US012662465B2

(12) United States Patent
Ahmad et al.

(10) Patent No.: US 12,662,465 B2
(45) Date of Patent: Jun. 23, 2026

(54) EGFR INHIBITORS

(71) Applicant: Blueprint Medicines Corporation, Cambridge, MA (US)

(72) Inventors: Omar Ahmad, Cambridge, MA (US); John Emmerson Campbell, Cambridge, MA (US); Thomas A. Dineen, Cambridge, MA (US); Meredith Suzanne Eno, Cambridge, MA (US); Dilinie Prasadhini Fernando, Cambridge, MA (US); Chandrasekhar V. Miduturu, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 850 days.

(21) Appl. No.: 17/883,743

(22) Filed: Aug. 9, 2022

(65) Prior Publication Data

US 2023/0019732 A1 Jan. 19, 2023

Related U.S. Application Data

(63) Continuation of application No. PCT/US2022/019597, filed on Mar. 9, 2022.

(60) Provisional application No. 63/158,998, filed on Mar. 10, 2021.

(51) Int. Cl.

| | |
|---|---|
| ***C07D 401/14*** | (2006.01) |
| ***A61P 35/00*** | (2006.01) |
| ***C07D 401/12*** | (2006.01) |
| ***C07D 403/14*** | (2006.01) |
| ***C07D 405/14*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 487/08*** | (2006.01) |
| ***C07D 487/10*** | (2006.01) |
| ***C07D 491/107*** | (2006.01) |
| ***C07D 495/10*** | (2006.01) |
| ***C07D 498/08*** | (2006.01) |

(52) U.S. Cl.
CPC ............ *C07D 401/14* (2013.01); *A61P 35/00* (2018.01); *C07D 401/12* (2013.01); *C07D 403/14* (2013.01); *C07D 405/14* (2013.01); *C07D 413/14* (2013.01); *C07D 417/14* (2013.01); *C07D 471/04* (2013.01); *C07D 487/04* (2013.01); *C07D 487/08* (2013.01); *C07D 487/10* (2013.01); *C07D 491/107* (2013.01); *C07D 495/10* (2013.01); *C07D 498/08* (2013.01)

(58) Field of Classification Search
CPC .. C07D 401/14; C07D 401/12; C07D 403/14; C07D 405/14; C07D 413/14; C07D 417/14; C07D 471/04; C07D 487/04; C07D 487/08; C07D 487/10; C07D 491/107; C07D 495/10; C07D 498/08
See application file for complete search history.

(56) References Cited

U.S. PATENT DOCUMENTS

| | | | | |
|---|---|---|---|---|
| 5,580,870 | A * | 12/1996 | Barker | C07D 401/12 514/249 |
| 7,696,214 | B2 | 4/2010 | Hennequin et al. | |
| 8,633,186 | B2 | 1/2014 | Tachdjian et al. | |
| 9,353,116 | B2 | 5/2016 | Garske et al. | |
| 2011/0275643 | A1 | 11/2011 | Liou et al. | |

FOREIGN PATENT DOCUMENTS

| | | | |
|---|---|---|---|
| CN | 102516232 | A | 6/2012 |
| CN | 103664938 | A | 3/2014 |
| CN | 104341437 | A | 2/2015 |
| CN | 108490184 | A | 9/2018 |
| EP | 1450808 | A1 | 9/2004 |
| WO | 2001/94341 | A1 | 12/2001 |

(Continued)

OTHER PUBLICATIONS

Cecil Textbook of Medicine, 1997, 20 Ed, vol. 1, pp. 1004-1010 (Year: 1997).*

(Continued)

*Primary Examiner* — Bruck Kifle
*Assistant Examiner* — Kevin S Martin
(74) *Attorney, Agent, or Firm* — McCarter & English, LLP; Xin Zhang; Sujatha Rochford

(57) ABSTRACT

The present disclosure provides a compound represented by structural formula (I-0):

(I-0)

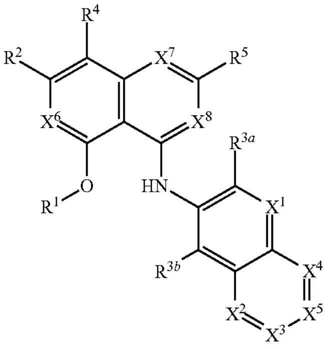

or a pharmaceutically acceptable salt thereof useful for treating a cancer.

18 Claims, No Drawings

(56) References Cited

FOREIGN PATENT DOCUMENTS

| | | | |
|---|---|---|---|
| WO | 03/045395 | A1 | 6/2003 |
| WO | 2003/064413 | A1 | 8/2003 |
| WO | 2005/014582 | A1 | 2/2005 |
| WO | 2011/053861 | A1 | 5/2011 |
| WO | 2012/116137 | A2 | 8/2012 |
| WO | 2016/061280 | A1 | 4/2016 |
| WO | 2018/226230 | A1 | 12/2018 |
| WO | 2019/027765 | A1 | 2/2019 |
| WO | 2020/033413 | A2 | 2/2020 |
| WO | 2020/168927 | A1 | 8/2020 |

OTHER PUBLICATIONS

Wu et al. Journal of Hematology & Oncology, 2022, 15, 143 (Year: 2022).*

Agarwal et al. (Curr Cancer Drug Targets 2017, 17(7), Abstract) (Year: 2017).*

Choudhary et al., Potential of substituted quinazolines to interact with multiple targets in the treatment of cancer. Bioorg Med Chem. Apr. 1, 2021;35:116061.

Yao et al., Synthesis and Evaluation of Vascular Endothelial Growth Factor Receptor-2 Inhibitory Activity of 6,7-Dimethoxycinnoline Derivatives. Letters in Drug Design & Discovery. 2013;10(10):984-988.

International Search Report and Written Opinion for Application No. PCT/US2022/019597, dated Jun. 3, 2022, 10 pages.

* cited by examiner

EGFR INHIBITORS

CROSS-REFERENCE TO RELATED APPLICATIONS

This application is a continuation of International Patent Application No. PCT/US2022/019597, filed Mar. 9, 2022, which claims priority from U.S. Provisional Application No. 63/158,998, filed Mar. 10, 2021. The entire contents of the aforementioned application are incorporated herein by reference.

BACKGROUND

EGFR (Epidermal Growth Factor Receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands and receptors, EGFR gene amplification and alterations such as mutations, deletions and the like, can promote malignant transformation of cells and play an important role in tumor cell proliferation, invasion, metastasis and angiogenesis. For example, alterations such as mutations and deletions in the EGFR gene are found in non-small lung cancer (NSCLC) tumors. The two most frequent EGFR alternations found in NSCLC tumors are short in-frame deletions in exon 19 (del19) and L858R, a single missense mutation in exon 21 (*Cancer Discovery* 2016 6(6) 601). These two alterations, referred to as sensitizing mutations, cause ligand-independent EGFR activation and are referred to as primary or activating mutations in EGFR mutant NSCLC (EGFR M+). Clinical experience shows an objective response rate (ORR) of approximately 60-85% in EGFR M+NSCLC patients treated first line (1L) with EGFR tyrosine kinase inhibitors (TKIs) erlotinib, gefitinib, afatinib and osimertinib (*Lancet Oncol.* 2010 Vol. 11, 121*; Lancet Oncol.* 2016 Vol. 17, 577*; N. Engl. J. Med.* 2017 Nov. 18 Doi: 10.1056/NEJMoa1713137*; Lancet Oncol.* 2011 Vol. 12, 735), thus demonstrating that EGFR mutant NSCLC tumors depend on oncogenic EGFR activity for survival and proliferation and establishing del19 and L858R mutated EGFR as oncogenic drivers of disease and thus, validating drug targets and biomarkers for the treatment of NSCLC.

Osimertinib is a covalent third ($3^{rd}$) generation EGFR TKI that is now the approved standard of care (SOC) in first line (1L) for the treatment of NSCLC harboring del19 and L858R mutations. With a progression-free survival (PFS) of 18.9 mo (JC Soria et al—NEJM, 2018 January; 378(2):113-125), it shows a transformative outcome for patients compared to first generation TKIs. However, after an average of 10-12 months of treatment, resistance has been observed in almost all NSCLC patients (Lancet Oncol. 2010 February; 11(2):121-8; Lancet Oncol. 2016 May; 17(5):577-89; Lancet Oncol. 2011 August; 12(8):735-42). Additional $3^{rd}$ generation TKIs are being used in front line (e.g. lazertinib) and relay on the same covalent mechanism of binding to EGFR. The most prominent on-target resistance mechanism is due to the secondary mutation in EGFR of C797X (where "X" can be an "S" or a "G" or an "N" or a "Y" or a "T" or a "D"), which occurs in 7% to 22% of patients progressing on 3rd generation EGFR inhibitors used in front line (Blakely, 2012; Kobayashi, 2005). This secondary C797S mutation reduces the affinity of the drug with the target, thereby producing drug resistance, and resulting in tumor recurrence or disease progression. The resulting "double mutant" tumors, that harbors the sensitizing mutations del19 or L858R and the resistance mutation C797X (e.g., C797S), are no longer sensitive to $2^{nd}$ and $3^{rd}$ generation TKIs. There is no approved drug to treat the double mutant patients. $1^{st}$ generation TKIs (gefitinib and erlotinib) are active against C797X (e.g., C797S) but they are poorly tolerated due to activity associated with wild-type EGFR inhibition, and do not control brain disease due to their low ability to cross the blood brain barrier (BBB).

There is an unmet need for a selective therapeutic agent that treats the double mutant tumors, that is brain penetrant and treats the brain disease, and with reduced toxicologies (diarrhea, skin rash) associated with wild-type EGFR inhibition.

SUMMARY

The applicant has discovered novel compounds which are effective inhibitors of certain mutant forms of EGFR (see Synthetic Examples 1-159). In particular, it has been demonstrated that the compounds of the present disclosure effectively inhibit certain mutant forms of EGFR. Compounds of the disclosure (also referred to herein as the "disclosed compounds") or pharmaceutically acceptable salts thereof effectively inhibit EGFR with one or more alterations, including L858R or exon 19 deletion mutation, and C797X (e.g., C797S) mutation (hereinafter "EGFR with LRCS mutations" or "double mutant EGFR") (see Biological Example 1) and can be used treat various cancers, for example, lung cancer (see Biological Example 2). Importantly, the disclosed compounds are selective EGFR inhibitors, i.e., the disclosed compounds have no or low activity against wild-type EGFR and the kinome. Advantages associated with such selectivity may include facilitating efficacious dosing and reducing EGFR-mediated on-target toxicities. Some of the disclosed compounds exhibit good penetration of the brain and blood brain barrier (e.g., a PGP efflux ratio of less than 5). As such, the compounds of the disclosure or pharmaceutically acceptable salts thereof are expected to be effective for the treatment of metastatic cancer, including brain metastesis, including leptomeningeal disease and other systemic metastesis. Some of the disclosed compounds also have the advantage of having high microsomal stability. Compounds of the disclosure also may have favorable toxicity profiles related to other non-kinase targets.

In one aspect, the present disclosure provides a compound represented by the following structural Formula (I-0):

(I-0)

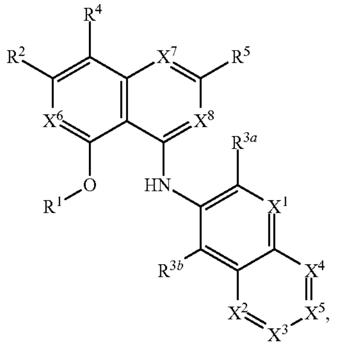

or a pharmaceutically acceptable salt thereof, the definition of each variable is provided below.

In another aspect, the present disclosure provides a pharmaceutical composition comprising a pharmaceutically acceptable carrier or diluent and one or more of the compounds disclosed herein, or a pharmaceutically acceptable salt thereof (a "pharmaceutical composition of the disclosure").

The present disclosure provides a method of treating a subject with cancer, comprising administering to the subject an effective amount of a compound of the disclosure (e.g., a compound of Formula (I)) or a pharmaceutically acceptable salt thereof or a pharmaceutical composition of the disclosure. In one embodiment, the cancer is non-small cell lung cancer. In another embodiment, the subject cancer has metastasized to the brain. In another embodiment, the subject has brain metastasis from non-small cell lung cancer.

In one embodiment, the cancer to be treated has epidermal growth factor receptor (EGFR) L858R mutation or exon 19 deletion mutation. In another embodiment, the cancer to be treated may further has epidermal growth factor receptor (EGFR) L858R mutation or exon 19 deletion mutation and the C797X (e.g., C797S) mutation. In another embodiment, the cancer to be treated in either of the foregoing embodiments is lung cancer, e.g., non-small cell lung cancer. In a specific embodiment, the cancer is non-small cell lung cancer with brain metastasis or leptomeningeal disease.

The treatment method disclosed herein further comprises administering to the subject an effective amount of an EGFR inhibitor (e.g., afatinib and/or osimertinib), and a MET inhibitor in combination with an effective amount of a compound of the disclosure.

The present disclosure also provides a method of inhibiting epidermal growth factor receptor (EGFR) in a subject in need thereof, comprising administering to the subject an effective amount of a compound of the disclosure (e.g., a compound of Formula (I-0)) or a pharmaceutically acceptable salt thereof or a pharmaceutical composition of the disclosure.

The present disclosure also provides the use of an effective amount of a compound of the disclosure (e.g., a compound of Formula (I-0)), or a pharmaceutically acceptable salt thereof, or a pharmaceutical composition of the disclosure, for the preparation of a medicament for the treatment of cancers.

In another aspect, provided herein a compound of Formula (I-0), or a pharmaceutically acceptable salt thereof, or a pharmaceutical composition of the disclosure for use in treating cancers.

DETAILED DESCRIPTION

Definitions

The term "halo" as used herein means halogen and includes chloro, fluoro, bromo and iodo.

The term "alkyl" used alone or as part of a larger moiety, such as "alkoxy" and the like, means saturated aliphatic straight-chain or branched monovalent hydrocarbon radical. Unless otherwise specified, an alkyl group typically has 1-6 carbon atoms, i.e. $(C_1\text{-}C_6)$alkyl. As used herein, a "$(C_1\text{-}C_6)$ alkyl" group means a radical having from 1 to 6 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "$(C_1\text{-}C_4)$alkoxy" includes methoxy, ethoxy, propoxy, and butoxy.

The term "cycloalkyl" refers to a monocyclic saturated hydrocarbon ring system. Unless otherwise specified, cycloalkyl has from 3-6 carbon atoms. For example, a $C_3$-$C_6$ cycloalkyl includes cyclopropyl, cyclobutyl, cyclopentyl and cyclohexyl. Unless otherwise described, a "cycloalkyl" has from three to six carbon atoms.

The term "heterocyclyl" or "heterocyclic" refers to a radical of a 4- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("4-12 membered heterocyclyl"). In some embodiments, a heterocyclyl group is a 4- to 8-membered non-aromatic ring system having ring carbon atoms and 1-4 (typically 1 to 2) ring heteroatoms, wherein each heteroatom is independently selected from nitrogen, oxygen, and sulfur ("4-8 membered heterocyclyl"). In heterocyclyl groups that contain one or more nitrogen atoms, the point of attachment can be a carbon or nitrogen atom, as valence permits. A heterocyclyl group can either be monocyclic ("monocyclic heterocyclyl") or polycyclic (e.g., a bicyclic system ("bicyclic heterocyclyl") or a tricyclic system ("tricyclic heterocyclyl")). A polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Exemplary polycyclic heterocyclic groups include 3-oxabicyclo[3.1.0]hexanyl, 8-oxa-3-azabicyclo[3.2.1]octanyl, 2-oxa-6-azaspiro[3.3]heptanyl, 6-oxa-3-azabicyclo[3.1.1]heptanyl, and the like. Substituents may be present on one or more rings in the polycyclic ring system.

A bridged bicyclic system has two non-aromatic rings containing from 7-12 ring atoms (heterocyclyl or cycloalkyl) and which share three or more atoms, with the two bridgehead atoms separated by a bridge containing at least one atom. "Bridged heterocyclyl" includes bicyclic or polycyclic hydrocarbon or aza-bridged hydrocarbon groups; examples include 3-oxabicyclo[3.1.0]hexanyl, 2-azabicyclo[2.2.1]heptanyl, 6-oxa-3-azabicyclo[3.1.1]heptanyl, 3-azabicyclo[3.2.1]octanyl, 6-oxa-2-azabicyclo[3.2.1]octanyl, 6-oxa-3-azabicyclo[3.2.1]octanyl, and 8-oxa-3-azabicyclo[3.2.1]octanyl.

A fused bicyclic system has two non-aromatic rings (heterocyclyl or cycloalkyl) containing from 7-12 ring atoms and which share two adjacent ring atoms. Examples of fused bicyclic systems include hexahydro-1H-furo[3,4-b]pyrrolyl, and hexahydro-1H-furo[3,4-c]pyrrolyl.

A spiro bicyclic system has two non-aromatic rings containing (heterocyclyl or cycloalkyl) from 7-12 ring atoms and which share one ring atom. Examples of spiro bicyclic systems include 1-oxa-7-azaspiro[3.5]nonan-7-yl, 2-oxa-6-azaspiro[3.3]heptanyl, 1,4-dioxa-8-azaspiro[4.5]decan-8-yl, and 1,4-dioxa-9-azaspiro[5.5]undecan-9-yl. "Heteroaryl" refers to a radical of a 4- to 12-membered aromatic ring system having ring carbon atoms and 1 to 4 ring heteroatoms, wherein each heteroatom is independently selected from nitrogen, oxygen, and sulfur. In some embodiments, a heteroaryl group is a 5 or 6 membered heteroaryl having ring carbon atoms and 1 to 4 ring heteroatoms (typically 1 to 2). Representative heteroaryl groups include ring systems where each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl.

Compounds of the Present Disclosure

Disclosed herein are embodiments of compounds having a general structure of Formula (I). These compounds are selective inhibitors of L858R, Ex19del, L858RC797S and Ex19DelC797S EGFR. In contrast to other EGFR inhibitors such as osimertinib which binds EGFR irreversibly, the compounds of the disclosure are non-covalent inhibitors.

In one embodiment, the present disclosure provides a compound represented by the following structural formula (I-0):

(I-0)

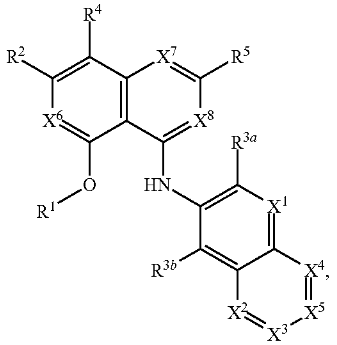

or a pharmaceutically acceptable salt thereof, wherein $X^1$, $X^2$, $X^3$, $X^4$, and $X^5$ is $CR^{3c}$, N, or $N^+—O^-$, provided that at least 3 of $X^1$, $X^2$, $X^3$, $X^4$, and $X^5$ is $CR^{3c}$;

$X^6$ is CH, CD, N, or $N^+—O^-$;

$X^7$ and $X^8$ is N or $N^+—O^-$; provided that no more than one of $X^1$, $X^2$, $X^3$, $X^4$, $X^5$, $X^6$, $X^7$, and $X^8$ is $N^+—O^-$;

$R^1$ is $C_1$-$C_6$alkyl, $C_3$-$C_6$cycloalkyl, or 4- to 12-membered heterocyclyl, wherein the alkyl, cycloalkyl, and heterocyclyl represented by $R^1$ is optionally substituted with 1 to 4 groups independently selected from deuterium, halo, $C_1$-$C_4$alkyl, =O, OH, $C_1$-$C_4$alkoxy, $NR^{1a}R^{1b}$, and 4 to 8 membered heterocyclyl, wherein the heterocyclyl is optionally substituted with methyl, ethyl, or $—(CH_2)_mNR^{1a}R^{1b}$;

$R^2$ is halo, $NR^{1a}R^{1b}$, $C_1$-$C_4$alkyl, $C_1$-$C_4$alkoxy, $C_3$-$C_6$cycloalkyl, 4- to 12-membered heterocyclyl, or 5 or 6 membered heteroaryl, wherein the alkyl, alkoxy, cycloalkyl, heterocycyl, and heteroaryl represented by $R^2$ are each optionally substituted with 1 to 4 groups selected from deuterium, halo, =O (as valence permits), OH, $NR^{1a}R^{1b}$, $C(O)CH_3$, $C_1$-$C_4$alkyl and $C_1$-$C_4$alkoxy, wherein the $C_1$-$C_4$alkyl and $C_1$-$C_4$alkoxy are each optionally substituted with 1 to 3 groups selected from deuterium, halo, OH, and $OCH_3$;

$R^{3a}$ is H, deuterium, halo, OH, $C_{1-4}$alkyl, or $C_1$-$C_4$alkoxy;

$R^{3b}$ is H, deuterium, halo, OH, $C_{1-4}$alkyl, or $C_1$-$C_4$alkoxy;

Each $R^{3c}$ is independently selected from H, deuterium, halo, OH, $C_{1-4}$alkyl, and $C_1$-$C_4$alkoxy, wherein no more than 3 $R^{3c}$ are halo, OH, $C_{1-4}$alkyl, or $C_1$-$C_4$alkoxy;

$R^{1a}$ is H, deuterium, $C_1$-$C_4$alkyl, or $C_3$-$C_6$cycloalkyl;

$R^{1b}$ is H, deuterium, $C_1$-$C_4$alkyl, or $C_3$-$C_6$cycloalkyl;

$R^4$ is H or deuterium;

$R^5$ is H or deuterium; and m is 0 or 1.

In a first embodiment, the present disclosure provides a compound represented by the following structural formula (I):

(I)

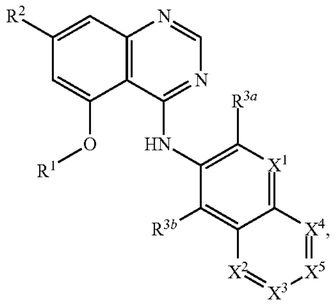

or a pharmaceutically acceptable salt thereof, wherein:

$X^1$, $X^2$, $X^3$, $X^4$, and $X^5$ is $CR^{3c}$ or N, provided that at least 3 of $X^1$, $X^2$, $X^3$, $X^4$, and $X^5$ is $CR^{3c}$;

$R^1$ is $C_1$-$C_6$ alkyl, $C_3$-$C_6$cycloalkyl, 4 to 12 membered heterocyclyl, wherein the alkyl, cycloalkyl, and heterocyclyl represented by $R^1$ is optionally substituted with 1 to 4 groups independently selected from halo, $C_1$-$C_4$alkyl, =O, OH, $C_1$-$C_4$alkoxy, $NR^{1a}R^{1b}$, and 4 to 8 membered heterocyclyl, wherein the heterocyclyl is optionally substituted with $—(CH_2)_mNR^{1a}R^{1b}$;

$R^2$ is $C_1$-$C_4$alkoxy, 4 to 12 membered heterocyclyl, 5 or 6 membered heteroaryl, wherein the alkyl, heterocycyl, and heteroaryl represented by $R^2$ are each optionally substituted with 1 to 4 groups selected from $C_1$-$C_4$alkyl and $C_1$-$C_4$alkoxy, wherein the $C_1$-$C_4$ alkyl and $C_1$-$C_4$alkoxy are each optionally substituted with 1 to 3 groups selected from halo, OH and $OCH_3$;

$R^{3a}$ is H, halo, OH, $C_{1-4}$alkyl, or $C_1$-$C_4$alkoxy;

$R^{3b}$ is H, halo, OH, $C_{1-4}$alkyl, or $C_1$-$C_4$ alkoxy;

Each $R^{3c}$ is independently selected from H, halo, OH, $C_{1-4}$alkyl, and $C_1$-$C_4$ alkoxy, wherein no more than 3 $R^{3c}$ are halo, OH, $C_{1-4}$alkyl, or $C_1$-$C_4$alkoxy;

$R^{1a}$ is H, $C_1$-$C_4$alkyl, or $C_3$-$C_6$cycloalkyl;

$R^{1b}$ is H, $C_1$-$C_4$alkyl, or $C_3$-$C_6$cycloalkyl; and m is 0 or 1.

In a second embodiment, the present disclosure provides a compound represented by structural formula (II):

(II)

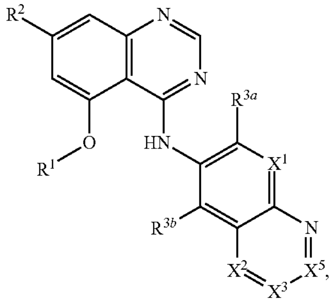

or a pharmaceutically acceptable salt thereof, wherein the variables are as defined in the first embodiment.

In a third embodiment, the present disclosure provides a compound represented by structural formula (IIA):

(IIA)

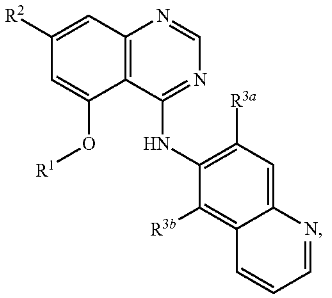

or a pharmaceutically acceptable salt thereof, wherein the variables are as defined in the first embodiment.

In a fourth embodiment, the present disclosure provides a compound represented by structural formula (IIB):

(IIB)

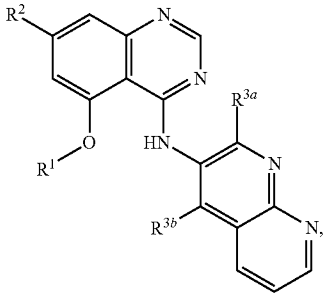

or a pharmaceutically acceptable salt thereof, wherein the variables are as defined in the first embodiment.

In a fifth embodiment, the present disclosure provides a compound represented by structural formula (IIC):

(IIC)

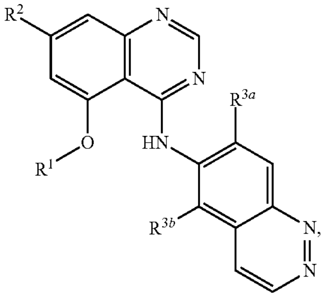

or a pharmaceutically acceptable salt thereof, wherein the variables are as defined in the first embodiment.

In a sixth embodiment, the present disclosure provides a compound represented by structural formula (IID):

(IID)

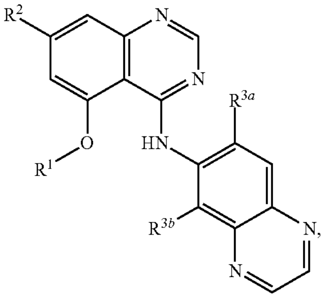

or a pharmaceutically acceptable salt thereof, wherein the variables are as defined in the first embodiment.

In a seventh embodiment, the present disclosure provides a compound represented by structural formula (III):

(III)

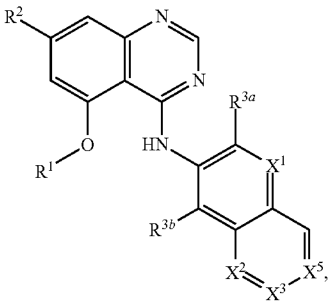

or a pharmaceutically acceptable salt thereof, wherein the variables are as defined in the first embodiment.

In an eighth embodiment, the present disclosure provides a compound represented by structural formula (IIIA):

(IIIA)

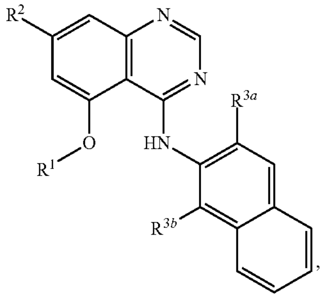

or a pharmaceutically acceptable salt thereof, wherein the variables are as defined in the first embodiment.

In a ninth embodiment, the present disclosure provides a compound represented by structural formula (IIIB):

(IIIB)

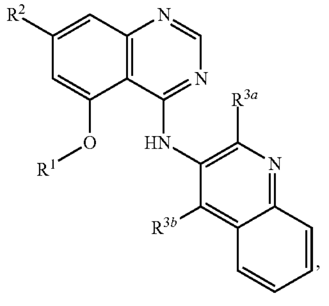

or a pharmaceutically acceptable salt thereof, wherein the variables are as defined in the first embodiment.

In a tenth embodiment, the present disclosure provides a compound represented by structural formula (IIIC):

(IIIC)

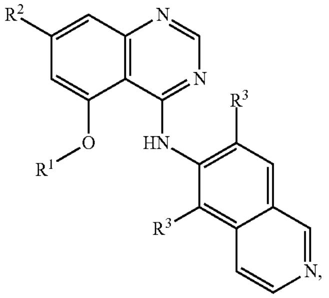

or a pharmaceutically acceptable salt thereof, wherein the variables are as defined in the first embodiment.

In an eleventh embodiment, the present disclosure provides a compound represented by structural formula (IIID):

(IIID)

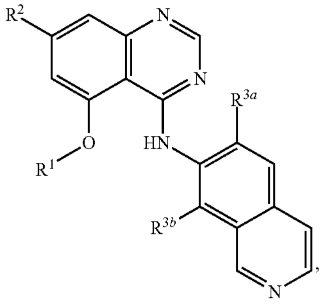

or a pharmaceutically acceptable salt thereof, wherein the variables are as defined in the first embodiment.

In a twelfth embodiment, the present disclosure provides a compound represented by structural formula (IIIE):

(IIIE)

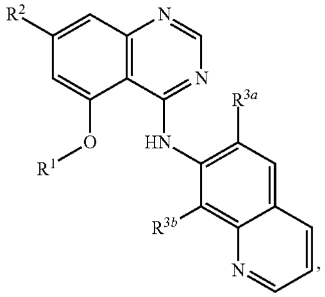

or a pharmaceutically acceptable salt thereof, wherein the variables are as defined in the first embodiment.

In a thirteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is $C_1$-$C_6$ alkyl optionally substituted with 1 to 4 groups independently selected from halo, =O, OH, $C_1$-$C_4$alkoxy, $NR^{1a}R^{1b}$, and 4 to 8 membered heterocyclyl, wherein the heterocyclyl is optionally substituted with $-(CH_2)_mNR^{1a}R^{1b}$; $R^{1a}$ is H, $C_1$-$C_4$alkyl, or $C_3$-$C_6$cycloakyl; and $R^{1b}$ is H or $C_1$-$C_4$alkyl, wherein the remainder of the variables are as defined in the first embodiment.

In a fourteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is $C_1$-$C_5$ alkyl optionally substituted with 1 to 3 groups independently selected from F, Cl, =O, OH, $OCH_3$, $NR^{1a}R^{1b}$, 3-oxabicyclo[3.1.0]hexanyl, azetidinyl, oxetanyl, tetrahydrofuranyl, and morpholinyl, wherein the oxetanyl is optionally substituted with $N(CH_3)_2$ or $CH_2N(CH_3)_2$; $R^{1a}$ is H, methyl, cyclopropyl, or cyclobutyl; and $R^{1b}$ is methyl, wherein the remainder of the variables are as defined in the first or thirteenth embodiment.

In a fifteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is ethyl substituted with oxetanyl, wherein the remainder of the variables are as defined in the first, thirteenth, or fourteenth embodiment. In a particular aspect, $R^1$ is $-CH(CH_3)$-oxetanyl.

In a sixteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is $C_3$alkyl substituted with $N(CH_3)_2$, wherein the remainder of the variables are as defined in the first, thirteenth, fourteenth, or fifteenth embodiment. In a particular aspect, $R^1$ is $—CH(CH_3)CH_2N(CH_3)_2$.

In a seventeenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is $C_3$-$C_6$cycloalkyl optionally substituted with 1 to 4 groups independently selected from halo, $C_1$-$C_4$alkyl, ═O, OH, $C_1$-$C_4$alkoxy, and $NR^{1a}R^{1b}$; $R^{1a}$ is H, $C_1$-$C_4$alkyl, or $C_3$-$C_6$cycloalkyl; and $R^{1b}$ is H or $C_1$-$C_4$alkyl, wherein the remainder of the variables are as defined in the first embodiment.

In an eighteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is cyclobutyl optionally substituted with OH or $N(CH_3)_2$, wherein the remainder of the variables are as defined in the first, or seventeenth embodiment.

In a nineteenth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is 4 to 8 membered monocyclic heterocyclyl optionally substituted with 1 to 2 groups independently selected from halo, $C_1$-$C_4$alkyl, ═O, OH, $C_1$-$C_4$alkoxy, and $NR^{1a}R^{1b}$; $R^{1a}$ is H, $C_1$-$C_4$alkyl, or $C_3$-$C_6$cycloalkyl; and $R^{1b}$ is H or $C_1$-$C_4$alkyl, wherein the remainder of the variables are as defined in the first embodiment.

In a twentieth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^1$ is piperidinyl or pyrrolidinyl, each optionally substituted with 1 or 2 groups selected from F, ═O, and $C_1$-$C_4$alkyl, wherein the remainder of the variables are as defined in the first or nineteenth embodiment.

In a twenty-first embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is $C_1$-$C_4$alkoxy, wherein the remainder of the variables are as defined in the first, thirteenth, fourteenth, fifteenth, sixteenth, seventeenth, eighteenth, nineteenth, or twentieth embodiment. In one specific embodiment, $R^2$ is $OCH_3$ or $OCH_2CH_3$.

In a twenty-second embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is 4 to 12 membered heterocyclyl optionally substituted with 1 to 3 groups selected from $C_1$-$C_4$ alkyl or $C_1$-$C_4$alkoxy, wherein the alkyl represented by $R^2$ is optionally substituted with OH, wherein the remainder of the variables are as defined in the first, thirteenth, fourteenth, fifteenth, sixteenth, seventeenth, eighteenth, nineteenth, or twentieth embodiment.

In a twenty-third embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is 8-oxa-3-azabicyclo[3.2.1]octanyl, 2-oxa-6-azaspiro[3.3]heptanyl, 6-oxa-3-azabicyclo[3.1.1]heptanyl, pyrrolidinyl, or morpholinyl, each of which is optionally substituted with 1 or 2 groups selected from methyl, $C(CH_3)_2OH$, and $OCH_3$, wherein the remainder of the variables are as defined in the first, thirteenth, fourteenth, fifteenth, sixteenth, seventeenth, eighteenth, nineteenth, twentieth, or twenty-second embodiment.

In a twenty-fourth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is 5 or 6 membered heteroaryl optionally substituted with 1 to 3 groups selected from $C_1$-$C_4$alkyl, and $C_1$-$C_4$alkoxy, wherein the $C_1$-$C_4$alkyl and $C_1$-$C_4$alkoxy represented by $R^2$ are each optionally substituted with 1 to 3 groups selected from halo and OH, wherein the remainder of the variables are as defined in the first, thirteenth, fourteenth, fifteenth, sixteenth, seventeenth, eighteenth, nineteenth, or twentieth embodiment.

In a twenty-fifth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is pyrazolyl optionally substituted with $C_1$-$C_4$alkyl or $C_1$-$C_4$alkoxy, each of which are optionally substituted with 1 to 3 groups selected from halo and OH, wherein the remainder of the variables are as defined in the first, thirteenth, fourteenth, fifteenth, sixteenth, seventeenth, eighteenth, nineteenth, twentieth, or twenty-fourth embodiment.

In a twenty-six embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^2$ is pyrazolyl optionally substituted with methyl, wherein the remainder of the variables are as defined in the first, thirteenth, fourteenth, fifteenth, sixteenth, seventeenth, eighteenth, nineteenth, twentieth, twenty-fourth, or twenty-fifth embodiment.

In a twenty-seventh embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^{3a}$ is halo; $R^{3b}$ is halo, and each $R^{3c}$ is H, wherein the remainder of the variables are as defined in the first, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a twenty-eighth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^{3a}$ is H; $R^{3b}$ is H, and each $R^{3c}$ is H, wherein the remainder of the variables are as defined in the first, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a twenty-ninth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^{3a}$ is H; $R^{3b}$ is halo, and each $R^{3c}$ is H, wherein the remainder of the variables are as defined in the first, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a thirtieth embodiment, the present disclosure provides a compound according to structural formula (I), (II), (IIA), (IIB), (IIC), (IID), (III), (IIIA), (IIIB), (IIIC), (IIID), or (IIIE), or a pharmaceutically acceptable salt thereof, wherein $R^{3a}$ is halo; $R^{3b}$ is H, and each $R^{3c}$ is H, wherein the remainder of the variables are as defined in the first, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a thirty-first embodiment, the present disclosure provides a compound represented by structural formula (IV):

(IV)

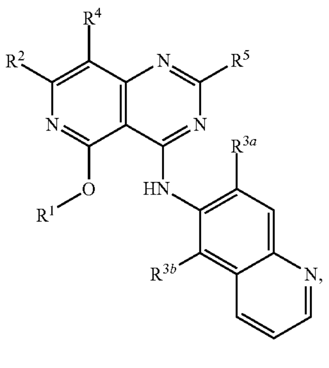

or a pharmaceutically acceptable salt thereof, wherein the variables are as defined in the embodiment of structural formula (I-0) and/or first, thirteenth through thirtieth embodiments.

In a thirty-second embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein $R^2$ is halo or $NR^{1a}R^{1b}$, wherein the remainder of the variables are as defined in the embodiment of structural formula (I-0) and/or first through twentieth, twenty-seventh through thirty-first embodiments.

In a thirty-third embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein $R^2$ is $C_1$-$C_4$alkyl or $C_1$-$C_4$alkoxy, wherein the alkyl and alkoxy, represented by $R^2$ are each optionally substituted with 1 to 4 groups selected from deuterium, halo, =O (as valence permits), OH, $NR^{1a}R^{1b}$, $C(O)CH_3$, $C_1$-$C_4$alkyl and $C_1$-$C_4$alkoxy, wherein the $C_1$-$C_4$alkyl and $C_1$-$C_4$alkoxy are each optionally substituted with 1 to 3 groups selected from deuterium, halo, OH, and $OCH_3$, wherein the remainder of the variables are as defined in the embodiment of structural formula (I-0) and/or first through twentieth, twenty-seventh through thirty-first embodiments. In one preferred embodiment, $R^2$ is $C_1$-$C_4$alkyl or $C_1$-$C_4$alkoxy, wherein the alkyl and alkoxy, represented by $R^2$ are each optionally substituted with 1 to 3 groups selected from halo.

In a thirty-fourth embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein $R^2$ is $C_3$-$C_6$cycloalkyl, 4- to 12-membered heterocyclyl, or 5 or 6 membered heteroaryl, wherein the cycloalkyl, heterocycyl, and heteroaryl represented by $R^2$ are each optionally substituted with 1 to 3 groups selected from deuterium, halo, =O (as valence permits), OH, $NR^{1a}R^{1b}$, $C(O)CH_3$, $C_1$-$C_4$alkyl and $C_1$-$C_4$alkoxy, wherein the $C_1$-$C_4$alkyl and $C_1$-$C_4$alkoxy are each optionally substituted with 1 to 3 groups selected from deuterium, halo, OH, and $OCH_3$, wherein the remainder of the variables are as defined in the embodiment of structural formula (I-0) and/or first through twentieth, twenty-seventh through thirty-first embodiments.

In a thirty-fifth embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one of $R^{3a}$, $R^{3b}$, and $R^{3c}$ is OH or $C_1$-$C_4$alkoxy, wherein the remainder of the variables are as defined in the embodiment of structural formula (I-0) and/or the first through thirty-fourth embodiment.

In a thirty-sixth embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or both of $R^{3a}$ and $R^{3b}$ are H or halo, and one $R^{3c}$ is OH or $C_1$-$C_4$alkoxy, wherein the remainder of the variables are as defined in the embodiment of structural formula (I-0) and/or the first through thirty-fourth embodiment.

In a thirty-seventh embodiment, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or both of $R^{3a}$ and $R^{3b}$ are H or halo, and one $R^{3c}$ is H or $C_1$-$C_4$alkyl, wherein the remainder of the variables are as defined in the embodiment of structural formula (I-0) and/or the first through thirty-fourth embodiment.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein $X^6$ is CD, wherein the remainder of the variables are as defined in the embodiment of structural formula (I-0) and/or the first through thirty-seventh embodiment.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or both of $R^{3a}$ and $R^{3b}$ is deuterium, wherein the remainder of the variables are as defined in the embodiment of structural formula (I-0) and/or the first through thirty-seventh embodiment. In a specific aspect, $R^{3a}$ is deuterium and $R^{3b}$ is hydrogen. Alternatively, $R^{3a}$ is hydrogen and $R^{3b}$ is deuterium. Alternatively, $R^{3a}$ is deuterium and $R^{3b}$ is deuterium.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or more optional substituents attached to $R^1$ and/or $R^2$ is deuterium, wherein the remainder of the variables are as defined in the embodiment of structural formula (I-0) and/or the first through thirty-seventh embodiment.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or more of $R^{3c}$ is deuterium, wherein the remainder of the variables are as defined in the embodiment of structural formula (I-0) and/or the first through thirty-seventh embodiment. In a specific aspect, one $R^{3c}$ is deuterium. In a specific aspect, two $R^{3c}$ are deuterium. In a specific aspect, three $R^{3c}$ are deuterium. In a specific aspect, four $R^{3c}$ are deuterium. In a specific aspect, five $R^{3c}$ are deuterium. In a specific aspect, six $R^{3c}$ are deuterium.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or both of $R^{1a}$ and $R^{1b}$ is deuterium, wherein the remainder of the variables are as defined in the embodiment of structural formula (I-0) and/or the first through thirty-seventh embodiment. In a specific aspect, $R^{1a}$ is deuterium and $R^{1b}$ is hydrogen. Alternatively, $R^{1a}$ is hydrogen and $R^{1b}$ is deuterium. Alternatively, $R^{1a}$ is deuterium and $R^{1b}$ is deuterium.

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or a pharmaceutically acceptable salt thereof, wherein one or both of $R^4$ and $R^5$ is deuterium, wherein the remainder of the variables are as defined in the embodiment of structural formula (I-0) and/or the first through thirty-seventh embodiment. In a specific aspect, $R^4$ is deuterium and $R^5$ is hydrogen. Alternatively, $R^4$ is hydrogen and $R^5$ is deuterium. Alternatively, $R^4$ is deuterium and $R^5$ is deuterium.

In one embodiment, a compound of the present disclosure is any one of the compounds disclosed in the examples (including neutral form, pharmaceutically acceptable salts, and intermediates) and Table 1, or a pharmaceutically acceptable salt thereof.

TABLE 1

| Example # | Structure |
|---|---|
| 1 | 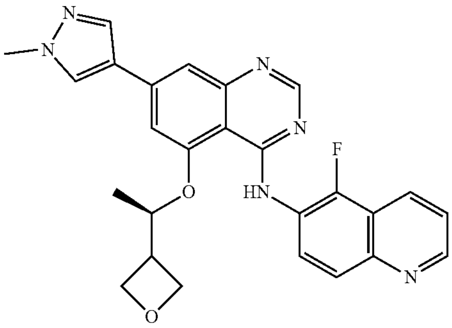 or 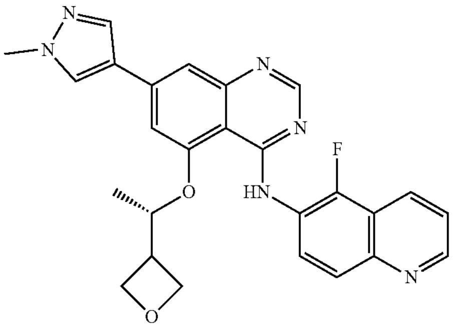 |
| 2 | 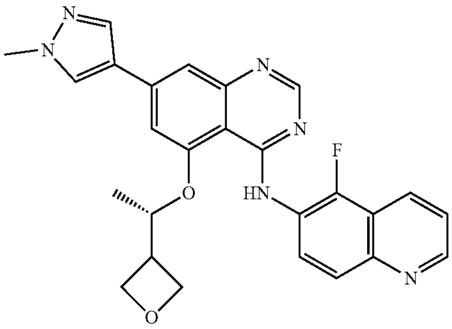 or 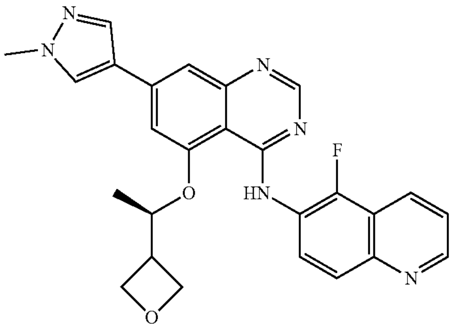 |
| 3 | 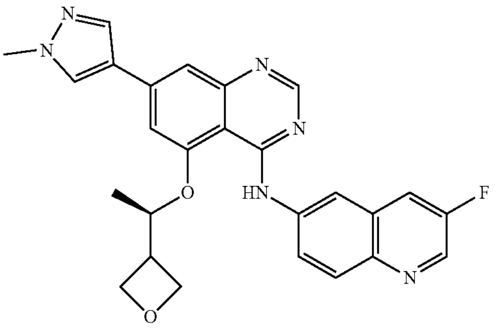 [SMILES: C[C@@H](Oc1cc(-c2cnn(C)c2)cc2ncnc(Nc3ccc4ncc(F)cc4c3)c12)C1COC1] |

TABLE 1-continued
| Example # | Structure | | |
|---|---|---|---|
| 4 | 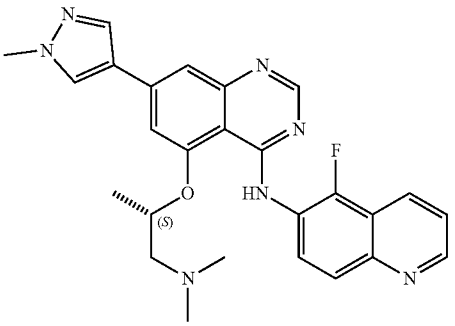 | or | 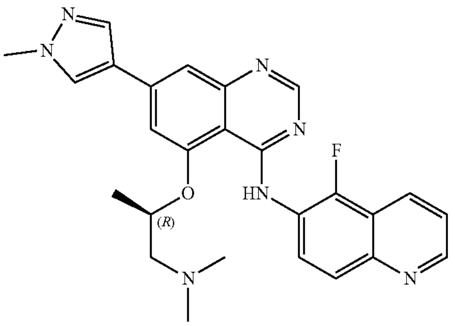 |
| 5 | 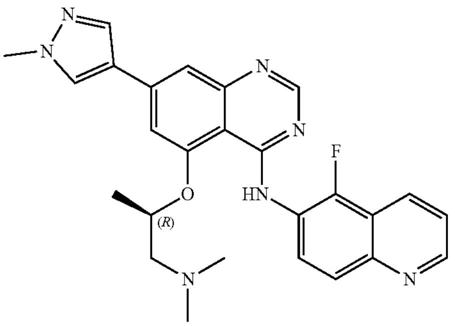 | or | 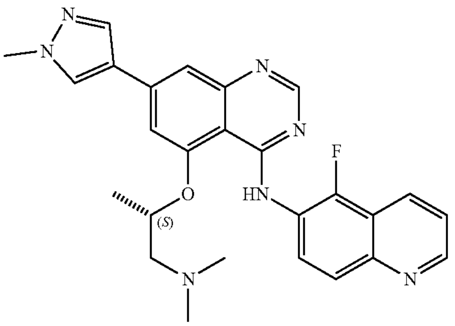 |
| 6 | 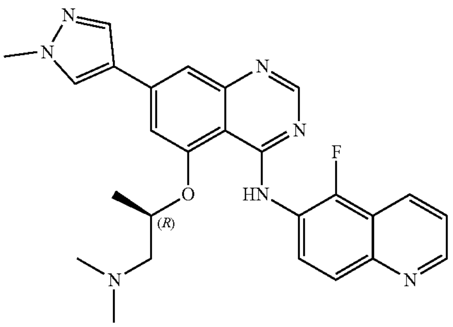 | | |
| 7 | 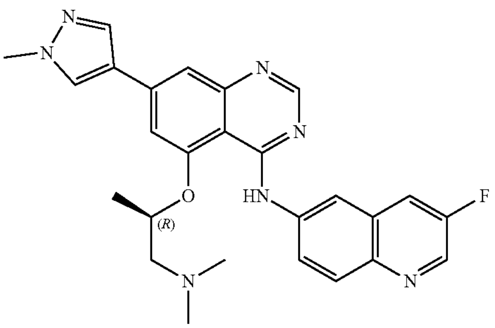 | | |

TABLE 1-continued
| Example # | Structure |
|---|---|
| 8 | 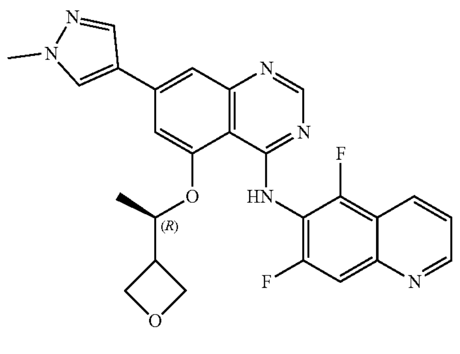 |
| 9 | 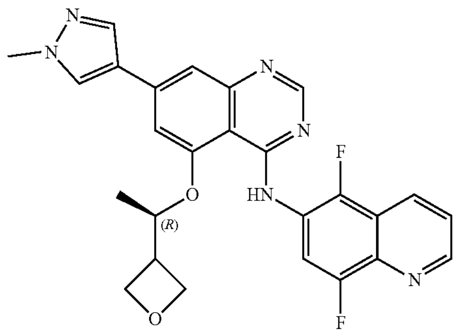 |
| 10 | 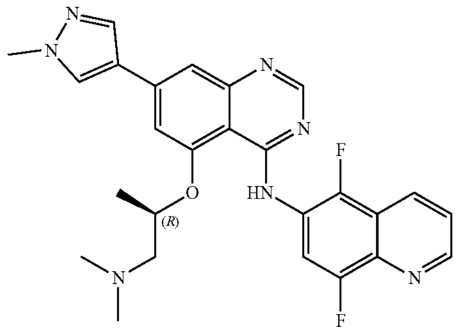 |
| 11 | 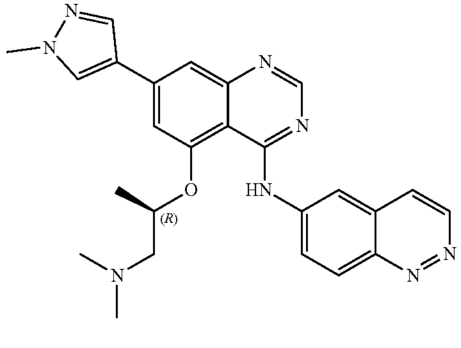 |

TABLE 1-continued
| Example # | Structure |
| --- | --- |
| 12 | 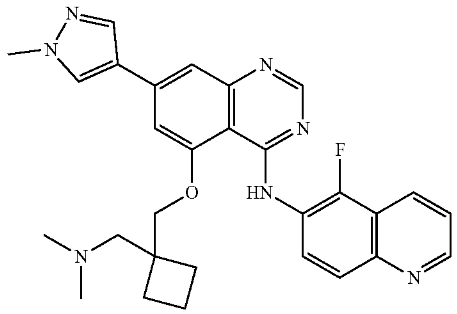 [SMILES: CN(C)CC1(COc2cc(-c3cnn(C)c3)cc3ncnc(Nc4ccc5ncccc5c4F)c23)CCC1] |
| 13 | 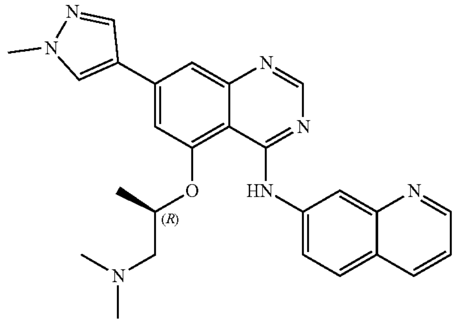 |
| 14 | 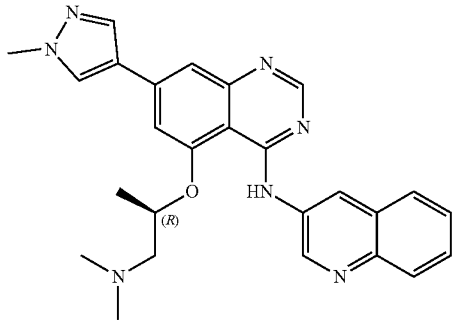 |
| 15 | 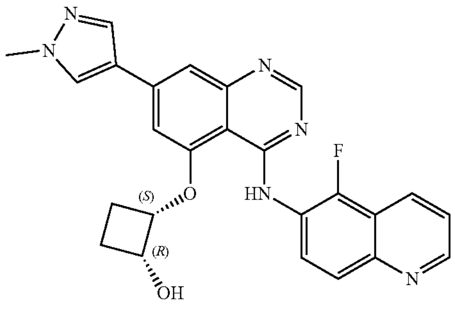 or 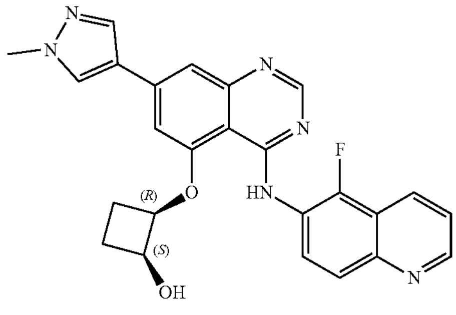 |

TABLE 1-continued
| Exam-ple # | Structure |
|---|---|
| 16 | 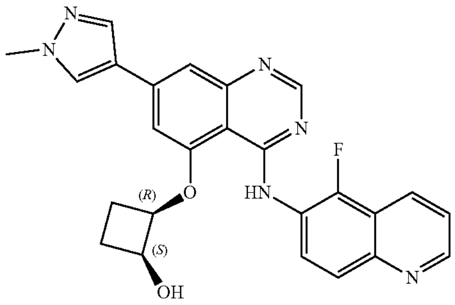 or 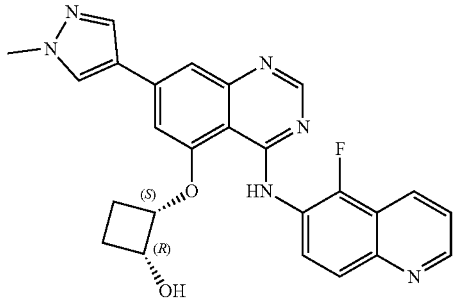 |
| 17 | 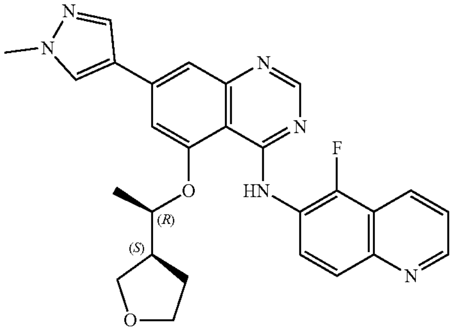 or 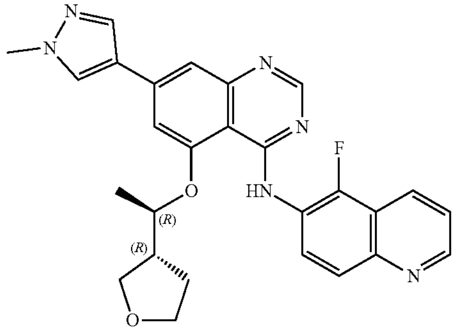 |
| 18 | 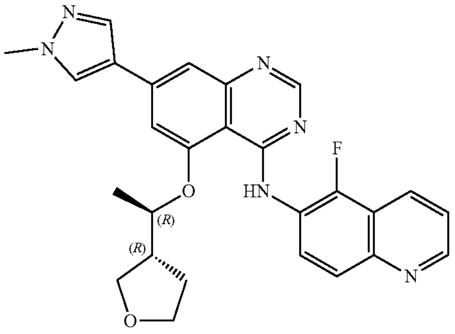 or 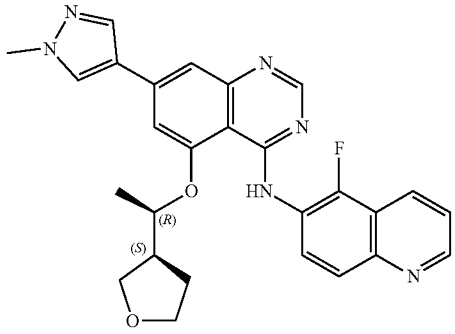 |
| 19 | 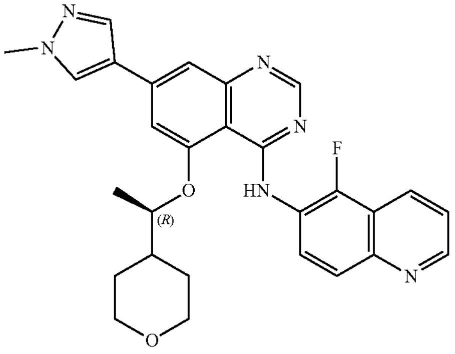 or 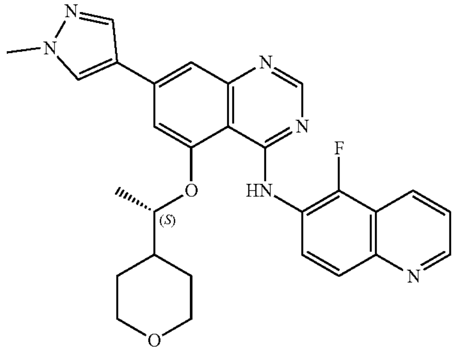 |

TABLE 1-continued
| Example # | Structure |
|---|---|
| 20 | 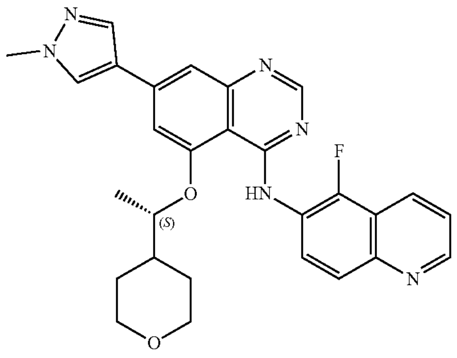 or 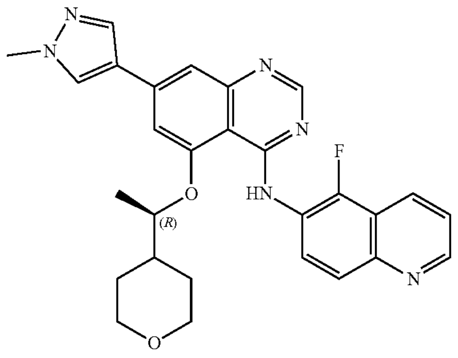 |
| 21 | 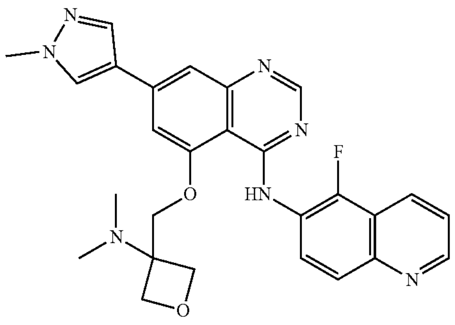 [SMILES: CN(C)C1(COc2cc(-c3cnn(C)c3)cc3ncnc(Nc4ccc5ncccc5c4F)c23)COC1] |
| 22 | 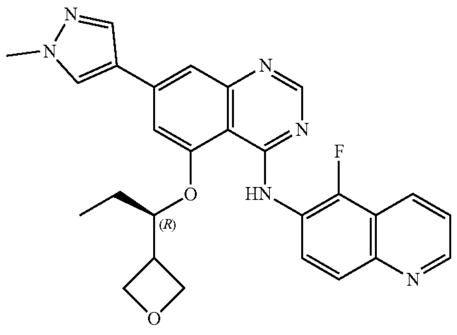 or 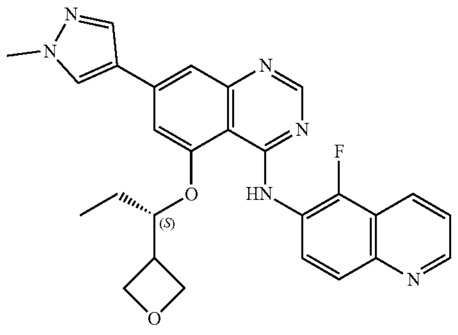 |
| 23 | 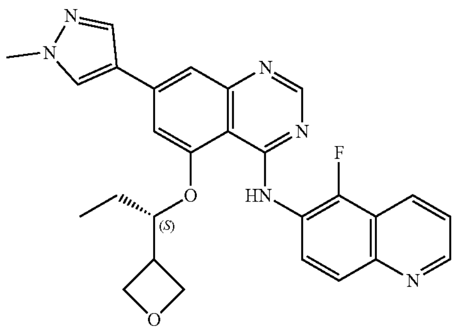 or 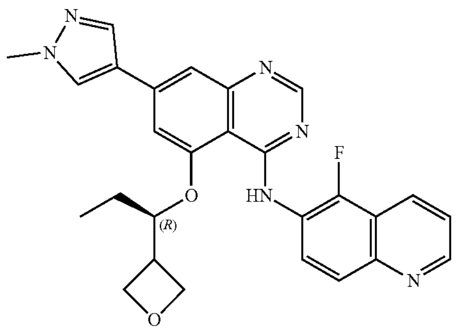 |

TABLE 1-continued
| Example # | Structure |
|---|---|
| 24 | 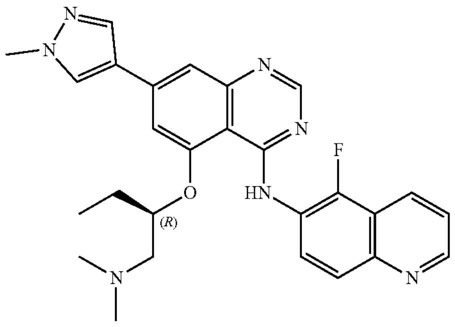 |
| 25 | 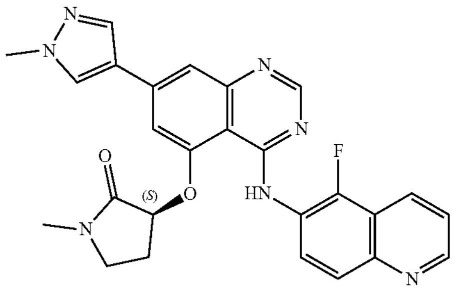 |
| 26 | 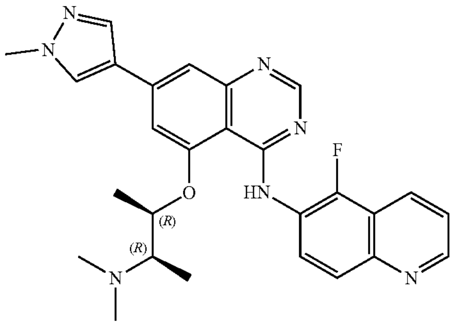 or 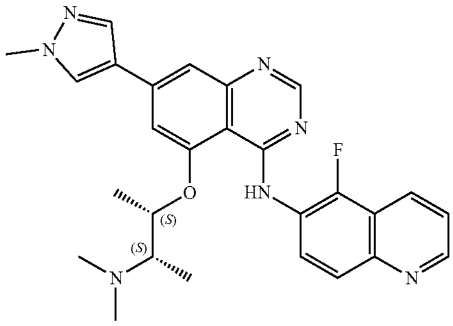 |
| 27 | 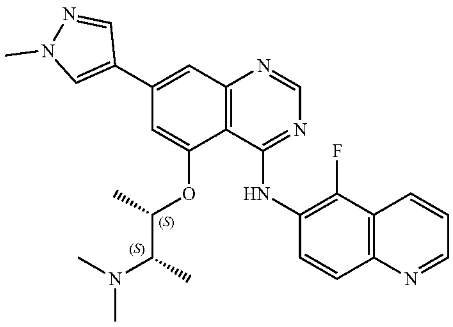 or 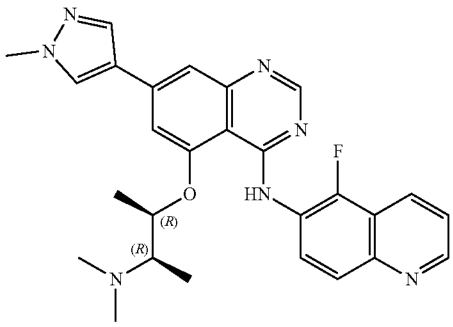 |

TABLE 1-continued
| Example # | Structure |
| --- | --- |
| 28 | 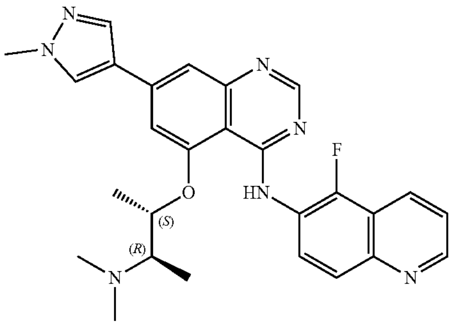 and 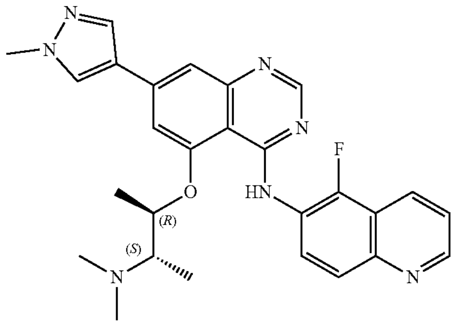 |
| 29 | 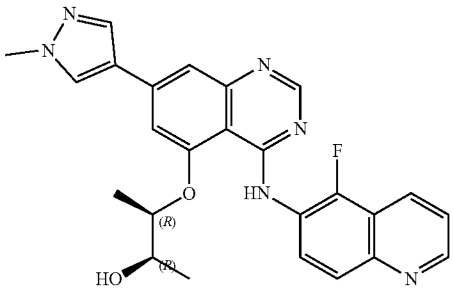 or 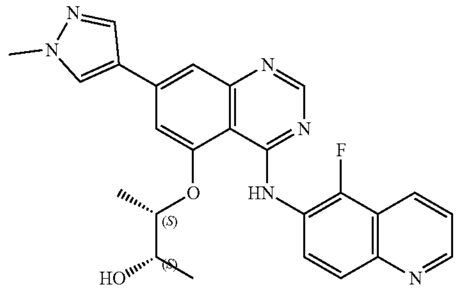 |
| 30 | 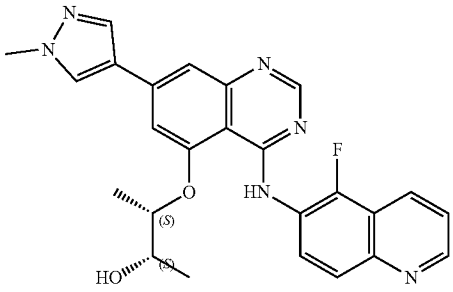 or 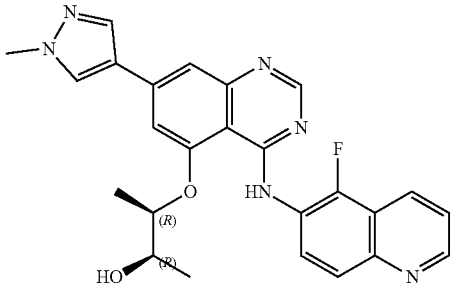 |
| 31 | 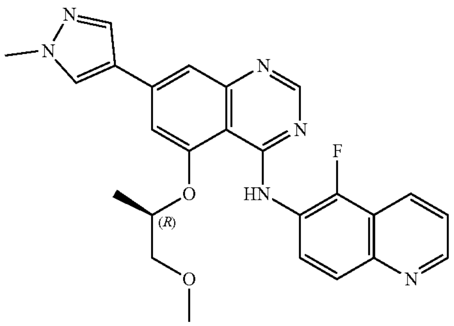 |

TABLE 1-continued
| Example # | Structure |
| --- | --- |
| 32 | 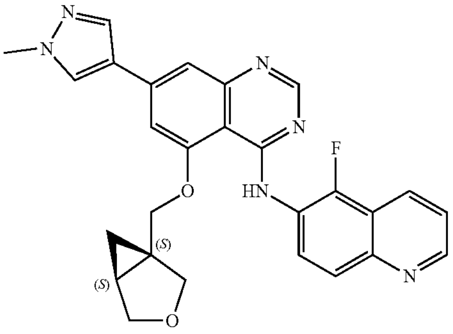 or 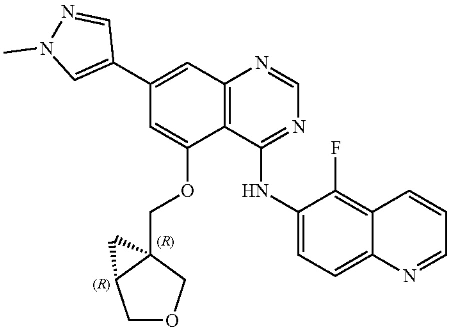 |
| 33 | 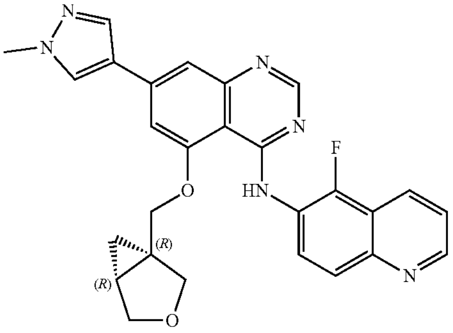 or 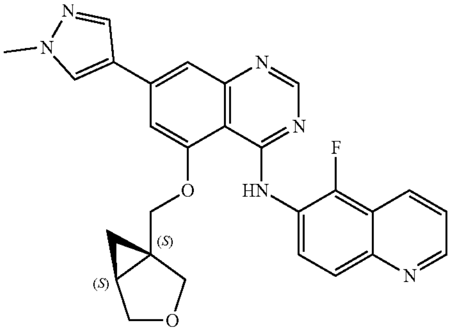 |
| 34 | 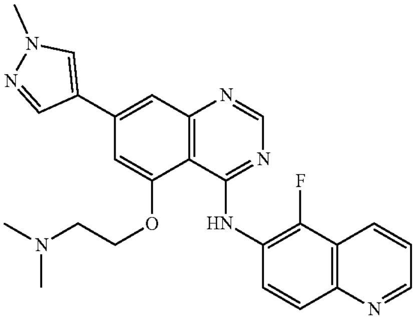 [SMILES: CN(C)CCOc1cc(-c2cnn(C)c2)cc2ncnc(Nc3ccc4ncccc4c3F)c12] |
| 35 | 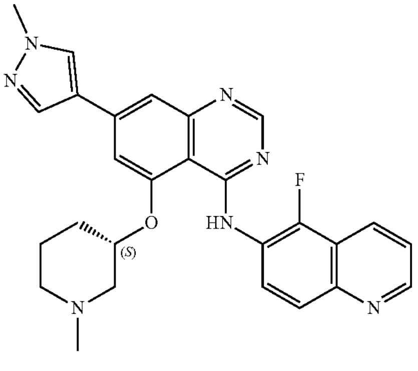 |

TABLE 1-continued
| Example # | Structure |
|---|---|
| 36 | 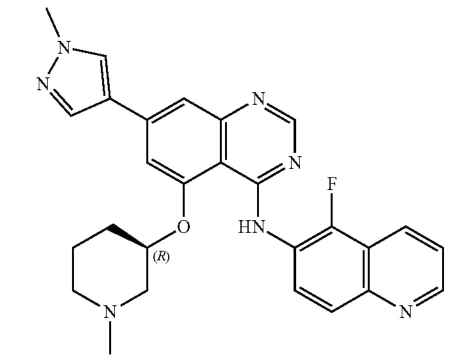 |
| 37 | 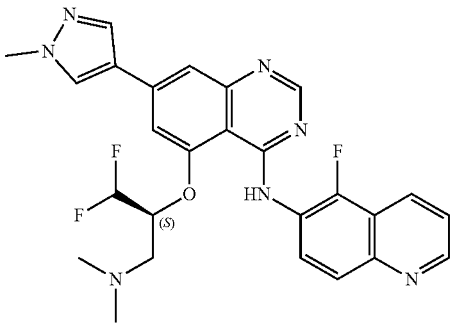 or 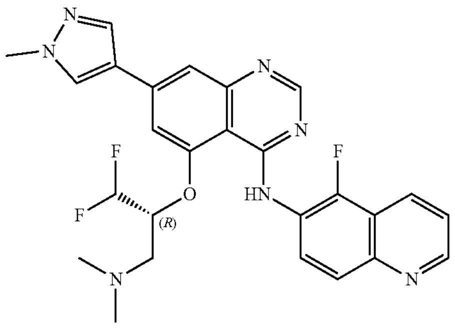 |
| 38 | 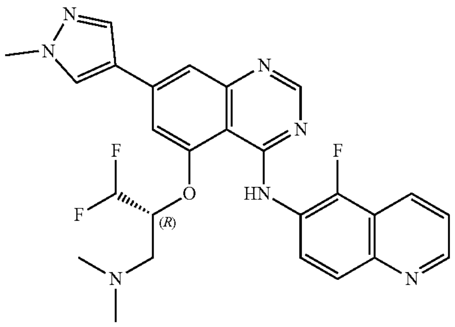 or 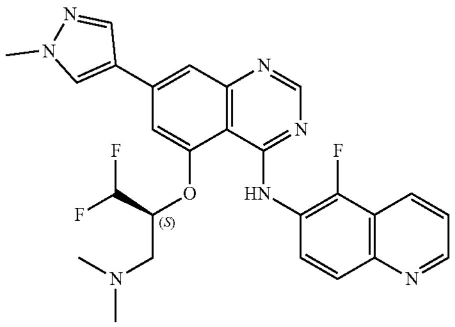 |
| 39 | 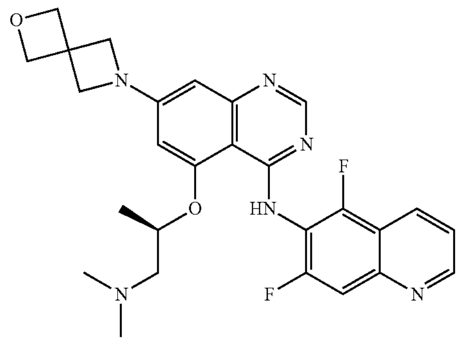 [SMILES: C[C@H](CN(C)C)Oc1cc(N2CC3(COC3)C2)cc2ncnc(Nc3c(F)cc4ncccc4c3F)c12] |

TABLE 1-continued
| Example # | Structure |
|---|---|
| 40 | 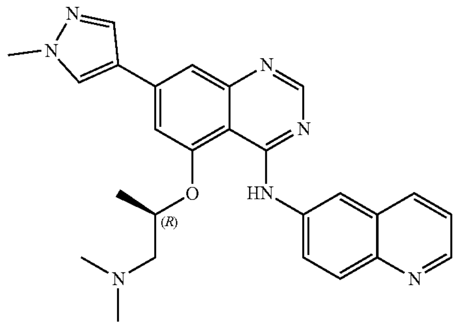 |
| 41 | 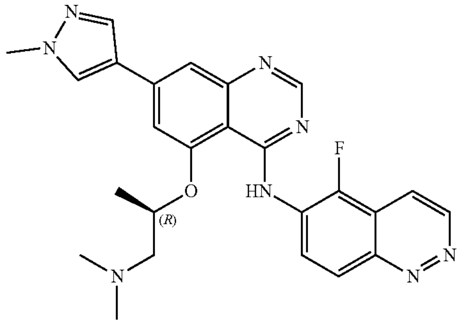 |
| 42 | 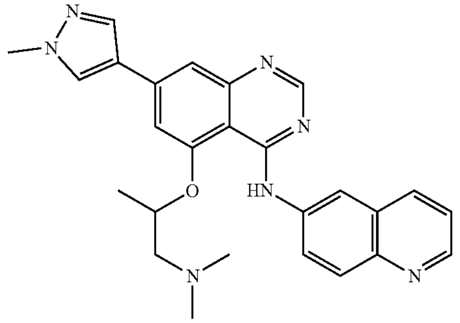 [SMILES: CC(CN(C)C)Oc1cc(-c2cnn(C)c2)cc2ncnc(Nc3ccc4ncccc4c3)c12] |
| 43 | 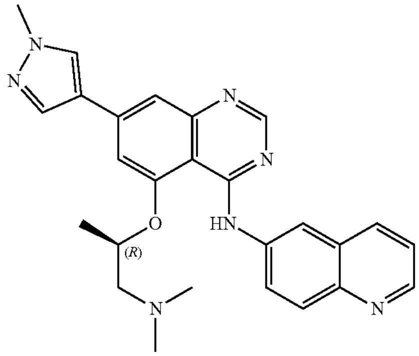 or 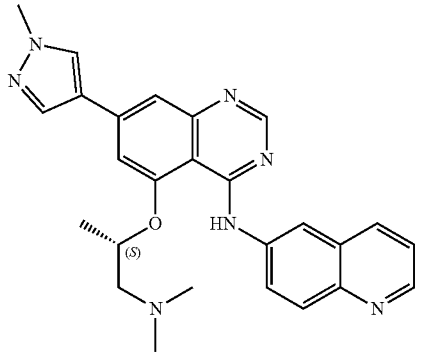 |

TABLE 1-continued
| Example # | Structure |
|---|---|
| 44 | 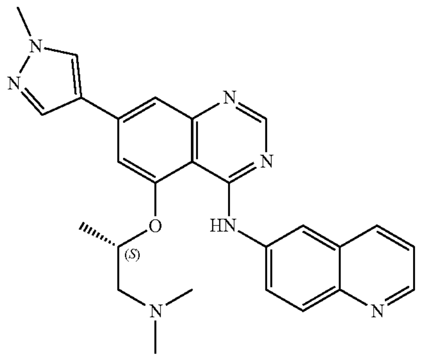 or 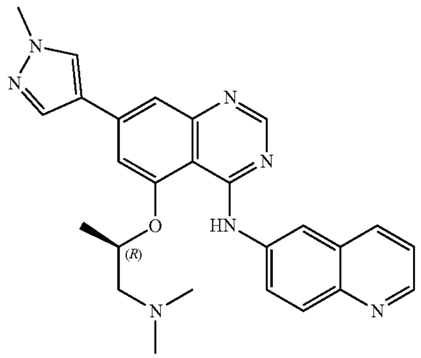 |
| 45 | 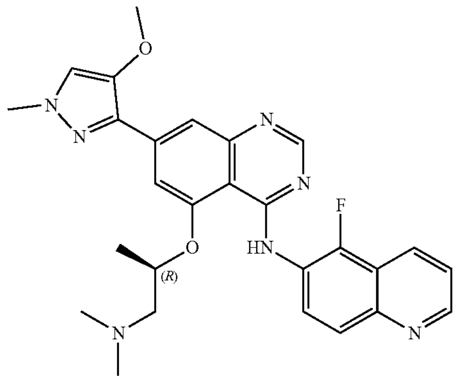 |
| 46 | 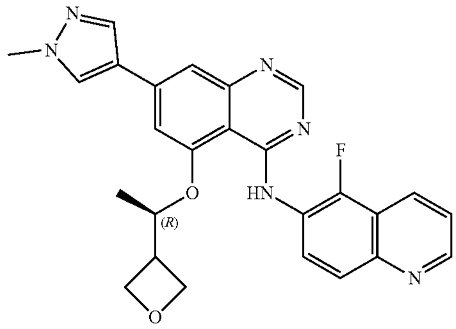 |
| 47 | 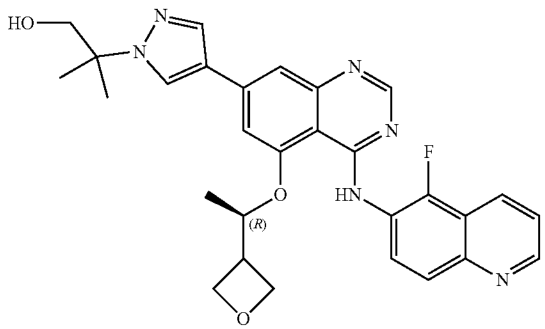 |

TABLE 1-continued
| Example # | Structure |
|---|---|
| 48 | 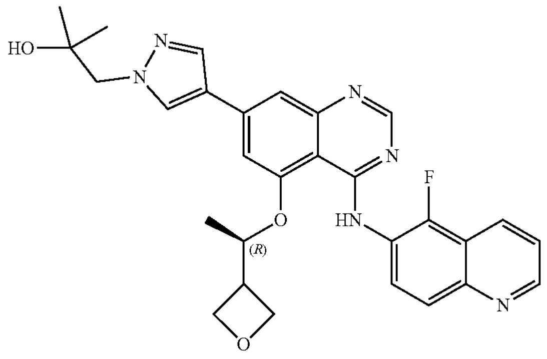 |
| 49 | 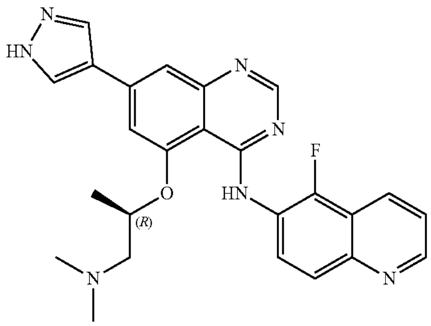 |
| 50 | 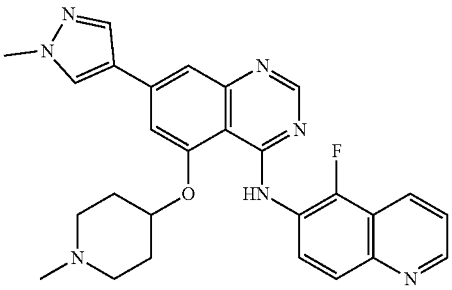 [SMILES: CN1CCC(Oc2cc(-c3cnn(C)c3)cc3ncnc(Nc4ccc5ncccc5c4F)c23)CC1] |
| 51 | 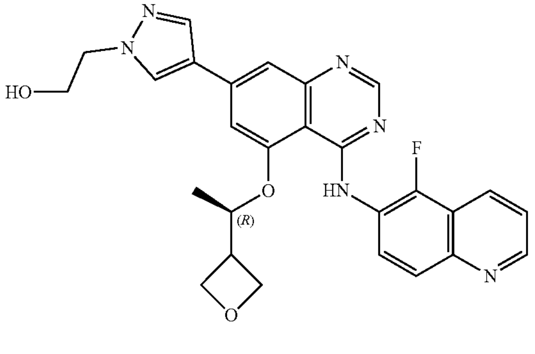 |

TABLE 1-continued
| Example # | Structure |
|---|---|
| 52 | 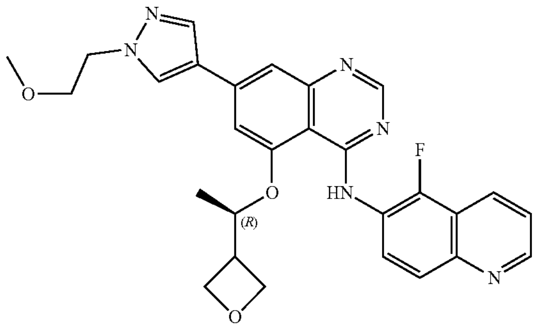 |
| 53 | 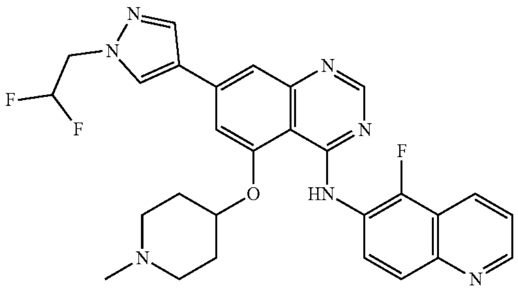 [SMILES: CN1CCC(Oc2cc(-c3cnn(CC(F)F)c3)cc3ncnc(Nc4ccc5ncccc5c4F)c23)CC1] |
| 54 | 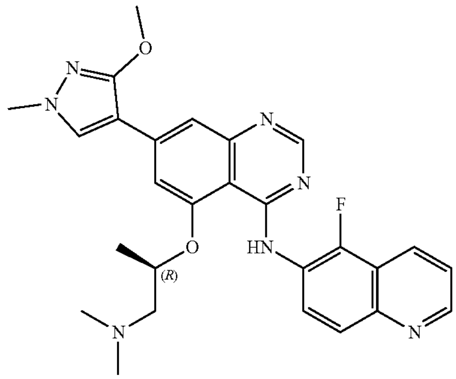 |
| 55 | 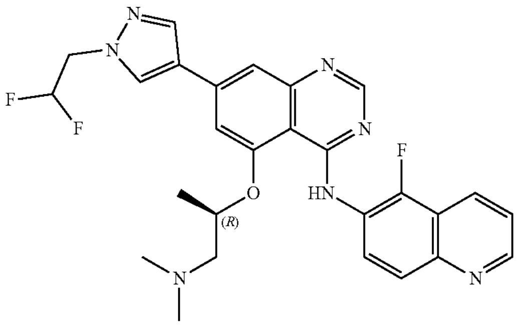 |

TABLE 1-continued
| Example # | Structure |
| --- | --- |
| 56 | 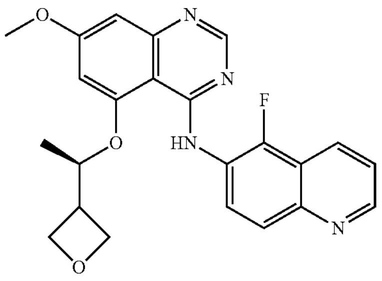 [SMILES: COc1cc(O[C@H](C)C2COC2)c2c(Nc3ccc4ncccc4c3F)ncnc2c1] |
| 57 | 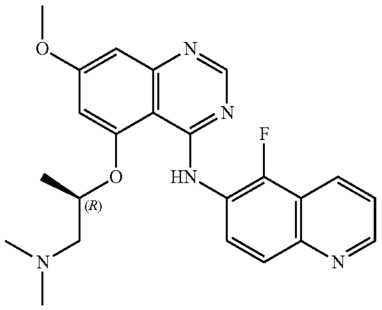 |
| 58 | 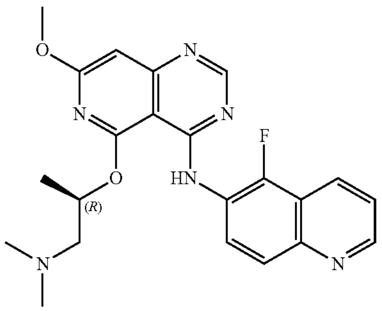 |
| 59 | 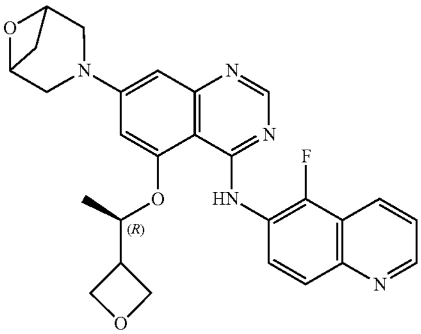 |

TABLE 1-continued
| Example # | Structure |
| --- | --- |
| 60 | 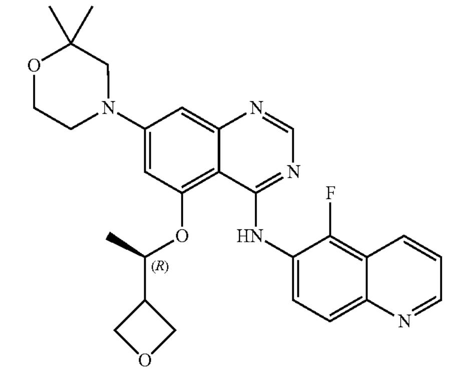 |
| 61 | 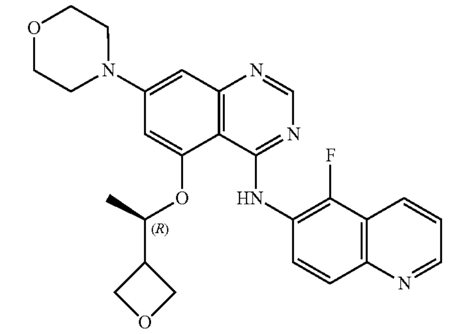 |
| 62 | 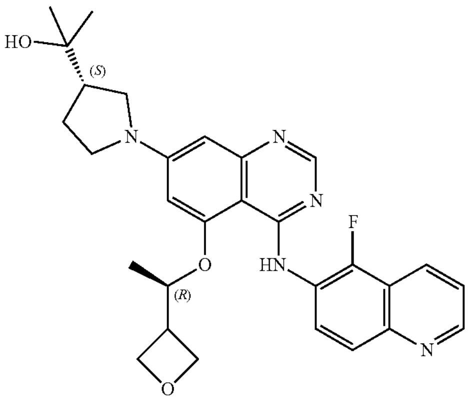 |
| 63 | 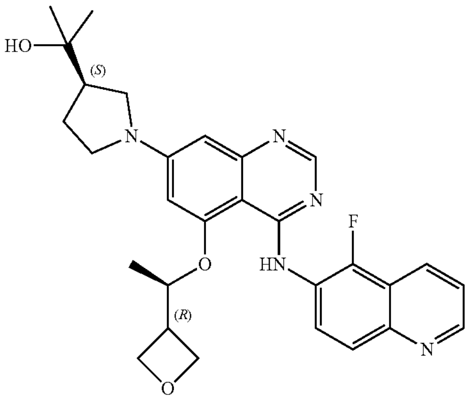 |

TABLE 1-continued
| Example # | Structure |
|---|---|
| 64 | 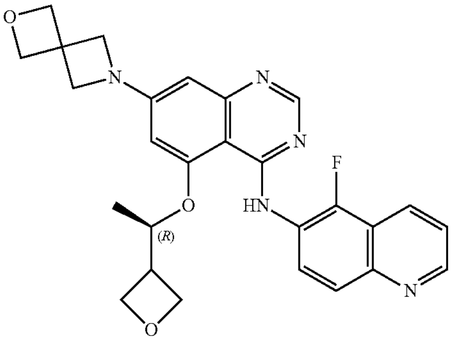 |
| 65 | 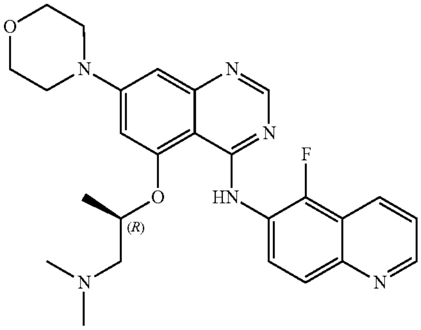 |
| 66 | 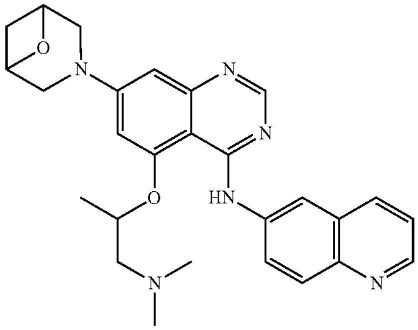 [SMILES: CC(CN(C)C)Oc1cc(N2CC3CC(C2)O3)cc2ncnc(Nc3ccc4ncccc4c3)c12] |
| 67 | 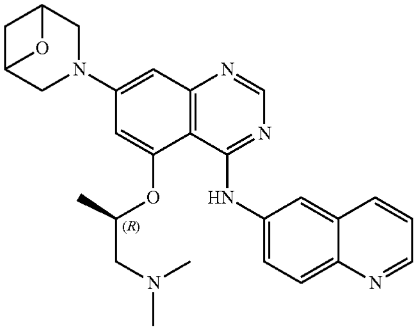 or 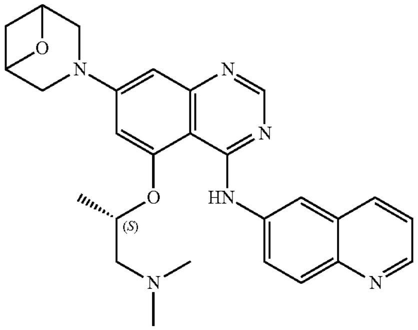 |

TABLE 1-continued
| Example # | Structure | | |
|---|---|---|---|
| 68 | 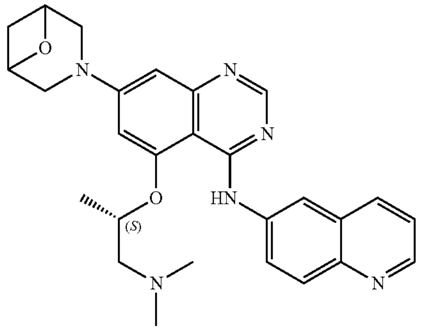 | or | 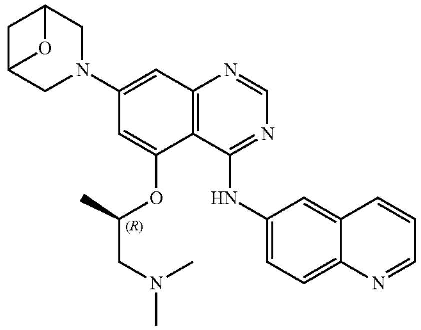 |
| 69 | 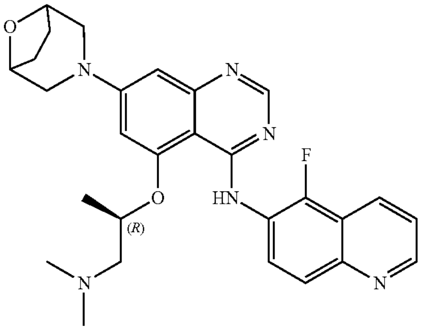 | | |
| 70 | 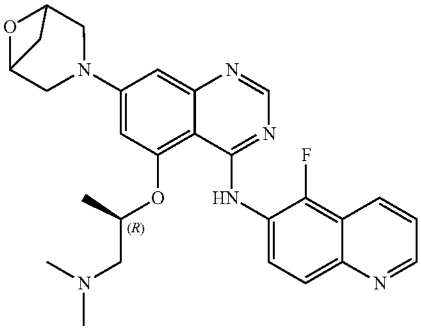 | | |
| 71 | 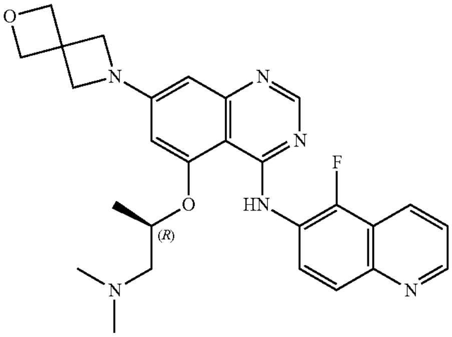 | | |

TABLE 1-continued
| Example # | Structure |
|---|---|
| 72 | 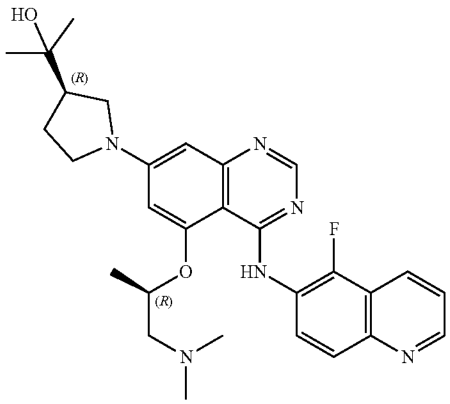 |
| 73 | 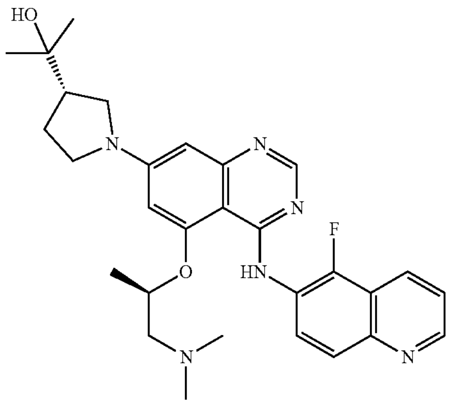 [SMILES: C[C@H](CN(C)C)Oc1cc(N2CC[C@H](C(C)(C)O)C2)cc2ncnc(Nc3ccc4ncccc4c3F)c12] |
| 74 | 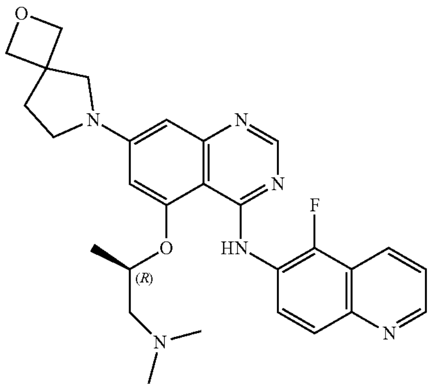 |

TABLE 1-continued
| Example # | Structure |
|---|---|
| 75 | 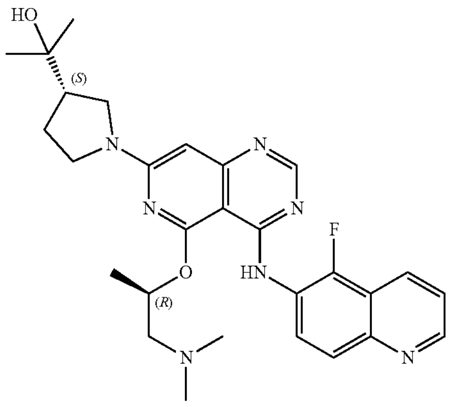 |
| 76 | 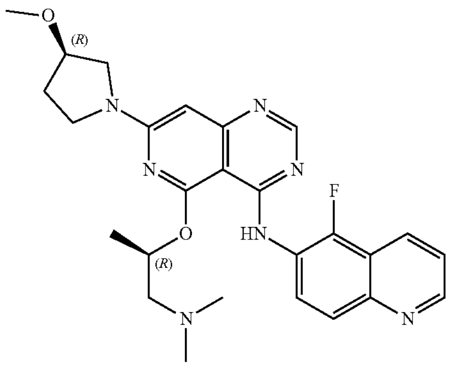 |
| 77 | 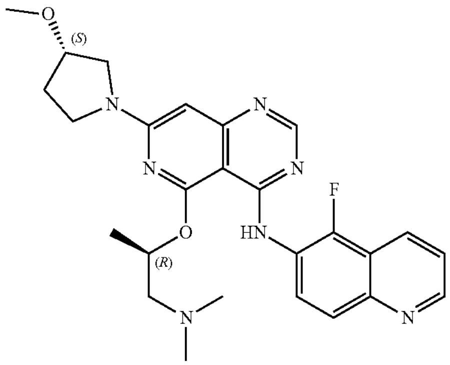 |
| 78 | 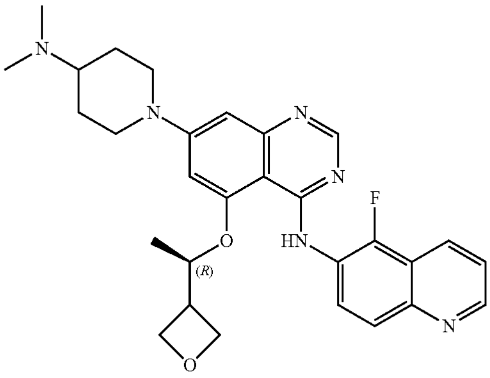 |

TABLE 1-continued
| Example # | Structure |
|---|---|
| 79 | 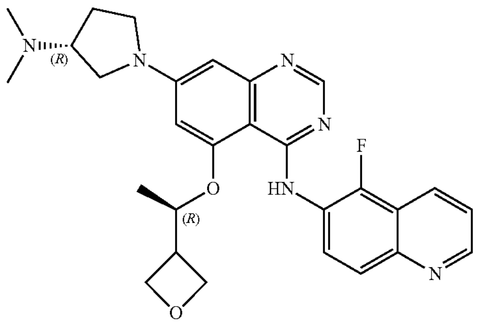 |
| 80 | 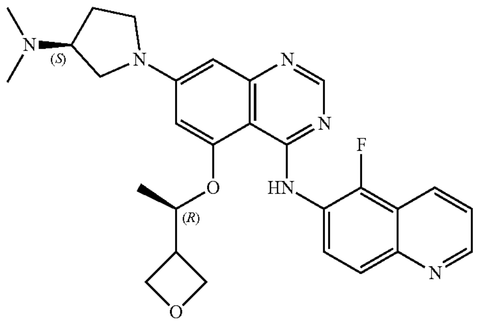 |
| 81 | 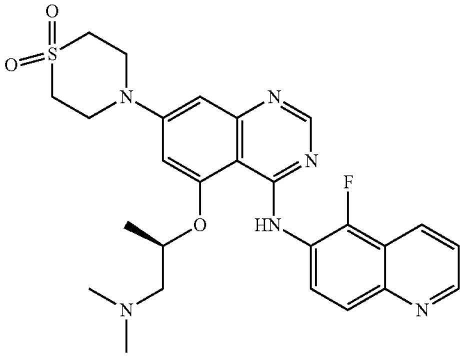 [SMILES: C[C@H](CN(C)C)Oc1cc(N2CCS(=O)(=O)CC2)cc2ncnc(Nc3ccc4ncccc4c3F)c12] |
| 82 | 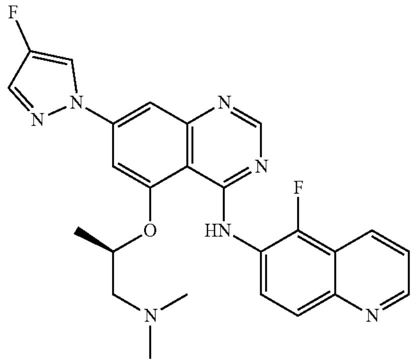 [SMILES: C[C@H](CN(C)C)Oc1cc(-n2cc(F)cn2)cc2ncnc(Nc3ccc4ncccc4c3F)c12] |

TABLE 1-continued
| Example # | Structure |
|---|---|
| 83 | 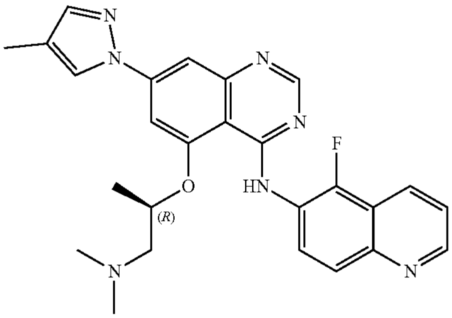 |
| 84 | 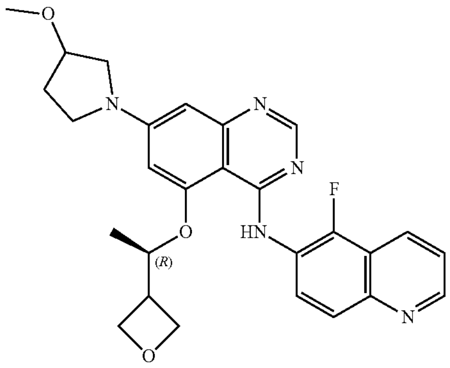 |
| 85a | 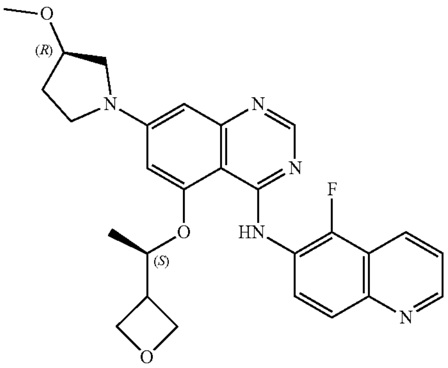 or 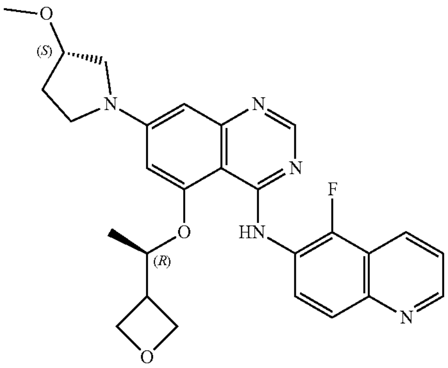 |
| 85b | 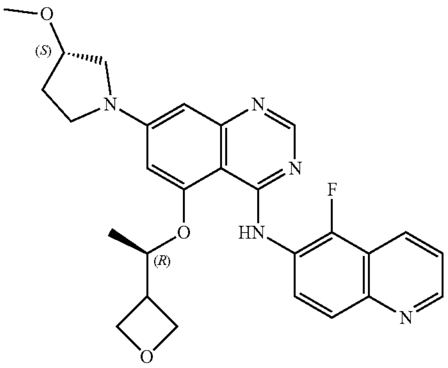 or 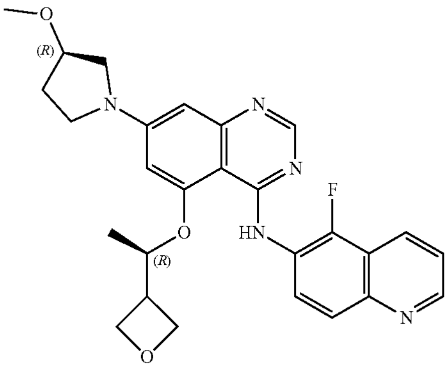 |

TABLE 1-continued
| Example # | Structure | | |
|---|---|---|---|
| 86 | 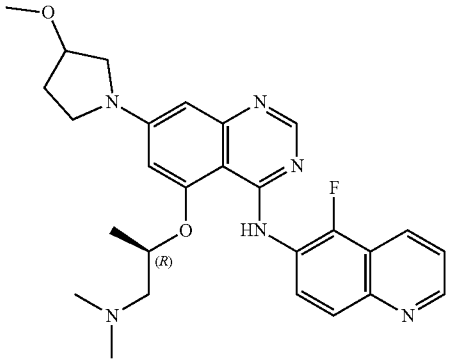 | | |
| 87a | 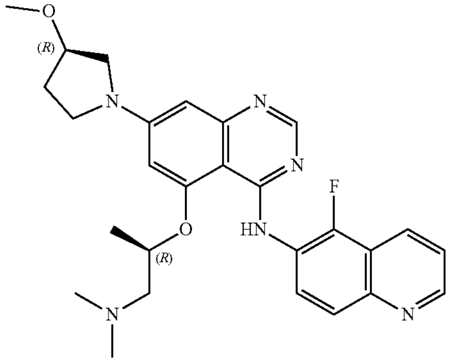 | or | 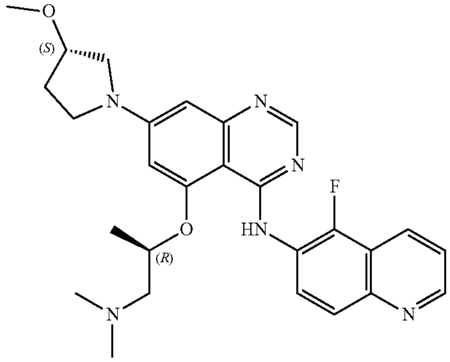 |
| 87b | 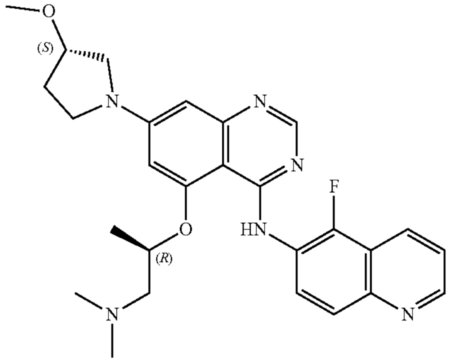 | or | 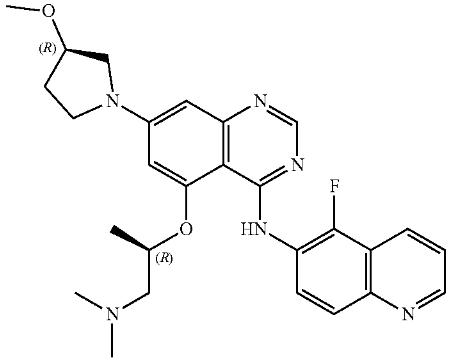 |
| 88 | 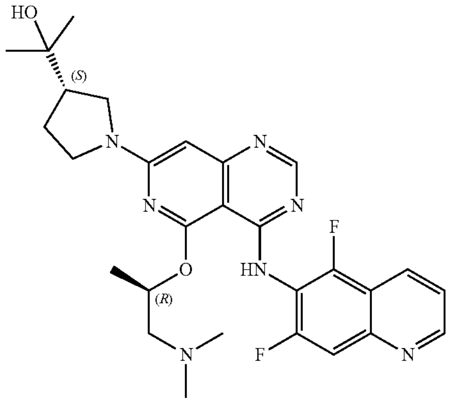 | | |

TABLE 1-continued
| Example # | Structure |
|---|---|
| 89 | 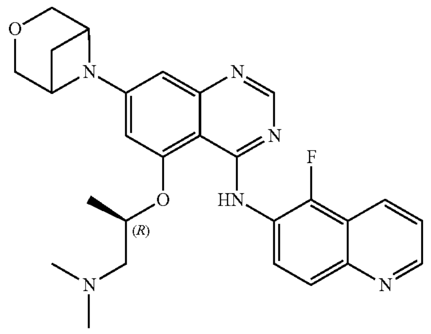 |
| 90 | 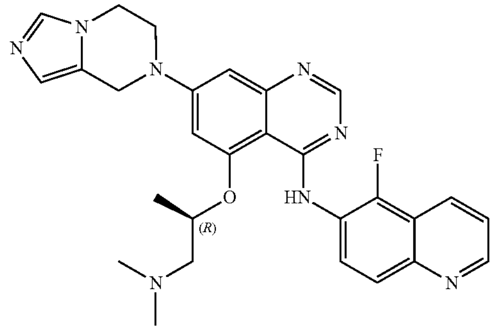 |
| 91 | 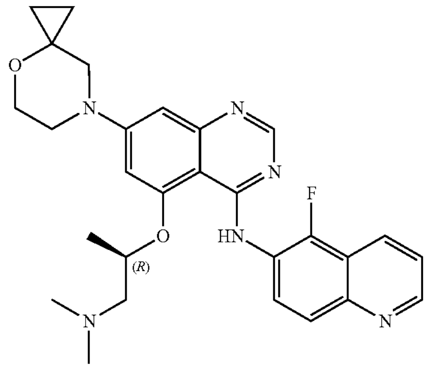 |
| 92 | 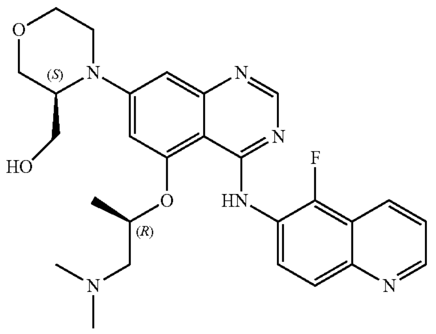 |

TABLE 1-continued
| Example # | Structure |
|---|---|
| 93 | 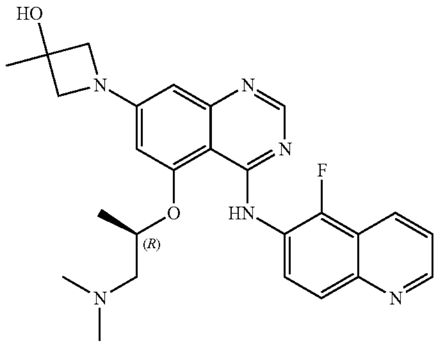 |
| 94 | 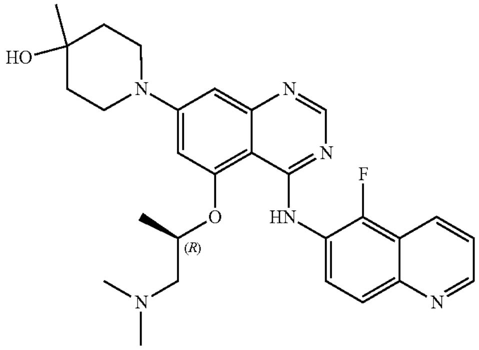 |
| 95 | 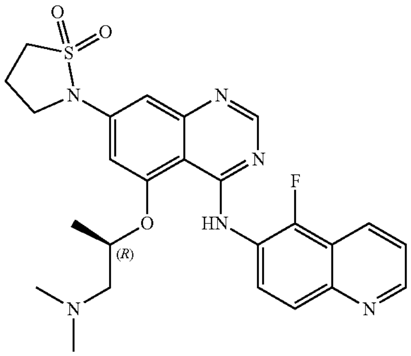 |
| 96 | 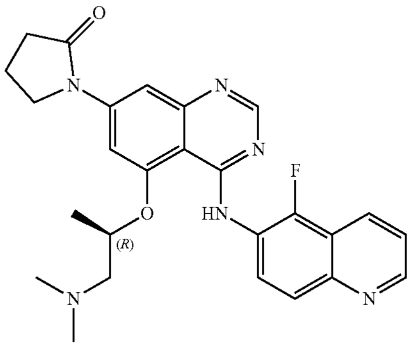 |

TABLE 1-continued
| Example # | Structure |
| --- | --- |
| 97 | 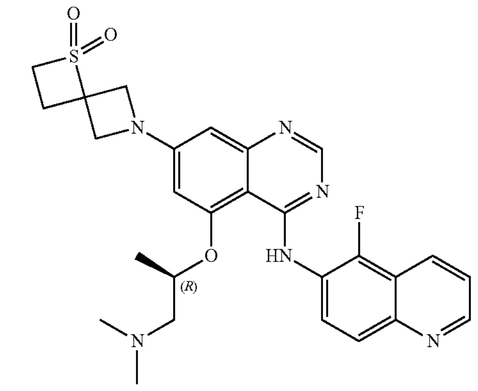 |
| 98 | 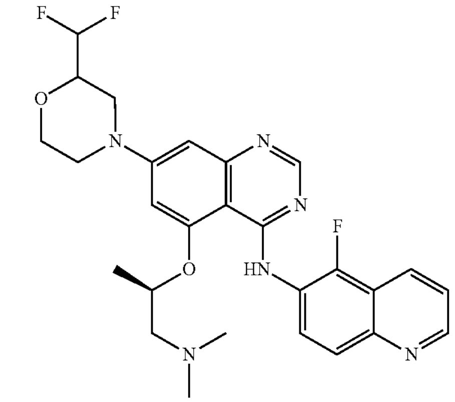 [SMILES: C[C@H](CN(C)C)Oc1cc(N2CCOC(C(F)F)C2)cc2ncnc(Nc3ccc4ncccc4c3F)c12] |
| 99a | 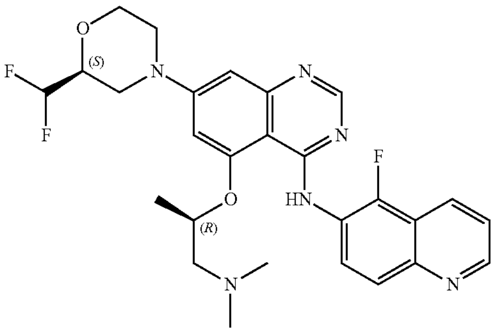 or 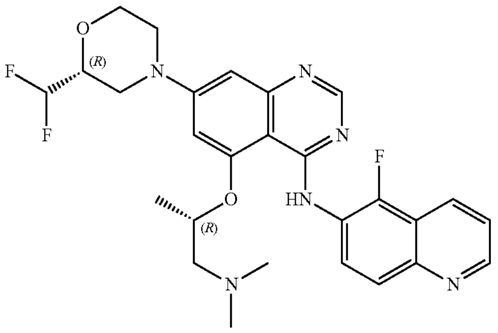 |
| 99b | 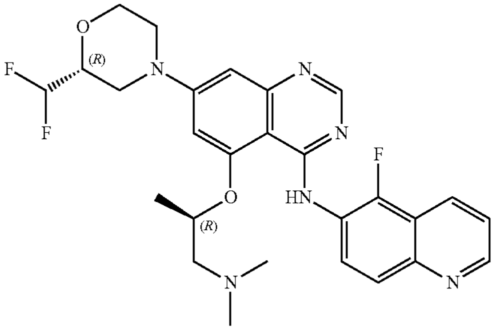 or 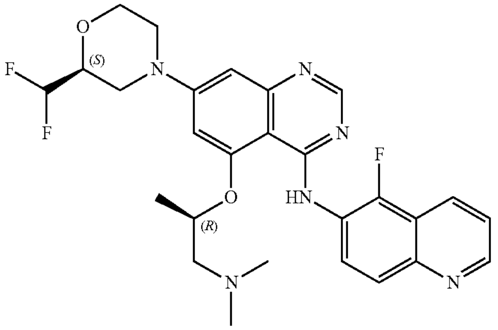 |

TABLE 1-continued
| Example # | Structure |
|---|---|
| 100 | 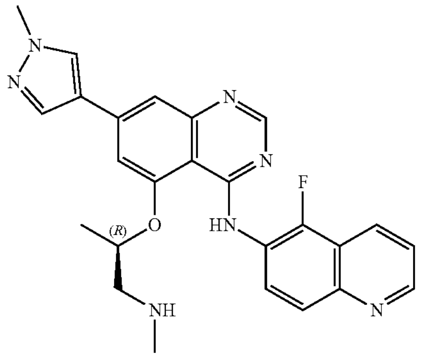 |
| 101 | 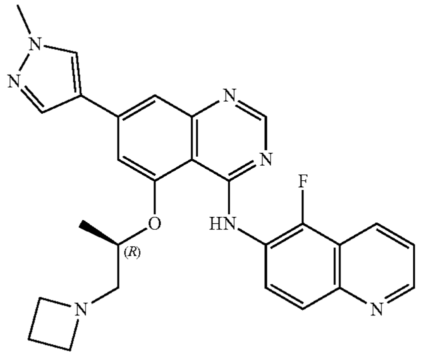 |
| 102 | 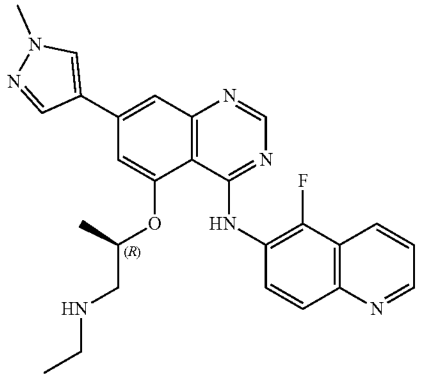 |
| 103 | 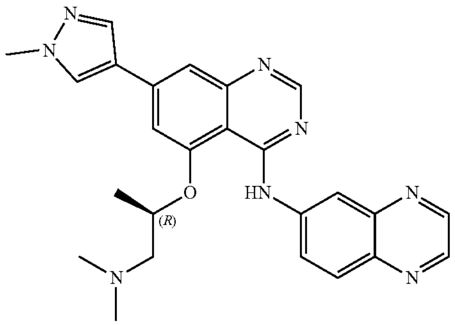 |

TABLE 1-continued
| Example # | Structure |
|---|---|
| 104 | 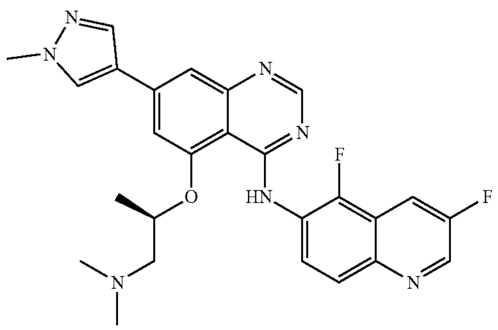 [SMILES: C[C@H](CN(C)C)Oc1cc(-c2cnn(C)c2)cc2ncnc(Nc3ccc4ncc(F)cc4c3F)c12] |
| 105 | 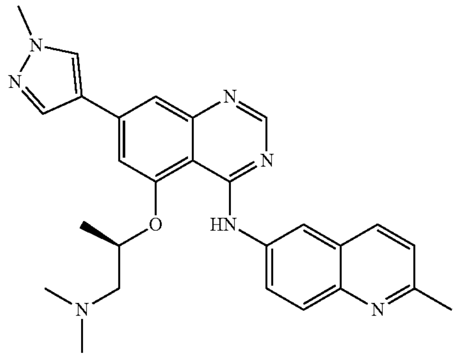 [SMILES: Cc1ccc2cc(Nc3ncnc4cc(-c5cnn(C)c5)cc(O[C@H](C)CN(C)C)c34)ccc2n1] |
| 106 | 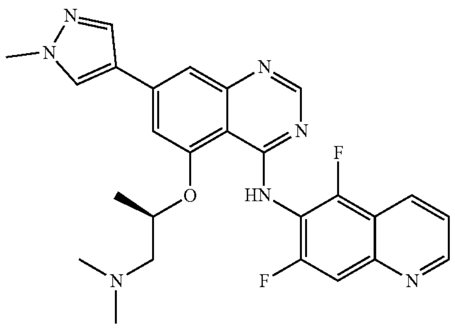 [SMILES: C[C@H](CN(C)C)Oc1cc(-c2cnn(C)c2)cc2ncnc(Nc3c(F)cc4ncccc4c3F)c12] |
| 107 | 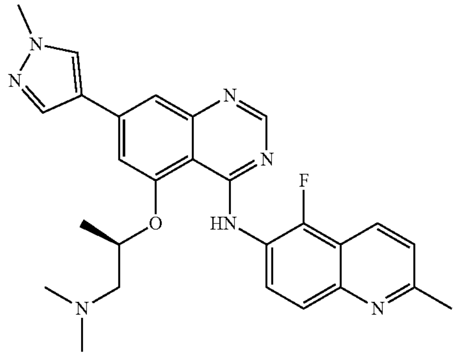 [SMILES: Cc1ccc2c(F)c(Nc3ncnc4cc(-c5cnn(C)c5)cc(O[C@H](C)CN(C)C)c34)ccc2n1] |

TABLE 1-continued
| Example # | Structure |
|---|---|
| 108 | 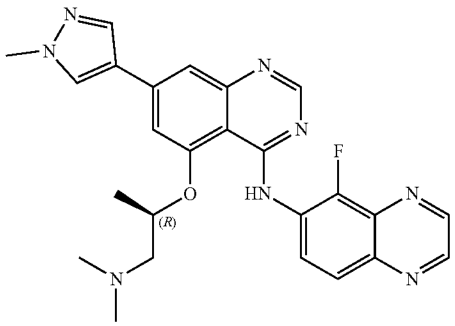 |
| 109 | 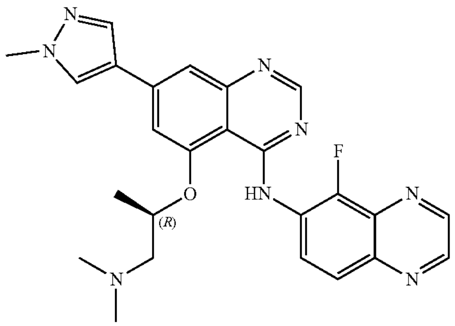 |
| 110 | 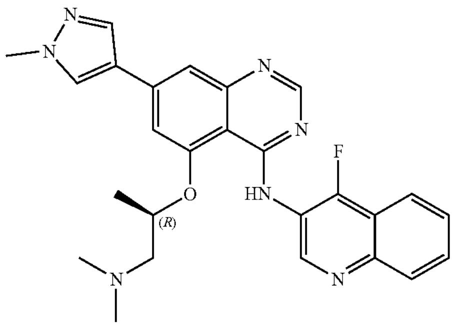 |
| 111 | 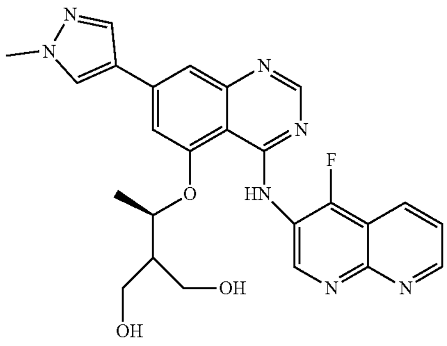 [SMILES: C[C@@H](Oc1cc(-c2cnn(C)c2)cc2ncnc(Nc3cnc4ncccc4c3F)c12)C(CO)CO] |

TABLE 1-continued
| Example # | Structure |
| --- | --- |
| 112 | 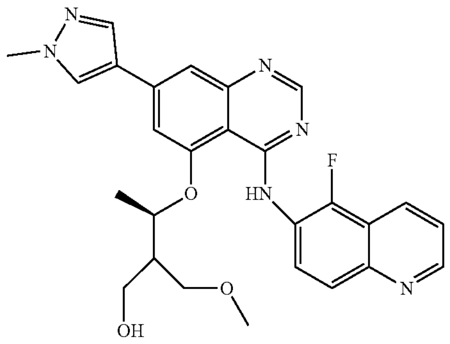 [SMILES: COCC(CO)[C@@H](C)Oc1cc(-c2cnn(C)c2)cc2ncnc(Nc3ccc4ncccc4c3F)c12] |
| 113 | 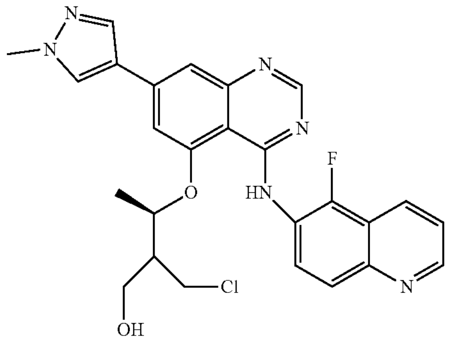 [SMILES: C[C@@H](Oc1cc(-c2cnn(C)c2)cc2ncnc(Nc3ccc4ncccc4c3F)c12)C(CO)CCl] |
| 114 | 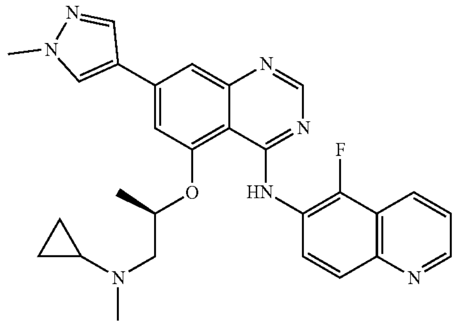 [SMILES: C[C@H](CN(C)C1CC1)Oc1cc(-c2cnn(C)c2)cc2ncnc(Nc3ccc4ncccc4c3F)c12] |
| 115 | 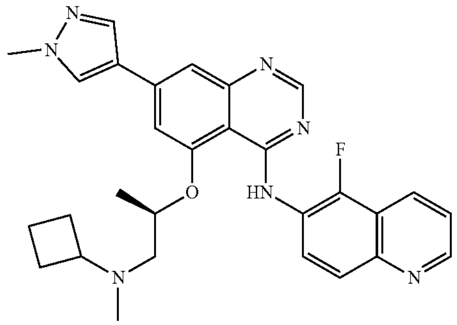 [SMILES: C[C@H](CN(C)C1CCC1)Oc1cc(-c2cnn(C)c2)cc2ncnc(Nc3ccc4ncccc4c3F)c12] |

TABLE 1-continued
| Example # | Structure |
| --- | --- |
| 116 | 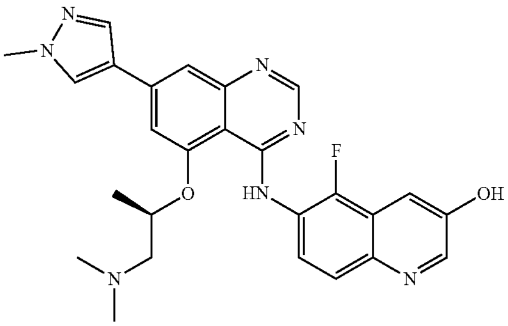 [SMILES: C[C@H](CN(C)C)Oc1cc(-c2cnn(C)c2)cc2ncnc(Nc3ccc4ncc(O)cc4c3F)c12] |
| 117 | 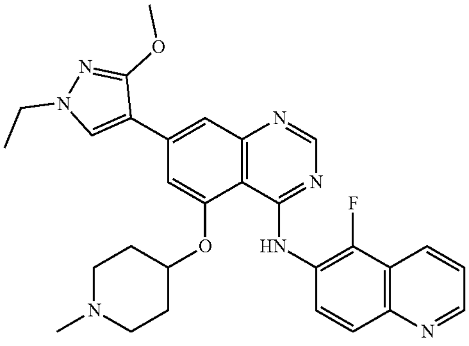 [SMILES: CCn1cc(-c2cc(OC3CCN(C)CC3)c3c(Nc4ccc5ncccc5c4F)ncnc3c2)c(OC)n1] |
| 118 | 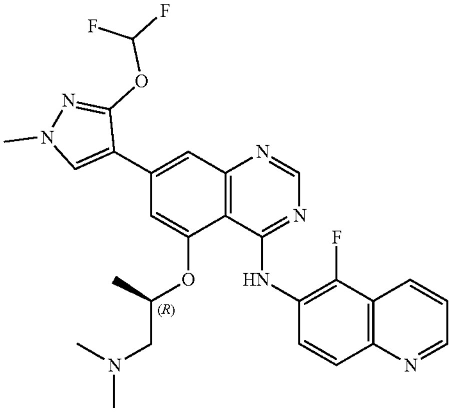 |
| 119 | 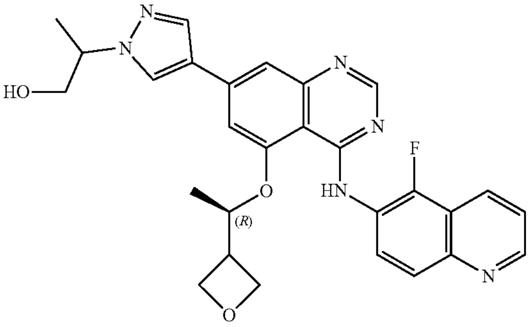 |

TABLE 1-continued
| Example # | Structure |
|---|---|
| 120 | 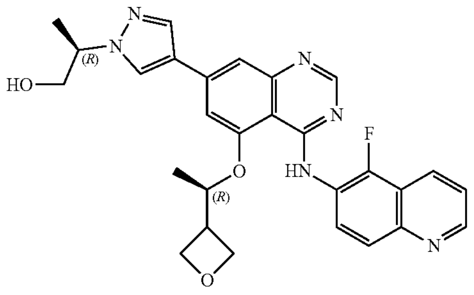 OR 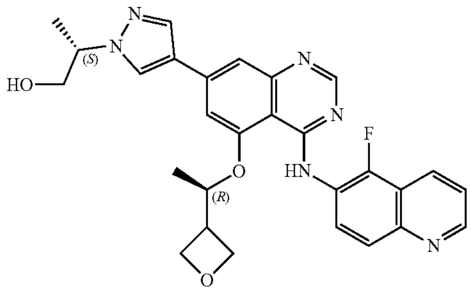 |
| 121 | 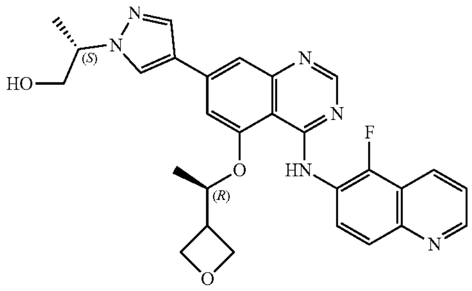 OR 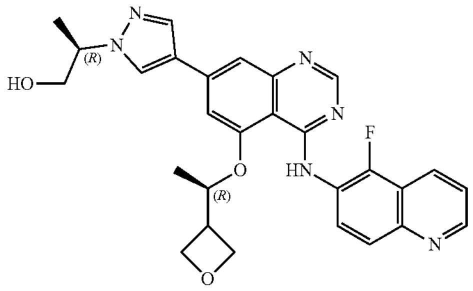 |
| 122 | 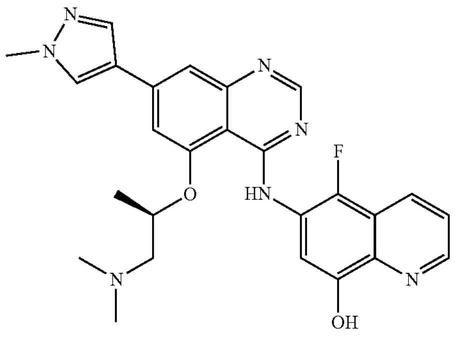 |
| 123 | 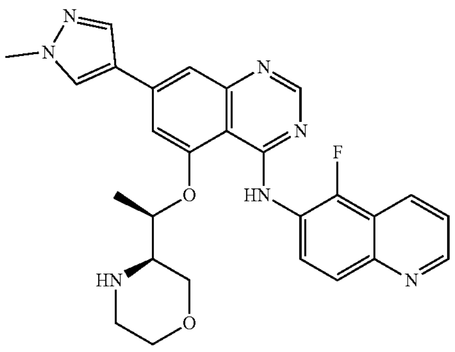 Or 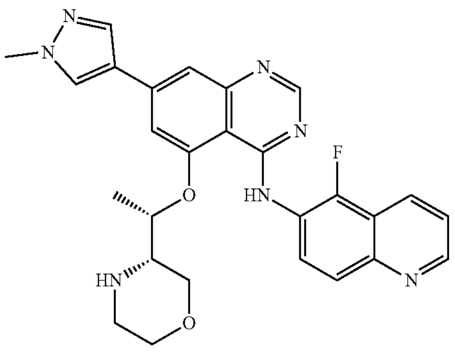 Or |

TABLE 1-continued
| Example # | Structure |
| --- | --- |
| | 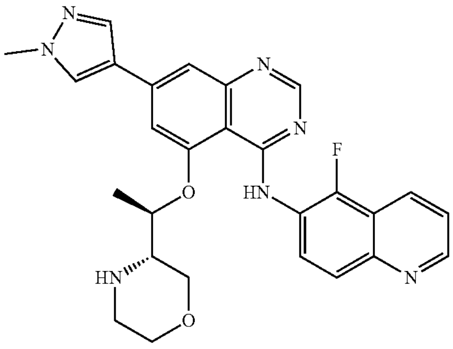 Or 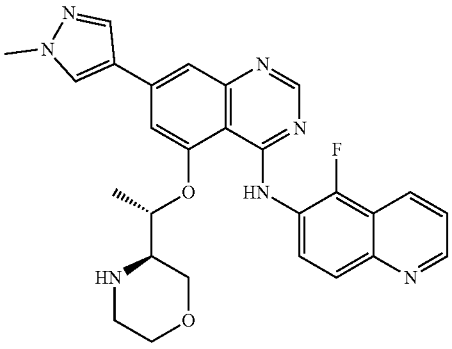 |
| 124 | 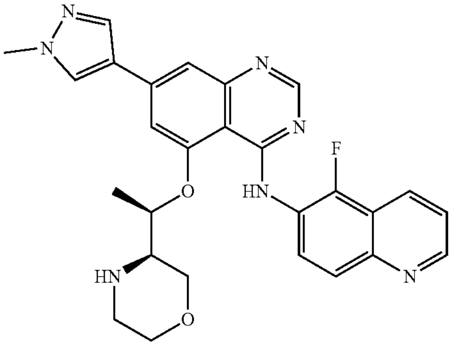 Or 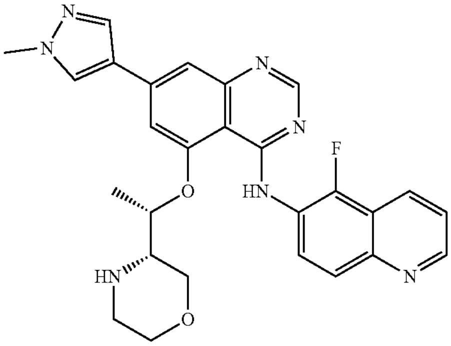 Or |
| | 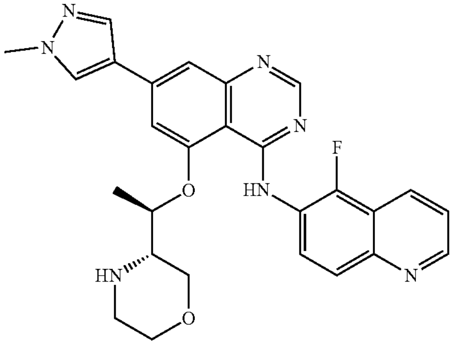 Or 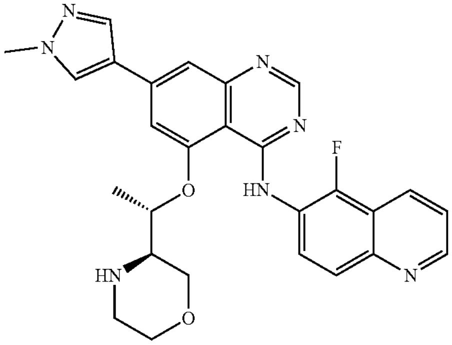 |
| 125 | 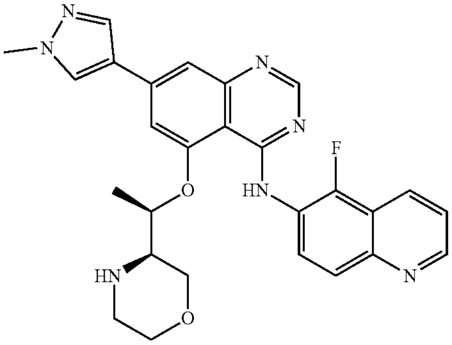 Or 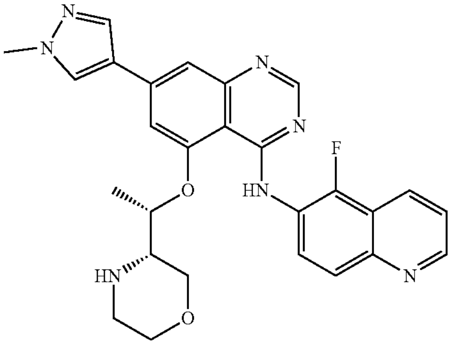 Or |

TABLE 1-continued
| Example # | Structure |
|---|---|
| | 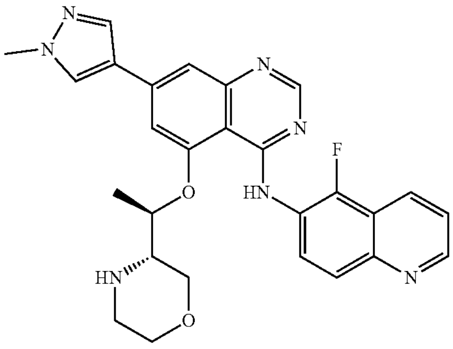 Or 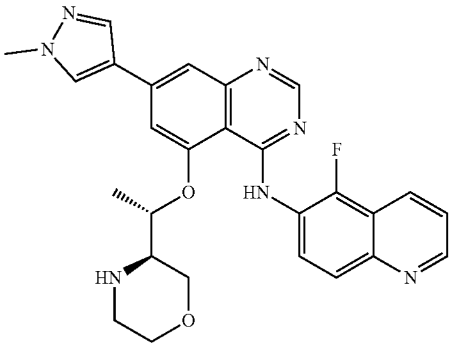 |
| 126 | 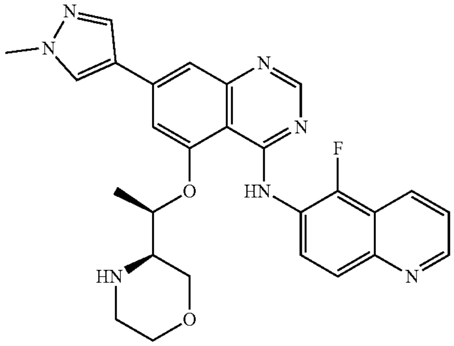 Or 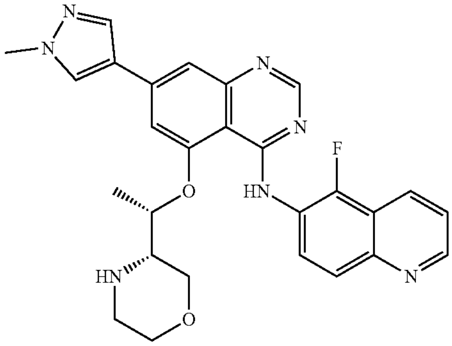 Or 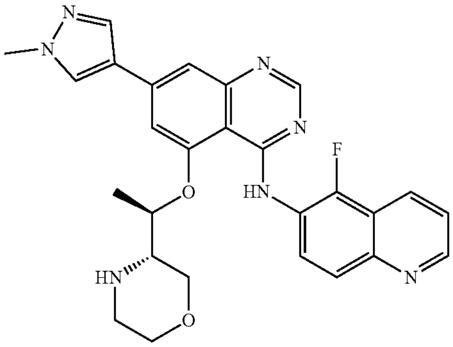 Or 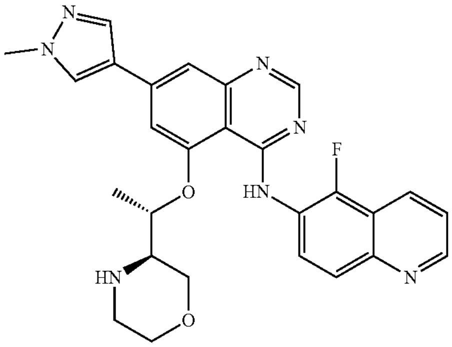 |
| 127 | 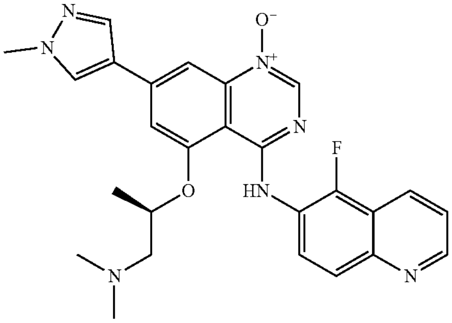 [SMILES: C[C@H](CN(C)C)Oc1cc(-c2cnn(C)c2)cc2c1c(Nc1ccc3ncccc3c1F)nc[n+]2[O-]] |

TABLE 1-continued
| Example # | Structure |
|---|---|
| 128 | 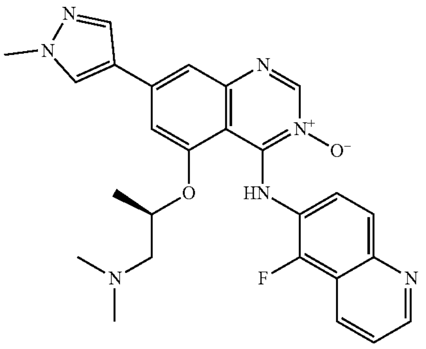 [SMILES: C[C@H](CN(C)C)Oc1cc(-c2cnn(C)c2)cc2nc[n+]([O-])c(Nc3ccc4ncccc4c3F)c12] |
| 129 | 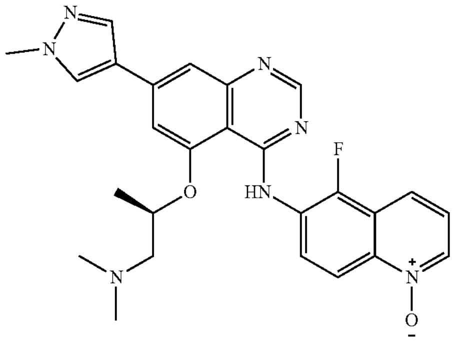 [SMILES: C[C@H](CN(C)C)Oc1cc(-c2cnn(C)c2)cc2ncnc(Nc3ccc4c(ccc[n+]4[O-])c3F)c12] |
| 130 | 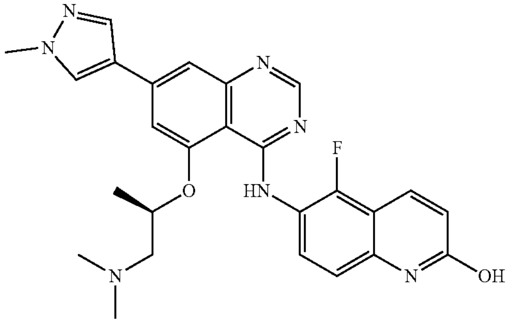 [SMILES: C[C@H](CN(C)C)Oc1cc(-c2cnn(C)c2)cc2ncnc(Nc3ccc4nc(O)ccc4c3F)c12] |
| 131 | 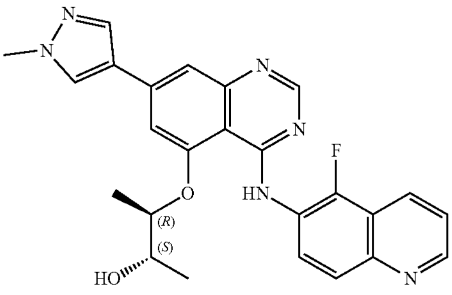 or 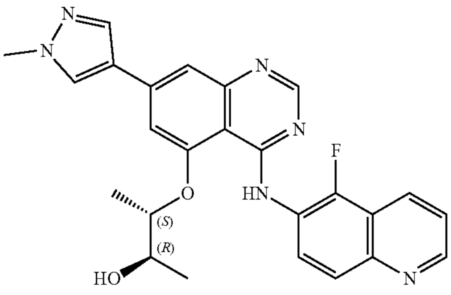 |

TABLE 1-continued
| Example # | Structure |
| --- | --- |
| 132 | 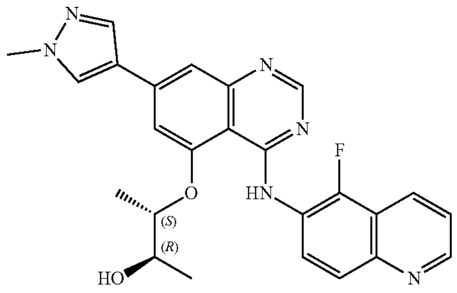 or 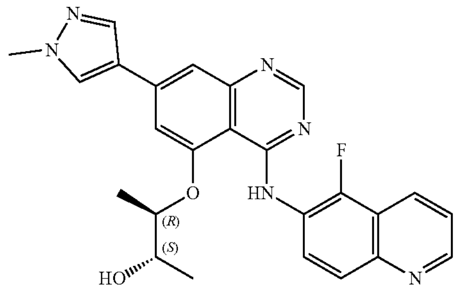 |
| 135 | 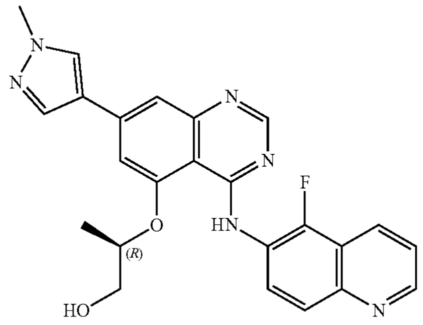 |
| 136 | 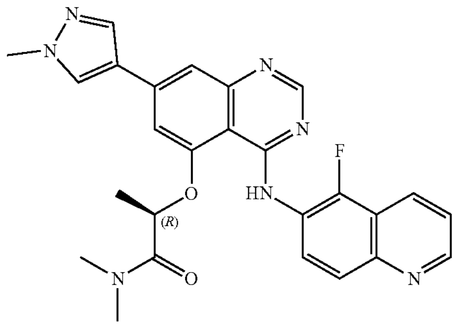 or 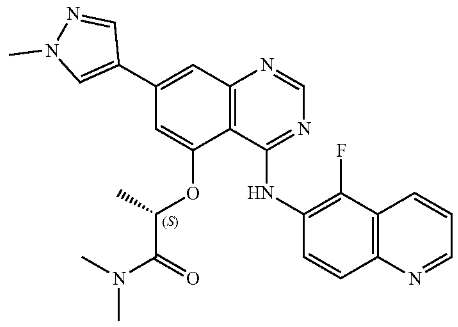 |
| 137 | 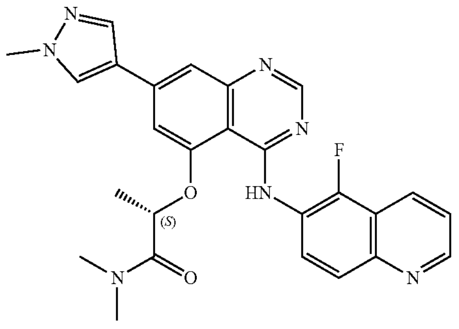 or 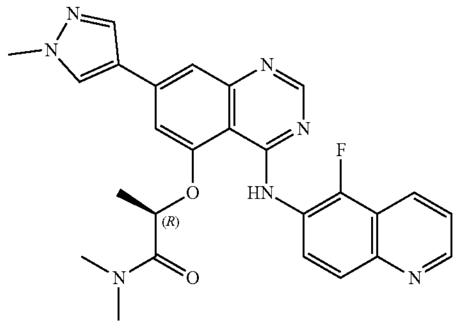 |

TABLE 1-continued
| Example # | Structure |
|---|---|
| 138 | 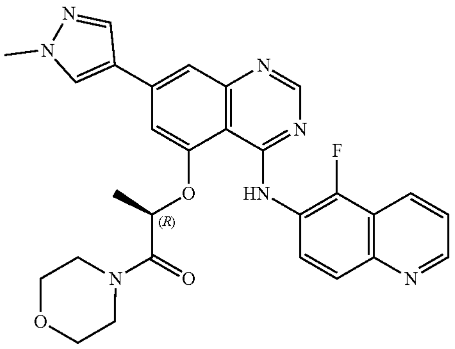 or 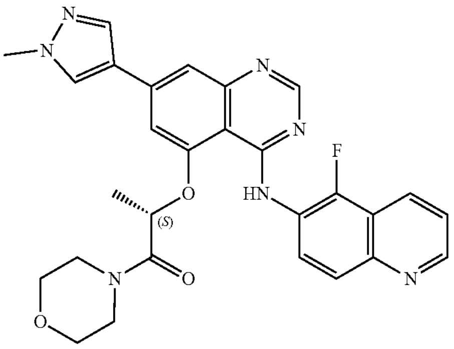 |
| 139 | 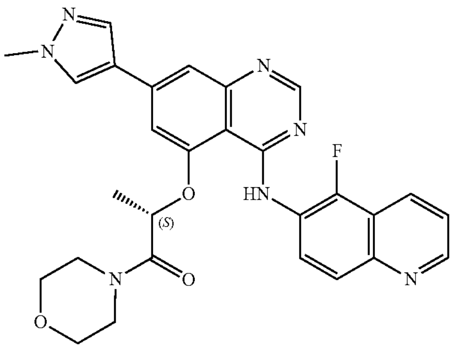 or 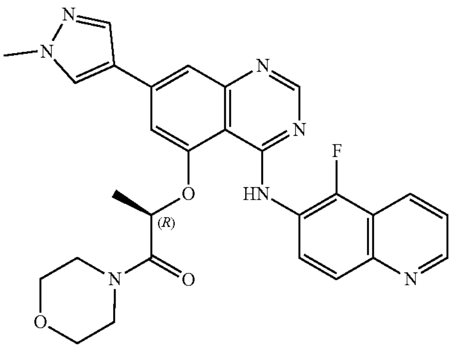 |
| 140 | 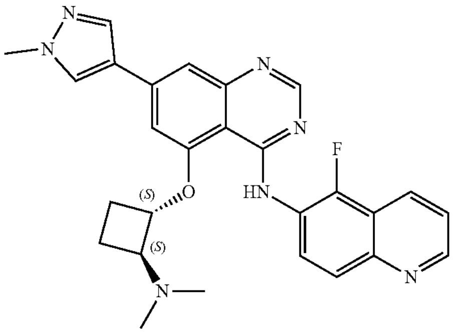 or 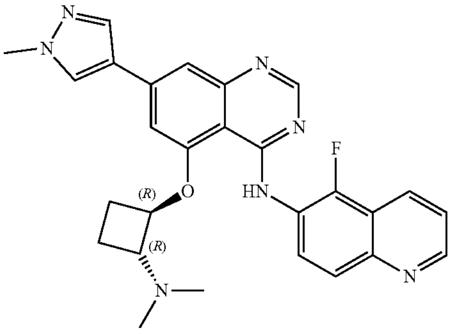 |
| 141 | 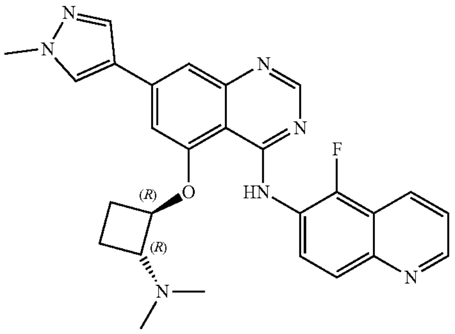 or 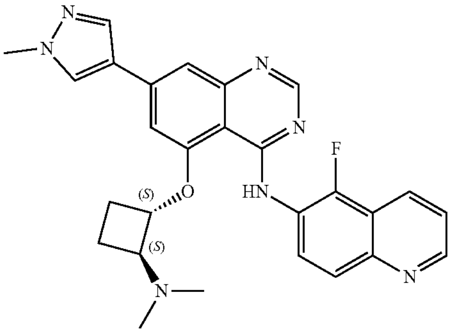 |

TABLE 1-continued
| Example # | Structure |
| --- | --- |
| 142 | 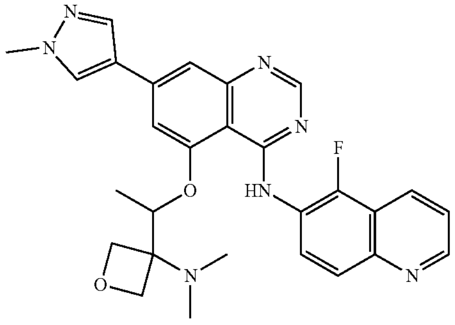 [SMILES: CC(Oc1cc(-c2cnn(C)c2)cc2ncnc(Nc3ccc4ncccc4c3F)c12)C1(N(C)C)COC1] |
| 143 | 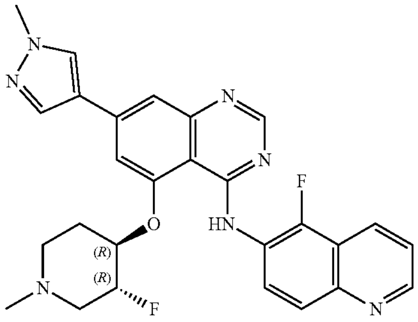 or 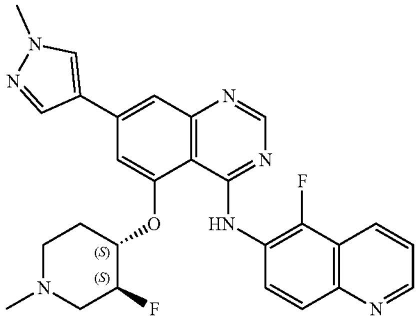 |
| 144 | 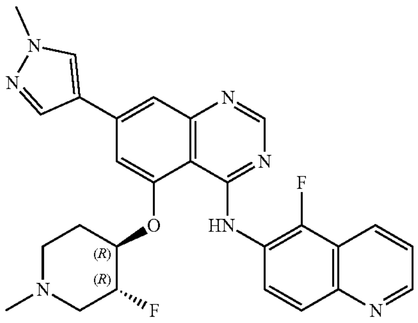 or 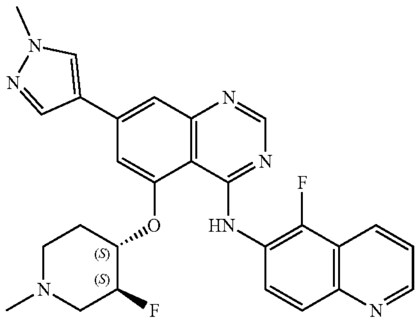 |
| 145 | 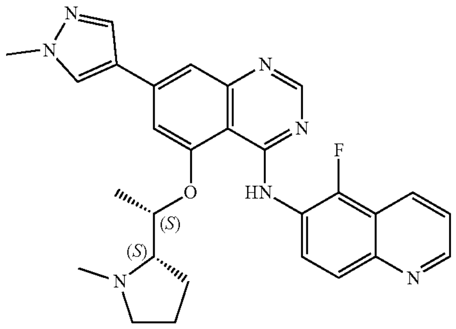 or 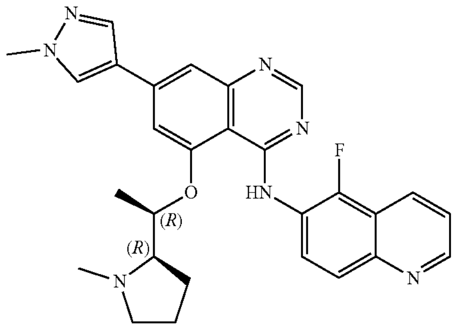 or |

TABLE 1-continued
| Example # | Structure |
| --- | --- |
| | 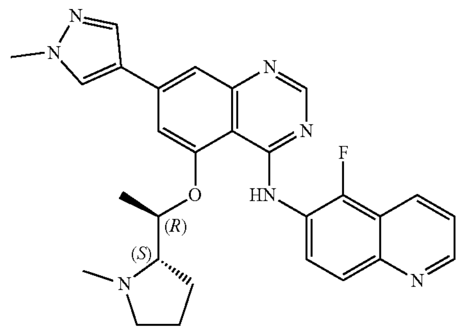 or 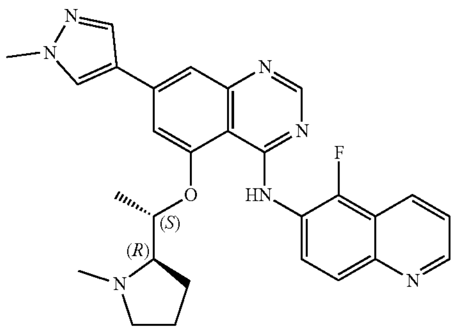 |
| 146 | |
| | 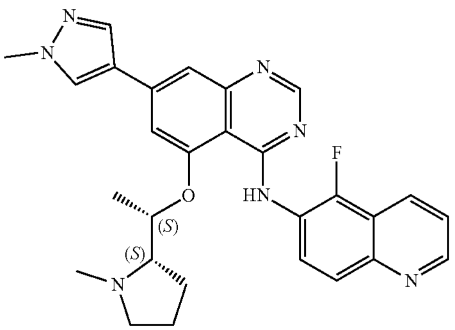 or 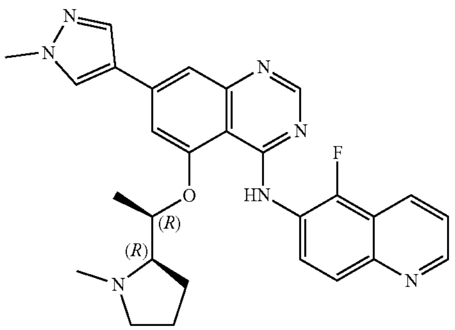 or |
| | 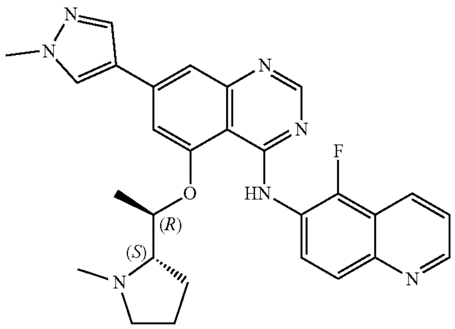 or 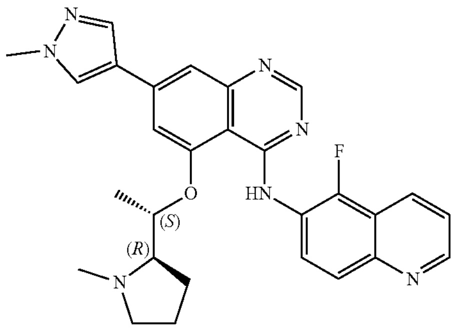 |
| 147 | 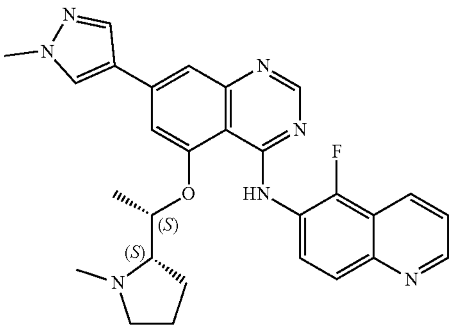 or 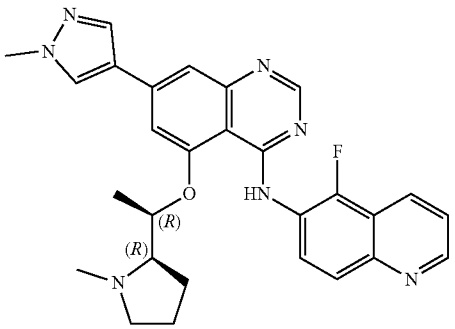 or |

TABLE 1-continued
| Example # | Structure |
|---|---|
| | 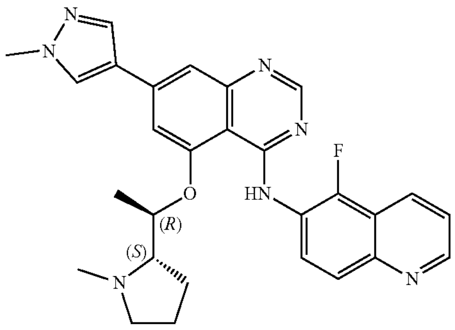 or 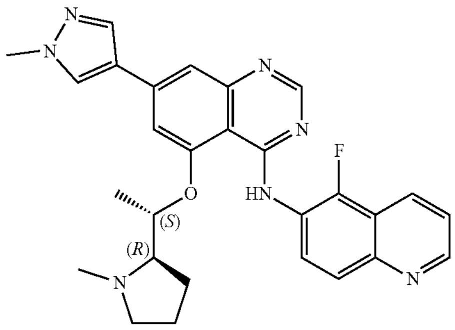 |
| 148 | 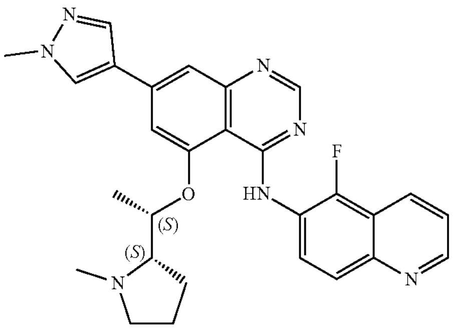 or 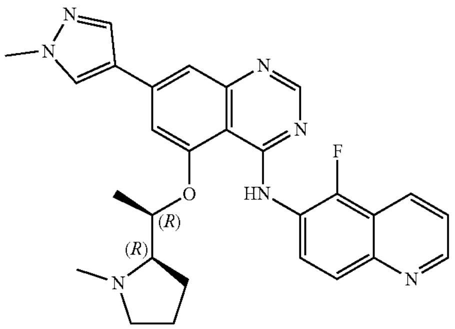 or 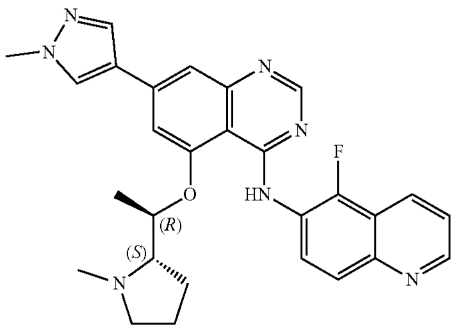 or 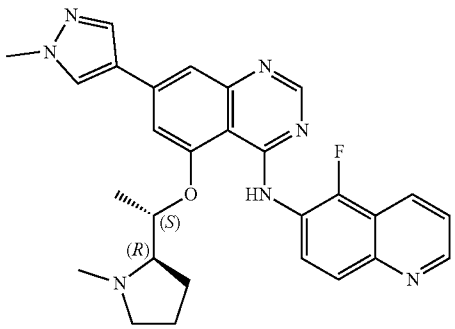 |
| 149 | 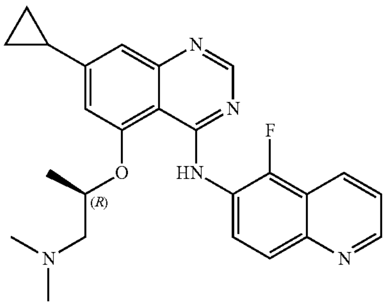 |

TABLE 1-continued
| Example # | Structure |
|---|---|
| 150 | 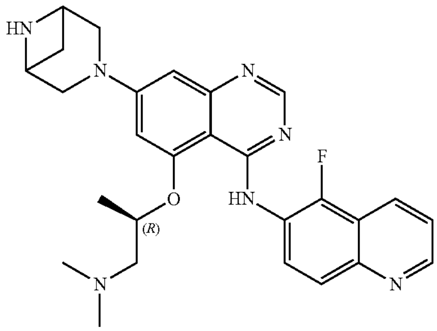 |
| 151 | 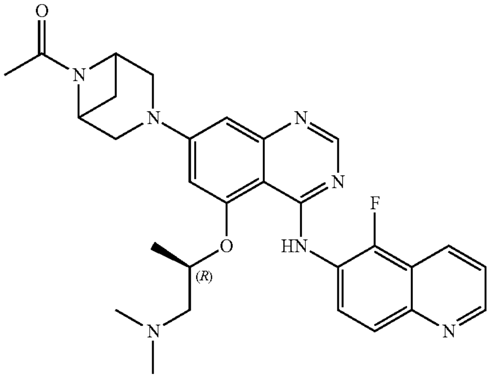 |
| 152 | 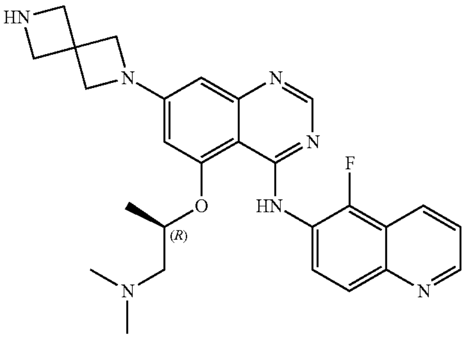 |
| 153 | 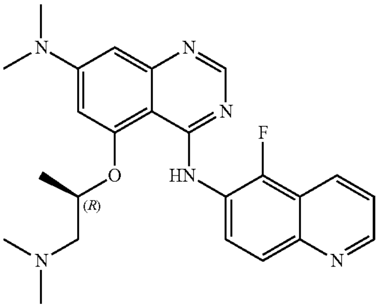 |

TABLE 1-continued
| Example # | Structure |
|---|---|
| 154 | 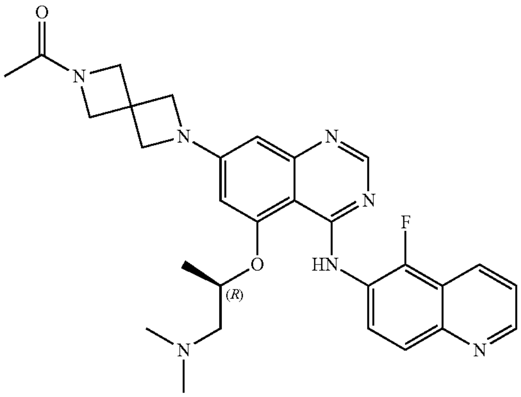 |
| 155 | 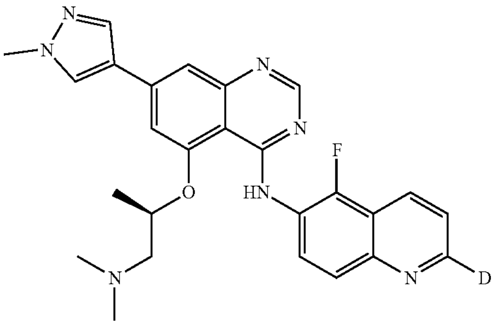 [SMILES: [2H]c1ccc2c(F)c(Nc3ncnc4cc(-c5cnn(C)c5)cc(O[C@H](C)CN(C)C)c34)ccc2n1] |
| 156 | 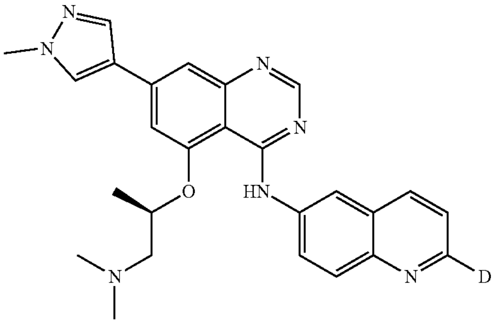 [SMILES: [2H]c1ccc2cc(Nc3ncnc4cc(-c5cnn(C)c5)cc(O[C@H](C)CN(C)C)c34)ccc2n1] |
| 157 | 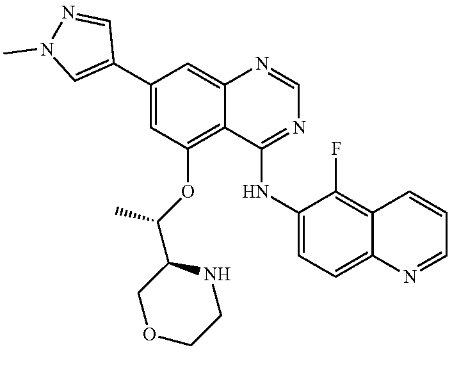 [SMILES: C[C@H](Oc1cc(-c2cnn(C)c2)cc2ncnc(Nc3ccc4ncccc4c3F)c12)[C@@H]1COCCN1] |

TABLE 1-continued

| Example # | Structure |
|---|---|
| 158 | 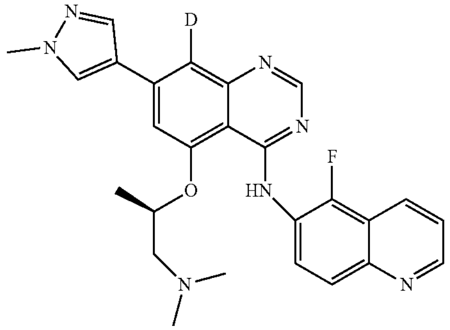 [SMILES: [2H]c1c(-c2cnn(C)c2)cc(O[C@H](C)CN(C)C)c2c(Nc3ccc4ncccc4c3F)ncnc12] |
| 159 | 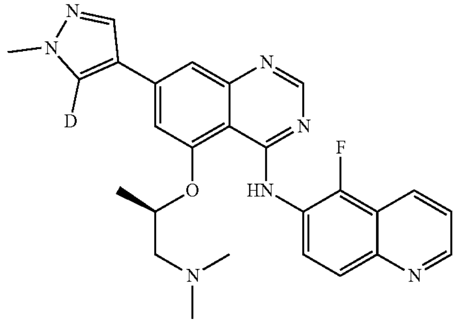 [SMILES: [2H]c1c(-c2cc(O[C@H](C)CN(C)C)c3c(Nc4ccc5ncccc5c4F)ncnc3c2)cnn1C] |

In some embodiments, the present disclosure provides a compound according to structural formula (I-0), (I), (II), (IIA), (IIB), (IIC), (IID), (III), (IIIA), (IIIB), (IIIC), (IIID), (IIIE), or (IV), or any one of the compounds of disclosed in the examples (including intermediates) and Table 1, or a pharmaceutically acceptable salt thereof, wherein one or more hydrogen is replaced with deuterium.

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically acceptable salts are well known in the art. For example, S. M. Berge et al. describes pharmacologically acceptable salts in *J. Pharm. Sci.,* 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Compounds having one or more chiral centers can exist in various stereoisomeric forms, i.e., each chiral center can have an R or S configuration or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

When two stereoisomers are depicted by their chemical names or structures, and the chemical names or structures are connected by an "and", a mixture of the two stereoisomers is intended.

When two stereoisomers are depicted by their chemical names or structures, and the names or structures are connected by an "or", one or the other of the two stereoisomers is intended, but not both.

A racemic mixture means a mixture of 50% of one enantiomer and 50% of its corresponding enantiomer. The present teachings encompass all enantiomerically-pure, enantiomerically-enriched, diastereomerically pure, diastereomerically-enriched, and racemic mixtures, and diastereomeric mixtures of the compounds disclosed herein.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

"First eluting compound" in the Experimental section refers to an intended reaction product compound obtained from a chromatography separation/purification that elutes earlier than a second intended reaction product compound from the same preceding reaction. The second intended product compound is referred to as "Second eluting compound".

In the compounds of the disclosure, any position specifically designated as "D" or "deuterium" is understood to have deuterium enrichment at 50, 80, 90, 95, 98 or 99%. "Deuterium enrichment" is a mole percent and is determined by dividing the number of compounds with deuterium at the indicated position by the total number of all of the compounds. When a position is designated as "H" or "hydrogen", the position has hydrogen at its natural abundance. When a position is silent as to whether hydrogen or deuterium is present, the position has hydrogen at its natural abundance. One specific alternative embodiment is directed to a compound of the disclosure having deuterium enrichment of at least 5, 10, 25, 50, 80, 90, 95, 98 or 99% at one or more positions not specifically designated as "D" or "deuterium".

As used herein, many moieties (e.g., alkyl, alkoxy, cycloalkyl or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Compounds of the disclosure are selective EGFR inhibitors. As used herein, the term "selective EGFR inhibitor" means a compound which selectively inhibits certain mutant EGFR kinases over wild-type EGFR and the kinome. Said another way, a selective EGFR inhibitor has no or low activity against wild-type EGFR and the kinome. A selective EGFR inhibitor's inhibitory activity against certain mutant EGFR kinases is more potent in terms of $IC_{50}$ value (i.e., the $IC_{50}$ value is subnanomolar) when compared with its inhibitory activity against wild-type EGFR and many other kinases. Potency can be measured using known biochemical assays.

Some compounds of the disclosure have the advantage of good penetration of the brain. The ability of a particular compound to cross the BBB and penetrate the brain can be assessed using a variety of known methods or combinations of such methods. One in vitro method that is frequently used to predict a compound's in vivo brain penetration is P-gp efflux ratio. P-glycoprotein (P-gp) is expressed at the blood-brain barrier (BBB) and restricts the penetration of its substrates into the central nervous system (CNS). Compounds that are found to be good P-gp substrates in vitro (i.e., have a high efflux ratio) are predicted to have poor in vivo brain penetration. In order to measure the P-gp efflux ratio, Madin-Darby canine kidney cells overexpressing P-gp (MDCK-MDR1 cells) the apparent apical to basolateral permeability (Papp[A-B]) and the apparent basolateral to apical permeability (Papp[B-A]) for compounds is determined. The P-gp efflux ratio is a measure of the ratio of Papp[B-A]/Papp[A-B]. In some embodiments, a compound of the disclosure has a P-gp efflux ratio of less than 2, less than 3, less than 4, less than 5.

Some compounds of the disclosure have the advantage of good metabolic stability. One indicator of good metabolic stability is high microsomal stability. Hepatic metabolism is a predominant route of elimination for small molecule drugs. The clearance of compounds by hepatic metabolism can be assessed in vitro using human liver microsomes (HLMs) or human hepatocytes. Compounds are incubated with HLMs plus appropriate co-factors or human hepatocytes and compound depletion is measured to determine an in vitro intrinsic clearance (Clint). The Clint is scaled to total body clearance (CL), and a hepatic extraction ratio (ER) is determined by dividing CL to standard human hepatic blood flow. Compounds that have a low hepatic extraction ratio are considered to have good metabolic stability. In some embodiments, a compound of the disclosure has a calculated ER of <0.3, <0.4, <0.5, <0.6.

Pharmaceutical Compositions

Pharmaceutical compositions of the disclosure (also referred to herein as the "disclosed pharmaceutical compositions") comprise one or more pharmaceutically acceptable carrier(s) or diluent(s) and a compound of the disclosure (e.g., a compound of Formula (I)), or a pharmaceutically acceptable salt thereof.

"Pharmaceutically acceptable carrier" and "pharmaceutically acceptable diluent" refer to a substance that aids the formulation and/or administration of an active agent to and/or absorption by a subject and can be included in the pharmaceutical compositions of the disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds or pharmaceutically acceptable salts thereof.

The pharmaceutical compositions of the disclosure optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present disclosure provides a method of inhibiting certain mutant forms of epidermal growth factor receptor (EGFR) in a subject in need thereof, comprising administering to the subject an effective amount of a compound disclosed herein, a pharmaceutically acceptable salt thereof or a pharmaceutical composition disclosed herein. Mutant forms of EGFR include for example, EGFR with LRCS mutation (the exon 19 deletion (del19) or exon 21 (L858R) substitution mutation, and C797X (e.g., C797S) mutation). Subjects "in need of inhibiting EGFR" are those having a disease for which a beneficial therapeutic effect can be achieved by inhibiting at least one mutant EGFR, e.g., a slowing in disease progression, alleviation of one or more symptoms associated with the disease or increasing the longevity of the subject in view of the disease.

In some embodiments, the disclosure provides a method of treating a disease/condition/or cancer associated with or modulated by mutant EGFR, wherein the inhibition of the mutant EGFR is of therapeutic benefit, including but not limited to the treatment of cancer in a subject in need thereof. The method comprises administering to the subject an effective amount of a compound disclosed herein, a pharmaceutically acceptable salt thereof, or pharmaceutical composition disclosed herein.

In another embodiment, the disclosure provides a method of treating a subject with cancer, comprising administering to the subject an effective amount of a compound disclosed herein, a pharmaceutically acceptable salt thereof, or a pharmaceutical composition disclosed herein. Cancers to be treated according to the disclosed methods include lung cancer, colon cancer, urothelial cancer, breast cancer, prostate cancer, brain cancers, ovarian cancer, gastric cancer, pancreatic cancer, head and neck cancer, bladder cancer, and mesothelioma, including metastasis (in particular brain metastasis) of all cancers listed. Typically, the cancer is characterized by at one or more EGFR mutations described herein. In a specific embodiment, the cancer has progressed on or after EGFR tyrosine kinase inhibitor (TKI) therapy. In a specific embodiment, the disease has progressed on or after first line 3rd generation TKI, e.g. osimertinib. In a specific embodiment, the cancer was not previously treated.

In a specific embodiment, the cancer to be treated is lung cancer. In a more specific embodiment, the cancer is non-small cell lung cancer (NSCLC). In some embodiments, the lung cancer is locally advanced or metastatic NSCLC, NSCLC adenocarcinoma, NSCLC with squamous histology and NSCLC with non-squamous histology. In another embodiment, the lung cancer is NSCLC adenocarcinoma. In another specific embodiment, the lung cancer (or non-small cell lung cancer) has metastasized to the brain.

In another embodiment, the disease/condition/or cancer associated with or modulated by mutant EGFR that is characterized by an EGFR genotype selected from genotypes 1-36 according the Table below (del18=Exon 18 deletion, specifically, e.g., del E709_T710 insD; and del19=Exon 19 deletion, specifically, e.g., delE746_A750 (most common), delE746_S752insV, del747_A750insP, delL747_P753insS, and delS752_I759; ex20ins—Exon 20 insertion, specifically, e.g., D761-E762insX, A763-Y764insX, Y764-V765insX, V765-M766insX, A767-S768insX, S768-D769insX, V769-D770insX, N771-P772insX, P772-H773insX, H773-V774insX, and V774-C775insX):

EGFR Genotype

| | |
|---|---|
| 1 | EGFR del19 |
| 2 | EGFR del19 C797S |
| 3 | EGFR del19 C797X (C797G or C797N or C797Y or C797T or C797D) |
| 4 | EGFR del19 L792X (L792F, L792H or L792Y) |
| 5 | EGFR del19 G796R (G796S) |
| 6 | EGFR del19 L792R (L792V or L792P) |
| 7 | EGFR del19 L718Q (L718V) |
| 8 | EGFR del19 G724S |
| 9 | EGFR del19 S768I (SV768IL) |
| 10 | EGFR del 19 V834L |
| 11 | EGFR del19 C797S L718Q (L718V) |
| 12 | EGFR del19 L718Q (L718V) A750P |
| 13 | EGFR L858R |
| 14 | EGFR L858R C797S |
| 15 | EGFR L858R C797X (797G or C797N or C797Y or C797T or C797D) |
| 16 | EGFR L858R L792X (L792F, L792H or L792Y) |
| 17 | EGFR L858R G796R (G796S) |
| 18 | EGFR L858R L792R (L792V or L792P) |
| 19 | EGFR L858R L718Q (L718V) |
| 20 | EGFR L858R G724S |
| 21 | EGFR L858R S768I (SV768IL) |
| 22 | EGFR L858R V834L |
| 23 | EGFR L858R C797S L718Q (L718V) |
| 24 | EGFR L858R L718Q (L718V) A750P |
| 25 | EGFR L861Q |
| 27 | EGFR L861Q C797S/G/N |
| 28 | EGFR del18 |
| 29 | EGFR G719X (G719A, G719S, G719C, G719R, G719D, or G719V) |
| 30 | EGFR E709X (E709K, E709H, or E709A) |
| 31 | EGFR E709X (E709K, E709H, or E709A) (G719A, G719S, G719C, G719D, G719R, or G719V) |
| 32 | EGFR G719X (G719A, G719S, G719C, G719D, G719R, or G719V) S768I |
| 33 | EGFR S768I |
| 34 | EGFR ex20ins |
| 35 | EGFR ex20ins L718Q |
| 36 | EGFR ex20ins C797S |

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del119.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del119 C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 C797X (C797G or C797N or C797Y or C797T or C797D).

In another embodiment, the disease/condition/or cancer (e.g., NSCLC) being treated with a disclosed compound, a pharmaceutically acceptable salt, or a pharmaceutical composition disclosed herein is characterized by EGFR comprising EGFR del19 L792X (L792F, L792H or L792Y).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 G796R (G796S).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L792R (L792V or L792P).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L718Q (L718V).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797S.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797X (797G or C797N or C797Y or C797T or C797D).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R L792X (L792F, L792H or L792Y).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R G796R (G796S).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L792R (L792V or L792P).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L718Q (L718V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del18.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719R, G719D, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A) (G719A, G719S, G719C, G719D, G719R, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719D, G719R, or G719V) S768I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR S768I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins L718Q.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins C797S.

In another embodiment, the disease/condition/or cancer (e.g., NSCLC) being treated with a disclosed compound, a pharmaceutically acceptable salt or a pharmaceutical composition disclosed herein is characterized by an EGFR genotype selected from genotypes 1-36.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to lazertinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to amivantamab.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to amivantamab and lazertinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to aumolertinib (formerly almonertinib).

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to olmutinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to nazartinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to avitinib.

Another embodiment is the treatment a subject with metastatic NSCLC with tumors harboring activating Exon 19 Deletion or L858R EGFR mutations, G719X (A, S, C, D, R, V), S768I and L861Q, as well as a resistance mutation disclosed herein as detected by an approved molecular testing methodology.

Another embodiment is a disclosed compound used in combination with a $2^{nd}$ or $3^{rd}$ generation TKI indicated for the treatment of subject with metastatic NSCLC with tumors harboring C797X mutations as detected by an approved test, and whose disease has progressed on or after 1 or 2 prior EGFR TKI therapies.

Another embodiment is a disclosed compound for the treatment of subjects with metastatic NSCLC whose disease with on-target EGFR resistance has progressed on or after any EGFR TKI. In a specific embodiment, the disclosed compound is used in combination with a $2^{nd}$ or $3^{rd}$ generation TKI indicated for the treatment of subject with metastatic NSCLC.

Another embodiment is a disclosed compound for the treatment of subjects with metastatic EGFR C797X mutation-positive NSCLC as detected by an approved molecular test, whose disease has progressed on or after first-line or second-line osimertinib. In a specific embodiment, the disclosed compound is used in combination with a $2^{nd}$ or $3^{rd}$ generation TKI indicated for the treatment of subject with metastatic NSCLC.

In a particular embodiment, the deletions, mutations, and insertions disclosed herein are detected by an FDA-approved test.

A person of ordinary skill in the art can readily determine the certain EGFR alterations a subject possesses in a cell, cancer, gene, or gene product, e.g., whether a subject has one or more of the mutations or deletions described herein using a detection method selected from those known in the art such as hybridization-based methods, amplification-based methods, microarray analysis, flow cytometry analysis, DNA sequencing, next-generation sequencing (NGS), primer extension, PCR, in situ hybridization, fluorescent in situ hybridization, dot blot, and Southern blot.

To detect one or more EGFR deletions and/or mutations, a primary tumor sample, circulating tumor DNA (ctDNA), circulating tumor cells (CTC), and/or circulating exosomes may be collected from a subject. The samples are processed, the nucleic acids are isolated using techniques known in the art, then the nucleic acids are sequenced using methods known in the art. Sequences are then mapped to individual exons, and measures of transcriptional expression (such as RPKM, or reads per kilobase per million reads mapped), are quantified. Raw sequences and exon array data are available from sources such as TCGA, ICGC, and the NCBI Gene Expression Omnibus (GEO). For a given sample, individual exon coordinates are annotated with gene identifier information, and exons belonging to kinase domains are flagged. The exon levels are then z-score normalized across all tumors samples.

The compounds of the disclosure, pharmaceutically acceptable salts thereof or pharmaceutical compositions disclosed herein may be used for treating to a subject who has become refractory to treatment with one or more other EGFR inhibitors. "Refractory" means that the subject's cancer previously responded to drugs but later responds poorly or not at all. In some embodiments, the subject has become refractory to one or more first generation EGFR inhibitors such as erlotinib, gefitinib, icotinib or lapatinib. In some embodiments, the subject has been become refractory to treatment with one or more second generation EGFR inhibitors such as afatinib, dacomitinib, poziotinib, or neratinib. In some embodiments the subject has become refractory to treatment with one or more first generation inhibitors and one or more second generation inhibitors. In some embodiments, the subject has become refractory to treatment with one or more third generation inhibitors such as osimertinib, nazartinib, or avitinib. In one embodiment, the subject has become refractory to treatment with one or more first generation EGFR inhibitors and one or more third generation EGFR inhibitors. In some embodiments, the subject has become refractory to treatment with one or more second generation EGFR inhibitors and one or more third generation EGFR inhibitors. In some embodiments, the subject has become refractory to treatment with one or more first generation inhibitors, and one or more third generation EGFR inhibitors.

Combinations

The compounds of the disclosure, pharmaceutically acceptable salts thereof, or pharmaceutical compositions disclosed herein can be used in combination with one or more additional pharmacologically active substances. For example, the disclosure includes methods of treating a condition/disease/or cancer comprising administering to a subject in need thereof a compound of the disclosure or a pharmaceutically acceptable salt or a pharmaceutical composition disclosed herein thereof in combination with an EGFR (or EGFR mutant) inhibitor, such as afatinib, osimertinib, lapatinib, erlotinib, dacomitinib, poziotinib, neratinib, gefitinib JBJ-04-125-02, alflutinib (AST 2818), aumolertinib (formerly almonertinib) (HS10296), BBT-176, BI-4020, BPI-361175, BPI-D0316, CH7233163, gilitertinib, icotinib, JND-3229, lazertinib, nazartinib (EGF 816), avitinib, PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)). For the treatment of cancer e.g., NSCLC using a compound of the disclosure or pharmaceutically acceptable salt thereof or pharmaceutical composition disclosed herein in combination with a first line therapy, for example a first, second, or third generation EGFR inhibitor (i.e., as an initial treatment before the cancer has become refractory) may forestall or delay the cancer from becoming refractory. Typically, the cancer is characterized by one of the EGFR genotypes described herein.

In one aspect, a compound of the disclosure, a pharmaceutically acceptable salt thereof or a pharmaceutical composition disclosed herein can be administered in combination with a compound disclosed in International Application Publication No. WO 2021/133809, a pharmaceutically acceptable salt thereof or a pharmaceutical composition comprising the same.

In one embodiment, a compound of the disclosure, a pharmaceutically acceptable salt thereof or a pharmaceutical composition disclosed herein can be administered in combination with a compound provided below, (3S,4R)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)-4-methylpiperidin-4-ol, (3R,4S)-3-fluoro-1-(4-(5-isopropyl-8-((2R,3S)-2-methyl-3-(methylsulfonylmethyl)azetidin-1-yl)isoquinolin-3-ylamino)pyrimidin-2-yl)-4-methylpiperidin-4-ol, N-(2-((3S,4R)-3-fluoro-4-methoxypiperidin-1-yl)pyrimidin-4-yl)-5-isopropyl-8-((2R,3S)-2-methyl-3-((methylsulfonyl)methyl)azetidin-1-yl)isoquinolin-3-amine, N-(2-((3R,4S)-3-fluoro-4-methoxypiperidin-1-yl)pyrimidin-4-yl)-5-isopropyl-8-((2R,3S)-2-methyl-3-((methylsulfonyl)methyl)azetidin-1-yl)isoquinolin-3-amine, N-(2-((3S,4R)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine, N-(2-((3R,4S)-3-fluoro-4-(methoxy-d3)piperidin-1-yl)pyrimidin-4-yl)-5-isopropyl-8-((2R,3S)-2-methyl-3-((methylsulfonyl)methyl)azetidin-1-yl)isoquinolin-3-amine, (3S,4R)-1-(4-(8-((2R,3S)-3-(ethylsulfonylmethyl)-2-methylazetidin-1-yl)-5-isopropyl-2,6-naphthyridin-3-ylamino)pyrimidin-2-yl)-3-fluoro-4-methylpiperidin-4-ol, (3S,4R)-1-(4-(8-((2R,3S)-3-(ethylsulfonylmethyl)-2-methylazetidin-1-yl)-5-isopropyl-2,7-naphthyridin-3-ylamino)pyrimidin-2-yl)-3-fluoro-4-methylpiperidin-4-ol, 2-((3S,4R)-1-(4-(8-((2R,3S)-3-(ethylsulfonylmethyl)-2-methylazetidin-1-yl)-5-isopropylisoquinolin-3-ylamino)pyrimidin-2-yl)-3-fluoropiperidin-4-yloxy)ethanol, (3S,4S)-5,5-difluoro-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol, (3R,4R)-5,5-difluoro-1-(4-(5-isopropyl-8-((2R,3S)-2-methyl-3-(methylsulfonylmethyl)azetidin-1-yl)isoquinolin-3-ylamino)pyrimidin-2-yl)-4-methoxypiperidin-3-ol, (3S,4S)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol, (3R,4R)-1-(4-(8-((2R,3S)-3-(ethylsulfonylmethyl)-2-methylazetidin-1-yl)-5-isopropylisoquinolin-3-ylamino)pyrimidin-2-yl)-4-methoxypiperidin-3-ol, a pharmaceutically acceptable salt thereof, or a pharmaceutical composition comprising the same.

Alternatively, a compound of the disclosure, a pharmaceutically acceptable salt thereof or a pharmaceutical composition disclosed herein can be administered in combination with other anti-cancer agents that are not EGFR inhibitors e.g., in combination with MEK, including mutant MEK inhibitors (trametinib, cobimtetinib, binimetinib, selumetinib, refametinib); c-MET, including mutant c-Met inhibitors (savolitinib, cabozantinib, foretinib, glumetinib, tepotinib) and MET antibodies (emibetuzumab, telisotuzumab vedotin (ABBV 339)); mitotic kinase inhibitors (CDK4/6 inhibitors such as palbociclib, ribociclib, abemacicilb, GIT38); anti-angiogenic agents e.g., bevacizumab, nintedanib; apoptosis inducers such as Bcl-2 inhibitors e.g, venetoclax, obatoclax, navitoclax, palcitoclax (APG-1252), and Mcl-1 inhibitors e.g., AZD-5991, AMG-176, S-64315; mTOR inhibitors e.g, rapamycin, temsirolimus, everolimus, ridoforolimus; RET inhibitors, like pralsetinib and selpercatinib, and PI3K inhibitors dactolisib (BEZ235), pictilisib (GDC-0941), LY294002, idelalisib (CAL-101); JAK inhibitors (e.g., AZD4205, itacitinib), Aurora A inhibitors (e.g., alisertib); BCR/ABL and/or Src family tyrosine kinase inhibitors (e.g., dasatinib); VEGF inhibitors (e.g., MP0250; ramucirumab); multi-kinase protein inhibitors (e.g., anlotinib, midostaurin); PARP inhibitors (e.g., niraparib); platinum therapies (e.g., cisplatin (CDDP), carboplatin (CBDCA), or nedaplatin (CDGP)); PD-L1 inhibitors (e.g., durvalumab (MEDI 4736)); HER2/neu receptor inhibitors (e.g., trastuzumab); anti-HER2 or anti-HER3 antibody-drug conjugates (e.g., patritumab deruxtecan (U3-1402), trastuzumab emtansine); or immunogene therapy (e.g., oncoprex).

A “subject” is a human in need of treatment.

Methods of Administration and Dosage Forms

The precise amount of compound administered to provide an “effective amount” to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an “effective amount” of any additional therapeutic agent(s) will depend on the type of drug used. Suitable dosages are known for approved therapeutic agents and can be adjusted by the skilled artisan according to the condition of the subject, the type of condition(s) being treated and the amount of a compound of Formula (I) being used by following, for example, dosages reported in the literature and recommended in the Physician's Desk Reference (57th Ed., 2003).

“Treating” or “treatment” refers to obtaining a desired pharmacological and/or physiological effect. The effect can be therapeutic, which includes achieving, partially or substantially, one or more of the following results: partially or substantially reducing the extent of the disease, condition or cancer; ameliorating or improving a clinical symptom or indicator associated with the disease, condition or cancer; delaying, inhibiting or decreasing the likelihood of the progression of the disease, condition or cancer; or decreasing the likelihood of recurrence of the disease, condition or cancer.

The term “effective amount” means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, a compound of the disclosure, a pharmaceutically acceptable salt thereof or a pharmaceutical composition of the disclosure can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds of the disclosure, a pharmaceutically acceptable salt thereof or a pharmaceutical composition of the disclosure will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed EGFR inhibitors for guidance.

The compounds of the disclosure or a pharmaceutically acceptable salt thereof can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the disclosure or a pharmaceutically acceptable salt thereof may be incorporated with excipient and used in the form of ingestible tablets, buccal tablets, troches, capsules, elixirs, suspensions, syrups, wafers, and the like.

Typically for parenteral administration, solutions of a compound of the disclosure can generally or a pharmaceutically acceptable salt thereof be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the disclosure for the extemporaneous preparation of sterile injectable solutions or dispersions are appropriate.

The following examples are intended to be illustrative and are not intended to be limiting in any way to the scope of the disclosure.

EXEMPLIFICATION

Preparation of Exemplary Compounds

Definitions

° C. degrees Celsius
CC Silica Column Chromatography
ACN acetonitrile
AcOH acetic Acid
DCM dichloromethane
DIEA diisopropylethylamine
DMF dimethyl formamide
DMF-DMA N,N-Dimethylformamide dimethyl acetal
DMSO dimethylsulfoxide
EA ethyl acetate
H, h, hr(s) hour(s)
HPLC high performance liquid chromatography
$IC_{50}$ inhibitory concentration 50%
i-PrOH isopropyl alcohol
IPA isopropyl alcohol
min minutes
MTBE methyl tert-butyl ether
MeOH methanol
PE petroleum ether
rt room temperature
TEA triethylamine
TFA trifluoracetic Acid
THF tetrahydrofuran
RT retention time
Prep HPLC preparative high-performance liquid chromatography
Prep-TLC preparative thin layer chromatography
TLC thin layer chromatography
MsCl methanesulfonyl chloride
Bpin boronic acid pinacol ester
BINAP (2,2'-bis(diphenylphosphino)-1,1'-binaphthyl)
$Pd(dppf)Cl_2$ [1,1'-Bis(diphenylphosphino)ferrocene]dichloropalladium Methods for preparing compounds of the invention can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^{1}H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: liquid chromatography-mass spectrometry (LC-MS) data (sample analyzed for purity and identity) were obtained with:

a) an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.10% formic acid in water and 0.10% formic acid in acetonitrile. A constant gradient from 95% aqueous/5% organic to 5% aqueous/95% organic mobile phase over the course of 4 minutes was utilized. The flow rate was constant at 1 mL/min; or b) Shimadzu LCMS system using a Shimadzu LCMS mass spectrometer utilizing ESI ionization fitted with an Agilent (Poroshel HPH-C18 2.7 um particle size, 3.0×50 mm dimensions) reverse-phase column at 22.4 degrees Celsius. The mobile phase consisted of a mixture of solvent 5 mM $NH_4HCO_3$ (or 0.05% TFA) in water and acetonitrile. A constant gradient from 90% aqueous/10% organic to 5% aqueous/95% organic mobile phase over the course of 2 minutes was utilized. The flow rate was constant at 1.5 mL/min.

Prep LC-MS: Preparative HPLC was performed on a a) Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.10% formic acid in water and 0.10% formic acid in acetonitrile. A constant gradient from 95% aqueous/5% organic to 5% aqueous/95% organic mobile phase over the course of 25 minutes was utilized. The flow rate was constant at 20 mL/min.

b) Manufacturer: Yantai Xinnuo Chemicals Co, particle size: 10-40 um, PH=6.2-7, Thickness: 1 mm, Binder: CMC, Specifications: 200*200 mm Silica gel chromatography: Silica gel chromatography was performed on either a Teledyne Isco CombiFlash® Rf unit or a Biotage® Isolera Four unit or a Biotage® Isolera Prime unit.

Proton NMR: $^{1}H$ NMR spectra were obtained with a) a Varian 400 MHz Unity Inova 400 MHz NMR instrument (acquisition time=3.5 seconds with a 1 second delay; 16 to 64 scans). Where characterized, all protons were reported in DMSO-d6 solvent as parts-per million (ppm) with respect to residual DMSO (2.50 ppm); or b) a Avance 400 MHz Unity Inova 400 MHz NM instrument (acquisition time=3.99 seconds with a 1 second delay; 4 to 64 scans) or a Avance 300 MHz Unity Inova 300 MHz NMR instrument (acquisition time=5.45 seconds with a 1 second delay; 4 to 64 scans).

Prep LC-MS: Preparative HPLC was performed on a Waters Preparative system fitted with Column: XBridge Shield RP18 OBD Column, 30*150 mm, 5 um; The mobile phase consisted of a solvent mixture of aqueous: (Water (10 mmol/L $NH_4HCO_3$+0.05% $NH_3 \cdot H_2O$)) and organic (acetonitrile). A constant gradient from 95% aqueous/5% organic to 5% aqueous/95% organic mobile phase was utilized. The flow rate was constant and typically 60 mL/min.

Reactions carried out in a microwave were done so in a Biotage Initiator microwave unit.

One of ordinary skill in the art will recognize that modifications of the gradient, column length, and flow rate are possible and that some conditions may be more suitable for compound characterization than others, depending on the chemical species being analyzed.

Generic Synthetic Schemes

Scheme 1

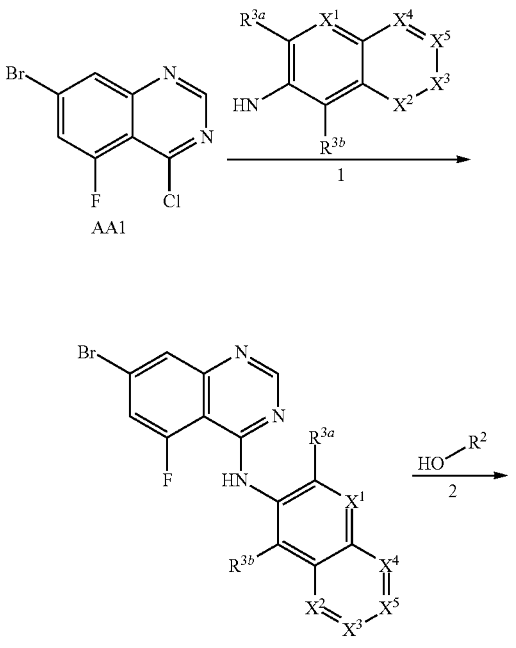

AA1

BB1

-continued

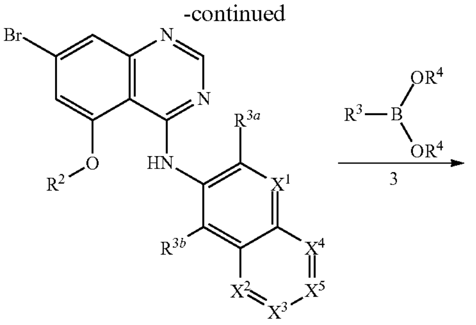

CC1

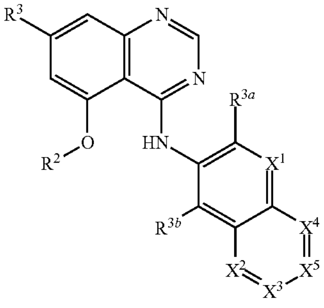

DD1

In certain embodiments optionally substituted bicyclic heteroaromatic, AA1, is reacted with an optionally substituted bicyclic aniline, 1, where $R_1$=H, F, OH, OAk and X=C or N to afford optionally substituted condensation products, BB1. The resulting species is further homologated with an optionally substituted alcohol, 2, via nucleophilic substitution to afford compounds of type CC1. The resulting species is further elaborated by Pd-mediated coupling with an optionally substituted alkyl, aryl, heteroaryl boronate or boronic acid, 3, to afford products, DD1.

Scheme 2

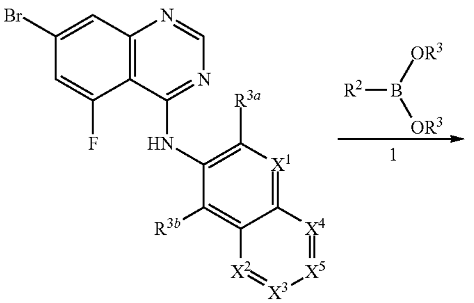

BB1

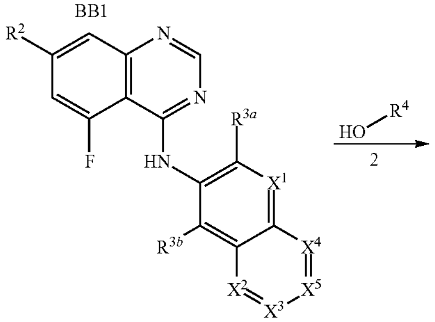

CC2

-continued

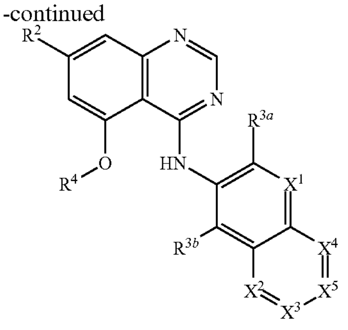

DD2

In certain embodiments BB1 is further homologated by Pd-mediated coupling with an optionally substituted alkyl, aryl, heteroaryl boronate or boronic acid, 1, to afford products, CC2. The resulting species is then reacted with an optionally substituted alcohol, 2, via nucleophilic substitution to afford compounds of type DD2.

Scheme 3

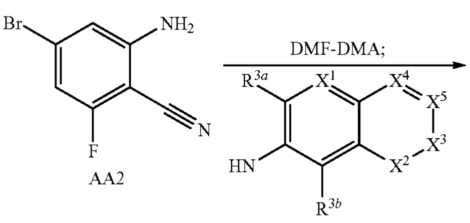

AA2

1

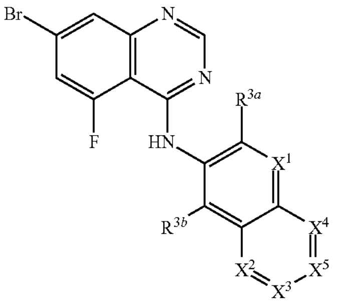

BB1

In certain embodiments BB1 is produced by reaction of aniline AA2 with DMF-DMA adduct followed by the addition of an optionally substituted bicyclic aniline, 1, where R1=H, F, OH, OAk and X=C or N.

Scheme 4
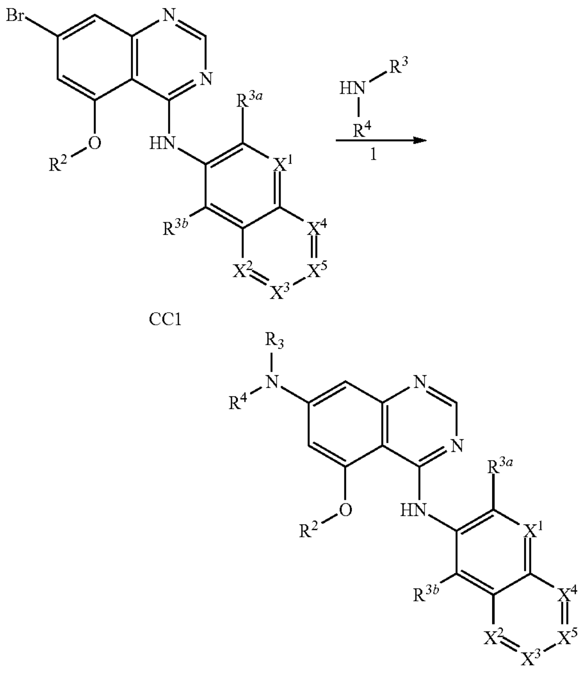
CC1
DD3
In certain embodiments CC1 is further elaborated by Pd-mediated coupling with an optionally substituted amine, 1, to afford products, DD3.
Scheme 5
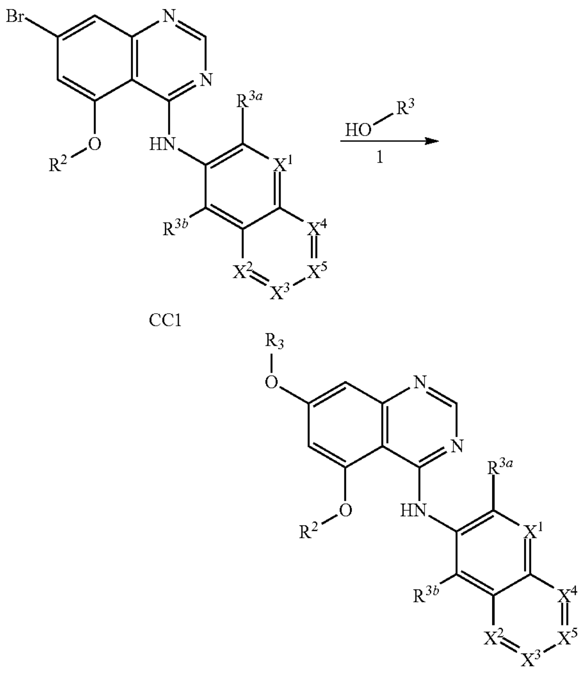
CC1
DD4
In certain embodiments CC1 is further elaborated by transition metal catalyzed coupling with an optionally substituted alcohol, 1, to afford products, DD4.
Scheme 6
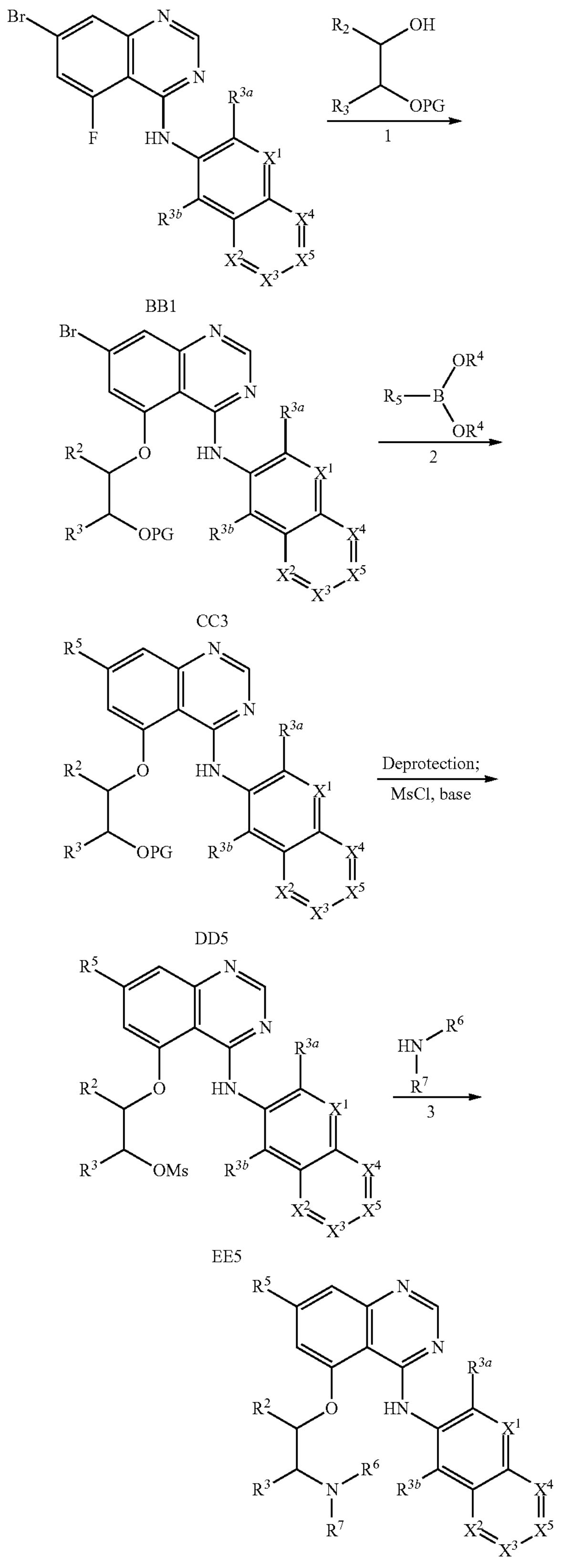
BB1
CC3
DD5
EE5
FF5

In certain embodiments BB1 is further homologated with an optionally substituted and monoprotected diol, 1, via nucleophilic substitution to afford compounds of type CC3. The resulting species is further elaborated by Pd-mediated coupling with an optionally substituted alkyl, aryl, heteroaryl boronate or boronic acid, 3, to afford products, DD5. The resulting protected alcohol is deprotected, treated with MsCl and organic base to afford the optionally substituted mesylate adduct EE5, which can be further elaborated through the addition of optionally substituted amine, 3, to afford products, FF5.

Intermediate 1: (E)-N'-(5-bromo-2-cyano-3-fluorophenyl)-N,N-dimethylformimidamide

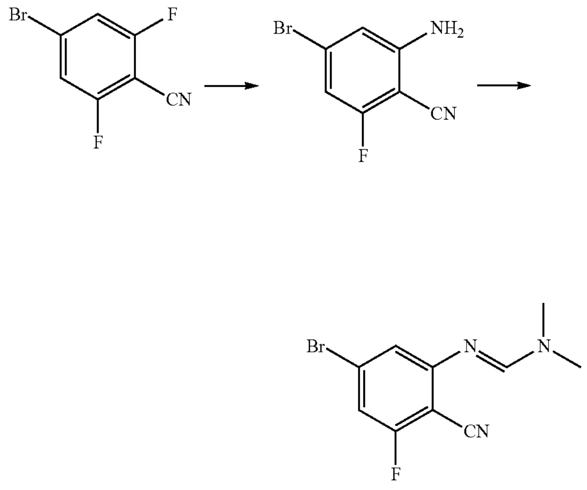

Intermediate 1

Step 1: 2-amino-4-bromo-6-fluorobenzonitrile

To a solution of 4-bromo-2,6-difluorobenzonitrile (10 g, 0.046 mol) in IPA (10 mL) was added ammonium hydroxide solution (10 mL) at rt. The mixture was stirred for 2 hours at 90° C. The solvent was evaporated and the crude product was used directly without further purification. LC-MS: (ES, m/z): RT=1.109 min, LCMS: m/z=213 [M−1].

Step 2: (E)-N'-(5-bromo-2-cyano-3-fluorophenyl)-N,N-dimethylformimidamide 2-amino-4-bromo-6-fluorobenzonitrile (5 g, 0.023 mol) was added to DMF-DMA (50 mL) at rt. The mixture was stirred at 120° C. for 2 hours. After cooling to rt the solvent was evaporated and the residue suspended in diethyl ether. The solid was collected by filtration and dried to obtain the title compound as white solid (4.9 g, 79.0%). LC-MS: (ES, m/z): RT=1.218 min, LCMS: m/z=270 [M+1].

Intermediate 2: 7-bromo-5-fluoro-N-(5-fluoroquinolin-6-yl)quinazolin-4-amine

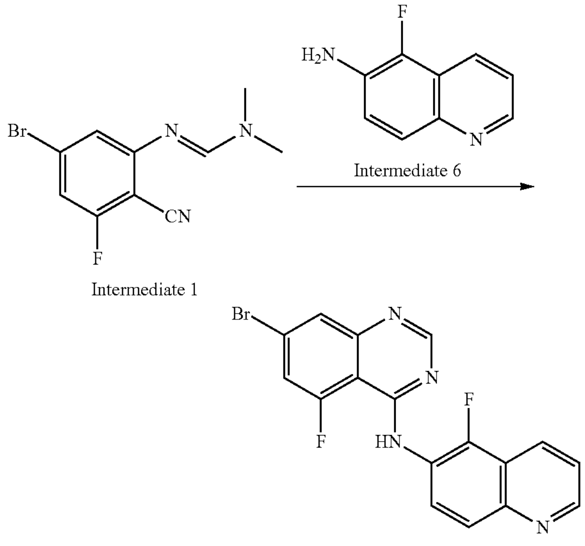

Intermediate 2

Intermediate 6 (17.0 g, 104 mmol) was added to Intermediate 1 (30.7 g, 114 mmol) in AcOH at rt. The resulting mixture was stirred at 100° C. The mixture was poured into water, and a solid was collected by filtration to give title compound (13.5 g, 34.9 mmol, 33.3% yield) as a white solid. LC-MS: (ES, m/z): RT=0.728 min, LCMS: m/z=387[M+1].

Intermediate 2: Alternate Route: 7-bromo-5-fluoro-N-(5-fluoroquinolin-6-yl) quinazolin-4-amine

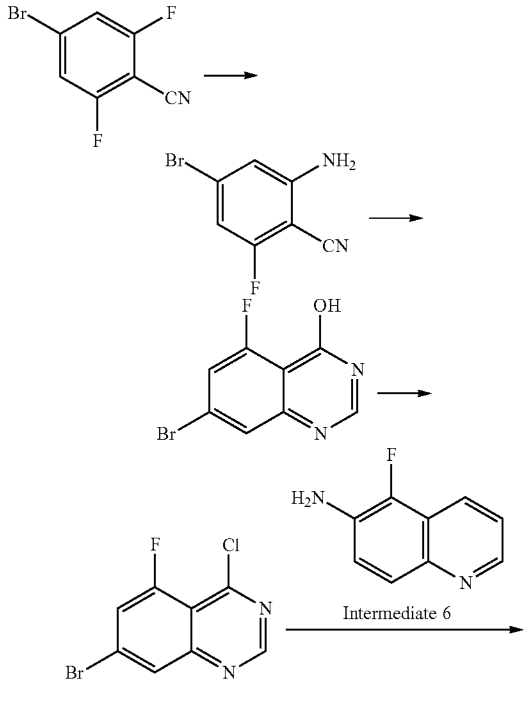

-continued

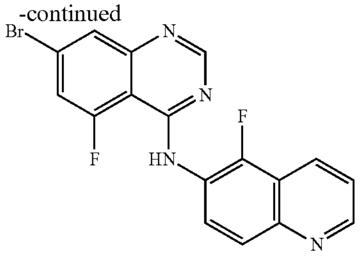

Intermediate 2

Step 1: 2-amino-4-bromo-6-fluorobenzonitrile

To a solution of 4-bromo-2, 6-difluorobenzonitrile (150 g, 688 mmol, 1.00 eq) in i-PrOH (300 mL) was added $NH_3 \cdot H_2O$ (673 g, 4.80 mol, 740 mL, 25% purity, 6.98 eq) under autoclave at 18-22° C. The reaction mixture was stirred at 80° C. for 16 hrs. TLC (Petroleum ether: Ethyl acetate=8:1) showed 4-bromo-2, 6-difluorobenzonitrile (Rf=0.60) was consumed and a main spot (Rf=0.10) was detected. The reaction mixture was poured into $H_2O$ (1.00 L) and extracted with Ethyl acetate (1.50 L×2). The combined organic layers were washed with brine (500 mL×3), dried over $Na_2SO_4$, filtered and concentrated under reduced pressure to give a residue. The residue was triturated with petroleum ether (450 mL) at 18-22° C. for 30 mins to give the title compound (141 g, 631 mmol, 91.7% yield, 96.1% purity) as a yellow solid. LC-MS: (ES, m/z): RT=2.353 mins; LCMS: m/z=214.9 [M−1]; $^1H$ NMR: (400 MHz, $CDCl_3$) δ 6.73 (s, 1H), 6.67-6.69 (m, 1H), 4.61 (s, 2H).

Step 2: 7-bromo-5-fluoroquinazolin-4-ol

To a solution of $H_2SO_4$ (287 g, 2.93 mol, 156 mL, 4.50 eq) and HCOOH (3.13 kg, 65.1 mol, 2.56 L, 100 eq) was added 2-amino-4-bromo-6-fluorobenzonitrile (140 g, 651 mmol, 1.00 eq) portion-wise at 100° C. The mixture was stirred at 100° C. for 2 hrs. The reaction mixture was concentrated under vacuum to give a residue. The residue was triturated with $H_2O$ (2.00 L) at 25° C. for 30 mins to give the title compound (100 g, 387 mmol, 59.4% yield, 94.0% purity) as a white solid. (ES, m/z): RT=0.983 min; LCMS: m/z=244.8 [M+1]; $^1H$ NMR: (400 MHz, DMSO-d6) δ 8.12 (s, 1H), 7.70 (s, 1H), 7.59-7.62 (m, 1H).

Step 3: 7-bromo-4-chloro-5-fluoroquinazoline

To a solution of 7-bromo-5-fluoroquinazolin-4-ol (50.0 g, 206 mmol, 1.00 eq) in toluene (500 mL) was added DIEA (120 g, 926 mmol, 161 mL, 4.50 eq) at 25° C. Then the reaction mixture was stirred at 25° C. for 30 mins. $POCl_3$ (63.1 g, 411 mmol, 38.2 mL, 2.00 eq) was added and the mixture was stirred at 100° C. for 2 hrs. The reaction mixture was cooled to 25° C., poured into $H_2O$ (450 mL) and extracted with ethyl acetate (400 mL×3). The organic layer was washed with brine (200 mL×2), dried over $Na_2SO_4$, filtered and concentrated under vacuum to give the title compound (50.0 g, crude) as a brown solid. The residue was used to the next step without purification. LC-MS: (ES, m/z): RT=0.625 min; LCMS: m/z=262.9 [M+1]

Step 4: 7-bromo-5-fluoro-N-(5-fluoroquinolin-6-yl) quinazolin-4-amine

A solution of Intermediate 6 (25.5 g, 157 mmol, 1.00 eq) and 7-bromo-4-chloro-5-fluoroquinazoline (49.3 g, 189 mmol, 1.20 eq) in i-PrOH (1.00 L) was stirred at 85° C. for 16 hrs. The reaction mixture was cooled to 25° C. and added ethyl acetate (400 mL) and stirred at 25° C. for 20 mins. Then the mixture was filtered and the filter cake was washed with ethyl acetate (300 mL) then concentrated under vacuum to give the title compound (47.5 g, 109.73 mmol, 69.8% yield, 97.9% purity, HCl) as a yellow solid. LC-MS: (ES, m/z): RT=0.540 min; LCMS: m/z=388.8 [M+1]; $^1H$ NMR: (400 MHz, DMSO-d6) δ 9.06-9.07 (m, 1H), 8.68 (s, 1H), 8.64 (m, 1H), 8.00-8.08 (m, 2H), 7.96-7.98 (m, 2H), 7.73-7.76 (m, 1H). FNMR: (400 MHz, DMSO-d6) δ −105.08, −126.64

Intermediate 3: 7-bromo-5-fluoroquinazolin-4(3H)-one

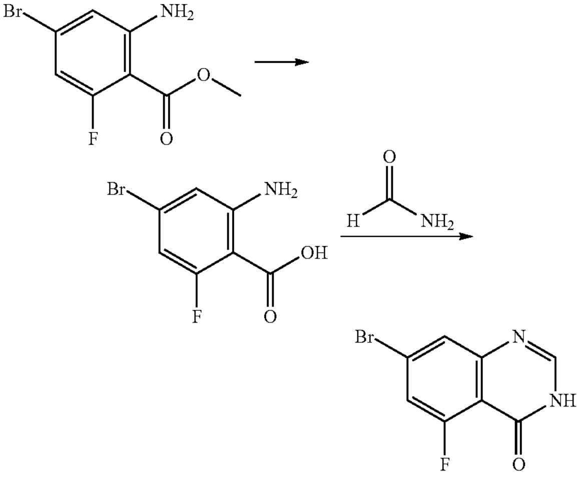

Intermediate 3

Step 1: 2-amino-4-bromo-6-fluorobenzoic acid

To a solution of methyl 2-amino-4-bromo-6-fluorobenzoate (3 g, 12.09 mmol, 1 eq) in dioxane (20 mL) and $H_2O$ (20 mL) was added $LiOH \cdot H_2O$ (5.08 g, 120.94 mmol, 10 eq). The mixture was stirred at rt for 2 hrs. The mixture was concentrated under reduced pressure. To the residue was added $H_2O$ (10 mL), and HCl (1 M) was added to adjust to pH=6. The mixture was filtered and the solid was concentrated under reduced pressure to afford the title compound (2.5 g, 10.68 mmol, 88.33% yield) as a brown solid. LC-MS: (ES, m/z): RT=1.056 min, LC-MS: m/z=233.9 [M+1].

Step 2: 7-bromo-5-fluoroquinazolin-4(3H)-one

A mixture of 2-amino-4-bromo-6-fluorobenzoic acid (2.5 g, 10.68 mmol, 1 eq) and formamide (12.03 g, 267.07 mmol, 10.65 mL, 25 eq) was heated to 170° C. for 3 hrs. The reaction mixture was quenched by addition of $H_2O$ (25 mL) at 25° C. The mixture was filtered and the filtrate was concentrated under reduced pressure to afford the title compound (2 g, 8.23 mmol, 77.03% yield) as a brown solid. LC-MS: (ES, m/z): RT=0.914 min, LC-MS: m/z=242.9 [M+1].

Intermediate 4: (R)-7-bromo-5-((1-(dimethylamino)propan-2-yl)oxy)-N-(5-fluoroquinolin-6-yl)quinazolin-4-amine

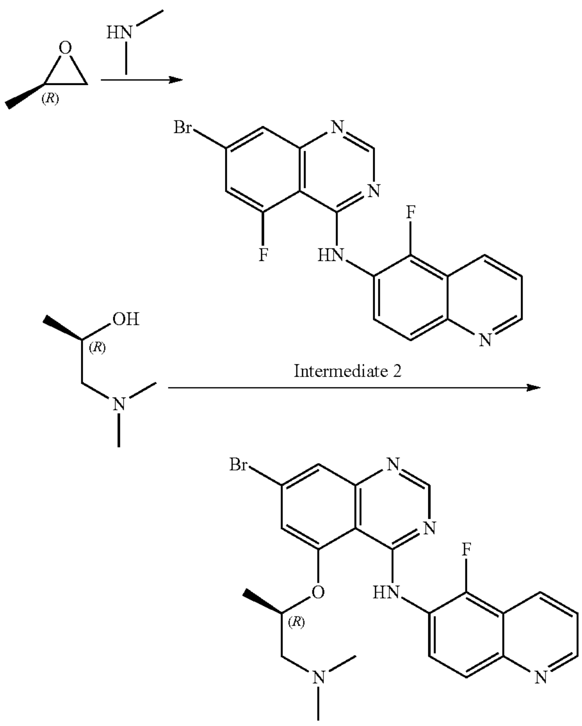

Intermediate 4

Step 1: (R)-1-(dimethylamino)propan-2-ol

Dimethylamine (60 mL, 33% in water) was added dropwise to (R)-2-methyloxirane (25 g, 0.431 mol) at 0° C. The resulting mixture was stirred at 40° C. for 16 h. The reaction mixture was diluted with DCM (300 mL) and washed with brine (2×100 mL), the organic layer was dried with $Na_2SO_4$ and concentrated under vacuum to afford the title compound (30 g, 67%) as a colorless oil. $^1$H NMR (400 MHz, DMSO-$d_6$) δ 3.73-3.65 (m, 1H), 2.26-2.04 (m, 8H), 1.03 (d, 3H).

Step 2: (R)-7-bromo-5-((1-(dimethylamino)propan-2-yl)oxy)-N-(5-fluoroquinolin-6-yl)quinazolin-4-amine NaH (6.15 g, 154 mmol) was added batch wise to (R)-1-(dimethylamino)propan-2-ol (15.8 g, 154 mmol) in THF (300 mL) at 0° C. for 30 min. Intermediate 2 (20 g, 51.6 mmol) was added to the mixture at 0° C. for 10 min. The reaction was stirred at 80° C. for 2 hours. The reaction was quenched with $H_2O$ (100 mL). The mixture was diluted with EA (300 mL) and washed with brine (150 mL×2), the organic layer was dried with $Na_2SO_4$ and concentrated under vacuum. The residue was purified by a silica gel column with DCM:MeOH=25:1 to afford the title compound as a yellow solid. (14 g, 58%). LC-MS: (ES, m/z): RT=0.787 min, LCMS: m/z=470 [M+1].

Intermediate 5: (R)-7-bromo-N-(5-fluoroquinolin-6-yl)-5-(1-(oxetan-3-yl)ethoxy)quinazolin-4-amine

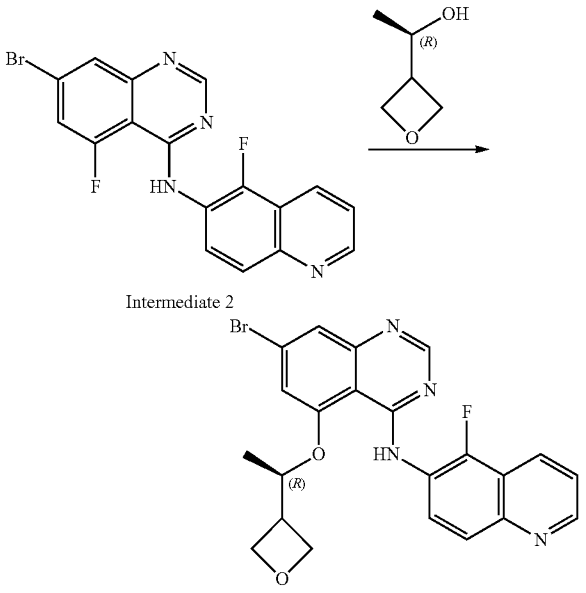

Intermediate 5

Potassium tert-butoxide (1.26 g, 11.23 mmol) was added to a mixture of Intermediate 2 (2.20 g, 5.68 mmol) and (R)-1-(oxetan-3-yl)ethan-1-ol (870 mg, 8.52 mmol) in THF at rt. The resulting mixture was stirred at 80° C. for 16 hr. The reaction mixture was diluted with EA (100 mL) and washed with brine (2×50 mL). The organic layer was dried with $Na_2SO_4$ and concentrated under vacuum. The residue was purified by a silica gel column chromatography eluting with 5:1, PE:EA to afford the title compound (1.6 g, 3.41 mmol, 60.0% yield) as a white solid. LC-MS: (ES, m/z): RT=0.808 min, LCMS: m/z=469[M+1], 1H NMR (400 MHz, DMSO-d6) δ 10.11 (s, 1H), 8.93 (dd, J=4.2, 1.7 Hz, 1H), 8.58 (t, J=8.8 Hz, 1H), 8.55-8.47 (m, 2H), 7.91 (dd, J=9.2, 1.3 Hz, 1H), 7.67-7.55 (m, 2H), 7.50 (d, J=1.9 Hz, 1H), 5.35 (p, J=6.1 Hz, 1H), 4.81 (ddd, J=10.9, 7.7, 6.3 Hz, 2H), 4.59 (dd, J=6.4, 5.5 Hz, 1H), 4.49 (t, J=5.9 Hz, 1H), 3.47-3.37 (m, 1H), 1.40 (d, J=6.0 Hz, 3H).

Intermediate 6: 5-fluoroquinolin-6-amine

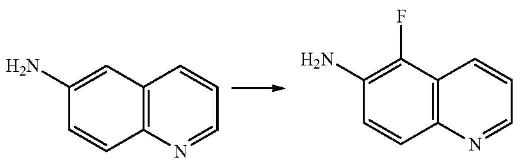

Intermediate 6

To a solution of quinolin-6-amine (100 g, 694 mmol, 1.00 eq) in dioxane (3.00 L) was added $NaHCO_3$ (175 g, 2.08 mol, 80.9 mL, 3.00 eq) at 18-22° C. Then SelectFluor (319 g, 901 mmol, 1.30 eq) was added slowly into the reaction mixture at 35-45° C. under $N_2$ and the reaction mixture was stirred at 40° C. for 4 hrs. The reaction mixture was cooled to 25° C. and filtered under reduced pressure. Then the filter cake was washed with ACN (1.60 L). The filtrate was quenched with water (18.0 mL) and dried over $Na_2SO_4$. Then the mixture was concentrated under vacuum to give the crude product. The crude product was purified by column chromatography (SiO2, PE/EA/DCM=150/1/1-15/5/1). The crude product was triturated with petroleum ether (40 mL) at 25° C. for 10 mins. The mixture was filtered to give the filter cake. The solid was dried under vacuum to afford the title compound (43.0 g, 264 mmol, 38.0% yield, 99.4% purity) as a pink solid. LC-MS: (ES, m/z): RT=1.441 mins; LCMS: m/z=163.0 [M+1]; $^1H$ NMR: (400 MHz, DMSO-d6) δ 8.58 (dd, J=4.25, 1.63 Hz, 1H), 8.16 (dd, J=8.50, 0.63 Hz, 1H), 7.62 (d, J=9.01 Hz, 1H), 7.42 (dd, J=8.51 Hz, 4.13 Hz, 1H), 7.34 (t, J=9.2 Hz, 1H), 5.62 (s, 2H).

Intermediate 7: 7-bromo-5-((1-(dimethylamino)propan-2-yl)oxy)-N-(quinolin-6-yl)quinazolin-4-amine

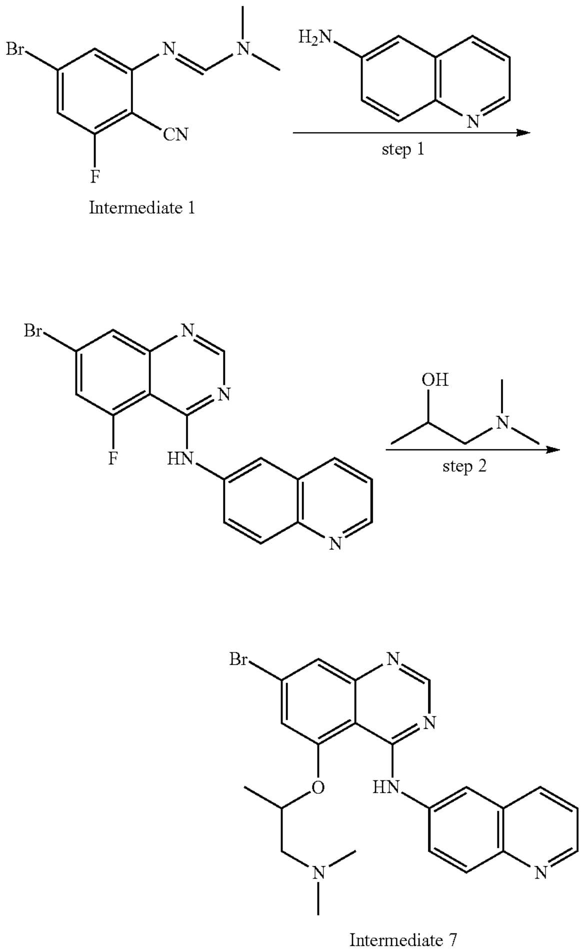

Intermediate 1

Intermediate 7

Step 1: 7-bromo-5-fluoro-N-(quinolin-6-yl)quinazolin-4-amine

A mixture of Intermediate 1 (0.975 g, 3.61 mmol) and 6-aminoquinoline (0.520 g, 3.61 mmol) in Toluene (7 ml) and AcOH (2.479 ml, 43.3 mmol) was heated to 90° C. for 16 hr. After cooling to rt the solid was filtered and washed with 1:1 mixture of MeOH and water to give the title compound (0.9904 g, 2.68 mmol, 74.3% yield). LC-MS: (ES, m/z): RT=2.582 min, LC-MS: m/z=371 [M+1]; $^1H$ NMR (500 MHz, DMSO-$d_6$) δ ppm: 9.54 (d, J=11.2 Hz, 1H), 8.86 (d, J=4.0 Hz, 1H), 8.66 (d, J=2.6 Hz, 1H), 8.41 (s, 1H), 8.35 (d, J=8.4 Hz, 1H), 8.06 (q, J=8.9, 8.5 Hz, 2H), 7.90 (s, 1H), 7.84 (d, J=11.4 Hz, 1H), 7.53 (dd, J=8.4, 4.0 Hz, 1H)

Step 2: 7-bromo-5-((1-(dimethylamino)propan-2-yl)oxy)-N-(quinolin-6-yl)quinazolin-4-amine To a solution of 1-Dimethylamino-2-propanol (84 mg, 0.810 mmol) in 5 ml of THF was added potassium t-butoxide (1557 µl, 1.557 mmol). Stirred for 10 min then added 7-bromo-5-fluoro-N-(quinolin-6-yl)quinazolin-4-amine (230 mg, 0.623 mmol). Reaction mixture was stirred and heated to 90° C. for 10 hr. After cooling to rt the reaction was concentrated under vacuum and purified on silica gel column (1:9:90=$NH_4OH$ (aq): MeOH:DCM) to afford the title compound (113.7 mg, 0.251 mmol, 40.3% yield). LC-MS: (ES, m/z): RT=1.709 min, LC-MS: m/z=453 [M+1].

Intermediate 8: 7-bromo-5-fluoro-N-(3-fluoroquinolin-6-yl)quinazolin-4-amine

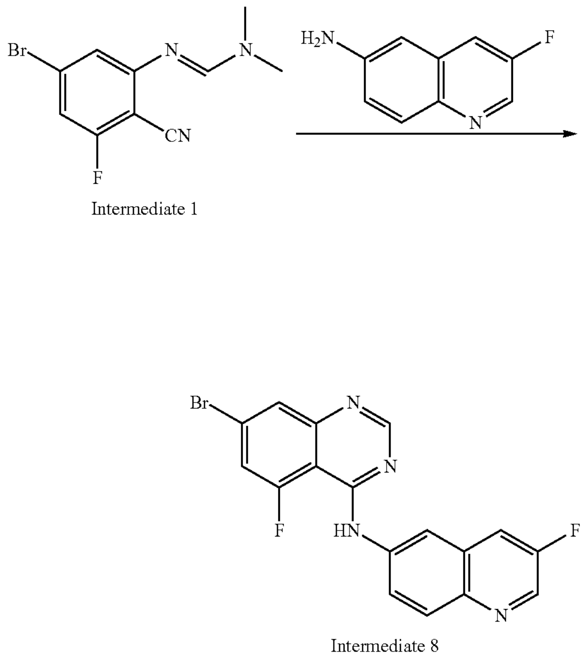

Intermediate 1

Intermediate 8

A mixture of Intermediate 1 (0.157 g, 0.581 mmol), 3-fluoroquinolin-6-amine (0.125 g, 0.581 mmol) Toluene (1 ml) and AcOH (0.399 ml) was heated to 90° C. for 16 hr. After cooling to rt a solid was collected by filtration and rinsed with 1:1 mixture of MeOH and water. The solid was collected by filtration and dried. This afforded the title compound (180.1 mg, 0.465 mmol, 80% yield). LC-MS: (ES, m/z): RT=3.1 min, LC-MS: m/z=388 [M+1].

Intermediate 9: (R)-2-((4-((5-fluoroquinolin-6-yl) amino)-7-(1-methyl-1H-pyrazol-4-yl)quinazolin-5-yl)oxy)propyl methanesulfonate

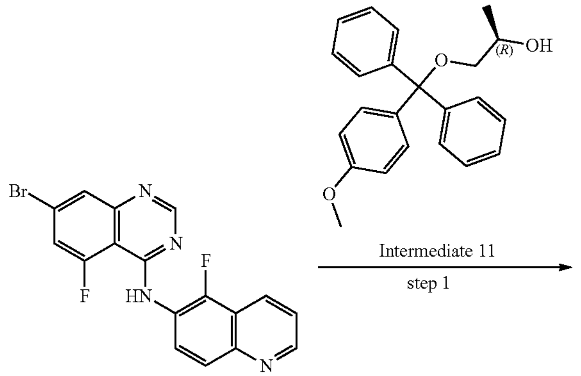

Intermediate 2

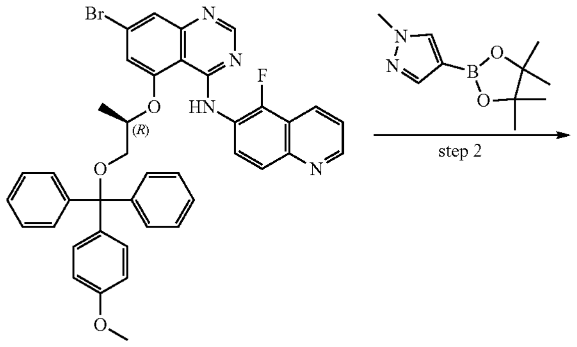

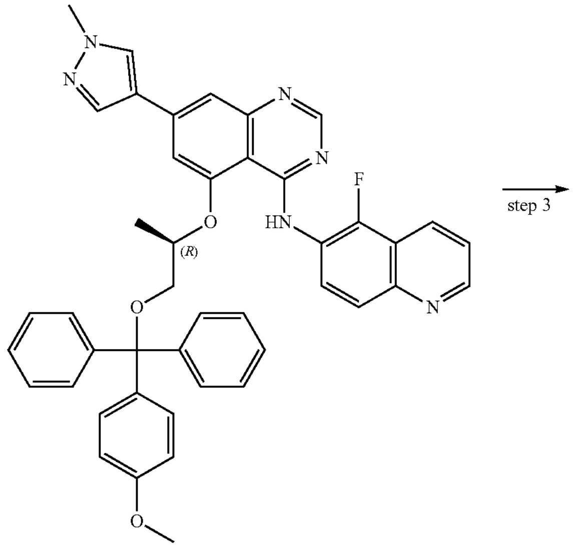

-continued

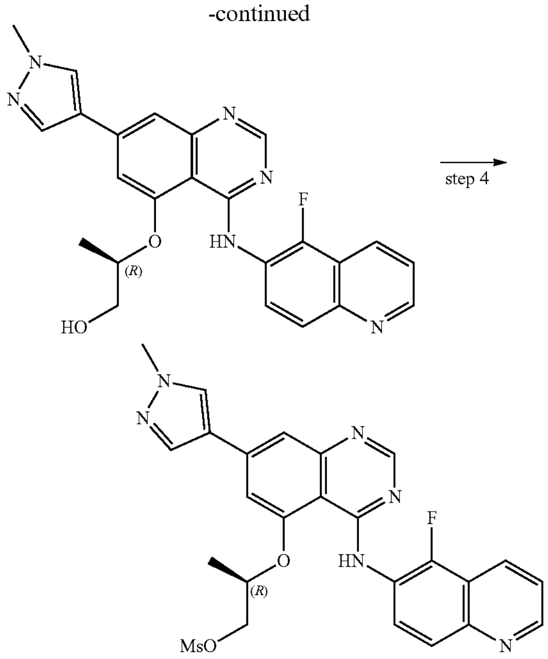

Intermediate 9

Step 1: (R)-7-bromo-N-(5-fluoroquinolin-6-yl)-5-((1-((4-methoxyphenyl) diphenylmethoxy)propan-2-yl)oxy)quinazolin-4-amine To a mixture of Intermediate 11 (898 mg, 2.58 mmol) in DMF (10 mL) was added NaH (133 mg, 3.33 mmol) at 0° C. The reaction mixture was stirred at 0° C. for 15 min, then Intermediate 2 (500 mg, 1.29 mmol) was added to the reaction mixture and stirred at 100° C. for 4 hr. The reaction mixture was added to the ice water and extracted with EA. The organic phase was concentrated under vacuum. The residue was purified by flash chromatography (50% EA in PE) to give the title compound (700 mg, yield: 75.8%) as a yellow solid. LC-MS: (ES, m/z): RT=1.398 min, LC-MS: m/z=715,717 [M+1]

Step 2: (R)—N-(5-fluoroquinolin-6-yl)-5-((1-((4-methoxyphenyl)diphenylmethoxy)propan-2-yl)oxy)-7-(1-methyl-1H-pyrazol-4-yl)quinazolin-4-amine To a solution of (R)-7-bromo-N-(5-fluoroquinolin-6-yl)-5-((1-((4-methoxyphenyl)diphenylmethoxy)propan-2-yl) oxy)quinazolin-4-amine (700 mg, 1.07 mmol) in 1,4-dioxane/$H_2O$ was added 1-methyl-4-(4,4,5,5-tetramethyl-1,3,2-dioxaborolan-2-yl)-1H-pyrazole (222 mg, 1.07 mmol), $K_2CO_3$ (269 mg, 1.95 mmol) and Pd(dppf)$Cl_2$ (71.4 mg, 97.8 umol) under nitrogen. The mixture was stirred at 80° C. for 4 hr. The reaction was cooled to room temperature. The reaction mixture was diluted with 25 ml of water, extracted with EA (2×40 mL). The organic layers were combined, washed with 20 mL of brine, dried over anhydrous sodium sulfate and concentrated under vacuum. The product was purified by chromatography with PE:EA (1:1) to give the title compound (600 mg, 71.3%) as a yellow solid. LC-MS: (ES, m/z): RT=1.424 min, LC-MS: m/z=717 [M+1]

Step 3: (R)-2-((4-((5-fluoroquinolin-6-yl)amino)-7-(1-methyl-1H-pyrazol-4-yl)quinazolin-5-yl)oxy) propan-1-ol The mixture of (R)—N-(5-fluoroquinolin-6-yl)-5-((1-((4-methoxyphenyl)diphenylmethoxy)propan-2-yl)oxy)-7-(1- methyl-1H-pyrazol-4-yl)quinazolin-4-amine (600 mg, 0.8370 mmol), TFA (3 mL) and DCM (9 mL) was stirred at 25° C. for 1 hr. The reaction mixture was concentrated under vacuum to afford the title compound (300 mg 80.6%) as yellow solid. LC-MS: (ES, m/z): RT=0.933 min, LC-MS: m/z=445 [M+1]

Step 4: (R)-2-((4-((5-fluoroquinolin-6-yl)amino)-7-(1-methyl-1H-pyrazol-4-yl)quinazolin-5-yl)oxy) propyl methanesulfonate To a solution of (R)-2-((4-((5-fluoroquinolin-6-yl) amino)-7-(1-methyl-1H-pyrazol-4-yl)quinazolin-5-yl)oxy) propan-1-ol (300 mg, 0.6749 mmol) in THF (5 mL) was added TEA (204 mg, 2.02 mmol, 3 eq), then MsCl (154 mg, 1.34 mmol) slowly at 0° C. The reaction was stirred at 25° C. for 2 hr. The mixture was concentrated to afford the title compound (200 mg 56.8%) as yellow solid. LC-MS: (ES, m/z): RT=1.043 min, LC-MS: m/z=523 [M+1]

Intermediate 10: (R)-7-bromo-N-(5,8-difluoroquinolin-6-yl)-5-(1-(oxetan-3-yl)ethoxy)quinazolin-4-amine

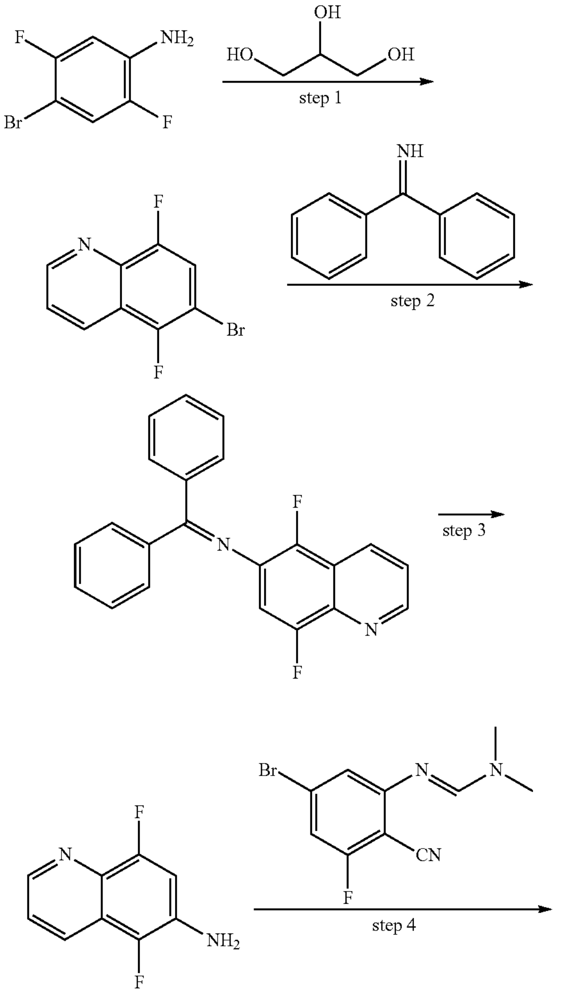

-continued

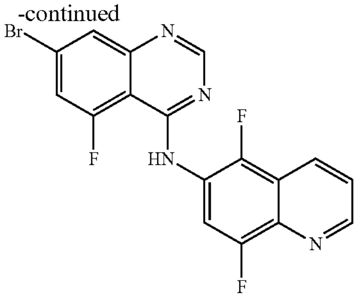

Intermediate 10

Step 1: 6-bromo-5,8-difluoroquinoline

To a mixture of 4-bromo-2,5-difluoroaniline (2 g, 9.61 mmol), propane-1,2,3-triol (2.65 g, 28.8 mmol) and sodium 3-nitrobenzene-1-sulfonate (5.40 g, 24.0 mmol) was added 12 mL of 70% sulfuric acid drop-wise. The reaction temperature was raised to 140° C. for 16 h. The mixture was then cooled, poured on ice water and filtered through Celite. The filtrate was neutralized with NaOH and extracted with $CH_2Cl_2$. The combined organic layers were dried over anhydrous $Na_2SO_4$ and concentrated on a rotary evaporator. The crude product was purified by flash chromatography on silica gel using PE:EA=2:1 to give 1.5 g (64.1%) of the title compound as a yellow solid. LC-MS: (ES, m/z): RT=1.063 min, LC-MS: m/z=244 [M+1]

Step 2: N-(5,8-difluoroquinolin-6-yl)-1,1-diphenylmethanimine

To a mixture of 6-bromo-5,8-difluoroquinoline (1.5 g, 6.14 mmol) and diphenylmethanimine (1.11 g, 6.14 mmol) in 1,4-dioxane (30.00 mL) was added XantPhos Pd G4 (552 mg, 614 umol), XantPhos (375 mg, 614 umol) and $Cs_2CO_3$ (3.97 g, 12.2 mmol) at 25° C., the reaction mixture was stirred at 100° C. for 3 hrs under $N_2$ atmosphere. The reaction mixture was concentrated under vacuum. The residue was purified by flash chromatography to afford the title compound (1.5 g, yield: 72.0%) as a yellow solid. LC-MS: (ES, m/z): RT=1.372 min, LC-MS: m/z=345 [M+1]

Step 3: 5,8-difluoroquinolin-6-amine

Into a 25 mL round-bottom flask, was placed N-(5,8-difluoroquinolin-6-yl)-1,1-diphenylmethanimine (1.5 g, 4.35 mmol) HCl (10 mL), and THF (10 mL). The resulting solution was stirred for 1 h at 25° C. The resulting mixture was concentrated under vacuum to afford the title compound (700 mg, 89.3%) as yellow solid. LC-MS: (ES, m/z): RT=0.715 min, LC-MS: m/z=181 [M+1]

Step 4: 7-bromo-N-(5,8-difluoroquinolin-6-yl)-5-fluoroquinazolin-4-amine

A solution of Intermediate 1 (524 mg, 1.94 mmol) in AcOH (5 mL) was added 5,8-difluoroquinolin-6-amine (350 mg, 1.94 mmol). The mixture was stirred for 18 h at 80° C. The resulting mixture was concentrated under vacuum, the mixture was dissolved with $CH_2Cl_2$ (120 mL), neutralize with saturated aqueous $NaHCO_3$. The organic layer was dried over anhydrous $Na_2SO_4$ and concentrated in vacuo to afford the title compound (500 mg, 63.6%) as yellow solid. LC-MS: (ES, m z): RT=0.857 min, LC-MS: m/z=405 [M+1]

Intermediate 11: (R)-1-((4-methoxyphenyl)diphenylmethoxy)propan-2-ol

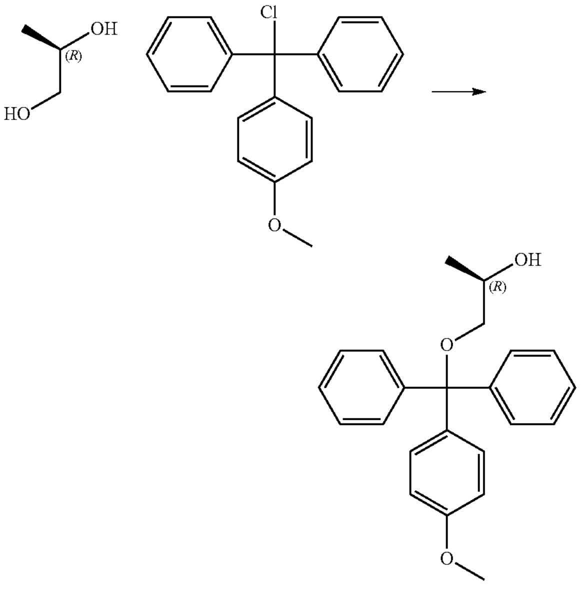

Intermediate 11

Step 1: (2R)-1-[(4-methoxyphenyl)diphenylmethoxy]propan-2-ol

To a solution of (2R)-propane-1,2-diol (1 g, 13.1 mmol, 1.00 equiv.) in DCM (20 mL) was added TEA (2.64 g, 26.2 mmol, 2.00 equiv.) and 1-(chlorodiphenylmethyl)-4-methoxybenzene (4.04 g, 13.1 mmol, 1.00 eq). The solution was stirred for 3 h at room temperature. The reaction mixture was washed with water (3×50 mL). The organic layer was dried over $MgSO_4$ and concentrated. The crude product was purified by flash chromatography (DCM:MeOH=10:1) to give the title compound as a light yellow solid. $^1H$ NMR (400 MHz, DMSO-d6) δ 7.44-7.39 (m, 4H), 7.35-7.29 (m, 5H), 7.27-7.22 (m, 4H), 6.98-6.84 (m, 2H), 3.82-3.76 (m, 1H), 3.74 (s, 3H), 2.94 (dd, J=8.8, 5.8 Hz, 1H), 2.69 (dd, J=8.8, 5.9 Hz, 1H), 1.07 (d, J=6.3 Hz, 3H).

Intermediate 12: 1-ethyl-4-iodo-3-methoxy-1H-pyrazole

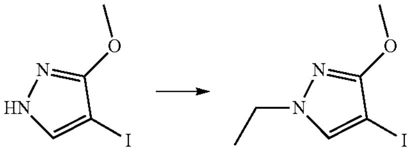

Intermediate 12

To a mixture of 4-iodo-3-methoxy-1H-pyrazole (3 g, 13.3 mmol, 1.00 eq) in DMF (40 mL) was added iodoethane (4.14 g, 26.6 mmol, 2.00 eq) and Cs2CO3 (8.67 g, 26.6 mmol, 2.00 eq), the reaction mixture was stirred at 80° C. for 16 hrs. The reaction mixture was added to the ice water. The resulting solution was extracted with 2×50 mL of ethyl acetate and the organic layers combined. The resulting mixture was washed with 50 mL of brine. The mixture was dried over anhydrous sodium sulfate and concentrated under vacuum. The crude product was purified by silica column chromatography (EA in PE=0% to 50%). This resulted in 2.8 g (83.5%) of the title compound as a white solid. LC-MS: (ES, m/z): RT=1.186 min, LCMS: m/z=253 [M+1], Intermediate 13: Cinnolin-6-amine

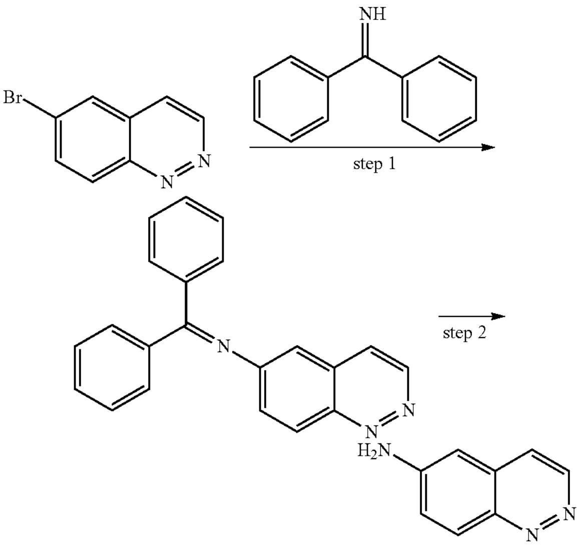

Intermediate 13

Step 1: N-(cinnolin-6-yl)-1,1-diphenylmethanimine

To a solution of 6-bromocinnoline (1_g, 4.78 mmol, 1.00 eq) in 1,4-dioxane (20 mL) was added diphenylmethanimine (951 mg, 5.25 mmol, 1.10 eq), $Cs_2CO_3$ (3.11 g, 9.56 mmol, 2.00 eq), Xantphos Pd G4 (430 mg, 478 μmol, 0.10 eq) and Xantphos (238 mg, 478 μmol, 0.10 eq) under nitrogen. The mixture was stirred at 100° C. for 3 hours. The reaction mixture was cooled to room temperature. The resulting solution was diluted with 50 mL of water. The resulting solution was extracted with 3×50 mL of ethyl acetate and the organic layers combined. The resulting mixture was washed with 50 mL of brine. The mixture was dried over anhydrous sodium sulfate and concentrated under vacuum. The residue was purified by flash chromatography (DCM:MeOH=10:1). To afford the title compound (1.2 g, 81.6%) as a yellow solid. LC-MS: (ES, m/z): RT=1.284 min, LCMS: m/z=310 [M+1].

Step 2: Cinnolin-6-amine

Into a 50 mL round-bottom flask was placed N-(cinnolin-6-yl)-1,1-diphenylmethanimine (3.23 mmol, 1.00 eq), HCl (10 mL), and THF (10 mL). The resulting solution was stirred for 1 h at 25° C. The resulting mixture was concentrated under vacuum. The product was purified by silica chromatography with DCM:MeOH=(10:1). To afford the title compound (450 mg, 96.1%) as a yellow solid. LC-MS: (ES, m/z): RT=0.341 min, LCMS: m/z=146 [M+1].

Intermediate 14: N-(7-bromo-5-fluoroquinazolin-4-yl)cinnolin-6-amine

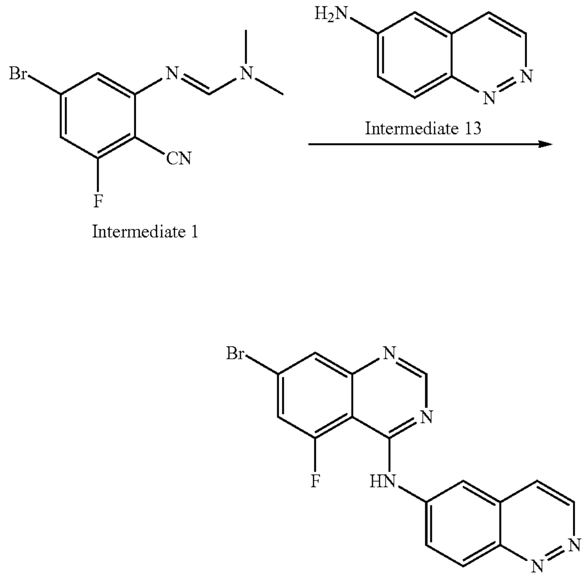

Intermediate 1

Intermediate 14

To a sealed tube containing Intermediate 13 (200 mg, 1.37 mmol, 1.00 eq) and Intermediate 1 (740 mg, 2.74 mmol, 2.00 eq) was added HOAc (3.00 mL). The reaction mixture was heated at 100° C. for 16 hr. After cooling, the mixture was concentrated under vacuum, leaving a tan residue. The solid was added to an ice-water mixture (100 mL) with cooling and allowed to stir at room temperature. The pH of the suspension was adjusted to about pH 9 via dropwise addition of 28% ammonium hydroxide. The resulting solution was extracted with 3×50 mL of ethyl acetate and the organic layers combined. The resulting mixture was washed with 50 mL of brine. The mixture was dried over anhydrous sodium sulfate and concentrated under vacuum. The residue was purified by flash chromatography (DCM:MeOH=20:1). This resulted in 200 mg (39.4%) of the title compound as a yellow solid. LC-MS: (ES, m/z): RT=0.750 min, LCMS: m/z=370 [M+1].

Intermediate 15 7-bromo-5-fluoro-N-(quinolin-7-yl)quinazolin-4-amine

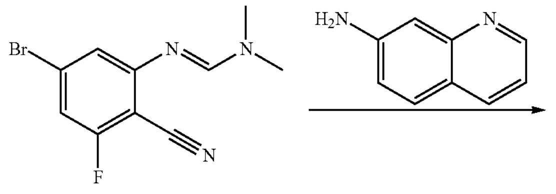

Intermediate 1

-continued

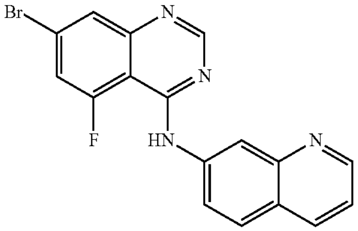

Intermediate 15

Quinolin-7-amine (127 mg, 887 μmol) and Intermediate 1 (200 mg, 740 μmol) in acetic acid (4 mL) was stirred at 100° C. for 2 hr. The resulting mixture was added to ice-water. Sat $Na_2CO_3$ (aq) was added to adjust to pH=8. The mixture was diluted with EA 100 mL and washed with brine (50 mL*2). The organic layer was dried with $Na_2SO_4$ and concentrated under vacuum. The residue was purified on a silica gel column using DCM:MeOH=25:1 to afford the title compound (200 mg, yield: 100%) as a yellow solid. LC-MS: (ES, m/z): RT=0.867 min, LCMS: m/z=369 [M+1].

Intermediate 16: 7-bromo-5-fluoro-N-(quinolin-3-yl)quinazolin-4-amine

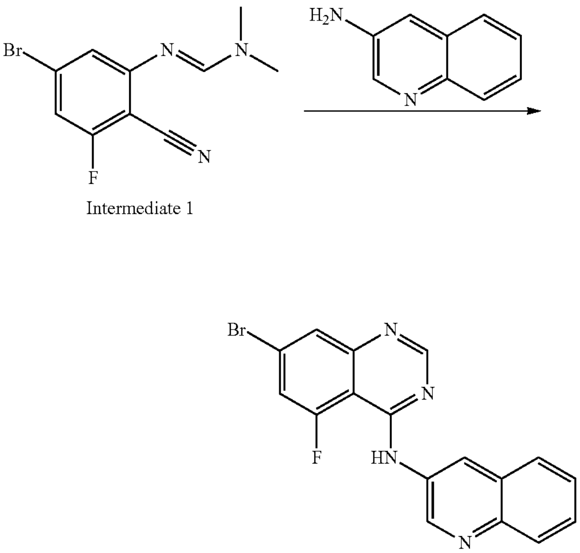

Intermediate 1

Intermediate 16

The reaction mixture of Intermediate 1 (591 mg, 2.18 mmol) and quinolin-3-amine (285 mg, 1.98 mmol) in AcOH (5 mL) was heated at 100° C. for 3 hr. The reaction mixture was diluted with EtOAc (120 mL) and washed with water (60 mL). The organic layer was dried over $Na_2SO_4$, filtered and evaporated to afford crude product. The crude product was purified by prep-TLC eluting with DCM:MeOH=10:1, to afford the title compound (220 mg) as a white solid. LC-MS: (ES, m/z): RT=1.077 min, LCMS: m/z=369 [M+1]

Intermediate 17: (R)-1-(dimethylamino)butan-2-ol

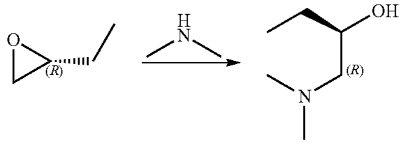

Intermediate 17

Dimethylamine solution (5 mL) was added to (2S)-2-ethyloxirane (2 mL) at 0° C. The reaction was then heated to 40° C. and stirred for 10 hr. The by-product was removed by distillation. The reaction residue was dried by $Na_2SO_4$, and concentrated to afford the title compound (300 mg, crude). LC-MS: (ES, m/z): RT=0.317 min, LCMS: m/z=118 [M+1].

Intermediate 19: (R,E)-N'-(5-bromo-2-cyano-3-((1-(dimethylamino)propan-2-yl)oxy)phenyl)-N,N-dimethylformimidamide

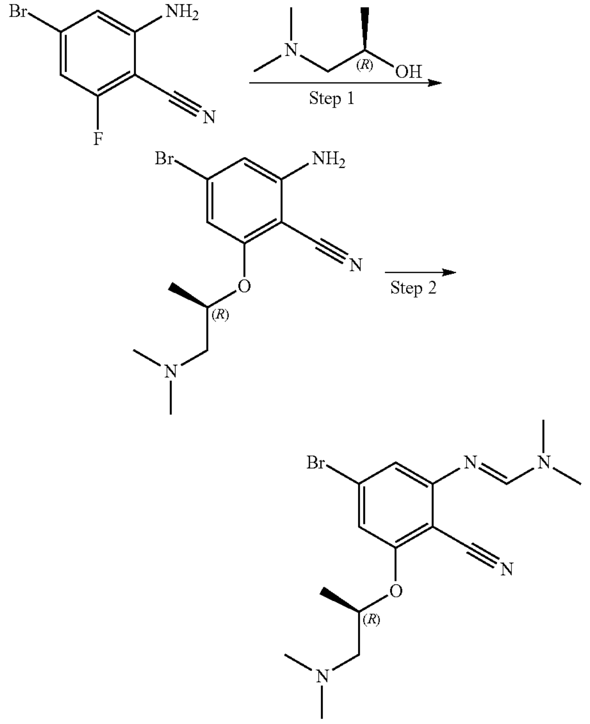

Intermediate 19

Step 1: (R)-2-amino-4-bromo-6-((1-(dimethylamino)propan-2-yl)oxy)benzonitrile

To a mixture of (2R)-1-(dimethylamino)propan-2-ol (7.18 g, 69.6 mmol) in THF (60 mL) was added NaH (1.67 g, 69.6 mmol, 60%) at 0° C., the reaction mixture was stirred at 0° C. for 15 min, then 2-amino-4-bromo-6-fluorobenzonitrile (5 g, 23.2 mmol) was added to the reaction mixture. The reaction was stirred at 80° C. for 16 h. The reaction mixture was added to the ice water (200 mL) and extracted with EA (200 mL*4). The organic phase was concentrated under vacuum. The residue was purified by flash chromatography (30% EA in PE) to give the title compound (6 g, yield: 86.8%) as a yellow oil. LC-MS: (ES, m/z): RT=1.274, LCMS: m/z=298 [M+1].

Step 2: (R,E)-N'-(5-bromo-2-cyano-3-((1-(dimethylamino)propan-2-yl)oxy)phenyl)-N,N-dimethylformimidamide To a solution of (R)-2-amino-4-bromo-6-((1-(dimethylamino)propan-2-yl)oxy)benzonitrile (6 g, 20.1 mmol, 1.00 eq) in DMF-DMA (70 mL) was stirred at 100° C. for 4 hours. The reaction mixture was cooled to room temperature. The resulting solution was concentrated under vacuum. The product was purified by flash chromatography with (10% MeOH in DCM). This resulted in (R,E)-N'-(5-bromo-2-cyano-3-((1-(dimethylamino)propan-2-yl)oxy)phenyl)-N,N-dimethylformimidamide (6 g) as a yellow oil. LC-MS: (ES, m/z): RT=1.208, LCMS: m/z=353 [M+1].

Intermediate 20: 3,5-difluoroquinolin-6-amine

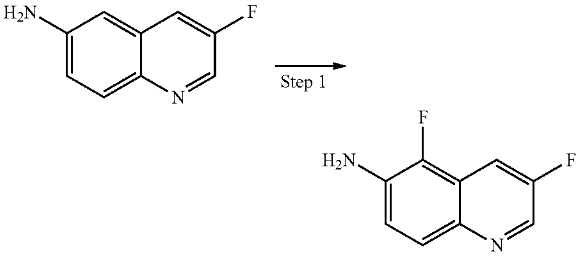

Intermediate 20

Into a 8 ml vial was added 3-fluoroquinolin-6-amine (50 mg, 0.3083 mmol) in ACN. The reaction solution was cooled to 0° C., SelectFluor (109 mg, 308 μmol) was added into the mixture in portions. The reaction was stirred at 0° C. for 1 hour. The reaction was diluted with water and extracted with EA (20 mL*3). The organic layer was dried with $Na_2SO_4$ and concentrated under vacuum. The crude compound was purified by prep-TLC: (DCM:MeOH=15:1) to afford the title compound as a red solid (23 mg, yield: 41.5%). LC-MS: (ES, m/z): RT=1.096 min, LCMS: m/z=181 [M+1]

Intermediate 21: 5,7-difluoroquinolin-6-amine

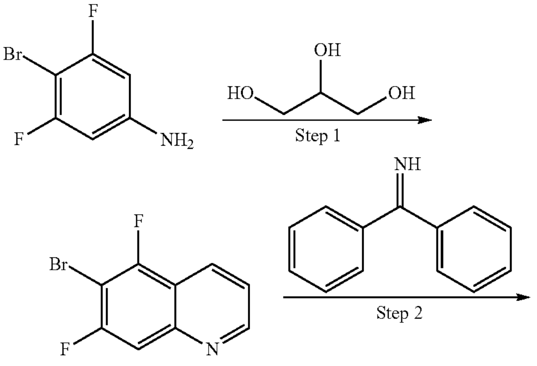

-continued

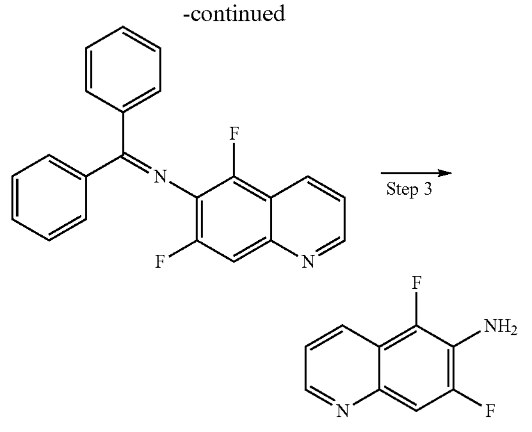

Intermediate 21

Step 1: 6-bromo-5,7-difluoroquinoline 4-bromo-3,5-difluoroaniline (3 g, 14.4 mmol) was added to propane-1,2,3-triol (3.97 g, 43.2 mmol) and 3-nitrobenzene-1-sulfonic acid (7.31 g, 36.0 mmol) in $H_2SO_4$ (10.00 mL) at 25° C. The reaction mixture was stirred at 140° C. for 3 h. The reaction mixture was cooled to room temperature. The reaction was diluted with 300 mL of water. The resulting solution was extracted with EA (2×200 mL). The organic layers were combined, washed with brine (200 ml), dried with anhydrous sodium sulfate and concentrated under vacuum. The residue was purified by flash chromatography with PE:EA=3:1 to afford the title compound (1.5 g, 42.7%) of as a yellow solid. LC-MS: (ES, m/z): RT=1.063 min, LC-MS: m/z=244 [M+1].

Step 2: N-(5,7-difluoroquinolin-6-yl)-1,1-diphenylmethanimine

XantPhos Pd G4 (368 mg, 409 umol) was added to 6-bromo-5,7-difluoroquinoline (1 g, 4.09 mmol), diphenylmethanimine (1.11 g, 6.13 mmol), XantPhos (249 mg, 409 umol) and $Cs_2CO_3$ (1.33 g, 4.09 mmol) in 1,4-dioxane (20 mL) at 25° C. The reaction mixture was stirred at 100° C. for 3 h under $N_2$ atmosphere. The reaction mixture was concentrated under vacuum. The residue was purified by flash chromatography to afford the title compound (1.0 g, yield: 71.4%) as a yellow solid. LC-MS: (ES, m/z): RT=1.402 min, LC-MS: m/z=345 [M+1].

Step 3: 5,7-difluoroquinolin-6-amine

Into a 50 mL round-bottom flask, was added: N-(5,7-difluoroquinolin-6-yl)-1,1-diphenylmethanimine (1.5 g, 4.35 mmol), HCl (10 mL), and THF (10 mL). The resulting solution was stirred for 1 h at 25° C. The resulting mixture was concentrated under vacuum to afford the title compound (700 mg 89.3%) as yellow solid. LC-MS: (ES, m/z): RT=0.493 min, LC-MS: m/z=181 [M+1].

Intermediate 22: 5-fluoro-2-methylquinolin-6-amine

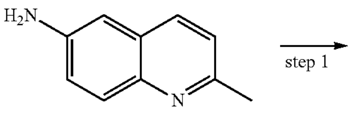

-continued

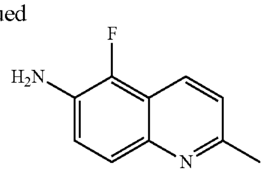

Intermediate 22

SelectFluor (892 mg, 2.52 mmol) was added to 2-methylquinolin-6-amine (400 mg, 2.52 mmol) in $CH_3CN$ (15 mL) at rt. The resulting mixture was stirred at r.t for 2 hr. The mixture was diluted with EA (100 mL and washed with brine (50 mL*2), the organic layer was dried with $Na_2SO_4$ and concentrated under vacuum. The residue was purified by a silica gel column using DCM:MeOH=15:1. This resulted in the title compound (150 mg, yield: 37.5%) as a yellow solid. LC-MS: (ES, m/z): RT=0.867 min, LCMS: m/z=177 [M+1].

Intermediate 23: 7-bromo-4-chloro-5-fluoroquinazoline

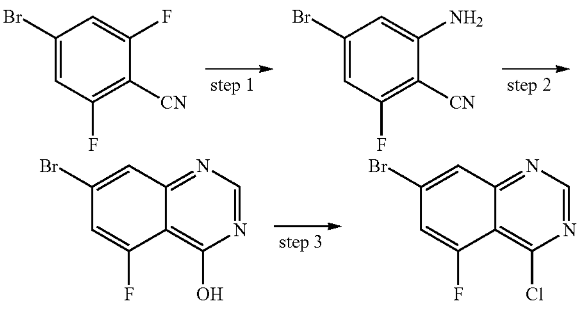

Intermediate 23

Step 1: 2-amino-4-bromo-6-fluorobenzonitrile

To a solution of 4-bromo-2, 6-difluorobenzonitrile (150 g, 688 mmol, 1.00 eq) in i-PrOH (300 mL) was added $NH_3 \cdot H_2O$ (673 g, 4.80 mol, 740 mL, 25% purity, 6.98 eq) under autoclave at 18-22° C. The reaction mixture was stirred at 80° C. for 16 hrs. TLC (Petroleum ether: Ethyl acetate=8:1) showed 4-bromo-2, 6-difluorobenzonitrile (Rf=0.60) was consumed and a main spot (Rf=0.10) was detected. The reaction mixture was poured into $H_2O$ (1.00 L) and extracted with Ethyl acetate (1.50 L×2). The combined organic layers were washed with brine (500 mL×3), dried over $Na_2SO_4$, filtered and concentrated under reduced pressure to give a residue. The residue was triturated with petroleum ether (450 mL) at 18-22° C. for 30 mins to give the title compound (141 g, 631 mmol, 91.7% yield, 96.1% purity) as a yellow solid. LC-MS: (ES, m/z): RT=2.353 mins; LCMS: m/z=214.9 [M−1]; $^1H$ NMR: (400 MHz, $CDCl_3$) δ 6.73 (s, 1H), 6.67-6.69 (m, 1H), 4.61 (s, 2H).

Step 2: 7-bromo-5-fluoroquinazolin-4-ol

To a solution of $H_2SO_4$ (287 g, 2.93 mol, 156 mL, 4.50 eq) and HCOOH (3.13 kg, 65.1 mol, 2.56 L, 100 eq) was added 2-amino-4-bromo-6-fluorobenzonitrile (140 g, 651 mmol, 1.00 eq) portion-wise at 100° C. The mixture was stirred at 100° C. for 2 hrs. The reaction mixture was concentrated under vacuum to give a residue. The residue was triturated with $H_2O$ (2.00 L) at 25° C. for 30 mins to give the title compound (100 g, 387 mmol, 59.4% yield, 94.0% purity) as a white solid. (ES, m/z): RT=0.983 min; LCMS: m/z=244.8 [M+1]; $^1H$ NMR: (400 MHz, DMSO-d6) δ 8.12 (s, 1H), 7.70 (s, 1H), 7.59-7.62 (m, 1H).

Step 3: 7-bromo-4-chloro-5-fluoroquinazoline

To a solution of 7-bromo-5-fluoroquinazolin-4-ol (50.0 g, 206 mmol, 1.00 eq) in toluene (500 mL) was added DIEA (120 g, 926 mmol, 161 mL, 4.50 eq) at 25° C. Then the reaction mixture was stirred at 25° C. for 30 mins. $POCl_3$ (63.1 g, 411 mmol, 38.2 mL, 2.00 eq) was added and the mixture was stirred at 100° C. for 2 hrs. The reaction mixture was cooled to 25° C., poured into $H_2O$ (450 mL) and extracted with ethyl acetate (400 mL×3). The organic layer was washed with brine (200 mL×2), dried over $Na_2SO_4$, filtered and concentrated under vacuum to give the title compound (50.0 g, crude) as a brown solid. The residue was used to the next step without purification. LC-MS: (ES, m/z): RT=0.625 min; LCMS: m/z=262.9 [M+1]

Intermediate 24: N-(7-bromo-5-fluoroquinazolin-4-yl)-5-fluorocinnolin-6-amine

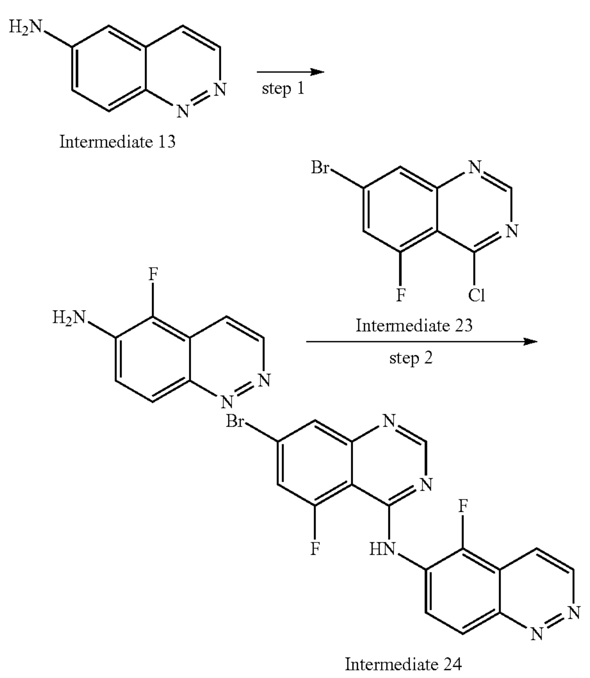

Step 1: 5-fluorocinnolin-6-amine

To a mixture of Intermediate 13 (400 mg, 2.75 mmol) in ACN (8 mL) was added Selectfluor (1.16 g, 3.29 mmol) at 0° C., the reaction mixture was stirred at 25° C. overnight. The reaction mixture was added to the ice water, the reaction mixture was concentrated under vacuum. The residue was purified by flash chromatography to give the title compound (120 mg, yield: 26.7%) as a yellow solid. LC-MS: (ES, m/z): RT=0.367 min, LCMS: m/z=164 [M+1]

Step 2: N-(7-bromo-5-fluoroquinazolin-4-yl)-5-fluorocinnolin-6-amine

To a mixture of 5-fluorocinnolin-6-amine (110 mg, 0.6742 mmol, 1 eq) in IPA (5 mL) was added Intermediate 23 (176 mg, 674 μmol, 1 eq) and TEA (204 mg, 2.02 mmol, 3 eq), the reaction mixture was stirred at 100° C. for 4 hrs. The reaction mixture was added to the ice water and extracted with EA. The organic phase was concentrated under vacuum. The residue was purified by flash chromatography (50% EA in PE) to give the title compound (70 mg, yield: 26.8%) as a yellow solid. LC-MS: (ES, m/z): RT=1.208 min, LCMS: m/z=388 [M+1]

Intermediate 25: 7-bromo-5-fluoro-N-(1,8-naphthyridin-3-yl)quinazolin-4-amine

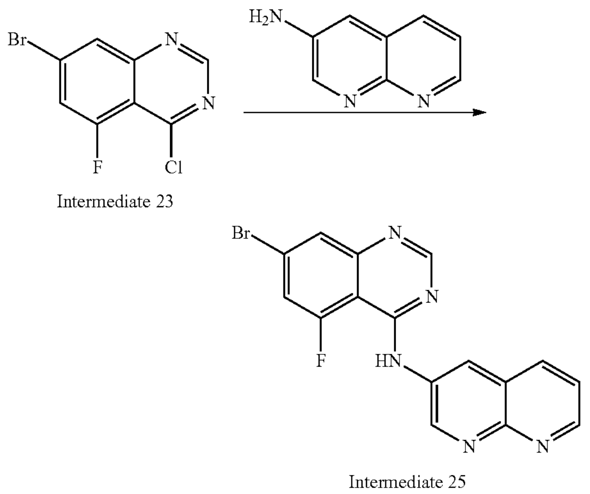

Step 1: 7-bromo-5-fluoro-N-(1,8-naphthyridin-3-yl) quinazolin-4-amine

A mixture of Intermediate 23_(150 mg, 573 μmol), 1,8-naphthyridin-3-amine (165 mg, 1.14 mmol) and TEA_(173 mg, 1.71 mmol) in iPrOH (10 mL) was stirred at 100° C. for 2 h then concentrated to dryness. The residue was purified on prep-TLC eluting with DCM:MeOH=10:1 to afford the title compound (110 mg, yield: 45%) as a yellow solid. LC-MS: (ES, m/z): RT=1.089 min, LCMS: m/z=370,372 [M+1]

Intermediate 26: 7-bromo-N-(5,7-difluoroquinolin-6-yl)-5-fluoroquinazolin-4-amine

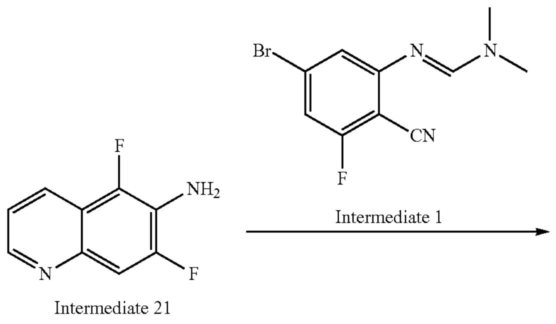

-continued

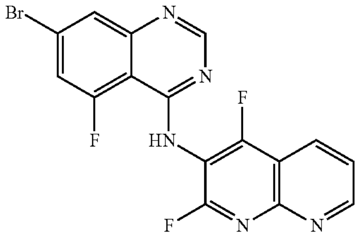

Intermediate 26

Step 1: 7-bromo-N-(5,7-difluoroquinolin-6-yl)-5-fluoroquinazolin-4-amine

Intermediate 1 (300 mg, 1.11 mmol) was added to Intermediate 21 (199 mg, 1.11 mmol) in AcOH (5 mL) at rt. The mixture was stirred for 18 hrs at 100° C. The resulting mixture was concentrated under vacuum. The residue was dissolved with DCM (80 mL), neutralized with saturated aqueous $NaHCO_3$ (30 mL). The organic layer was dried over anhydrous $Na_2SO_4$ and concentrated in vacuo to afford the title compound. LC-MS: (ES, m/z): RT=1.122 min, LC-MS: m/z=405 [M+1].

Intermediate 27: (R)-7-chloro-5-((1-(dimethylamino)propan-2-yl)oxy)-N-(5-fluoroquinolin-6-yl)pyrido[4,3-d]pyrimidin-4-amine

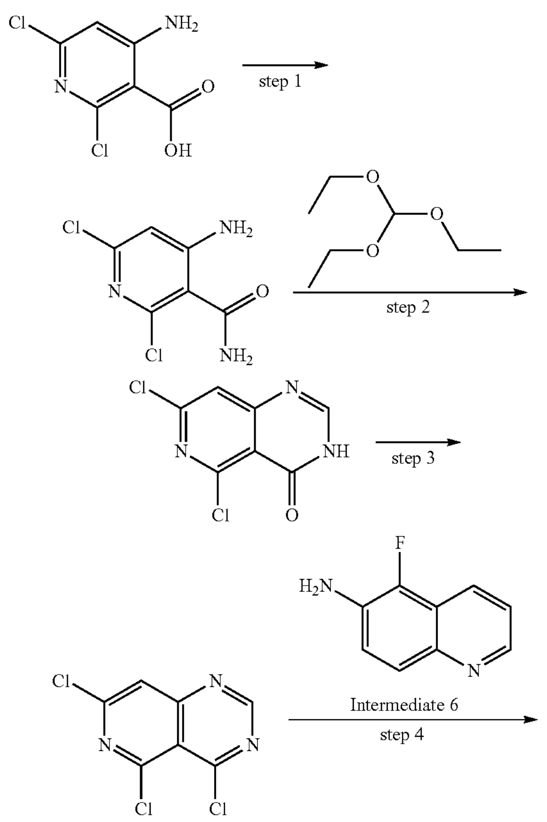

-continued

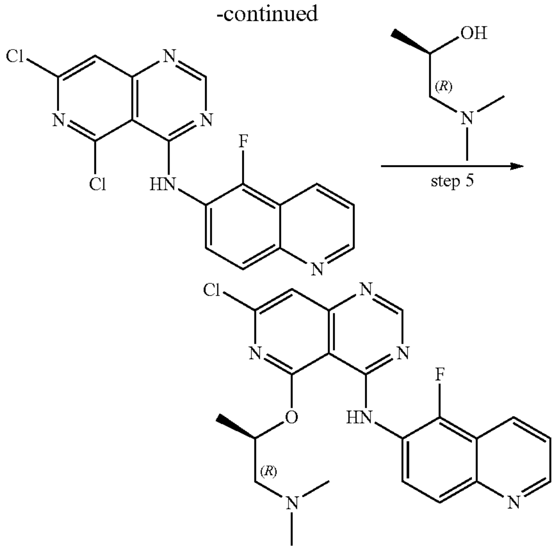

Intermediate 27

Step 1: 4-amino-2,6-dichloronicotinamide

To a solution of 4-amino-2,6-dichloropyridine-3-carboxylic acid (2 g, 9.66 mmol, 1.00 eq) in DCE (40 mL) was added $SOCl_2$ (7 mL) at 0° C. The reaction mixture was stirred at 80° C. for 3 h. The mixture was concentrated under reduced pressure, the residue was diluted with DCM (50 mL), and the solution was added to ice-cold 30% aq $NH_4OH$ (30 mL). The mixture was stirred at 0° C. for 1 h. The organic layer was then concentrated under reduced pressure to give the title compound (1.5 g, yield: 75.3%) as a white solid. LC-MS: (ES, m/z): RT=0.330 min, LCMS: m/z=206 [M+1]

Step 2: 5,7-dichloropyrido[4,3-d]pyrimidin-4(3H)-one

To a solution of 4-amino-2,6-dichloronicotinamide (1.4 g, 6.79 mmol, 1.00 eq) in triethoxymethane (30 mL), The reaction mixture was stirred at 120° C. for 4 hr. Then it was cooled to room temperature. The mixture was concentrated under vacuum. The product was purified by prep-TLC eluting with DCM:MeOH (20:1). This resulted in the title compound (600 mg, 41.0%) as a white solid. LC-MS: (ES, m/z): RT=0.970 min, LCMS: m/z=216 [M+1]

Step 3: 4,5,7-trichloropyrido[4,3-d]pyrimidine $POCl_3$ (1.77 g, 11.5 mmol) and TEA (1.40 g, 13.8 mmol) were added to 5,7-dichloropyrido[4,3-d]pyrimidin-4(3H)-one (500 mg, 2.31 mmol) in ACN (8 mL) at rt. The reaction mixture was heated to 80° C. for 2 hr. The resulting mixture was added to ice-water, then $Na_2CO_3$ (1.00 M) was added until pH=8. The solution was extracted with EA and concentrated under vacuum. The residue was purified by a silica gel column using DCM. This resulted in the title compound (400 mg, 73%) as an off-white solid. LC-MS: (ES, m/z): RT=0.887 min, LCMS: m/z=234 [M+1]

Step 4: 5,7-dichloro-N-(5-fluoroquinolin-6-yl)pyrido[4,3-d]pyrimidin-4-amine

To a solution of 4,5,7-trichloropyrido[4,3-d]pyrimidine (600 mg, 2.55 mmol, 1 eq) in IPA was added Intermediate 6 (494 mg, 3.05 mmol, 1.2 eq) and TEA (771 mg, 7.64 mmol, 3 eq). The mixture was stirred at 80° C. for 16 hours. The mixture was filtered and filter cake collected to give the title compound (600 mg, yield: 65.3%) as a yellow solid.

Step 5: (R)-7-chloro-5-((1-(dimethylamino)propan-2-yl)oxy)-N-(5-fluoroquinolin-6-yl)pyrido[4,3-d]pyrimidin-4-amine To a mixture of (2R)-1-(dimethylamino)propan-2-ol (2 eq) in THF (15 mL) was added NaH (79.6 mg, 3.32 mmol, 2 eq) at 0° C., the reaction mixture was stirred at 0° C. for 15 min, then 5,7-dichloro-N-(5-fluoroquinolin-6-yl)pyrido[4,3-d]pyrimidin-4-amine (600 mg, 1.66 mmol, 1 eq) was added to the reaction mixture. The reaction mixture was stirred at 50° C. for 4 hrs. The reaction mixture was added to the ice water and extracted with EA. The organic phase was concentrated under vacuum. The residue was purified by prep-TLC (PE:EA=2:1) to give the title compound (360 mg, yield: 50.8%) as a yellow solid. LC-MS: (ES, m/z): RT=1.441 min, LCMS: m/z=427 [M+1].

Intermediate 28: (R)-5-((1-(dimethylamino)propan-2-yl)oxy)-7-(1-methyl-1H-pyrazol-4-yl)quinazolin-4-amine Intermediate 28b: (R,E)-N'-(2-cyano-3-((1-(dimethylamino)propan-2-yl)oxy)-5-(1-methyl-1H-pyrazol-4-yl)phenyl)-N,N-dimethylformimidamide

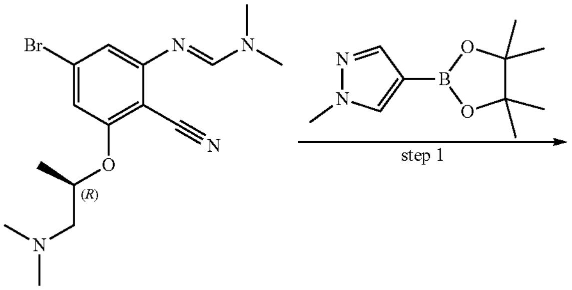

Intermediate 19

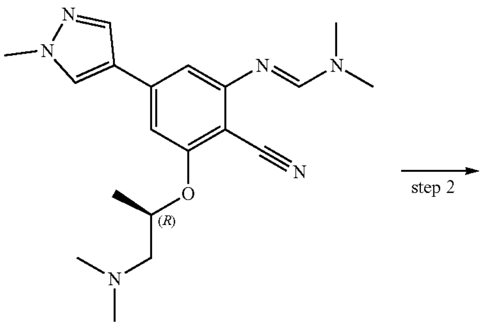

Intermediate 28b

-continued

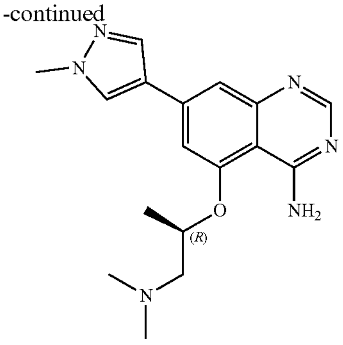

Intermediate 28

Step 1: Intermediate 28b, (R,E)-N'-(2-cyano-3-((1-(dimethylamino)propan-2-yl)oxy)-5-(1-methyl-1H-pyrazol-4-yl)phenyl)-N,N-dimethylformimidamide $Pd(dppf)Cl_2$ (217 mg, 297 μmol) and $K_2CO_3$ (614 mg, 4.45 mmol) were added Intermediate 19 (1.05 g, 2.97 mmol) and 1-methyl-4-(4,4,5,5-tetramethyl-1,3,2-dioxaborolan-2-yl)-1H-pyrazole (925 mg, 4.45 mmol) in dioxane (16 mL) and $H_2O$ (4 mL) at rt. The reaction mixture was heated to 80° C. for 2 h under $N_2$. The resulting solution was extracted with 3×100 mL of EA. The organic layer was dried with $Na_2SO_4$ and concentrated under vacuum. The crude product was purified by a silica gel column using DCM:MeOH=15:1. This resulted in the title compound (970 mg, yield: 92%) as a yellow solid. LC-MS: (ES, m/z): RT=1.134 min, LCMS: m/z=355 [M+1]

Step 2: (R)-5-((1-(dimethylamino)propan-2-yl)oxy)-7-(1-methyl-1H-pyrazol-4-yl)quinazolin-4-amine (1,1-dimethoxyethyl)dimethylamine (72.7 mg, 546 μmol) was added to Intermediate 28b (970 mg, 2.73 mmol) in formamide (15 mL) at rt. The reaction mixture was heated to 150° C. for 1 hr. The resulting solution was purified by C18-flash chromatography, elution gradient 0% to 50% ACN in water. This resulted in the title compound (560 mg, yield: 62%) as an off-white solid. LC-MS: (ES, m z): RT=0.999 min, LCMS: m/z=327 [M+1]

Intermediate 29: 6-amino-5-fluoroquinolin-3-ol

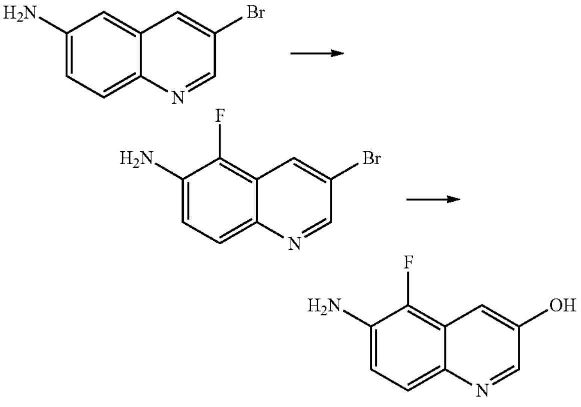

Intermediate 29

Step 1: 3-bromo-5-fluoroquinolin-6-amine

Selectfluor (2.37 g, 6.72 mmol) was added to 3-bromoquinolin-6-amine (1 g, 4.48 mmol) in DMF (100 mL) at −40° C., and warmed to rt slowly and stirred for 10 hrs. The mixture was extracted with DCM, washed with saturated $NaHCO_3$, water and brine. The organic layers were dried with $Na_2SO_4$, and concentrated. Purified by silica column chromatography to afford the title compound (470 mg, yield: 45%). LC-MS: (ES, m/z): RT=0.804 min, LCMS: m/z=241 243 [M+1].

Step 2: 6-amino-5-fluoroquinolin-3-ol 3-bromo-5-fluoroquinolin-6-amine (300 mg, 1.24 mmol), KOH (69.4 mg, 1.24 mmol), $Pd_2(dba)_3$ (113 mg, 0.124 mmol) and ligand (CAS: 857356-94-6, 59.6 mg, 0.124 mmol) in dioxane (2.5 mL) and $H_2O$ (2.5 mL) was stirred at 100° C. under $N_2$ for 10 hr. The reaction was concentrated and purified by prep-TLC (PE/EA=4/1) to afford the title compound (210 mg, yield: 60%). LC-MS: (ES, m/z): RT=0.678 min, LCMS: m/z=178.9 [M+1].

Intermediate 30: 7-bromo-8-fluoroquinoline

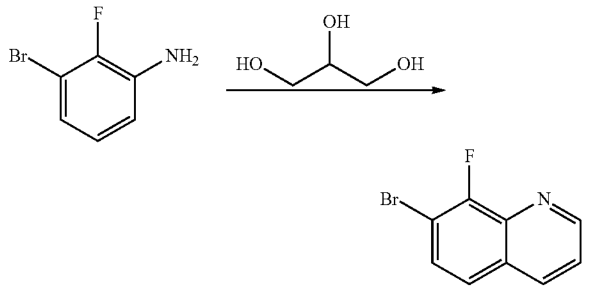

Intermediate 30

$H_2SO_4$ (4 mL) was added to 3-bromo-2-fluoroaniline (100 mg, 421 μmol), sodium 3-nitrobenzene-1-sulfonate (118 mg, 526 μmol), propane-1,2,3-triol (2.5 mL) and $H_2O$ (2 mL) at rt. The reaction was stirred at 120° C. for 6 hr under $N_2$. The resulting mixture was poured into ice-water and adjusted to pH=8 with sat NaOH (aq). The mixture was diluted with EA (100 mL) and washed with brine (50 mL*2). The organic layer was dried with $Na_2SO_4$ and concentrated under vacuum. The residue was purified by a silica gel column using DCM:MeOH=25:1. This resulted in the title compound (90 mg, yield: 90%) as a yellow solid. LC-MS: (ES, m/z): RT=1.179 min, LCMS: m/z=226[M+1].

Intermediate 31: 6-bromo-5-fluoroquinoxaline

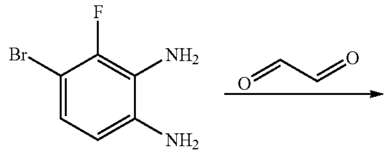

-continued

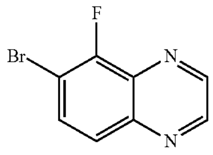

Intermediate 31

Glyoxal (40% in water, 1 mL) was added to 4-bromo-3-fluorobenzene-1,2-diamine (200 mg, 975 μmol) in EtOH (4 mL) at rt. The reaction mixture was heated to 80° C. for 2 hr. The resulting solution was extracted with 3×50 mL of EA. The organic layer was dried with $Na_2SO_4$ and concentrated under vacuum. The crude product was purified by prep-TLC eluting with PE:EA=2:1. This resulted in the title compound (150 mg, yield: 67%) as a white solid. LC-MS: (ES, m/z): RT=1.006 min, LCMS: m/z=227 [M+1].

Intermediate 32: 7-bromo-N-(5-fluoroquinolin-6-yl)-5-((1-methylpiperidin-4-yl)oxy)quinazolin-4-amine

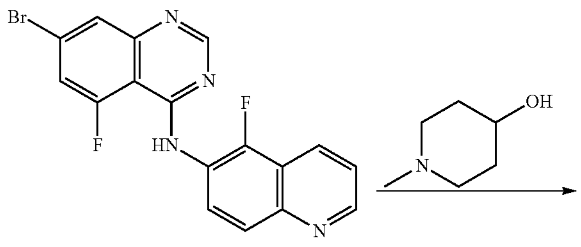

Intermediate 2

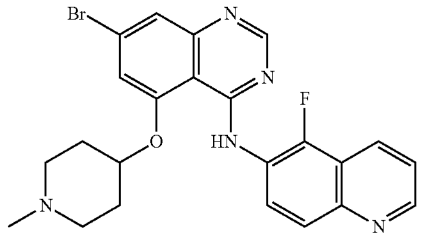

Intermediate 32

NaH (824 mg, 20.6 mmol) was added to 1-methylpiperidin-4-ol (891 mg, 7.74 mmol) in THF at 0° C. The resulting mixture was stirred at 0° C. for 10 min. Intermediate 2 (1 g, 2.58 mmol) was added to the mixture at 0° C. The resulting mixture was heated at 80° C. for 3 hr. The reaction mixture was diluted with EA (120 mL), and washed with water (60 mL). The organic layer was dried over $Na_2SO_4$, filtered and evaporated under vacuum. The crude product was purified by prep-TLC eluting with DCM:MeOH=10:1 to afford the title compound (700 mg) as a white solid. LC-MS: (ES, m/z): RT=0.852 min, LCMS: m/z=482 [M+1]

Intermediate 33: 7-bromo-4-((5-fluoroquinolin-6-yl) amino)quinazolin-5-ol

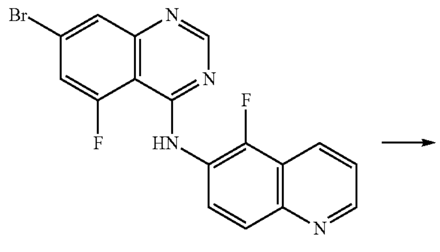

Intermediate 2

-continued

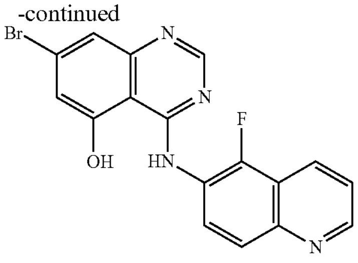

Intermediate 33 t-BuOK (581 mg, 5.15 mmol) was added to Intermediate 2 (400 mg, 1.03 mmol) in THF (10 mL) at rt. The resulting mixture was heated at 80° C. for 6 hr. The reaction mixture was diluted with EA (120 mL), and washed with water (60 mL). The organic layer was dried over $Na_2SO_4$, filtered and evaporated to afford the title compound (300 mg) a white solid. LC-MS: (ES, m/z): RT=0.894 min, LCMS: m/z=385 [M+1], Intermediate 34: (R)—N-(5-fluoroquinolin-6-yl)-5-((1-((4-methoxyphenyl)diphenylmethoxy)propan-2-yl)oxy)-7-(1-methyl-1H-pyrazol-4-yl)quinazolin-4-amine

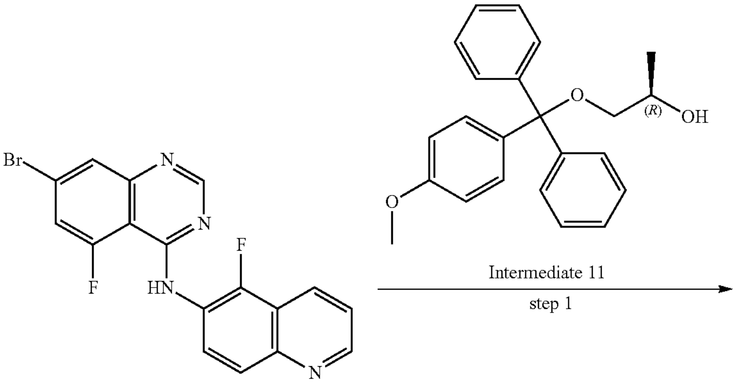

Intermediate 2

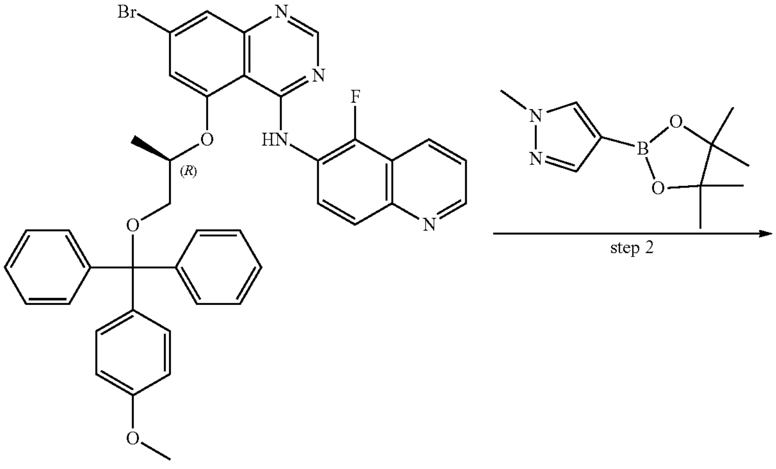

-continued

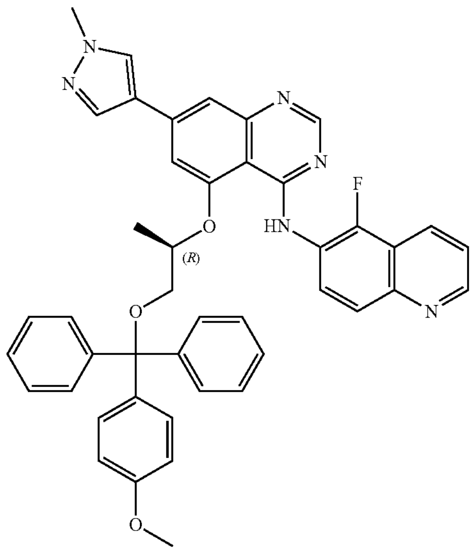

Intermediate 34

Step 1: (R)-7-bromo-N-(5-fluoroquinolin-6-yl)-5-((1-((4-methoxyphenyl) diphenylmethoxy)propan-2-yl)oxy)quinazolin-4-amine To a mixture of Intermediate 11 (898 mg, 2.58 mmol) in DMF (10 mL) was added NaH (133 mg, 3.33 mmol) at 0° C. and was stirred for 15 min. Intermediate 2 (500 mg, 1.29 mmol) was added to the reaction mixture and stirred at 100° C. for 4 hrs. The reaction mixture was added to the ice water and extracted with EA. The organic phase was concentrated under vacuum. The residue was purified by flash chromatography (50% EA in PE) to give the title compound (700 mg, yield: 75.8%) as a yellow solid. LC-MS: (ES, m/z): RT=1.398 min, LCMS: m/z=715,717 [M+1]

Step 2: (R)—N-(5-fluoroquinolin-6-yl)-5-((1-((4-methoxyphenyl)diphenylmethoxy)propan-2-yl)oxy)-7-(1-methyl-1H-pyrazol-4-yl)quinazolin-4-amine To a solution of (R)-7-bromo-N-(5-fluoroquinolin-6-yl)-5-((1-((4-methoxyphenyl) diphenylmethoxy)propan-2-yl)oxy)quinazolin-4-amine (700 mg, 1.07 mmol) in 1,4-dioxane/$H_2O$ was added 1-methyl-4-(4,4,5,5-tetramethyl-1,3,2-dioxaborolan-2-yl)-1H-pyrazole (222 mg, 1.07 mmol), $K_2CO_3$ (269 mg, 1.95 mmol) and Pd(dppf)$Cl_2$ (71.4 mg, 97.8 umol) under nitrogen. The mixture was stirred at 80° C. for 4 hours. The reaction mixture was cooled to room temperature. The resulting solution was diluted with 25 mL of water, extracted with 2×40 mL of ethyl acetate. The organic layers were combined and washed with 20 mL of brine. The mixture was dried over anhydrous sodium sulfate and concentrated under vacuum. The product was purified by chromatography with PE:EA (1:1). This resulted in the title compound (600 mg, 71.3%) as a yellow solid.

Example 1: (R)—N-(5-fluoroquinolin-6-yl)-7-(1-methyl-1H-pyrazol-4-yl)-5-(1-(oxetan-3-yl)ethoxy) quinazolin-4-amine or (S)—N-(5-fluoroquinolin-6-yl)-7-(1-methyl-1H-pyrazol-4-yl)-5-(1-(oxetan-3-yl) ethoxy)quinazolin-4-amine Example 2: (S)—N-(5-fluoroquinolin-6-yl)-7-(1-methyl-1H-pyrazol-4-yl)-5-(1-(oxetan-3-yl)ethoxy) quinazolin-4-amine or (R)—N-(5-fluoroquinolin-6-yl)-7-(1-methyl-1H-pyrazol-4-yl)-5-(1-(oxetan-3-yl) ethoxy)quinazolin-4-amine

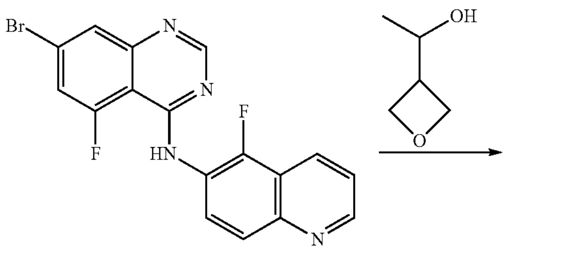

Intermediate 2

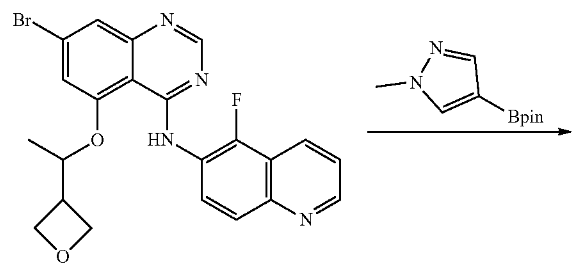

-continued

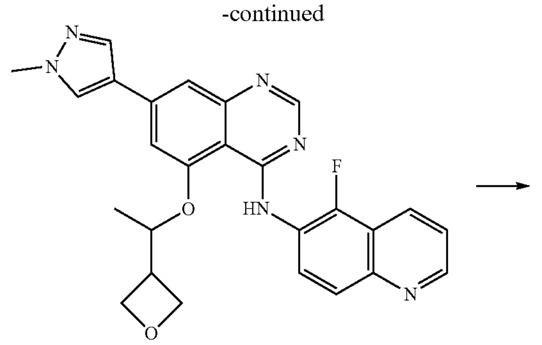

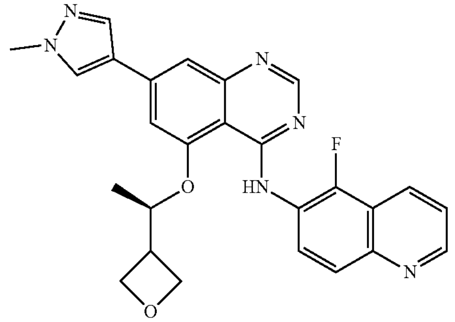

or

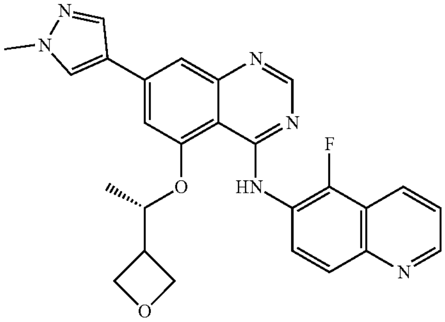

Step 1: 7-bromo-N-(5-fluoroquinolin-6-yl)-5-[1-(oxetan-3-yl)ethoxy]quinazolin-4-amine To a solution of 1-(oxetan-3-yl)ethan-1-ol (28.9 mg, 283 μmol) in DMF was added NaH (12.3 mg, 516 μmol) at 0° C. The mixture was stirred at rt for 0.5 hrs. Intermediate 2 (100 mg, 258 μmol) was added to the mixture and stirred at 60° C. for 2 hrs. The reaction was quenched with water/ice, filtered and the filter cake collected to afford the desired product. The crude material was used in the next step. LC-MS: (ES, m/z): RT=1.205 min, LC-MS: m/z=467 [M+1].

Step 2: N-(5-fluoroquinolin-6-yl)-7-(1-methyl-1H-pyrazol-4-yl)-5-(1-(oxetan-3-yl)ethoxy)quinazolin-4-amine To a reaction vessel under $N_2$ was added: 7-bromo-N-(5-fluoroquinolin-6-yl)-5-[1-(oxetan-3-yl)ethoxy]quinazolin-4-amine (100 mg, 213 μmol), 1-methyl-4-(4,4,5,5-tetramethyl-1,3,2-dioxaborolan-2-yl)-1H-pyrazole (48.6 mg, 234 μmol), 1,4-dioxane, $H_2O$, Pd(dppf)$Cl_2$ (7.69 mg, 10.6 μmol) and $K_2CO_3$ (58.7 mg, 426 μmol). The mixture was stirred at 100° C. for 2 h. After cooling to rt, the reaction was extracted with DCM and purified by Prep-TLC (DCM/MeOH=10:1) to give the title compound (80 mg (79.9%) as yellow solid. LC-MS: (ES, m/z): RT=0.658 min, LC-MS: m/z=471 [M+1].

Chiral Separation:

The product of Step 2 (100 mg, 212 μmol) was separated by PREP-CHIRAL-HPLC (Column: CHIRALPAK IE, 2×25 cm, 5 um; Mobile Phase A=MTBE (0.5% 2M $NH_3$-MeOH), Mobile Phase B=EtOH; Flow rate: 18 mL/min; Gradient: 40% B isocratic 15 min; 220/254 nm; RT1: 10.936; RT2: 13.141, to give:

Example 1: First Eluting Isomer: (R)—N-(5-fluoroquinolin-6-yl)-7-(1-methyl-1H-pyrazol-4-yl)-5-(1-(oxetan-3-yl)ethoxy)quinazolin-4-amine or (S)—N-(5-fluoroquinolin-6-yl)-7-(1-methyl-1H-pyrazol-4-yl)-5-(1-(oxetan-3-yl)ethoxy)quinazolin-4-amine: (34 mg, 34.1%, as a white solid. LC-MS: (ES, m/z): RT=0.993 min, LC-MS: m/z=471 [M+1]; $^1$H NMR (300 MHz, DMSO-$d_6$) δ 10.21 (s, 1H), 8.95 (dd, J=4.2, 1.7 Hz, 1H), 8.76 (t, J=8.9 Hz, 1H), 8.60-8.49 (m, 3H), 8.21 (s, 1H), 7.95 (d, J=9.3 Hz, 1H), 7.70-7.59 (m, 2H), 7.53 (d, J=1.5 Hz, 1H), 5.54-5.44 (m, 1H), 4.90-4.78 (m, 2H), 4.62 (t, J=5.9 Hz, 1H), 4.52 (t, J=6.0 Hz, 1H), 3.93 (s, 3H), 3.48 (q, J=6.4 Hz, 1H), 1.43 (d, J=5.9 Hz, 3H).

Example 2: Second eluting isomer: (S)—N-(5-fluoroquinolin-6-yl)-7-(1-methyl-1H-pyrazol-4-yl)-5-(1-(oxetan-3-yl)ethoxy)quinazolin-4-amine or (R)—N-(5-fluoroquinolin-6-yl)-7-(1-methyl-1H-pyrazol-4-yl)-5-(1-(oxetan-3-yl)ethoxy)quinazolin-4-amine: (37.9 mg, 38.0%, as a white solid. LC-MS: (ES, m/z): RT=0.989 min, LC-MS: m/z=471 [M+1]; $^1$H NMR (300 MHz, DMSO-$d_6$) δ 10.20 (s, 1H), 8.95 (dd, J=4.2, 1.6 Hz, 1H), 8.77 (t, J=8.9 Hz, 1H), 8.60-8.52 (m, 3H), 8.21 (s, 1H), 7.95 (d, J=9.3 Hz, 1H), 7.70-7.59 (m, 2H), 7.53 (s, 1H), 5.54-5.43 (m, 1H), 4.90-4.78 (m, 2H), 4.62 (t, J=5.9 Hz, 1H), 4.52 (t, J=6.0 Hz, 1H), 3.93 (s, 3H), 3.48 (d, J=7.1 Hz, 1H), 1.43 (d, J=5.9 Hz, 3H).

Example 3: (R)—N-(3-fluoroquinolin-6-yl)-7-(1-methyl-1H-pyrazol-4-yl)-5-(1-(oxetan-3-yl)ethoxy)quinazolin-4-amine

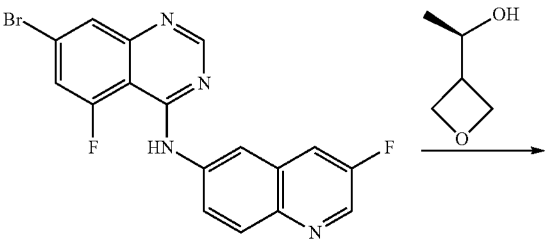

Intermediate 8

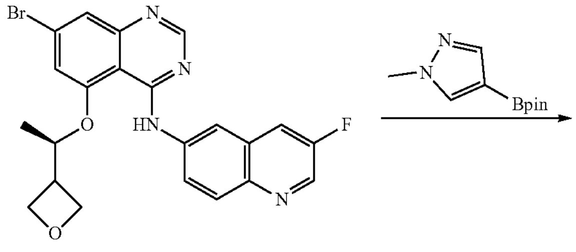

-continued

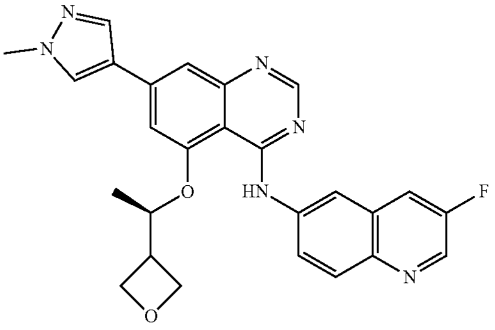

Step 1: (R)-7-bromo-N-(3-fluoroquinolin-6-yl)-5-(1-(oxetan-3-yl)ethoxy)quinazolin-4-amine Potassium t-butoxide (581 μl, 0.581 mmol) was added to a solution of (R)-1-(oxetan-3-yl)ethan-1-ol (35.6 mg, 0.349 mmol) in THF (2 mL) and the mixture was stirred at rt for 10 min. Solid Intermediate 8 (90 mg, 0.232 mmol) was added and the reaction was stirred at rt for 16 h. Adjusted to pH=5 with acetic acid and concentrated under vacuum. Crude solid was purified on silica gel using 0-20% MeOH in DCM gradient to afford the title compound (79.3 mg, 0.169 mmol, 72.7% yield). LC-MS: (ES, m/z): RT=2.6 min, LC-MS: m/z=470 [M+1].

Step 2: (R)—N-(3-fluoroquinolin-6-yl)-7-(1-methyl-1H-pyrazol-4-yl)-5-(1-(oxetan-3-yl)ethoxy)quinazolin-4-amine To a mixture of (R)-7-bromo-N-(3-fluoroquinolin-6-yl)-5-(1-(oxetan-3-yl)ethoxy)quinazolin-4-amine (79.4 mg, 0.169 mmol), 1-methyl-4-(4,4,5,5-tetramethyl-1,3,2-dioxaborolan-2-yl)-1H-pyrazole (52.8 mg, 0.254 mmol), methanesulfonato[9,9-dimethyl-4,5-bis(diphenylphosphino)xanthene][2'-amino-1,1'-biphenyl]palladium(II) dichloromethane adduct (8.03 mg, 8.46 μmol) in DMF (5 ml) was added potassium phosphate 2M solution (169 μl, 0.338 mmol). The mixture was sparged with nitrogen and heated to 90° C. for 16 h. Adjusted the pH with acetic acid. Diluted with water and extracted with DCM. The organic layers were concentrated under vacuum and purified using a silica gel column eluting with a gradient of 0-20% MeOH in DCM. Further purified by prep-HPLC: Xbridge Prep OBD C18 5.0 μm column with 5-45% 1% acetic acid modified acetonitrile/water to afford the title compound (39.7 mg, 0.084 mmol, 50% yield). LC-MS: (ES, m/z): RT=2.7 min, LC-MS: m/z=471 [M+1]; $^1H$ NMR (500 MHz, DMSO-$d_6$) δ ppm: 10.48 (s, 1H), 8.80 (s, 1H), 8.63 (s, 1H), 8.46 (s, 1H), 8.40 (s, 1H), 8.20 (d, J=9.9 Hz, 1H), 8.12 (s, 1H), 8.03 (d, J=9.4 Hz, 1H), 7.90 (d, J=9.3 Hz, 1H), 7.49 (s, 2H), 5.49-5.32 (m, 1H), 4.79 (dt, J=11.1, 6.3 Hz, 2H), 4.59 (d, J=5.6 Hz, 1H), 4.49 (d, J=5.7 Hz, 1H), 3.87 (d, J=3.6 Hz, 4H), 1.36 (d, J=6.0 Hz, 3H).

Example 4: (S)-5-((1-(dimethylamino)propan-2-yl)oxy)-N-(5-fluoroquinolin-6-yl)-7-(1-methyl-1H-pyrazol-4-yl)quinazolin-4-amine or (R)-5-((1-(dimethylamino)propan-2-yl)oxy)-N-(5-fluoroquinolin-6-yl)-7-(1-methyl-1H-pyrazol-4-yl)quinazolin-4-amine Example 5: (R)-5-((1-(dimethylamino)propan-2-yl)oxy)-N-(5-fluoroquinolin-6-yl)-7-(1-methyl-1H-pyrazol-4-yl)quinazolin-4-amine or (S)-5-((1-(dimethylamino)propan-2-yl)oxy)-N-(5-fluoroquinolin-6-yl)-7-(1-methyl-1H-pyrazol-4-yl)quinazolin-4-amine

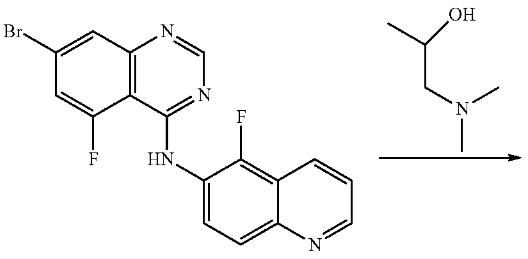

Intermediate 2

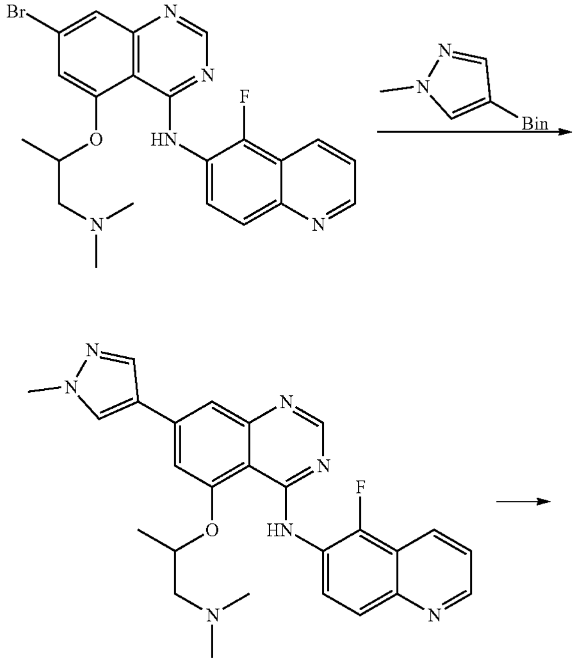

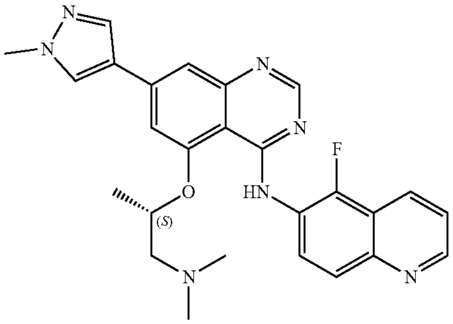

or

-continued

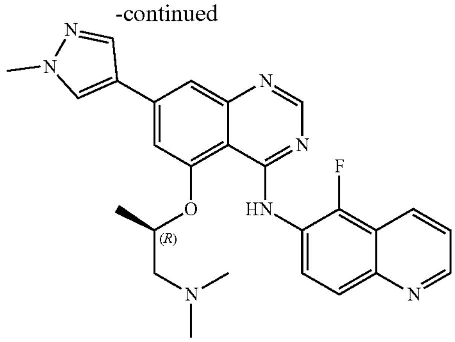

Step 1: 7-bromo-5-((1-(dimethylamino)propan-2-yl)oxy)-N-(5-fluoroquinolin-6-yl)quinazolin-4-amine Into a 40 ml vial was added Intermediate 2 (200 mg, 0.5165 mmol), 1-(dimethylamino)propan-2-ol (106 mg, 1.03 mmol) in DMF. NaH (41.1 mg, 1.03 mmol) was added into the mixture at 0° C. The reaction was stirred at 80° C. for 2 h. Water was added and extracted with EA. The crude compound was purified by prep-TLC (EA) to afford the title compound (150 mg, 0.319 mmol) as a white solid. LC-MS: (ES, m/z): RT=1.239 min, LC-MS: m/z=472 [M+1].

Step 2: 5-((1-(dimethylamino)propan-2-yl)oxy)-N-(5-fluoroquinolin-6-yl)-7-(1-methyl-1H-pyrazol-4-yl)quinazolin-4-amine Into a 25 ml vial and maintained under an inert atmosphere was added: 7-bromo-5-((1-(dimethylamino)propan-2-yl)oxy)-N-(5-fluoroquinolin-6-yl)quinazolin-4-amine (150 mg, 478 μmol), 1-methyl-4-(4,4,5,5-tetramethyl-1,3,2-dioxaborolan-2-yl)-1H-pyrazole (99.4 mg, 478 μmol), $Pd(dppf)Cl_2$ (50.2 mg, 0.06378 mmol), $K_2CO_3$ (88.0 mg, 0.6378 mmol), 1,4-dioxane and $H_2O$. The mixture was stirred at 80° C. for 2 h. The reaction was extracted by EA and purified by prep-TLC, eluting with (10:1, DCM: MeOH). To afford the title compound (120 mg, 0.254 mmol) as a white solid. LC-MS: (ES, m/z): RT=1.070 min, LC-MS: m/z=472 [M+1].

Chiral Separation: 5-((1-(dimethylamino)propan-2-yl)oxy)-N-(5-fluoroquinolin-6-yl)-7-(1-methyl-1H-pyrazol-4-yl)quinazolin-4-amine (80 mg, 0.1696 mmol) was separated by chiral HPLC: Column: CHIRAL ART Cellulose-SB, 2×25 cm, 5 μm; Mobile Phase A: MTBE (0.3% IPA), Mobile Phase B: EtOH; Flow rate: 20 mL/min; Gradient: 20% B to 20% B in 12 min; Wavelength: 220/254 nm; RT1 (min): 8.7; RT2 (min): 9.8.

Example 4: First eluting compound: (S)-5-((1-(dimethylamino)propan-2-yl)oxy)-N-(5-fluoroquinolin-6-yl)-7-(1-methyl-1H-pyrazol-4-yl)quinazolin-4-amine or (R)-5-((1-(dimethylamino)propan-2-yl)oxy)-N-(5-fluoroquinolin-6-yl)-7-(1-methyl-1H-pyrazol-4-yl)quinazolin-4-amine: (17.2 mg, 0.03647 mmol, as a light yellow solid: LC-MS: (ES, m/z): RT=0.895 min, LC-MS: m/z=472.15 [M+1]; $^1H$ NMR (300 MHz, DMSO-d6) δ 10.52 (s, 1H), 8.91 (dd, J=4.2, 1.6 Hz, 1H), 8.70 (t, J=8.9 Hz, 1H), 8.54-8.42 (m, 3H), 8.14 (d, J=0.8 Hz, 1H), 7.93 (dd, J=9.3, 1.3 Hz, 1H), 7.67-7.53 (m, 2H), 7.42 (d, J=1.6 Hz, 1H), 5.15 (s, 1H), 3.90 (s, 3H), 2.95 (m, 1H), 2.58 (m, 1H), 2.23 (s, 6H), 1.49 (d, J=6.0 Hz, 3H).

Example 5: Second eluting compound: (R)-5-((1-(dimethylamino)propan-2-yl)oxy)-N-(5-fluoroquinolin-6-yl)-7-(1-methyl-1H-pyrazol-4-yl)quinazolin-4-amine or (S)-5-((1-(dimethylamino)propan-2-yl)oxy)-N-(5-fluoroquinolin-6-yl)-7-(1-methyl-1H-pyrazol-4-yl)quinazolin-4-amine: (16.9 mg, 0.0358 mmol, as a light yellow solid: LC-MS: (ES, m/z): RT=0.896 min, LC-MS: m/z=472.15 [M+1]; $^1H$ NMR (300 MHz, DMSO-d6) δ 10.52 (s, 1H), 8.91 (dd, J=4.2, 1.6 Hz, 1H), 8.70 (t, J=8.9 Hz, 1H), 8.54-8.42 (m, 3H), 8.14 (d, J=0.8 Hz, 1H), 7.93 (dd, J=9.3, 1.3 Hz, 1H), 7.67-7.53 (m, 2H), 7.42 (d, J=1.6 Hz, 1H), 5.15 (s, 1H), 3.90 (s, 3H), 2.95 (m, 1H), 2.58 (m, 1H), 2.23 (s, 6H), 1.49 (d, J=6.0 Hz, 3H).

Example 6: (R)-5-((1-(dimethylamino)propan-2-yl)oxy)-N-(5-fluoroquinolin-6-yl)-7-(1-methyl-1H-pyrazol-4-yl)quinazolin-4-amine

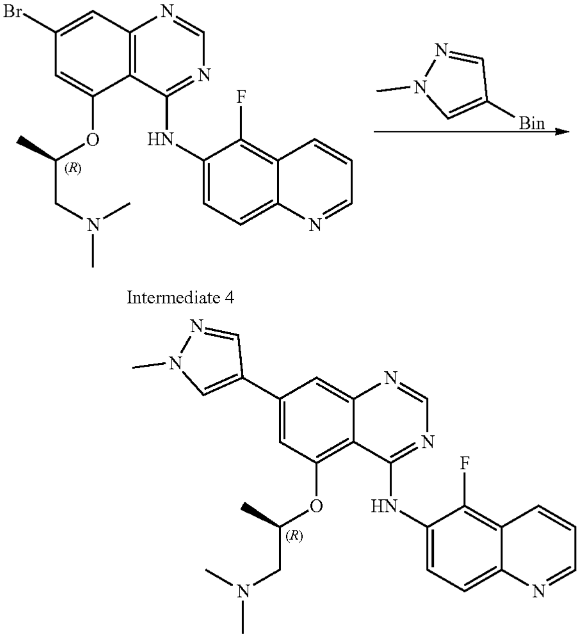

Into a 40 mL vial and maintained an inert $N_2$ atmosphere was added Intermediate 4 (1.5 g, 3.18 mmol), 1-methyl-4-(4,4,5,5-tetramethyl-1,3,2-dioxaborolan-2-yl)-1H-pyrazole (726 mg, 3.49 mmol), $Pd(dppf)Cl_2$ (167 mg, 212 μmol), $K_2CO_3$ (292 mg, 2.12 mmol), 1,4-dioxane and $H_2O$. The mixture was stirred at 80° C. for 2 h. The reaction was extracted with EA (100 mL) and washed with brine (50 mL×2), the organic layer was dried with $Na_2SO_4$ and concentrated under vacuum. The residue was purified by prep-HPLC using the following conditions: Column: YMC-Actus Triart C18 ExRS, 30 mm×150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 32 B to 65 B in 7 min, 254/220 nm to afford the title compound (700 mg, 46.6%) as an off-white solid. LC-MS: (ES, m/z): RT=1.447 min, LCMS: m/z=472 [M+1]. $^1H$ NMR (300 MHz, DMSO-d6) δ 10.59 (s, 1H), 8.94 (dd, J=4.3, 1.6 Hz, 1H), 8.71 (t, J=8.8 Hz, 1H), 8.50 (m, 3H), 8.16 (s, 1H), 7.95 (d, J=9.3 Hz, 1H), 7.64 (dd, J=8.5, 4.2 Hz, 1H), 7.58 (d, J=1.4 Hz, 1H), 7.44 (d, J=1.6 Hz, 1H), 5.14 (s, 1H), 3.92 (s, 3H), 2.91 (m, 1H), 2.55 (m, 1H), 2.20 (s, 6H), 1.52 (d, J=5.9 Hz, 3H).

Example 7: (R)-5-((1-(dimethylamino)propan-2-yl)oxy)-N-(3-fluoroquinolin-6-yl)-7-(1-methyl-1H-pyrazol-4-yl)quinazolin-4-amine

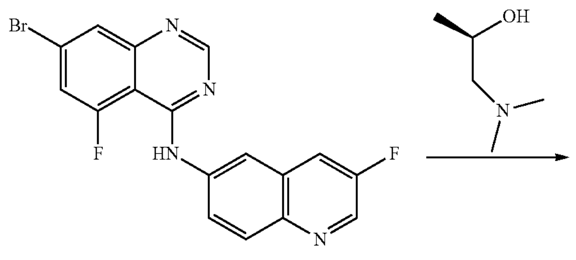

Intermediate 8

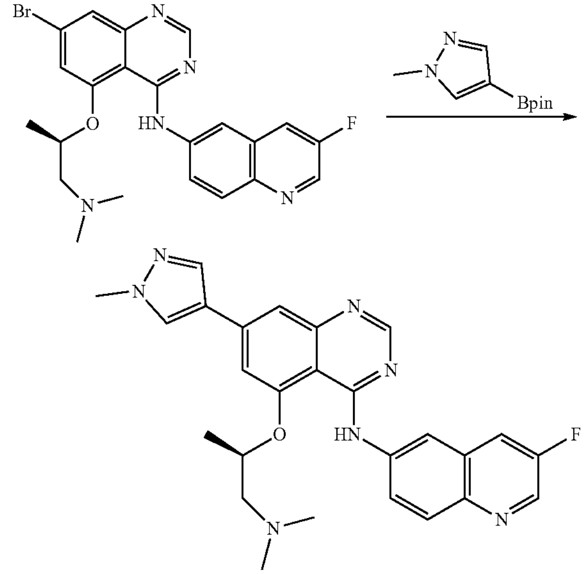

Step 1: (R)-7-bromo-5-((1-(dimethylamino)propan-2-yl)oxy)-N-(3-fluoroquinolin-6-yl)quinazolin-4-amine To a solution of (R)-1-(dimethylamino)propan-2-ol (103 mg, 0.998 mmol) in THF (2 ml), potassium t-butoxide (1M in THF) (581 μl, 0.581 mmol) was added and the reaction was stirred at rt for 10 min. Solid Intermediate 8 (90 mg, 0.232 mmol) was added. Stirred at rt for 16 hr. Due to only partial conversion the reaction mixture was heated to 90° C. for 5 h. Cooled to rt, added water and adjusted to pH=5 with acetic acid. Extracted with DCM twice and the combined organic layers were concentrated under vacuum. The resulting crude material was taken to the next step. LC-MS: (ES, m z): RT=2.4 min, LC-MS: m/z=471 [M+1].

Step 2: (R)-5-((1-(dimethylamino)propan-2-yl)oxy)-N-(3-fluoroquinolin-6-yl)-7-(1-methyl-1H-pyrazol-4-yl)quinazolin-4-amine To the crude (R)-7-bromo-5-((1-(dimethylamino)propan-2-yl)oxy)-N-(3-fluoroquinolin-6-yl)quinazolin-4-amine (109 mg, 0.232 mmol) was added: 1-methyl-4-(4,4,5,5-tetramethyl-1,3,2-dioxaborolan-2-yl)-1H-pyrazole (72.3 mg, 0.348 mmol), methanesulfonato[9,9-dimethyl-4,5-bis(diphenylphosphino)xanthene][2'-amino-1,1'-biphenyl]palladium(II) dichloromethane adduct (11.00 mg, 0.012 mmol), potassium phosphate 2M solution (232 μl, 0.463 mmol) and DMF (2 ml). Sparged with nitrogen and heated to 90° C. for 16 h. Cooled to rt and diluted with water and extracted with DCM. The combined organic layers were concentrated under vacuum and purified by silica gel column chromatography eluting with 0-20% MeOH/DCM. The resulting material was further purified by prep-HPLC: Xbridge Prep OBD C18 5.0 μm column with 5-45% 1% Acetic acid Acetonitrile/Water to afford the title compound (8.9 mg, 0.019 mmol, 8.06% yield). LC-MS: (ES, m z): RT=2.2 min, LC-MS: m/z=472 [M+1]; $^1$H NMR (500 MHz, DMSO-$d_6$) δ ppm: 8.60 (s, 2H), 8.45 (d, J=3.6 Hz, 1H), 8.12 (s, 1H), 8.03-7.90 (m, 3H), 7.85 (d, J=9.2 Hz, 1H), 7.40 (s, 1H), 7.28 (s, 1H), 5.02 (s, 1H), 3.88 (d, J=3.5 Hz, 3H), 3.00 (t, J=11.2 Hz, 1H), 2.54 (d, J=13.8 Hz, 1H), 2.26 (d, J=3.3 Hz, 6H), 1.50 (dd, J=5.7, 3.3 Hz, 3H).

Example 8: (R)—N-(5,7-difluoroquinolin-6-yl)-7-(1-methyl-1H-pyrazol-4-yl)-5-(1-(oxetan-3-yl)ethoxy)quinazolin-4-amine

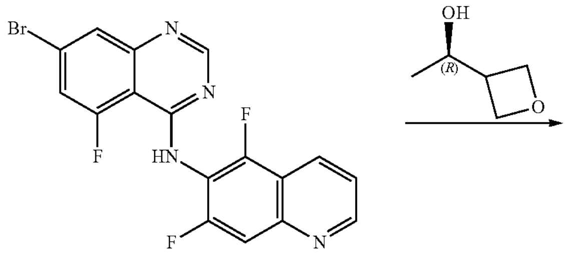

Intermediate 26

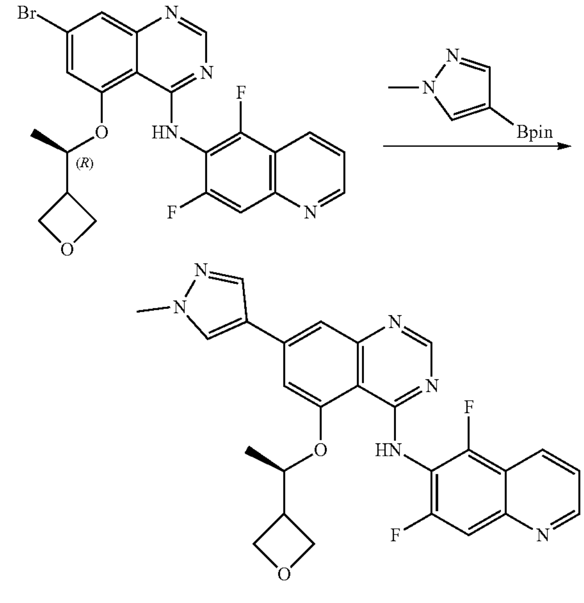

Step 1: (R)-7-bromo-N-(5,7-difluoroquinolin-6-yl)-5-(1-(oxetan-3-yl)ethoxy)quinazolin-4-amine t-BuOK (290 mg, 2.59 mmol) was added to Intermediate 26 (350 mg, 863 μmol) and (1R)-1-(oxetan-3-yl)ethan-1-ol (263 mg, 2.58 mmol) in THF (10 mL). The mixture was stirred at 80° C. for 16 h. LC-MS showed that the reaction was completed. The reaction mixture was cooled to rt. The reaction mixture was diluted with 25 mL of water. The resulting solution was extracted with EA (2×40 mL) and the organic layers combined. The resulting mixture was washed with 20 mL of brine. The mixture was dried over anhydrous sodium sulfate and concentrated under vacuum. The product was purified by chromatography with PE:EA (1:1) to afford the title compound (300 mg) as a yellow solid. LC-MS: (ES, m/z): RT=1.119 min, LC-MS: m/z=487 [M+1].

Step 2: (R)—N-(5,7-difluoroquinolin-6-yl)-7-(1-methyl-1H-pyrazol-4-yl)-5-(1-(oxetan-3-yl)ethoxy)quinazolin-4-amine Pd(dppf)$Cl_2$ (122 mg, 150 μmol), $K_2CO_3$ (138 mg, 1 mmol), (R)-7-bromo-N-(5,7-difluoroquinolin-6-yl)-5-(1-(oxetan-3-yl)ethoxy)quinazolin-4-amine, (244 mg, 500 μmol), 1-methyl-4-(4,4,5,5-tetramethyl-1,3,2-dioxaborolan-2-yl)-1H-pyrazole (208 mg, 1 mmol), 1,4-dioxane (8.00 mL) and $H_2O$ (2.00 mL) were combined at 25° C. The reaction mixture was stirred at 80° C. for 3 hrs under $N_2$. The resulting solution was diluted with 20 mL of water. The mixture was extracted with 2×20 mL of ethyl acetate and the organic layers combined and washed with 20 mL of brine. The mixture was dried over anhydrous sodium sulfate and concentrated under vacuum. The product was purified by prep-TLC eluting with DCM:MeOH (10:1). The crude product was purified by Prep-HPLC with the following conditions: Column: YMC-Actus Triart C18, 30 mm×150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 30% B to 50% B in 10 min, Wavelength: 254/220 nm; RT1(min): 8.68, to afford the title compound as a white solid. LC-MS: (ES, m/z): RT=1.217 min, LC-MS: m/z=489 [M+1]; $^1$H NMR (300 MHz, DMSO-$d_6$) δ 9.68 (s, 1H), 9.00 (dd, J=4.4, 1.6 Hz, 1H), 8.50 (d, J=6.4 Hz, 2H), 8.34 (s, 1H), 8.17 (s, 1H), 7.81 (dd, J=10.8, 1.7 Hz, 1H), 7.69-7.62 (m, 1H), 7.62-7.54 (m, 1H), 7.43 (d, J=1.6 Hz, 1H), 5.30 (q, J=5.7 Hz, 1H), 4.82 (q, J=6.8 Hz, 2H), 4.59 (t, J=5.7 Hz, 1H), 4.55-4.43 (m, 1H), 3.91 (s, 3H), 3.40-3.30 1.40 (d, J=5.9 Hz, 3H).

Example 9: (R)—N-(5,8-difluoroquinolin-6-yl)-7-(1-methyl-1H-pyrazol-4-yl)-5-(1-(oxetan-3-yl)ethoxy)quinazolin-4-amine

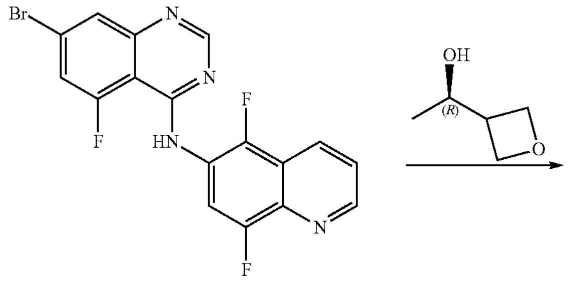

Intermediate 10

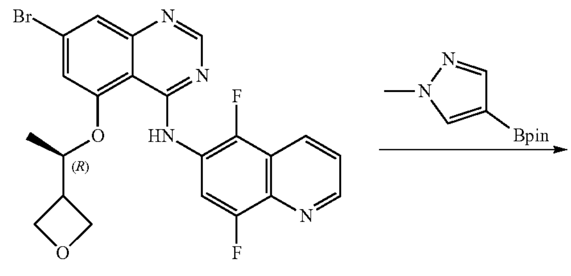

-continued

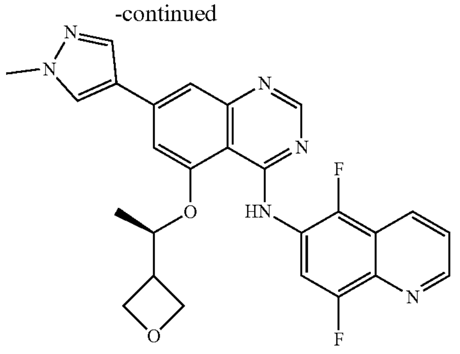

Step 1: (R)-7-bromo-N-(5,8-difluoroquinolin-6-yl)-5-(1-(oxetan-3-yl)ethoxy)quinazolin-4-amine To a solution of Intermediate 10 (350 mg, 0.8638 mmol) in THF was added (1R)-1-(oxetan-3-yl)ethan-1-ol (264 mg, 2.59 mmol) and t-BuOK (290 mg, 2.59 mmol). The mixture was stirred at 80° C. for 16 hrs. LC-MS show the reaction was completed. The reaction mixture was cooled to room temperature. The resulting solution was diluted with 25 mL of water. The resulting solution was extracted with 2×40 mL of ethyl acetate and the organic layers combined. The resulting mixture was washed with 20 mL of brine. The mixture was dried over anhydrous sodium sulfate and concentrated under vacuum. The product was purified by chromatography with PE:EA (1:1). This resulted in 300 mg of the title compound as a yellow solid. LC-MS: (ES, m/z): RT=1.261 min, LC-MS: m/z=487 [M+1]; $^1$H NMR (400 MHz, Chloroform-d) δ 10.23 (s, 1H), 9.07-8.93 (m, 2H), 8.73 (s, 1H), 8.44 (dt, J=8.6, 1.6 Hz, 1H), 7.73 (d, J=1.7 Hz, 1H), 7.57 (dd, J=8.6, 4.2 Hz, 1H), 7.17 (dd, J=1.7, 0.7 Hz, 1H), 5.22-5.08 (m, 1H), 5.06-4.96 (m, 2H), 4.67 (dd, J=6.7, 5.4 Hz, 1H), 4.58 (dd, J=6.6, 5.4 Hz, 1H), 3.53 (q, J=6.0 Hz, 1H), 1.55 (d, J=6.1 Hz, 3H).

Step 2: (R)—N-(5,8-difluoroquinolin-6-yl)-7-(1-methyl-1H-pyrazol-4-yl)-5-(1-(oxetan-3-yl)ethoxy)quinazolin-4-amine To a mixture of (R)-7-bromo-N-(5,8-difluoroquinolin-6-yl)-5-(1-(oxetan-3-yl)ethoxy)quinazolin-4-amine (200 mg, 0.4104 mmol) and 1-methyl-4-(4,4,5,5-tetramethyl-1,3,2-dioxaborolan-2-yl)-1H-pyrazole (93.8 mg, 451 μmol) in 1,4-dioxane (8 mL) and $H_2O$ (2 mL) was added pd(dppf)$Cl_2$ (29.9 mg, 41.0 μmol) and $K_2CO_3$ (169 mg, 1.23 mmol) at 25° C., the reaction mixture was stirred at 80° C. for 4 h under $N_2$. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The crude product was purified by Prep-HPLC with the following conditions: Column: YMC-Actus Triart C18, 30 mm×150 mm, 5 um; Mobile Phase A: Water (10 mmol/L $NH_4HCO_3$+0.1% $NH_3 \cdot H_2O$), Mobile Phase B:ACN; Flow rate: 60 mL/min; Gradient: 34 B to 64 B in 8 min, 254/220 nm; RTL 6.53. This resulted in 67.9 mg (33.9%) of the title compound as a white solid. LC-MS: (ES, m/z): RT=0.966 min, LC-MS: m/z=489 [M+1]; $^1$H NMR (300 MHz, DMSO-$d_6$) δ 10.24 (s, 1H), 8.93 (dd, J=4.2, 1.5 Hz, 1H), 8.85 (dd, J=12.9, 6.9 Hz, 1H), 8.60-8.51 (m, 2H), 8.49 (s, 1H), 8.18 (s, 1H), 7.71 (dd, J=8.6, 4.2 Hz, 1H), 7.59 (d, J=1.4 Hz, 1H), 7.52 (d, J=1.5 Hz, 1H), 5.48 (q, J=6.4 Hz, 1H), 4.82 (ddd, J=7.9, 6.3, 3.0 Hz, 2H), 4.58 (t, J=6.0 Hz, 1H), 4.49 (t, J=6.0 Hz, 1H), 3.90 (s, 3H), 3.47 (q, J=6.8 Hz, 1H), 1.41 (d, J=5.9 Hz, 3H).

Example 10: (R)—N-(5,8-difluoroquinolin-6-yl)-5-((1-(dimethylamino) propan-2-yl)oxy)-7-(1-methyl-1H-pyrazol-4-yl)quinazolin-4-amine

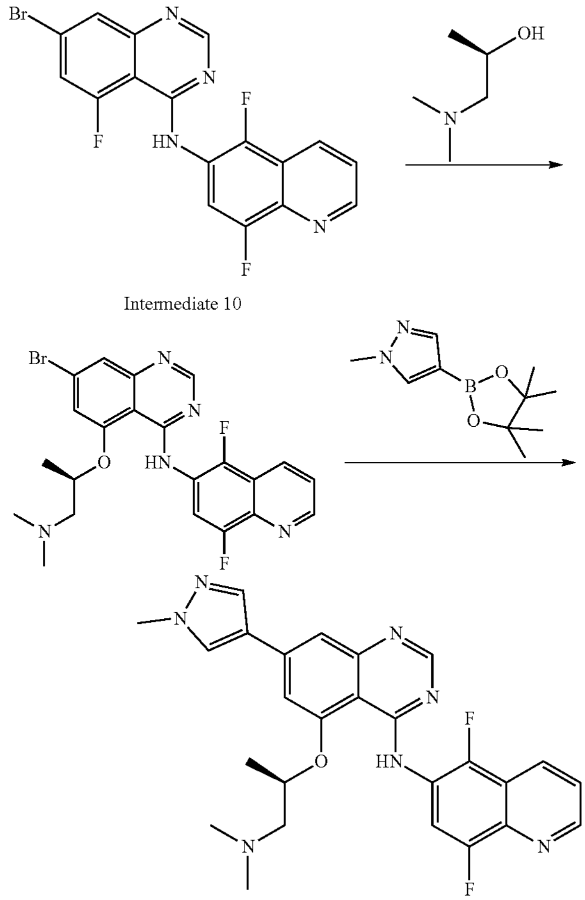

Step 1: (R)-7-bromo-N-(5,8-difluoroquinolin-6-yl)-5-((1-(dimethylamino)propan-2-yl)oxy)quinazolin-4-amine NaH (39.3 mg, 983 μmol) was added to (2R)-1-(dimethylamino)propan-2-ol (101 mg, 983 μmol) in THF (10 ml) at 0° C. After stirring for 30 min Intermediate 10 (100 mg, 246 μmol) was added to the mixture. The reaction was stirred for 80° C. for 16 h. The reaction mixture was diluted with EA (100 mL), washed with water (3×100 mL) and saturated brine (100 mL). The organic layer was dried over $Na_2SO_4$, filtered and evaporated. The crude product was purified by prep-TLC, eluting with DCM:MeOH, 25:1. This resulted in the title compound (95 mg, 79.8%) as a light-yellow solid. LC-MS: (ES, m/z): RT=0.529 min, LC-MS: m/z=488, 490 [M+], [M+2].

Step 2: (R)—N-(5,8-difluoroquinolin-6-yl)-5-((1-(dimethylamino)propan-2-yl)oxy)-7-(1-methyl-1H-pyrazol-4-yl)quinazolin-4-amine $Pd(dppf)Cl_2$ (15.2 mg, 18.4 μmol), $K_2CO_3$ (38.0 mg, 276 μmol), (R)-7-bromo-N-(5,8-difluoroquinolin-6-yl)-5-((1-(dimethylamino)propan-2-yl)oxy)quinazolin-4-amine (90 mg, 184 μmol), 1-methyl-4-(4,4,5,5-tetramethyl-1,3,2-dioxaborolan-2-yl)-1H-pyrazole (45.7 mg, 220 μmol), dioxane (0.6 mL) and $H_2O$ (0.2 mL) were combined in a reaction vessel at rt. The resulting mixture was heated at 100° C. for 16 h under $N_2$. The reaction mixture was diluted with DCM (100 mL), washed with water (3×100 mL) and saturated brine (100 mL). The organic layer was dried over $Na_2SO_4$, filtered and evaporated. The crude product was purified by prep-TLC, eluting with DCM:MeOH, 25:1. This resulted in 90 mg crude product. The residue was purified by Prep-HPLC using the following conditions: Column: YMC-Actus Triart C18, 30×150 mm, 5 μm; Mobile Phase A: $H_2O$ (10 mmol/L $NH_4HCO_3$+0.1% $NH_3 \cdot H_2O$), Mobile Phase B: ACN, Flow rate: 60 mL/min; Gradient: 45% B to 60% B over 8 min. Wavelength: 254/220 nm; to afford the title compound (48.9 mg (54.3%) as a white solid. LC-MS: (ES, m/z): RT=0.615 min, LC-MS: m/z=490 [M+1]; $^1H$ NMR (400 MHz, DMSO-d6) δ 10.68-10.63 (m, 1H), 8.97 (dd, J=4.2, 1.6 Hz, 1H), 8.84 (dd, J=12.8, 6.9 Hz, 1H), 8.56 (d, J=8.9 Hz, 2H), 8.49 (s, 1H), 8.17 (d, J=0.7 Hz, 1H), 7.74 (dd, J=8.6, 4.2 Hz, 1H), 7.60 (d, J=1.4 Hz, 1H), 7.47 (d, J=1.6 Hz, 1H), 5.16 (d, J=6.9 Hz, 1H), 3.92 (s, 3H), 2.50-2.59 (s, 1H), 2.90 (dd, J=13.0, 8.1 Hz, 1H), 2.5 (m, 1H), 2.20 (s, 6H), 1.52 (d, J=6.0 Hz, 3H).

Example 11: (R)—N-(5-((1-(dimethylamino)propan-2-yl)oxy)-7-(1-methyl-1H-pyrazol-4-yl)quinazolin-4-yl)cinnolin-6-amine

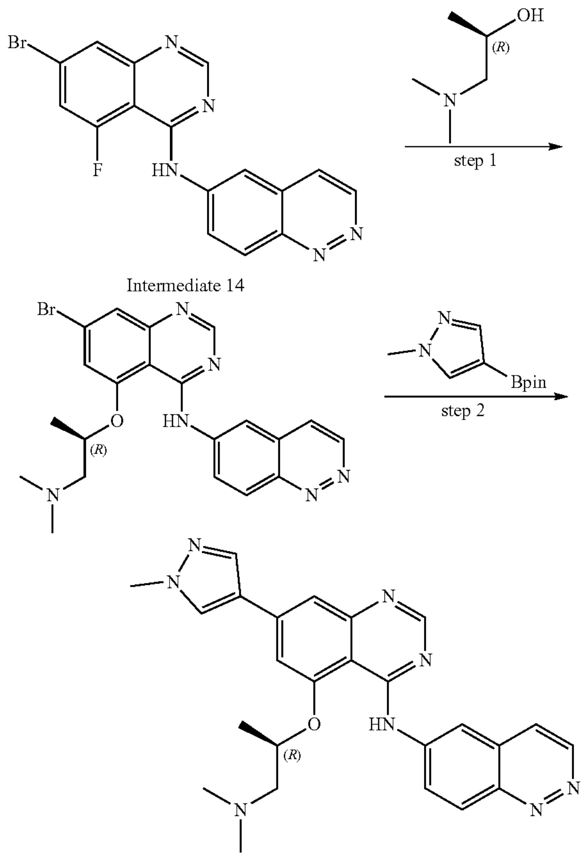

Step 1: (R)—N-(7-bromo-5-((1-(dimethylamino) propan-2-yl)oxy)quinazolin-4-yl)cinnolin-6-amine To a mixture of (2R)-1-(dimethylamino)propan-2-ol (167 mg, 1.62 mmol, 3 eq) in THF (10 mL) was added NaH (38.8 mg, 3.33 mmol) at 0° C., the reaction mixture was stirred at 0° C. for 15 min, then Intermediate 14 (200 mg, 0.5402 mmol, 1 eq) was added to the reaction mixture and was stirred at 80° C. for 4 hrs. The reaction mixture was added to the ice water and extracted with EA. The organic phase was concentrated under vacuum. The residue was purified by flash chromatography (50% EA in PE) to afford the title compound (150 mg, yield: 61.4%) as a yellow solid. LC-MS: (ES, m/z): RT=1.345 min, LCMS: m/z=453 [M+1].

Step 2: (R)—N-(5-((1-(dimethylamino)propan-2-yl) oxy)-7-(1-methyl-1H-pyrazol-4-yl)quinazolin-4-yl) cinnolin-6-amine To a solution of (R)—N-(7-bromo-5-((1-(dimethylamino) propan-2-yl)oxy)quinazolin-4-yl)cinnolin-6-amine (150 mg, 0.3308 mmol) in 1,4-dioxane/$H_2O$ was added 1-methyl-4-(4,4,5,5-tetramethyl-1,3,2-dioxaborolan-2-yl)-1H-pyrazole (75.5 mg, 363 μmol), $K_2CO_3$ (91.2 mg, 661 μmol) and Pd(dppf)$Cl_2$ (24.1 mg, 33.0 μmol) under nitrogen. The reaction was stirred for 3 hr at 80° C. then it was cooled to room temperature. The resulting solution was diluted with 50 mL of water. Extracted with 2×50 mL of ethyl acetate and the organic layers combined. The resulting mixture was washed with 50 mL of brine. The mixture was dried over anhydrous sodium sulfate and concentrated under vacuum. The residue was purified by prep-HPLC (Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 23% B to 56% B in 7 min; Wavelength: 254/220 nm) to afford the title compound (44.7 mg, yield: 30.0%) as a white solid. LC-MS: (ES, m/z): RT=1.169 min, LCMS: m/z=455 [M+1]. $^1H$ NMR (300 MHz, DMSO-$d_6$) δ 10.87 (s, 1H), 9.27 (d, J=5.9 Hz, 1H), 8.68 (s, 1H), 8.48 (d, J=10.9 Hz, 2H), 8.26-8.07 (m, 3H), 7.62 (d, J=1.4 Hz, 1H), 7.45 (s, 1H), 5.14 (d, J=10.9 Hz, 1H), 3.92 (s, 3H), 3.09 (dd, J=12.9, 8.9 Hz, 1H), 2.43 (s, 1H), 2.28 (s, 6H), 1.54 (d, J=5.8 Hz, 3H).

Example 12: 5-((3-((dimethyl amino) methyl) oxetan-3-yl) methoxy)-N-(5-fluoroquinolin-6-yl)-7-(1-methyl-1H-pyrazol-4-yl) quinazolin-4-amine

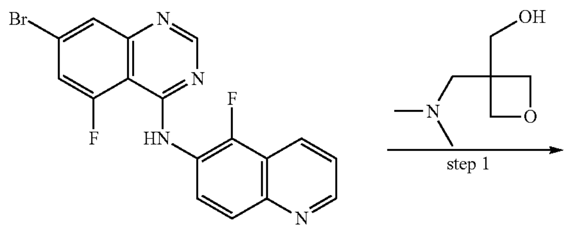

Intermediate 2

-continued

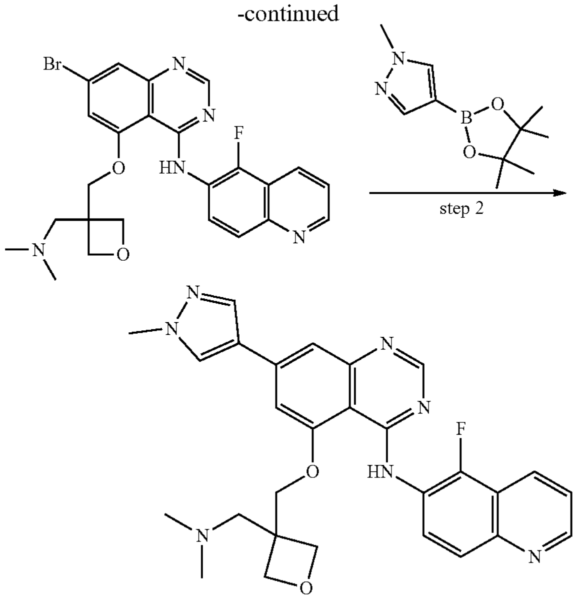

Step 1: 7-bromo-5-((3-((dimethyl amino) methyl) oxetan-3-yl) methoxy)-N-(5-fluoroquinolin-6-yl) quinazolin-4-amine To a mixture of (3-((dimethylamino)methyl)oxetan-3-yl) methanol (56.1 mg, 387 μmol) in THF (10 mL) was added NaH (18.5 mg, 774 μmol) at 0° C., the reaction mixture was stirred at 0° C. for 15 min, then Intermediate 2 (150 mg, 387 μmol) was added the reaction and was stirred at 80° C. for 4 hrs. The reaction mixture was added to ice water; then concentrated under vacuum. The residue was purified by flash chromatography to give the title compound (100 mg, yield: 50.5%) as a white solid. LC-MS: (ES, m/z): RT=1.271 min, LCMS: m/z=513 [M+1].

Step 2: 5-((3-((dimethyl amino) methyl) oxetan-3-yl) methoxy)-N-(5-fluoroquinolin-6-yl)-7-(1-methyl-1H-pyrazol-4-yl) quinazolin-4-amine To a mixture of 7-bromo-5-((3-((dimethylamino)methyl) oxetan-3-yl)methoxy)-N-(5-fluoroquinolin-6-yl)quinazolin-4-amine (100 mg, 195 μmol) and 1-methyl-4-(4,4,5,5-tetramethyl-1,3,2-dioxaborolan-2-yl)-1H-pyrazole (48.6 mg, 234 μmol) in 1,4-dioxane (4.00 mL) and $H_2O$ (1.00 mL) was added Pd(dppf)$Cl_2$ (15.9 mg, 19.5 μmol) and $K_2CO_3$ (53.8 mg, 390 μmol) at 25° C., the reaction mixture was stirred at 80° C. overnight under $N_2$. The reaction mixture was diluted with 20 mL of water. The resulting solution was extracted with 2×20 mL of ethyl acetate and the organic layers combined. The organic layer was washed with 20 mL of brine and dried over anhydrous sodium sulfate. Concentrated under vacuum. The product was purified by prep-TLC eluting with DCM:MeOH (10:1). The product was further purified by Prep-HPLC with the following conditions: (Column: Bridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 25% B to 45% B in 8 min; Wavelength: 254; 220 nm.) to afford the title compound (42.8 mg, yield: 42.7%). LC-MS: (ES, m/z): RT=1.110 min, LCMS: m/z=514 [M+1], H NMR (300 MHz, DMSO-d6) δ 10.10 (s, 1H), 8.96 (m, J=4.2, 1.7 Hz, 1H), 8.51 (d, J=14.4 Hz, 2H), 8.42 (s, 1H), 8.19 (s, 1H), 8.11 (t, J=8.6 Hz, 1H), 7.90 (d, J=9.1 Hz, 1H), 7.71-7.56 (m, 2H), 7.42 (s, 1H), 4.72 (d, J=6.2 Hz, 2H), 4.67-4.50 (m, 4H), 3.93 (s, 3H), 2.08 (d, J=2.6 Hz, 8H).

Example 13: (R)-5-((1-(dimethylamino)propan-2-yl)oxy)-7-(1-methyl-1H-pyrazol-4-yl)-N-(quinolin-7-yl)quinazolin-4-amine

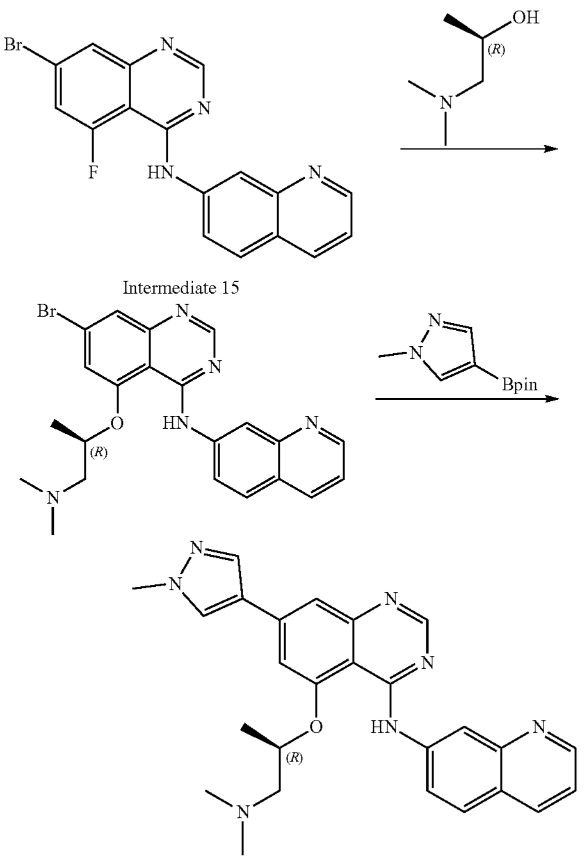

Step 1: (R)-7-bromo-5-((1-(dimethylamino)propan-2-yl)oxy)-N-(quinolin-7-yl)quinazolin-4-amine NaH (30.9 mg, 1.29 mmol) was added to Intermediate 15 (200 mg, 648 μmol) and (2R)-1-(dimethylamino)propan-2-ol (133 mg, 1.29 mmol) in THF (10 mL) at 0° C. The resulting mixture was stirred at 60° C. for 3 h under $N_2$. The reaction mixture was diluted with DCM 100 mL and washed with brine 50 mL*2, the organic layer was dried with $Na_2SO_4$ and concentrated under vacuum. The residue was purified by a silica gel column using PE:EA=15:1 to afford the title compound (150 mg, yield: 75%) as a light yellow solid. LC-MS: (ES, m/z): RT=1.452 min, LCMS: m/z=452 [M+1].

Step 2: (R)-5-((1-(dimethylamino)propan-2-yl)oxy)-7-(1-methyl-1H-pyrazol-4-yl)-N-(quinolin-7-yl)quinazolin-4-amine The reaction mixture of Pd(dppf)$Cl_2$ (10.1 mg, 13.2 μmol), $K_2CO_3$ (27.3 mg, 198 μmol), (R)-7-bromo-5-((1-(dimethylamino)propan-2-yl)oxy)-N-(quinolin-7-yl)quinazolin-4-amine (60 mg, 132 μmol) and 1-methyl-4-(4,4,5,5-tetramethyl-1,3,2-dioxaborolan-2-yl)-1H-pyrazole (54.9 mg, 264 μmol) in $H_2O$ (4 mL) and dioxane (16 mL) was stirred at 80° C. for 2 h under $N_2$. The mixture was diluted with DCM, washed with water, the organic layer dried with $Na_2SO_4$ and concentrated under vacuum. The residue was purified by a silica gel column using DCM:MeOH=20:1. The residue was purified by prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 21% B to 54% B in 8 min, 54% B; Wavelength: 254/220 nm; This resulted in the title compound (22 mg, yield: 16%) as an off-white solid. LC-MS: (ES, m/z): RT=1.357 min, LCMS: m/z=454 [M+1]. $^1H$ NMR (400 MHz, DMSO-$d_6$) δ 10.72 (s, 1H), 8.88 (dd, J=4.3, 1.8 Hz, 1H), 8.76 (d, J=2.1 Hz, 1H), 8.62 (s, 1H), 8.48 (s, 1H), 8.32 (d, J=8.3 Hz, 1H), 8.16 (s, 1H), 8.01 (d, J=8.8 Hz, 1H), 7.92 (dd, J=8.8, 2.2 Hz, 1H), 7.58 (s, 1H), 7.49-7.40 (m, 2H), 5.19-5.10 (m, 1H), 3.92 (s, 3H), 3.04 (dd, J=13.0, 8.7 Hz, 1H), 2.58 (s, 1H), 2.28 (s, 6H), 1.53 (d, J=5.8 Hz, 3H).

Example 14: (R)-5-((1-(dimethylamino)propan-2-yl)oxy)-7-(1-methyl-1H-pyrazol-4-yl)-N-(quinolin-3-yl)quinazolin-4-amine

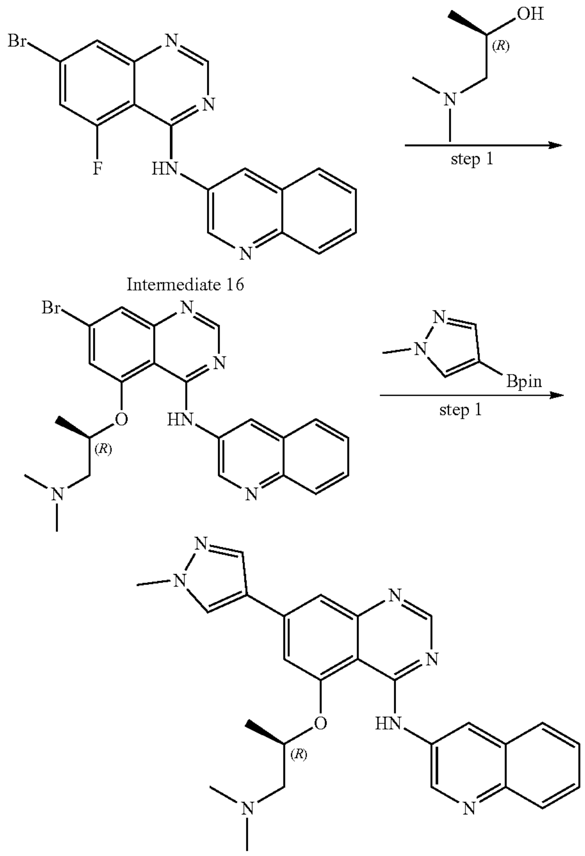

Step 1: (R)-7-bromo-5-((1-(dimethylamino)propan-2-yl)oxy)-N-(quinolin-3-yl)quinazolin-4-amine NaH (43.2 mg, 1.08 mmol) was added to Intermediate 16 (100 mg, 270 μmol) and (2R)-1-(dimethylamino) propan-2- ol (111 mg, 1.08 mmol) in THF (10 mL) at 0° C. The resulting mixture was heated at 80° C. for 3 hr. The reaction mixture was diluted with EtOAc (120 mL) and washed with water (60 mL). The organic layer was dried over $Na_2SO_4$, filtered and evaporated under vacuum. The crude product was purified by Prep-TLC eluting with DCM:MeOH=10:1 to afford the title compound (90 mg) as a white solid. LC-MS: (ES, m/z): RT=0.494 min, LCMS: m/z=452 [M+1], Step 2: (R)-5-((1-(dimethylamino)propan-2-yl)oxy)-7-(1-methyl-1H-pyrazol-4-yl)-N-(quinolin-3-yl)quinazolin-4-amine $Pd(dppf)Cl_2$ (12.5 mg, 15.4 μmol) and $K_2CO_3$ (31.8 mg, 231 μmol) were added to (R)-7-bromo-5-((1-(dimethylamino)propan-2-yl)oxy)-N-(quinolin-3-yl)quinazolin-4-amine (70 mg, 154 μmol) and 1-methyl-4-(4,4,5,5-tetramethyl-1,3,2-dioxaborolan-2-yl)-1H-pyrazole (48.0 mg, 231 μmol) in dioxane/$H_2O$ (4 mL/1 mL) at rt. This resulting mixture was heated to 80° C. for 3 hr. The reaction mixture was diluted with EtOAc (120 mL) and washed with water (60 mL). The organic layer was dried over $Na_2SO_4$, filtered and evaporated to afford crude product. The mixture was concentrated under vacuum. The crude product was purified by Prep-TLC with DCM:MeOH=20:1. This residue was purified by Prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 38% B to 71% B in 7 min, 71% B; Wavelength: 254/220 nm to afford the title compound (38 mg) as an off-white solid. LC-MS: (ES, m/z): RT=1.068 min, LCMS: m/z=454 [M+1], 1H NMR (400 MHz, DMSO-d6) δ 10.74 (s, 1H), 9.09 (d, J=2.5 Hz, 1H), 8.95 (d, J=2.5 Hz, 1H), 8.59 (s, 1H), 8.49 (s, 1H), 8.17 (s, 1H), 8.05-7.97 (m, 2H), 7.69 (ddd, J=8.4, 6.9, 1.6 Hz, 1H), 7.66-7.56 (m, 2H), 7.41 (d, J=1.5 Hz, 1H), 5.11 (d, J=9.5 Hz, 1H), 3.93 (s, 3H), 3.09 (dd, J=12.8, 9.1 Hz, 1H), 2.53 (s, 1H), 2.27 (s, 6H), 1.54 (d, J=5.9 Hz, 3H).

Example 15: (1R,2S)-2-((4-((5-fluoroquinolin-6-yl)amino)-7-(1-methyl-1H-pyrazol-4-yl)quinazolin-5-yl)oxy)cyclobutan-1-ol or (1S,2R)-2-((4-((5-fluoroquinolin-6-yl)amino)-7-(1-methyl-1H-pyrazol-4-yl)quinazolin-5-yl)oxy)cyclobutan-1-ol Example 16: (1S,2R)-2-((4-((5-fluoroquinolin-6-yl)amino)-7-(1-methyl-1H-pyrazol-4-yl)quinazolin-5-yl)oxy)cyclobutan-1-ol or (1R,2S)-2-((4-((5-fluoroquinolin-6-yl)amino)-7-(1-methyl-1H-pyrazol-4-yl)quinazolin-5-yl)oxy)cyclobutan-1-ol

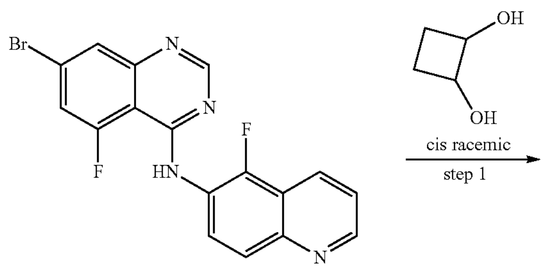

Intermediate 2

-continued

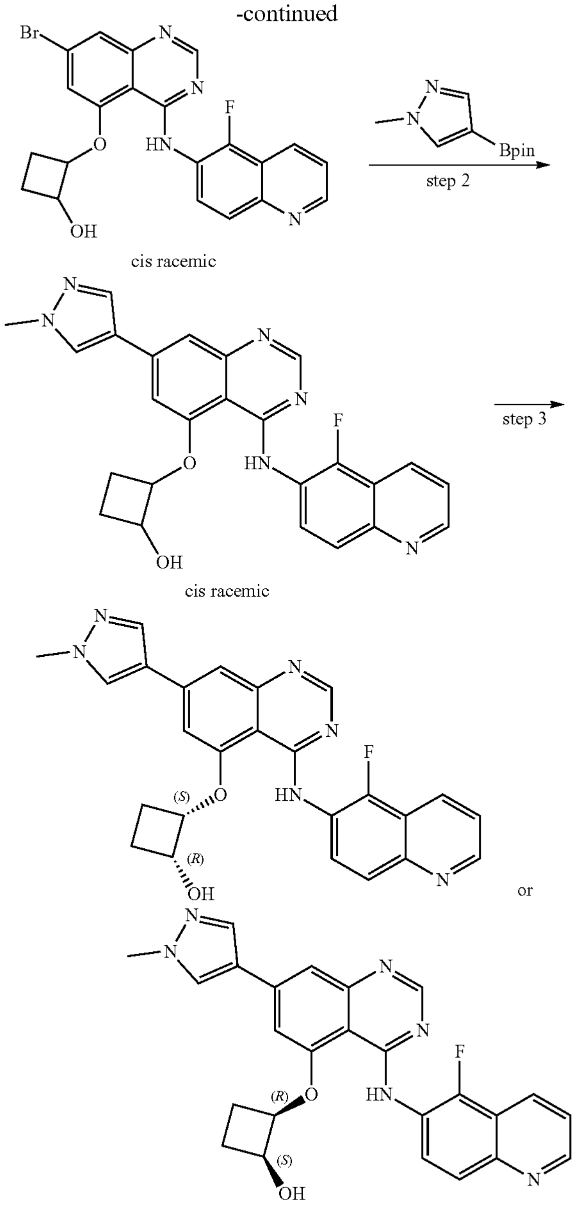

Step 1: Cis-rac-2-((7-bromo-4-((5-fluoroquinolin-6-yl)amino)quinazolin-5-yl)oxy)cyclobutan-1-ol t-BuOK (115 mg, 1.03 mmol) was added to Intermediate 2 (200 mg, 516 μmol) and cis-rac-cyclobutane-1,2-diol (90.7 mg, 1.03 mmol) in THF (10 mL) at rt. The resulting mixture was stirred at 80° C. for 3 h under $N_2$. The mixture was diluted with EA 100 mL and washed with brine 50 mL*2, the organic layer was dried with $Na_2SO_4$ and concentrated under vacuum. The residue was purified by a silica gel column using DCM: EA=15:1 to afford the title compound (120 mg, yield: 60%) as a light yellow solid. LC-MS: (ES, m/z): RT=1.176 min, LCMS: m/z=455 [M+1].

Step 2: Cis-rac-2-((4-((5-fluoroquinolin-6-yl)amino)-7-(1-methyl-1H-pyrazol-4-yl)quinazolin-5-yl)oxy)cyclobutan-1-ol The reaction mixture of $Pd(dppf)Cl_2$ (21.4 mg, 26.3 μmol),_$K_2CO_3$ (54.3 mg, 394 μmol), 1-methyl-4-(4,4,5,5- tetramethyl-1,3,2-dioxaborolan-2-yl)-1H-pyrazole (120 mg, 263 μmol) and cis-rac-2-((7-bromo-4-((5-fluoroquinolin-6-yl)amino)quinazolin-5-yl)oxy)cyclobutan-1-ol (70.9 mg, 263 μmol) in $H_2O$ (4 mL) and dioxane (16 mL) was stirred at 80° C. for 2 h under $N_2$. The mixture was diluted with DCM 100 mL and washed with water 50 mL*2, the organic layer was dried with $Na_2SO_4$ and concentrated under vacuum. The residue was purified by a silica gel column using DCM:MeOH=20:1 to afford the title compound (12 mg, yield: 10%) as a yellow oil. LC-MS: (ES, m/z): RT=1.171 min, LCMS: m/z=457 [M+1].

Step 3: Chiral Separation

Cis-rac 2-((4-((5-fluoroquinolin-6-yl)amino)-7-(1-methyl-1H-pyrazol-4-yl)quinazolin-5-yl)oxy)cyclobutan-1-ol (12 mg, 21.9 μmol) in MeOH was purified by Prep-Chiral-HPLC with following conditions: Column: Column: CHIRALPAK IF-3, 4.6*50 mm, 3.0 um; Flow rate: 1 mL/min; Gradient: 0% B to 0% B; to afford:

Example 15: First eluting isomer, (2 mg) LC-MS: (ES, m/z): RT=1.251 min, LCMS: m/z=457 [M+1]. Chiral-HPLC R=1.913, $^1$H NMR (400 MHz, DMSO-$d_6$) δ 10.57 (s, 1H), 8.97 (dd, J=4.3, 1.7 Hz, 1H), 8.56-8.49 (m, 1H), 8.46 (d, J=5.5 Hz, 2H), 8.44-8.36 (m, 1H), 8.13 (d, J=0.8 Hz, 1H), 7.95 (d, J=9.2 Hz, 1H), 7.66 (dd, J=8.5, 4.2 Hz, 1H), 7.58 (d, J=1.5 Hz, 1H), 7.15 (d, J=1.6 Hz, 1H), 5.72 (d, J=5.1 Hz, 1H), 5.20 (s, 1H), 4.61 (t, J=5.5 Hz, 1H), 3.92 (s, 3H), 2.37 (d, J=7.2 Hz, 1H), Example 16: Second eluting isomer, (1 mg), LC-MS: (ES, m/z): RT=0.898 min, LCMS: m/z=457 [M+1]. Chiral-HPLC R=3.119, $^1$H NMR (400 MHz, DMSO-$d_6$) δ 10.57 (s, 1H), 8.97 (dd, J=4.3, 1.7 Hz, 1H), 8.57-8.50 (m, 1H), 8.46 (d, J=6.0 Hz, 2H), 8.40 (t, J=8.7 Hz, 1H), 8.13 (d, J=0.9 Hz, 1H), 7.95 (d, J=9.2 Hz, 1H), 7.66 (dd, J=8.5, 4.2 Hz, 1H), 7.58 (d, J=1.5 Hz, 1H), 7.15 (d, J=1.6 Hz, 1H), 5.72 (d, J=5.2 Hz, 1H), 5.20 (s, 1H), 4.65-4.58 (m, 1H), 3.92 (s, 3H), 2.38 (s, 1H), 2.22 (s, 2H), 2.14-2.03 (m, 1H).

Example 17: N-(5-fluoroquinolin-6-yl)-7-(1-methyl-1H-pyrazol-4-yl)-5-((R)-1-((S)-tetrahydrofuran-3-yl)ethoxy)quinazolin-4-amine or N-(5-fluoroquinolin-6-yl)-7-(1-methyl-1H-pyrazol-4-yl)-5-((R)-1-((R)-tetrahydrofuran-3-yl)ethoxy)quinazolin-4-amine Example 18: N-(5-fluoroquinolin-6-yl)-7-(1-methyl-1H-pyrazol-4-yl)-5-((R)-1-((R)-tetrahydrofuran-3-yl)ethoxy)quinazolin-4-amine or N-(5-fluoroquinolin-6-yl)-7-(1-methyl-1H-pyrazol-4-yl)-5-((R)-1-((S)-tetrahydrofuran-3-yl)ethoxy)quinazolin-4-amine

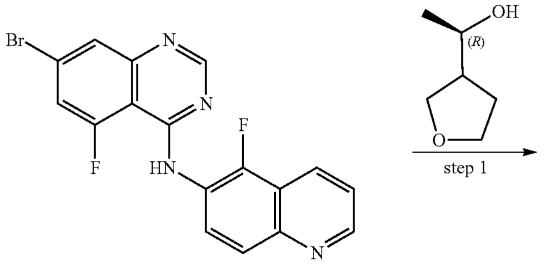

Intermediate 2

-continued

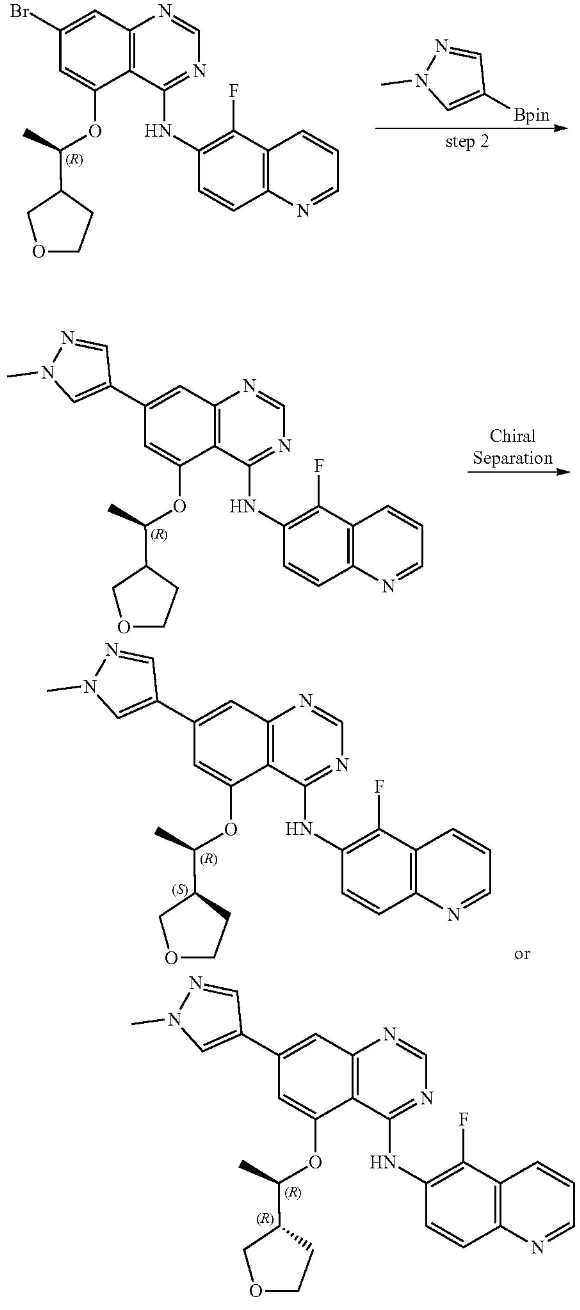

Step 1: 7-bromo-N-(5-fluoroquinolin-6-yl)-5-((1R)-1-(tetrahydrofuran-3-yl)ethoxy)quinazolin-4-amine To a mixture of (1R)-1-(tetrahydrofuran-3-yl)ethan-1-ol (89.9 mg, 774 μmol) in THF (5 mL) was added NaH (18.5 mg, 774 μmol) at 0° C. The reaction mixture was stirred at 0° C. for 15 min, then Intermediate 2 (150 mg, 387 μmol) was added to the reaction mixture. Stirred at 80° C. overnight. The reaction mixture was added to ice water and concentrated under vacuum. The residue was purified by flash chromatography to give the title compound (100 mg, yield=53.4%) as a white solid. LC-MS: (ES, m/z): RT=1.063 min, LCMS: m/z=484 [M+1]

Step 2: N-(5-fluoroquinolin-6-yl)-7-(1-methyl-1H-pyrazol-4-yl)-5-((1R)-1-(tetrahydrofuran-3-yl)ethoxy)quinazolin-4-amine To a mixture of 7-bromo-N-(5-fluoroquinolin-6-yl)-5-((1R)-1-(tetrahydrofuran-3-yl)ethoxy)quinazolin-4-amine (100 mg, 206 μmol) and 1-methyl-4-(4,4,5,5-tetramethyl-1,3,2-dioxaborolan-2-yl)-1H-pyrazole (64.2 mg, 309 μmol) in 1,4-dioxane (4.00 mL) and $H_2O$ (1.00 mL) was added Pd(dppf)$Cl_2$ (16.8 mg, 20.6 μmol) and $K_2CO_3$ (85.2 mg, 618 μmol) at 25° C., the reaction mixture was stirred at 80° C. for 4 hrs under $N_2$. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum to afford the title compound.

Chiral Separation:

The product of step 2 was purified by prep-HPLC (Column: YMC-Actus Triart C18, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 50% B to 60% B in 8 min; Wavelength: 254/220 nm). To afford:

Example 17: First eluting isomer, white solid 36.9 mg (36.9%): LC-MS: (ES, m/z): RT=1.382 min, LCMS: m/z=484 [M+1]. 1H NMR (400 MHz, DMSO-d6) δ 10.34 (s, 1H), 8.95 (dd, J=4.2, 1.6 Hz, 1H), 8.69 (t, J=8.8 Hz, 1H), 8.63-8.41 (m, 3H), 8.17 (d, J=0.8 Hz, 1H), 7.96 (d, J=9.3 Hz, 1H), 7.66-7.56 (m, 2H), 7.47 (d, J=1.7 Hz, 1H), 5.05 (p, J=6.1 Hz, 1H), 4.14 (q, J=6.9 Hz, 1H), 3.92 (s, 3H), 3.69-3.51 (m, 2H), 2.20-2.01 (m, 1H), 1.99-1.62 (m, 3H), 1.49 (d, J=6.1 Hz, 3H).

Example 18: Second eluting isomer, white solid and 11.6 mg (11.6%): LC-MS: (ES, m/z): RT=1.043 min, LCMS: m/z=484 [M+1]. 1H NMR (400 MHz, DMSO-d6) δ 10.29 (s, 1H), 8.95 (dd, J=4.2, 1.6 Hz, 1H), 8.75 (t, J=8.9 Hz, 1H), 8.51 (d, J=10.7 Hz, 2H), 8.18 (s, 1H), 7.96 (d, J=9.3 Hz, 1H), 7.66-7.57 (m, 2H), 7.53 (d, J=1.5 Hz, 1H), 5.14 (p, J=6.0 Hz, 1H), 4.27 (td, J=7.0, 4.5 Hz, 1H), 3.92 (s, 3H), 3.80 (dt, J=8.0, 6.5 Hz, 1H), 3.69 (dt, J=8.2, 6.6 Hz, 1H), 2.16-2.01 (m, 1H), 1.95-1.71 (m, 3H), 1.47 (d, J=6.1 Hz, 3H).

Example 19: (R)—N-(5-fluoroquinolin-6-yl)-7-(1-methyl-1H-pyrazol-4-yl)-5-(1-(tetrahydro-2H-pyran-4-yl)ethoxy)quinazolin-4-amine. or (S)—N-(5-fluoroquinolin-6-yl)-7-(1-methyl-1H-pyrazol-4-yl)-5-(1-(tetrahydro-2H-pyran-4-yl)ethoxy)quinazolin-4-amine Example 20: (S)—N-(5-fluoroquinolin-6-yl)-7-(1-methyl-1H-pyrazol-4-yl)-5-(1-(tetrahydro-2H-pyran-4-yl)ethoxy)quinazolin-4-amine. or (R)—N-(5-fluoroquinolin-6-yl)-7-(1-methyl-1H-pyrazol-4-yl)-5-(1-(tetrahydro-2H-pyran-4-yl)ethoxy)quinazolin-4-amine

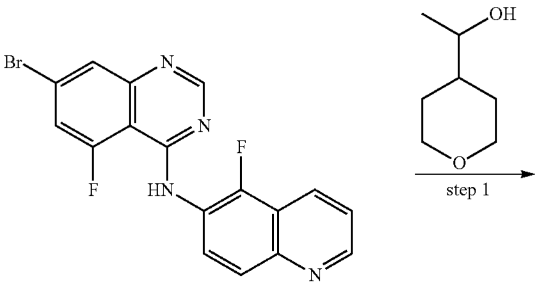

Intermediate 2

-continued

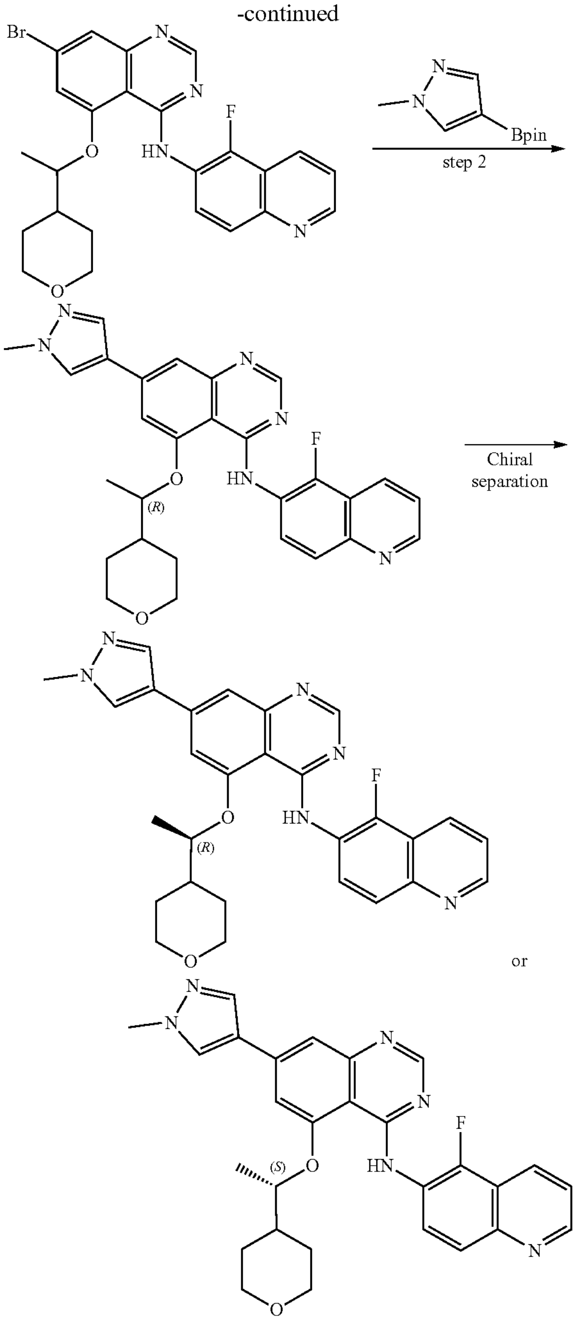

Step 1: 7-bromo-N-(5-fluoroquinolin-6-yl)-5-(1-(tetrahydro-2H-pyran-4-yl)ethoxy)quinazolin-4-amine To a mixture of 1-(oxan-4-yl)ethan-1-ol (134 mg, 1.03 mmol) in THF (5 mL) was added NaH (24.7 mg, 1.03 mmol) at 0° C., the reaction mixture was stirred at 0° C. for 15 min, then Intermediate 2 (200 mg, 516 μmol) was added to the reaction mixture. The reaction mixture was stirred at 80° C. overnight. The reaction mixture was added to the ice water and concentrated under vacuum. The residue was purified by flash chromatography to give the title compound (150 mg, yield: 58.5%) as a white solid. LC-MS: (ES, m/z): RT=1.597 min, LCMS: m/z=497 [M+1]

Step 2: N-(5-fluoroquinolin-6-yl)-7-(1-methyl-1H-pyrazol-4-yl)-5-(1-(tetrahydro-2H-pyran-4-yl)ethoxy)quinazolin-4-amine To a mixture of 7-bromo-N-(5-fluoroquinolin-6-yl)-5-(1-(tetrahydro-2H-pyran-4-yl)ethoxy)quinazolin-4-amine (150 mg, 301 μmol) and 1-methyl-4-(4,4,5,5-tetramethyl-1,3,2-dioxaborolan-2-yl)-1H-pyrazole (93.8 mg, 451 μmol) in 1,4-dioxane (4.00 mL) and $H_2O$ (1.00 mL) was added $Pd(dppf)Cl_2$ (24.5 mg, 30.1 μmol) and $K_2CO_3$ (124 mg, 903 μmol) at 25° C., the reaction mixture was stirred at 80° C. for 4 hrs under $N_2$. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The product was purified by TLC eluting with DCM:MeOH (10:1) to afford the title compound (90 mg, yield: 60.0%) as a yellow solid.

Chiral Separation: The product of step 2 (90 mg, 180 μmol) was Purified by Prep-Chiral-HPLC with following conditions: Column: CHIRALPAK IH, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 15% B to 15% B in 20 min; Wavelength: 220/254 nm to afford:

Example 19: First eluting isomer 18.5 mg (20.6%) white solid: LC-MS: (ES, m/z): RT=1.407 min, LCMS: m/z=499 [M+1]. Chiral-HPLC R=3.42, 1H NMR (400 MHz, DMSO-d6) δ 10.40 (d, J=2.3 Hz, 1H), 9.08 (t, J=9.0 Hz, 1H), 8.93 (dd, J=4.2, 1.6 Hz, 1H), 8.63-8.35 (m, 3H), 8.19 (s, 1H), 7.97 (d, J=9.3 Hz, 1H), 7.73-7.56 (m, 2H), 7.46 (d, J=1.6 Hz, 1H), 4.99 (p, J=6.2 Hz, 1H), 3.93 (s, 5H), 3.47-3.37 (m, 2H), 2.21-2.10 (m, 1H), 1.94 (s, 1H), 1.71 (d, J=13.1 Hz, 1H), 1.52-1.34 (m, 5H), 1.22 (s, 1H), 0.84 (d, J=7.1 Hz, 0H).

Example 20: Second eluting isomer, 18.3 mg (20.4%), white solid: LC-MS: (ES, m/z): RT=1.403 min, LCMS: m/z=499 [M+1]. Chiral-HPLC R=4.77, 1H NMR (400 MHz, DMSO-d6) δ 10.41 (d, J=2.2 Hz, 1H), 9.08 (t, J=8.9 Hz, 1H), 8.93 (dd, J=4.2, 1.6 Hz, 1H), 8.67-8.48 (m, 3H), 8.19 (s, 1H), 7.97 (d, J=9.3 Hz, 1H), 7.68-7.49 (m, 2H), 7.46 (d, J=1.5 Hz, 1H), 4.99 (p, J=6.1 Hz, 1H), 3.93 (s, 5H), 3.49-3.37 (m, 2H), 2.22-2.10 (m, 1H), 1.95 (d, J=13.1 Hz, 1H), 1.71 (d, J=12.8 Hz, 1H), 1.56-1.32 (m, 5H), 1.23 (s, 1H), 0.85 (d, J=7.1 Hz, 0H).

Example 21: 5-((3-(dimethylamino)oxetan-3-yl)methoxy)-N-(5-fluoroquinolin-6-yl)-7-(1-methyl-1H-pyrazol-4-yl)quinazolin-4-amine

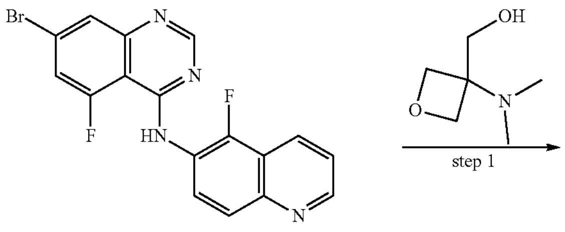

Intermediate 2

-continued

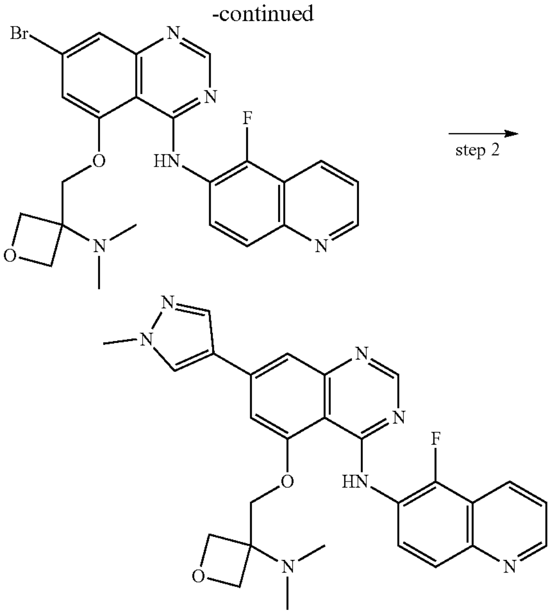

Step 1: 7-bromo-5-((3-(dimethylamino)oxetan-3-yl)methoxy)-N-(5-fluoroquinolin-6-yl)quinazolin-4-amine To a solution of (3-(dimethylamine) oxetan-3-yl)methanol (67.6 mg, 516 μmol, 1 eq) in THF (5 ml). was added NaH (18.5 mg, 774 μmol) at 0° C., the reaction mixture was stirred at 0° C. for 15 min, then Intermediate 2 (100 mg, 258 μmol) was added to the reaction mixture at 25° C., the resulting solution was stirred for 4 hours at 80° C. Then it was cooled to room temperature. The resulting solution was diluted with 20 mL of water. The resulting solution was extracted with 2×20 mL of ethyl acetate, the organic layers combined, and the resulting mixture was washed with 20 mL of brine. The mixture was dried over anhydrous sodium sulfate and concentrated under vacuum. The product was purified by chromatography with DCM:MeOH to afford the title compound (120 mg, yield: 93.7%) as a yellow solid. LC-MS: (ES, m/z): RT=1.037 min, LCMS: m/z=498 [M+1].

Step 2: 5-((3-(dimethylamino)oxetan-3-yl)methoxy)-N-(5-fluoroquinolin-6-yl)-7-(1-methyl-1H-pyrazol-4-yl)quinazolin-4-amine To a mixture of the product of Step 1 (120 mg, 240 μmol) and 1-methyl-4-(4,4,5,5-tetramethyl-1,3,2-dioxaborolan-2-yl)-1H-pyrazole (59.7 mg, 287 μmol) in 1,4-dioxane (4.00 mL) and $H_2O$ (1.00 mL) was added $Pd(dppf)Cl_2$ (19.5 mg, 24.0 μmol) and $K_2CO_3$ (66.2 mg, 480 μmol) at 25° C., the reaction mixture was stirred at 80° C. overnight under N2. The resulting solution was diluted with 20 mL of water. The solution was extracted with 2×20 mL of ethyl acetate and the organic layers combined. The resulting mixture was washed with 20 mL of brine. The mixture was dried over anhydrous sodium sulfate and concentrated under vacuum. The product was purified by TLC eluting with DCM: Me OH (10:1). The crude product was purified by Prep-HPLC with the following conditions: Column: Bridge Shield RP18 OBD Column, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 8% B to 51% B in 7 min;

Wavelength: 254/220 nm to afford the title compound (72.2 mg, yield: 60.6%). LC-MS: (ES, m/z): RT=1.103 min, LCMS: m/z=500 [M+1], 1H NMR (300 MHz, DMSO-d6) δ 10.03 (s, 1H), 8.84 (m, J=4.2, 1.7 Hz, 1H), 8.43-8.20 (m, 3H), 8.10 (d, J=0.8 Hz, 1H), 7.89 (m, J=9.1, 8.0 Hz, 1H), 7.78 (d, J=9.1 Hz, 1H), 7.61-7.44 (m, 2H), 7.38 (d, J=1.5 Hz, 1H), 4.62-4.44 (m, 6H), 3.81 (s, 3H), 2.16 (s, 6H).

Example 22: ((R)—N-(5-fluoroquinolin-6-yl)-7-(1-methyl-1H-pyrazol-4-yl)-5-(1-(oxetan-3-yl)propoxy)quinazolin-4-amine or (S)—N-(5-fluoroquinolin-6-yl)-7-(1-methyl-1H-pyrazol-4-yl)-5-(1-(oxetan-3-yl)propoxy)quinazolin-4-amine Example 23: (S)—N-(5-fluoroquinolin-6-yl)-7-(1-methyl-1H-pyrazol-4-yl)-5-(1-(oxetan-3-yl)propoxy)quinazolin-4-amine or ((R)—N-(5-fluoroquinolin-6-yl)-7-(1-methyl-1H-pyrazol-4-yl)-5-(1-(oxetan-3-yl)propoxy)quinazolin-4-amine

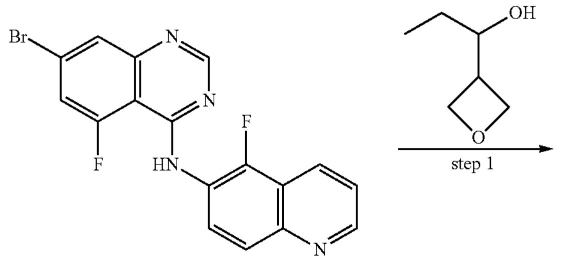

Intermediate 2

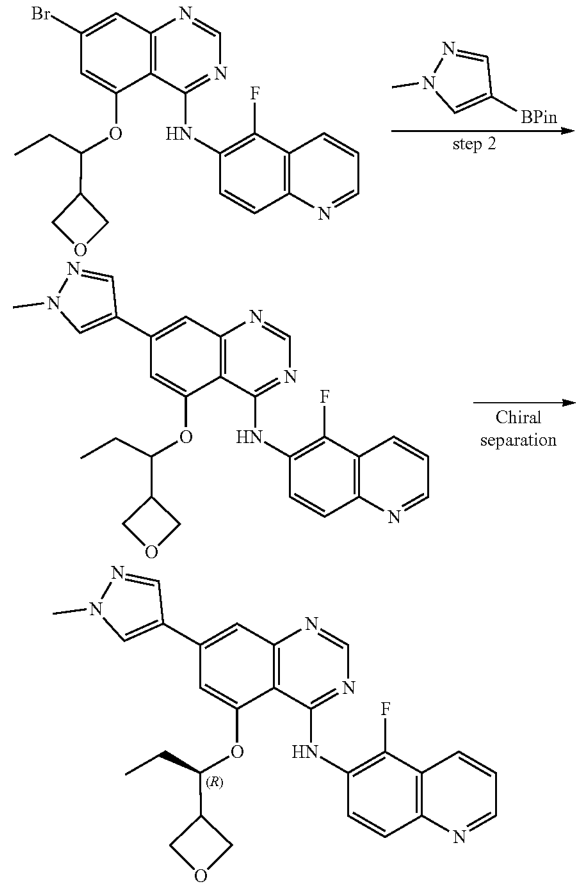

or

-continued

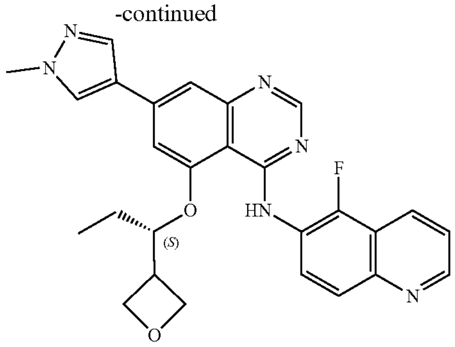

Step 1: 7-bromo-N-(5-fluoroquinolin-6-yl)-5-(1-(oxetan-3-yl)propoxy)quinazolin-4-amine t-BuOK (86.6 mg, 774 μmol) was added into Intermediate 2 (150 mg, 0.3874 mmol) and 1-(oxetan-3-yl)propan-1-ol (89.9 mg, 774 μmol) in THF. The mixture was stirred at 80° C. for 3 hours. The reaction was extracted by EA and purified by Prep-TLC (DCM:MeOH=20:1) to afford the title compound (130 mg, yield: 69.5%) as a light yellow solid. LC-MS: (ES, m/z): RT=1.408 min, LCMS: m/z=485 [M+1].

Step 2: (N-(5-fluoroquinolin-6-yl)-7-(1-methyl-1H-pyrazol-4-yl)-5-(1-(oxetan-3-yl)propoxy)quinazolin-4-amine Into a 8 ml vial and maintained a $N_2$ atmosphere was added 7-bromo-N-(5-fluoroquinolin-6-yl)-5-(1-(oxetan-3-yl)propoxy)quinazolin-4-amine (120 mg, 0.2482 mmol), 1-methyl-4-(4,4,5,5-tetramethyl-1,3,2-dioxaborolan-2-yl)-1H-pyrazole (61.7 mg, 0.297 mmol), Pd(dppf)$Cl_2$ (20.2 mg, 24.8 μmol) and $K_2CO_3$ (68.4 mg, 0.496 mmol) in 4 ml 1,4-dioxane and 1 ml $H_2O$. The mixture was stirred at 80° C. for 3 hours. The reaction was extracted by EA and the organic layer was concentrated in vacuum. The reaction was purified by Prep-HPLC: Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 35% B to 65% B in 8 min, 65% B; Wavelength: 254/220 nm; RT1 (min): 6.28; To afford the title compound (70 mg, 58.3%) as a white solid. LC-MS: (ES, m/z): RT=0.772 min, LCMS: m/z=485 [M+1]

Chiral separation: The product of Step 2 (70 mg, 0.1444 mmol) was separated by Chiral HPLC: Column: CHIRALPAK IA-3, 4.6*50 mm 3 um; Mobile Phase A: Hex (0.1% DEA): EtOH=70:30; Flow rate: 1 mL/min; Gradient: 0% B to 0% B; to afford:

Example 22: First eluting isomer, (27.9 mg, 79.9%) as a white solid LC-MS: (ES, m/z): RT=0.980 min, LCMS: m/z=485[M+1]; Chiral-HPLC: 3.286; 1H NMR (400 MHz, DMSO-d6) δ 10.27 (d, J=1.9 Hz, 1H), 8.95 (dd, J=4.2, 1.6 Hz, 1H), 8.90 (t, J=8.9 Hz, 1H), 8.59-8.50 (m, 3H), 8.21 (s, 1H), 7.97 (d, J=9.3 Hz, 1H), 7.70-7.60 (m, 2H), 7.57 (d, J=1.5 Hz, 1H), 5.48 (q, J=6.0 Hz, 1H), 4.79 (ddd, J=8.0, 6.3, 2.0 Hz, 2H), 4.62 (t, J=6.2 Hz, 1H), 4.55 (t, J=6.2 Hz, 1H), 3.94 (s, 3H), 3.64 (h, J=7.3 Hz, 1H), 1.92-1.81 (m, 2H), 0.95 (t, J=7.4 Hz, 3H).

Example 23: Second eluting isomer, (30.2 mg, 86.5%) as a white solid, LC-MS: (ES, m/z): RT=0.877 min, LCMS: m/z=485 [M+1], Chiral-HPLC: 3.099, 1H NMR (400 MHz, DMSO-d6) δ 10.27 (d, J=1.8 Hz, 1H), 8.95 (dd, J=4.2, 1.7 Hz, 1H), 8.90 (t, J=8.9 Hz, 1H), 8.59-8.50 (m, 3H), 8.21 (s, 1H), 7.97 (d, J=9.2 Hz, 1H), 7.70-7.60 (m, 2H), 7.57 (d, J=1.6 Hz, 1H), 5.48 (q, J=6.0 Hz, 1H), 4.79 (ddd, J=8.0, 6.2, 2.0 Hz, 2H), 4.62 (t, J=6.2 Hz, 1H), 4.55 (t, J=6.2 Hz, 1H), 3.94 (s, 3H), 3.65 (p, J=7.2 Hz, 1H), 1.92-1.81 (m, 2H), 0.95 (t, J=7.4 Hz, 3H).

Example 24: (R)-5-((1-(dimethylamino)butan-2-yl)oxy)-N-(5-fluoroquinolin-6-yl)-7-(1-methyl-1H-pyrazol-4-yl)quinazolin-4-amine

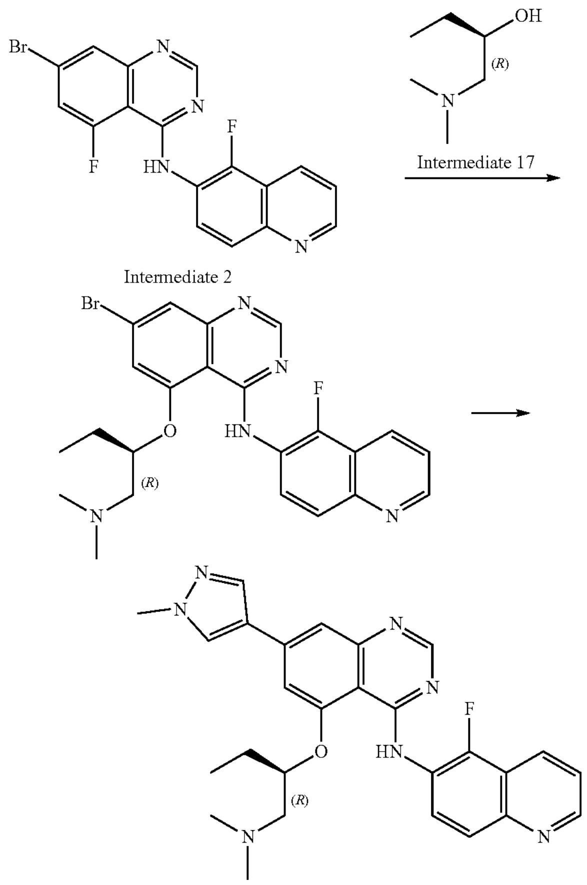

Step 1: (R)-7-bromo-5-((1-(dimethylamino)butan-2-yl)oxy)-N-(5-fluoroquinolin-6-yl)quinazolin-4-amine NaH (97 mg, 2 mmol) was added to the mixture of Intermediate 17 (150 mg, 1.27 mmol), Intermediate 2 (491 mg, 1.27 mmol) in DMF (3 mL) at rt, and stirred at 80° C. for 10 hrs. The reaction was poured into ice-water, the solid was collected by filtration and purified by prep-TLC (DCM/$CH_3OH$=20/1) to afford the title compound (180 mg, yield=31%) LC-MS: (ES, m/z): RT=0.850 min, LCMS: m/z=484 486 [M+1].

Step 2: (R)-5-((1-(dimethylamino)butan-2-yl)oxy)-N-(5-fluoroquinolin-6-yl)-7-(1-methyl-1H-pyrazol-4-yl)quinazolin-4-amine The reaction mixture of (R)-7-bromo-5-((1-(dimethylamino)butan-2-yl)oxy)-N-(5-fluoroquinolin-6-yl)quinazolin-4-amine (160 mg, 0.33 mmol), 1-methyl-4-(4,4,5,5-tetramethyl-1,3,2-dioxaborolan-2-yl)-1H-pyrazole (68.6 mg, 0.33 mmol), $Pd(dppf)Cl_2$ (25.7 mg, 0.03 mmol), $K_2CO_3$ (91 mg, 0.66 mmol) in dioxane (5 mL) was stirred at 80° C. for 4 hrs under $N_2$. After completion, concentrated and purified by prep-HPLC to afford the title compound as a white solid (19.2 mg, yield: 12%). LC-MS: (ES, m/z): RT=1.058 min, LCMS: m/z=486 [M+1], $^1H$ NMR (400 MHz, DMSO-$d_6$) δ 10.61-10.56 (m, 1H), 8.94 (dd, J=4.2, 1.6 Hz, 1H), 8.87 (t, J=8.9 Hz, 1H), 8.54 (s, 1H), 8.57-8.50 (m, 1H), 8.48 (s, 1H), 8.16 (d, J=0.8 Hz, 1H), 7.97 (d, J=9.3 Hz, 1H), 7.65 (dd, J=8.5, 4.2 Hz, 1H), 7.59 (d, J=1.4 Hz, 1H), 7.47 (d, J=1.5 Hz, 1H), 5.10 (dd, J=7.9, 4.7 Hz, 1H), 3.93 (s, 3H), 2.87 (dd, J=13.1, 7.8 Hz, 1H), 2.56 (dd, J=13.1, 4.2 Hz, 1H), 2.20 (s, 6H), 2.04-1.84 (m, 2H), 1.06 (t, J=7.5 Hz, 3H).

Example 25: (S)-3-((4-((5-fluoroquinolin-6-yl)amino)-7-(1-methyl-1H-pyrazol-4-yl)quinazolin-5-yl)oxy)-1-methylpyrrolidin-2-one

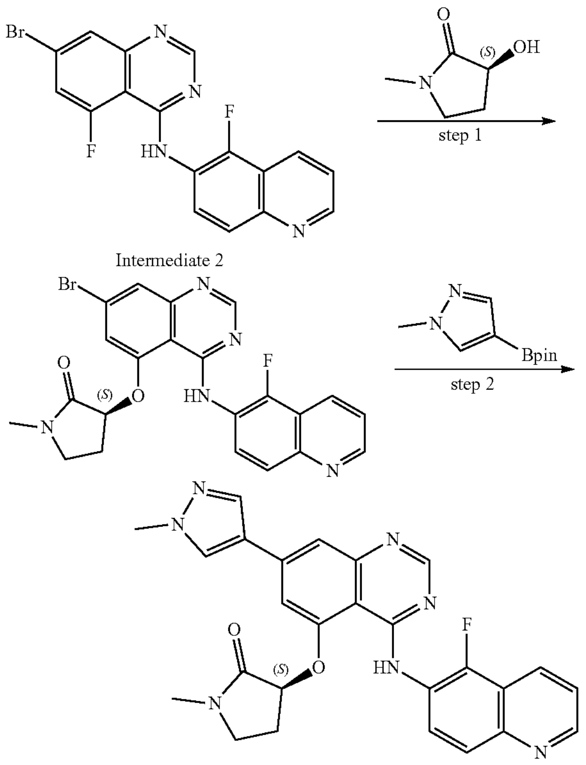

Step 1: (S)-3-((7-bromo-4-((5-fluoroquinolin-6-yl)amino)quinazolin-5-yl)oxy)-1-methylpyrrolidin-2-one NaH (82.4 mg, 2.06 mmol) was added to (3S)-3-hydroxy-1-methylpyrrolidin-2-one (237 mg, 2.06 mmol) in THF (10 mL) at 0° C. and the mixture was stirred at 0° C. for 10 min. Intermediate 2 (200 mg, 516 μmol) was added to the mixture at 0° C. The resulting mixture was heated at 80° C. for 3 hr. The reaction mixture was diluted with EtOAc (120 mL) and washed with water (60 mL). The organic layer was dried over $Na_2SO_4$, filtered and evaporated to afford the title compound (155 mg) as a gray solid. LC-MS: (ES, m/z): RT=1.220 min, LCMS: m/z=482 [M+1], Step 2: (S)-3-((4-((5-fluoroquinolin-6-yl)amino)-7-(1-methyl-1H-pyrazol-4-yl)quinazolin-5-yl)oxy)-1-methylpyrrolidin-2-one Pd(dppf)$Cl_2$ (23.6 mg, 29.0 μmol) and $K_2CO_3$ (60.0 mg, 435 μmol) were added to (S)-3-((7-bromo-4-((5-fluoroquinolin-6-yl)amino)quinazolin-5-yl)oxy)-1-methylpyrrolidin-2-one (140 mg, 290 μmol) and 1-methyl-4-(4,4,5,5-tetramethyl-1,3,2-dioxaborolan-2-yl)-1H-pyrazole (90.5 mg, 435 μmol) in dioxane/$H_2O$ (6 mL/2 mL) at rt. This resulting mixture was heated to 80° C. for 3 h under $N_2$. The reaction mixture was diluted with EtOAc (120 mL) and washed with water (60 mL). The organic layer was dried over $Na_2SO_4$, filtered and evaporated to afford crude product (30.1 mg) as a gray solid. LC-MS: (ES, m/z): RT=0.858 min, LCMS: m/z=484 [M+1], 1H NMR (400 MHz, DMSO-d6) δ 10.28 (s, 1H), 8.96 (s, 1H), 8.49 (d, J=11.1 Hz, 4H), 8.17 (s, 1H), 7.96 (d, J=9.0 Hz, 1H), 7.66 (s, 2H), 7.46 (s, 1H), 5.46 (s, 1H), 3.93 (s, 3H), 3.52 (t, J=11.7 Hz, 2H), 3.01 (s, 1H), 2.88 (s, 3H), 2.29 (s, 1H).

Example 26: 5-(((2R,3R)-3-(dimethylamino)butan-2-yl)oxy)-N-(5-fluoroquinolin-6-yl)-7-(1-methyl-1H-pyrazol-4-yl)quinazolin-4-amine or 5-(((2S,3S)-3-(dimethylamino)butan-2-yl)oxy)-N-(5-fluoroquinolin-6-yl)-7-(1-methyl-1H-pyrazol-4-yl)quinazolin-4-amine Example 27: 5-(((2S,3S)-3-(dimethylamino)butan-2-yl)oxy)-N-(5-fluoroquinolin-6-yl)-7-(1-methyl-1H-pyrazol-4-yl)quinazolin-4-amine or 5-(((2R,3R)-3-(dimethylamino)butan-2-yl)oxy)-N-(5-fluoroquinolin-6-yl)-7-(1-methyl-1H-pyrazol-4-yl)quinazolin-4-amine

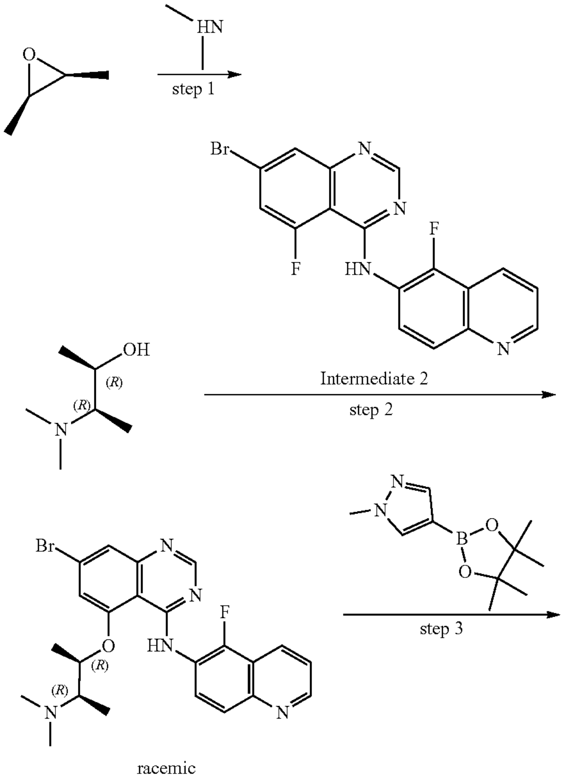

racemic

-continued

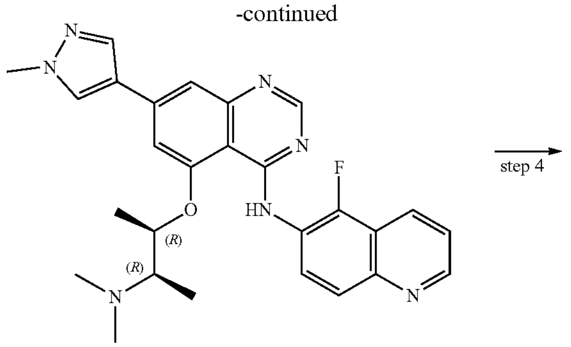

racemic

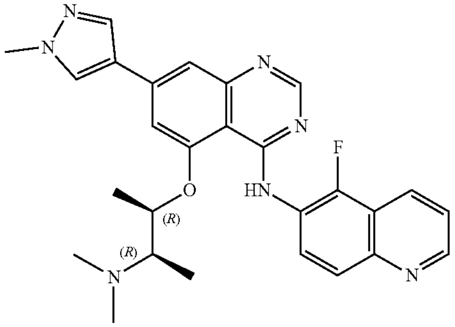

or

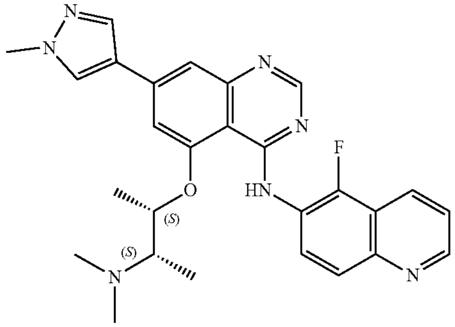

Step 1:(2R,3R)-3-(dimethylamino)butan-2-ol and (2S,3S)-3-(dimethylamino)butan-2-ol (2R,3S)-2,3-dimethyloxirane (1 g, 13.8 mmol) was added dropwise to dimethylamine (20 mL, 33% aq) at 0° C., then the reaction was stirred at 50° C. for 16 hr. The mixture was diluted with DCM 100 mL and washed with brine 10×2 mL. The organic layer was dried with $Na_2SO_4$ and concentrated under vacuum. This resulted in the title compound (1.25 g) as a colorless oil. LC-MS: (ES, m/z): RT=0.219 min, LCMS: m/z=118 [M+1].

Step 2: 7-bromo-5-(((2R,3R)-3-(dimethylamino)butan-2-yl)oxy)-N-(5-fluoroquinolin-6-yl)quinazolin-4-amine and 7-bromo-5-(((2S,3S)-3-(dimethylamino)butan-2-yl)oxy)-N-(5-fluoroquinolin-6-yl)quinazolin-4-amine NaH (92.6 mg, 3.86 mmol) was added slowly into solution of the product of step 1 (452 mg, 3.86 mmol) in THF (10 mL) at rt. The resulted mixture was stirred at rt for 10 min then Intermediate 2 (300 mg, 774 μmol) was added to the mixture and stirred at 80° C. for 24 hr. After reaction, the solution was extracted with EA 3×50 mL and dried with $Na_2SO_4$, the crude product was purified by Prep-TLC eluting with DCM:MeOH=20:1 to afford the title compound (180 mg) as a yellow solid. LC-MS: (ES, m/z): RT=1.475 min, LCMS: m/z=485 [M+1]

Step 3: 5-(((2R,3R)-3-(dimethylamino)butan-2-yl)oxy)-N-(5-fluoroquinolin-6-yl)-7-(1-methyl-1H-pyrazol-4-yl)quinazolin-4-amine and 5-(((2S,3S)-3-(dimethylamino)butan-2-yl)oxy)-N-(5-fluoroquinolin-6-yl)-7-(1-methyl-1H-pyrazol-4-yl)quinazolin-4-amine $Pd(dppf)Cl_2$ (15.0 mg, 20.6 μmol), $K_2CO_3$ (56.8 mg, 412 μmol) were added into solution of the product of step 2 (100 mg, 206 μmol) and 1-methyl-4-(4,4,5,5-tetramethyl-1,3,2-dioxaborolan-2-yl)-1H-pyrazole (85.7 mg, 412 μmol) in dioxane/$H_2O$ (10 mL/2 mL) at rt. The reaction mixture was stirred at 80° C. under $N_2$ for 2 hr. The reaction was extracted with EA 3×50 mL, the organic layer was dried with $Na_2SO_4$ and evaporated under vacuum. The crude product was purified by Prep-HPLC using the following conditions: Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 53% B to 63% B in 8 min, 63% B; Wavelength: 254/220 nm; This resulted in the title compound (50 mg) as white solid. LC-MS: (ES, m/z): RT=1.319 min, LCMS: m/z=486 [M+1].

Step 4: Chiral Separation

The product of Step 3 (50 mg, 102 μmol) in MeOH was purified by Chiral-HPLC using the following conditions: Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 53% B to 63% B in 8 min, 63% B; Wavelength: 254/220 nm; to afford:

Example 26: First eluting isomer (20 mg) as a white solid, LC-MS: (ES, m/z): RT=1.069 min, LCMS: m/z=486 [M+1], Chiral-HPLC (ES): RT=3.99 min; $^1H$ NMR (300 MHz, DMSO-$d_6$) δ ppm 10.96 (s, 1H), 8.97 (dd, J=4.0 Hz, 1.3 Hz, 1H), 8.55-8.36 (m, 4H), 8.15 (s, 1H), 7.95 (d, J=8.8 Hz, 1H), 7.65 (q, J=4.2 Hz, 1H), 7.55 (s, 1H), 7.35 (s, 1H), 4.80 (dd, J=9.0 Hz, 5.6 Hz, 1H), 3.93 (s, 3H), 3.02 (dd, J=9.0 Hz, 6.4 Hz, 1H), 2.04 (s, 6H), 1.54 (d, J=5.8 Hz, 3H), 0.99 (d, J=6.5 Hz, 3H).

Example 27: Second eluting isomer (22 mg) as a white solid, LC-MS: (ES, m/z): RT=1.066 min, LCMS: m/z=486 [M+1], Chiral-HPLC (ES): RT=5.53 min; $^1H$ NMR (300 MHz, DMSO-$d_6$) δ ppm 10.96 (s, 1H), 8.96 (dd, J=4.2 Hz, 1.6 Hz, 1H), 8.55-8.36 (m, 4H), 8.15 (s, 1H), 7.95 (d, J=9.2 Hz, 1H), 7.65 (q, J=4.3 Hz, 1H), 7.54 (d, J=1.2 Hz, 1H), 7.35 (d, J=0.7 Hz, 1H), 4.80 (dd, J=9.3 Hz, 5.9 Hz, 1H), 3.93 (s, 3H), 3.02 (dd, J=9.0 Hz, 6.8 Hz, 1H), 2.04 (s, 6H), 1.53 (d, J=5.8 Hz, 3H), 0.99 (d, J=6.6 Hz, 3H).

Example 28: 5-(((2R,3S)-3-(dimethylamino)butan-2-yl)oxy)-N-(5-fluoroquinolin-6-yl)-7-(1-methyl-1H-pyrazol-4-yl)quinazolin-4-amine and 5-(((2S,3R)-3-(dimethylamino)butan-2-yl)oxy)-N-(5-fluoroquinolin-6-yl)-7-(1-methyl-1H-pyrazol-4-yl)quinazolin-4-amine

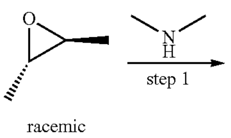

-continued

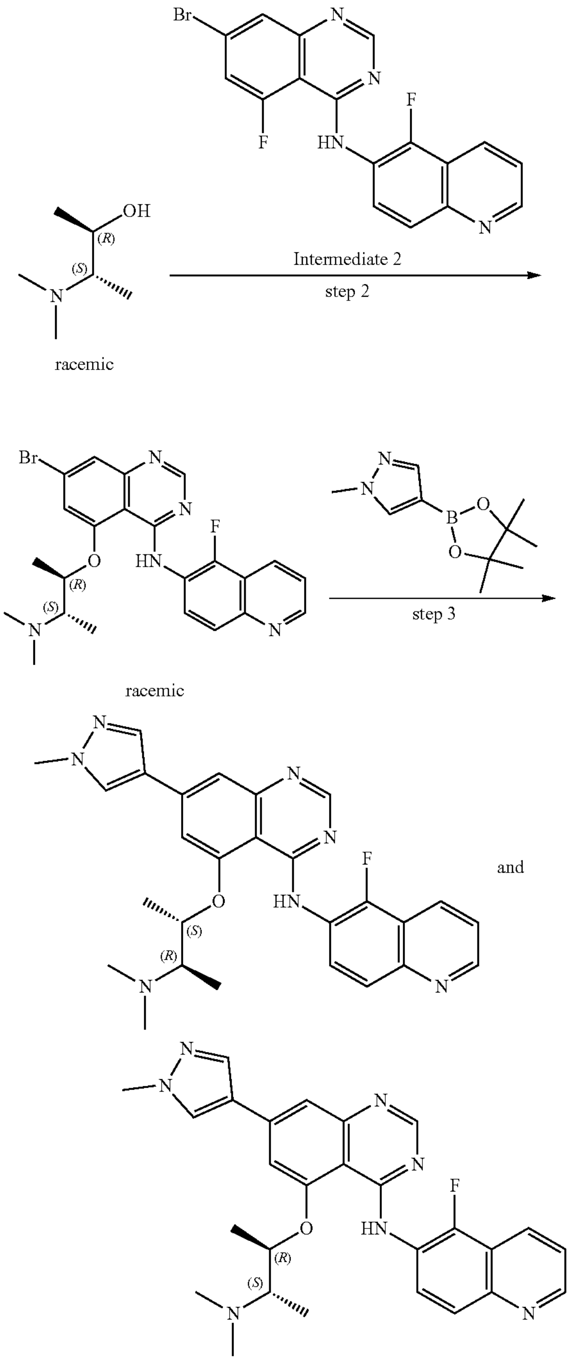

Step 1: (2R,3S)-3-(dimethylamino)butan-2-ol and (2S,3R)-3-(dimethylamino)butan-2-ol trans-rac-2,3-dimethyloxirane (1 g, 13.8 mmol) was added dropwise to dimethylamine (20 mL) at 0° C. After adding, the solution was warmed to 50° C. for 16 hr. The mixture was diluted with DCM (100 mL) and washed with brine (2×10 mL). The organic layer was dried with $Na_2SO_4$ and concentrated under vacuum to afford the title compound (1.2 g) as a colorless oil. LC-MS: (ES, m/z): RT=0.156 min, LCMS: m/z=118 [M+1]

Step 2: 7-bromo-5-(((2R,3S)-3-(dimethylamino)butan-2-yl)oxy)-N-(5-fluoroquinolin-6-yl)quinazolin-4-amine and 7-bromo-5-(((2S,3R)-3-(dimethylamino)butan-2-yl)oxy)-N-(5-fluoroquinolin-6-yl)quinazolin-4-amine NaH (92.6 mg, 3.86 mmol) was added slowly into solution the product of step 1 (452 mg, 3.86 mmol) in THF (10 mL) at rt. The resulting mixture was stirred at rt for 10 min. Intermediate 2 (300 mg, 774 μmol) was added to the mixture and was stirred at 80° C. for 24 hr. The solution was extracted with EA 3×50 mL and dried with $Na_2SO_4$. The crude product was purified by Prep-TLC eluting with DCM: MeOH=20:1 to afford the title compound (180 mg) as a yellow solid. LC-MS: (ES, m/z): RT=1.092 min, LCMS: m/z=485 [M+1]

Step 3: 5-(((2R,3S)-3-(dimethylamino)butan-2-yl)oxy)-N-(5-fluoroquinolin-6-yl)-7-(1-methyl-1H-pyrazol-4-yl)quinazolin-4-amine and 5-(((2S,3R)-3-(dimethylamino)butan-2-yl)oxy)-N-(5-fluoroquinolin-6-yl)-7-(1-methyl-1H-pyrazol-4-yl)quinazolin-4-amine $Pd(dppf)Cl_2$ (15.0 mg, 20.6 μmol) and $K_2CO_3$ (56.8 mg, 412 μmol) were added into solution of the product of step 2 (100 mg, 206 μmol) and 1-methyl-4-(4,4,5,5-tetramethyl-1,3,2-dioxaborolan-2-yl)-1H-pyrazole (85.7 mg, 412 μmol), the solution was stirred at 80° C. under $N_2$ for 3 hr. The reaction was extracted with EA 3×50 mL, the organic layer was dried with $Na_2SO_4$ and concentrated under vacuum, the crude product was purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 28% B to 62% B in 7 min, 62% B; Wavelength: 254/220 nm; This resulted in the title compound (45.6 mg) as a white solid. LC-MS: (ES, m/z): RT=1.149 min, LCMS: m/z=486; [M+1]; $^1H$ NMR (300 MHz, DMSO-d6) δ ppm 10.42 (s, 1H), 8.95 (dd, J=4.2 Hz, 1.5 Hz, 1H), 8.71 (t, J=8.9 Hz, 1H), 8.55-8.50 (m, 3H), 8.20 (s, 1H), 7.97 (d, J=9.2 Hz, 1H), 7.65 (q, J=4.2 Hz, 1H), 7.59 (d, J=1.1 Hz, 1H), 7.48 (d, J=1 Hz. 1H), 5.03 (t, J=5.7 Hz, 1H), 3.93 (s, 3H), 2.95 (t, J=6.8 Hz, 1H), 2.24 (s, 6H), 1.50 (d, J=6.1 Hz, 3H), 1.11 (d, J=6.5 Hz).

Example 29: (2R,3R)-3-((4-((5-fluoroquinolin-6-yl)amino)-7-(1-methyl-1H-pyrazol-4-yl)quinazolin-5-yl)oxy)butan-2-ol or (2S,3S)-3-((4-((5-fluoroquinolin-6-yl)amino)-7-(1-methyl-1H-pyrazol-4-yl)quinazolin-5-yl)oxy)butan-2-ol Example 30: (2S,3S)-3-((4-((5-fluoroquinolin-6-yl)amino)-7-(1-methyl-1H-pyrazol-4-yl)quinazolin-5-yl)oxy)butan-2-ol or (2R,3R)-3-((4-((5-fluoroquinolin-6-yl)amino)-7-(1-methyl-1H-pyrazol-4-yl)quinazolin-5-yl)oxy)butan-2-ol

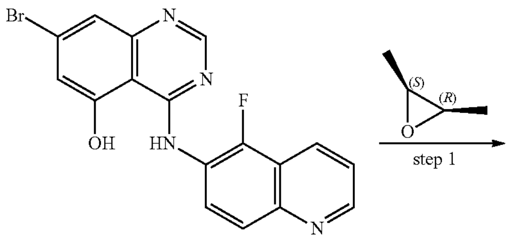

Intermediate 33

-continued

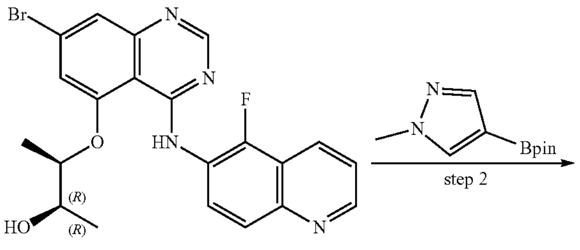

racemic

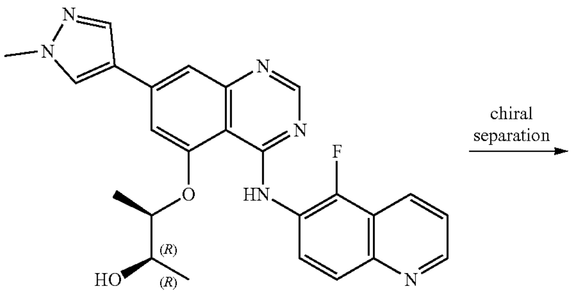

racemic

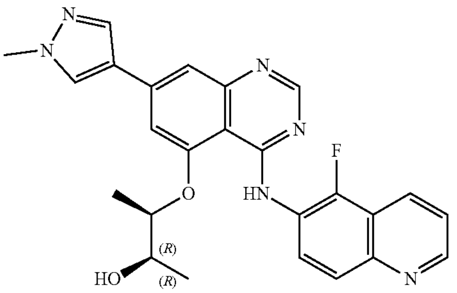

or

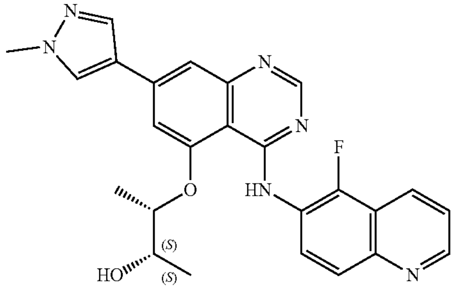

Step 1: ((2R,3R)-3-((7-bromo-4-((5-fluoroquinolin-6-yl)amino)quinazolin-5-yl)oxy)butan-2-ol and ((2S,3S)-3-((7-bromo-4-((5-fluoroquinolin-6-yl)amino)quinazolin-5-yl)oxy)butan-2-ol NaOH (206 mg, 5.18 mmol) was added to Intermediate 33 (400 mg, 1.038 mmol) and rel-(2R,3S)-2,3-dimethyloxirane (372 mg, 5.18 mmol) in dioxane/$H_2O$ (3 mL/1 mL) at rt. This resulting mixture was heated to 100° C. for 3 hr. The reaction mixture was diluted with EtOAc (120 mL) and washed with water (60 mL). The organic layer was dried over $Na_2SO_4$, filtered and evaporated to afford the title compound (505 mg) as a yellow solid. LC-MS: (ES, m/z): RT=0.930 min, LCMS: m/z=457 [M+1], Step 2: (2R,3R)-3-((4-((5-fluoroquinolin-6-yl)amino)-7-(1-methyl-1H-pyrazol-4-yl)quinazolin-5-yl)oxy)butan-2-ol and (2S,3S)-3-((4-((5-fluoroquinolin-6-yl)amino)-7-(1-methyl-1H-pyrazol-4-yl)quinazolin-5-yl)oxy)butan-2-ol Pd(dppf)$Cl_2$ (88.9 mg, 109 μmol) and $K_2CO_3$ (224 mg, 1.63 mmol) were added to the product of Step 1 (500 mg, 1.09 mmol) and 1-methyl-4-(4,4,5,5-tetramethyl-1,3,2-dioxaborolan-2-yl)-1H-pyrazole (339 mg, 1.63 mmol) in dioxane/$H_2O$ (3 mL/1 mL) at rt. The resulting mixture was heated to 80° C. for 3 h under $N_2$. The reaction mixture was diluted with EtOAc (120 mL) and washed with water (60 mL). The organic layer was dried over $Na_2SO_4$, filtered and evaporated to afford to afford the title compound (100 mg) as a yellow solid. LC-MS: (ES, m/z): RT=0.890 min, LCMS: m/z=459 [M+1], Chiral Separation: The product of step 2 (100 mg, 218 μmol) in MeOH was Purified by Prep-Chiral-HPLC with following conditions: Column: CHIRAL ART Amylose-SA, 2*25 cm, 5 μm; Mobile Phase A: Hex (0.5% 2M $NH_3$-MeOH)-HPLC, Mobile Phase B: EtOH-HPLC; Flow rate: 20 mL/min; Gradient: 30% B to 30% B in 15 min; Wavelength: 220/254 nm; RT1(min): 8.9; RT2(min): 13.76; Sample Solvent: EtOH-HPLC to afford:

Example 29: First eluting isomer as a yellow solid (14 mg). LC-MS: (ES, m/z): RT=1.415 min, LCMS: m/z=459 [M+1], Chiral-HPLC (ES): RT=1.729 min, 1H NMR (400 MHz, DMSO-d6) δ 10.54 (s, 1H), 8.96 (dd, J=4.3, 1.6 Hz, 1H), 8.57-8.46 (m, 4H), 8.17 (s, 1H), 7.95 (d, J=9.2 Hz, 1H), 7.66 (dd, J=8.5, 4.2 Hz, 1H), 7.57 (d, J=1.5 Hz, 1H), 7.44 (d, J=1.6 Hz, 1H), 5.30 (d, J=4.4 Hz, 1H), 4.90 (dd, J=6.3, 4.3 Hz, 1H), 3.96 (s, 4H), 1.45 (d, J=6.2 Hz, 3H), 1.25 (d, J=6.4 Hz, 3H).

Example 30: Second eluting isomer as a yellow solid (12 mg) LC-MS: (ES, m/z): RT=1.415 min, LCMS: m/z=459 [M+1], Chiral-HPLC (ES): RT=2.559 min, 1H NMR (400 MHz, DMSO-d6) δ 10.61 (s, 1H), 8.97 (dd, J=4.2, 1.6 Hz, 1H), 8.53 (d, J=9.9 Hz, 4H), 8.18 (s, 1H), 7.96 (d, J=9.2 Hz, 1H), 7.66 (dd, J=8.5, 4.2 Hz, 1H), 7.56 (d, J=1.5 Hz, 1H), 7.46 (d, J=1.6 Hz, 1H), 5.33 (s, 1H), 4.96-4.87 (m, 1H), 3.93 (s, 4H), 1.45 (d, J=6.2 Hz, 3H), 1.25 (d, J=6.4 Hz, 3H), 1.17 (d, J=6.5 Hz, 1H).

Example 31: (R)—N-(5-fluoroquinolin-6-yl)-5-((1-methoxypropan-2-yl)oxy)-7-(1-methyl-1H-pyrazol-4-yl)quinazolin-4-amine

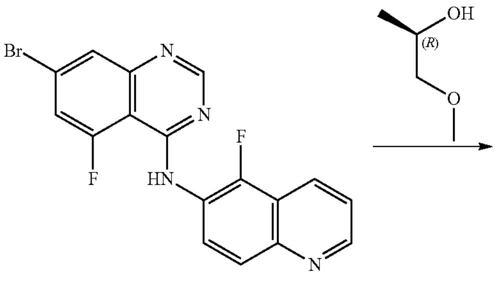

Interemediate 2

-continued

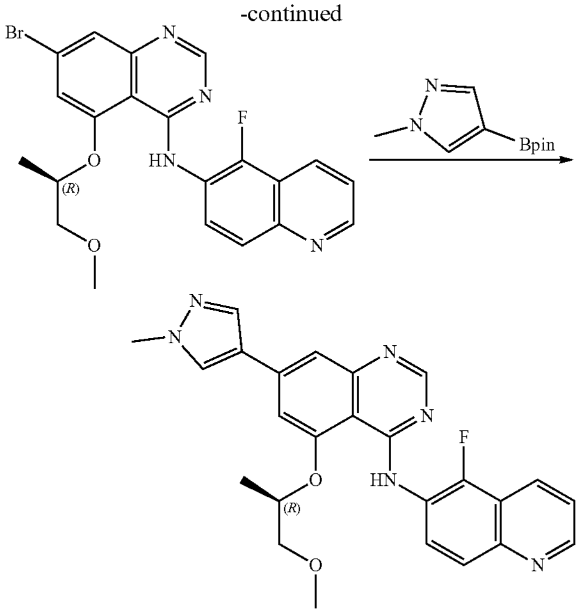

Step 1: (R)-7-bromo-N-(5-fluoroquinolin-6-yl)-5-((1-methoxypropan-2-yl)oxy)quinazolin-4-amine To a solution of Intermediate 2 and (2R)-1-methoxypropan-2-ol (209 mg, 2.32 mmol) in THF (10 mL), was added t-BuOK (260 mg, 2.32 mmol) under $N_2$ atmosphere. The resulting mixture was stirred at 80° C. for 3 hr. The reaction was concentrated and purified by prep-TLC (DCM:MeOH=10:1) to afford the title compound (390 mg, yield: 85.2%) as green solid. LC-MS: (ES, m/z): RT=1.588 min, LCMS: m/z=457[M+1].

Step 2: (R)-7-bromo-N-(5-fluoroquinolin-6-yl)-5-((1-methoxypropan-2-yl)oxy)quinazolin-4-amine To a solution of (R)-7-bromo-N-(5-fluoroquinolin-6-yl)-5-((1-methoxypropan-2-yl)oxy)quinazolin-4-amine (200 mg, 437 μmol) in dioxane (4 mL) and $H_2O$ (1 mL), was added 1-methyl-4-(4,4,5,5-tetramethyl-1,3,2-dioxaborolan-2-yl)-1H-pyrazole (118 mg, 568 μmol), $K_2CO_3$ (132 mg, 961 μmol) and Pd(dppf)$Cl_2$ (47.9 mg, 65.5 μmol) under $N_2$. The resulting solution was stirred at 100° C. for 3 hr. The mixture was diluted with EA (20 mL*3) and washed with brine (10 mL). The organic layer was dried with $Na_2SO_4$ and concentrated under vacuum. The residue was purified by prep-TLC (DCM:MeOH=10:1) to give the crude product. The crude product was purified by prep-HPLC (Column: YMC-Actus Triart C18, 30*150 mm, 5 μm; Mobile Phase A: water (10 mmol/L $NH_4HCO_3$+0.1% $NH_3·H_2O$), Mobile Phase B: ACN; Flow rate: 60 mL/min; Gradient: 45% B to 55% B in 8 min, 55% B; Wavelength: 254/220 nm) to afford the title compound (69.5 mg, yield: 90.9%) as a white solid. LC-MS: (ES, m/z): RT=1.337 min, LCMS: m/z=459 [M+1], 1H NMR (400 MHz, DMSO-d6) δ 10.38 (s, 1H), 8.95 (dd, J=4.2, 1.7 Hz, 1H), 8.87-8.78 (m, 1H), 8.57-8.47 (m, 3H), 8.18 (s, 1H), 7.97 (d, J=9.2 Hz, 1H), 7.65 (dd, J=8.5, 4.1 Hz, 1H), 7.61 (d, J=1.5 Hz, 1H), 7.49 (s, 1H), 5.28 (d, J=5.8 Hz, 1H), 3.92 (s, 3H), 3.27 (s, 3H), 3.78-3.73 (m, 2H), 1.50 (d, J=6.2 Hz, 3H).

Example 32: 5-(((1S,5S)-3-oxabicyclo[3.1.0]hexan-1-yl)methoxy)-N-(5-fluoroquinolin-6-yl)-7-(1-methyl-1H-pyrazol-4-yl)quinazolin-4-amine or 5-(((1R,5R)-3-oxabicyclo[3.1.0]hexan-1-yl)methoxy)-N-(5-fluoroquinolin-6-yl)-7-(1-methyl-1H-pyrazol-4-yl)quinazolin-4-amine

Example 33: 5-(((1R,5R)-3-oxabicyclo[3.1.0]hexan-1-yl)methoxy)-N-(5-fluoroquinolin-6-yl)-7-(1-methyl-1H-pyrazol-4-yl)quinazolin-4-amine or 5-(((1S,5S)-3-oxabicyclo[3.1.0]hexan-1-yl)methoxy)-N-(5-fluoroquinolin-6-yl)-7-(1-methyl-1H-pyrazol-4-yl)quinazolin-4-amine

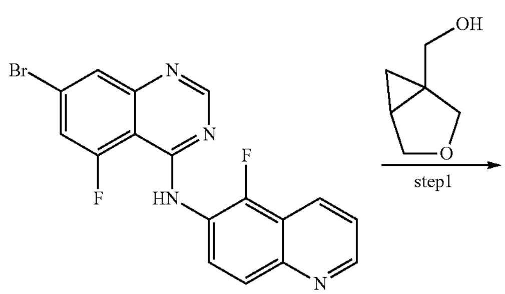

Intermediate 2

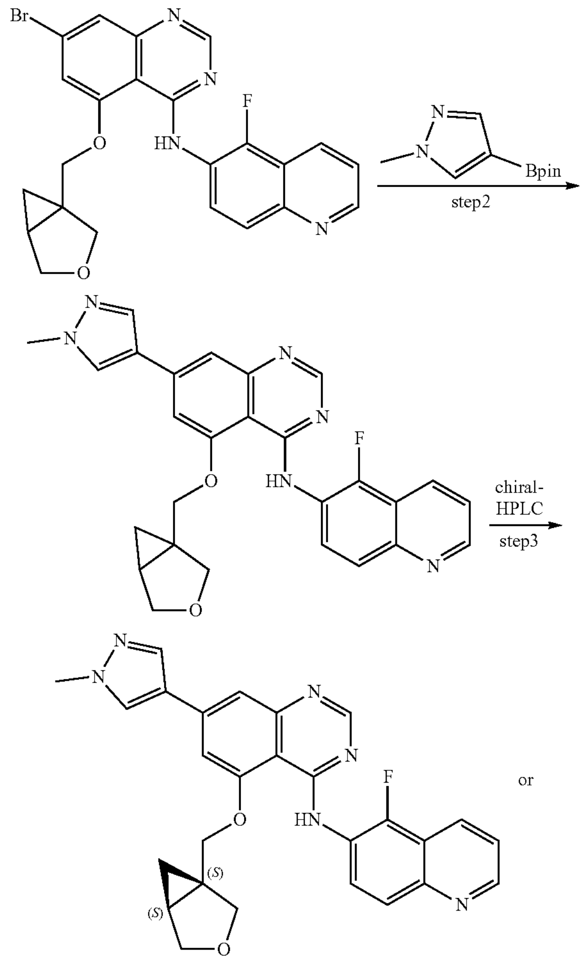

or

-continued

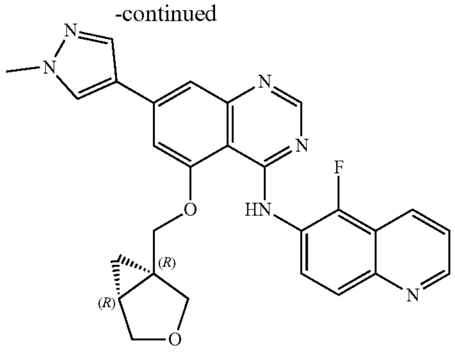

Step 1: 5-((3-oxabicyclo[3.1.0]hexan-1-yl)methoxy)-7-bromo-N-(5-fluoroquinolin-6-yl)quinazolin-4-amine t-BuOK (86.6 mg, 774 μmol) was added to Intermediate 2 (150 mg, 387 μmol) and (3-oxabicyclo[3.1.0]hexan-1-yl)methanol (88.3 mg, 774 μmol) in THF (10 mL) at rt. The resulting mixture was stirred at 80° C. for 3 hr under $N_2$. The mixture was diluted with EA 100 mL and washed with brine 50 mL*2, the organic layer was dried with $Na_2SO_4$ and concentrated under vacuum. The residue was purified by a silica gel column using DCM: EA=15:1 to afford the title compound (100 mg, yield: 66.7%) as a light yellow solid. LC-MS: (ES, m/z): RT=1.182 min, LCMS: m/z=455 [M+1].

Step 2: 5-((3-oxabicyclo[3.1.0]hexan-1-yl)methoxy)-N-(5-fluoroquinolin-6-yl)-7-(1-methyl-1H-pyrazol-4-yl)quinazolin-4-amine The reaction mixture of Pd(dppf)$Cl_2$ (16.8 mg, 20.7 μmol), 1-methyl-4-(4,4,5,5-tetramethyl-1,3,2-dioxaborolan-2-yl)-1H-pyrazole (64.5 mg, 310 μmol), 5-((3-oxabicyclo[3.1.0]hexan-1-yl)methoxy)-7-bromo-N-(5-fluoroquinolin-6-yl)quinazolin-4-amine (100 mg, 207 μmol), $K_2CO_3$ (42.7 mg, 310 μmol) in $H_2O$ (4 mL) and dioxane (16 mL) at rt. The resulting mixture was stirred at 80° C. for 2 h under $N_2$. The mixture was diluted with DCM 100 mL and washed with water 50 mL*2, the organic layer was dried with $Na_2SO_4$ and concentrated under vacuum. The residue was purified by a silica gel column using DCM:MeOH=20:1. The residue was purified by prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 29% B to 62% B in 7 min, 62% B; Wavelength: 254/220 nm; This resulted in the title compound (50 mg) as a white solid. LC-MS: (ES, m/z): RT=1.171 min, LCMS: m/z=457 [M+1].

Step 3: Chiral Separation

The product of step 2 (50 mg, 103 μmol) in MeOH was purified by prep-Chiral-HPLC with following conditions: Column: Column: NB_ASA CHIRAL ART Cellulose-SC (IC), 5*25 cm, 10 μm; Mobile Phase A: Hex: DCM=3:1 (0.5% 2M $NH_3$-MeOH)-HPLC, Mobile Phase B: MeOH-HPLC; Flow rate: 20 mL/min; Gradient: 20% B to 20% B in 20 min; Wavelength: 220/254 nm to afford:

Example 32: First eluting isomer (22.5 mg): LC-MS: (ES, m/z): RT=1.251 min, LCMS: m/z=457 [M+1]. Chiral-HPLC R=1.913, $^1H$ NMR (400 MHz, DMSO-$d_6$) δ 10.57 (s, 1H), 8.97 (dd, J=4.3, 1.7 Hz, 1H), 8.56-8.49 (m, 1H), 8.46 (d, J=5.5 Hz, 2H), 8.44-8.36 (m, 1H), 8.13 (d, J=0.8 Hz, 1H), 7.95 (d, J=9.2 Hz, 1H), 7.66 (dd, J=8.5, 4.2 Hz, 1H), 7.58 (d, J=1.5 Hz, 1H), 7.15 (d, J=1.6 Hz, 1H), 5.72 (d, J=5.1 Hz, 1H), 5.20 (s, 1H), 4.61 (t, J=5.5 Hz, 1H), 3.92 (s, 3H), 2.37 (d, J=7.2 Hz, 1H), 2.24 (s, 2H), 2.14-2.04 (m, 1H).

Example 33: Second eluting isomer (20.2 mg), LC-MS: (ES, m/z): RT=0.898 min, LCMS: m/z=457 [M+1]. Chiral-HPLC R=3.119, $^1$H NMR (400 MHz, DMSO-$d_6$) δ 10.57 (s, 1H), 8.97 (dd, J=4.3, 1.7 Hz, 1H), 8.57-8.50 (m, 1H), 8.46 (d, J=6.0 Hz, 2H), 8.40 (t, J=8.7 Hz, 1H), 8.13 (d, J=0.9 Hz, 1H), 7.95 (d, J=9.2 Hz, 1H), 7.66 (dd, J=8.5, 4.2 Hz, 1H), 7.58 (d, J=1.5 Hz, 1H), 7.15 (d, J=1.6 Hz, 1H), 5.72 (d, J=5.2 Hz, 1H), 5.20 (s, 1H), 4.65-4.58 (m, 1H), 3.92 (s, 3H), 2.38 (s, 1H), 2.22 (s, 2H), 2.14-2.03 (m, 1H).

Example 34: 5-(2-(dimethylamino)ethoxy)-N-(5-fluoroquinolin-6-yl)-7-(1-methyl-1H-pyrazol-4-yl)quinazolin-4-amine

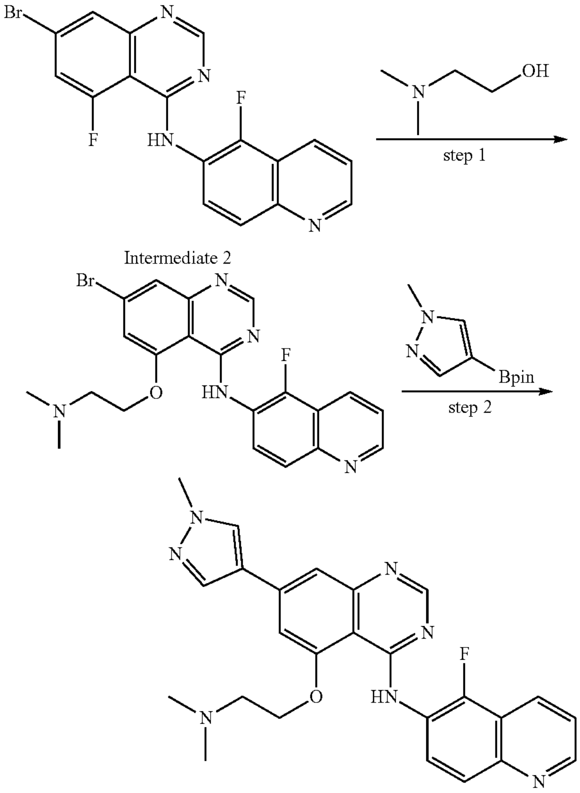

Step 1: 7-bromo-5-(2-(dimethylamino)ethoxy)-N-(5-fluoroquinolin-6-yl)quinazolin-4-amine NaH (123 mg, 3.09 mmol) was added to 2-(dimethylamino) ethan-1-ol (275 mg, 3.09 mmol) in THF (10 mL) at 0° C. The resulting mixture was stirred at 0° C. Intermediate 2 (300 mg, 774 μmol) was added to the mixture at this temperature. The resulting mixture was heated at 80° C. for 3 hr. The reaction mixture was diluted with EtOAc (120 mL) and washed with water (60 mL). The organic layer was dried over $Na_2SO_4$, filtered and evaporated to afford the title compound (344.5 mg) as a yellow solid. LC-MS: (ES, m/z): RT=0.860 min, LCMS: m/z=456 [M+1].

Step 2: 5-(2-(dimethylamino)ethoxy)-N-(5-fluoroquinolin-6-yl)-7-(1-methyl-1H-pyrazol-4-yl)quinazolin-4-amine $Pd(dppf)Cl_2$ (35.7 mg, 43.8 μmol) and $K_2CO_3$ (90.6 mg, 657 μmol) were add to 7-bromo-5-(2-(dimethylamino) ethoxy)-N-(5-fluoroquinolin-6-yl) quinazolin-4-amine (200 mg, 438 μmol) and 1-methyl-4-(3,3,4,4-tetramethylborolan-1-yl)-1H-pyrazole (134 mg, 657 μmol) in dioxane/$H_2O$ (9 mL/3 mL) at rt. The resulting mixture was heated to 80° C. for 3 h under $N_2$. The reaction mixture was diluted with EtOAc (120 mL) and washed with water (60 mL). The organic layer was dried over $Na_2SO_4$, filtered and evaporated to give the title compound (32.5 mg) as a yellow solid. LC-MS: (ES, m/z): RT=0.733 min, LCMS: m/z=458 [M+1]. 1H NMR (400 MHz, DMSO-d6) δ 10.55 (s, 1H), 8.97 (dd, J=4.2, 1.7 Hz, 1H), 8.66 (s, 3H), 8.56-8.50 (m, 1H), 8.46 (d, J=10.7 Hz, 1H), 8.33 (t, J=8.7 Hz, 1H), 8.17 (d, J=0.8 Hz, 1H), 7.95 (d, J=9.1 Hz, 1H), 7.66 (dd, J=8.5, 4.2 Hz, 1H), 4.49 (t, J=5.4 Hz, 2H), 3.92 (s, 3H), 2.82 (t, J=5.4 Hz, 2H), 2.17 (s, 6H).

Example 35: (S)—N-(5-fluoroquinolin-6-yl)-7-(1-methyl-1H-pyrazol-4-yl)-5-((1-methylpiperidin-3-yl)oxy)quinazolin-4-amine

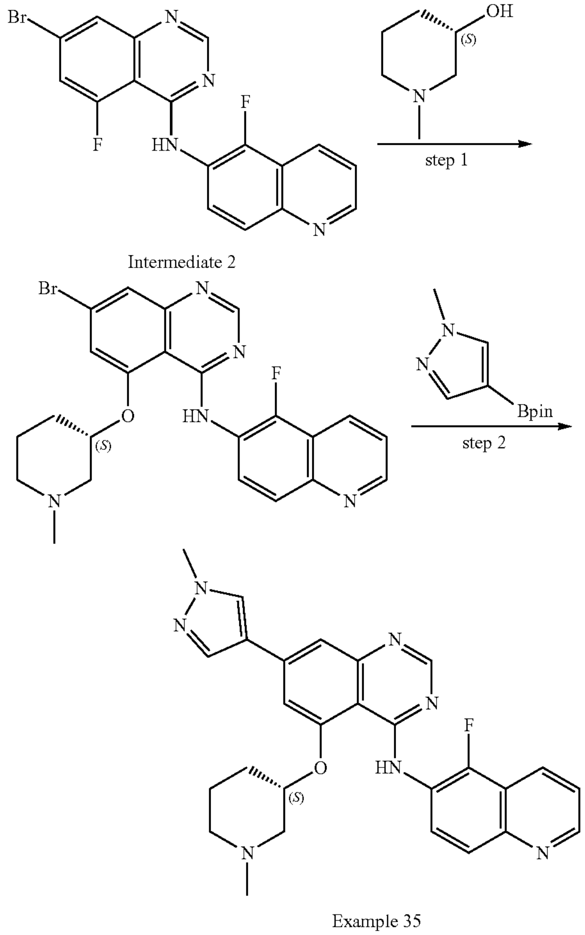

Example 35

Step 1: (S)-7-bromo-N-(5-fluoroquinolin-6-yl)-5-((1-methylpiperidin-3-yl)oxy)quinazolin-4-amine NaH (123 mg, 3.09 mmol) was added to (3S)-1-methylpiperidin-3-ol (355 mg, 3.09 mmol) in THF at 0° C. The reaction mixture was stirred at this temperature for 10 min. Intermediate 2 (300 mg, 774 μmol) was added to the mixture at 0° C. The resulting mixture was heated at 80° C. for 3 hr. The reaction mixture was diluted with EtOAc (120 mL) and washed with water (60 mL). The organic layer was dried over $Na_2SO_4$, filtered and evaporated to afford the title compound (442.1 mg) as a white solid. LC-MS: (ES, m/z): RT=1.497 min, LCMS: m/z=482 [M+1], Step 2: (S)—N-(5-fluoroquinolin-6-yl)-7-(1-methyl-1H-pyrazol-4-yl)-5-((1-methylpiperidin-3-yl)oxy)quinazolin-4-amine Pd(dppf)$Cl_2$ (16.8 mg, 20.7 μmol) and $K_2CO_3$ (42.7 mg, 310 μmol) were added to (S)-7-bromo-N-(5-fluoroquinolin-6-yl)-5-((1-methylpiperidin-3-yl)oxy)quinazolin-4-amine (100 mg, 207 μmol) and 1-methyl-4-(3,3,4,4-tetramethylborolan-1-yl)-1H-pyrazole (63.2 mg, 310 μmol) in dioxane/$H_2O$ (3 mL/1 mL) at rt. This resulting mixture was heated to 80° C. for 3 h under $N_2$. The reaction mixture was diluted with EtOAc (120 mL) and washed with water (60 mL). The organic layer was dried over $Na_2SO_4$, filtered and evaporated under vacuum. The crude product was purified by Prep-TLC eluting with DCM:MeOH=20:1. The residue was purified by Prep-HPLC using the following conditions: Column: YMC-Actus Triart C18, 30*150 mm, 5 μm; Mobile Phase A: Water (0.1% FA), Mobile Phase B: ACN; Flow rate: 60 mL/min; Gradient: 5% B to 30% B in 8 min, 30% B; Wavelength: 254/220 nm; to afford the title compound (7.8 mg) as a white solid. LC-MS: (ES, m/z): RT=1.132 min, LCMS: m/z=484 [M+1], 1H NMR (400 MHz, DMSO-d6) δ 10.72 (s, 1H), 8.97 (dd, J=4.2, 1.6 Hz, 1H), 8.57-8.50 (m, 3H), 8.24 (t, J=8.6 Hz, 1H), 8.16 (s, 1H), 7.94 (d, J=9.1 Hz, 1H), 7.66 (dd, J=8.5, 4.2 Hz, 1H), 7.58 (d, J=1.5 Hz, 1H), 7.46 (d, J=1.6 Hz, 1H), 5.22 (s, 1H), 3.92 (s, 3H), 2.95 (d, J=11.8 Hz, 1H), 2.66 (s, 2H), 2.45 (d, J=14.5 Hz, 5H), 1.92 (s, 1H), 1.79 (t, J=11.6 Hz, 1H), 1.69 (d, J=13.2 Hz, 1H).

Example 36: (R)—N-(5-fluoroquinolin-6-yl)-7-(1-methyl-1H-pyrazol-4-yl)-5-((1-methylpiperidin-3-yl)oxy)quinazolin-4-amine

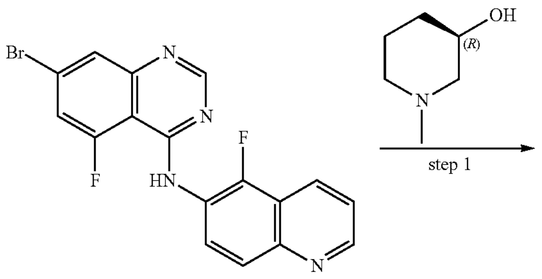

-continued

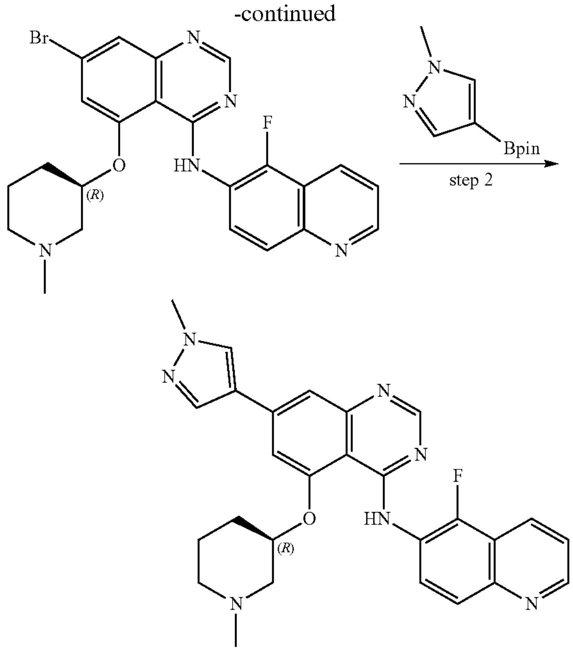

Step 1: (R)-7-bromo-N-(5-fluoroquinolin-6-yl)-5-((1-methylpiperidin-3-yl)oxy)quinazolin-4-amine NaH (123 mg, 3.09 mmol) was added to (3R)-1-methylpiperidin-3-ol (355 mg, 3.09 mmol) in THF (10 mL) at 0° C. The resulting mixture was stirred at 0° C. for 10 min. Intermediate 2 (300 mg, 774 μmol) was added to the mixture at this temperature. The resulting mixture was heated at 80° C. for 3 hours under $N_2$. The reaction mixture was diluted with EtOAc (120 mL) and washed brine (60 mL). The organic layer was dried over $Na_2SO_4$, filtered and evaporated to afford the title compound (364 mg) as an off-white solid. LC-MS: (ES, m/z): RT=1.502 min, LCMS: m/z=482 [M+1], Step 2: (R)—N-(5-fluoroquinolin-6-yl)-7-(1-methyl-1H-pyrazol-4-yl)-5-((1-methylpiperidin-3-yl)oxy)quinazolin-4-amine Pd(dppf)$Cl_2$ (16.8 mg, 20.7 μmol) and $K_2CO_3$ (42.7 mg, 207 μmol) were added to (R)-7-bromo-N-(5-fluoroquinolin-6-yl)-5-((1-methylpiperidin-3-yl)oxy)quinazolin-4-amine (100 mg, 207 μmol) and 1-methyl-4-(3,3,4,4-tetramethylborolan-1-yl)-1H-pyrazole (63.2 mg, 310 μmol) in dioxane/$H_2O$ (3 mL/1 mL) at rt. The resulting mixture was heated at 80° C. for 3 hours under $N_2$. The reaction mixture was diluted with EtOAc (120 mL) and washed with water (60 mL). The organic layer was dried over $Na_2SO_4$, filtered and concentrated under vacuum. The crude product was purified by Prep-TLC eluting with DCM:MeOH=20:1. The residue was purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 28% B to 64% B in 7 min, 64% B; Wavelength: 254/220 nm; to give the title compound (15.9 mg) as an off-white solid. LC-MS: (ES, m/z): RT=1.128 min, LCMS: m/z=484 [M+1], 1H NMR (400 MHz, DMSO-d6) δ 10.72 (s, 1H), 8.97 (dd, J=4.2, 1.7 Hz, 1H), 8.53 (dd, J=8.5, 1.7 Hz, 3H), 8.16 (s, 2H), 7.94 (d, J=9.2 Hz, 1H), 7.65 (dd, J=8.5, 4.2 Hz, 1H), 7.58 (d, J=1.5 Hz, 1H), 7.46 (d, J=1.6 Hz, 1H), 5.22 (s, 1H), 3.92 (s, 3H), 2.95 (d, J=11.5 Hz, 1H), 2.45 (d, J=13.0 Hz, 2H), 2.14 (d, J=10.5 Hz, 5H), 1.79 (t, J=11.7 Hz, 1H), 1.69 (d, J=13.6 Hz, 1H), 1.57-1.49 (m, 1H).

Example 37: (S)-5-((3-(dimethylamino)-1,1-difluoropropan-2-yl)oxy)-N-(5-fluoroquinolin-6-yl)-7-(1-methyl-1H-pyrazol-4-yl)quinazolin-4-amine or (R)-5-((3-(dimethylamino)-1,1-difluoropropan-2-yl)oxy)-N-(5-fluoroquinolin-6-yl)-7-(1-methyl-1H-pyrazol-4-yl)quinazolin-4-amine Example 38: (R)-5-((3-(dimethylamino)-1,1-difluoropropan-2-yl)oxy)-N-(5-fluoroquinolin-6-yl)-7-(1-methyl-1H-pyrazol-4-yl)quinazolin-4-amine or (S)-5-((3-(dimethylamino)-1,1-difluoropropan-2-yl)oxy)-N-(5-fluoroquinolin-6-yl)-7-(1-methyl-1H-pyrazol-4-yl)quinazolin-4-amine

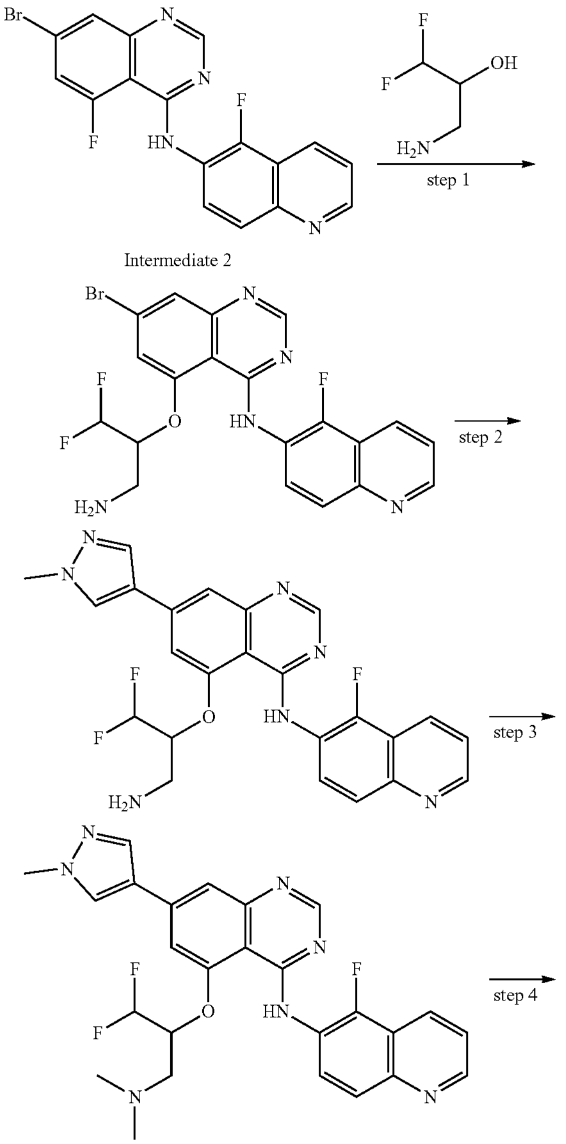

-continued

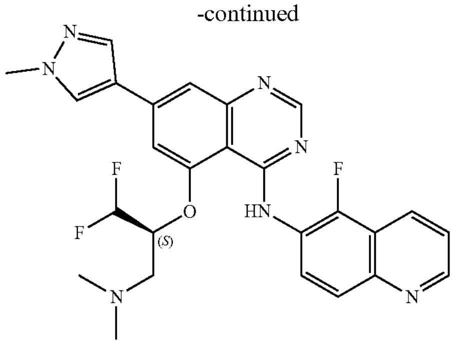

or

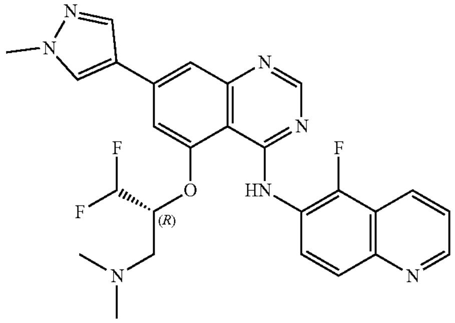

Step 1: 5-((3-amino-1,1-difluoropropan-2-yl)oxy)-7-bromo-N-(5-fluoroquinolin-6-yl)quinazolin-4-amine NaH (41.1 mg, 1.03 mmol) was added to 3-amino-1,1-difluoropropan-2-ol (114 mg, 1.03 mmol) in THF then stirred for 10 min. Intermediate 2 (200 mg, 0.5165 mmol) was added into the reaction mixture and stirred at 80° C. for 3 hours. The reaction was quenched into ice and water and extracted with EA. The crude compound was purified by Prep-TLC: (DCM:MeOH=10:1) to afford the title compound (150 mg, yield: 60.9%) as a light yellow solid. LC-MS: (ES, m/z): RT=1.168 min, LCMS: m/z=478 [M+1]

Step 2: 5-((3-amino-1,1-difluoropropan-2-yl)oxy)-N-(5-fluoroquinolin-6-yl)-7-(1-methyl-1H-pyrazol-4-yl)quinazolin-4-amine Into a 8 ml vial and maintained a $N_2$ atmosphere was added 5-((3-amino-1,1-difluoropropan-2-yl)oxy)-7-bromo-N-(5-fluoroquinolin-6-yl)quinazolin-4-amine (140 mg, 0.2927 mmol)), 1-methyl-4-(3,3,4,4-tetramethylborolan-1-yl)-1H-pyrazole (72.6 mg, 351 μmol), Pd(dppf)$Cl_2$ (23.8 mg, 29.2 μmol) and $K_2CO_3$ (80.7 mg, 585 μmol) in 1,4-dioxane (4 mL) and $H_2O$ (1 mL). The mixture was stirred at 80° C. for 3 hours. The solution was extracted by EA and purified by Prep-TLC: (DCM: MeOH=10:1) to afford the title compound (110 mg, yield: 78.5%) as a white solid. LC-MS: (ES, m/z): RT=0.538 min, LCMS: m/z=480 [M+1]

Step 3: 5-((3-(dimethylamino)-1,1-difluoropropan-2-yl)oxy)-N-(5-fluoroquinolin-6-yl)-7-(1-methyl-1H-pyrazol-4-yl)quinazolin-4-amine 5-((3-amino-1,1-difluoropropan-2-yl)oxy)-N-(5-fluoroquinolin-6-yl)-7-(1-methyl-1H-pyrazol-4-yl)quinazolin-4-amine (100 mg, 0.2085 mmol)) and formaldehyde solution (0.5 ml) was added in DCM. Then STAB (132 mg, 625 μmol) was added into the reaction at room temperature. The reaction was stirred at room temperature for 1 hour. The reaction was quenched with $NH_4Cl$ solution and extracted by DCM. The crude compound was purified by prep-HPLC: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 33% B to 72% B in 7 min, 72% B; Wavelength: 254/220 nm; RT1(min): 6.33, to afford the title compound (45 mg, yield: 42.8%) as a white solid. LC-MS: (ES, m/z): RT=1.272 min, LCMS: m/z=506 [M+1]

Step 4: Chiral Separation 5-((3-(dimethylamino)-1,1-difluoropropan-2-yl)oxy)-N-(5-fluoroquinolin-6-yl)-7-(1-methyl-1H-pyrazol-4-yl)quinazolin-4-amine (40 mg, 0.07881 mmol) was separated by chiral HPLC: Column: CHIRALPAK IG, 2*25 cm, 5 μm; Mobile Phase A: Hex: DCM=3:1 (0.5% 2M NH3-MeOH)-HPLC, Mobile Phase B: EtOH-HPLC; Flow rate: 20 mL/min; Gradient: 20% B to 20% B in 50 min; Wavelength: 220/254 nm; RT1(min): 18.6; RT2(min): 28.5; Sample Solvent: EtOH-HPLC; Injection Volume: 1.5 mL; Number Of Runs: 3, to afford:

Example 37: First eluting isomer, (5 mg), LC-MS: (ES, m/z): RT=0.779 min, LCMS: m/z=508[M+1]; Chiral-HPLC: 3.678; $^1H$ NMR (300 MHz, Methanol-$d_4$) δ 8.95-8.83 (m, 2H), 8.61 (d, J=8.5 Hz, 1H), 8.54 (s, 1H), 8.27 (s, 1H), 8.09 (d, J=0.8 Hz, 1H), 7.96 (d, J=9.1 Hz, 1H), 7.71-7.59 (m, 3H), 6.39 (d, J=2.5 Hz, 1H), 5.45 (d, J=11.4 Hz, 1H), 4.01 (s, 3H), 3.15 (dd, J=13.8, 8.4 Hz, 1H), 2.87 (dd, J=13.7, 4.0 Hz, 1H), 2.35 (s, 6H).

Example 38: Second eluting isomer, (5 mg), LC-MS: (ES, m/z): RT=0.757 min, LCMS: m/z=508 [M+1], Chiral-HPLC: 4.938, (s, 1H), 8.27 (s, 1H), 8.09 (d, J=0.8 Hz, 1H), 8.00-7.91 (m, 1H), 7.71-7.58 (m, 3H), 6.39 (d, J=2.4 Hz, 0H), 5.45 (d, J=10.6 Hz, 1H), 4.00 (s, 3H), 3.15 (dd, J=13.7, 8.3 Hz, 1H), 2.87 (dd, J=13.7, 3.9 Hz, 1H), 2.35 (s, 6H).

Example 39: (R)—N-(5,7-difluoroquinolin-6-yl)-5-((1-(dimethylamino)propan-2-yl)oxy)-7-(2-oxa-6-azaspiro[3.3]heptan-6-yl)quinazolin-4-amine

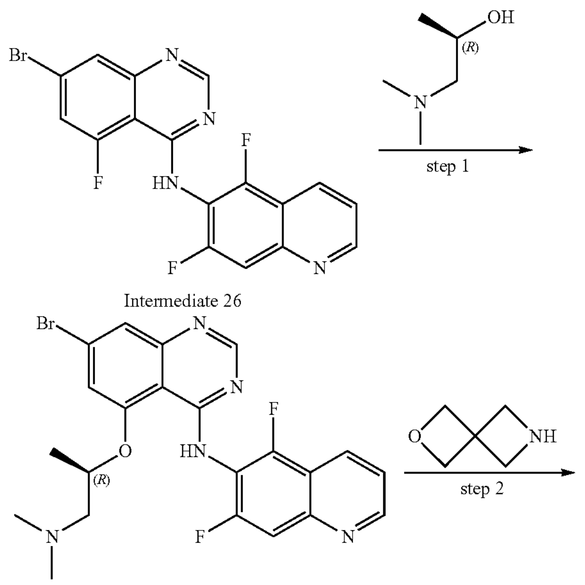

-continued

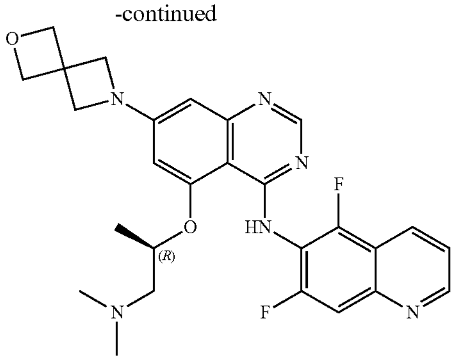

Step 1: (R)-7-bromo-N-(5,7-difluoroquinolin-6-yl)-5-((1-(dimethylamino) propan-2-yl)oxy)quinazolin-4-amine To a mixture of (2R)-1-(dimethyl amino) propan-2-ol (76.2 mg, 739 μmol) in THF (10 mL) was added NaH (23.6 mg, 985 μmol) at 0° C. Intermediate 26 (200 mg, 493 μmol) was added to the reaction mixture at 25° C., the reaction mixture was stirred at 80° C. for 4 hrs. The reaction mixture was added to the ice water, the reaction mixture was concentrated under vacuum. The residue was purified by flash chromatography to give the title compound (110 mg, yield: 45.8%) as a white solid. LC-MS: (ES, m/z): RT=0.814 min, LCMS: m/z=489 [M+1].

Step 2: (R)—N-(5,7-difluoroquinolin-6-yl)-5-((1-(dimethylamino)propan-2-yl)oxy)-7-(2-oxa-6-azaspiro[3.3]heptan-6-yl)quinazolin-4-amine To a solution of (R)-7-bromo-N-(5,7-difluoroquinolin-6-yl)-5-((1-(dimethylamino)propan-2-yl)oxy)quinazolin-4-amine (110 mg, 225 μmol) in 1,4-dioxane (5 ml) was added 2-oxa-6-azaspiro [3.3] heptane (33.4 mg, 337 μmol), $Cs_2CO_3$ (219 mg, 675 μmol) and RuPhos Pd (18.8 mg, 22.5 μmol) under nitrogen. The mixture was stirred at 100° C. for 4 hours. The reaction mixture was cooled to room temperature. The resulting solution was diluted with 20 mL of water and extracted with 2×20 mL of ethyl acetate and the organic layers combined. The resulting mixture was washed with 20 mL of brine. The mixture was dried over anhydrous sodium sulfate and concentrated under vacuum. The crude product was purified by Prep-HPLC with the following conditions: Column: Bridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 32% B to 52% B in 8 min; Wavelength: 254; 220 nm to afford the title compound (13.1 mg, yield: 11.5%). LC-MS: (ES, m/z): RT=0.792 min, LCMS: m/z=507 [M+1], $^1H$ NMR (400 MHz, DMSO, 23° C.) δ 1.46 (3H, d), 2.18 (6H, d), 2.68 (1H, s), 4.21 (4H, s), 4.77 (4H, s), 4.94 (1H, s), 6.17 (1H, d), 6.32 (1H, s), 7.65 (1H, m), 7.82 (1H, d), 8.15 (1H, s), 8.52 (1H, m), 9.01 (1H, m), 9.93 (1H, s).

Example 40: (R)-5-((1-(dimethylamino)propan-2-yl)oxy)-7-(1-methyl-1H-pyrazol-4-yl)-N-(1,8-naphthyridin-3-yl)quinazolin-4-amine

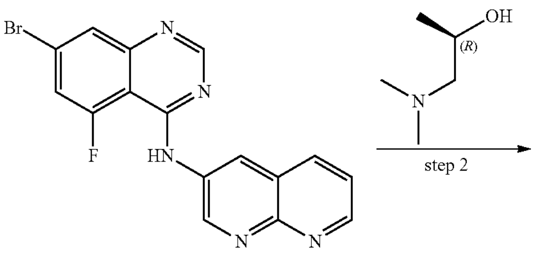

Intermediate 25

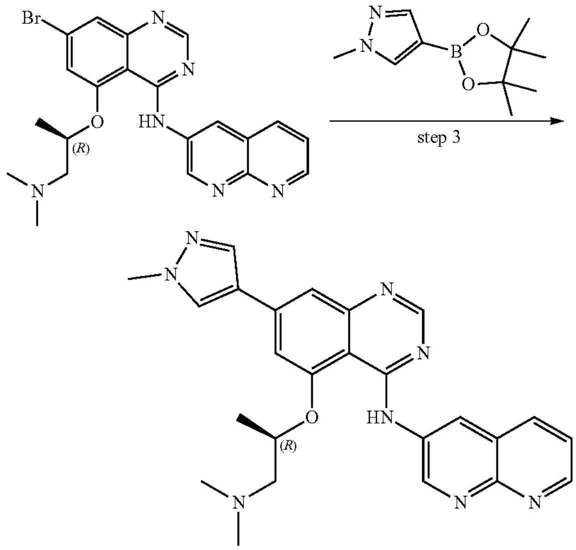

Step 1: (R)-7-bromo-5-((1-(dimethylamino)propan-2-yl)oxy)-N-(1,8-naphthyridin-3-yl)quinazolin-4-amine To a solution of (2R)-1-(dimethylamino)propan-2-ol_(61 mg, 594 μmol) in DMF (10 mL) was added NaH_(60%, 24 mg, 594 μmol). Stirred at 25° C. for 10 min. Then added Intermediate 25_(110 mg, 297 μmol). Stirred at 80° C. for 2 h. Quenched with water. Concentrated to dryness. The residue was purified on prep-TLC eluting with DCM: MeOH=15:1 to afford the title compound (60 mg, yield: 44%) as a yellow solid. LC-MS: (ES, m/z): RT=1.247 min, LCMS: m/z=453,455 [M+1]

Step 2: (R)-5-((1-(dimethylamino)propan-2-yl)oxy)-7-(1-methyl-1H-pyrazol-4-yl)-N-(1,8-naphthyridin-3-yl)quinazolin-4-amine A mixture of (R)-7-bromo-5-((1-(dimethylamino)propan-2-yl)oxy)-N-(1,8-naphthyridin-3-yl)quinazolin-4-amine_ (55 mg, 121 μmol), 1-methyl-4-(4,4,5,5-tetramethyl-1,3,2-dioxaborolan-2-yl)-1H-pyrazole_(38 mg, 182 μmol), $Pd(PPh_3)_4$ (15 mg, 12.9 μmol) and $K_3PO_4$ (38 mg, 182 μmol) in dioxane (5 mL) and $H_2O$ (2 mL) was stirred at 80° C. for 2 h. Concentrated to dryness. The residue was purified on prep-TLC eluting with DCM:MeOH=20:1 to afford the title compound (17.8 mg) as a light yellow solid. LC-MS: (ES, m/z): RT=1.292 min, LCMS: m/z=455 [M+1], $^1$H NMR (400 MHz, DMSO-d6): δ 10.82 (s, 1H), 9.24 (d, J=2.8 Hz, 1H), 9.08 (d, J=2.8 Hz, 1H), 9.00 (dd, J=4.3, 2.0 Hz, 1H), 8.61 (s, 1H), 8.54-8.48 (m, 1H), 8.49 (s, 1H), 8.17 (s, 1H), 7.64 (dd, J=8.1, 4.2 Hz, 1H), 7.60 (d, J=1.4 Hz, 1H), 7.42 (d, J=1.6 Hz, 1H), 5.11 (dd, J=10.2, 5.1 Hz, 1H), 3.93 (s, 3H), 3.11 (m, 1H), 2.49 (s, 1H), 2.27 (s, 6H), 1.55 (d, J=5.9 Hz, 3H).

Example 41: (R)—N-(5-((1-(dimethylamino)propan-2-yl)oxy)-7-(1-methyl-1H-pyrazol-4-yl)quinazolin-4-yl)-5-fluorocinnolin-6-amine

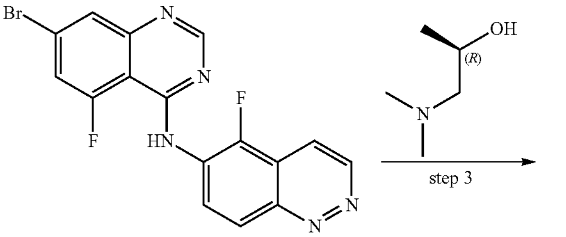

Intermediate 24

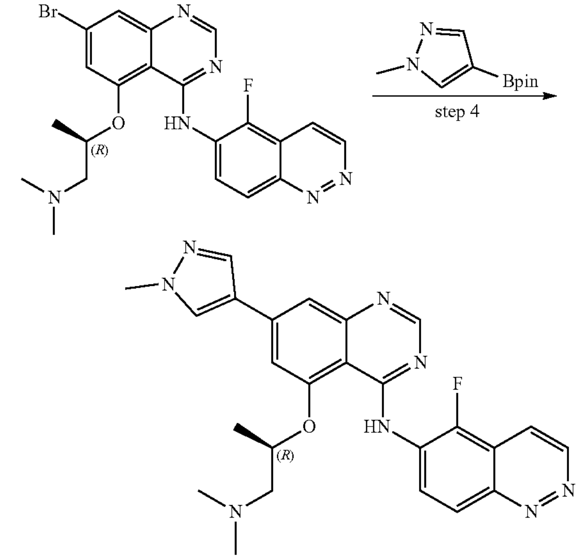

Step 1: (R)—N-(7-bromo-5-((1-(dimethylamino)propan-2-yl)oxy)quinazolin-4-yl)-5-fluorocinnolin-6-amine To a mixture of (2R)-1-(dimethylamino)propan-2-ol (55.7 mg, 540 μmol, 3 eq) in THF (5 mL) was added NaH (12.9 mg, 540 μmol, 3 eq) at 0° C., the reaction mixture was stirred at 0° C. for 15 min, then Intermediate 24 (70 mg, 0.1803 mmol, 1 eq) was added to the reaction mixture, the reaction mixture was stirred at 80° C. for 4 hrs. The reaction mixture was added to the ice water and extracted with EA. The organic phase was concentrated under vacuum. The residue was purified by flash chromatography (10% MeOH in DCM) to give the title compound (20 mg, yield: 23.5%) as a yellow solid. LC-MS: (ES, m/z): RT=1.308 min, LCMS: m/z=471 [M+1].

Step 2: (R)—N-(5-((1-(dimethylamino)propan-2-yl)oxy)-7-(1-methyl-1H-pyrazol-4-yl)quinazolin-4-yl)-5-fluorocinnolin-6-amine To a mixture of (R)—N-(7-bromo-5-((1-(dimethylamino)propan-2-yl)oxy)quinazolin-4-yl)-5-fluorocinnolin-6-amine (20 mg, 0.042 mmol, 1.00 eq) and 1-methyl-4-(4,4,5,5-tetramethyl-1,3,2-dioxaborolan-2-yl)-1H-pyrazole (9.69 mg, 46.6 μmol, 1.10 eq) in 1,4-dioxane (4.00 mL) and $H_2O$ (0.50 mL) was added Pd(dppf)$Cl_2$ (585 μg, 4.24 μmol, 0.10 eq) and $K_2CO3$ (11.7 mg, 84.8 μmol, 2.00 eq) at 25° C., the reaction mixture was stirred at 80° C. for 4 hrs under $N_2$. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The crude product was purified by Prep-HPLC with the following conditions: Column: Xselect CSH OBD Column 30*150 mm 5 um, n; Mobile Phase A: Water (0.1% FA), Mobile Phase B: ACN; Flow rate: 60 mL/min; Gradient: 5% B to 20% B in 8 min; Wavelength: 254, 220 nm. This resulted in 7.3 mg (36.5%) of the title compound as a yellow solid. LC-MS: (ES, m/z): RT=1.236 min, LCMS: m/z=471 [M+1]. $^1$H NMR (300 MHz, DMSO-$d_6$) δ 10.77 (s, 1H), 9.42 (d, J=6.0 Hz, 1H), 9.14 (dd, J=9.4, 8.0 Hz, 1H), 8.65-8.39 (m, 3H), 8.32 (d, J=5.8 Hz, 1H), 8.19 (s, 1H), 7.63 (d, J=1.4 Hz, 1H), 7.50 (s, 1H), 5.18 (s, 1H), 3.92 (s, 3H), 2.91 (dd, J=13.0, 8.0 Hz, 1H), 2.44 (s, 1H), 2.20 (s, 6H), 1.53 (d, J=6.0 Hz, 3H).

Example 42: (R)-5-((1-(dimethylamino)propan-2-yl)oxy)-7-(1-methyl-1H-pyrazol-4-yl)-N-(quinolin-6-yl)quinazolin-4-amine and (S)-5-((1-(dimethylamino)propan-2-yl)oxy)-7-(1-methyl-1H-pyrazol-4-yl)-N-(quinolin-6-yl)quinazolin-4-amine Example 43: (R)-5-((1-(dimethylamino)propan-2-yl)oxy)-7-(1-methyl-1H-pyrazol-4-yl)-N-(quinolin-6-yl)quinazolin-4-amine or (S)-5-((1-(dimethylamino)propan-2-yl)oxy)-7-(1-methyl-1H-pyrazol-4-yl)-N-(quinolin-6-yl)quinazolin-4-amine Example 44: (S)-5-((1-(dimethylamino)propan-2-yl)oxy)-7-(1-methyl-1H-pyrazol-4-yl)-N-(quinolin-6-yl)quinazolin-4-amine or (R)-5-((1-(dimethylamino)propan-2-yl)oxy)-7-(1-methyl-1H-pyrazol-4-yl)-N-(quinolin-6-yl)quinazolin-4-amine

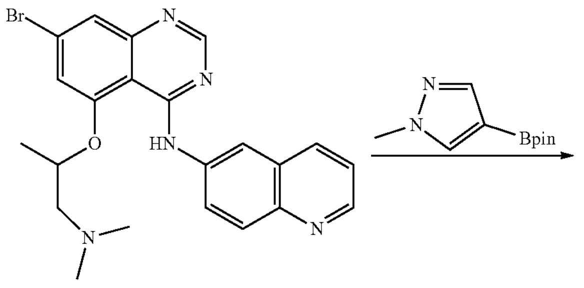

Intermediate 7

-continued

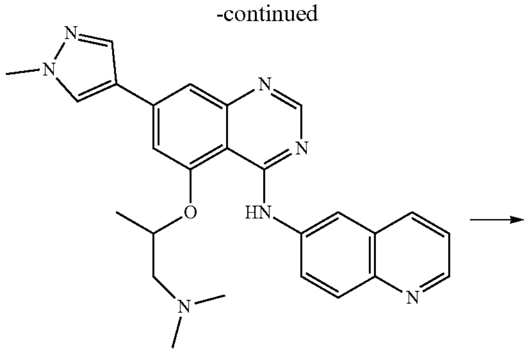

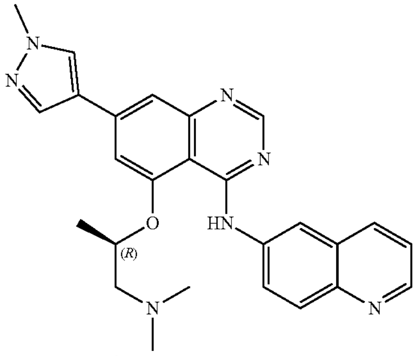

or

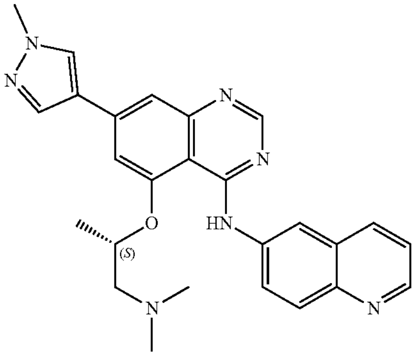

Example 42: (R)-5-((1-(dimethylamino)propan-2-yl)oxy)-7-(1-methyl-1H-pyrazol-4-yl)-N-(quinolin-6-yl)quinazolin-4-amine and (S)-5-((1-(dimethylamino)propan-2-yl)oxy)-7-(1-methyl-1H-pyrazol-4-yl)-N-(quinolin-6-yl)quinazolin-4-amine Step 1: A heterogeneous mixture of Intermediate 7 (61 mg, 0.135 mmol), (2'-amino-[1,1'-biphenyl]-2-yl)((5-(diphenylphosphaneyl)-9,9-dimethyl-9H-xanthen-4-yl)diphenyl-15-phosphaneyl)palladium(III) methanesulfonate (6.40 mg, 6.74 μmol), 1-methyl-1H-pyrazole-4-boronic acid pinacol ester (28.1 mg, 0.135 mmol), DMA (1.5 mL) and potassium phosphate (135 μl, 0.270 mmol) were combined and sparged with nitrogen. The reaction was heated to 90° C. for 16 hr. Cooled to rt and added few drops of TFA to neutralize the reaction and then concentrated under vacuum. Purified by prep-HPLC using 0.1% TFA ACN/Water. Isolated the title compound as the TFA salt (81 mg, 0.143 mmol, 106% yield): LC-MS: (ES, m/z): RT=1.461 min, LC-MS: m/z=454 [M+1].

Chiral Separation:

The racemic product of step 1 was further purified by prep-HPLC with following conditions: Column: XBridge Shield RP18 OBD Column, 30*150 mm, 5 μm; Mobile Phase A: Water (10 mM $NH_4HCO_3$+0.1% $NH_3 \cdot H_2O$), Mobile Phase B: ACN; Flow rate: 60 mL/min; Gradient: 35% B to 50% B in 8 min, Wavelength: 254; 220 nm; RT1 (min): 6.68 gave: (32.6 mg) as a white solid.

The solid was dissolved in MeOH and purified by Chiral-HPLC using the following conditions: Column: CHIRALPAK ID, 2*25 cm, 5 μm; Mobile Phase A: MTBE (0.5% 2M $NH_3$-MeOH, Mobile Phase B: EtOH; Flow rate: 18 mL/min; Isocratic 90% B over 27 min; Wavelength: 220/254 nm; RT1(min): 19.093; RT2 (min): 23.882. to afford:

Example 43: First eluting isomer: (7.4 mg) white solid. LC-MS: (ES, m/z): RT=0.878 min, LC-MS: m/z=454 [M+1], Chiral-HPLC (ES): RT=4.271, 1H NMR (300 MHz, DMSO-d6) δ 10.70 (s, 1H), 8.83 (dd, J=4.2, 1.7 Hz, 1H), 8.59 (d, J=3.3 Hz, 2H), 8.48 (s, 1H), 8.36 (dd, J=8.5, 1.7 Hz, 1H), 8.16 (s, 1H), 8.06 (d, J=1.4 Hz, 2H), 7.60-7.48 (m, 2H), 7.41 (d, J=1.5 Hz, 1H), 5.16-5.10 (m, 1H), 3.92 (s, 3H), 3.05 (dd, J=13.0, 8.9 Hz, 1H), 2.53-2.50 (m, 1H), 2.27 (s, 6H), 1.53 (d, J=5.9 Hz, 3H)

Example 44: Second eluting isomer: (5.8 mg) white solid. LC-MS: (ES, m/z): RT=0.884 min, LC-MS: m/z=454 [M+1], Chiral-HPLC (ES): RT=5.259, 1H NMR (300 MHz, DMSO-d6) δ 10.70 (s, 1H), 8.83 (dd, J=4.2, 1.7 Hz, 1H), 8.59 (d, J=3.1 Hz, 2H), 8.48 (s, 1H), 8.36 (dd, J=8.5, 1.7 Hz, 1H), 8.16 (s, 1H), 8.06 (d, J=1.4 Hz, 2H), 7.60-7.48 (m, 2H), 7.41 (d, J=1.6 Hz, 1H), 5.16-5.10 (m, 1H), 3.92 (s, 3H), 3.05 (dd, J=12.9, 8.9 Hz, 1H), 2.53-2.50 (m, 1H), 2.27 (s, 6H), 1.53 (d, J=5.8 Hz, 3H).

Example 45: (R)-5-((1-(dimethylamino)propan-2-yl)oxy)-N-(5-fluoroquinolin-6-yl)-7-(4-methoxy-1-methyl-1H-pyrazol-3-yl)quinazolin-4-amine

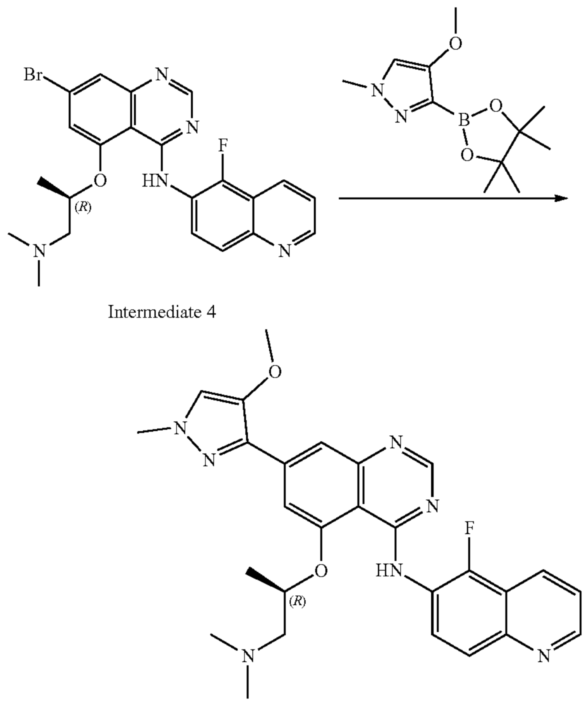

Intermediate 4

Pd(dppf)$Cl_2$ (16.2 mg, 21.2 μmol, 0.10 eq), $K_2CO_3$ (43.8 mg, 318 μmol, 1.50 eq), Intermediate 4 (100 mg, 212 μmol, 1.00 eq), 4-methoxy-1-methyl-3-(4,4,5,5-tetramethyl-1,3,2-dioxaborolan-2-yl)-1H-pyrazole (100 mg, 424 μmol, 2.00 eq), $H_2O$ (0.5 mL) and dioxane (2 mL) were combined at rt. The resulting mixture was stirred at 80° C. for 2 h under $N_2$. The reaction mixture was extracted with 3×20 mL of EA. The organic layer was dried with $Na_2SO_4$ and concentrated under vacuum. The crude product was purified by prep-HPLC. Column: XBridge Shield RP18 OBD Column, 30×150 mm, 5 μm; Mobile Phase A: Water (10 mM $NH_4HCO_3$+0.1% $NH_3 \cdot H_2O$), Mobile Phase B: ACN; Flow rate: 60 mL/min; Gradient: 42 B to 58 B over 8 min, 254/220 nm; RT1: 6.55 min. The resulting material was further purified by prep-Chiral-HPLC. Column: CHIRAL ART Cellulose-SB, 2×25 cm, 5 μm; Mobile Phase A: MTBE (MeOH, 0.5% 2M $NH_3$ in THF), Mobile Phase B: EtOH-HPLC; Flow rate: 20 mL/min; Gradient: 20% B to 20% B in 9 min; afforded the title compound (31.2 mg, 62%) as a white solid. LC-MS: (ES, m/z): RT=0.790 min, LC-MS: m/z=502 [M+1]; $^1H$ NMR (400 MHz, DMSO-$d_6$) δ 10.67 (s, 1H), 8.95 (dd, J=4.3, 1.7 Hz, 1H), 8.62-8.51 (m, 2H), 8.49 (s, 1H), 7.96 (d, J=9.2 Hz, 1H), 7.89 (d, J=1.3 Hz, 1H), 7.72 (d, J=5.2 Hz, 2H), 7.65 (dd, J=8.5, 4.2 Hz, 1H), 4.96-4.87 (m, 1H), 3.87 (d, J=10.7 Hz, 6H), 2.90 (dd, J=12.8, 8.5 Hz, 1H), 2.47 (d, J=4.3 Hz, 1H), 2.17 (s, 6H), 1.55 (d, J=6.0 Hz, 3H).

Example 46: (R)—N-(5-fluoroquinolin-6-yl)-7-(1-methyl-1H-pyrazol-4-yl)-5-(1-(oxetan-3-yl)ethoxy)quinazolin-4-amine

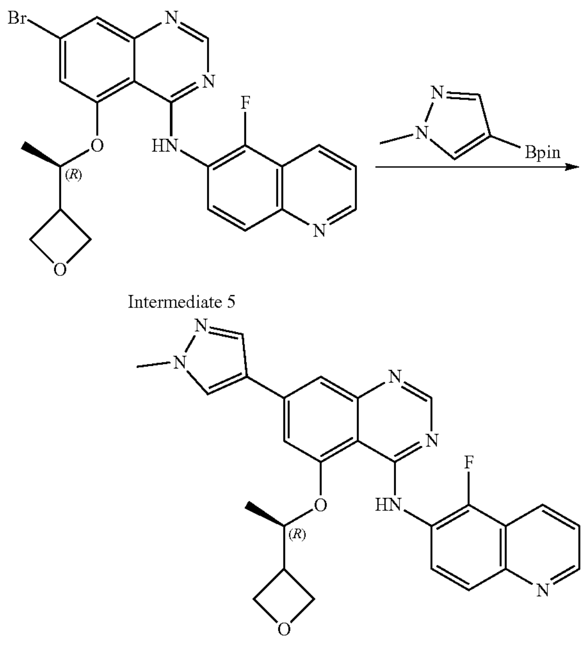

Intermediate 5

$K_2CO_3$ (749 mg, 5.43 mmol), Pd(dppf)$Cl_2$·DCM (295 mg, 362 μmol), Intermediate 5 (1.7 g, 3.62 mmol), 1-methyl-4-(4,4,5,5-tetramethyl-1,3,2-dioxaborolan-2-yl)-1H-pyrazole (1.12 g, 5.43 mmol), dioxane (30 mL), $H_2O$ (10 mL) were combined at rt. The resulting mixture was stirred at 80° C. for 3 h under $N_2$. The mixture was diluted with EA (100 mL). The organic layer was washed with brine (50 mL×2), dried with $Na_2SO_4$ and concentrated under vacuum. The residue was purified by a silica gel column using DCM: MeOH=10:1 to afford the title compound (720 mg) as a white solid. LC-MS: (ES, m/z): RT=1.026 min, LCMS: m/z=471 [M+1]; $^1H$ NMR (300 MHz, DMSO-d6) δ 10.21

(s, 1H), 8.94 (dd, J=4.3, 1.6 Hz, 1H), 8.75 (t, J=8.9 Hz, 1H), 8.59-8.49 (m, 3H), 8.21 (s, 1H), 7.95 (d, J=9.3 Hz, 1H), 7.70-7.58 (m, 2H), 7.53 (d, J=1.5 Hz, 1H), 5.54-5.43 (m, 1H), 4.90-4.78 (m, 2H), 4.62 (t, J=5.9 Hz, 1H), 4.52 (t, J=6.0 Hz, 1H), 3.93 (s, 3H), 3.52-3.42 (m, 1H), 1.43 (d, J=5.9 Hz, 3H).

Example 47: (R)-2-(4-(4-(5-fluoroquinolin-6-ylamino)-5-(1-(oxetan-3-yl)ethoxy)quinazolin-7-yl)-1H-pyrazol-1-yl)-2-methylpropan-1-ol

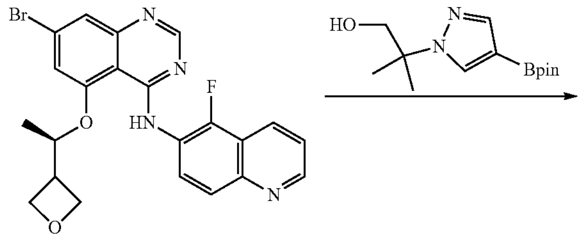

Intermediate 5

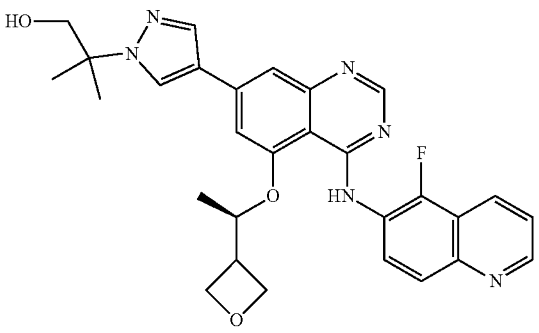

A mixture of Intermediate 5 (80 mg, 170 μmol), 2-methyl-2-[4-(4,4,5,5-tetramethyl-1,3,2-dioxaborolan-2-yl)-1H-pyrazol-1-yl]propan-1-ol (90.4 mg, 340 μmol), $K_2CO_3$ (46.9 mg, 340 μmol), Pd(dppf)$Cl_2$ (25 mg, 30.6 μmol), dioxane (15 mL) and water (5 mL) was stirred at 100° C. for 2 h. The mixture was concentrated to dryness. The residue was purified by prep-TLC eluting with DCM:MeOH=20:1. The resulting crude product was purified by prep-HPLC to afford 28.6 mg of the title compound as an off-white solid. LC-MS: (ES, m/z): RT=1.042 min, LC-MS: m/z=529 [M+1]; $^1$H NMR (DMSO-$d_6$, 400 MHz): δ=10.19 (s, 1H), 8.92 (dd, J=4.2, 1.7 Hz, 1H), 8.72 (t, J=8.8 Hz, 1H), 8.59-8.48 (m, 3H), 8.19 (s, 1H), 7.92 (d, J=9.3 Hz, 1H), 7.67-7.59 (m, 2H), 7.54 (d, J=1.5 Hz, 1H), 5.48 (p, J=6.1 Hz, 1H), 5.02 (t, J=5.4 Hz, 1H), 4.87-4.77 (m, 2H), 4.60 (t, J=6.0 Hz, 1H), 4.51 (t, J=6.0 Hz, 1H), 3.63 (d, J=4.6 Hz, 2H), 3.51-3.43 (m, 1H), 1.53 (s, 6H), 1.40 (d, J=5.9 Hz, 3H).

Example 48: (R)-1-(4-(4-(5-fluoroquinolin-6-ylamino)-5-(1-(oxetan-3-yl)ethoxy)quinazolin-7-yl)-1H-pyrazol-1-yl)-2-methylpropan-2-ol

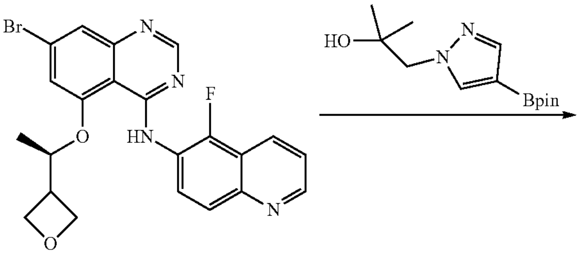

Intermediate 5

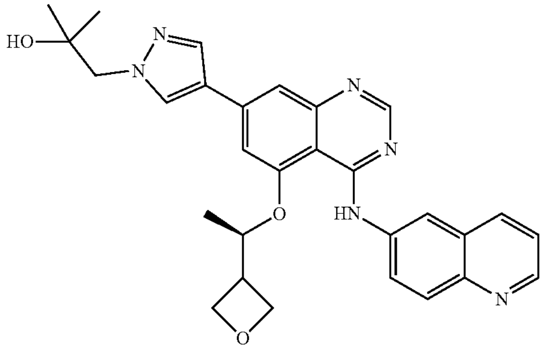

A mixture of Intermediate 5 (80 mg, 145 μmol), 2-methyl-1-[4-(4,4,5,5-tetramethyl-1,3,2-dioxaborolan-2-yl)-1H-pyrazol-1-yl]propan-2-ol (77.1 mg, 290 μmol), potassium carbonate (29.9 mg, 217 μmol), Pd(dppf)$Cl_2$ (25 mg, 30.6 μmol) in dioxane (15 mL) and water (5 mL) was stirred at 100° C. for 2 h. The mixture was concentrated to dryness. The residue was purified on prep-TLC eluting with DCM: MeOH, 20:1. The resulting crude product was purified on prep-HPLC to afford 51.5 mg of the title compound as a white solid. LC-MS: (ES, m/z): RT=0.829 min, LC-MS: m/z=529 [M+1]; $^1$H NMR (DMSO-$d_6$, 300 MHz): δ=10.20 (s, 1H), 8.94 (dd, J=4.2, 1.7 Hz, 1H), 8.77 (t, J=8.9 Hz, 1H), 8.59-8.46 (m, 3H), 8.22 (s, 1H), 7.94 (d, J=9.3 Hz, 1H), 7.70-7.60 (m, 2H), 7.55 (s, 1H), 5.56-5.46 (m, 1H), 4.90-4.78 (m, 3H), 4.62 (t, J=6.0 Hz, 1H), 4.52 (t, J=6.0 Hz, 1H), 4.09 (s, 2H), 3.48 (q, J=6.8 Hz, 1H), 1.43 (d, J=5.9 Hz, 3H), 1.14 (d, J=1.5 Hz, 6H)

Example 49: (R)-5-((1-(dimethylamino)propan-2-yl)oxy)-N-(5-fluoroquinolin-6-yl)-7-(1H-pyrazol-4-yl)quinazolin-4-amine

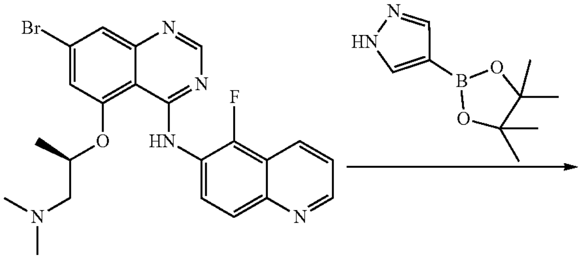

Intermediate 4

-continued

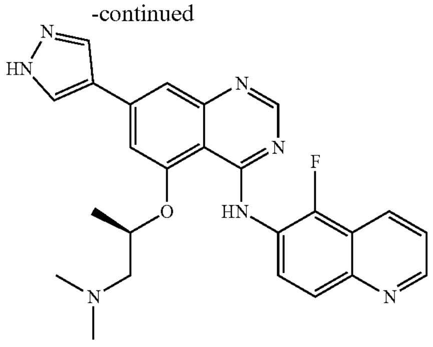

Pd(dppf)$Cl_2$ (52.8 mg, 63.6 μmol), $K_2CO_3$ (117 mg, 848 μmol), Intermediate 4 (100 mg, 212 μmol), 4-(4,4,5,5-tetramethyl-1,3,2-dioxaborolan-2-yl)-1H-pyrazole (111 mg, 424 μmol), dioxane (6 mL) and $H_2O$ (2 mL) at rt. The resulting mixture was heated to 100° C. for 16 h under $N_2$. The reaction mixture was diluted with EA (100 mL), washed with water (100 mL×3) and saturated brine (100 mL). The organic layer was dried over $Na_2SO_4$, filtered and evaporated to afford crude product. The crude product was purified by prep-TLC eluting with 20:1, DCM:MeOH. The mixture was concentrated under vacuum. The residue was purified by Prep-HPLC using the following conditions: Column: XBridge Shield RP18 OBD Column, 30×150 mm, 5 μm; Mobile Phase A: water (10 mM $NH_4HCO_3$+0.1% $NH_3·H_2O$), Mobile Phase B: ACN; Flow rate: 60 mL/min; Gradient: 21% B to 51% B in 7 min, Wavelength: 254/220 nm; RT1 (min): 6.93, to afford the title compound (6.0 mg, 6.19%) as a white solid. LC-MS: (ES, m/z): RT=0.689 min, LC-MS: m/z=458 [M+1]; $^1$H NMR (300 MHz, DMSO-d6) δ 13.17 (s, 1H), 10.62 (s, 1H), 8.95 (dd, J=4.2, 1.7 Hz, 1H), 8.71 (t, J=8.8 Hz, 1H), 8.58-8.47 (m, 3H), 8.22 (s, 1H), 7.96 (d, J=9.3 Hz, 1H), 7.70-7.60 (m, 2H), 7.49 (s, 1H), 5.15 (s, 1H), 2.90 (dd, J=12.9, 8.2 Hz, 1H), 2.41-2.31 (m, 1H), 2.19 (s, 6H), 1.53 (d, J=5.9 Hz, 3H).

Example 50: N-(5-fluoroquinolin-6-yl)-7-(1-methyl-1H-pyrazol-4-yl)-5-((1-methylpiperidin-4-yl)oxy)quinazolin-4-amine

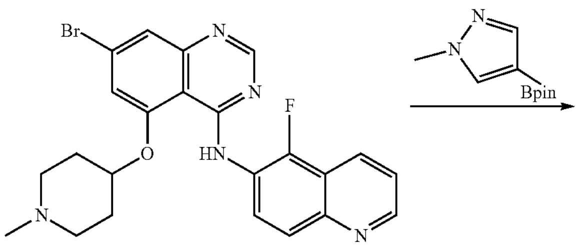

Intermediate 32

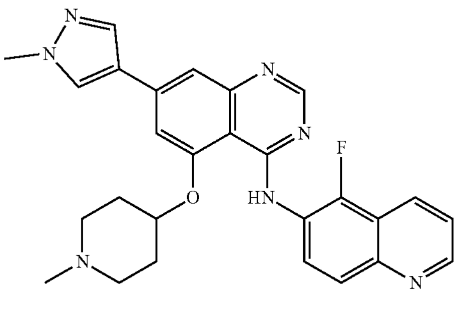

The reaction mixture of Pd(dppf)$Cl_2$ (16.8 mg, 20.7 μmol), $K_2CO_3$ (42.7 mg, 310 μmol), Intermediate 32 (100 mg, 207 μmol) and 1-methyl-4-(4,4,5,5-tetramethyl-1,3,2-dioxaborolan-2-yl)-1H-pyrazole (64.5 mg, 310 μmol) in dioxane/$H_2O$ (10 mL/2 mL) was heated at 80° C. for 3 h under $N_2$. The reaction mixture was diluted with EtOAc (120 mL) and washed with water (60 mL). The organic layer was dried over $Na_2SO_4$, filtered and evaporated under vacuum. The crude product was purified by Prep-TLC with DCM:MeOH=10:1. The residue was purified by Prep-HPLC using the following conditions: Column: YMC-Actus Triart C18 ExRS, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 27% B to 60% B in 7 min, 60% B; Wavelength: 254/220 nm, to afford the title compound (38.5 mg) as an off-white solid. LC-MS: (ES, m/z): RT=0.610 min, LCMS: m/z=484 [M+1], 1H NMR (400 MHz, DMSO-d6) δ 10.32 (s, 1H), 8.99 (t, J=8.9 Hz, 2H), 8.58-8.47 (m, 3H), 8.18 (s, 1H), 7.97 (d, J=9.3 Hz, 1H), 7.68-7.58 (m, 2H), 7.46 (s, 1H), 5.03 (s, 1H), 3.92 (s, 3H), 2.75 (d, J=11.3 Hz, 2H), 2.28 (t, J=11.2 Hz, 7H), 1.95 (dd, J=11.3, 7.8 Hz, 2H).

Example 51: (R)-2-(4-(4-((5-fluoroquinolin-6-yl)amino)-5-(1-(oxetan-3-yl)ethoxy)quinazolin-7-yl)-1H-pyrazol-1-yl)ethan-1-ol

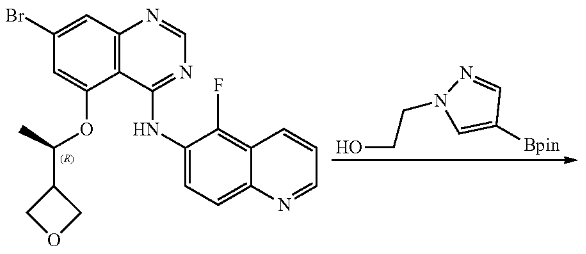

Intermediate 5

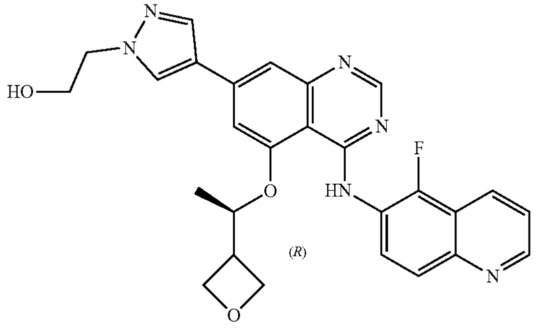

Pd(dppf)$Cl_2$ (13.0 mg, 17.0 μmol) and $K_2CO_3$ (35.0 mg, 254 μmol) were added to Intermediate 5 (80 mg, 170 μmol), 2-[4-(4,4,5,5-tetramethyl-1,3,2-dioxaborolan-2-yl)-1H-pyrazol-1-yl]ethan-1-ol (80.9 mg, 340 μmol), $H_2O$ (2 mL) and dioxane (8 mL) at rt. The resulting mixture was stirred at 80° C. for 2 h under $N_2$. The mixture was diluted with DCM 100 mL and washed with water 50 mL*2, the organic layer was dried with $Na_2SO_4$ and concentrated under vacuum. The residue was purified by a Prep-TLC with DCM:MeOH=20:1. The residue was purified by prep-HPLC using the following conditions: Column: YMC-Actus Triart C18 ExRS, 30*150 mm, 5 μm; Mobile Phase A: Water (10 mmol/L $NH_4HCO_3$+0.1% $NH_3·H_2O$), Mobile Phase B:

ACN; Flow rate: 60 mL/min; Gradient: 25% B to 55% B in 7 min, 55% B; Wavelength: 254 nm to afford the title compound (17.3 mg, yield: 21.6%) of as a white solid. LC-MS: (ES, m/z): RT=1.105 min, LCMS: m/z=501 [M+1]. $^1$H NMR (400 MHz, DMSO-$d_6$) δ 10.20 (s, 1H), 8.94 (dd, J=4.2, 1.6 Hz, 1H), 8.77 (t, J=8.9 Hz, 1H), 8.58-8.50 (m, 3H), 8.22 (s, 1H), 7.95 (d, J=9.3 Hz, 1H), 7.69-7.61 (m, 2H), 7.55 (s, 1H), 5.54-5.46 (m, 1H), 4.99 (t, J=5.3 Hz, 1H), 4.88-4.79 (m, 2H), 4.62 (t, J=5.9 Hz, 1H), 4.52 (t, J=5.9 Hz, 1H), 4.22 (t, J=5.6 Hz, 2H), 3.82 (q, J=5.5 Hz, 2H), 3.49 (q, J=6.3 Hz, 1H), 1.43 (d, J=6.0 Hz, 3H).

Example 52: (R)—N-(5-fluoroquinolin-6-yl)-7-(1-(2-methoxyethyl)-1H-pyrazol-4-yl)-5-(1-(oxetan-3-yl)ethoxy)quinazolin-4-amine

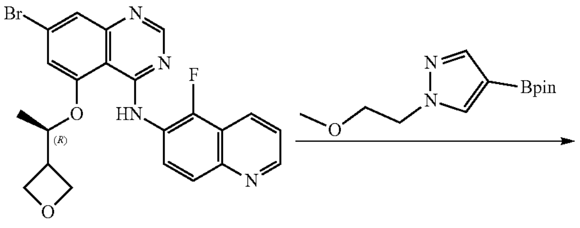

Intermediate 5

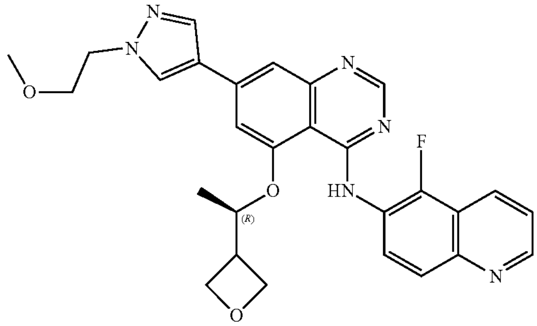

$Pd(dppf)Cl_2$ (8.14 mg, 10.6 μmol), $K_2CO_3$ (21.9 mg, 159 μmol) were added to Intermediate 5 (50 mg, 106 μmol), 1-(2-methoxyethyl)-4-(4,4,5,5-tetramethyl-1,3,2-dioxaborolan-2-yl)-1H-pyrazole (26.7 mg, 106 μmol), $H_2O$ (2 mL) and dioxane (8 mL) at rt. The resulting mixture was stirred at 80° C. for 2 h under $N_2$. The mixture was diluted with DCM 100 mL and washed with water 50 mL*2, the organic layer was dried with $Na_2SO_4$ and concentrated under vacuum. The residue was purified by a silica gel column using DCM:MeOH=20:1. The residue was further purified by prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 210% B to 54% B in 8 min, 54% B; Wavelength: 254/220 nm; to afford the title compound (17.3 mg, yield: 34.6%) as a white solid. LC-MS: (ES, m/z): RT=1.171 min, LCMS: m/z=515 [M+1]. $^1$H NMR (300 MHz, DMSO-$d_6$) δ 10.21 (s, 1H), 8.95 (d, J=3.4 Hz, 1H), 8.77 (t, J=8.9 Hz, 3H), 8.54 (d, J=7.7 Hz, 1H), 8.24 (s, 1H), 7.71-7.61 (m, 2H), 7.54 (s, 1H), 5.50 (t, J=6.3 Hz, 1H), 4.84 (q, J=6.5 Hz, 2H), 4.62 (t, J=5.9 Hz, 2H), 4.34 (t, J=5.3 Hz, 2H), 3.77 (t, J=5.2 Hz, 1H), 3.49 (d, J=6.8 Hz, 3H), 1.43 (d, J=5.9 Hz, 3H).

Example 53: 7-(1-(2,2-difluoroethyl)-1H-pyrazol-4-yl)-N-(5-fluoroquinolin-6-yl)-5-((1-methylpiperidin-4-yl)oxy)quinazolin-4-amine

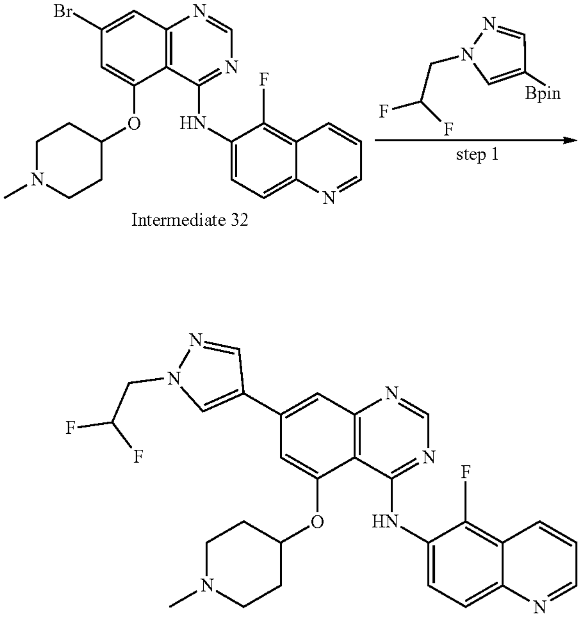

The reaction mixture of $Pd(dppf)Cl_2$ (16.8 mg, 20.7 μmol), $K_2CO_3$ (42.7 mg, 310 μmol), Intermediate 32 (100 mg, 207 μmol), 1-(2,2-difluoroethyl)-4-(4,4,5,5-tetramethyl-1,3,2-dioxaborolan-2-yl)-1H-pyrazole (80.0 mg, 310 μmol) in dioxane/$H_2O$ (3 mL/1 mL) was heated at 80° C. for 3 hr under $N_2$. The reaction mixture was diluted with EtOAc (120 mL) and washed with water (60 mL). The organic layer was dried over $Na_2SO_4$, filtered and evaporated under vacuum. The crude product was purified by Prep-TLC eluting with DCM:MeOH=10:1. The residue was further purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 30% B to 58% B in 7 min, 58% B; Wavelength: 254/220 nm; to afford the title compound (34.8 mg) as an off-white solid. LC-MS: (ES, m/z): RT=0.616 min, LCMS: m/z=534 [M+1], $^1$H NMR (400 MHz, DMSO-d6) δ 10.31 (s, 1H), 8.98 (t, J=8.9 Hz, 2H), 8.58 (d, J=8.5 Hz, 3H), 8.31 (s, 1H), 7.96 (d, J=9.3 Hz, 1H), 7.67-7.60 (m, 2H), 7.51-7.46 (m, 1H), 6.45 (t, J=3.7 Hz, 1H), 5.05 (dt, J=9.4, 5.0 Hz, 1H), 4.70 (td, J=15.1, 3.8 Hz, 2H), 2.78-2.70 (m, 2H), 2.33-2.23 (m, 7H), 2.01-1.94 (m, 2H).

Example 54: (R)-5-((1-(dimethylamino)propan-2-yl)oxy)-N-(5-fluoroquinolin-6-yl)-7-(3-methoxy-1-methyl-1H-pyrazol-4-yl)quinazolin-4-amine

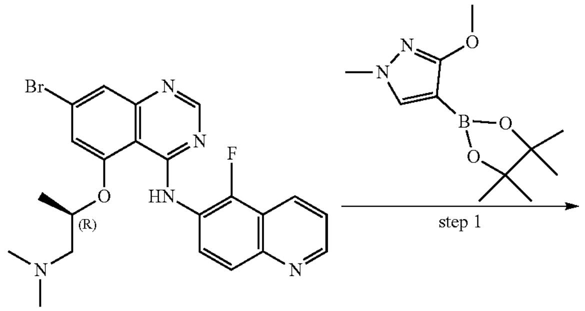

Intermediate 4

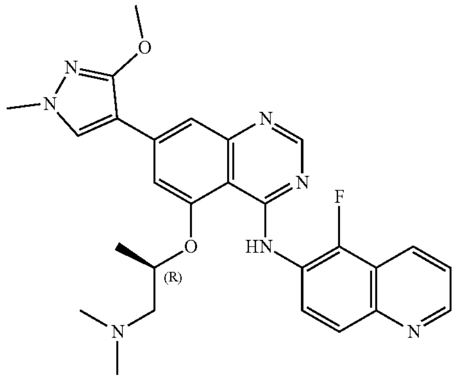

To a solution of Intermediate 4 (100 mg, 212 μmol, 1 eq) in 1,4-dioxane (4 ml) and $H_2O$ (1 ml) was added 3-methoxy-1-methyl-4-(4,4,5,5-tetramethyl-1,3,2-dioxaborolan-2-yl)-1H-pyrazole (60.4 mg, 254 μmol), 1.2 eq), Pd(dppf)$Cl_2$·DCM (17.2 mg 21.2 μmol, 0.1 eq) and $K_2CO_3$ (58.5 mg, 424 μmol, 2 eq). The mixture was stirred at 80° C. for 3 hours under $N_2$. The reaction was diluted with 20 mL of water. The resulting solution was extracted with 2×20 mL of ethyl acetate and the organic layers combined. The resulting mixture was washed with 20 mL of brine then dried over anhydrous sodium sulfate and concentrated under vacuum. The crude product was purified by Prep-HPLC with the following conditions: (Column: XBridge Shield RP18 OBD Column, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 33% B to 69% B in 7 min; Wavelength: 254/220 nm) to afford the title compound (22.1 mg, yield: 20.8%). LC-MS: (ES, m/z): RT=min, LCMS: m/z=[M+1]. $^1$H NMR (300 MHz, DMSO-d6) δ 10.47 (s, 1H), 8.82 (dd, J=4.3, 1.8 Hz, 1H), 8.56 (t, J=8.8 Hz, 1H), 8.45-8.28 (m, 2H), 8.24 (s, 1H), 7.84 (d, J=9.2 Hz, 1H), 7.63-7.46 (m, 2H), 7.35 (s, 1H), 4.88 (s, 1H), 3.87 (d, J=2.1 Hz, 3H), 3.67 (d, J=2.1 Hz, 3H), 2.86-2.65 (m, 1H), 2.61 (s, 1H), 2.06 (d, J=2.1 Hz, 6H), 1.42 (dd, J=6.1, 2.1 Hz, 3H)

Example 55: (R)-7-(1-(2,2-difluoroethyl)-1H-pyrazol-4-yl)-5-((1-(dimethylamino)propan-2-yl)oxy)-N-(5-fluoroquinolin-6-yl)quinazolin-4-amine

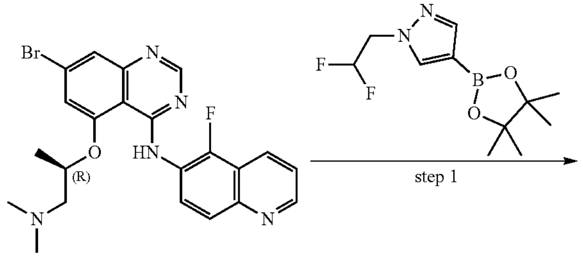

Intermediate 4

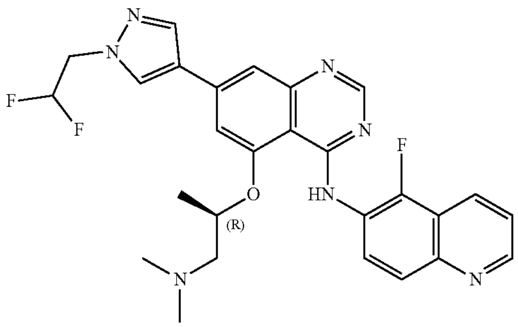

Pd(dppf)$Cl_2$ (17.2 mg, 21.2 μmol) and $K_2CO_3$ (29.2 mg, 212 μmol) were added to Intermediate 4 (100 mg, 212 μmol) and 1-(2,2-difluoroethyl)-4-(4,4,5,5-tetramethyl-1,3,2-dioxaborolan-2-yl)-1H-pyrazole (80.8 mg, 318 μmol) in dioxane/$H_2O$ (3 mL: 1 mL) at rt. This resulting mixture was heated at 80° C. for 3 h under $N_2$. The reaction mixture was diluted with EtOAc (120 mL) and washed with water (60 mL). The organic layer was dried over $Na_2SO_4$, filtered and evaporated under vacuum. The crude product was purified by Prep-TLC with DCM:MeOH=20:1. The residue was purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 36% B to 66% B in 8 min, 66% B; Wavelength: 254; 220 nm to afford the title compound (32.8 mg) as a white solid. LC-MS: (ES, m/z): RT=1.481 min, LCMS: m/z=522 [M+1], $^1$H NMR (400 MHz, DMSO-d6) δ 10.63 (s, 1H), 8.95 (dd, J=4.2, 1.7 Hz, 1H), 8.69 (t, J=8.8 Hz, 1H), 8.59 (s, 1H), 8.57-8.49 (m, 2H), 8.30 (s, 1H), 7.96 (d, J=9.2 Hz, 1H), 7.69-7.60 (m, 2H), 7.47 (d, J=1.6 Hz, 1H), 6.45 (t, J=3.7 Hz, 1H), 5.14 (d, J=9.7 Hz, 1H), 4.71 (td, J=15.2, 3.7 Hz, 2H), 2.91 (dd, J=13.0, 8.3 Hz, 1H), 2.48 (s, 6H), 2.19 (s, 6H), 1.53 (d, J=6.0 Hz, 3H).

Example 56: (R)—N-(5-fluoroquinolin-6-yl)-7-methoxy-5-(1-(oxetan-3-yl)ethoxy)quinazolin-4-amine

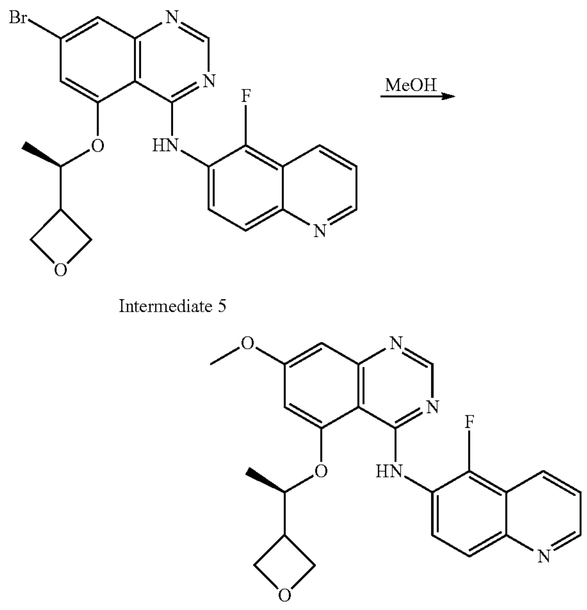

Intermediate 5

A mixture of Intermediate 5 (100 mg, 182 μmol), $K_2CO_3$ (50.3 mg, 364 μmol), RockPhosPdG3 (25 mg, 29.8 μmol) in dioxane (15 mL) and MeOH (0.5 mL) was stirred at 100° C. for 2 hr. Concentrated to dryness. The residue was purified by prep-TLC eluting with DCM:MeOH=20:1. The resulting crude product was purified on prep-HPLC to afford 19 mg of the title compound as a white solid. LC-MS: (ES, m/z): RT=1.041 min, LC-MS: m/z=421 [M+1]; $^1$H NMR (DMSO-$d_6$, 300 MHz): δ=10.05 (s, 1H), 8.94 (dd, J=4.2, 1.7 Hz, 1H), 8.67 (t, J=8.9 Hz, 1H), 8.57-8.45 (m, 2H), 7.93 (d, J=9.3 Hz, 1H), 7.64 (dd, J=8.5, 4.2 Hz, 1H), 6.90 (dd, J=16.2, 2.3 Hz, 2H), 5.26 (q, J=6.3 Hz, 1H), 4.80 (q, J=7.8 Hz, 2H), 4.53 (dt, J=26.9, 5.9 Hz, 2H), 3.94 (s, 3H), 3.49-3.39 (m, 1H), 1.39 (d, J=6.0 Hz, 3H).

Example 57: (R)-5-((1-(dimethylamino)propan-2-yl)oxy)-N-(5-fluoroquinolin-6-yl)-7-methoxyquinazolin-4-amine

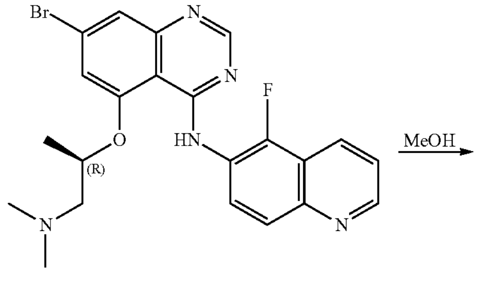

Intermediate 4

-continued

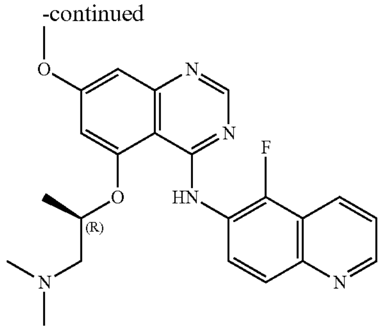

RockPhos Pd (17.7 mg, 21.2 μmol), $Cs_2CO_3$ (103 mg, 318 μmol), Intermediate 4 (100 mg, 212 μmol), MeOH (34.6 mg, 1.05 mmol) and dioxane were combined at rt. The resulting mixture was heated to 80° C. for 16 h. The reaction mixture was concentrated under vacuum. The residue was purified by Prep-HPLC using the following conditions: Column: XBridge Shield RP18 OBD Column, 30×150 mm, 5 um, Mobile Phase A: Water (10 mM, $NH_4HCO_3$+0.1% $NH_3 \cdot H_2O$), Mobile Phase B: ACN, Flow rate: 60 mL/min; Gradient: 37 B to 57 B in 8 min, 254; 220 nm, RTL: 7.22 min, to afford the title compound (40.5 mg, 45%) as a white solid. LC-MS: (ES, m/z): RT=1.213 min, LC-MS: m/z=422.10 [M+1]; $^1$H NMR (400 MHz, DMSO-$d_6$) δ 10.47 (s, 1H), 8.94 (dd, J=4.2, 1.7 Hz, 1H), 8.65 (t, J=8.8 Hz, 1H), 8.55-8.34 (m, 2H), 7.94 (dd, J=9.2, 1.4 Hz, 1H), 7.64 (dd, J=8.5, 4.2 Hz, 1H), 6.89-6.80 (m, 2H), 5.00-4.91 (m, 1H), 3.93 (s, 3H), 2.86 (dd, J=12.9, 8.4 Hz, 1H), 2.45 (dd, J=12.9, 4.2 Hz, 1H), 2.16 (s, 6H), 1.47 (d, J=6.0 Hz, 3H).

Example 58: (R)-5-((1-(dimethylamino)propan-2-yl)oxy)-7-ethoxy-N-(5-fluoroquinolin-6-yl)pyrido[4,3-d]pyrimidin-4-amine

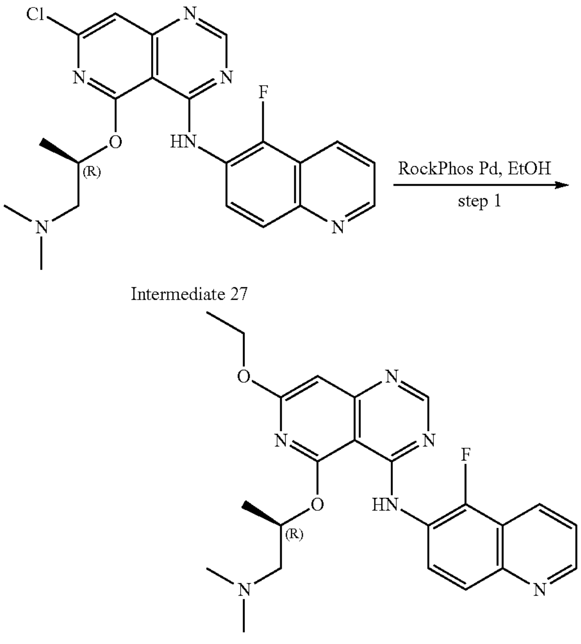

Intermediate 27

RockPhos Pd (17.7 mg, 21.2 μmol) and $Cs_2CO_3$ (103 mg, 318 μmol) were added to Intermediate 27 (100 mg, 234

μmol), EtOH (99.1 mg, 2.11 mmol) and dioxane (10 mL) at rt. The resulting mixture was heated at 80° C. for 16 hours under $N_2$. The reaction mixture was diluted with EtOAc (120 mL) and washed with water (60 mL). The organic layer was dried over $Na_2SO_4$, filtered and concentrated under vacuum. The crude product was purified by Prep-TLC with DCM:MeOH=20:1. The residue was purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 47% B to 59% B in 8 min, 59% B; Wavelength: 254; 220 nm; to afford the title compound (41.8 mg) as a white solid. LC-MS: (ES, m/z): RT=1.276 min, LCMS: m/z=437 [M+1], $^1$H NMR (400 MHz, DMSO-d6) δ 10.28 (s, 1H), 8.95 (dd, J=4.2, 1.6 Hz, 1H), 8.61 (t, J=8.8 Hz, 1H), 8.56-8.48 (m, 2H), 7.95 (dd, J=9.3, 1.4 Hz, 1H), 7.65 (dd, J=8.5, 4.2 Hz, 1H), 6.50 (s, 1H), 5.58-5.45 (m, 1H), 4.37 (q, J=7.0 Hz, 2H), 2.90 (dd, J=12.8, 8.9 Hz, 1H), 2.46 (dd, J=12.8, 4.4 Hz, 1H), 2.18 (s, 6H), 1.55 (d, J=6.1 Hz, 3H), 1.39 (t, J=7.0 Hz, 3H).

Example 59: 7-(6-oxa-3-azabicyclo[3.1.1]heptan-3-yl)-N-(5-fluoroquinolin-6-yl)-5-((R)-1-(oxetan-3-yl)ethoxy)quinazolin-4-amine

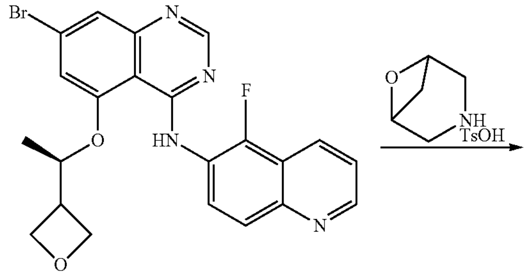

Intermediate 5

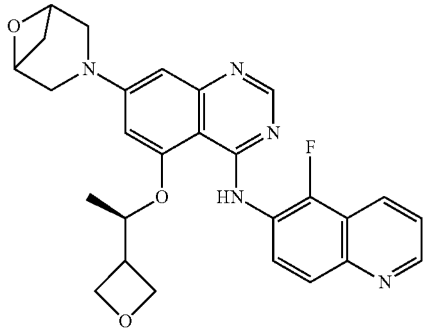

RuPhos Pd (1.06 g, 1.27 mmol, 0.20 eq), $Cs_2CO_3$ (6.22 g, 19.2 mmol, 3.00 eq), Intermediate 5 (3 g, 6.39 mmol, 1.00 eq), 6-oxa-3-azabicyclo[3.1.1]heptane 4-methylbenzene-1-sulfonic acid salt (3.44 g, 12.7 mmol, 2.00 eq) and dioxane (40 mL) were combined at rt. The resulting mixture was stirred at 100° C. for 2 h under $N_2$. The resulting solution was extracted with 2×50 mL of EA. The organic layers were combined, washed with 20 mL of brine, dried over anhydrous sodium sulfate and concentrated under vacuum. The product was purified by a silica gel column using DCM: MeOH (20:1) to afford the title compound (1.53 g, 49%) as a light-yellow solid. LC-MS: (ES, m/z): RT=0.826 min, LC-MS: m/z=488 [M+1]; $^1$H NMR (300 MHz, DMSO-$d_6$) δ 10.01 (s, 1H), 8.96-8.71 (m, 2H), 8.53 (dd, J=8.5, 1.5 Hz, 1H), 8.38 (s, 1H), 7.92 (d, J=9.3 Hz, 1H), 7.63 (dd, J=8.5, 4.2 Hz, 1H), 6.78 (s, 1H), 6.56 (d, J=2.1 Hz, 1H), 5.40 (q, J=6.6 Hz, 1H), 4.80 (dd, J=7.9, 6.0 Hz, 4H), 4.59 (t, J=6.0 Hz, 1H), 4.51 (t, J=6.0 Hz, 1H), 3.84-3.55 (m, 4H), 3.47 (q, J=6.9 Hz, 1H), 3.19 (q, J=7.4 Hz, 1H), 1.95 (d, J=8.8 Hz, 1H), 1.42 (d, J=5.9 Hz, 3H).

Example 60: (R)-7-(2,2-dimethylmorpholino)-N-(5-fluoroquinolin-6-yl)-5-(1-(oxetan-3-yl)ethoxy)quinazolin-4-amine

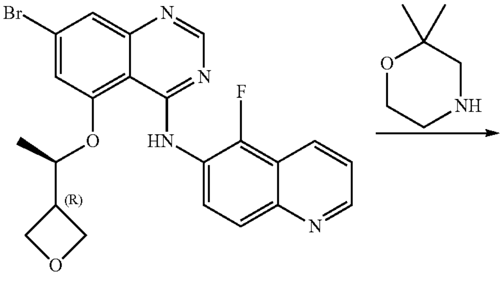

Intermediate 5

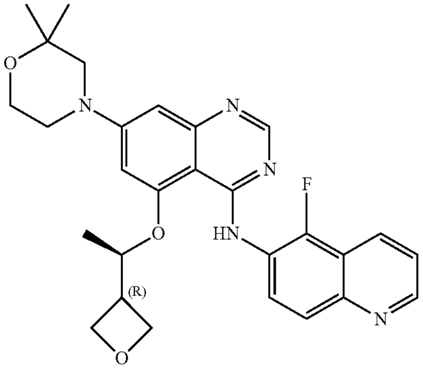

A mixture of Intermediate 5 (70 mg, 149 μmol), 2,2-dimethylmorpholine (68.6 mg, 596 μmol), $Pd_2(dba)_3{\cdot}CHCl_3$ (15 mg, 14.6 μmol), CPhos (10 mg, 22.9 μmol), $Cs_2CO_3$ (72.6 mg, 223 μmol) and dioxane (15 mL) was stirred at 100° C. for 6 h. The mixture was concentrated to dryness. The residue was purified on prep-TLC eluting with DCM: MeOH=20:1. The resulting material was purified on prep-HPLC to afford the title compound (7.6 mg) as a light-yellow solid. LC-MS: (ES, m z): RT=1.123 min, LC-MS: m/z=504 [M+1]; $^1$H NMR (300 MHz, DMSO-d6) δ 10.00 (s, 1H), 8.92 (dd, J=4.2, 1.6 Hz, 1H), 8.83 (t, J=8.9 Hz, 1H), 8.53 (dt, J=8.4, 1.5 Hz, 1H), 8.39 (s, 1H), 7.92 (d, J=9.3 Hz, 1H), 7.63 (dd, J=8.5, 4.2 Hz, 1H), 6.93 (d, J=2.3 Hz, 1H), 6.69 (d, J=2.1 Hz, 1H), 5.47-5.36 (m, 1H), 4.81 (ddd, J=8.0, 6.3, 4.5 Hz, 2H), 4.58 (t, J=6.0 Hz, 1H), 4.50 (t, J=6.0 Hz, 1H), 3.80 (t, J=5.0 Hz, 2H), 3.43 (dd, J=12.9, 7.3 Hz, 3H), 3.32 (s, 1H), 3.26 (d, J=12.6 Hz, 1H), 1.37 (d, J=5.9 Hz, 3H), 1.26 (s, 6H).

Example 61: (R)—N-(5-fluoroquinolin-6-yl)-7-morpholino-5-(1-(oxetan-3-yl)ethoxy)quinazolin-4-amine

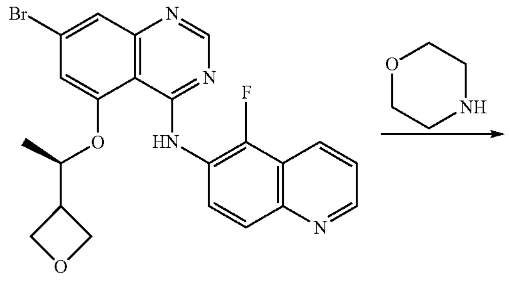

Intermediate 5

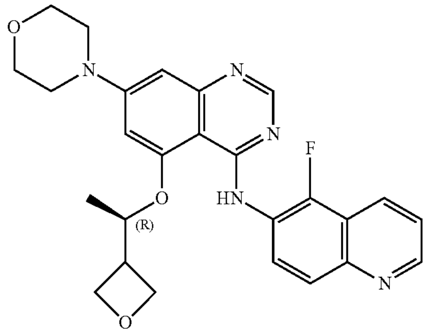

To a reaction vessel was added: RuPhos Pd (71.3 mg, 85.2 μmol, 0.20 eq), $Cs_2CO_3$ (277 mg, 852 μmol, 2.00 eq), Intermediate 5 (200 mg, 426 μmol, 1.00 eq), morpholine (185 mg, 2.13 mmol, 5.00 eq.) and dioxane (2 mL) at rt. The mixture was stirred at 100° C. for 2 h under $N_2$. The resulting solution was extracted with 3×30 mL of EA. The organic layer was dried with $Na_2SO_4$ and concentrated under vacuum. The crude product was purified by HPLC: Column=XBridge Prep OBD C18 30×150 mm, 5 um. Mobile Phase A=Water (10 mM $NH_4HCO_3$+0.1% $NH_3 \cdot H_2O$). Mobile Phase B=ACN. Flow rate=60 mL/min. Gradient: 30% B to 45% B over 8 min, 254 and 220 nm; RT=6.75 min. Afforded (114.4 mg, 56%) of the title compound as a white solid. LC-MS: (ES, m/z): RT=1.594 min, LC-MS: m/z=476 [M+1]; $^1$H NMR (300 MHz, DMSO-d6) δ 10.03 (s, 1H), 8.92 (dd, J=4.2, 1.6 Hz, 1H), 8.84 (t, J=8.9 Hz, 1H), 8.53 (d, J=8.5 Hz, 1H), 8.41 (s, 1H), 7.92 (d, J=9.3 Hz, 1H), 7.64 (dd, J=8.5, 4.2 Hz, 1H), 7.00 (s, 1H), 6.71 (d, J=2.0 Hz, 1H), 5.41 (t, J=6.7 Hz, 1H), 4.87-4.75 (m, 2H), 4.53 (dt, J=27.0, 6.0 Hz, 2H), 3.80 (t, J=4.5 Hz, 4H), 3.41 (d, J=9.8 Hz, 5H), 1.37 (d, J=5.9 Hz, 3H).

Example 62: 2—((S)-1-(4-((5-fluoroquinolin-6-yl)amino)-5-((R)-1-(oxetan-3-yl)ethoxy)quinazolin-7-yl)pyrrolidin-3-yl)propan-2-ol

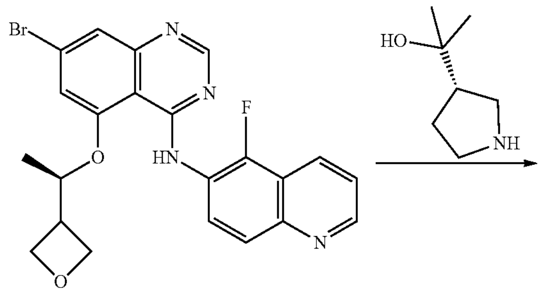

Intermediate 5

-continued

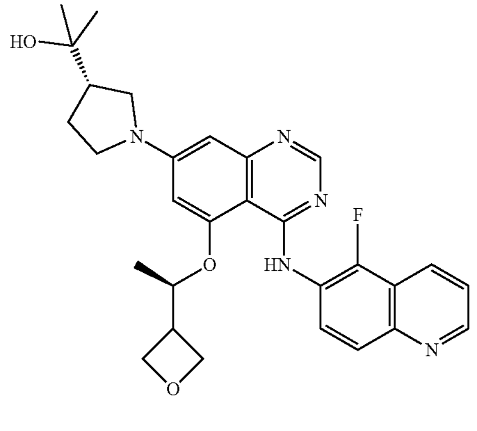

A mixture of Intermediate 5 (70 mg, 149 μmol), 2-[(3S)-pyrrolidin-3-yl]propan-2-ol (77.0 mg, 596 μmol), $Cs_2CO_3$ (72.6 mg, 222 μmol), BINAP-Pd G2 (139 mg, 148 μmol) and dioxane (15 mL) was stirred at 100° C. for 6 h. The mixture was concentrated to dryness. The residue was purified on prep-TLC eluting with 20:1, DCM:MeOH. The resulting material was purified by prep-HPLC to afford 23.1 mg of the title compound as a yellow solid. LC-MS: (ES, m/z): RT=2.088 min, LC-MS: m/z=518 [M+1]; $^1$H NMR (300 MHz, DMSO-d6) δ 9.99 (s, 1H), 8.92 (dd, J=4.2, 1.7 Hz, 1H), 8.82 (t, J=9.0 Hz, 1H), 8.52 (d, J=8.1 Hz, 1H), 8.34 (s, 1H), 7.91 (d, J=9.3 Hz, 1H), 7.63 (dd, J=8.5, 4.2 Hz, 1H), 6.56 (s, 1H), 6.31 (d, J=2.0 Hz, 1H), 5.38 (t, J=6.7 Hz, 1H), 4.87-4.74 (m, 2H), 4.54 (dt, J=21.4, 6.0 Hz, 2H), 4.44 (s, 1H), 3.61 (t, J=9.0 Hz, 1H), 3.49 (t, J=8.9 Hz, 3H), 3.28-3.40 (t, 1H), 2.43-2.31 (m, 1H), 1.96 (d, J=10.7 Hz, 2H), 1.40 (d, J=5.9 Hz, 3H), 1.20 (d, J=7.9 Hz, 6H).

Example 63: 2—((R)-1-(4-((5-fluoroquinolin-6-yl)amino)-5-((R)-1-(oxetan-3-yl)ethoxy)quinazolin-7-yl)pyrrolidin-3-yl)propan-2-ol

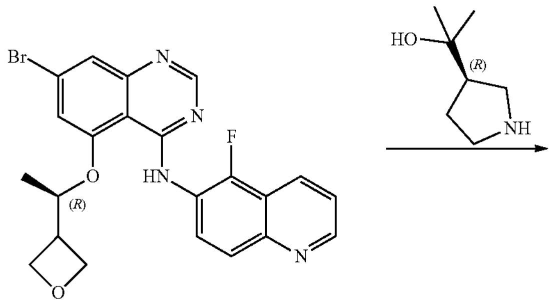

Intermediate 5

-continued

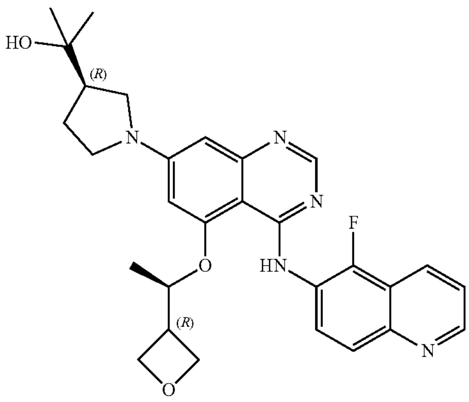

BINAP-Pd G2 (29.7 mg, 0.032 mmol), $Cs_2CO_3$ (155 mg, 0.478 mmol) was added to Intermediate 5 (150 mg, 0.319 mmol) and 2-[(3R)-pyrrolidin-3-yl]propan-2-ol (82.4 mg, 0.638 mmol) in dioxane (10 ml) at rt. The resulting mixture was heated to 80° C. for 16 h. The reaction mixture was diluted with EA (100 mL), washed with water (100 mL×3) and saturated brine (100 mL). The organic layer was dried over $Na_2SO_4$, filtered and evaporated to afford crude product. The crude product was purified by Prep-TLC with 20:1, DCM:MeOH. The resulting residue was purified by prep-HPLC using the following conditions: Column: XBridge Shield RP18 OBD Column, 30×150 mm, 5 um, Mobile Phase A: Water (10 mM, $NH_4HCO_3$+0.1% $NH_3$. $H_2O$), Mobile Phase B: ACN; Flow rate: 60 mL/min; Gradient: 35 B to 46 B in 10 min, 254/220 nm; rt: 7.83 min; affording the title compound (29.4 mg) as a light-yellow solid. LC-MS: (ES, m/z): RT=0.924 min, LC-MS: m/z=518.15 [M+1]; $^1$H NMR (400 MHz, DMSO-d6)$^1$H NMR (400 MHz, DMSO-d6) δ 9.96 (s, 1H), 8.93-8.82 (m, 2H), 8.50 (dd, J=6.7, 4.4 Hz, 1H), 8.32 (s, 1H), 7.90 (d, J=9.3 Hz, 1H), 7.62 (ddd, J=8.6, 4.3, 2.3 Hz, 1H), 6.55 (d, J=3.0 Hz, 1H), 6.30 (d, J=2.1 Hz, 1H), 5.36 (p, J=6.2 Hz, 1H), 4.80 (ddd, J=9.4, 7.9, 6.3 Hz, 2H), 4.58 (t, J=6.0 Hz, 1H), 4.51 (t, J=6.0 Hz, 1H), 4.44 (s, 1H), 3.56 (t, J=8.9 Hz, 1H), 3.45 (ddd, J=18.6, 9.3, 5.2 Hz, 4H), 2.41-2.32 (m, 1H), 2.00-1.89 (m, 2H), 1.40 (d, J=6.0 Hz, 3H), 1.19 (d, J=9.9 Hz, 6H).

Example 64: ((R)—N-(5-fluoroquinolin-6-yl)-5-(1-(oxetan-3-yl)ethoxy)-7-(2-oxa-6-azaspiro[3.3]heptan-6-yl)quinazolin-4-amine

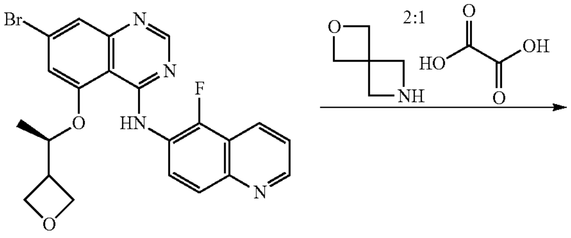

Intermediate 5

-continued

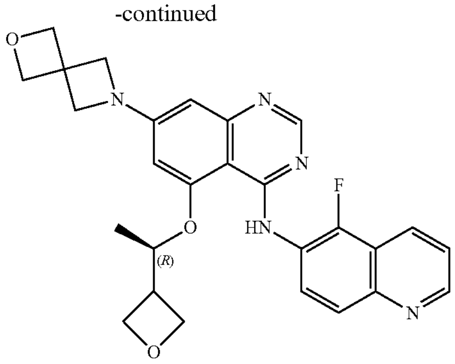

To a mixture of Intermediate 5 (75 mg, 0.160 mmol), 2-oxa-6-azaspiro[3.3]heptane hemioxalate (69.1 mg, 0.240 mmol), RuPhos Pd G3 (6.68 mg, 7.99 μmol), 2,2'-bis (diphenylphospheneyl)-1,1'-binaphthalene (4.98 mg, 7.99 μmol), tris(dibenzylideneacetone)dipalladium(0) (4.39 mg, 4.79 μmol) and sodium t-butoxide (46.1 mg, 0.479 mmol) was added DMF (2.91 mL). The reaction was sparged with nitrogen then heated to 95° C. for 6 h. Concentrated to a crude solid and purified by silica gel 0-25% MeOH in DCM. Further purified by reverse phase purification using Xbridge Prep OBD C18 5.0 μm column with 0-40% gradient of ACN, in water (0.1% acetic acid) to obtain the title compound (4.4 mg, 0.0088 mmol, 5.5% yield) with 98% purity. LC-MS: (ES, m/z): RT=2.112 min, LC-MS: m/z=488 [M+1]; $^1$H NMR (500 MHz, DMSO-$d_6$) δ ppm: 10.56 (s, 1H), 9.01 (s, 1H), 8.63 (s, 1H), 8.60-8.37 (m, 1H), 8.11 (s, 1H), 7.95 (d, J=8.2 Hz, 1H), 7.69 (s, 1H), 6.45 (d, J=3.8 Hz, 1H), 6.07 (s, 1H), 5.32 (s, 1H), 4.92-4.70 (m, 6H), 4.57 (s, 1H), 4.45 (s, 1H), 4.35 (s, 4H), 3.38 (s, 1H), 1.40 (t, J=5.0 Hz, 3H).

Example 65: (R)-5-((1-(dimethylamino)propan-2-yl)oxy)-N-(5-fluoroquinolin-6-yl)-7-morpholinoquinazolin-4-amine

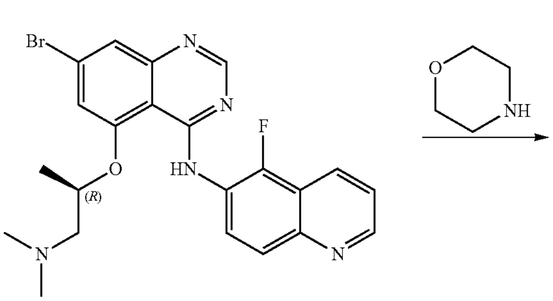

Intermediate 4

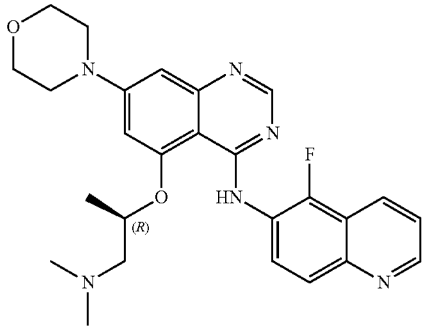

RuPhos Pd G3 (46.2 mg, 55.2 μmol, 0.20 eq), $Cs_2CO_3$ (134 mg, 414 μmol, 1.50 eq), Intermediate 4 (130 mg, 276 μmol, 1.00 eq), morpholine (120 mg, 1.38 mmol, 5.00 eq) and dioxane (4 mL) were combined at rt. The resulting mixture was stirred at 100° C. for 2 h under $N_2$. The reaction mixture was extracted with EA (3×20 mL). The organic layer was dried with $Na_2SO_4$ and concentrated under vacuum. The crude product was purified by HPLC. Column: YMC-Actus Triart C18, 30 mm×150 mm, 5 um; Mobile Phase A: water (10 mM $NH_4HCO_3$+0.1% $NH_3$ $H_2O$), Mobile Phase B: ACN; Flow rate: 60 mL/min; Gradient: 50 B to 60 B in 8 min; 254/220 nm; RTL: 7.47 min. The resulting material was further purified by prep-chiral-HPLC. Column: CHIRALPAK IG, 2×25 cm, 5 um; Mobile Phase A: MTBE (0.5% 2M NH3-MeOH)-HPLC, Mobile Phase B: EtOH-HPLC; Flow rate: 20 mL/min; Gradient: 20 B to 20 B in 13 min; 220/254 nm; to afford the title compound (35 mg, 57%) as a white solid. LC-MS: (ES, m/z): RT=0.906 min, LC-MS: m/z=477 [M+1]; $^1H$ NMR (300 MHz, DMSO-$d_6$) δ 10.40 (s, 1H), 8.93 (dd, J=4.3, 1.7 Hz, 1H), 8.77 (t, J=8.9 Hz, 1H), 8.51 (d, J=8.5 Hz, 1H), 8.38 (s, 1H), 7.94 (d, J=9.3 Hz, 1H), 7.63 (dd, J=8.5, 4.2 Hz, 1H), 6.93 (d, J=2.3 Hz, 1H), 6.68 (d, J=2.1 Hz, 1H), 5.10-5.04 (m, 1H), 3.79 (t, J=4.8 Hz, 4H), 3.38 (t, J=4.8 Hz, 4H), 2.86 (dd, J=12.9, 8.0 Hz, 1H), 2.45 (d, J=4.2 Hz, 1H), 2.18 (s, 6H), 1.47 (d, J=5.9 Hz, 3H).

Example 66: 7-(6-oxa-3-azabicyclo[3.1.1]heptan-3-yl)-5-(((R)-1-(dimethylamino)propan-2-yl)oxy)-N-(quinolin-6-yl)quinazolin-4-amine and 7-(6-oxa-3-azabicyclo[3.1.1]heptan-3-yl)-5-(((S)-1-(dimethylamino)propan-2-yl)oxy)-N-(quinolin-6-yl)quinazolin-4-amine Example 67: 7-(6-oxa-3-azabicyclo[3.1.1]heptan-3-yl)-5-(((R)-1-(dimethylamino)propan-2-yl)oxy)-N-(quinolin-6-yl)quinazolin-4-amine or 7-(6-oxa-3-azabicyclo[3.1.1]heptan-3-yl)-5-(((S)-1-(dimethylamino)propan-2-yl)oxy)-N-(quinolin-6-yl)quinazolin-4-amine Example 68: 7-(6-oxa-3-azabicyclo[3.1.1]heptan-3-yl)-5-(((S)-1-(dimethylamino)propan-2-yl)oxy)-N-(quinolin-6-yl)quinazolin-4-amine or 7-(6-oxa-3-azabicyclo[3.1.1]heptan-3-yl)-5-(((R)-1-(dimethylamino)propan-2-yl)oxy)-N-(quinolin-6-yl)quinazolin-4-amine

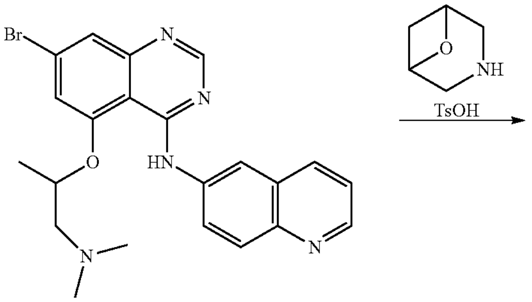

Intermediate 7

-continued

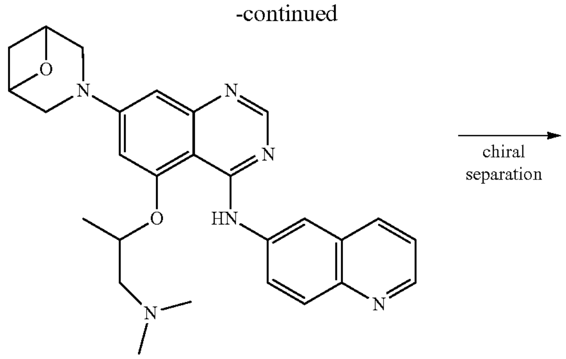

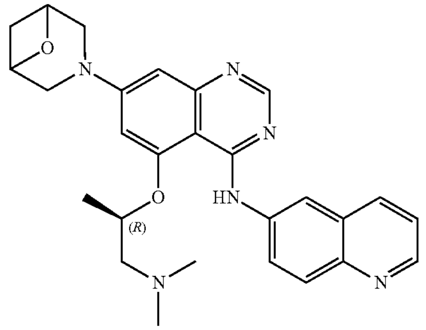

or

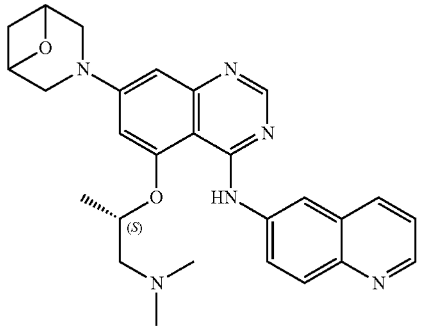

Example 66: 7-(6-oxa-3-azabicyclo[3.1.1]heptan-3-yl)-5-(((R)-1-(dimethylamino)propan-2-yl)oxy)-N-(quinolin-6-yl)quinazolin-4-amine and 7-(6-oxa-3-azabicyclo[3.1.1]heptan-3-yl)-5-(((S)-1-(dimethylamino)propan-2-yl)oxy)-N-(quinolin-6-yl)quinazolin-4-amine Intermediate 7 (62 mg, 0.137 mmol), 6-Oxa-3-azabicyclo[3.1.1]heptane tosylate (54 mg, 0.199 mmol), XantPhos Pd G3 (6.51 mg, 6.85 μmol), sodium t-butoxide (39.5 mg, 0.411 mmol) and DMA (2 mL) were combined under nitrogen. Sparged with nitrogen for 5 min. Heated the reaction to 90° C. for 16 h. Cooled to rt and added few drops of TFA neutralize the reaction then concentrated under vacuum. Purified by prep-HPLC, using 0.10% TFA ACN/Water to afford the title compound (57 mg, 0.094 mmol, 68.5% yield). LC-MS: (ES, m/z): RT=1.461 min, LC-MS: m/z=471 [M+1].

Chiral Separation:

The product was further purified by Prep-HPLC with the following conditions: Column: YMC-Actus Triart C18, 30*150 mm, 5 μm; Mobile Phase A: Water (10 mmol/L $NH_4HCO_3$+0.1% $NH_3$·$H_2O$), Mobile Phase B: ACN; Flow rate: 60 mL/min; Gradient: 45% B to 62% B in 8 min, 62% B; Wavelength: 254/220 nm; RT1 (min): 7.05; Resulted in 8.4 mg of a white solid. The solid was dissolved in MeOH and purified by Chiral HPLC using the following conditions: Column: CHIRALPAK ID, 2*25 cm, 5 μm; Mobile Phase A: MTBE (0.5% 2M NH3-MeOH)-HPLC, Mobile Phase B: MeOH; Flow rate: 18 mL/min; Gradient: 90% B to 90% B in 24 min; Wavelength: 220/254 nm; RT1(min): 4.19; RT2 (min): 8.683. This afforded:

Example 67: First eluting isomer: 7-(6-oxa-3-azabicyclo[3.1.1]heptan-3-yl)-5-(((R)-1-(dimethylamino)propan-2-yl)oxy)-N-(quinolin-6-yl)quinazolin-4-amine or 7-(6-oxa-3-azabicyclo[3.1.1]heptan-3-yl)-5-(((S)-1-(dimethylamino)propan-2-yl)oxy)-N-(quinolin-6-yl)quinazolin-4-amine: (1.2 mg) of as a white solid. LC-MS: (ES, m/z): RT=0.864 min, LC-MS: m/z=471 [M+1], Chiral-HPLC (ES): RT=5.333, $^1$H NMR (300 MHz, DMSO-d6) δ 10.49 (s, 1H), 8.80 (dd, J=4.2, 1.7 Hz, 1H), 8.58 (s, 1H), 8.43 (s, 1H), 8.33 (dd, J=8.4, 1.7 Hz, 1H), 8.03 (d, J=1.7 Hz, 2H), 7.51 (dd, J=8.3, 4.2 Hz, 1H), 6.69 (d, J=2.1 Hz, 1H), 6.52 (d, J=2.1 Hz, 1H), 5.04 (m, 1H), 4.78 (d, J=6.3 Hz, 2H), 3.81-3.47 (m, 4H), 3.30-2.96 (m, 2H), 2.52-2.50 (m, 1H), 2.27 (s, 6H), 1.94 (d, J=8.8 Hz, 1H), 1.53 (d, J=5.9 Hz, 3H).

Example 68: Second eluting isomer: 7-(6-oxa-3-azabicyclo[3.1.1]heptan-3-yl)-5-(((S)-1-(dimethylamino)propan-2-yl)oxy)-N-(quinolin-6-yl)quinazolin-4-amine or 7-(6-oxa-3-azabicyclo[3.1.1]heptan-3-yl)-5-(((R)-1-(dimethylamino)propan-2-yl)oxy)-N-(quinolin-6-yl)quinazolin-4-amine: (1 mg) as a white solid. LC-MS: (ES, m/z): RT=0.861 min, LC-MS: m/z=471 [M+1], Chiral-HPLC (ES): RT=7.103, 1H NMR (300 MHz, DMSO-d6) δ 10.49 (s, 1H), 8.80 (dd, J=4.2, 1.7 Hz, 1H), 8.58 (s, 1H), 8.43 (s, 1H), 8.33 (dd, J=8.4, 1.7 Hz, 1H), 8.03 (d, J=1.7 Hz, 2H), 7.51 (dd, J=8.3, 4.2 Hz, 1H), 6.69 (d, J=2.2 Hz, 1H), 6.52 (d, J=2.1 Hz, 1H), 5.06-5.02 (m, 1H), 4.78 (d, J=6.4 Hz, 2H), 4.02-3.56 (m, 4H), 3.10 (ddd, J=45.8, 13.9, 8.1 Hz, 2H), 2.53-2.50 (m, 1H), 2.27 (s, 6H), 1.94 (d, J=8.8 Hz, 1H), 1.53 (d, J=5.9 Hz, 3H).

Example 69: 7-(8-oxa-3-azabicyclo[3.2.1]octan-3-yl)-5-(((R)-1-(dimethylamino)propan-2-yl)oxy)-N-(5-fluoroquinolin-6-yl)quinazolin-4-amine

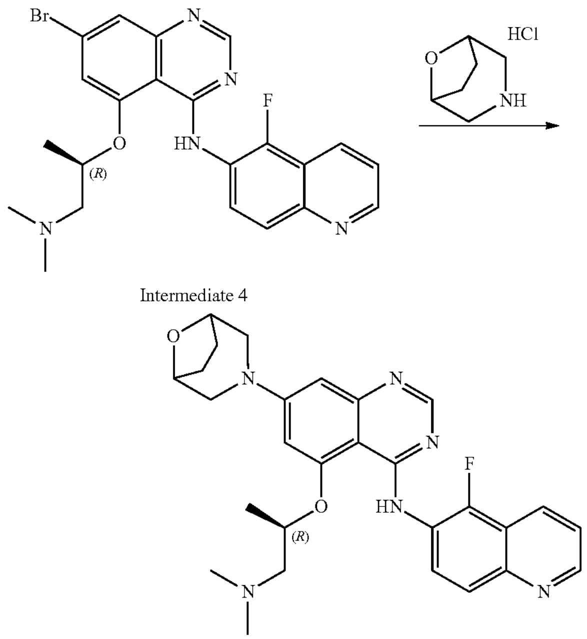

RuPhos Pd G3 (35.5 mg, 42.4 μmol, 0.20 eq), $Cs_2CO_3$ (276 mg, 848 μmol, 4.00 eq), Intermediate 4 (100 mg, 212 μmol, 1.00 eq), 8-oxa-3-azabicyclo[3.2.1]octane hydrochloride (63.4 mg, 424 μmol, 2.00 eq) and dioxane (4 mL) were combined at rt. The resulting mixture was stirred at 100° C. for 2 h under $N_2$. The resulting solution was extracted with 3×20 mL of ethyl acetate. The organic layer was dried with $Na_2SO_4$ and concentrated under vacuum. The crude product was purified by HPLC: Column: YMC-Actus Triart C18, 30 mm×150 mm, 5 um; MP-A: Water (10 mM $NH_4HCO_3$+0.1% $NH_3$—$H_2O$), MP-B: ACN; Flow rate: 60 mL/min, Gradient: 55% B to 65% B over 8 min, 254/220 nm; RT1: 7.55 min. The resulting residue was further purified by prep-Chiral-HPLC. Column: CHIRAL ART Cellulose-SB, 2×25 cm, 5 μm; Mobile Phase A: MTBE (0.5% 2M $NH_3$ in MeOH, Mobile Phase B: EtOH, Flow rate: 20 mL/min, Gradient: 10% B to 10% B in 10 min, to afford the title compound (42.6 mg 85%) as a white solid. LC-MS: (ES, m/z): RT=0.770 min, LC-MS: m/z=503 [M+1]; $^1$H NMR (400 MHz, DMSO-d$_6$) δ 10.39 (s, 1H), 8.92 (dd, J=4.2, 1.7 Hz, 1H), 8.78 (t, J=8.9 Hz, 1H), 8.54-8.47 (m, 1H), 8.36 (s, 1H), 7.93 (d, J=9.3 Hz, 1H), 7.63 (dd, J=8.5, 4.2 Hz, 1H), 6.84 (d, J=2.2 Hz, 1H), 6.58 (d, J=2.2 Hz, 1H), 5.03 (q, J=6.2 Hz, 1H), 4.50 (s, 2H), 3.68 (t, J=11.8 Hz, 2H), 3.01 (dt, J=11.7, 2.8 Hz, 2H), 2.85 (dd, J=13.0, 8.0 Hz, 1H), 2.50-2.42 (m, 1H), 2.18 (s, 6H), 1.88-1.87 (m, 4H), 1.48 (d, J=6.0 Hz, 3H).

Example 70: 7-(6-oxa-3-azabicyclo[3.1.1]heptan-3-yl)-5-(((R)-1-(dimethylamino)propan-2-yl)oxy)-N-(5-fluoroquinolin-6-yl)quinazolin-4-amine

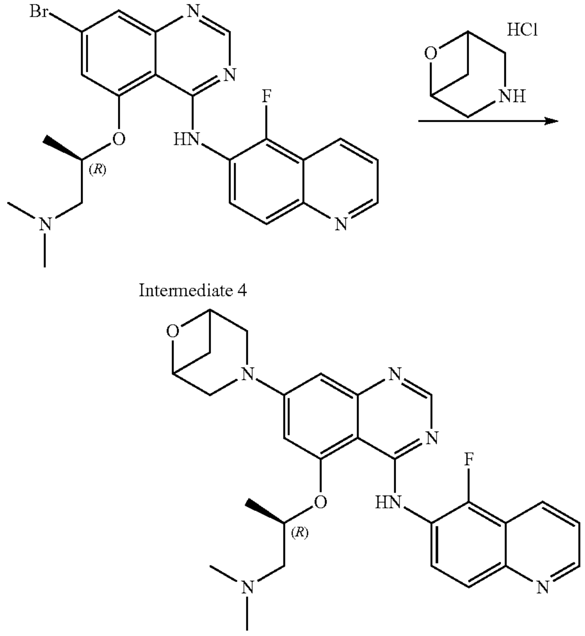

RuPhos Pd (212 mg, 254 μmol, 0.20 eq), $Cs_2CO_3$ (1.65 g, 5.08 mmol, 4.00 eq), Intermediate 4 (600 mg, 1.27 mmol, 1.00 eq), 6-oxa-3-azabicyclo[3.1.1]heptane hydrochloride (344 mg, 2.504 mmol, 2.00 eq) and dioxane (20 mL) were combined at rt. The resulting mixture was stirred at 100° C. for 2 h under $N_2$. The reaction mixture was extracted with 3×100 mL of EA. The organic layer was dried with $Na_2SO_4$ then concentrated under vacuum. The crude product was purified by HPLC. Column: YMC-Actus Triart C18 ExRS, 30 mm×150 mm, 5 um; Mobile Phase A: Water (10 mM $NH_4HCO_3$+0.1% $NH_3·H_2O$), Mobile Phase B: ACN; Flow rate: 60 mL/min; Gradient: 30 B to 55 B in 9 min, 254/220 nm; RT1: 8.58 min. The resulting material further purified by prep-Chiral-HPLC. Column: CHIRAL ART Cellulose-SB, 5×25 cm, 5 μm; Mobile Phase A: MTBE (0.5% 2M NH3-MeOH), Mobile Phase B: EtOH; Flow rate: 20 mL/min; Isocratic 20% B for 9 min to afford the title compound (176 mg, 73%) as a white solid. LC-MS: (ES, m/z): RT=0.738 min, LC-MS: m/z=489 [M+1]; $^1$H NMR (400 MHz, DMSO-$d_6$) δ 10.39 (s, 1H), 8.92 (dd, J=4.2, 1.7 Hz, 1H), 8.79 (t, J=8.9 Hz, 1H), 8.50 (dt, J=8.2, 1.4 Hz, 1H), 8.35 (s, 1H), 7.93 (d, J=9.3 Hz, 1H), 7.63 (dd, J=8.5, 4.2 Hz, 1H), 6.73 (d, J=2.2 Hz, 1H), 6.53 (d, J=2.2 Hz, 1H), 5.04 (q, J=6.3 Hz, 1H), 4.78 (d, J=6.5 Hz, 2H), 3.78-3.55 (m, 4H), 3.18 (q, J=7.2 Hz, 1H), 2.88 (dd, J=12.9, 8.0 Hz, 1H), 2.51-2.43 (m, 1H), 2.19 (s, 6H), 1.94 (d, J=8.8 Hz, 1H), 1.52 (d, J=6.0 Hz, 3H).

Example 71: (R)-5-((1-(dimethylamino)propan-2-yl) oxy)-N-(5-fluoroquinolin-6-yl)-7-(2-oxa-6-azaspiro [3.3]heptan-6-yl)quinazolin-4-amine

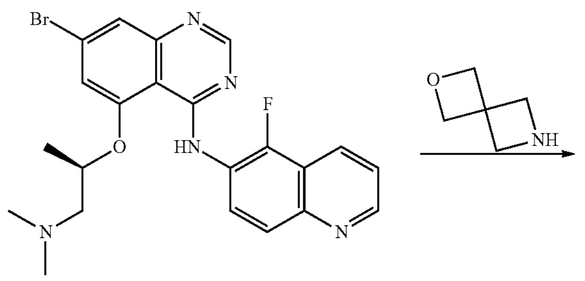

Intermediate 4

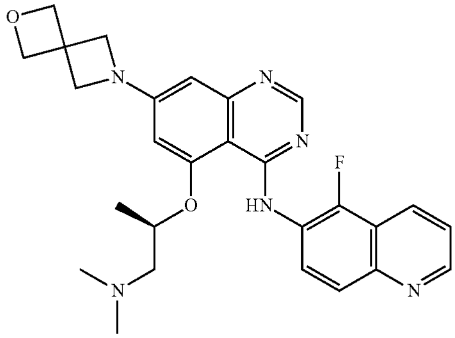

RuPhos Pd (17.7 mg, 21.2 μmol, 0.20 eq), $Cs_2CO_3$ (138 mg, 424 μmol, 2 eq), 2-oxa-6-azaspiro [3.3]heptane (42.0 mg, 424 μmol, 2 eq), Intermediate 4 (42.0 mg, 424 μmol, 2 eq) and dioxane were combined at rt. The resulting mixture was heated to 80° C. for 16 h under $N_2$. The reaction mixture was diluted with DCM (100 mL), washed with water thrice (100 mL) and washed with saturated brine (100 mL). The organic layer was dried over $Na_2SO_4$, filtered and evaporated to afford crude product. The crude product was purified by prep-TLC eluting with 20:1, DCM. The resulting material was purified by prep-HPLC using the following conditions: Column: YMC-Actus Triart C18 ExRS, 30×150 mm, 5 μm; Mobile Phase A: Water (10 mM, $NH_4HCO_3$+0.1% $NH_3·H_2O$), Mobile Phase B: ACN, Flow rate: 60 mL/min; Gradient: 28% B to 61% B over 7 min, Wavelength: 254/220 nm; RT1 (min): 6.6. Afforded the title compound (54.8 mg, 53.2%) as an off-white solid. LC-MS: (ES, m/z): RT=0.742 min, LC-MS: m/z=489.40 [M+1]; $^1$H NMR (300 MHz, Chloroform-d) δ 10.35 (s, 1H), 8.98 (t, J=8.9 Hz, 1H), 8.89 (dd, J=4.3, 1.7 Hz, 1H), 8.53 (s, 1H), 8.49-8.37 (m, 1H), 7.98 (d, J=9.3 Hz, 1H), 7.46 (dd, J=8.5, 4.3 Hz, 1H), 6.36 (d, J=2.0 Hz, 1H), 6.18 (d, J=2.1 Hz, 1H), 4.91 (s, 4H), 4.79 (h, J=6.3 Hz, 1H), 4.21 (s, 4H), 2.96 (dd, J=13.1, 7.2 Hz, 1H), 2.57 (dd, J=13.1, 4.7 Hz, 1H), 2.32 (s, 6H), 1.58 (d, J=6.1 Hz, 3H).

Example 72: 2—((R)-1-(5-(((R)-1-(dimethylamino) propan-2-yl)oxy)-4-((5-fluoroquinolin-6-yl)amino) quinazolin-7-yl)pyrrolidin-3-yl)propan-2-ol

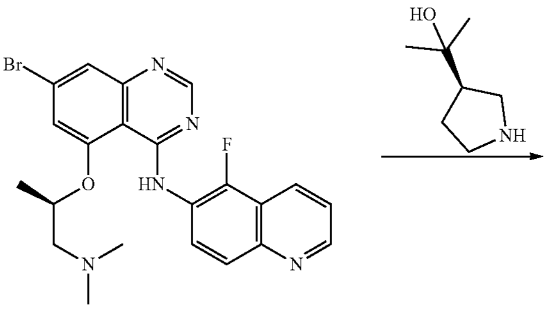

Intermediate 4

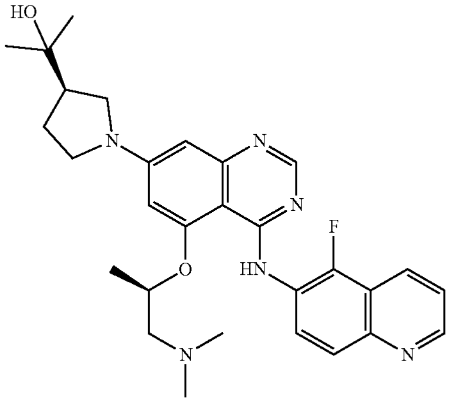

RuPhos Pd (26.5 mg, 31.8 μmol), $Cs_2CO_3$ (207 mg, 636 μmol), Intermediate 4 (150 mg, 318 μmol), (R)-2-(pyrrolidin-3-yl)propan-2-ol (82.1 mg, 636 μmol) and dioxane (10 mL) were combined at rt. The resulting mixture was heated to 80° C. for 16 h. The reaction mixture was diluted with EA (100 mL), washed with water (100 mL×3) and saturated brine (100 mL×1). The organic layer was dried over $Na_2SO_4$, filtered and evaporated to afford crude product. The crude product was purified by prep-TLC eluting with 20:1, DCM:MeOH. The resulting residue was purified by prep-HPLC using the following conditions: Column: XBridge Shield RP18 OBD Column, 30×150 mm, 5 um, Mobile Phase A: Water (10 mM $NH_4HCO_3$+0.1% $NH_3·H_2O$), Mobile Phase B: ACN, Flow rate: 60 mL/min, gradient: 39 B to 55 B in 8 min, 254, 220 nm, RT1=6.98; to afford the title compound (122 mg) as a yellow solid. LC-MS: (ES, m/z): RT=0.789 min, LC-MS: m/z=519.50 [M+1]; $^1$H NMR (300 MHz, DMSO-d6) δ 10.33 (s, 1H), 8.91 (dd, J=4.2, 1.6 Hz, 1H), 8.82 (t, J=8.9 Hz, 1H), 8.49 (dd, J=8.4, 1.5 Hz, 1H), 8.31 (s, 1H), 7.92 (d, J=9.3 Hz, 1H), 7.62 (dd, J=8.5, 4.2 Hz, 1H), 6.52 (d, J=2.1 Hz, 1H), 6.28 (d, J=2.0 Hz, 1H), 5.00 (q, J=5.7 Hz, 1H), 4.43 (s, 1H), 3.58-3.53 (m, 1H), 3.45-3.36 (m, 1H), 3.36-3.33 (m, 1H), 3.31-3.28 (m, 1H), 2.85 (dd, J=12.9, 7.6 Hz, 1H), 2.48-2.30 (m, 2H), 2.19 (s, 6H), 1.97 (m, 2H), 1.51 (d, J=5.9 Hz, 3H), 1.18 (d, J=5.4 Hz, 6H).

Example 73: 2—((S)-1-(5-(((R)-1-(dimethylamino) propan-2-yl)oxy)-4-((5-fluoroquinolin-6-yl)amino) quinazolin-7-yl)pyrrolidin-3-yl)propan-2-ol

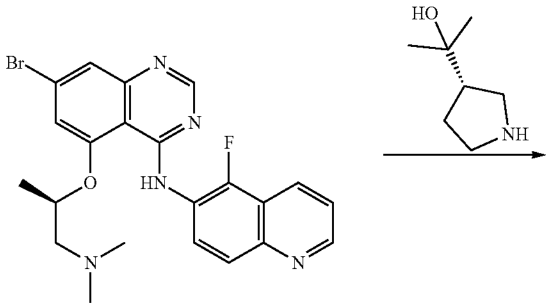

Intermediate 4

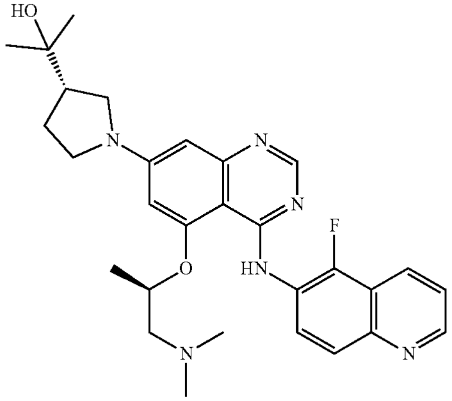

RuPhos Pd (26.5 mg, 31.8 μmol), $Cs_2CO_3$ (207 mg, 636 μmol) was added to Intermediate 4 (150 mg, 318 μmol) and 2-[(3S)-pyrrolidin-3-yl]propan-2-ol (82.1 mg, 636 μmol) in dioxane (10 mL) at rt. The resulting mixture was heated to 80° C. for 16 h. The reaction mixture was diluted with EA (100 mL) washed with water (100 mL×3) and saturated brine (100 mL). The organic layer was dried over $Na_2SO_4$, filtered and evaporated to afford crude product. This material was purified by prep-TLC eluting with 20:1, DCM:MeOH. The resulting residue was purified by prep-HPLC using the following conditions: Column: XBridge Shield RP18 OBD Column, 30×150 mm, 5 um, Mobile Phase A: Water (10 mM $NH_4HCO_3$+0.1% $NH_3 \cdot H_2O$), Mobile Phase B: ACN; Flow rate: 60 mL/min; Gradient: 39 B to 55 B in 8 min, 254; 220 nm; RT1: 6.95 min, afforded 123 mg of the title compound as a yellow solid. LC-MS: (ES, m/z): RT=0.788 min, LC-MS: m/z=519.45 [M+1]; $^1$H NMR (300 MHz, DMSO-$d_6$) δ 10.32 (s, 1H), 8.90 (dd, J=4.2, 1.7 Hz, 1H), 8.81 (t, J=8.9 Hz, 1H), 8.48 (d, J=8.5 Hz, 1H), 8.30 (s, 1H), 7.91 (d, J=9.3 Hz, 1H), 7.61 (dd, J=8.5, 4.2 Hz, 1H), 6.50 (d, J=2.4 Hz, 1H), 6.27 (d, J=2.0 Hz, 1H), 5.04-4.99 (m, 1H), 4.43 (s, 1H), 3.57 (t, J=8.9 Hz, 1H), 3.43-3.33 (m, 1H), 3.33-3.27 (m, 2H), 2.85 (dd, J=12.8, 7.7 Hz, 1H), 2.50-2.29 (m, 2H), 2.18 (s, 6H), 1.95 (q, J=10.6, 9.5 Hz, 2H), 1.50 (d, J=5.9 Hz, 3H), 1.18 (d, J=6.3 Hz, 6H).

Example 74: (R)-5-((1-(dimethylamino)propan-2-yl) oxy)-N-(5-fluoroquinolin-6-yl)-7-(2-oxa-6-azaspiro [3.4]octan-6-yl)quinazolin-4-amine

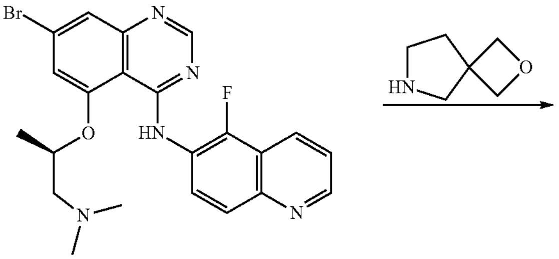

Intermediate 4

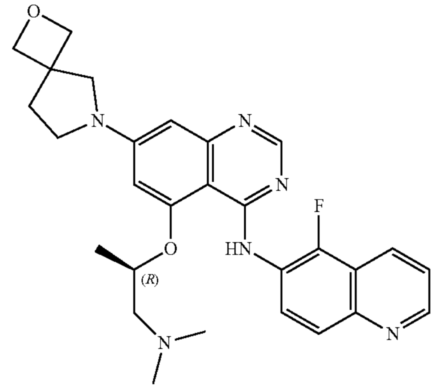

A mixture of Intermediate 4 (75 mg, 0.160 mmol), 2-oxa-6-azaspiro[3.4]octane (27.1 mg, 0.239 mmol), RuPhos Pd G3 (6.67 mg, 7.97 μmol), 2,2'-bis(diphenylphosphaneyl)-1,1'-binaphthalene (4.96 mg, 7.97 μmol), tris(dibenzylideneacetone)dipalladium(0) (4.38 mg, 4.78 μmol), sodium t-butoxide (46.0 mg, 0.478 mmol) in DMF (2.90 ml) was sparged with nitrogen and heated to 90° C. for 8 hr. Concentrated to a crude solid and purified 0-25% (MeOH/DCM to obtain title compound LC-MS: (ES, m/z): RT=1.623 min, LC-MS: m/z=503 [M+1]; $^1$H NMR (DMSO) δ:10.22 (s, 1H), 0.17-9.95 (brs, 1H), 9.04 (s, 1H), 8.66 (s, 1H), 8.60 (d, J=8.6 Hz, 1H), 8.26-8.15 (m, 1H), 8.02 (d, J=9.1 Hz, 1H), 7.74-7.69 (m, 1H), 6.65 (s, 1H), 6.32 (s, 1H), 5.57 (brs, 1H), 4.68-4.58 (m, 4H), 4.14-4.01 (m, 1H), 3.90-3.72 (m, 2H), 3.61-3.43 (m, 3H), 2.94 (d, J=12.8 Hz, 6H), 2.37 (brs, 2H), 1.48 (brs, 3H).

Example 75: 2—((S)-1-(5-(((R)-1-(dimethylamino) propan-2-yl)oxy)-4-((5-fluoroquinolin-6-yl)amino) pyrido[4,3-d]pyrimidin-7-yl)pyrrolidin-3-yl)propan-2-ol

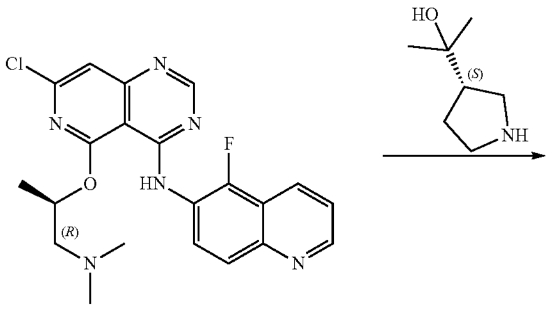

Intermediate 27

-continued

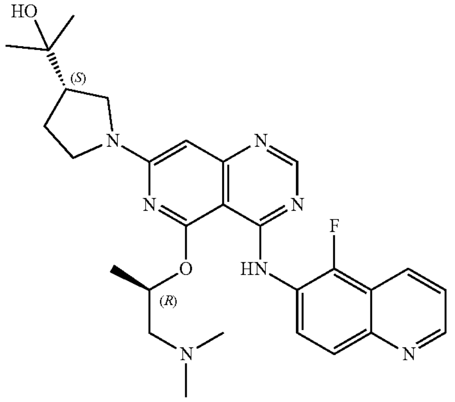

To a solution of Intermediate 27 (150 mg, 0.3513 mmol, 1.00 eq) in 1,4-dioxane was added 2-[(3S)-pyrrolidin-3-yl] propan-2-ol (54.3 mg, 421 μmol, 1.20 eq), $Cs_2CO_3$ (228 mg, 702 μmol, 2.00 eq) and RuPhos Pd G3 (24.5 mg, 35.1 μmol, 0.10 eq) under nitrogen. The mixture was stirred at 100° C. for 3 hours. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The crude product was purified by Prep-HPLC with the following conditions: Column: YMC-Actus Triart C18 ExRS, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 49% B to 79% B in 7 min; Wavelength: 254 nm. This resulted in 64.2 mg (35.2%) of the title compound as an off-white solid. LC-MS: (ES, m/z): RT=1.586 min, LCMS: m/z=594 [M+1]. $^1$H NMR (400 MHz, DMSO-$d_6$) δ 10.12 (d, J=1.9 Hz, 1H), 8.92 (dd, J=4.2, 1.7 Hz, 1H), 8.76 (t, J=8.9 Hz, 1H), 8.50 (dt, J=8.3, 1.4 Hz, 1H), 8.34 (s, 1H), 7.92 (d, J=9.3 Hz, 1H), 7.62 (dd, J=8.5, 4.2 Hz, 1H), 5.98 (s, 1H), 5.55 (dt, J=8.3, 5.7 Hz, 1H), 4.41 (s, 1H), 3.33 (s, 4H), 2.84 (s, 1H), 2.44 (dd, J=12.6, 5.1 Hz, 1H), 2.36-2.28 (m, 1H), 2.19 (s, 6H), 1.94 (d, J=8.7 Hz, 2H), 1.54 (d, J=6.2 Hz, 3H), 1.16 (d, J=4.4 Hz, 6H).

Example 76: 5—(((R)-1-(dimethylamino)propan-2-yl)oxy)-N-(5-fluoroquinolin-6-yl)-7-((R)-3-methoxypyrrolidin-1-yl)pyrido[4,3-d]pyrimidin-4-amine

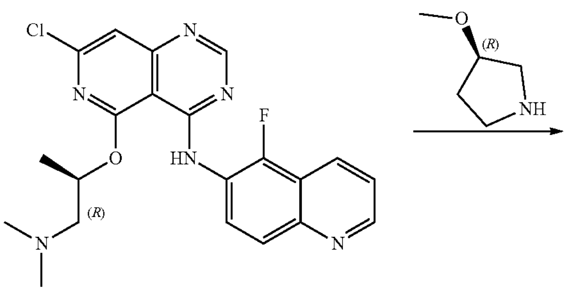

Intermediate 27

-continued

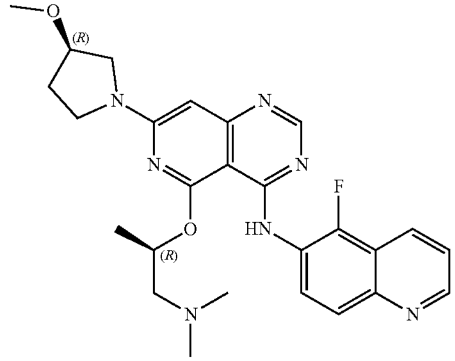

To a solution of Intermediate 27 (160 mg, 374 μmol) in 1,4-dioxane (8 mL) was added (3R)-3-methoxypyrrolidine (56.7 mg, 561 μmol), $Cs_2CO_3$ (365 mg, 1.12 mmol) and RuPhos Pd (31.2 mg, 37.4 μmol) under nitrogen. The mixture was stirred at 100° C. overnight. The reaction mixture was cooled to room temperature. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The product was purified by chromatography with DCM: MEOH (10:1). The crude product was purified by Prep-HPLC with the following conditions: Column: YMC-Acts Trait C18, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 55% B to 85% B in 8 min; Wavelength: 254/220 nm.) to afford the title compound (69.9 mg, yield: 38.1%). LC-MS: (ES, m/z): RT=1.645 min, LCMS: m/z=492 [M+1], $^1$H NMR (300 MHz, DMSO-d6) δ 10.12 (s, 1H), 8.90 (m, J=4.3, 1.7 Hz, 1H), 8.73 (t, J=8.9 Hz, 1H), 8.48 (d, J=8.5 Hz, 1H), 8.34 (s, 1H), 7.91 (d, J=9.3 Hz, 1H), 7.61 (m, J=8.5, 4.2 Hz, 1H), 6.01 (s, 1H), 5.54 (d, J=7.1 Hz, 1H), 4.09 (s, 1H), 3.50 (d, J=37.3 Hz, 4H), 3.27 (s, 3H), 2.84 (m, J=12.6, 8.5 Hz, 1H), 2.44-2.34 (m, 1H), 2.17 (s, 6H), 2.09 (s, 2H), 1.51 (d, J=6.1 Hz, 3H).

Example 77: 5—(((S)-1-(dimethylamino)propan-2-yl)oxy)-N-(5-fluoroquinolin-6-yl)-7-((S)-3-methoxy-pyrrolidin-1-yl)pyrido[4,3-d]pyrimidin-4-amine

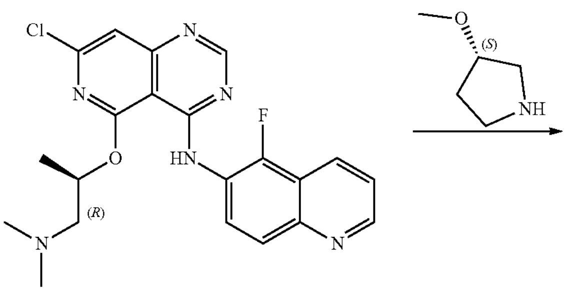

Intermediate 27

-continued

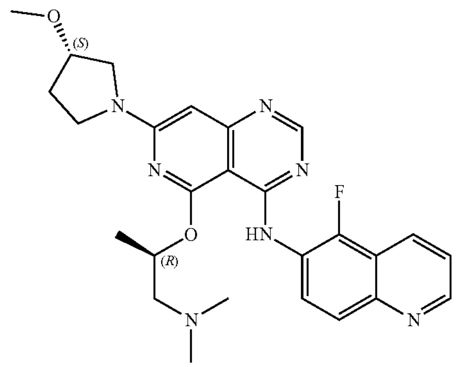

To a solution of Intermediate 27 (160 mg, 374 μmol) in 1,4-dioxane (8 mL) was added (3S)-3-methoxypyrrolidine (56.7 mg, 561 μmol), $Cs_2CO_3$ (365 mg, 1.12 mmol) and RuPhos Pd (31.2 mg, 37.4 μmol) under nitrogen. The mixture was stirred at 100° C. overnight. The reaction mixture was cooled to room temperature and diluted with 20 mL of water. Extracted with 2×20 mL of ethyl acetate and the organic layers combined. The organic layers were washed with 20 mL of brine, dried over anhydrous sodium sulfate and concentrated under vacuum. The product was purified by silica chromatography with DCM: MEOH (10: 1). The crude product was purified by Prep-HPLC with the following conditions: Column: YMC-Acts Trait C18 Expr's, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 56% B to 86% B in 7 min; Wavelength: 254 nm to afford the title compound (84.9 mg, yield: 46.3%). LC-MS: (ES, m/z): RT=1.644 min, LCMS: m/z=492 [M+1], $^1H$ NMR (300 MHz, DMSO-d6) δ 10.10 (s, 1H), 8.89 (d, J=4.2 Hz, 1H), 8.74 (t, J=8.9 Hz, 1H), 8.47 (d, J=8.5 Hz, 1H), 8.33 (s, 1H), 7.89 (d, J=9.3 Hz, 1H), 7.60 (m, J=8.5, 4.2 Hz, 1H), 5.99 (s, 1H), 5.53 (q, J=6.5 Hz, 1H), 4.08 (s, 1H), 3.55 (s, 4H), 3.27 (s, 3H), 2.83 (m, J=12.6, 8.4 Hz, 1H), 2.44-2.37 (m, 1H), 2.17 (s, 8H), 1.51 (d, J=6.1 Hz, 3H).

-continued

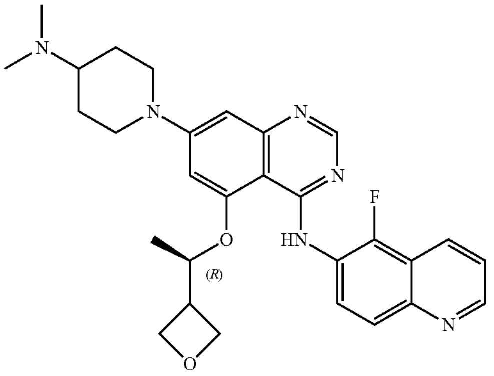

The reaction mixture of BINAP-Pd (19.8 mg, 21.3 μmol), $Cs_2CO_3$ (138 mg, 426 μmol), Intermediate 5 (100 mg, 213 μmol) and N,N-dimethylpiperidin-4-amine (54.6 mg, 426 μmol) in dioxane (6 mL) was heated to 100° C. for 16 hr under $N_2$. The reaction mixture was diluted with EA (100 mL), washed with water (100 mL*3) and saturated brine (100 mL*1). The organic layer was dried over $Na_2SO_4$, filtered and evaporated to afford crude product. Purified by a silica gel column using DCM:MeOH=20:1. The residue was purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 30% B to 47% B in 8 min, 47% B; Wavelength: 254; 220 nm, to afford the title compound (27.8 mg, yield: 25.2%) as an off-white solid. LC-MS: (ES, m/z): RT=0.751 min, LCMS: m/z=517 [M+1], 1H NMR (300 MHz, DMSO-d6) δ 10.00 (s, 1H), 8.92-8.84 (m, 2H), 8.53 (d, J=8.1 Hz, 1H), 8.38 (s, 1H), 7.92 (d, J=9.4 Hz, 1H), 7.64 (dd, J=8.6, 4.3 Hz, 1H), 6.97 (s, 1H), 6.68 (d, J=2.0 Hz, 1H), 5.41 (t, J=6.6 Hz, 1H), 4.80 (q, J=6.4 Hz, 2H), 4.58 (t, J=6.1 Hz, 1H), 4.50 (t, J=6.0 Hz, 1H), 4.06 (d, J=12.8 Hz, 2H), 3.51-3.41 (m, 1H), 2.93 (t, J=12.3 Hz, 2H), 2.36 (s, 1H), 2.21 (s, 6H), 1.88 (d, J=12.4 Hz, 2H), 1.57-1.44 (m, 2H), 1.37 (d, J=5.8 Hz, 3H).

Example 78: (R)-7-(4-(dimethylamino)piperidin-1-yl)-N-(5-fluoroquinolin-6-yl)-5-(1-(oxetan-3-yl) ethoxy)quinazolin-4-amine

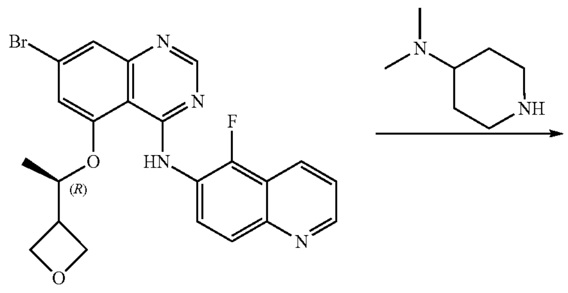

Intermediate 5

Example 79: 7—((R)-3-(dimethylamino)pyrrolidin-1-yl)-N-(5-fluoroquinolin-6-yl)-5-((R)-1-(oxetan-3-yl)ethoxy)quinazolin-4-amine

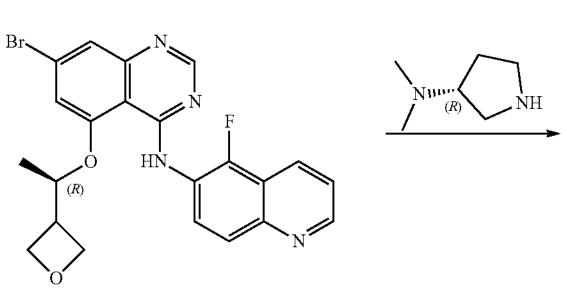

Intermediate 5

-continued

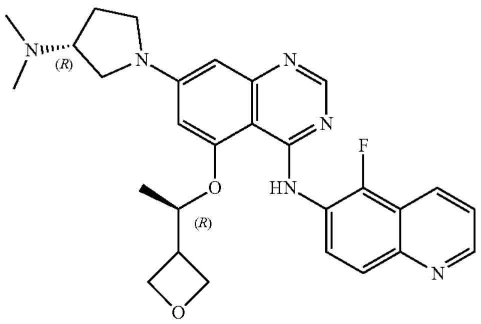

BINAP-Pd (19.8 mg, 21.3 μmol), $Cs_2CO_3$ (138 mg, 426 μmol), Intermediate 5 (100 mg, 213 μmol) and (3R)—N,N-dimethylpyrrolidin-3-amine (48.6 mg, 426 μmol) in dioxane (6 mL) was heated to 100° C. for 16 hr under $N_2$. The reaction mixture was diluted with EA (100 mL), washed with water (100 mL*3) and saturated brine (100 mL*1). The organic layer was dried over $Na_2SO_4$, filtered and evaporated to afford crude product. The crude product was purified by a silica gel column using DCM:MeOH=15:1. The residue was further purified by Prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 33% B to 63% B in 7 min, 63% B; Wavelength: 254 nm. This resulted in the title compound (48.2 mg, yield: 45%) as a light yellow solid. LC-MS: (ES, m/z): RT=0.742 min, LCMS: m/z=503 [M+1], $^1H$ NMR (300 MHz, DMSO-d6) δ 9.98 (s, 1H), 8.95-8.80 (m, 2H), 8.52 (d, J=8.5 Hz, 1H), 8.33 (s, 1H), 7.92 (d, J=9.2 Hz, 1H), 7.63 (dd, J=8.5, 4.2 Hz, 1H), 6.59 (s, 1H), 6.34 (d, J=2.0 Hz, 1H), 5.38 (t, J=6.7 Hz, 1H), 4.87-4.75 (m, 2H), 4.54 (dt, J=22.2, 6.1 Hz, 2H), 3.62 (dt, J=18.1, 8.7 Hz, 2H), 3.45 (t, J=8.2 Hz, 2H), 3.23 (t, J=8.9 Hz, 1H), 2.88 (s, 1H), 2.26 (m, 7H), 1.90 (d, J=10.0 Hz, 1H), 1.40 (d, J=5.9 Hz, 3H).

Example 80: 7—((S)-3-(dimethylamino)pyrrolidin-1-yl)-N-(5-fluoroquinolin-6-yl)-5-((R)-1-(oxetan-3-yl)ethoxy)quinazolin-4-amine

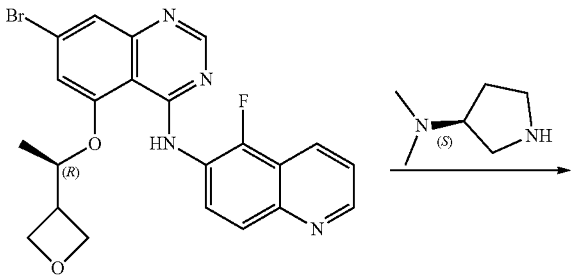

Intermediate 5

-continued

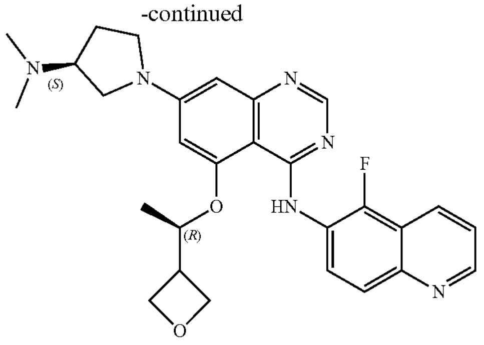

The reaction mixture of BINAP-Pd (19.8 mg, 21.3 μmol) and $Cs_2CO_3$ (69.4 mg, 213 μmol), Intermediate 5 (100 mg, 213 μmol) and (3S)—N,N-dimethylpyrrolidin-3-amine (48.6 mg, 426 μmol) in dioxane (6 mL) was heated to 100° C. for 16 h under $N_2$. The reaction mixture was diluted with EA (100 mL), washed with water (100 mL*3) and saturated brine (100 mL*1). The organic layer was dried over $Na_2SO_4$, filtered and evaporated to afford crude product. The crude product was purified by a silica gel column using DCM:MeOH=15:1. The residue was purified by Prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 32% B to 62% B in 7 min, 62% B; Wavelength: 254 nm. This resulted in the title compound (27.3 mg, yield: 25.5%) as an off-white solid. LC-MS: (ES, m/z): RT=0.735 min, LCMS: m/z=503 [M+1], 1H NMR (300 MHz, DMSO-d6) δ 9.98 (s, 1H), 8.91-8.86 (m, 2H), 8.52 (d, J=8.3 Hz, 1H), 8.33 (s, 1H), 7.92 (d, J=9.3 Hz, 1H), 7.63 (dd, J=8.6, 4.3 Hz, 1H), 6.58 (s, 1H), 6.34 (d, J=1.9 Hz, 1H), 5.39 (t, J=6.8 Hz, 1H), 4.80 (dd, J=7.5, 5.5 Hz, 2H), 4.54 (dt, J=21.3, 6.0 Hz, 2H), 3.68 (dd, J=21.0, 11.4 Hz, 2H), 3.48-3.38 (m, 2H), 3.19 (t, J=8.8 Hz, 1H), 2.85 (s, 1H), 2.26 (m, 7H), 1.93-1.80 (m, 1H), 1.40 (d, J=5.9 Hz, 3H).

Example 81: (R)-4-(5-((1-(dimethylamino)propan-2-yl)oxy)-4-((5-fluoroquinolin-6-yl)amino)quinazolin-7-yl)thiomorpholine 1,1-dioxide

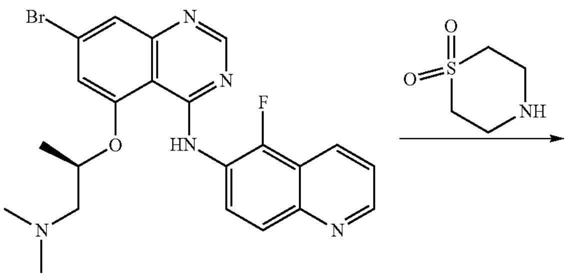

Intermediate 4

-continued

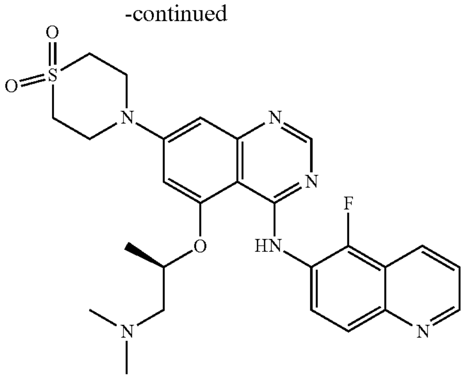

BINAP-Pd(19.7 mg, 21.2 μmol) and $Cs_2CO_3$ (138 mg, 424 μmol) were added to Intermediate 4 (100 mg, 212 μmol) and thiomorpholine 1,1-dioxide (57.3 mg, 424 μmol) in dioxane at rt. The resulting mixture was heated at 100° C. for 3 hours under $N_2$. The reaction mixture was diluted with EtOAc (120 mL) and washed with water (60 mL). The organic layer was dried over $Na_2SO_4$, filtered and evaporated concentrated under vacuum. The crude product was purified by Prep-TLC eluting with DCM:MeOH=20:1. The residue was purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 23% B to 56% B in 7 min, 56% B; Wavelength: 254/220 nm; afforded the title compound (78.5 mg,) as a white solid. LC-MS: (ES, m/z): RT=0.967 min, LCMS: m/z=525 [M+1], $^1H$ NMR (400 MHz, DMSO-d6) δ 10.40 (s, 1H), 8.93 (dd, J=4.2, 1.7 Hz, 1H), 8.74 (t, J=8.9 Hz, 1H), 8.51 (d, J=8.4 Hz, 1H), 8.40 (s, 1H), 7.94 (d, J=9.3 Hz, 1H), 7.64 (dd, J=8.5, 4.2 Hz, 1H), 6.96 (d, J=2.3 Hz, 1H), 6.81 (d, J=2.2 Hz, 1H), 5.09 (s, 1H), 4.03 (d, J=6.1 Hz, 4H), 3.21 (t, J=5.2 Hz, 4H), 2.87 (dd, J=13.0, 8.0 Hz, 1H), 2.51 (s, 1H), 2.18 (s, 6H), 1.48 (d, J=5.9 Hz, 3H).

Example 82: (R)-5-((1-(dimethylamino)propan-2-yl)oxy)-7-(4-fluoro-1H-pyrazol-1-yl)-N-(5-fluoroquinolin-6-yl)quinazolin-4-amine

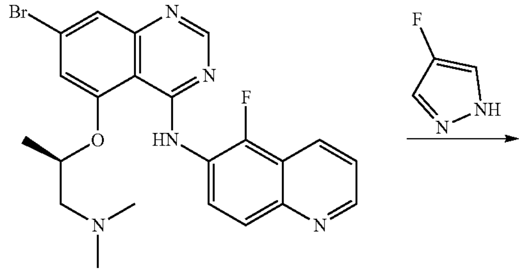

Intermediate 4

-continued

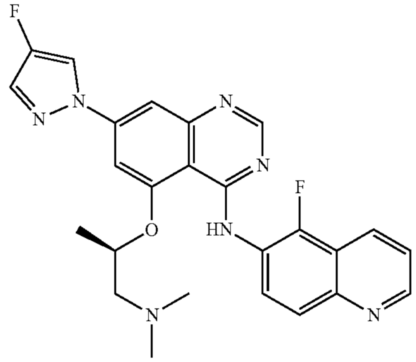

Ephos Pd G4 (68.1 mg, 74.2 μmol) and $Cs_2CO_3$ (103 mg, 318 μmol) were added to Intermediate 4 (50 mg, 106 mg) and 4-fluoro-1H-pyrazole (22.8 mg, 265 μmol) in dioxane at rt. This resulting mixture was heated at 100° C. for 3 hr. The reaction mixture was diluted with EtOAc (120 mL) and washed with water (60 mL). The organic layer was dried over $Na_2SO_4$, filtered and evaporated to afford crude product. The mixture was concentrated under vacuum. The crude product was purified by Prep-TLC eluting with DCM:MeOH=10:1. The residue was further purified by prep-HPLC using the following conditions: Column: YMC-Actus Triart C18 ExRS, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 57% B to 87% B in 7 min, 87% B; Wavelength: 254 nm; RT1(min): 6.45; This afforded the title compound (20.4 mg) as an off-white solid. LC-MS: (ES, m/z): RT=1.161 min, LCMS: m/z=476 [M+1], 1H NMR (400 MHz, DMSO-d6) δ 10.62 (s, 1H), 9.07 (d, J=4.4 Hz, 1H), 8.97 (dd, J=4.2, 1.7 Hz, 1H), 8.60-8.51 (m, 3H), 8.02 (d, J=4.2 Hz, 2H), 7.79 (s, 1H), 7.71 (s, 2H), 5.12 (s, 1H), 2.94 (s, 1H), 2.54 (s, 1H), 2.20 (s, 6H), 1.54 (d, J=5.9 Hz, 3H).

Example 83: (R)-5-((1-(dimethylamino)propan-2-yl)oxy)-N-(5-fluoroquinolin-6-yl)-7-(4-methyl-1H-pyrazol-1-yl)quinazolin-4-amine

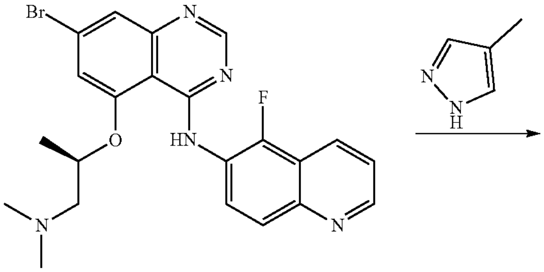

Intermediate 4

-continued

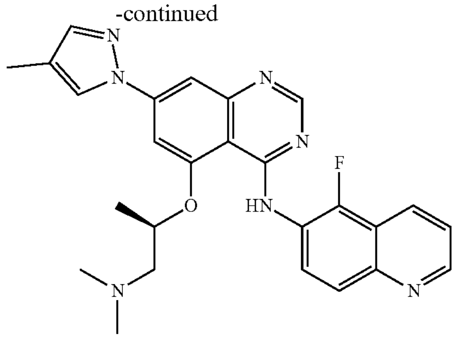

EPhos Pd G4 (68.1 mg, 74.2 μmol) and $Cs_2CO_3$ (103 mg, 318 μmol) were added to Intermediate 4 (50 mg, 106 μmol) and 4-methyl-1H-pyrazole (21.7 mg, 265 μmol) in dioxane (10 mL) at rt. This resulting mixture was heated at 100° C. for 3 hours. The reaction mixture was diluted with EtOAc (120 mL) and washed with water (60 mL). The organic layer was dried over $Na_2SO_4$, filtered and evaporated under vacuum. The crude product was purified by Prep-TLC using DCM: MeOH=10:1. The residue was purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 37% B to 73% B in 7 min, 73% B; Wavelength: 254/220 nm; RT1(min): 6.23; gave the title compound (20.3 mg) as a white solid. LC-MS: (ES, m/z): RT=1.155 min, LCMS: m/z=472 [M+1], 1H NMR (400 MHz, DMSO-d6) δ 10.62 (s, 1H), 8.96 (dd, J=4.2, 1.7 Hz, 1H), 8.65-8.50 (m, 4H), 7.97 (d, J=9.2 Hz, 1H), 7.77-7.69 (m, 3H), 7.66 (dd, J=8.5, 4.2 Hz, 1H), 5.10 (s, 1H), 2.93 (s, 1H), 2.17 (d, J=10.7 Hz, 9H), 1.54 (d, J=6.0 Hz, 3H).

Example 84: N-(5-fluoroquinolin-6-yl)-7-((R)-3-methoxypyrrolidin-1-yl)-5-((R)-1-(oxetan-3-yl)ethoxy)quinazolin-4-amine and N-(5-fluoroquinolin-6-yl)-7-((S)-3-methoxypyrrolidin-1-yl)-5-((R)-1-(oxetan-3-yl)ethoxy)quinazolin-4-amine Example 85a: N-(5-fluoroquinolin-6-yl)-7-((R)-3-methoxypyrrolidin-1-yl)-5-((R)-1-(oxetan-3-yl)ethoxy)quinazolin-4-amine or N-(5-fluoroquinolin-6-yl)-7-((S)-3-methoxypyrrolidin-1-yl)-5-((R)-1-(oxetan-3-yl)ethoxy)quinazolin-4-amine Example 85b: N-(5-fluoroquinolin-6-yl)-7-((S)-3-methoxypyrrolidin-1-yl)-5-((R)-1-(oxetan-3-yl)ethoxy)quinazolin-4-amine or N-(5-fluoroquinolin-6-yl)-7-((R)-3-methoxypyrrolidin-1-yl)-5-((R)-1-(oxetan-3-yl)ethoxy)quinazolin-4-amine

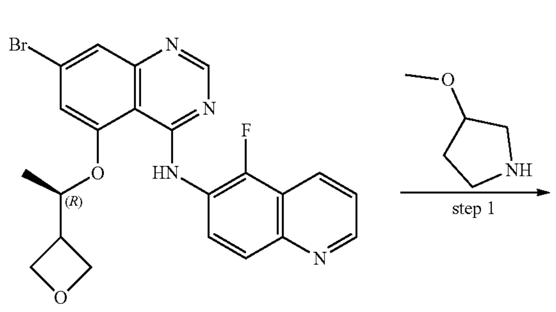

Intermediate 5

-continued

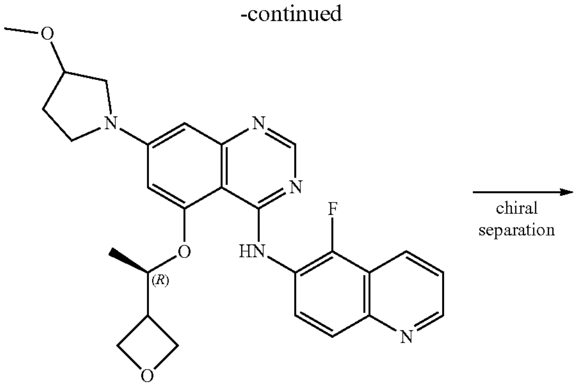

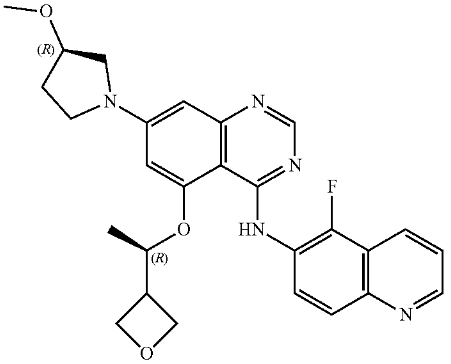

or

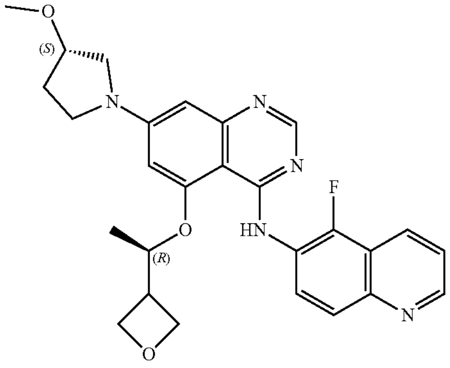

Example 84: N-(5-fluoroquinolin-6-yl)-7-((R)-3-methoxypyrrolidin-1-yl)-5-((R)-1-(oxetan-3-yl)ethoxy)quinazolin-4-amine and N-(5-fluoroquinolin-6-yl)-7-((S)-3-methoxypyrrolidin-1-yl)-5-((R)-1-(oxetan-3-yl)ethoxy)quinazolin-4-amine To a solution of Intermediate 5 (100 mg, 213 μmol, 1 eq) in 1,4-dioxane (5 mL) was added 3-methoxypyrrolidine hydrochloride (73.2 mg, 532 μmol, 2.5 eq), $Cs_2CO_3$ (277 mg, 852 μmol, 4 eq) and Xantphos Pd G4 (37.8 mg, 42.6 μmol, 0.2 eq) under nitrogen. The mixture was stirred at 100° C. for 3 hours. The reaction mixture was cooled to room temperature. The reaction was diluted with 20 mL of water and extracted with 2×20 mL of ethyl acetate. The organic layers were combined and washed with 20 mL of brine. The mixture was dried over anhydrous sodium sulfate and concentrated under vacuum. The crude product was purified by prep-HPLC using the following conditions: (Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 40% B to 70% B in 8 min 70% B; Wavelength:

254/220 nm) to afford the title compound (46.5 mg, yield: 44.7%). LC-MS: (ES, m/z): RT=1.321 min, LCMS: m/z=490 [M+1] 1H NMR (300 MHz, DMSO-d6) δ 9.94 (t, J=2.6 Hz, 1H), 8.96-8.63 (m, 2H), 8.49 (dt, J=8.4, 1.5 Hz, 1H), 8.31 (s, 1H), 7.88 (d, J=9.3 Hz, 1H), 7.60 (dd, J=8.5, 4.2 Hz, 1H), 6.55 (s, 1H), 6.31 (d, J=2.0 Hz, 1H), 5.35 (q, J=6.1 Hz, 1H), 4.85-4.65 (m, 2H), 4.59-4.31 (m, 2H), 4.13 (s, 1H), 3.62-3.30 (m, 8H), 2.12 (t, J=5.9 Hz, 2H), 1.38 (dd, J=6.0, 2.8 Hz, 3H).

Chiral Separation:

Example 84: (46.5 mg, 94.9 μmol, 1 eq) was Purified by Prep-Chiral-HPLC with following conditions: (Column: CHIRALPAK ID, 2*25 cm, 5 mi; Mobile Phase A: Hex: DCM=3:1 (0.5% 2M NH3-MeOH)-HPLC, Mobile Phase B: IPA-HPLC; Flow rate: 20 mL/min; Gradient: 30% B to 30% B in 20 min; Wavelength: 220/254 nm) to afford:

Example 85a: First eluting isomer, (13.3 mg), off-white solid: LC-MS: (ES, m/z): RT=1.328 min, LCMS: m/z=490 [M+1]. Chiral-HPLC R=2.47, $^{1}$H NMR (300 MHz, DMSO-d6) δ 9.98 (d, J=1.8 Hz, 1H), 9.06-8.69 (m, 2H), 8.65-8.48 (m, 1H), 8.34 (s, 1H), 7.92 (d, J=9.3 Hz, 1H), 7.63 (dd, J=8.5, 4.2 Hz, 1H), 6.59 (d, J=2.1 Hz, 1H), 6.34 (d, J=2.0 Hz, 1H), 5.37 (p, J=6.0 Hz, 1H), 4.93-4.72 (m, 2H), 4.54 (dt, J=22.3, 6.0 Hz, 2H), 4.16 (d, J=4.3 Hz, 1H), 3.66-3.40 (m, 5H), 3.33 (d, J=3.9 Hz, 3H), 2.15 (t, J=5.7 Hz, 2H), 1.41 (d, J=5.9 Hz, 3H).

Example 85b: Second eluting isomer, (8.2 mg) off-white solid: LC-MS: (ES, m/z): RT=1.325 min, LCMS: m/z=490 [M+1]. Chiral-HPLC R=3.127, 1H NMR (300 MHz, DMSO-d6) δ 9.98 (s, 1H), 8.99-8.72 (m, 2H), 8.69-8.46 (m, 1H), 8.34 (s, 1H), 7.92 (d, J=9.3 Hz, 1H), 7.63 (dd, J=8.5, 4.2 Hz, 1H), 6.58 (d, J=2.1 Hz, 1H), 6.34 (d, J=2.0 Hz, 1H), 5.43-5.28 (m, 1H), 4.91-4.74 (m, 2H), 4.54 (dt, J=23.5, 6.0 Hz, 2H), 4.16 (s, 1H), 3.58-3.26 (m, 8H), 2.22-2.05 (m, 2H), 1.40 (d, J=5.9 Hz, 3H).

Example 86: 5—(((R)-1-(dimethylamino)propan-2-yl)oxy)-N-(5-fluoroquinolin-6-yl)-7-((R)-3-methoxypyrrolidin-1-yl)quinazolin-4-amine and 5-(((R)-1-(dimethylamino)propan-2-yl)oxy)-N-(5-fluoroquinolin-6-yl)-7-((S)-3-methoxypyrrolidin-1-yl)quinazolin-4-amine Example 87a: 5-(((R)-1-(dimethylamino)propan-2-yl)oxy)-N-(5-fluoroquinolin-6-yl)-7-((R)-3-methoxypyrrolidin-1-yl)quinazolin-4-amine or 5-(((R)-1-(dimethylamino)propan-2-yl)oxy)-N-(5-fluoroquinolin-6-yl)-7-((S)-3-methoxypyrrolidin-1-yl)quinazolin-4-amine Example 87a: 5-(((R)-1-(dimethylamino)propan-2-yl)oxy)-N-(5-fluoroquinolin-6-yl)-7-((S)-3-methoxy-pyrrolidin-1-yl)quinazolin-4-amine or 5-(((R)-1-(dimethylamino)propan-2-yl)oxy)-N-(5-fluoroquinolin-6-yl)-7-((R)-3-methoxypyrrolidin-1-yl)quinazolin-4-amine

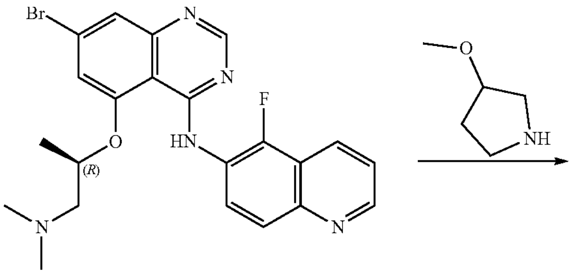

Intermediate 4

-continued

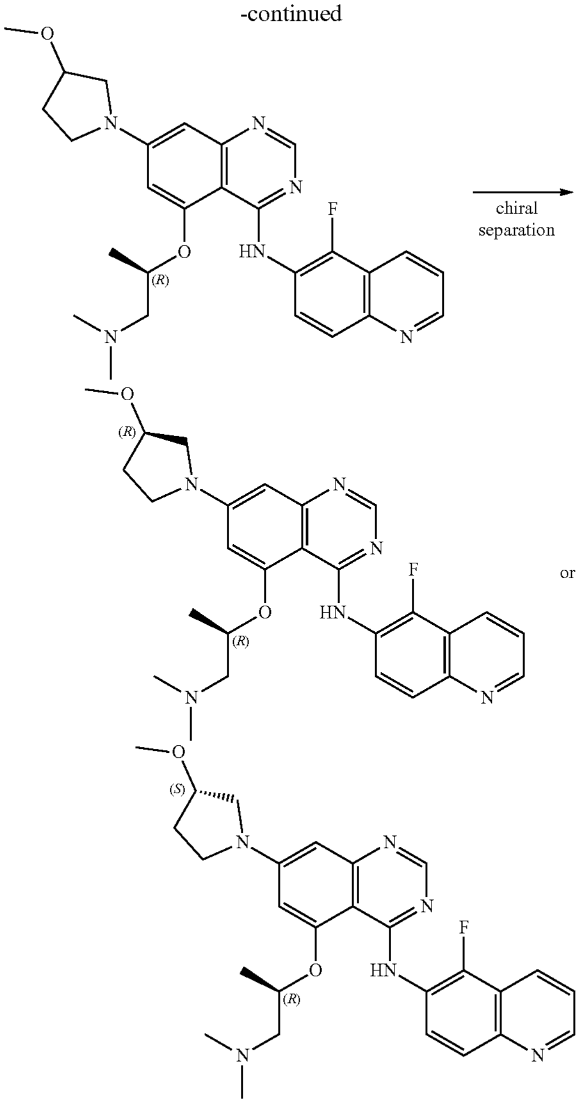

or

Example 86: 5—(((R)-1-(dimethylamino)propan-2-yl)oxy)-N-(5-fluoroquinolin-6-yl)-7-((R)-3-methoxypyrrolidin-1-yl)quinazolin-4-amine and 5-(((R)-1-(dimethylamino)propan-2-yl)oxy)-N-(5-fluoroquinolin-6-yl)-7-((S)-3-methoxypyrrolidin-1-yl)quinazolin-4-amine To a solution of Intermediate 4 (100 mg, 212 μmol, 1 eq) in 1,4-dioxane (5 mL) was added 3-methoxypyrrolidine hydrochloride (72.9 mg, 530 μmol, 2.5 eq), $Cs_2CO_3$ (276 mg, 848 μmol, 4 eq) and Xantphos Pd G4 (37.6 mg, 42.4 μmol, 0.2 eq) under nitrogen. The mixture was stirred at 100° C. for 3 hours. The reaction mixture was cooled to room temperature, diluted with 20 mL of water, and extracted with 2×20 mL of ethyl acetate. The organic layers were combined and washed with 20 mL of brine. Dried over anhydrous sodium sulfate and concentrated under vacuum. The crude product was purified by Prep-HPLC with the following conditions: (Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 41% B to 61% B in 8 min; Wavelength: 254; 220 nm) to afford the title compound (30.8 mg, yield: 29.6%) as a white solid. LC-MS: (ES, m/z): RT=1.493 min, LCMS: m/z=491 [M+1]. $^1$H NMR (400 MHz, DMSO-d6) δ 10.33 (s, 1H), 8.99-8.78 (m, 2H), 8.58-8.41 (m, 1H), 8.31 (d, J=1.7 Hz, 1H), 7.92 (d, J=9.3 Hz, 1H), 7.62 (dd, J=8.5, 4.2 Hz, 1H), 6.53 (t, J=2.4 Hz, 1H), 6.31 (d, J=2.0 Hz, 1H), 5.01 (d, J=6.5 Hz, 1H), 4.14 (d, J=4.4 Hz, 1H), 3.64-3.30 (m, 7H), 2.85 (ddd, J=13.0, 7.8, 2.9 Hz, 1H), 2.48-2.01 (m, 9H), 1.50 (dd, J=6.0, 3.6 Hz, 3H).

Chiral Separation:

Example 86 (30.8 mg, 62.7 μmol, 1 eq) was Purified by Prep-Chiral-HPLC with following conditions: (Column: Lux 5 um Cellulose-4, 2.12*25 cm, 5 μm; Mobile Phase A: Hex (0.5% 2M $NH_3$-MeOH)-HPLC, Mobile Phase B: EtOH-HPLC; Flow rate: 20 mL/min; Gradient: 45% B to 45% B in 45 min; Wavelength: 220/254 nm) to afford:

Example 87a: First eluting isomer, (3.7 mg): LC-MS: (ES, m/z): RT=1.500 min, LCMS: m/z=491 [M+1]. Chiral-HPLC R=4.18, $^1$H NMR (300 MHz, DMSO-d6) δ 10.31 (s, 1H), 8.89 (dd, J=4.2, 1.7 Hz, 1H), 8.79 (t, J=8.9 Hz, 1H), 8.48 (dd, J=8.4, 1.5 Hz, 1H), 8.29 (s, 1H), 7.90 (d, J=9.2 Hz, 1H), 7.60 (dd, J=8.5, 4.2 Hz, 1H), 6.51 (d, J=2.1 Hz, 1H), 6.29 (d, J=2.0 Hz, 1H), 5.08-4.89 (m, 1H), 4.12 (d, J=4.4 Hz, 1H), 3.55 (dd, J=11.2, 4.8 Hz, 1H), 3.43 (d, J=12.8 Hz, 3H), 3.29 (d, J=2.5 Hz, 3H), 2.83 (dd, J=12.9, 7.7 Hz, 1H), 2.48 (p, J=1.8 Hz, 1H), 2.17 (s, 8H), 1.49 (d, J=6.0 Hz, 3H).

Example 87b: Second eluting isomer, (4.4 mg): (ES, m/z): RT=1.502 min, LCMS: m/z=491 [M+1]. Chiral-HPLC R=5.094, $^1$H NMR (300 MHz, DMSO-d6) δ 10.98 (s, 1H), 8.93 (dd, J=4.2, 1.7 Hz, 1H), 8.65-8.41 (m, 3H), 8.40 (s, 1H), 8.12 (s, 1H), 7.94 (d, J=9.2 Hz, 1H), 7.63 (dd, J=8.5, 4.2 Hz, 1H), 7.57 (d, J=1.4 Hz, 1H), 7.43 (d, J=1.6 Hz, 1H), 5.97 (q, J=6.4 Hz, 1H), 3.91 (s, 3H), 3.16 (s, 3H), 2.85 (s, 3H), 1.65 (d, J=6.4 Hz, 3H).

Example 88: 2—((S)-1-(4-((5,7-difluoroquinolin-6-yl)amino)-5-(((R)-1-(dimethylamino)propan-2-yl)oxy)quinazolin-7-yl)pyrrolidin-3-yl)propan-2-ol

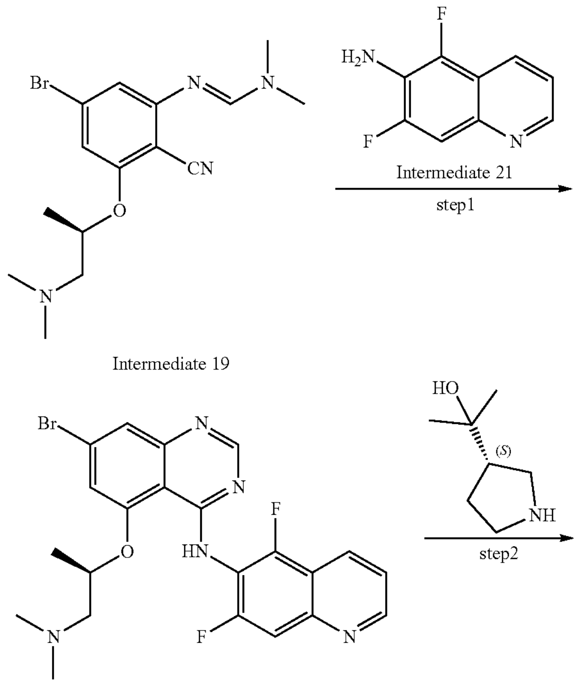

-continued

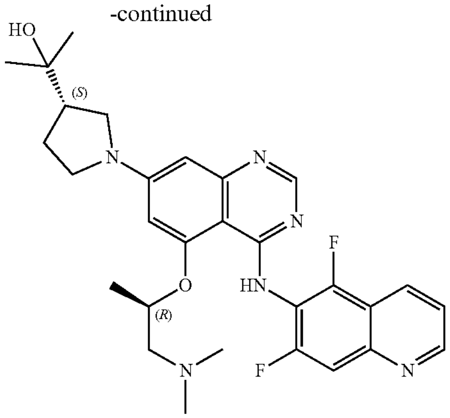

Step 1: (R)-7-bromo-N-(5,7-difluoroquinolin-6-yl)-5-((1-(dimethylamino)propan-2-yl)oxy)quinazolin-4-amine To a mixture of Intermediate 21 (100 mg, 555 μmol) in AcOH (10 mL) was added Intermediate 19 (586 mg, 1.66 mmol) at 25° C. The reaction mixture was stirred at 100° C. overnight. The reaction mixture was concentrated under vacuum. The residue was purified by flash chromatography to give the title compound (80 mg, yield: 29.5%) as a white solid. LC-MS: (ES, m/z): RT=1.403 min, LCMS: m/z=489 [M+1], Step 2: 2—((S)-1-(4-((5,7-difluoroquinolin-6-yl)amino)-5-(((R)-1-(dimethylamino)propan-2-yl)oxy)quinazolin-7-yl)pyrrolidin-3-yl)propan-2-ol To a solution of (R)-7-bromo-N-(5,7-difluoroquinolin-6-yl)-5-((1-(dimethylamino)propan-2-yl)oxy)quinazolin-4-amine (80 mg, 163 μmol) in 1,4-dioxane was added 2-[(3S)-pyrrolidin-3-yl]propan-2-ol (31.5 mg, 244 μmol), $Cs_2CO_3$ (13.6 mg, 16.3 μmol) and RuPhos Pd (159 mg, 489 μmol). The mixture was stirred at 100° C. for 3 hours. The resulting solution was diluted with 20 mL of water. The resulting solution was extracted with 2×20 mL of ethyl acetate and the organic layers combined. The organic layer was washed with 20 mL of brine. The mixture was dried over anhydrous sodium sulfate and concentrated under vacuum. The crude product was purified by Prep-HPLC with the following conditions: Column: Column: Bridge Shield RP18 OBD Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 28% B to 64% B in 7 min; Wavelength: 254/220 nm to afford the title compound (7.9 mg, yield: 9.03%). LC-MS: (ES, m/z): RT=0.755 min, LCMS: 537 m/z=[M+1], $^1$H NMR (400 MHz, DMSO-d6) δ 10.10 (s, 1H), 9.01 (m, J=4.3, 1.7 Hz, 1H), 8.57-8.46 (m, 1H), 8.11 (s, 1H), 7.82 (d, J=10.7 Hz, 1H), 7.65 (m, J=8.5, 4.3 Hz, 1H), 6.45 (d, J=2.1 Hz, 1H), 6.26 (d, J=2.0 Hz, 1H), 4.89 (s, 1H), 4.43 (s, 1H), 3.62-3.51 (m, 1H), 3.46 (t, J=9.1 Hz, 1H), 3.32 (d, J=13.0 Hz, 2H), 2.83 (m, J=12.9, 9.2 Hz, 1H), 2.42-2.31 (m, 2H), 2.13 (s, 6H), 2.01-1.90 (m, 2H), 1.49 (d, J=5.9 Hz, 3H), 1.24 (s, 0H), 1.18 (s, 6H).

Example 89: 7-(3-oxa-6-azabicyclo[3.1.1]heptan-6-yl)-5-(((R)-1-(dimethylamino)propan-2-yl)oxy)-N-(5-fluoroquinolin-6-yl)quinazolin-4-amine

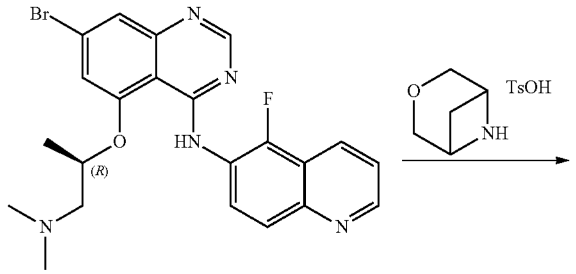

Intermediate 4

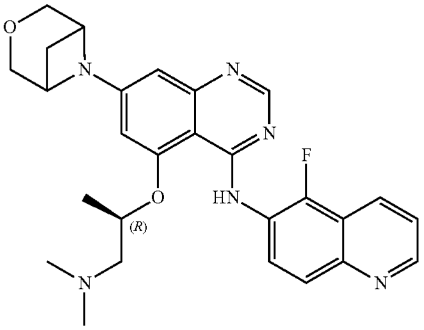

RuPhos Pd (6.7 mg, 7.97 μmol, 0.05 eq.), 2,2'-bis(diphenylphosphaneyl)-1,1'-binaphthalene (4.96 mg, 7.97 μmol), Tris(dibenzylideneacetone)dipalladium(0) (4.38 mg, 4.78 μmol), sodium t-butoxide (46.0 mg, 0.478 mmol, 3.00 eq), Intermediate 4 (75 mg, 0.159 mmol, 1.00 eq), 3-oxa-6-azabicyclo[3.1.1]heptane 4-methylbenzenesulfonate (64.9 mg, 0.239 mmol, 1.5 eq) and dimethylformamide (2.9 mL) were combined at rt and sparged with nitrogen. The resulting mixture was stirred at 90° C. for 8 h under $N_2$. The reaction mixture was concentrated and purified on a silica gel column using 0-25% (Methanol/dichloromethane) gradient to afford the title compound (24.6 mg, 32%) as a solid. LC-MS: (ES, m/z): RT=1.59 min, LC-MS: m/z=489 [M+1]; $^1$H NMR (DMSO) δ: 10.26 (s, 1H), 9.04 (s, 1H), 8.66 (d, J=3.6 Hz, 1H), 8.63-8.57 (m, 1H), 8.18 (s, 1H), 8.02 (d, J=8.9 Hz, 1H), 7.75-7.69 (m, 1H), 6.72 (s, 1H), 6.38 (s, 1H), 5.51 (s, 1H), 4.61 (s, 2H), 4.18 (d, J=11.6 Hz, 1H), 4.13 (s, 1H), 4.08 (d, J=11.4 Hz, 1H), 3.84 (t, J=12.8 Hz, 2H), 3.53 (d, J=14.0 Hz, 1H), 2.93 (d, J=17.0 Hz, 6H), 2.82 (s, 1H), 1.96 (d, J=8.1 Hz, 1H), 1.44 (dd, J=6.2, 3.4 Hz, 3H).

Example 90: (R)-7-(5,6-dihydroimidazo[1,5-a]pyrazin-7(8H)-yl)-5-((1-(dimethylamino)propan-2-yl)oxy)-N-(5-fluoroquinolin-6-yl)quinazolin-4-amine

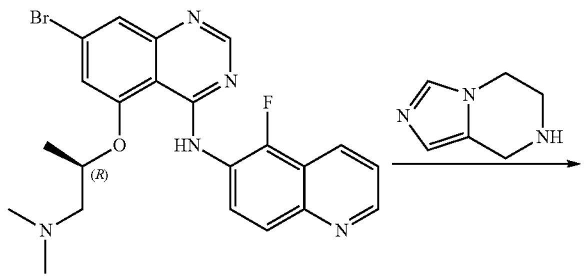

Intermediate 4

-continued

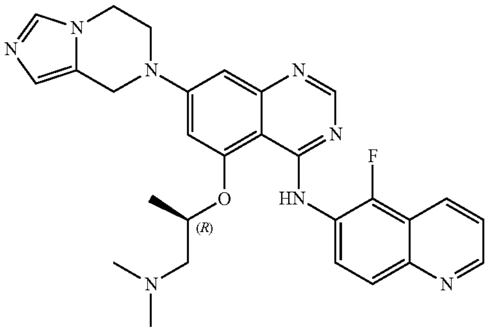

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 5,6,7,8-tetrahydroimidazo[1,5-a]pyrazine (50.0 mg, 0.406 mmol, 3.2 eq) and dimethylformamide (2.3 mL) were combined at rt and sparged with nitrogen. The resulting mixture was stirred at 100° C. for 8 h under $N_2$. The reaction mixture was concentrated down and purified on a silica gel column using 0-25% (Methanol/dichloromethane) gradient and concentrated the desired product peak and repurified on reverse phase on the C18 column to afford the title compound (47.5 mg, 73%) as a solid. LC-MS: (ES, m/z): RT=1.30 min, LC-MS: m/z=513 [M+1]; $^1$H NMR (MeOD) δ: 9.12-8.90 (m, 2H), 8.79-8.52 (m, 3H), 8.03 (d, J=9.3 Hz, 1H), 7.75 (td, J=8.4, 4.3 Hz, 1H), 7.57 (d, J=1.6 Hz, 1H), 7.22 (d, J=2.4 Hz, 1H), 6.94-6.70 (m, 1H), 5.90-5.64 (m, 1H), 5.10-4.93 (m, 2H), 4.86 (bs, 1H), 4.63 (t, J=5.4 Hz, 2H), 4.22 (tt, J=5.0, 2.3 Hz, 2H), 4.12-3.91 (m, 1H), 3.70 (dd, J=14.3, 1.9 Hz, 1H), 3.11 (s, 6H), 1.63 (d, J=6.1 Hz, 3H).

Example 91: (R)-5-((1-(dimethylamino)propan-2-yl)oxy)-N-(5-fluoroquinolin-6-yl)-7-(4-oxa-7-azaspiro[2.5]octan-7-yl)quinazolin-4-amine

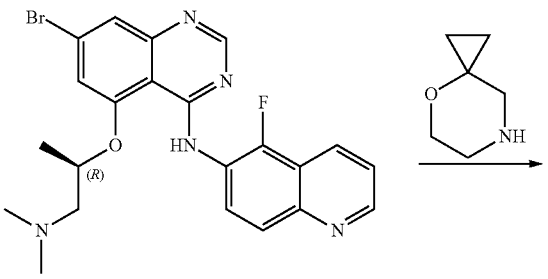

Intermediate 4

-continued

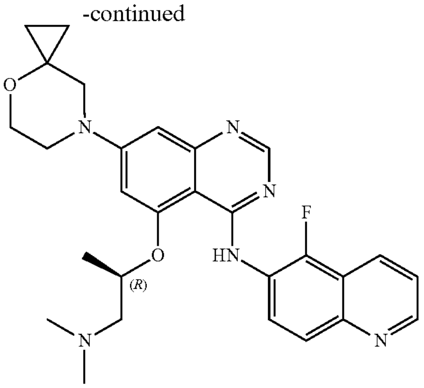

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 4-oxa-7-azaspiro[2.5]octane (50.0 mg, 0.406 mmol, 3.5 eq) and dimethylformamide (2.3 mL) were combined at rt and sparged with nitrogen. The resulting mixture was stirred at 100° C. for 8 h under $N_2$. The reaction mixture was concentrated down and purified on a silica gel column using 0-25% (Methanol/dichloromethane) gradient and concentrated the desired product peak and repurified on reverse phase on the C18 column to afford the title compound (23.5 mg, 34%) as a solid. LC-MS: (ES, m/z): RT=1.73 min, LC-MS: m/z=503 [M+1]; $^1H$ NMR (MeOD) δ: 9.07-8.99 (m, 1H), 8.80 (bs, 1H), 8.70 (s, 1H), 8.62 (s, 1H), 8.04 (d, J=9.0 Hz, 1H), 7.80 (s, 1H), 7.08 (d, J=2.3 Hz, 1H), 6.67 (d, J=8.6 Hz, 1H), 5.70 (s, 1H), 4.86 (s, 1H), 4.06-4.00 (m, 1H), 3.98 (q, J=5.9, 5.0 Hz, 2H), 3.72 (d, J=5.3 Hz, 1H), 3.70-3.62 (m, 2H), 3.60 (d, J=3.7 Hz, 2H), 3.09 (d, J=2.7 Hz, 6H), 1.59 (d, J=6.1 Hz, 3H), 0.91 (d, J=2.4 Hz, 2H), 0.82-0.73 (m, 2H)

Example 92: ((S)-4-(5-(((R)-1-(dimethylamino)propan-2-yl)oxy)-4-((5-fluoroquinolin-6-yl)amino)quinazolin-7-yl)morpholin-3-yl)methanol

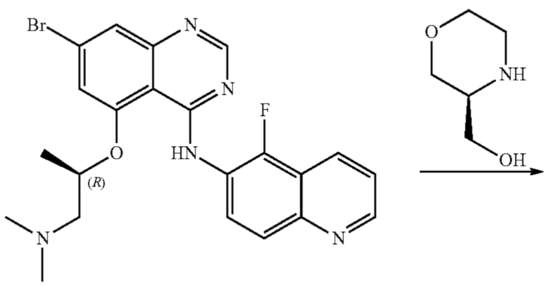

Intermediate 4

-continued

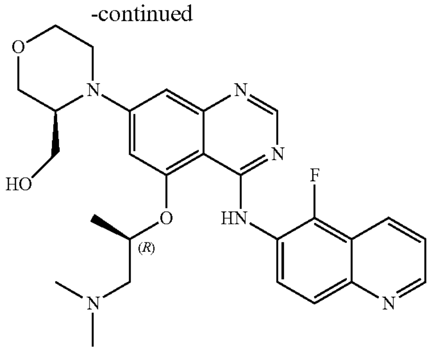

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), morpholin-3S-ylmethanol (44.8 mg, 0.383 mmol, 3.0 eq) and dimethylformamide (2.3 mL) were combined at rt and sparged with nitrogen. The resulting mixture was stirred at 100° C. for 2 h under $N_2$. The reaction mixture was concentrated and purified on a silica gel column using 0-25% (Methanol/dichloromethane) gradient to afford the title compound (53.1 mg, 82%) as a solid. LC-MS: (ES, m/z): RT=1.51 min, LC-MS: m/z=507 [M+1]; $^1H$ NMR (MeOD) δ: 9.00 (dd, J=4.5, 2.0 Hz, 1H), 8.72 (d, J=9.5 Hz, 1H), 8.64 (d, J=9.6 Hz, 1H), 8.57 (s, 1H), 8.01 (d, J=9.3 Hz, 1H), 7.74 (dt, J=8.5, 3.9 Hz, 1H), 6.88 (d, J=2.2 Hz, 1H), 6.50 (d, J=2.2 Hz, 1H), 5.70-5.60 (m, 1H), 4.17-4.05 (m, 1H), 4.05-3.96 (m, 1H), 3.67 (dd, J=14.2, 2.1 Hz, 1H), 3.28 (s, 5H), 3.09 (d, J=5.7 Hz, 7H), 1.62 (d, J=6.3 Hz, 4H), 1.40 (s, 1H), 1.31 (m, J=17.0 Hz, 1H), OH broad peak.

Example 93: (R)-1-(5-((1-(dimethylamino)propan-2-yl)oxy)-4-((5-fluoroquinolin-6-yl)amino)quinazolin-7-yl)-3-methylazetidin-3-ol

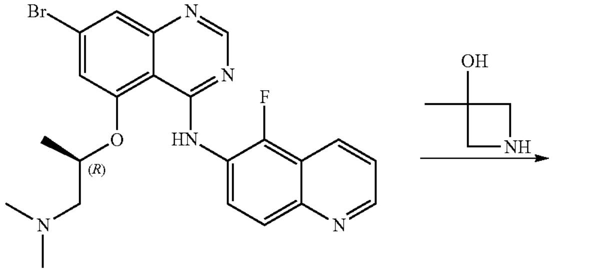

Intermediate 4

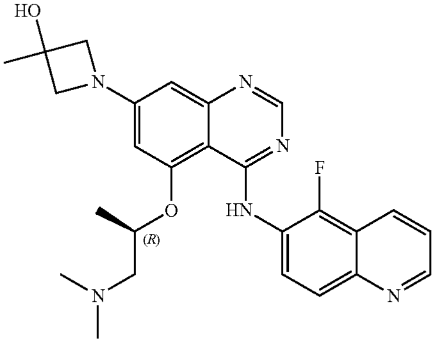

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 3-methylazetidin-3-ol (33.3 mg, 0.383 mmol, 3.0 eq) and dimethylformamide (2.3 mL) were combined at rt and sparged with nitrogen. The resulting mixture was stirred at 100° C. for 2 h under $N_2$. The reaction mixture was concentrated down and purified on a silica gel column using 0-25% (Methanol/dichloromethane) to afford the title compound (65.7 mg, 98%) as a solid. LC-MS: (ES, m/z): RT=1.52 min, LC-MS: m/z=477 [M+1]; $^1$H NMR (MeOD) δ: 9.01 (dd, J=4.4, 1.7 Hz, 1H), 8.74 (dd, J=8.6, 2.1 Hz, 1H), 8.65 (td, J=8.8, 2.2 Hz, 1H), 8.55 (s, 1H), 8.01 (d, J=9.3 Hz, 1H), 7.76 (ddd, J=8.6, 4.5, 1.7 Hz, 1H), 6.58 (d, J=1.8 Hz, 1H), 6.18 (d, J=1.8 Hz, 1H), 5.62 (p, J=6.8 Hz, 1H), 4.19-4.11 (m, 2H), 4.08 (t, J=8.9 Hz, 2H), 4.01 (dd, J=14.2, 9.6 Hz, 1H), 3.66 (dd, J=14.1, 2.0 Hz, 1H), 3.08 (s, 6H), 1.64-1.58 (m, 6H).

Example 94: (R)-1-(5-((1-(dimethylamino)propan-2-yl)oxy)-4-((5-fluoroquinolin-6-yl)amino)quinazolin-7-yl)-4-methylpiperidin-4-ol

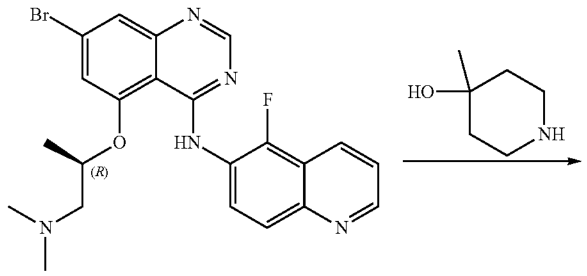

Intermediate 4

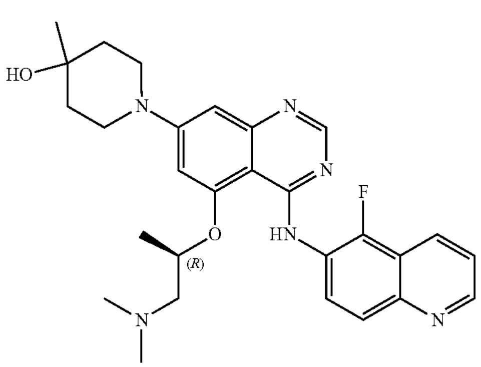

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 4-methylpiperidin-4-ol (44.1 mg, 0.383 mmol, 3.0 eq) and dimethylformamide (2.3 mL) were combined at rt and sparged with nitrogen. The resulting mixture was stirred at 100° C. for 2 h under $N_2$. The reaction mixture was concentrated down and purified on a silica gel column using 0-25% (Methanol/dichloromethane) to afford the title compound (65.7 mg, 98%) as a solid. LC-MS: (ES, m/z): RT=1.47 min, LC-MS: m/z=505 [M+1]; $^1$H NMR (MeOD) δ: 9.00 (dd, J=4.4, 1.7 Hz, 1H), 8.71-8.57 (m, 3H), 8.01 (d, J=9.3 Hz, 1H), 7.73 (ddd, J=8.5, 4.5, 1.7 Hz, 1H), 7.09 (d, J=2.2 Hz, 1H), 6.68 (d, J=2.1 Hz, 1H), 5.66 (s, 1H), 4.01 (dd, J=14.2, 9.6 Hz, 1H), 3.92 (d, J=13.6 Hz, 2H), 3.71-3.64 (m, 1H), 3.59 (ddd, J=14.7, 11.0, 4.3 Hz, 2H), 3.10 (s, 6H), 1.83-1.70 (m, 4H), 1.60 (d, J=6.1 Hz, 3H), 1.33 (s, 3H).

Example 95: (R)-2-(5-((1-(dimethylamino)propan-2-yl)oxy)-4-((5-fluoroquinolin-6-yl)amino)quinazolin-7-yl)isothiazolidine 1,1-dioxide

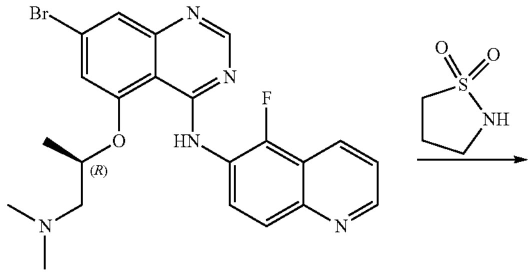

Intermediate 4

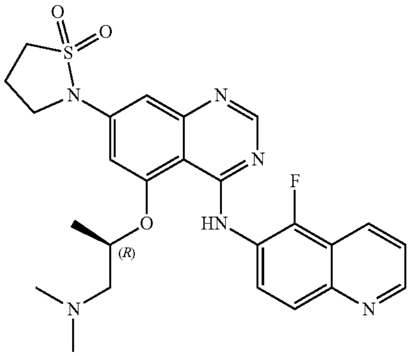

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), isothiazolidine 1,1-dioxide (46.4 mg, 0.383 mmol, 3.0 eq) and dimethylformamide (2.3 mL) were combined at rt and sparged with nitrogen. The resulting mixture was stirred at 100° C. for 2 h under $N_2$. The reaction mixture was concentrated and purified on a silica gel column using 0-25% (Methanol/dichloromethane) to afford the title compound (65.7 mg, 98%) as a solid. LC-MS: (ES, m/z): RT=1.54 min, LC-MS: m/z=511 [M+1]; $^1$H NMR (MeOD) δ: 9.04 (dt, J=3.6, 1.7 Hz, 1H), 8.80-8.74 (m, 1H), 8.75 (s, 1H), 8.61 (td, J=8.9, 2.9 Hz, 1H), 8.05 (d, J=9.3 Hz, 1H), 7.78 (ddd, J=8.8, 4.5, 2.5 Hz, 1H), 7.35 (d, J=2.0 Hz, 1H), 7.22 (t, J=1.8 Hz, 1H), 5.62-5.54 (m, 1H), 4.08 (dddd, J=11.3, 9.2, 6.4, 3.2 Hz, 3H), 3.73-3.62 (m, 3H), 3.09 (s, 6H), 2.66 (p, J=6.8 Hz, 2H), 1.67 (d, J=6.1 Hz, 3H).

Example 96: (R)-1-(5-((1-(dimethylamino)propan-2-yl)oxy)-4-((5-fluoroquinolin-6-yl)amino)quinazolin-7-yl)pyrrolidin-2-one

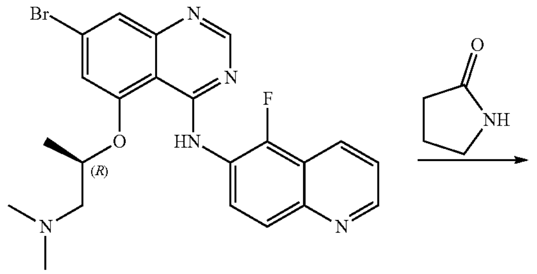

Intermediate 4

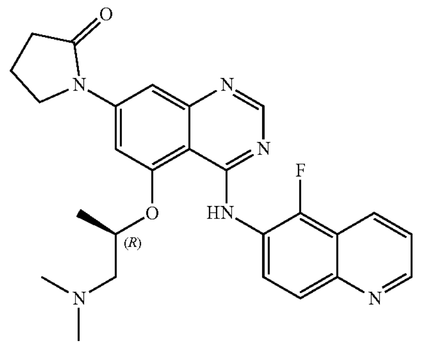

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), pyrrolidin-2-one (32.6 mg, 0.383 mmol, 3.0 eq) and dimethylformamide (2.3 mL) were combined at rt and sparged with nitrogen. The resulting mixture was stirred at 95° C. for 2 h under $N_2$. The reaction mixture was concentrated down and purified on a silica gel column using 0-25% (Methanol/dichloromethane) followed by reverse phase purification using 0-40% (1% TFA modified water/Acetonitrile gradient to afford the title compound (56.8 mg, 94%) as a solid. LC-MS: (ES, m/z): RT=1.65 min, LC-MS: m/z=475 [M+1]; $^1$H NMR (MeOD) δ: 9.07 (dd, J=4.6, 1.5 Hz, 1H), 8.84 (d, J=8.5 Hz, 1H), 8.79 (s, 1H), 8.67 (t, J=8.7 Hz, 1H), 8.20 (d, J=1.9 Hz, 1H), 8.07 (d, J=9.3 Hz, 1H), 7.83 (dd, J=8.5, 4.5 Hz, 1H), 7.75 (d, J=1.9 Hz, 1H), 5.60 (dtt, J=11.5, 7.6, 3.7 Hz, 1H), 4.20-4.05 (m, 3H), 3.68 (dd, J=14.2, 2.0 Hz, 1H), 3.10 (s, 6H), 2.76 (t, J=8.1 Hz, 2H), 2.29 (p, J=7.6 Hz, 2H), 1.68 (d, J=6.2 Hz, 3H)

Example 97: (R)-6-(5-((1-(dimethylamino)propan-2-yl)oxy)-4-((5-fluoroquinolin-6-yl)amino)quinazolin-7-yl)-1-thia-6-azaspiro[3.3]heptane 1,1-dioxide

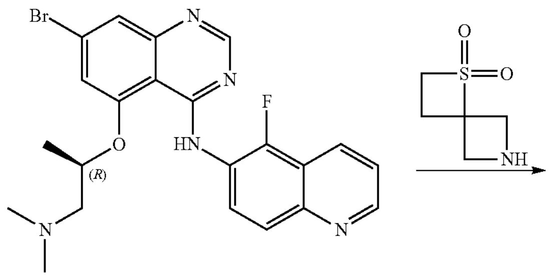

Intermediate 4

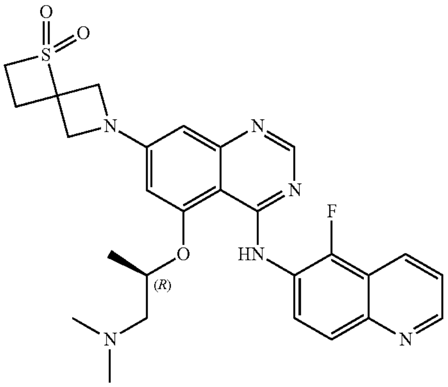

RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 1-thia-6-azaspiro[3.3]heptane 1,1-dioxide (28.2 mg, 0.191 mmol, 1.5 eq) and dimethylformamide (2.3 mL) were combined at rt and sparged with nitrogen. The resulting mixture was stirred at 100° C. for 1 h under $N_2$. The reaction mixture was diluted with dichloromethane and water. Extracted product into organic layer. Concentrated down the organic layer and purified by reverse phase purification using 0-40% (1% TFA modified water/Acetonitrile gradient to afford the title compound (25.3 mg, 36%) as a solid. LC-MS: (ES, m/z): RT=1.62 min, LC-MS: m/z=537 [M+1]; $^1$H NMR (MeOD) δ: 8.88 (dd, J=4.3, 1.8 Hz, 1H), 8.57 (d, J=8.5 Hz, 1H), 8.50-8.44 (m, 2H), 7.89 (d, J=9.2 Hz, 1H), 7.61 (dd, J=8.6, 4.3 Hz, 1H), 6.56 (d, J=2.0 Hz, 1H), 6.15 (d, J=1.9 Hz, 1H), 5.51 (t, J=7.8 Hz, 1H), 4.67 (dd, J=16.3, 10.2 Hz, 2H), 4.33 (d, J=10.2 Hz, 2H), 4.10-4.02 (m, 2H), 3.90 (dd, J=14.2, 9.6 Hz, 1H), 3.54 (dd, J=14.4, 2.0 Hz, 1H), 2.97 (s, 6H), 2.44 (dd, J=10.1, 7.4 Hz, 2H), 1.50 (d, J=6.1 Hz, 3H).

Example 98: 7—((S)-2-(difluoromethyl)morpholino)-5-(((R)-1-(dimethylamino)propan-2-yl)oxy)-N-(5-fluoroquinolin-6-yl) and 7-((R)-2-(difluoromethyl)morpholino)-5-(((R)-1-(dimethylamino)propan-2-yl)oxy)-N-(5-fluoroquinolin-6-yl)quinazolin-4-amine Example 99a: 7-((S)-2-(difluoromethyl)morpholino)-5-(((R)-1-(dimethylamino)propan-2-yl)oxy)-N-(5-fluoroquinolin-6-yl) or 7-((R)-2-(difluoromethyl)morpholino)-5-(((R)-1-(dimethylamino)propan-2-yl)oxy)-N-(5-fluoroquinolin-6-yl)quinazolin-4-amine Example 99b: 7-((R)-2-(difluoromethyl)morpholino)-5-(((R)-1-(dimethylamino)propan-2-yl)oxy)-N-(5-fluoroquinolin-6-yl)quinazolin-4-amine or 7-((S)-2-(difluoromethyl)morpholino)-5-(((R)-1-(dimethylamino)propan-2-yl)oxy)-N-(5-fluoroquinolin-6-yl)

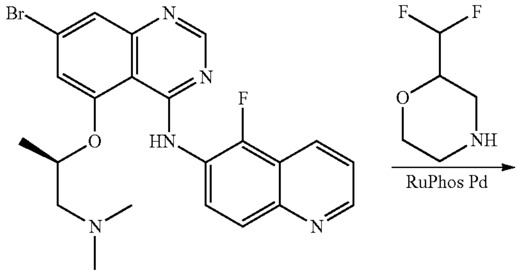

Intermediate 4

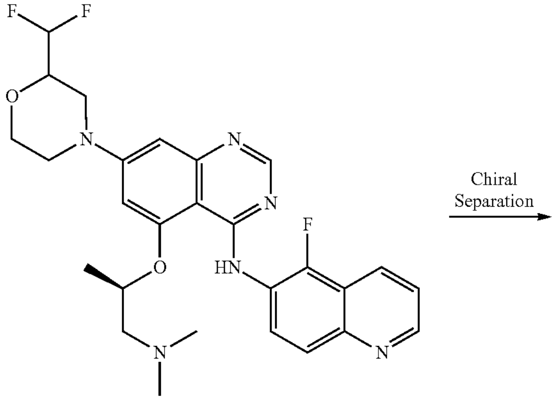

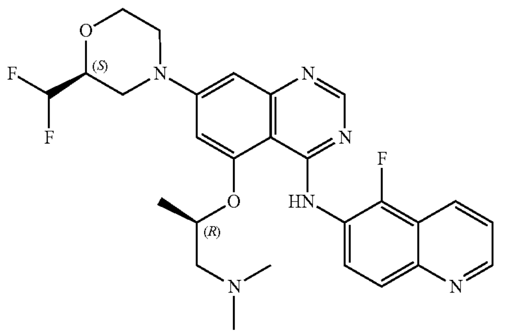

or

-continued

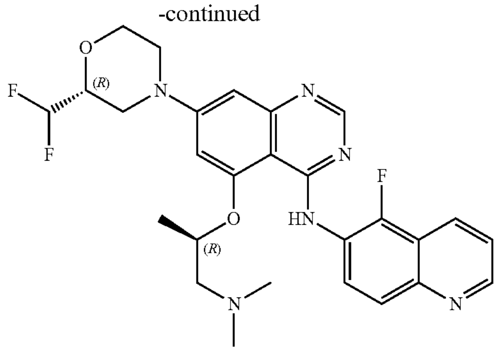

Example 98: 7—((S)-2-(difluoromethyl)morpholino)-5-(((R)-1-(dimethylamino)propan-2-yl)oxy)-N-(5-fluoroquinolin-6-yl) and 7-((R)-2-(difluoromethyl)morpholino)-5-(((R)-1-(dimethylamino)propan-2-yl)oxy)-N-(5-fluoroquinolin-6-yl)quinazolin-4-amine The reaction mixture of RuPhos Pd (71.0 mg, 85.0 μmol), $Cs_2CO_3$ (554 mg, 1.70 mmol), Intermediate 4 (400 mg, 850 μmol) and 2-(difluoromethyl)morpholine (233 mg, 1.70 mmol) in dioxane (20 mL) was heated to 100° C. for 16 h under $N_2$. The reaction mixture was diluted with EA (100 mL) and washed with water (100 mL*3) and saturated brine (100 mL*1). The organic layer was dried over $Na_2SO_4$, filtered and evaporated to afford crude product. The crude product was purified by a silica gel column using DCM: MeOH=20:1. The residue was purified by prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 25% B to 70% B in 8 min, 70% B; Wavelength: 254/220 nm, to afford the title compound (256 mg, yield: 57.2%) as a white solid. LC-MS: (ES, m/z): RT=0.760 min, LCMS: m/z=527 [M+1], 1H NMR (400 MHz, DMSO-d6) δ 10.42 (s, 1H), 8.93 (dd, J=4.2, 1.6 Hz, 1H), 8.75 (td, J=9.0, 2.0 Hz, 1H), 8.51 (dd, J=8.3, 1.4 Hz, 1H), 8.40 (s, 1H), 7.94 (d, J=9.3 Hz, 1H), 7.64 (dd, J=8.5, 4.2 Hz, 1H), 6.98 (t, J=2.2 Hz, 1H), 6.72 (d, J=2.2 Hz, 1H), 6.18 (d, J=3.2 Hz, 1H), 5.08-5.02 (m, 1H), 4.09 (d, J=11.5 Hz, 1H), 3.92 (m, 3H), 3.80-3.70 (m, 1H), 3.05-2.95 (m, 1H), 2.94-2.82 (m, 2H), 2.50-2.43 (m, 1H), 2.18 (s, 6H), 1.48 (dd, J=6.1, 1.5 Hz, 3H).

Step 2: Chiral Separation

Example 98, 7—((S)-2-(difluoromethyl)morpholino)-5-(((R)-1-(dimethylamino)propan-2-yl)oxy)-N-(5-fluoroquinolin-6-yl) and 7-((R)-2-(difluoromethyl)morpholino)-5-(((R)-1-(dimethylamino)propan-2-yl)oxy)-N-(5-fluoroquinolin-6-yl)quinazolin-4-amine (10.3 mg, 19.5 μmol) in MeOH was Purified by Prep-Chiral-HPLC with following conditions: Column: CHIRALPAK IF, 2*25 cm, 5 μm; Mobile Phase A: Hex (0.5% 2M $NH_3$-MeOH)-HPLC, Mobile Phase B: EtOH-HPLC; Flow rate: 16 mL/min; Gradient: 50% B to 50% B in 26 min; Wavelength: 220/254 nm; RT1 (min): 19.595; RT2(min): 22.461; Sample Solvent: EtOH-HPLC to afford:

Example 99a: First eluting isomer, (0.2 mg) as a white solid. LC-MS: (ES, m/z): RT=1.615 min, LCMS: m/z=527 [M+1], Chiral-HPLC (ES): RT=3.330 min, 1H NMR (400 MHz, DMSO-d6) δ 10.41 (s, 1H), 8.93 (dd, J=4.2, 1.7 Hz, 1H), 8.76 (t, J=8.9 Hz, 1H), 8.55-8.48 (m, 1H), 8.40 (s, 1H), 7.94 (d, J=9.3 Hz, 1H), 7.64 (dd, J=8.5, 4.2 Hz, 1H), 6.98 (d, J=2.4 Hz, 1H), 6.72 (d, J=2.2 Hz, 1H), 6.18 (d, J=3.3 Hz, 1H), 5.06 (s, 1H), 4.09 (dd, J=11.2, 3.0 Hz, 1H), 3.93 (q, J=11.5, 10.4 Hz, 3H), 3.81-3.70 (m, 1H), 3.02-2.83 (m, 3H), 2.57 (s, 1H), 2.19 (s, 6H), 1.48 (d, J=6.0 Hz, 3H).

Example 99b: Second eluting isomer, (1 mg) as a white solid. LC-MS: (ES, m/z): RT=1.626 min, LCMS: m/z=527 [M+1], Chiral-HPLC (ES): RT=3.993 min, 1H NMR (400 MHz, DMSO-d6) δ 10.41 (s, 1H), 8.93 (dd, J=4.2, 1.7 Hz, 1H), 8.75 (t, J=8.9 Hz, 1H), 8.51 (dt, J=8.4, 1.4 Hz, 1H), 8.40 (s, 1H), 7.94 (d, J=9.3 Hz, 1H), 7.64 (dd, J=8.5, 4.2 Hz, 1H), 6.99 (d, J=2.3 Hz, 1H), 6.72 (d, J=2.3 Hz, 1H), 6.17 (d, J=3.3 Hz, 1H), 5.06 (s, 1H), 4.13-4.06 (m, 1H), 3.91 (dd, J=24.5, 12.0 Hz, 3H), 3.74 (td, J=11.5, 2.7 Hz, 1H), 2.98 (td, J=12.1, 3.5 Hz, 1H), 2.87 (dd, J=12.5, 10.9 Hz, 2H), 2.54 (s, 1H), 2.19 (s, 6H), 1.48 (d, J=6.0 Hz, 3H).

Example 100: (R)—N-(5-fluoroquinolin-6-yl)-7-(1-methyl-1H-pyrazol-4-yl)-5-((1-(methylamino)propan-2-yl)oxy)quinazolin-4-amine

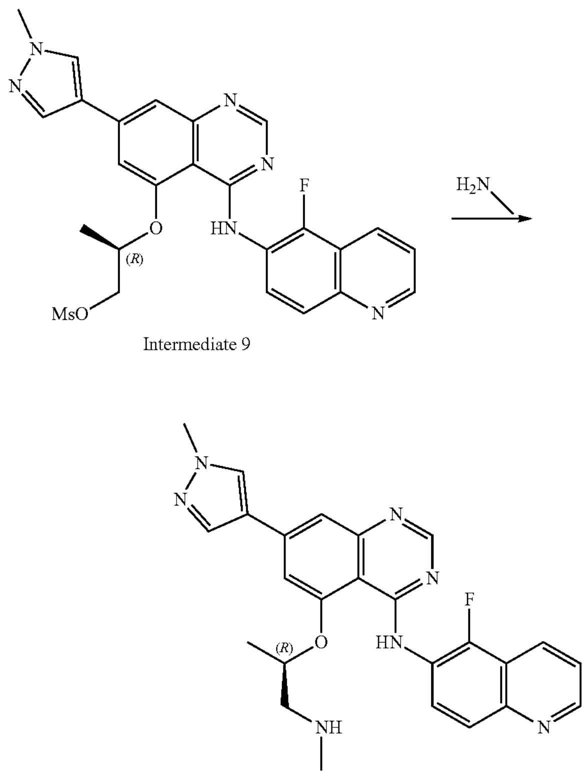

To a solution of Intermediate 9 (120 mg, 0.2296 mmol) in EtOH was added methanamine (71.1 mg, 2.29 mmol). The mixture was stirred at 80° C. for 3 h. The solution was concentrated under vacuum. The residue was purified by prep-HPLC [XBridge Prep OBD C18 Column, 30×150 mm, 5 μm, 50-80% methanol in water (buffered with 10 mM $NH_4HCO_3$ and 0.1% ammonia) over 8 min, flow rate: 60 mL/min, UV detection (λ=220, 254 nm], RT=1.635 min to afford the title compound (33.4 mg, yield: 32.1%) as an off-white solid. LC-MS: (ES, m/z): RT=1.261 min, LC-MS: m/z=488 [M+1]; HPLC: RT=2.944 min: $^1$H NMR (400 MHz, DMSO-$d_6$) δ 8.93 (dd, J=4.2, 1.6 Hz, 1H), 8.74 (t, J=8.8 Hz, 1H), 8.55-8.42 (m, 3H), 8.16 (d, J=0.8 Hz, 1H), 7.95 (dd, J=9.3, 1.3 Hz, 1H), 7.63 (dd, J=8.5, 4.2 Hz, 1H), 7.57 (d, J=1.4 Hz, 1H), 7.43 (d, J=1.6 Hz, 1H), 5.13 (dt, J=11.3, 5.9 Hz, 1H), 3.92 (s, 3H), 2.99 (dd, J=12.7, 6.2 Hz, 1H), 2.94-2.83 (m, 1H), 2.30 (s, 3H), 1.50 (d, J=6.1 Hz, 3H).

Example 101: (R)-5-((1-(azetidin-1-yl)propan-2-yl)oxy)-N-(5-fluoroquinolin-6-yl)-7-(1-methyl-1H-pyrazol-4-yl)quinazolin-4-amine

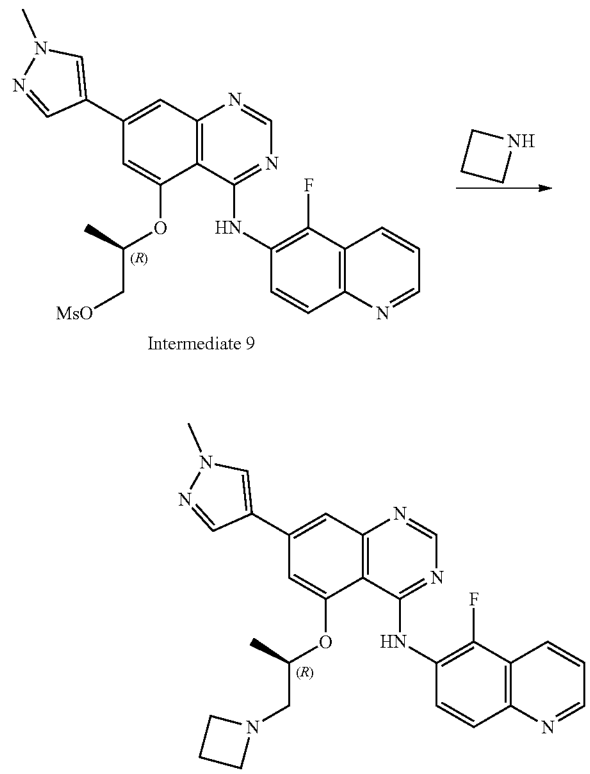

To a solution of azetidine (8.73 mg, 153 μmol) in MeOH was added Intermediate 9 (40 mg, 76.5 μmol). The mixture was stirred at 80° C. for 2 hrs. The reaction was concentrated under vacuum and purified by prep-HPLC (Column: XBridge Shield RP18 OBD Column, 30×150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 35% B to 52% B in 8 min, Wavelength: 254; 220 nm; RT1 (min): 7.12 to afford the title compound (2 mg, 5.4%) as white solid. LC-MS: (ES, m/z): RT=1.156 min, LC-MS: m/z=484 [M+1]; $^1$H NMR (300 MHz, DMSO-d6) δ 10.75 (s, 1H), 8.96 (dd, J=4.3, 1.6 Hz, 1H), 8.74 (dt, J=11.9, 8.9 Hz, 1H), 8.60-8.46 (m, 3H), 8.17 (s, 1H), 7.98 (d, J=9.2 Hz, 1H), 7.66 (dd, J=8.5, 4.2 Hz, 1H), 7.59 (d, J=1.4 Hz, 1H), 7.43 (s, 1H), 5.01 (d, J=5.6 Hz, 1H), 3.92 (s, 3H), 3.16 (t, J=7.0 Hz, 4H), 2.83 (t, J=5.0 Hz, 2H), 1.73 (t, J=7.1 Hz, 2H), 1.47 (d, J=6.1 Hz, 3H).

Example 102: (R)-5-((1-(ethylamino)propan-2-yl)oxy)-N-(5-fluoroquinolin-6-yl)-7-(1-methyl-1H-pyrazol-4-yl)quinazolin-4-amine

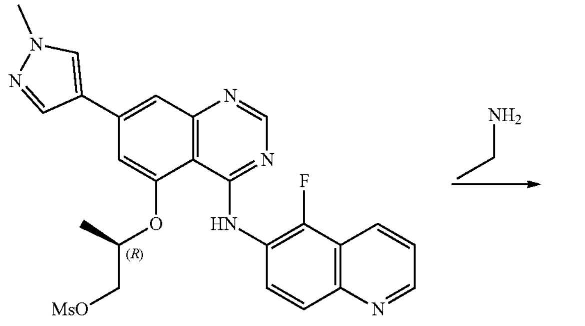

Intermediate 9

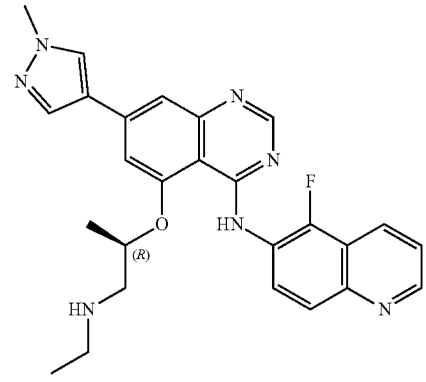

Intermediate 9 (100 mg, 191 μmol) and $EtNH_3$ in MeOH (1M) were stirred at 80° C. for 2 hrs. The reaction was concentrated under vacuum and purified by Prep-HPLC (Column: XBridge Shield RP18 OBD Column, 30×150 mm, 5 um; Mobile Phase A: water (10 mmol/L $NH_4HCO_3$+0.1% $NH_3 \cdot H_2O$), Mobile Phase B: ACN; Flow rate: 60 mL/min; Gradient: 35% B to 45% B in 8 min, wavelength: 254; 220 nm; RT1 (min): 7.1 to afford the title compound (9.5 mg, 10.5%) as white solid. LC-MS: (ES, m/z): RT=1.036 min, LC-MS: m/z=472.1 [M+1]; $^1$H NMR (300 MHz, DMSO-d6) δ 8.94 (dd, J=4.2, 1.7 Hz, 1H), 8.74 (t, J=8.9 Hz, 1H), 8.56-8.46 (m, 3H), 8.17 (s, 1H), 7.95 (d, J=9.3 Hz, 1H), 7.65 (dd, J=8.5, 4.2 Hz, 1H), 7.58 (d, J=1.4 Hz, 1H), 7.45 (d, J=1.5 Hz, 1H), 5.13 (q, J=5.6 Hz, 1H), 3.92 (s, 3H), 3.10-2.86 (m, 2H), 2.63-2.53 (m, 2H), 1.50 (d, J=6.1 Hz, 3H), 0.82 (t, J=7.1 Hz, 3H).

Example 103: (R)-5-((1-(dimethylamino)propan-2-yl)oxy)-7-(1-methyl-1H-pyrazol-4-yl)-N-(quinoxalin-6-yl)quinazolin-4-amine

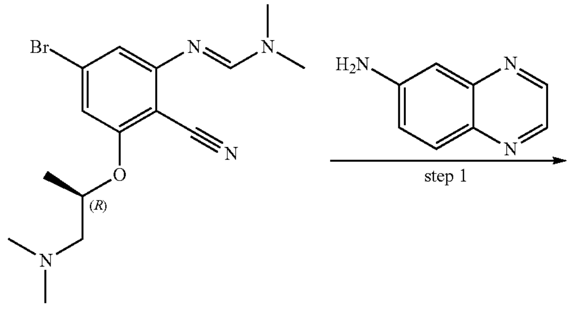

Intermediate 19

-continued

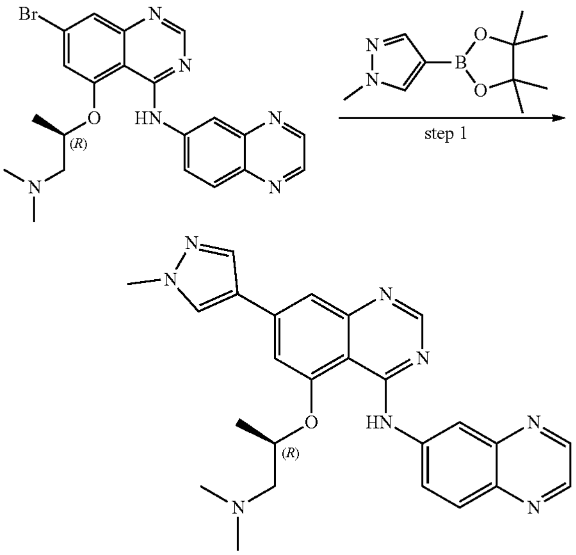

Step 1: (R)-7-bromo-5-((1-(dimethylamino)propan-2-yl)oxy)-N-(quinoxalin-6-yl)quinazolin-4-amine To a solution of Intermediate 19 (100 mg, 0.283 mmol) in AcOH (2 mL) was added quinoxalin-6-amine (41.0 mg, 283 μmol). The mixture was stirred at 80° C. for 3 h. $H_2O$ (20 mL) was added to the mixture. A solid was collected by filtration and washed with $H_2O$ (50 mL) and PE (50 mL) to afford the desired product (110 mg) as an off-white solid. LC-MS: (ES, m/z): RT=0.859, LCMS: m/z=453 [M+1].

Step 2: (R)-5-((1-(dimethylamino)propan-2-yl)oxy)-7-(1-methyl-1H-pyrazol-4-yl)-N-(quinoxalin-6-yl)quinazolin-4-amine Into a 40-mL sealed tube was placed (R)-7-bromo-5-((1-(dimethylamino)propan-2-yl)oxy)-N-(quinoxalin-6-yl)quinazolin-4-amine (100 mg, 484 μmol) in dioxane (2 mL), $H_2O$ (0.5 mL), was added 1-methyl-4-(4,4,5,5-tetramethyl-1,3,2-dioxaborolan-2-yl)-1H-pyrazole (110 mg, 484 μmol), $K_2CO_3$ (100 mg, 484 μmol) and Pd(dppf)$Cl_2$ (17.6 mg, 24.2 μmol) under $N_2$. The resulting solution was stirred at 100° C. for 2 h. The mixture was diluted with EA (20 mL) and washed with brine (10 mL*2). The organic layer was dried with $Na_2SO_4$ and concentrated under vacuum. The residue was purified by prep-TLC (DCM:MeOH=10:1). The residue was concentrated under vacuum and purified by prep-HPLC (Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 48% B to 58% B in 8 min, 58% B; Wavelength: 254/220 nm). This resulted in the title compound (21.2 mg, yield: 19.4%) as a white solid. LC-MS: (ES, m/z): RT=0.958 min, LCMS: m/z=455 [M+1], $^1$H NMR (400 MHz, DMSO-d6) δ 10.82 (s, 1H), 8.95-8.87 (m, 2H), 8.85 (d, J=1.9 Hz, 1H), 8.66 (s, 1H), 8.50 (s, 1H), 8.20-8.11 (m, 3H), 7.61 (d, J=1.4 Hz, 1H), 7.44 (d, J=1.5 Hz, 1H), 5.16 (s, 1H), 3.92 (s, 3H), 3.07 (dd, J=12.9, 8.8 Hz, 1H), 2.54 (d, J=4.3 Hz, 1H), 2.29 (s, 6H), 1.53 (d, J=5.8 Hz, 3H).

Example 104: (R)—N-(3,5-difluoroquinolin-6-yl)-5-((1-(dimethylamino)propan-2-yl)oxy)-7-(1-methyl-1H-pyrazol-4-yl)quinazolin-4-amine

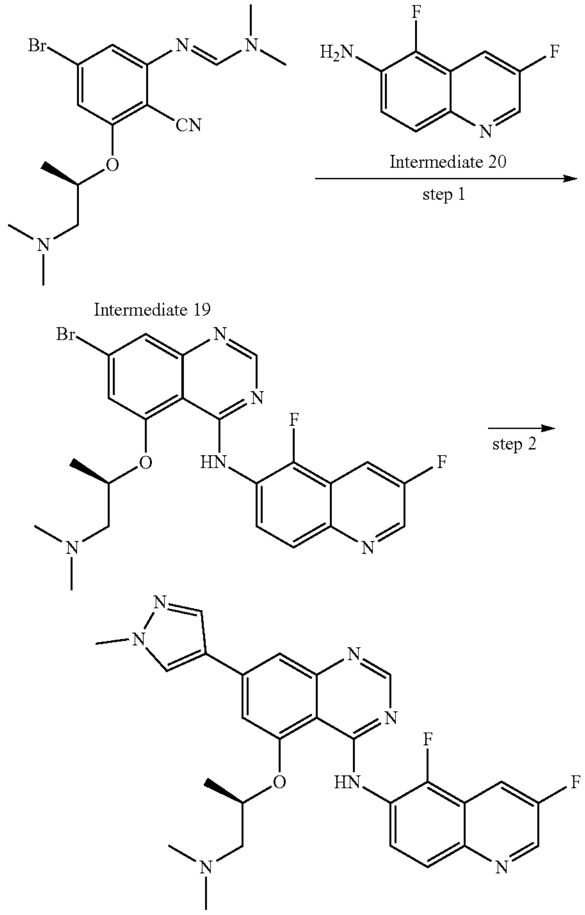

Step 1: (R)-7-bromo-N-(3,5-difluoroquinolin-6-yl)-5-((1-(dimethylamino)propan-2-yl)oxy)quinazolin-4-amine Intermediate 19 (60 mg, 203 μmol), Intermediate 20 (36.5 mg, 203 μmol) and $CH_3COOH$ were stirred at 100° C. for 12 hours. The solution was concentrated under vacuum. The crude compound was purified by prep-TLC: (DCM: MeOH=20:1) to afford the title compound (35 mg, yield: 42.4%) as a light yellow solid. LC-MS: (ES, m/z): RT=1.715 min, LCMS: m/z=488 [M+1]

Step 2: (R)—N-(3,5-difluoroquinolin-6-yl)-5-((1-(dimethylamino)propan-2-yl)oxy)-7-(1-methyl-1H-pyrazol-4-yl)quinazolin-4-amine Into a 8 ml vial and maintained a $N_2$ atmosphere was added (R)-7-bromo-N-(3,5-difluoroquinolin-6-yl)-5-((1-(dimethylamino)propan-2-yl)oxy)quinazolin-4-amine (20 mg, 0.0409 mmol), 1-methyl-4-(4,4,5,5-tetramethyl-1,3,2-dioxaborolan-2-yl)-1H-pyrazole (10.2 mg, 49.1 μmol), $Pd(dppf)Cl_2$ (3.22 mg, 4.09 μmol), $K_2CO_3$ (11.3 mg, 81.9 μmol), 2 mL 1,4-dioxane and 0.5 mL $H_2O$. The mixture was stirred at 80° C. for 3 hours. The reaction was extracted with EA and the organic layer was concentrated under vacuum. The crude compound was purified by prep-HPLC: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 46% B to 79% B in 7 min, 79% B; Wavelength: 254/220 nm; RT1(min): 6.72; To afford the title compound (4.3 mg, yield: 21.5%) as a light yellow solid. LC-MS: (ES, m/z): RT=1.117 min, LCMS: m/z=490 [M+1]; 1H NMR (300 MHz, Methanol-d4) δ 8.97-8.85 (m, 1H), 8.82 (dd, J=2.8, 0.9 Hz, 1H), 8.51 (s, 1H), 8.28-8.18 (m, 2H), 8.07 (d, J=0.9 Hz, 1H), 8.01-7.92 (m, 1H), 7.54 (d, J=1.5 Hz, 1H), 7.44 (d, J=1.5 Hz, 1H), 5.17 (s, 1H), 3.98 (s, 3H), 3.13-3.00 (m, 1H), 2.61 (dd, J=13.3, 3.6 Hz, 1H), 2.30 (s, 6H), 1.58 (d, J=6.1 Hz, 3H).

Example 105: (R)-5-((1-(dimethylamino)propan-2-yl)oxy)-7-(1-methyl-1H-pyrazol-4-yl)-N-(2-methylquinolin-6-yl)quinazolin-4-amine

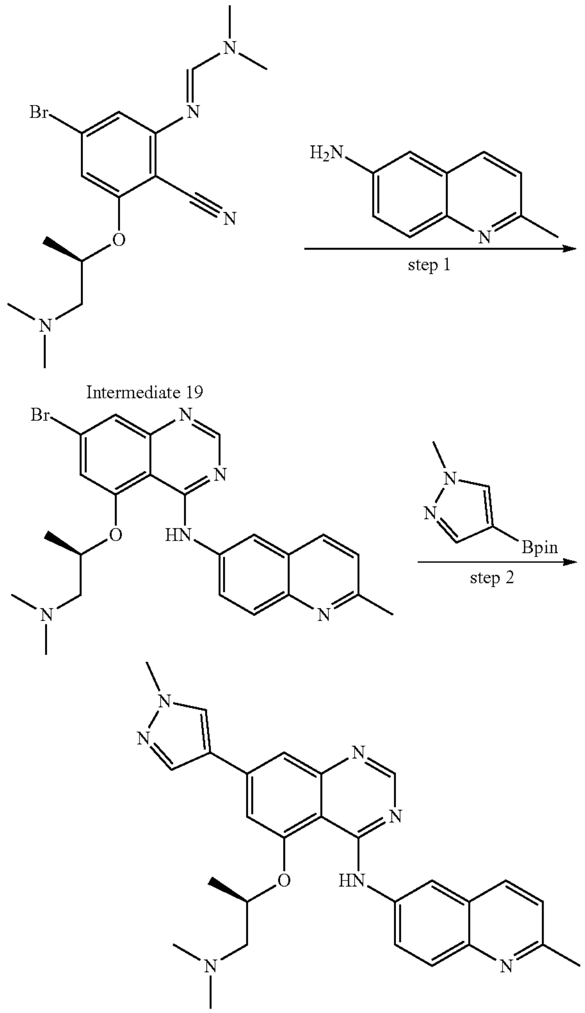

Step 1: (R)-7-bromo-5-((1-(dimethylamino)propan-2-yl)oxy)-N-(2-methylquinolin-6-yl)quinazolin-4-amine The reaction mixture of Intermediate 19 (150 mg, 424 μmol) and 2-methylquinolin-6-amine (134 mg, 848 μmol) in AcOH (5 mL) was heated at 100° C. for 3 hours under $N_2$. The reaction mixture was diluted with EtOAc (120 mL) and washed with water (60 mL). The organic layer was dried over $Na_2SO_4$, filtered and concentrated under vacuum. The crude product was purified by prep-TLC with DCM: MeOH=20:1 to afford the title compound (100 mg) as a white solid. LC-MS: (ES, m/z): RT=0.803 min, LCMS: m/z=466 [M+1].

Step 2: (R)-5-((1-(dimethylamino)propan-2-yl)oxy)-7-(1-methyl-1H-pyrazol-4-yl)-N-(2-methylquinolin-6-yl)quinazolin-4-amine Pd(dppf)$Cl_2$ (14.8 mg, 18.2 μmol) and $K_2CO_3$ (25.1 mg, 182 μmol) were added to (R)-7-bromo-5-((1-(dimethylamino)propan-2-yl)oxy)-N-(2-methylquinolin-6-yl)quinazolin-4-amine (85 mg, 182 μmol) and 1-methyl-4-(4,4,5,5-tetramethyl-1,3,2-dioxaborolan-2-yl)-1H-pyrazole (37.8 mg, 182 μmol) in dioxane/$H_2O$ (4 mL/1 mL) at rt. The reaction was heated at 80° C. for 3 hrs under $N_2$. The reaction mixture was diluted with EtOAc (120 mL) and washed with water (60 mL). The organic layer was dried over $Na_2SO_4$, filtered and concentrated under vacuum. The crude product was purified by prep-TLC with DCM: MeOH=20:1. The residue was purified by prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 41% B to 60% B in 8 min, 60% B; Wavelength: 254,220 nm. This afforded the title compound (46.5 mg) as a white solid. LC-MS: (ES, m/z): RT=1.924 min, LCMS: m/z=468 [M+1], $^1H$ NMR (400 MHz, DMSO-d6) δ 10.63 (s, 1H), 8.55 (s, 1H), 8.48 (d, J=10.1 Hz, 2H), 8.23 (d, J=8.5 Hz, 1H), 8.14 (s, 1H), 8.01 (dd, J=9.0, 2.3 Hz, 2H), 7.55 (s, 1H), 7.40 (d, J=9.4 Hz, 2H), 5.12 (s, 1H), 3.91 (s, 3H), 3.03 (s, 1H), 2.65 (s, 6H), 2.53 (s, 1H), 2.26 (s, 6H), 1.52 (d, J=5.9 Hz, 3H).

Example 106: (R)—N-(5,7-difluoroquinolin-6-yl)-5-((1-(dimethylamino)propan-2-yl)oxy)-7-(1-methyl-1H-pyrazol-4-yl)quinazolin-4-amine

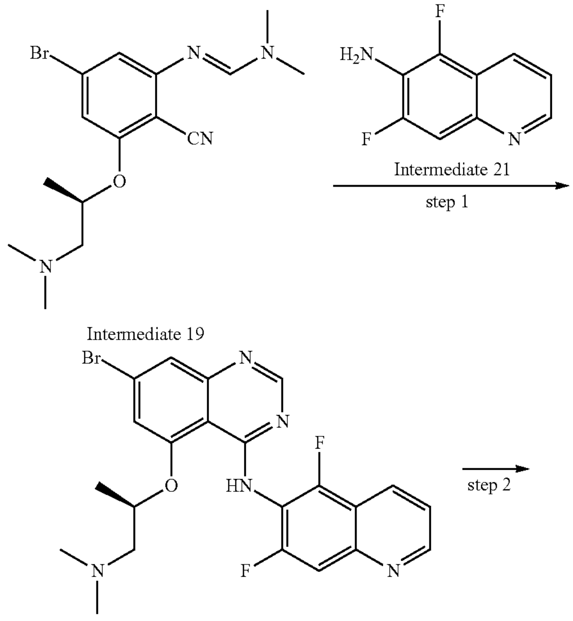

-continued

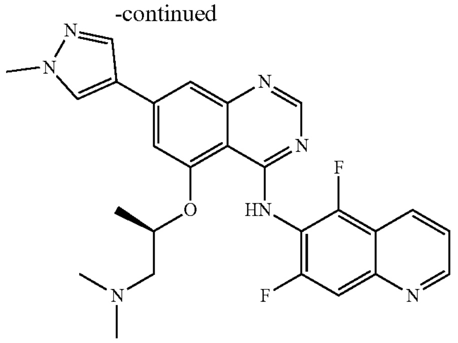

Step 1: (R)-7-bromo-N-(5,7-difluoroquinolin-6-yl)-5-((1-(dimethylamino)propan-2-yl)oxy)quinazolin-4-amine Intermediate 19 (200 mg, 566 μmol) was added to Intermediate 21 (304 mg, 1.69 mmol) in AcOH (5 mL) at rt. The reaction was stirred for 18 hrs. at 100° C. The resulting mixture was concentrated under vacuum. The residue was dissolved with $CH_2Cl_2$ (80 mL), neutralized with saturated aqueous $NaHCO_3$ (30 mL). The organic layer was dried over anhydrous $Na_2SO_4$ and concentrated. This resulted in the title compound (100 mg, yield: 36.2%) as a yellow solid. LC-MS: (ES, m/z): RT=1.378 min, LCMS: m/z=489 [M+1].

Step 2: (R)—N-(5,7-difluoroquinolin-6-yl)-5-((1-(dimethylamino)propan-2-yl)oxy)-7-(1-methyl-1H-pyrazol-4-yl)quinazolin-4-amine To a mixture of (R)-7-bromo-N-(5,7-difluoroquinolin-6-yl)-5-((1-(dimethylamino)propan-2-yl)oxy)quinazolin-4-amine (100 mg, 204 μmol) and 1-methyl-4-(4,4,5,5-tetramethyl-1,3,2-dioxaborolan-2-yl)-1H-pyrazole (84.8 mg, 408 μmol), 1,4-dioxane (8.00 mL) and $H_2O$ (2.00 mL), was added Pd(dppf)$Cl_2$ (49.9 mg, 61.2 μmol) and $K_2CO_3$ (56.3 mg, 408 μmol) at 25° C. The reaction mixture was stirred at 80° C. for 3 hrs under N2. The resulting solution was diluted with 20 mL of water. The resulting solution was extracted with 2×20 mL of ethyl acetate and the organic layers combined. The resulting mixture was washed with 20 mL of brine. The organic layer was dried over anhydrous sodium sulfate and concentrated under vacuum. The residue was purified by prep-TLC eluting with DCM: Me OH (10:1). The crude product was purified by Prep-HPLC with the following conditions: Column: YMC-Acts Trait C18 Expr's, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 30% B to 63% B in 7 min; Wavelength: 254/220 nm, to afford the title compound (39.3 mg, yield: 39.3%). LC-MS: (ES, m/z): RT=1.334 min, LCMS: m/z=490 [M+1], 1H NMR (300 MHz, DMSO-d6) δ 10.40 (s, 1H), 9.01 (m, J=4.3, 1.6 Hz, 1H), 8.59-8.44 (m, 2H), 8.32 (s, 1H), 8.13 (d, J=0.8 Hz, 1H), 7.83 (m, J=10.8, 1.7 Hz, 1H), 7.69-7.45 (m, 2H), 7.35 (d, J=1.5 Hz, 1H), 4.96 (m, J=9.7, 4.3 Hz, 1H), 3.90 (s, 3H), 2.85 (m J=12.9, 9.2 Hz, 1H), 2.48-2.12 (m, 1H), 2.11 (s, 6H), 1.51 (d, J=5.9 Hz, 3H), 1.21 (s, 1H).

Example 107: (R)-5-((1-(dimethylamino)propan-2-yl)oxy)-N-(5-fluoro-2-methylquinolin-6-yl)-7-(1-methyl-1H-pyrazol-4-yl)quinazolin-4-amine

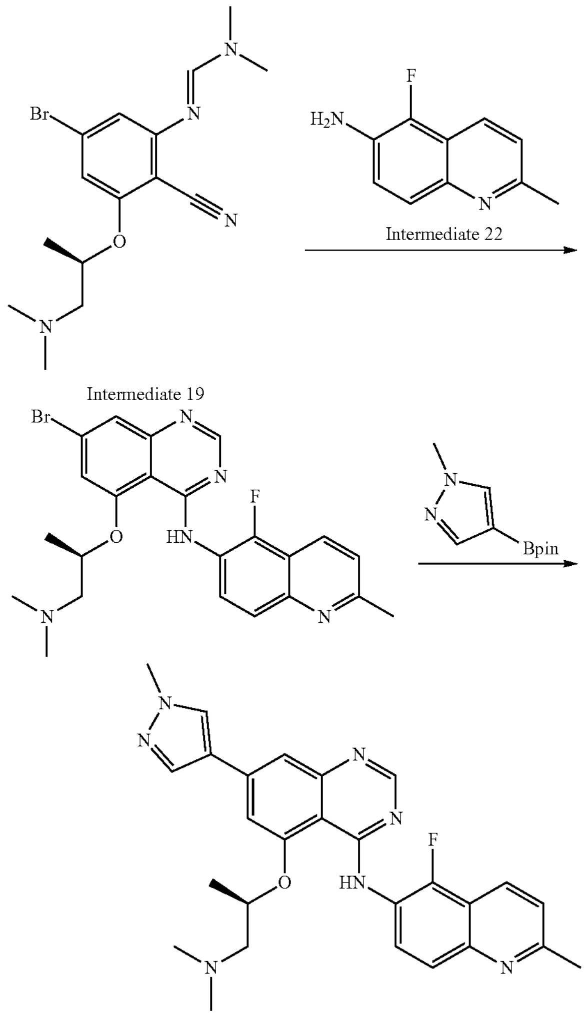

Step 1: (R)-7-bromo-5-((1-(dimethylamino)propan-2-yl)oxy)-N-(5-fluoro-2-methylquinolin-6-yl)quinazolin-4-amine The reaction mixture of Intermediate 22 (150 mg, 851 μmol) and Intermediate 19 (240 mg, 680 μmol) in acetic acid (4 mL) was stirred at 100° C. for 2 hr. The resulting mixture was added to ice-water and adjusted to pH=8 with sat $NaHCO_3$ (aq). The mixture was diluted with EA (100 mL) and washed with brine (50 mL*2). The organic layer was dried with $Na_2SO_4$ and concentrated under vacuum. The residue was purified by a silica gel column using DCM: MeOH=20:1, to afford the title compound (50 mg, yield: 33.4%) as a yellow solid. LC-MS: (ES, m/z): RT=0.867 min, LCMS: m/z=484 [M+1].

Step 2: (R)-5-((1-(dimethylamino)propan-2-yl)oxy)-N-(5-fluoro-2-methylquinolin-6-yl)-7-(1-methyl-1H-pyrazol-4-yl)quinazolin-4-amine The reaction mixture of $Pd(dppf)Cl_2$ (8.6 mg, 10.3 μmol), $K_2CO_3$ (21.2 mg, 154 μmol), (R)-7-bromo-5-((1-(dimethylamino)propan-2-yl)oxy)-N-(5-fluoro-2-methylquinolin-6-yl)quinazolin-4-amine (50 mg, 103 μmol), 1-methyl-4-(4,4,5,5-tetramethyl-1,3,2-dioxaborolan-2-yl)-1H-pyrazole (32.0 mg, 154 μmol), $H_2O$ (4 mL) and dioxane (16 mL) was stirred at 80° C. for 2 h under $N_2$. The reaction was cooled and diluted with DCM (100 mL) and washed with water (50 mL*2). The organic layer was dried with $Na_2SO_4$ and concentrated under vacuum. The residue was purified by a silica gel column using DCM:MeOH=20:1. The residue was purified by prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 16% B to 64% B in 10 min, 64% B; Wavelength: 254/220 nm. This resulted in the title compound (13.5 mg) as an off-white solid. LC-MS: (ES, m/z): RT=1.357 min, LCMS: m/z=486 [M+1]. $^1H$ NMR (400 MHz, DMSO-$d_6$) δ 10.55 (s, 1H), 8.60 (t, J=8.8 Hz, 1H), 8.47 (d, J=1.4 Hz, 2H), 8.40 (d, J=8.7 Hz, 1H), 8.15 (d, J=0.8 Hz, 1H), 7.84 (d, J=9.2 Hz, 1H), 7.59-7.49 (m, 2H), 7.42 (d, J=1.6 Hz, 1H), 5.11 (s, 1H), 3.92 (s, 3H), 2.88 (dd, J=13.0, 8.3 Hz, 1H), 2.69 (s, 3H), 2.48 (d, J=4.1 Hz, 1H), 2.18 (s, 6H), 1.51 (d, J=6.0 Hz, 3H).

Example 108: (R)-5-((1-(dimethylamino)propan-2-yl)oxy)-N-(8-fluoroquinolin-7-yl)-7-(1-methyl-1H-pyrazol-4-yl)quinazolin-4-amine

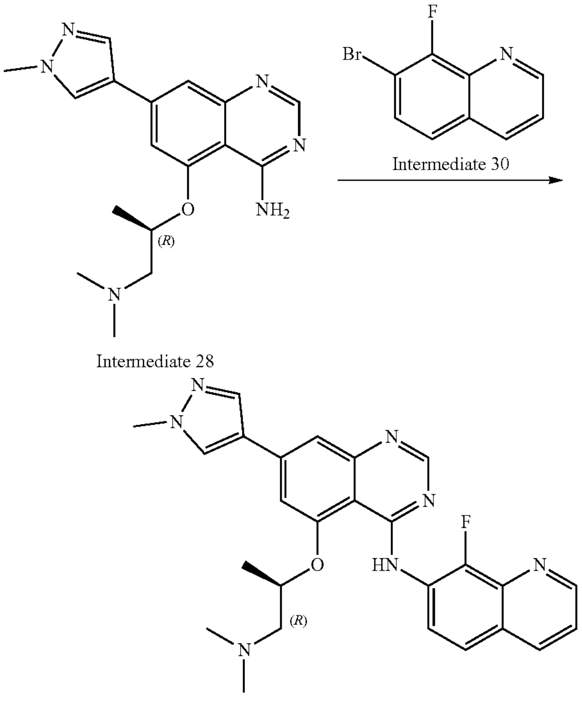

The reaction mixture of Xantphos (47.3 mg, 39.8 μmol), $Pd_2(dba)_3$ (23.0 mg, 39.8 μmol), $Cs_2CO_3$ (194 mg, 597 μmol) Intermediate 30 (90 mg, 398 μmol), Intermediate 28 (155 mg, 477 μmol) and dioxane (4 mL) was stirred at 80° C. for 5 h under $N_2$. The mixture was diluted with DCM 100 mL and washed with brine 40 mL*2, the organic layer was dried with $Na_2SO_4$ and concentrated under vacuum. The residue was purified by a silica gel column using DCM: EA=15:1. The residue was purified by prep-HPLC using the following conditions: Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 31% B to 51% B in 8 min, 51% B; Wavelength: 254; 220 nm; This resulted in the title compound (65.6 mg) as an off-white solid. LC-MS: (ES, m/z): RT=1.357 min, LCMS: m/z=472[M+1]. $^1$H NMR (300 MHz, DMSO-$d_6$) δ 10.56 (d, J=1.9 Hz, 1H), 8.83 (dd, J=4.2, 1.6 Hz, 1H), 8.58 (dd, J=9.1, 7.1 Hz, 1H), 8.41 (s, 1H), 8.39-8.26 (m, 2H), 8.04 (d, J=0.8 Hz, 1H), 7.75 (dd, J=9.1, 1.5 Hz, 1H), 7.51-7.40 (m, 2H), 7.34 (d, J=1.6 Hz, 1H), 5.04 (q, J=6.2 Hz, 1H), 3.80 (s, 3H), 2.78 (dd, J=13.0, 8.0 Hz, 1H), 2.42 (d, J=4.3 Hz, 1H), 2.07 (s, 6H), 1.40 (d, J=5.9 Hz, 3H).

Example 109: (R)-5-((1-(dimethylamino)propan-2-yl)oxy)-N-(5-fluoroquinoxalin-6-yl)-7-(1-methyl-1H-pyrazol-4-yl)quinazolin-4-amine

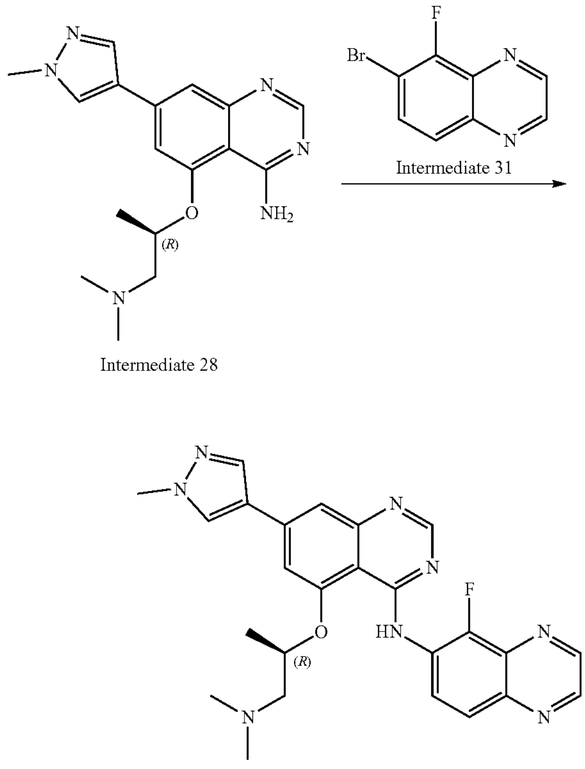

The reaction mixture of XantPhos (40.7 mg, 70.4 μmol), $Pd_2(dba)_3$ (32.2 mg, 35.2 μmol), $Cs_2CO_3$ (172 mg, 528 μmol), Intermediate 28 (114 mg, 352 μmol), Intermediate 31 (80 mg, 352 μmol) and dioxane (6 mL) was heated to 100° C. for 2 h under $N_2$. The reaction was extracted with EA (3×30 mL). The organic layer was dried with $Na_2SO_4$ and concentrated under vacuum. The crude product was purified by Prep-HPLC with the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 16% B to 59% B in 8 min; Wavelength: 254/220 nm. This resulted in the title compound (45.0 mg, yield: 27%) as an off-white solid. LC-MS: (ES, m/z): RT=0.963 min, LCMS: m/z=473 [M+1], $^1$H NMR (300 MHz, DMSO-$d_6$) δ 10.75 (s, 1H), 9.04-8.95 (m, 3H), 8.56 (s, 1H), 8.50 (s, 1H), 8.18 (s, 1H), 8.03 (dd, J=9.4, 1.5 Hz, 1H), 7.61 (d, J=1.4 Hz, 1H), 7.48 (s, 1H), 5.18 (s, 1H), 3.93 (s, 3H), 2.91 (dd, J=12.9, 8.0 Hz, 1H), 2.55 (m, 1H), 2.20 (s, 6H), 1.53 (d, J=5.9 Hz, 3H).

Example 110: (R)-5-((1-(dimethylamino)propan-2-yl)oxy)-N-(4-fluoroquinolin-3-yl)-7-(1-methyl-1H-pyrazol-4-yl)quinazolin-4-amine

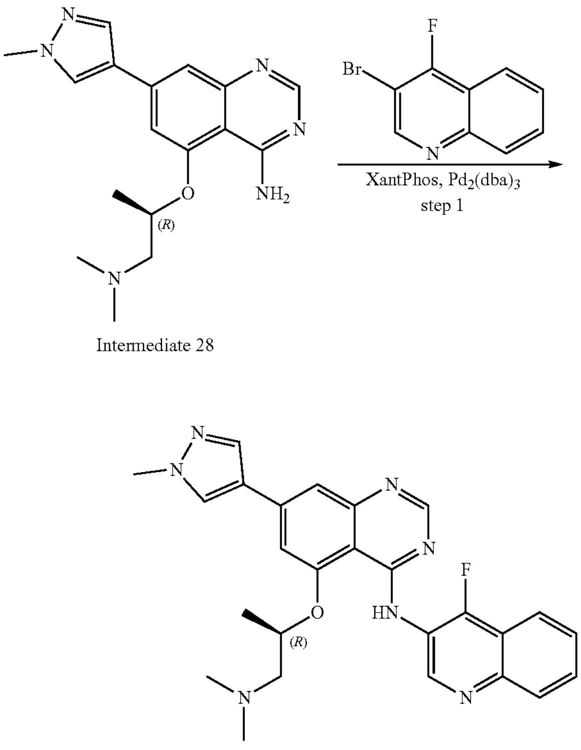

The reaction mixture of XantPhos (31.8 mg, 55.0 μmol), $Pd_2(dba)_3$ (25.1 mg, 27.5 μmol), Intermediate 28 (90 mg, 275 μmol), 3-bromo-4-fluoroquinoline (93.1 mg, 412 μmol) in dioxane (2 mL) was heated to 100° C. for 2 h under $N_2$. Diluted with water and extracted with EA. The organic layer was dried with $Na_2SO_4$ and concentrated under vacuum. Purified by prep-HPLC using following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 23% B to 66% B in 7 min; Wavelength: 254/220 nm. This resulted in the title compound (74.7 mg, yield: 57%) as a white solid. LC-MS: (ES, m/z): RT=1.067 min, LCMS: m/z=472 [M+1], $^1$H NMR (400 MHz, DMSO-$d_6$) δ 10.55 (s, 1H), 9.47 (d, J=9.7 Hz, 1H), 8.47 (d, J=18.2 Hz, 2H), 8.18-8.10 (m, 3H), 7.85 (ddd, J=8.4, 5.0, 1.5 Hz, 1H), 7.75 (t, J=7.6 Hz, 1H), 7.59 (d, J=1.4 Hz, 1H), 7.42 (d, J=1.5 Hz, 1H), 5.11-5.04 (m, 1H), 3.92 (s, 3H), 2.92 (dd, J=12.9, 8.8 Hz, 1H), 2.49-2.44 (m, 1H), 2.18 (s, 6H), 1.53 (d, J=5.9 Hz, 3H).

Example 111: (R)-2-(1-((4-((5-fluoroquinolin-6-yl)amino)-7-(1-methyl-1H-pyrazol-4-yl)quinazolin-5-yl)oxy)ethyl)propane-1,3-diol Example 112: (3R)-3-((4-((5-fluoroquinolin-6-yl)amino)-7-(1-methyl-1H-pyrazol-4-yl)quinazolin-5-yl)oxy)-2-(methoxymethyl)butan-1-ol

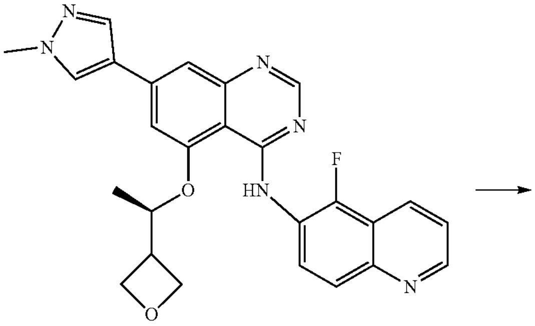

Example 3

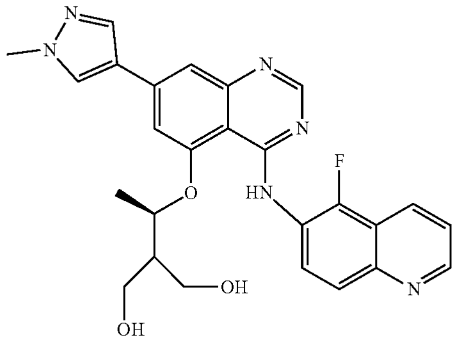

Example 111

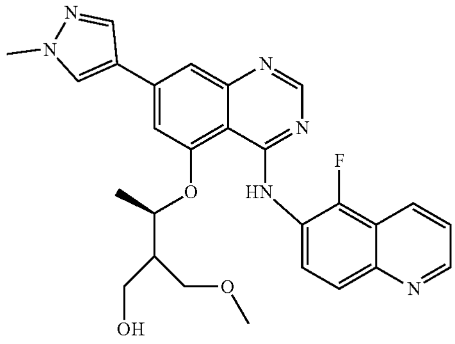

Example 112

A mixture of Example 3 (20.7 mg, 0.044 mmol) in 1 mL of TFA and 200 μL of MeOH was heated to 90° C. for 1 hr. Both products were observed. Reaction mixture was concentrated down under vacuum and dissolved in DMSO. Followed by reverse phase purification using Xbridge Prep OBD C18 5.0 mm column with 0-40% 0.1% TFA modified Acetonitrile/Water. Appropriate fractions were combined to give:

Example 111: (R)-2-(1-((4-((5-fluoroquinolin-6-yl)amino)-7-(1-methyl-1H-pyrazol-4-yl)quinazolin-5-yl)oxy)ethyl)propane-1,3-diol (14.4 mg, 0.029 mmol, 68.0% yield). LC-MS: (ES, m z): RT=2.4 min, LC-MS: m/z=489 [M+1]; $^1$H NMR (500 MHz, DMSO-$d_6$) δ ppm: 8.79 (s, 1H), 8.53-8.45 (m, 1H), 8.40 (d, J=9.6 Hz, 1H), 8.32-8.28 (m, 1H), 8.14-8.09 (m, 1H), 7.97-7.90 (m, 1H), 7.86-7.79 (m, 1H), 7.53 (dd, J=9.3, 4.6 Hz, 1H), 7.40 (s, 1H), 7.35 (s, 1H), 5.22 (d, J=7.6 Hz, 1H), 3.95-3.86 (m, 3H), 3.84 (d, J=11.7 Hz, 3H), 3.71 (dd, J=20.7, 9.3 Hz, 2H), 2.14 (s, 1H), 1.53 (t, J=4.9 Hz, 3H).

Example 112: (3R)-3-((4-((5-fluoroquinolin-6-yl)amino)-7-(1-methyl-1H-pyrazol-4-yl)quinazolin-5-yl)oxy)-2-(methoxymethyl)butan-1-ol (1.3 mg, 2.59 μmol, 5.97% yield). LC-MS: (ES, m/z): RT=2.55 min, LC-MS: m/z=503 [M+1].

Example 113: (3R)-2-(chloromethyl)-3-((4-((5-fluoroquinolin-6-yl)amino)-7-(1-methyl-1H-pyrazol-4-yl)quinazolin-5-yl)oxy)butan-1-ol

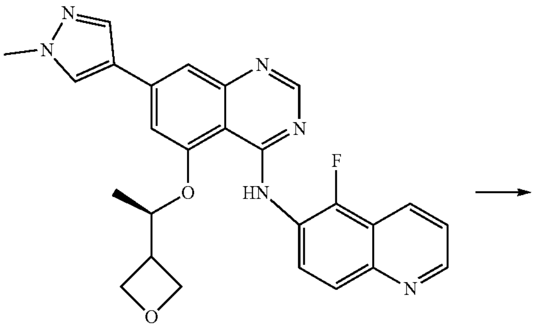

Example 3

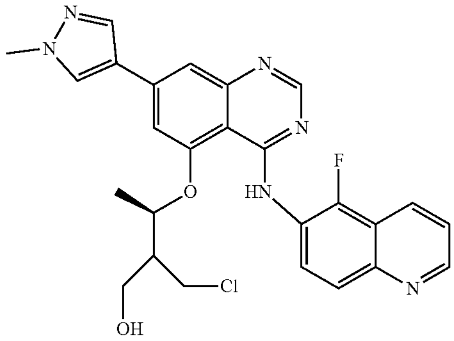

A mixture of Example 3, in 1 mL of 1N HCl (aq) was heated to 45° C. for 16 h. Reaction mixture was concentrated under vacuum and the residue dissolved in DMSO. Followed by reverse phase purification: Xbridge Prep OBD C18 5.0 mm column with 0-40% 0.1% TFA modified Acetonitrile/Water. Isolated the title compound (8.5 mg, 0.017 mmol, 77% yield). LC-MS: (ES, m z): RT=2.6 min, LC-MS: m/z=507 [M+1]; $^1$H NMR (500 MHz, DMSO-$d_6$) δ 11.29-10.67 (m, 1H), 9.09-8.96 (m, 1H), 8.71-8.50 (m, 3H), 8.45 (s, 0.2H), 8.21-8.14 (m, 1H), 8.06 (s, 0.8H), 7.98 (s, 1H), 7.74-7.63 (m, 1H), 7.63-7.45 (m, 2H), 5.44 (s, 1H), 5.28 (s, 1H), 4.04-3.86 (m, 6H), 3.83-3.65 (m, 1H), 2.23 (s, 1H), 1.64-1.48 (m, 3H).

Example 114: (R)-5-((1-(cyclopropyl(methyl)amino)propan-2-yl)oxy)-N-(5-fluoroquinolin-6-yl)-7-(1-methyl-1H-pyrazol-4-yl)quinazolin-4-amine

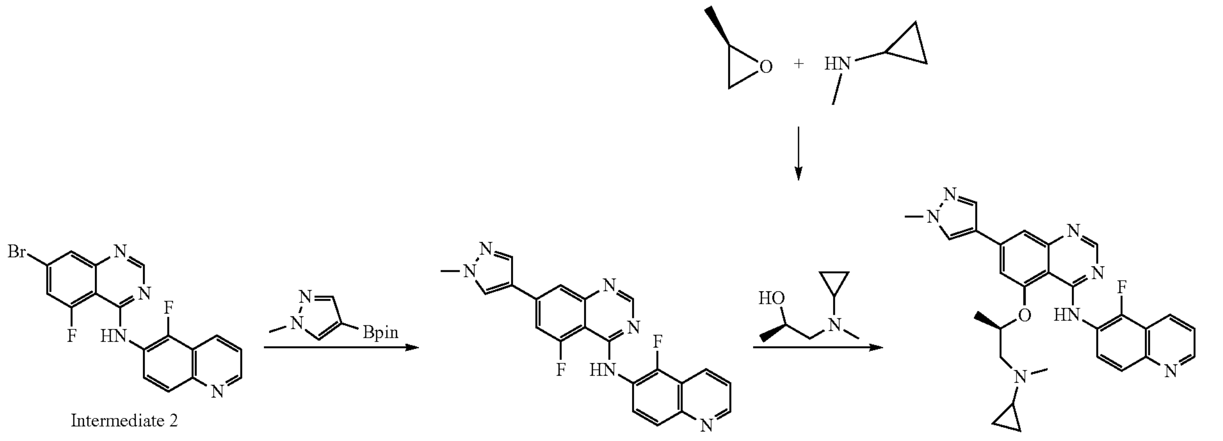

Intermediate 2

Step 1: 5-fluoro-N-(5-fluoroquinolin-6-yl)-7-(1-methyl-1H-pyrazol-4-yl)quinazolin-4-amine Intermediate 2 (500 mg, 1.291 mmol), Xantphos Pd G3 (61.3 mg, 0.065 mmol), 1-methyl-4-(4,4,5,5-tetramethyl-1,3,2-dioxaborolan-2-yl)-1H-pyrazole (322 mg, 1.550 mmol), DMF (5 mL) and potassium phosphate (2M solution, 1291 µl, 2.58 mmol) were combined. The reaction was sparged with nitrogen and heated 100° C. for 16 h. Cooled to rt, extracted with DCM and washed with water. The combined organic layers were concentrated and the residue was purified by CC eluting with 0-20%, 1% $NH_4OH$ modified MeOH/DCM to afford the title compound (379.0 mg, 0.976 mmol, 76% yield). LC-MS: (ES, m/z): RT=2.5 min, LC-MS: m/z=389 [M+1].

Step 2: (R)-1-(cyclopropyl(methyl)amino)propan-2-ol

Cyclopropyl-methyl-amine hydrochloride (0.713 g, 6.63 mmol) was free-based with 2 mL of ACN and 500 mg of solid supported carbonate. Stirred for 2 hr at rt and then filtered the resin away. The filtrate was added dropwise to a rt solution of (R)-Propylene oxide (0.35 g, 6.03 mmol) in ACN (2 mL) then heated to 80° C. for 1 h. Concentrated to a minimum volume under vacuum and the crude material was used in the next step without isolation.

Step 3: (R)-5-((1-(cyclopropyl(methyl)amino)propan-2-yl)oxy)-N-(5-fluoroquinolin-6-yl)-7-(1-methyl-1H-pyrazol-4-yl)quinazolin-4-amine (R)-1-(cyclopropyl(methyl)amino)propan-2-ol (33.3 mg, 0.257 mmol), 5-fluoro-N-(5-fluoroquinolin-6-yl)-7-(1-methyl-1H-pyrazol-4-yl)quinazolin-4-amine (50.0 mg, 0.129 mmol), sodium hydride (15.45 mg, 0.386 mmol) and DMA (2 mL) were heated to 90° C. for 1 h. Cooled to rt and concentrated under vacuum. Added 2 mL DCM and 1 mL of water. Extracted with DCM multiple times. Combined organic layers and concentrated. The residue was dissolved in a minimum amount of DMSO and purified by prep-HPLC: Xbridge Prep OBD C18 5.0 um column with 0-40% 0.1% TFA modified Acetonitrile/Water to afford the title compound (28.1 mg, 0.056 mmol, 43.4% yield). LC-MS: (ES, m/z): RT=2.2 min, LC-MS: m/z=498 [M+1]; $^1$H NMR (MeOD) δ: 9.03 (d, J=5.2 Hz, 1H), 8.79 (d, J=3.7 Hz, 1H), 8.74 (d, J=9.4 Hz, 2H), 8.67 (d, J=9.7 Hz, 1H), 8.42 (d, J=3.8 Hz, 1H), 8.18 (d, J=3.8 Hz, 1H), 8.04 (d, J=9.4 Hz, 1H), 7.82-7.71 (m, 2H), 7.62 (d, J=3.9 Hz, 1H), 5.95 (s, 1H), 4.19 (t, J=11.7 Hz, 1H), 4.01 (d, J=3.8 Hz, 3H), 3.85 (d, J=14.5 Hz, 1H), 3.15 (d, J=3.8 Hz, 3H), 3.00 (q, J=5.9, 5.4 Hz, 1H), 1.65 (t, J=5.1 Hz, 3H), 1.05 (s, 3H), 0.95 (d, J=8.0 Hz, 1H).

Example 115: (R)-5-((1-(cyclopropyl(methyl)amino)propan-2-yl)oxy)-N-(5-fluoroquinolin-6-yl)-7-(1-methyl-1H-pyrazol-4-yl)quinazolin-4-amine

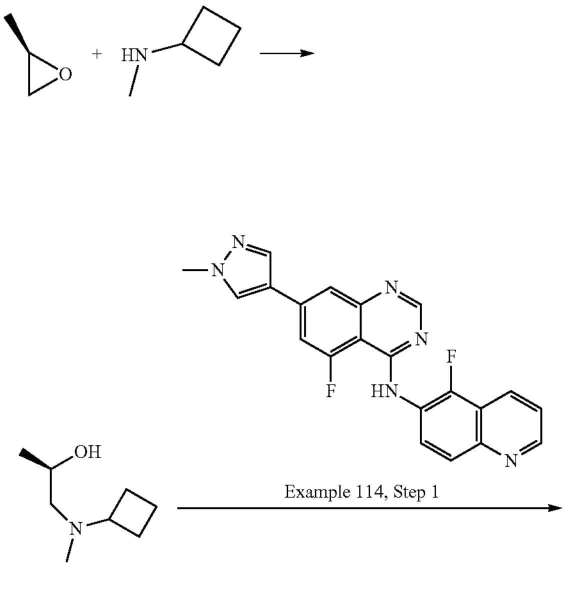

-continued

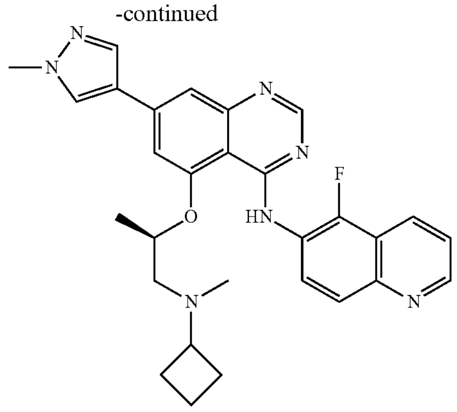

Step 1: (R)-1-(cyclobutyl(methyl)amino)propan-2-ol

Cyclopbutan-methyl-amine hydrochloride (0.230 g, 1.891 mmol) was freebased using 2 mL of acetonitrile and 200 mg of solid supported carbonate resin. Stirred for 2 hr at rt and then filtered solution. The filtrate was added dropwise to a solution of (R)-propylene oxide (0.12 g, 2.03 mmol) in acetonitrile (2 mL) at rt and then heated to 80° C. for 1 hr. Concentrated to a minimum volume under vacuum and taken to the next step crude.

Step 2: (R)-5-((1-(cyclobutyl(methyl)amino)propan-2-yl)oxy)-N-(5-fluoroquinolin-6-yl)-7-(1-methyl-1H-pyrazol-4-yl)quinazolin-4-amine (R)-1-(cyclobutyl(methyl)amino)propan-2-ol (36.9 mg, 0.257 mmol), 5-fluoro-N-(5-fluoroquinolin-6-yl)-7-(1-methyl-1H-pyrazol-4-yl)quinazolin-4-amine [[Product example 114, Step 1]] (50.0 mg, 0.129 mmol) and sodium hydride (15.45 mg, 0.386 mmol) were combined with DMA (2 mL) and heated to 90° C. for 1 hr. Cooled to rt and concentrated under vacuum. Added 2 mL DCM and 1 mL of water. Extracted several times with DCM (2 mL). Combined organic layers and concentrated. Dissolved in minimum amount of DMSO and purified by prep-HPLC using Xbridge Prep OBD C18 5.0 um column with 0-40% 0.1% TFA modified Acetonitrile/Water. Isolated the title compound (27.8 mg, 0.054 mmol, 41.8% yield). LC-MS: (ES, m/z): RT=2.2 min, LC-MS: m/z=512 [M+1]; $^{1}$H NMR (500 MHz, DMSO-$d_6$) δ ppm: 9.02 (d, J=4.8 Hz, 1H), 8.79 (d, J=3.6 Hz, 1H), 8.70 (d, J=8.6 Hz, 1H), 8.62 (d, J=9.4 Hz, 1H), 8.42 (d, J=3.6 Hz, 1H), 8.18 (d, J=3.8 Hz, 1H), 8.07-7.99 (m, 1H), 7.82-7.71 (m, 2H), 7.63 (d, J=3.8 Hz, 1H), 5.78 (d, J=8.5 Hz, 1H), 4.01 (d, J=3.6 Hz, 3H), 3.99-3.82 (m, 3H), 2.95 (d, J=3.6 Hz, 3H), 2.36 (q, J=13.5, 11.5 Hz, 4H), 1.80 (q, J=10.8, 10.1 Hz, 2H), 1.65 (t, J=5.0 Hz, 3H).

Example 116: (R)-6-((5-((1-(dimethylamino)propan-2-yl)oxy)-7-(1-methyl-1H-pyrazol-4-yl)quinazolin-4-yl)amino)-5-fluoroquinolin-3-ol

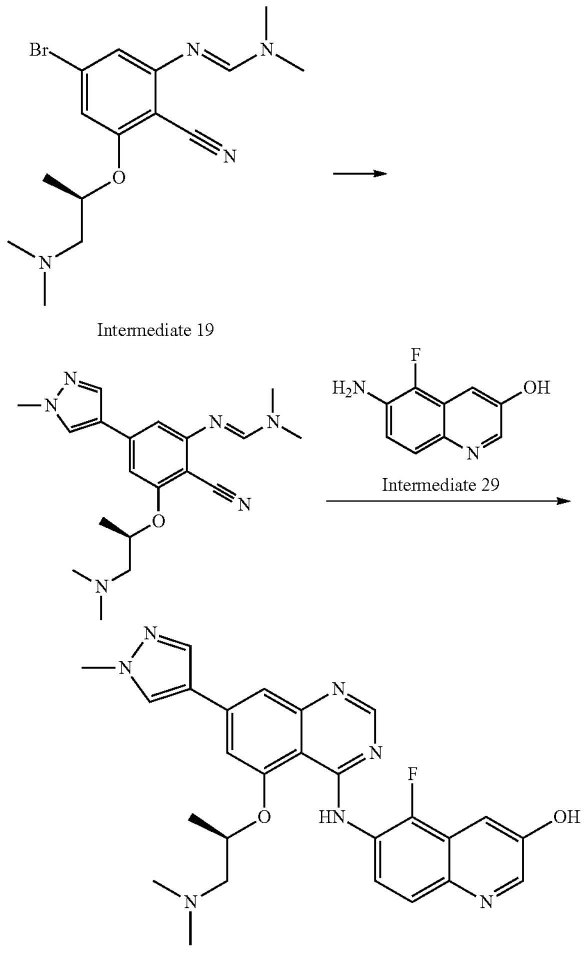

Step 1: (R,E)-N'-(2-cyano-3-((1-(dimethylamino)propan-2-yl)oxy)-5-(1-methyl-1H-pyrazol-4-yl)phenyl)-N,N-dimethylformimidamide The reaction mixture of Intermediate 19 (500 mg, 1.41 mmol), 1-methyl-4-(4,4,5,5-tetramethyl-1,3,2-dioxaborolan-2-yl)-1H-pyrazole (29 3 mg, 1.41 mmol), Pd(dppf)$Cl_2$ (109 mg, 0.141 mmol), $K_2CO_3$ (389 mg, 2.82 mmol) in dioxane (6 mL)/$H_2O$ (2 mL) was stirred at 80° C. for 4 h, then concentrated and purified by prep-HPLC (DCM/$CH_3OH$=20/1) to afford the title compound (400 mg, yield: 70%). LC-MS: (ES, m/z): RT=0.736 min, LCMS: m/z=355 [M+1].

Step 2: (R)-6-((5-((1-(dimethylamino)propan-2-yl)oxy)-7-(1-methyl-1H-pyrazol-4-yl)quinazolin-4-yl)amino)-5-fluoroquinolin-3-ol The reaction mixture of (R,E)-N'-(2-cyano-3-((1-(dimethylamino)propan-2-yl)oxy)-5-(1-methyl-1H-pyrazol-4-yl)phenyl)-N,N-dimethylformimidamide (354 mg, 0.1 mmol) and Intermediate 29 (354 mg, 0.2 mmol) in HOAc (2 mL) was stirred at 100° C. for 10 hr. The reaction was concentrated and purified by prep-HPLC (Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 8% B to 45% B in 10 min, 45% B; Wavelength: 254/220 nm; RT1(min): 9; Number Of Runs: 0) to afford the title compound as a white solid (30.7 mg) LC-MS: (ES, m/z): RT=0.857 min, LCMS: m/z=488 [M+1], $^1$H NMR (300 MHz, DMSO-$d_6$) δ 10.71 (s, 1H), 10.56 (s, 1H), 8.58 (d, J=2.7 Hz, 1H), 8.52-8.39 (m, 3H), 8.16 (s, 1H), 7.81 (d, J=9.2 Hz, 1H), 7.56 (dd, J=6.4, 2.1 Hz, 2H), 7.43 (s, 1H), 5.13 (d, J=10.8 Hz, 1H), 3.92 (s, 3H), 2.89 (dd, J=12.9, 8.2 Hz, 1H), 2.50 (d, J=17.3 Hz, 1H), 2.18 (s, 6H), 1.51 (d, J=5.9 Hz, 3H).

Example 117: 7-(1-ethyl-3-methoxy-1H-pyrazol-4-yl)-N-(5-fluoroquinolin-6-yl)-5-((1-methylpiperidin-4-yl)oxy)quinazolin-4-amine

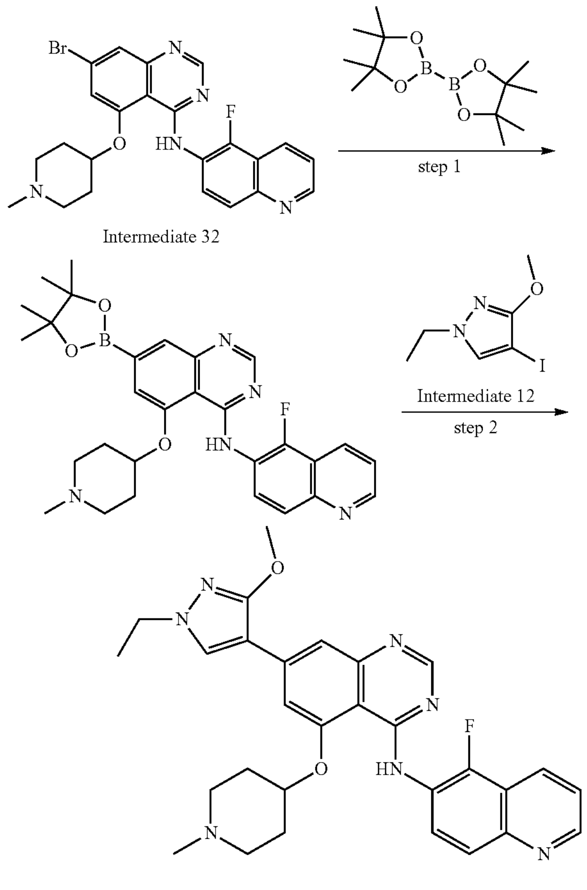

Step 1: N-(5-fluoroquinolin-6-yl)-5-((1-methylpiperidin-4-yl)oxy)-7-(4,4,5,5-tetramethyl-1,3,2-dioxaborolan-2-yl)quinazolin-4-amine The reaction mixture of Pd(dppf)$Cl_2$ (8.40 mg, 10.3 μmol), KOAc (30.5 mg, 309 μmol), Intermediate 32 (50 mg, 103 μmol), 4,4,5,5-tetramethyl-2-(4,4,5,5-tetramethyl-1,3,2-dioxaborolan-2-yl)-1,3,2-dioxaborolane (78.4 mg, 309 μmol) in dioxane (3 mL) was heated at 100° C. for 3 h under $N_2$. The mixture was evaporated to afford crude title compound (50 mg) as a white solid. LC-MS: (ES, m/z): RT=1.350 min, LCMS: m/z=530 [M+1], Step 2: 7-(1-ethyl-3-methoxy-1H-pyrazol-4-yl)-N-(5-fluoroquinolin-6-yl)-5-((1-methylpiperidin-4-yl)oxy)quinazolin-4-amine The reaction mixture of Pd(dppf)$Cl_2$ (7.70 mg, 9.44 μmol), $K_2CO_3$ (19.4 mg, 141 μmol), N-(5-fluoroquinolin-6-yl)-5-((1-methylpiperidin-4-yl)oxy)-7-(4,4,5,5-tetramethyl-1,3,2-dioxaborolan-2-yl)quinazolin-4-amine (50 mg, 94.4 μmol), Intermediate 12 (11.8 mg, 47.2 μmol) in dioxane/$H_2O$ (3 mL/1 mL) was heated at 80° C. for 3 h under $N_2$. The reaction mixture was diluted with EtOAc (120 mL) and washed with water (60 mL). The organic layer was dried over $Na_2SO_4$, filtered and evaporated under vacuum. The crude product was purified by prep-TLC using DCM: MeOH=20:1. The residue was further purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 35% B to 71% B in 7 min, 71% B; Wavelength: 254/220 nm; to afford the title compound (4.0 mg) as an off-white solid. LC-MS: (ES, m/z): RT=0.633 min, LCMS: m/z=528 [M+1], 1H NMR (400 MHz, DMSO-d6) δ 10.29 (s, 1H), 9.00 (t, J=8.9 Hz, 2H), 8.53 (d, J=10.5 Hz, 2H), 8.43 (s, 1H), 7.97 (d, J=9.4 Hz, 1H), 7.71 (d, J=1.4 Hz, 2H), 7.49 (s, 1H), 4.96 (s, 1H), 2.75 (s, 2H), 2.32-2.19 (m, 7H), 1.95 (d, J=11.0 Hz, 2H), 1.42 (t, J=7.3 Hz, 3H).

Example 118: (R)-7-(3-(difluoromethoxy)-1-methyl-1H-pyrazol-4-yl)-5-((1-(dimethylamino)propan-2-yl)oxy)-N-(5-fluoroquinolin-6-yl)quinazolin-4-amine

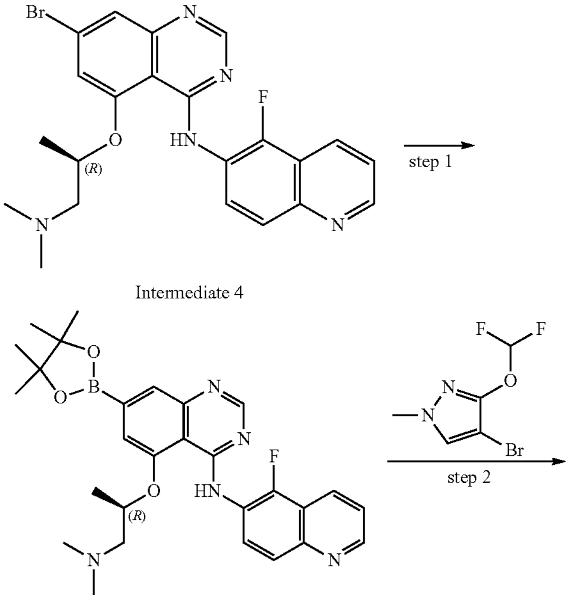

-continued

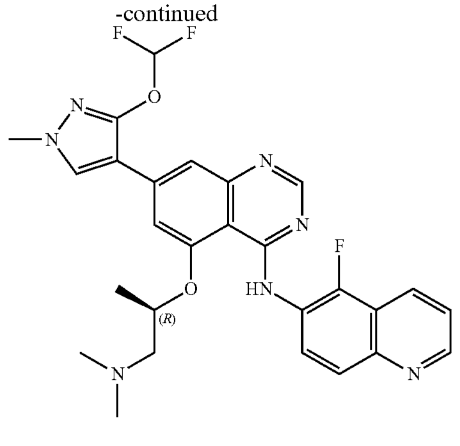

Step 1: (R)-5-((1-(dimethylamino)propan-2-yl)oxy)-N-(5-fluoroquinolin-6-yl)-7-(4,4,5,5-tetramethyl-1,3,2-dioxaborolan-2-yl)quinazolin-4-amine To a solution of Intermediate 4 (120 mg, 255 μmol), 4,4,5,5-tetramethyl-2-(4,4,5,5-tetramethyl-1,3,2-dioxaborolan-2-yl)-1,3,2-dioxaborolane (129 mg, 509 μmol) in 1,4-dioxane (5 mL) was added Pd(dppf)$Cl_2$·DCM (20.7 mg 25.4 μmol) and KOAc (49.9 mg, 509 μmol). The mixture was stirred at 100° C. overnight under $N_2$. The reaction was diluted with 20 mL of water, extracted with 2×20 mL of ethyl acetate and the organic layers combined. The organic layer was washed with 20 mL of brine, dried over anhydrous sodium sulfate and concentrated under vacuum. The residue was purified by flash chromatography to give the title compound (80 mg, yield: 61.0%) as a white solid. LC-MS: (ES, m/z): RT=0.792 min, LCMS: m/z=518 [M+1], Step 2: (R)-7-(3-(difluoromethoxy)-1-methyl-1H-pyrazol-4-yl)-5-((1-(dimethylamino)propan-2-yl)oxy)-N-(5-fluoroquinolin-6-yl)quinazolin-4-amine To a solution of (R)-5-((1-(dimethylamino)propan-2-yl)oxy)-N-(5-fluoroquinolin-6-yl)-7-(4,4,5,5-tetramethyl-1,3,2-dioxaborolan-2-yl)quinazolin-4-amine (80 mg, 158 μmol) and 4-bromo-3-(difluoromethoxy)-1-methyl-1H-pyrazole (53.8 mg, 237 μmol) in 1,4-dioxane (4 mL) and $H_2O$ (1 mL) was added Pd(dppf)$Cl_2$·DCM (12.8 mg 15.8 μmol) and $K_2CO_3$ (43.6 mg, 316 μmol). The mixture was stirred at 80° C. for 3 hours under $N_2$. The reaction was diluted with 20 mL of water, extracted with 2×20 mL of ethyl acetate and the organic layers combined. The organic layer was washed with 20 mL of brine, dried over anhydrous sodium sulfate and concentrated under vacuum. The crude product was purified by prep-HPLC using the following conditions: Column: YMC-Altus Trait C18, 30*150 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 65% B to 75% B in 8 min; Wavelength: 254/220 nm to afford the title compound (32.6 mg, yield: 20.5%) as a white solid. LC-MS: (ES, m/z): RT=1.654 min, LCMS: m/z=538 [M+1]. $^1$H NMR (400 MHz, DMSO-d6) δ 10.63 (s, 1H), 8.95 (m, J=4.3, 1.7 Hz, 1H), 8.63 (t, J=8.8 Hz, 1H), 8.55-8.39 (m, 3H), 7.96 (d, J=9.2 Hz, 1H), 7.65 (m, J=8.4, 4.4 Hz, 1H), 7.63-7.19 (m, 3H), 5.13-4.73 (m, 1H), 3.85 (s, 3H), 2.91 (m, J=12.9, 8.5 Hz, 1H), 2.17 (s, 7H), 1.54 (d, J=6.0 Hz, 3H).

Example 119: (R)-2-(4-(4-((5-fluoroquinolin-6-yl)amino)-5-((R)-1-(oxetan-3-yl)ethoxy)quinazolin-7-yl)-1H-pyrazol-1-yl)propan-1-ol and (S)-2-(4-(4-((5-fluoroquinolin-6-yl)amino)-5-((R)-1-(oxetan-3-yl)ethoxy)quinazolin-7-yl)-1H-pyrazol-1-yl)propan-1-ol Example 120: (R)-2-(4-(4-((5-fluoroquinolin-6-yl)amino)-5-((R)-1-(oxetan-3-yl)ethoxy)quinazolin-7-yl)-1H-pyrazol-1-yl)propan-1-ol or (S)-2-(4-(4-((5-fluoroquinolin-6-yl)amino)-5-((R)-1-(oxetan-3-yl)ethoxy)quinazolin-7-yl)-1H-pyrazol-1-yl)propan-1-ol Example 121: (S)-2-(4-(4-((5-fluoroquinolin-6-yl)amino)-5-((R)-1-(oxetan-3-yl)ethoxy)quinazolin-7-yl)-1H-pyrazol-1-yl)propan-1-ol or (R)-2-(4-(4-((5-fluoroquinolin-6-yl)amino)-5-((R)-1-(oxetan-3-yl)ethoxy)quinazolin-7-yl)-1H-pyrazol-1-yl)propan-1-ol

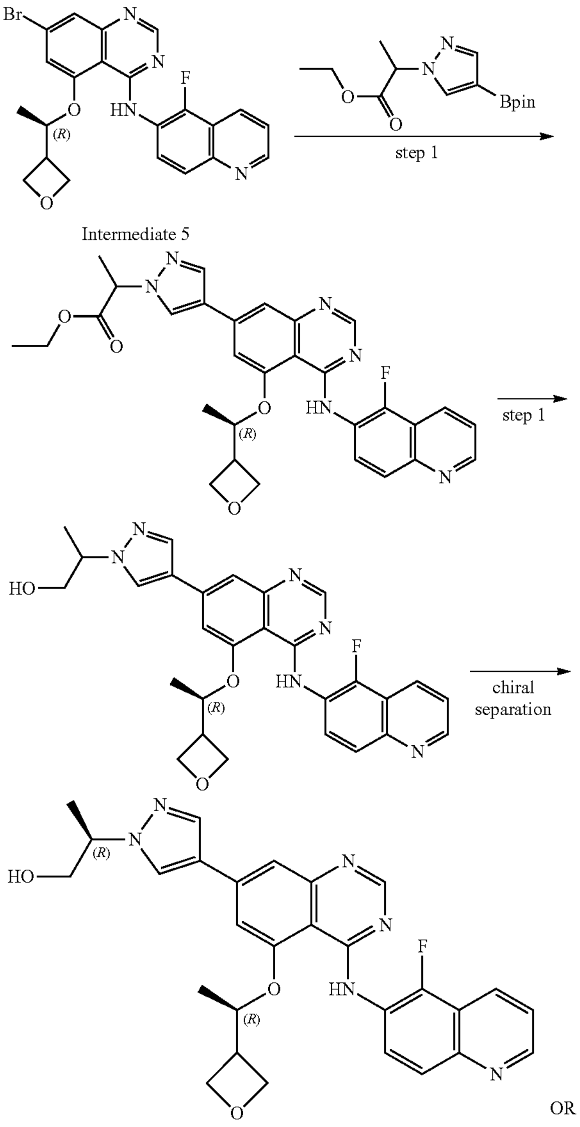

OR

-continued

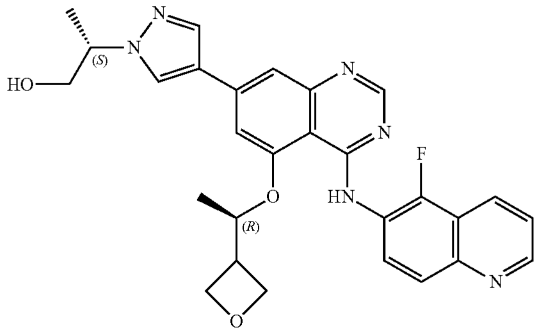

Step 1: ethyl 2-(4-(4-((5-fluoroquinolin-6-yl) amino)-5-((R)-1-(oxetan-3-yl)ethoxy) quinazolin-7-yl)-1H-pyrazol-1-yl)propanoate $Pd(dppf)Cl_2$ (34.7 mg, 42.6 μmol), $K_2CO_3$ (88.1 mg, 639 μmol), ethyl 2-[4-(4,4,5,5-tetramethyl-1,3,2-dioxaborolan-2-yl)-1H-pyrazol-1-yl]propanoate (187 mg, 639 μmol), Intermediate 5 (200 mg, 426 μmol), $H_2O$ (4 mL) and dioxane (16 mL) were stirred at 80° C. for 2 h under $N_2$. The reaction was diluted with DCM (100 mL) and washed with water (50 mL*2). The organic layer was dried with $Na_2SO_4$ and concentrated under vacuum. The residue was purified by silica gel column using DCM:MeOH=20:1 to afford the title compound (150 mg, yield: 75%) as a white solid. LC-MS: (ES, m/z): RT=1.227 min, LCMS: m/z=557 [M+1].

Step 2, Example 119: (R)-2-(4-(4-((5-fluoroquinolin-6-yl)amino)-5-((R)-1-(oxetan-3-yl)ethoxy)quinazolin-7-yl)-1H-pyrazol-1-yl)propan-1-ol and (S)-2-(4-(4-((5-fluoroquinolin-6-yl)amino)-5-((R)-1-(oxetan-3-yl)ethoxy)quinazolin-7-yl)-1H-pyrazol-1-yl)propan-1-ol $LiBH_4$ (1.14 mg, 35.9 μmol) was added to ethyl 2-(4-(4-((5-fluoroquinolin-6-yl)amino)-5-((R)-1-(oxetan-3-yl) ethoxy) quinazolin-7-yl)-1H-pyrazol-1-yl)propanoate (20 mg, 35.9 μmol) in THF (2 mL) for 2 h under $N_2$. The reaction was diluted with EA (100 mL), washed with brine (50 mL*2), the organic layer dried with $Na_2SO_4$ and concentrated under vacuum. The residue was purified by prep-TLC using PE:EA=15:1, The residue was further purified by prep-HPLC using the following conditions: Column: Xselect CSH C18 OBD Column 30*150 mm 5 m, n; Mobile Phase A: Water (10 mmol/L $NH_4HCO_3$+0.1% $NH_3 \cdot H_2O$), Mobile Phase B: ACN; Flow rate: 60 mL/min; Gradient: 31% B to 41% B in 10 min, 41% B; Wavelength: 254; 220 nm; to afford the title compound (1.8 mg, yield: 9%) of as a white solid. LC-MS: (ES, m/z): RT=1.171 min, LCMS: m/z=515 [M+1]. $^1$H NMR (300 MHz, DMSO-$d_6$) δ 10.17 (s, 1H), 8.92 (s, 1H), 8.74 (t, J=8.8 Hz, 1H), 8.52 (d, J=11.7 Hz, 3H), 8.19 (s, 1H), 7.93 (d, J=9.3 Hz, 1H), 7.62 (s, 2H), 7.52 (s, 1H), 5.48 (s, 1H), 4.98 (s, 1H), 4.82 (s, 2H), 4.60 (s, 1H), 4.50 (s, 1H), 3.67 (s, 2H), 3.47 (s, 1H), 1.43 (dd, J=11.1, 6.4 Hz, 6H), 1.22 (s, 1H).

Step 3: Chiral Separation

Example 119, (R)-2-(4-(4-((5-fluoroquinolin-6-yl) amino)-5-((R)-1-(oxetan-3-yl)ethoxy)quinazolin-7-yl)-1H-pyrazol-1-yl)propan-1-ol and (S)-2-(4-(4-((5-fluoroquinolin-6-yl)amino)-5-((R)-1-(oxetan-3-yl)ethoxy)quinazolin-7-yl)-1H-pyrazol-1-yl)propan-1-ol (60 mg, 97.1 μmol) was dissolved in MeOH was Purified by Prep-Chiral-HPLC with following conditions: Column: CHIRALPAK ID, 2*25 cm, 5 μm; Mobile Phase A: Hex: DCM=3:1 (0.5% 2M NH3-MeOH)-HPLC, Mobile Phase B: EtOH-HPLC; Flow rate: 20 mL/min; Gradient: 20% B to 20% B in 23 min; Wavelength: 254/220 nm; RT1(min): 14.32; RT2(min): 18.21; Sample Solvent: EtOH-HPLC. This resulted in:

Example 120: First eluting isomer, (18 mg), as an off-white solid, LC-MS: (ES, m/z): RT=1.448 min, LCMS: m/z=401 [M+1]. Chiral-HPLC R=1.90, $^1$H NMR (300 MHz, DMSO-$d_6$) δ 10.17 (d, J=1.4 Hz, 1H), 8.92 (dd, J=4.2, 1.7 Hz, 1H), 8.74 (t, J=8.9 Hz, 1H), 8.52 (d, J=12.3 Hz, 3H), 8.19 (s, 1H), 7.93 (d, J=9.3 Hz, 1H), 7.68-7.58 (m, 2H), 7.53 (s, 1H), 5.53-5.42 (m, 1H), 4.97 (t, J=5.4 Hz, 1H), 4.82 (q, J=6.4 Hz, 2H), 4.60 (t, J=6.0 Hz, 1H), 4.50 (t, J=5.9 Hz, 1H), 4.45-4.32 (m, 1H), 3.69 (dq, J=16.8, 5.8, 5.4 Hz, 2H), 3.47 (d, J=7.2 Hz, 1H), 1.43 (dd, J=10.9, 6.4 Hz, 6H).

Example 121: Second eluting isomer, (18 mg), as a white solid, LC-MS: (ES, m/z): RT=1.452 min, LCMS: m/z=401 [M+1]. Chiral-HPLC R=2.44, $^1$H NMR (300 MHz, DMSO-$d_6$) δ 10.18 (s, 1H), 8.92 (dd, J=4.2, 1.7 Hz, 1H), 8.74 (t, J=8.9 Hz, 1H), 8.52 (d, J=11.6 Hz, 3H), 8.19 (s, 1H), 7.93 (d, J=9.3 Hz, 1H), 7.68-7.58 (m, 2H), 7.53 (s, 1H), 5.53-5.43 (m, 1H), 4.98 (t, J=5.4 Hz, 1H), 4.82 (q, J=6.5 Hz, 2H), 4.60 (t, J=5.9 Hz, 1H), 4.50 (t, J=5.9 Hz, 1H), 4.39 (q, J=6.6 Hz, 1H), 3.75-3.62 (m, 2H), 3.46 (d, J=7.1 Hz, 1H), 1.43 (dd, J=11.3, 6.4 Hz, 6H).

Example 122: (R)-6-((5-((1-(dimethylamino)propan-2-yl)oxy)-7-(1-methyl-1H-pyrazol-4-yl)quinazolin-4-yl)amino)-5-fluoroquinolin-8-ol

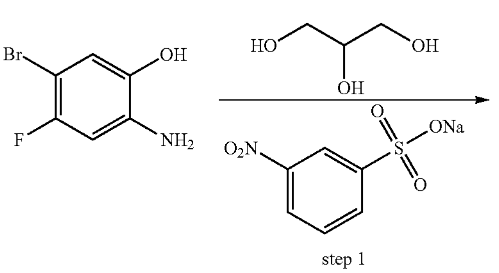

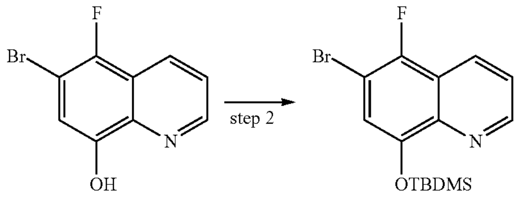

-continued

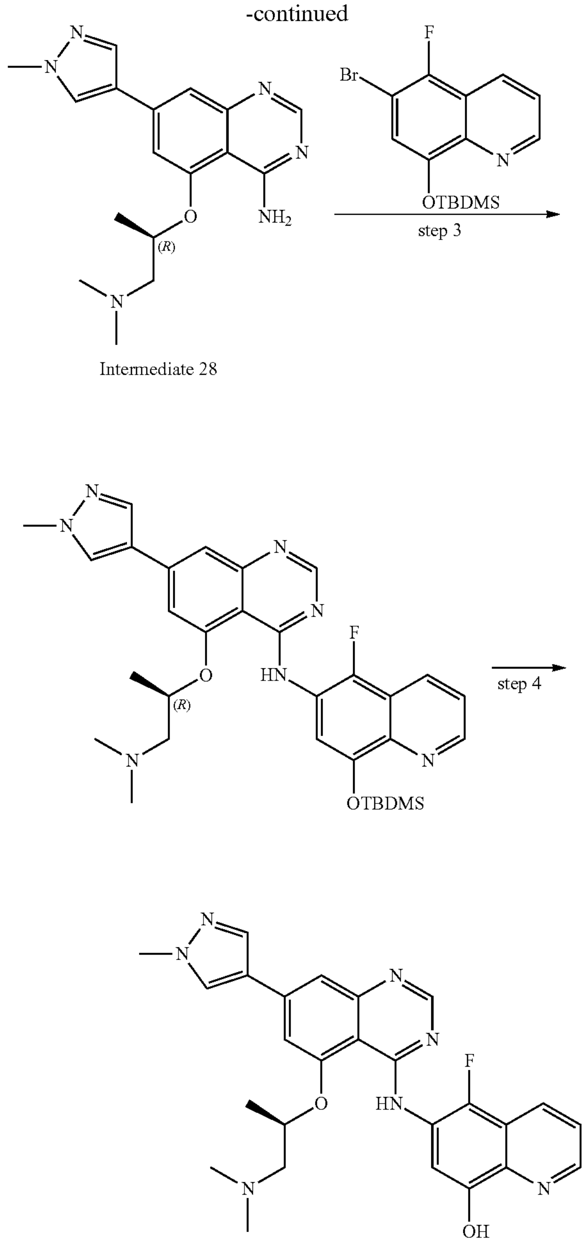

Intermediate 28

Step 1: 6-bromo-5-fluoroquinolin-8-ol

To a mixture of 2-amino-5-bromo-4-fluorophenol (500 mg, 2.42 mmol) in 70% $H_2SO_4$ (4 mL) was added propane-1,2,3-triol (667 mg, 7.25 mmol) and sodium 3-nitrobenzene-1-sulfonate (1.63 g, 7.25 mmol), the reaction mixture was stirred at 100° C. for 16 hrs. The reaction mixture was cooled to rt, diluted with 30 mL ice/water mixture. The aqueous phase was adjusted to pH=6-7 by slow addition of 6N NaOH. The resulting black precipitate was collected by filtration. The aqueous solution was extracted with ethyl acetate 3 times. The organic extracts were combined with the black precipitate, concentrated in vacuo, and purified on silica gel column using 0-10% MeOH/DCM. This resulted in 240 mg (41.0%) the title compound as an off-white solid. LC-MS: (ES, m/z): RT=0.900 min, LCMS: m/z=242 [M+1].

Step 2: 6-bromo-8-((tert-butyldimethylsilyl)oxy)-5-fluoroquinoline

To a mixture of 6-bromo-5-fluoroquinolin-8-ol (260 mg, 1.07 mmol) in DMF (8 mL) was added imdazole (145 mg, 2.14 mmol) and TBDMSCl (321 mg, 2.14 mmol), the reaction mixture was stirred at 25° C. for 3 hrs. The reaction mixture was diluted with 30 mL water and extracted with ethyl acetate 3 times. The organic extracts were combined, concentrated in vacuo, and purified on silica gel column using 0-20% EA/PE. This resulted in 200 mg (52.4%) the title compound as an off-white solid. LC-MS: (ES, m/z): RT=1.803 min, LCMS: m/z=356 [M+1].

Step 3: (R)—N-(8-((tert-butyldimethylsilyl)oxy)-5-fluoroquinolin-6-yl)-5-((1-(dimethylamino)propan-2-yl)oxy)-7-(1-methyl-1H-pyrazol-4-yl)quinazolin-4-amine To a solution of Intermediate 28 (100 mg, 0.3063 mmol, 1.00 eq) in 1,4-dioxane (5 mL) was added 6-bromo-8-((tert-butyldimethylsilyl)oxy)-5-fluoroquinoline (109 mg, 306 μmol, 2.00 eq), $Cs_2CO_3$ (299 mg, 918 μmol, 3.00 eq), Xantphos (18.6 mg, 30.6 μmol, 0.1 eq) and $Pd_2(dba)_3$ (31.6 mg, 30.6 μmol, 0.10 eq). The resulting solution was stirred for 16 hour at 100° C. Then cooled to room temperature. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The product was purified by prep-TLC eluting with DCM:MeOH=(10:1). This resulted in 100 mg (54.3%) of title compound as yellow solid. LC-MS: (ES, m/z): RT=1.069 min, LCMS: m/z=602 [M+1].

Step 4: (R)-6-((5-((1-(dimethylamino)propan-2-yl)oxy)-7-(1-methyl-1H-pyrazol-4-yl)quinazolin-4-yl)amino)-5-fluoroquinolin-8-ol The mixture of (R)—N-(8-((tert-butyldimethylsilyl)oxy)-5-fluoroquinolin-6-yl)-5-((1-(dimethylamino)propan-2-yl)oxy)-7-(1-methyl-1H-pyrazol-4-yl)quinazolin-4-amine (50 mg, 0.083 mmol, 1.00 eq) in HCl (0.50 mL) and EtOH (5.00 mL) was stirred at 25° C. for 1 hr. The mixture was concentered in vacuum. The residue was purified by prep-HPLC (Column: YMC-Actus Triart C18, 30 mm×150 mm, 5 um; Mobile Phase A: Water (0.1% FA), Mobile Phase B: ACN; Flow rate: 60 mL/min; Gradient: 30% B to 60% B in 8 min; Wavelength: 254/220 nm) to afford the title compound (7.4 mg, yield: 18.3%) as a yellow solid. LC-MS: (ES, m/z): RT=0.778 min, LCMS: m/z=488 [M+1]. $^1H$ NMR (400 MHz, Chloroform-d) δ 10.51 (s, 1H), 8.97-8.65 (m, 3H), 8.38 (d, J=8.4 Hz, 1H), 8.19 (s, 1H), 7.99 (s, 1H), 7.73 (s, 2H), 7.55 (dd, J=8.4, 4.3 Hz, 1H), 5.77 (s, 1H), 4.02 (s, 3H), 3.34 (d, J=65.5 Hz, 2H), 2.85 (s, 6H), 1.59 (d, J=6.0 Hz, 3H).

Intermediate 35
N-(5-fluoroquinolin-6-yl)-7-(1-methyl-1H-pyrazol-4-yl)-5-((R)-1-((R)-morpholin-3-yl)ethoxy)quinazolin-4-amine and N-(5-fluoroquinolin-6-yl)-7-(1-methyl-1H-pyrazol-4-yl)-5-((S)-1-((S)-morpholin-3-yl)ethoxy)quinazolin-4-amine
Or
N-(5-fluoroquinolin-6-yl)-7-(1-methyl-1H-pyrazol-4-yl)-5-((R)-1-((S)-morpholin-3-yl)ethoxy)quinazolin-4-amine and N-(5-fluoroquinolin-6-yl)-7-(1-methyl-1H-pyrazol-4-yl)-5-((S)-1-((R)-morpholin-3-yl)ethoxy)quinazolin-4-amine
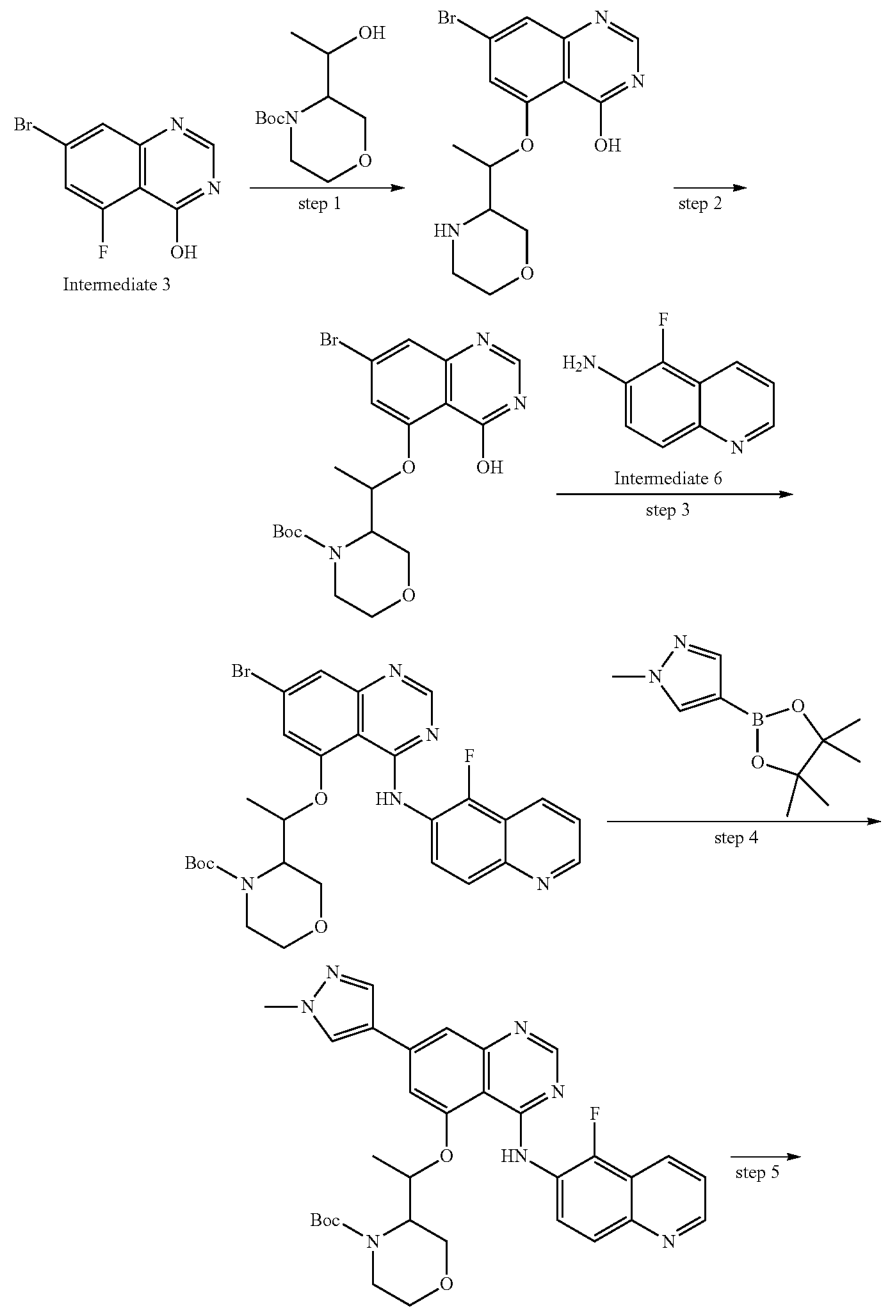

-continued

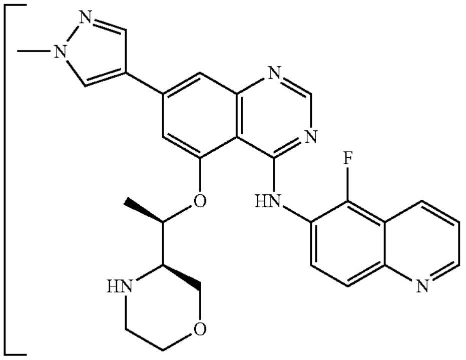

and

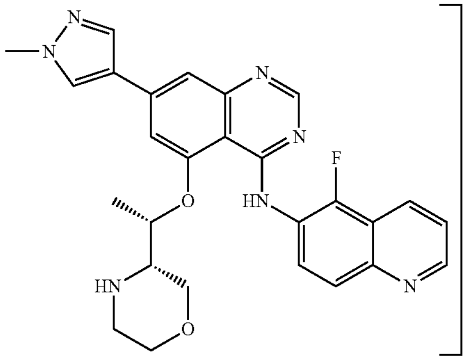

or

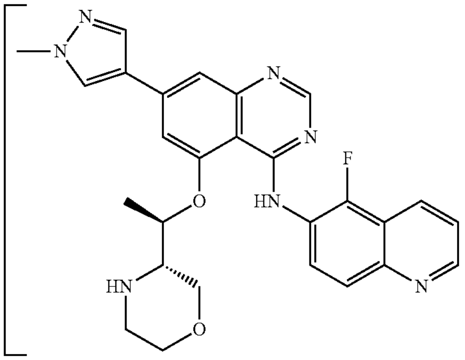

and

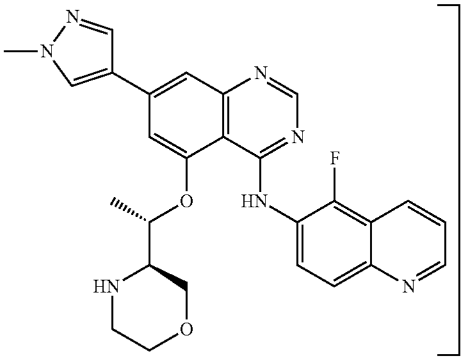

Intermediate 35

Step 1: 7-bromo-5-(1-(morpholin-3-yl)ethoxy)quinazolin-4-ol t-BuOK (1.37 g, 12.3 mmol) was added to Intermediate 3 (600 mg, 2.46 mmol) and tert-butyl 3-(1-hydroxyethyl) morpholine-4-carboxylate (851 mg, 3.68 mmol, from Nantong XianXing Biological Medicine technology co., LTD) in THF (30 mL) at rt. The reaction mixture was heated to 80° C. for 2 hr. The resulting solution was extracted with 3×100 mL of EA. The organic layer was dried with $Na_2SO_4$ and concentrated under vacuum. The crude product was purified by a silica gel column using DCM:MeOH=10:1. This resulted in the title compound (600 mg, yield: 68%) as a white solid. LC-MS: (ES, m/z): RT=0.808 min, LCMS: m/z=354 [M+1].

Step 2: tert-butyl 3-(1-((7-bromo-4-hydroxyquinazolin-5-yl)oxy)ethyl)morpholine-4-carboxylate The reaction mixture of DIEA (657 mg, 5.06 mmol), DMAP (103 mg, 845 μmol), 7-bromo-5-(1-(morpholin-3-yl)ethoxy)quinazolin-4-ol (600 mg, 1.69 mmol) and $(Boc)_2O$ (1.10 g, 5.06 mmol) in DCM (20 mL) was stirred at rt for 2 hr. The resulting solution was extracted with 3×100 mL of EA. The organic layer was dried with $Na_2SO_4$ and concentrated under vacuum. The crude product was purified by a silica gel column using DCM:MeOH=20:1. This resulted in the title compound (270 mg, yield: 35%) as a yellow solid. LC-MS: (ES, m/z): RT=1.090 min, LCMS: m/z=454 [M+1]

Step 3: tert-butyl 3-(1-((7-bromo-4-((5-fluoroquinolin-6-yl)amino)quinazolin-5-yl)oxy)ethyl)morpholine-4-carboxylate $CCl_4$ (605 mg, 3.96 mmol) was added to tert-butyl 3-(1-((7-bromo-4-hydroxyquinazolin-5-yl)oxy)ethyl)morpholine-4-carboxylate (300 mg, 660 μmol) and $PPh_3$ (520 mg, 1.98 mmol) in DCE (15 mL) at rt. The reaction mixture was heated to 80° C. for 2 hr. Intermediate 6 (160 mg, 990 μmol) was added to the reaction mixture at rt. The resulting mixture was heated to 60° C. for 1 hr. The resulting solution was extracted with 3×60 mL of EA. The organic layer was dried with $Na_2SO_4$ and concentrated under vacuum. The crude product was purified by a Prep-TLC with DCM:MeOH=25:1. This resulted in the title compound (380 mg, yield: 96%) as a yellow solid. LC-MS: (ES, m/z): RT=0.843 min, LCMS: m/z=598 [M+1]

Step 4: N-(5-fluoroquinolin-6-yl)-7-(1-methyl-1H-pyrazol-4-yl)-5-(1-(morpholin-3-yl)ethoxy)quinazolin-4-amine $Pd(dppf)Cl_2$ (61.1 mg, 83.5 μmol) and $K_2CO_3$ (172 mg, 1.25 mmol) were added to tert-butyl 3-(1-((7-bromo-4-((5- fluoroquinolin-6-yl)amino)quinazolin-5-yl)oxy)ethyl)morpholine-4-carboxylate (500 mg, 835 μmol) and 1-methyl-4-(4,4,5,5-tetramethyl-1,3,2-dioxaborolan-2-yl)-1H-pyrazole (260 mg, 1.25 mmol) in dioxane (8 mL) and $H_2O$ (2 mL) at rt. The reaction mixture was heated to 80° C. for 2 h under $N_2$. The resulting solution was extracted with 3×80 mL of EA. The organic layer was dried with $Na_2SO_4$ and concentrated under vacuum. The crude product was purified by a silica gel column using DCM:MeOH=20:1. This resulted in the title compound (400 mg, yield: 80%) as a yellow solid. LC-MS: (ES, m/z): RT=1.027 min, LCMS: m/z=600 [M+1]

Step 5: Intermediate 35

TFA (2 mL) was added to N-(5-fluoroquinolin-6-yl)-7-(1-methyl-1H-pyrazol-4-yl)-5-(1-(morpholin-3-yl)ethoxy) quinazolin-4-amine (150 mg, 250 μmol) in DCM (4 mL) at 0° C. The reaction mixture was stirred at rt for 2 hr. The mixture was concentrated under vacuum. The crude product was purified by Prep-HPLC using the following conditions: Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 20% B to 53% B in 7 min; Wavelength: 254/220 nm. This resulted in Intermediate 35 (50 mg, yield: 40%) as a white solid. LC-MS: (ES, m/z): RT=0.771 min, LCMS: m/z=500 [M+1]. Note: Only one pair of enantiomers was isolated.

Examples 123 and 124: are enantiomers that can be represented by any of these 4 structures with the constraint that they are both from pair 1 or both from pair 2

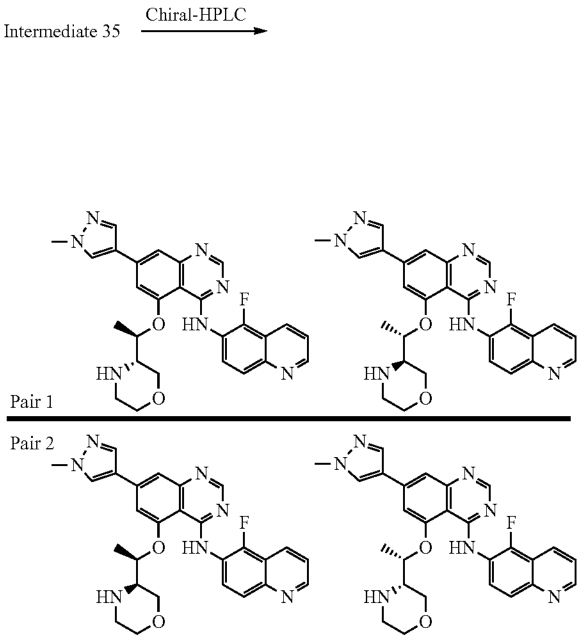

Example 123

N-(5-fluoroquinolin-6-yl)-7-(1-methyl-1H-pyrazol-4-yl)-5-((R)-1-((S)-morpholin-3-yl)ethoxy)quinazolin-4-amine Or N-(5-fluoroquinolin-6-yl)-7-(1-methyl-1H-pyrazol-4-yl)-5-((S)-1-((R)-morpholin-3-yl)ethoxy)quinazolin-4-amine Or N-(5-fluoroquinolin-6-yl)-7-(1-methyl-1H-pyrazol-4-yl)-5-((R)-1-((R)-morpholin-3-yl)ethoxy)quinazolin-4-amine Or N-(5-fluoroquinolin-6-yl)-7-(1-methyl-1H-pyrazol-4-yl)-5-((S)-1-((S)-morpholin-3-yl)ethoxy)quinazolin-4-amine Example 124

N-(5-fluoroquinolin-6-yl)-7-(1-methyl-1H-pyrazol-4-yl)-5-((R)-1-((S)-morpholin-3-yl)ethoxy)quinazolin-4-amine Or N-(5-fluoroquinolin-6-yl)-7-(1-methyl-1H-pyrazol-4-yl)-5-((S)-1-((R)-morpholin-3-yl)ethoxy)quinazolin-4-amine Or N-(5-fluoroquinolin-6-yl)-7-(1-methyl-1H-pyrazol-4-yl)-5-((R)-1-((R)-morpholin-3-yl)ethoxy)quinazolin-4-amine Or N-(5-fluoroquinolin-6-yl)-7-(1-methyl-1H-pyrazol-4-yl)-5-((S)-1-((S)-morpholin-3-yl)ethoxy)quinazolin-4-amine Chiral Separation:

Intermediate 35 (50 mg, 100 μmol) in MeOH was purified by Prep-Chiral-HPLC using the following conditions: Column: CHIRALPAK IE, 2*25 cm, 5 μm; Mobile Phase A: (Hex: DCM=3:1)(0.5% 2M $NH_3$-MeOH)-HPLC, Mobile Phase B: IPA-HPLC; Flow rate: 20 mL/min; Gradient: 10% B to 10% B in 15 min; Wavelength: 220/254 nm; RT1(min): 9.78; RT2(min): 13.412; Sample Solvent: IPA-HPLC; Injection Volume: 0.5 mL; to afford:

Example 123: First eluting isomer, (19 mg), LC-MS: (ES, m/z): RT=1.390 min, LCMS: m/z=500 [M+1], chiral-HPLC: (ES, m/z): R=2.649 min, $^1H$ NMR (400 MHz, DMSO-$d_6$) δ 10.83 (s, 1H), 8.96 (dd, J=4.2, 1.7 Hz, 1H), 8.55-8.46 (m, 2H), 8.46-8.37 (m, 2H), 8.16 (s, 1H), 7.95 (d, J=9.1 Hz, 1H), 7.66 (dd, J=8.5, 4.2 Hz, 1H), 7.56 (d, J=1.4 Hz, 1H), 7.35 (d, J=1.6 Hz, 1H), 4.92 (dd, J=6.3, 4.2 Hz, 1H), 3.92 (s, 3H), 3.83 (dd, J=10.8, 2.9 Hz, 1H), 3.58 (d, J=10.8 Hz, 1H), 3.40 (t, J=10.4 Hz, 1H), 3.18 (td, J=11.0, 2.5 Hz, 1H), 3.04 (d, J=10.9 Hz, 2H), 2.76 (dd, J=12.8, 9.6 Hz, 1H), 2.59 (d, J=11.8 Hz, 1H), 1.46 (d, J=6.2 Hz, 3H).

Example 124: Second eluting isomer, (22 mg), LC-MS: (ES, m/z): RT=0.612 min, LCMS: m/z=500 [M+1], chiral-HPLC: (ES, m/z): R=3.523 min, $^1H$ NMR (400 MHz, DMSO-$d_6$) δ 10.83 (s, 1H), 8.96 (dd, J=4.2, 1.6 Hz, 1H), 8.56-8.47 (m, 2H), 8.45-8.37 (m, 2H), 8.16 (d, J=0.8 Hz, 1H), 7.95 (d, J=9.2 Hz, 1H), 7.66 (dd, J=8.5, 4.2 Hz, 1H), 7.56 (d, J=1.4 Hz, 1H), 7.35 (d, J=1.6 Hz, 1H), 4.92 (dd, J=6.3, 4.3 Hz, 1H), 3.92 (s, 3H), 3.83 (dd, J=10.8, 3.0 Hz, 1H), 3.58 (d, J=10.7 Hz, 1H), 3.40 (t, J=10.4 Hz, 1H), 3.22-3.14 (m, 1H), 3.05 (dd, J=8.7, 5.1 Hz, 1H), 2.80-2.71 (m, 1H), 2.59 (d, J=11.8 Hz, 1H), 1.46 (d, J=6.2 Hz, 3H).

Examples 125 and 126: are enantiomers that can be represented by any of these 4 structures with the constraint that they are both from pair 1 or both from pair 2

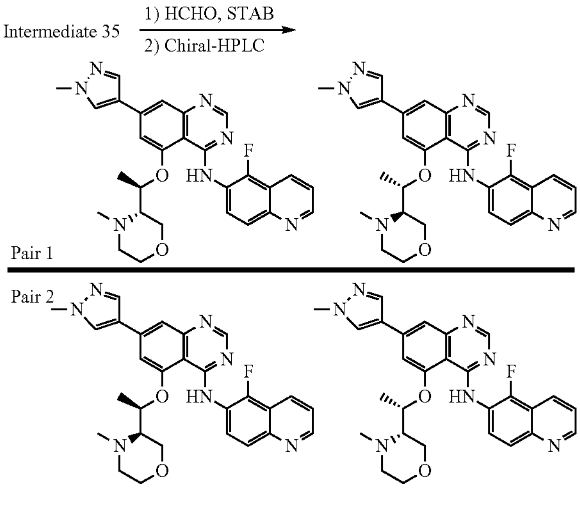

Example 125

N-(5-fluoroquinolin-6-yl)-7-(1-methyl-1H-pyrazol-4-yl)-5-((R)-1-((S)-4-methylmorpholin-3-yl)ethoxy)quinazolin-4-amine Or N-(5-fluoroquinolin-6-yl)-7-(1-methyl-1H-pyrazol-4-yl)-5-((S)-1-((R)-4-methylmorpholin-3-yl)ethoxy)quinazolin-4-amine Or N-(5-fluoroquinolin-6-yl)-7-(1-methyl-1H-pyrazol-4-yl)-5-((R)-1-((R)-4-methylmorpholin-3-yl)ethoxy)quinazolin-4-amine Or N-(5-fluoroquinolin-6-yl)-7-(1-methyl-1H-pyrazol-4-yl)-5-((S)-1-((S)-4-methylmorpholin-3-yl)ethoxy)quinazolin-4-amine Example 126

N-(5-fluoroquinolin-6-yl)-7-(1-methyl-1H-pyrazol-4-yl)-5-((R)-1-((S)-4-methylmorpholin-3-yl)ethoxy)quinazolin-4-amine Or N-(5-fluoroquinolin-6-yl)-7-(1-methyl-1H-pyrazol-4-yl)-5-((S)-1-((R)-4-methylmorpholin-3-yl)ethoxy)quinazolin-4-amine Or N-(5-fluoroquinolin-6-yl)-7-(1-methyl-1H-pyrazol-4-yl)-5-((R)-1-((R)-4-methylmorpholin-3-yl)ethoxy)quinazolin-4-amine Or N-(5-fluoroquinolin-6-yl)-7-(1-methyl-1H-pyrazol-4-yl)-5-((S)-1-((S)-4-methylmorpholin-3-yl)ethoxy)quinazolin-4-amine Intermediate 35 (200 mg, 400 μmol) and formaldehyde solution (0.4 mL) in DCM (5 mL) was stirred at rt for 20 min. STAB (169 mg, 800 μmol) was added to the reaction mixture at 0° C. and stirred at rt for 2 hr. The resulting solution was extracted with 3×40 mL of EA. The organic layer was dried with $Na_2SO_4$ and concentrated under vacuum. The crude product was purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: MeOH-HPLC; Flow rate: 60 mL/min; Gradient: 46% B to 71% B in 8 min; Wavelength: 254; 220 nm to give (80 mg, yield: 39%) as a white solid. LC-MS: (ES, m/z): RT=0.615 min, LCMS: m/z=514 [M+1]

The solid (80 mg, 155 μmol) in MeOH was purified by Prep-Chiral-HPLC using the following conditions: Column: CHIRALPAK IH, 2*25 cm, 5 μm; Mobile Phase A: MtBE (0.5% 2M $NH_3$-MeOH)-HPLC, Mobile Phase B: EtOH-HPLC; Flow rate: 20 mL/min; Gradient: 10% B to 10% B in 15 min; Wavelength: 220/254 nm; RT1(min): 9.98; RT2 (min): 13.203; Sample Solvent: EtOH-HPLC; to afford:

Example 125: First eluting isomer, (21 mg), as a white solid, LC-MS: (ES, m/z): RT=0.962 min, LCMS: m/z=514 [M+1], chiral-HPLC: (ES, m/z): R=2.207 min, $^1H$ NMR (400 MHz, DMSO-d6) δ 10.48 (s, 1H), 8.96 (dd, J=4.2, 1.7 Hz, 1H), 8.60-8.51 (m, 2H), 8.48 (d, J=2.2 Hz, 2H), 8.16 (s, 1H), 7.96 (d, J=9.2 Hz, 1H), 7.65 (dd, J=8.5, 4.2 Hz, 1H), 7.60 (d, J=1.4 Hz, 1H), 7.39 (d, J=1.6 Hz, 1H), 5.23 (dd, J=6.6, 4.2 Hz, 1H), 3.93 (s, 3H), 3.84 (dd, J=11.4, 3.2 Hz, 1H), 3.63 (dt, J=11.2, 3.0 Hz, 1H), 3.50 (dd, J=11.3, 9.6 Hz, 1H), 3.40 (td, J=10.8, 2.4 Hz, 1H), 2.62 (dt, J=9.7, 3.6 Hz, 2H), 2.39 (s, 3H), 2.35-2.27 (m, 1H), 1.59 (d, J=6.4 Hz, 3H).

Example 126: Second eluting isomer, (16 mg), as a white solid, LCMS: m/z=514 [M+1], chiral-HPLC: (ES, m/z): R=2.818 min, $^1H$ NMR (400 MHz, DMSO-$d_6$) δ 10.48 (s, 1H), 8.96 (dd, J=4.2, 1.7 Hz, 1H), 8.60-8.51 (m, 2H), 8.48 (d, J=1.8 Hz, 2H), 8.16 (s, 1H), 7.96 (d, J=9.2 Hz, 1H), 7.66 (dd, J=8.5, 4.2 Hz, 1H), 7.60 (d, J=1.4 Hz, 1H), 7.40 (d, J=1.6 Hz, 1H), 5.23 (dd, J=6.6, 4.2 Hz, 1H), 3.93 (s, 3H), 3.84 (dd, J=11.0, 3.2 Hz, 1H), 3.66-3.60 (m, 1H), 3.50 (dd, J=11.3, 9.6 Hz, 1H), 3.40 (td, J=10.9, 2.5 Hz, 1H), 2.62 (dt, J=9.8, 3.6 Hz, 2H), 2.39 (s, 3H), 2.35-2.27 (m, 1H), 1.59 (d, J=6.4 Hz, 3H).

Example 127: (R)-5-((1-(dimethylamino)propan-2-yl)oxy)-4-((5-fluoroquinolin-6-yl)amino)-7-(1-methyl-1H-pyrazol-4-yl)quinazoline 1-oxide Example 128: (R)-5-((1-(dimethylamino)propan-2-yl)oxy)-4-((5-fluoroquinolin-6-yl)amino)-7-(1-methyl-1H-pyrazol-4-yl)quinazoline 3-oxide Example 129: (R)-6-((5-((1-(dimethylamino)propan-2-yl)oxy)-7-(1-methyl-1H-pyrazol-4-yl)quinazolin-4-yl)amino)-5-fluoroquinoline 1-oxide

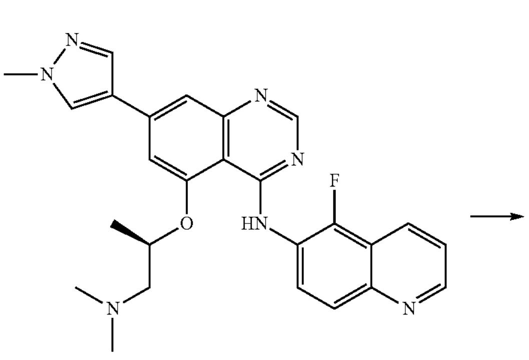

Example 6

-continued

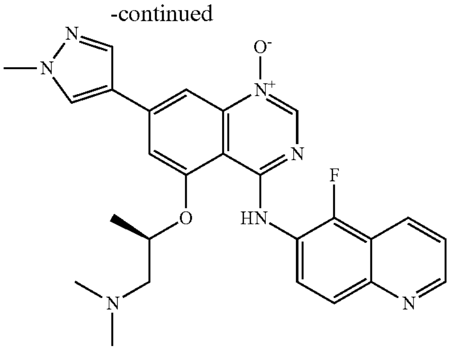

Example 127

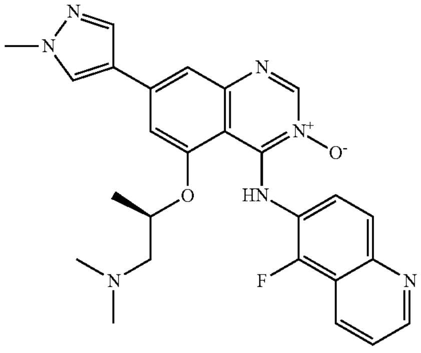

Example 128

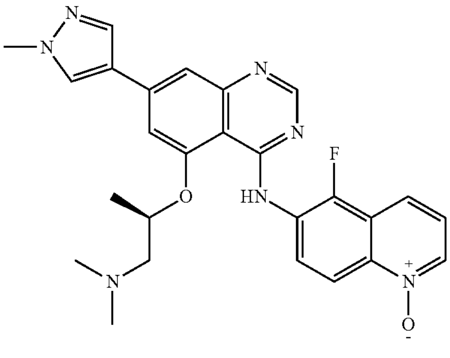

Example 129 m-CPBA (43.7 mg, 253 μmol) was added to Example 6 (80 mg, 169 μmol) in DCM (5 mL) at rt. The resulting mixture was stirred at r.t for 2 hr. The mixture was diluted with EA 100 mL and washed with brine 50 mL*2, the organic layer was dried with $Na_2SO_4$ and concentrated under vacuum. The residue was purified by a silica gel column using DCM:MeOH=25:1 to afford 50 mg of a yellow solid. The solid was dissolved in MeOH and Purified by Prep-HPLC with following conditions: Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 17% B to 32% B in 8 min, 32% B; Wavelength: 254; 220 nm;

Example 127: First eluting isomer (6.4 mg, yield: 12.8%) as a white solid. LC-MS: (ES, m/z): RT=0.719 min, LCMS: m/z=488 [M+1]. $^1$H NMR (400 MHz, DMSO-$d_6$) δ 11.66 (s, 1H), 8.92 (dd, J=4.2, 1.6 Hz, 1H), 8.54-8.45 (m, 2H), 8.38 (s, 2H), 8.35-8.24 (m, 1H), 8.15 (s, 1H), 7.88 (d, J=9.1 Hz, 1H), 7.62 (dd, J=8.5, 4.2 Hz, 1H), 7.58-7.51 (m, 2H), 5.61-5.53 (m, 1H), 3.92 (s, 4H), 3.84 (dd, J=13.7, 8.2 Hz, 1H), 3.17 (d, J=4.6 Hz, 6H), 1.52 (d, J=6.1 Hz, 3H).

Example 128: Second eluting isomer (3.3 mg, yield: 6.6%) as a white solid. LC-MS: (ES, m/z): RT=0.876 min, LCMS: m/z=488 [M+1]. $^1$H NMR (400 MHz, DMSO-$d_6$) δ 11.93 (s, 1H), 8.93 (dd, J=4.2, 1.7 Hz, 1H), 8.52-8.45 (m, 2H), 8.30 (s, 1H), 8.13 (s, 1H), 7.98 (t, J=8.6 Hz, 1H), 7.86 (d, J=9.1 Hz, 1H), 7.61 (dd, J=8.5, 4.2 Hz, 1H), 7.52 (d, J=1.5 Hz, 1H), 7.34 (d, J=1.6 Hz, 1H), 4.70 (d, J=10.9 Hz, 2H), 3.91 (s, 3H), 3.51 (s, 1H), 3.21 (s, 3H), 3.04 (s, 3H), 1.51 (d, J=6.8 Hz, 3H).

Example 129: Third eluting isomer (17.5 mg, yield: 35%) as an off-white solid. LC-MS: (ES, m/z): RT=1.679 min, LCMS: m/z=488 [M+1]. $^1$H NMR (300 MHz, DMSO-$d_6$) δ 11.79 (s, 1H), 8.92 (dd, J=4.2, 1.6 Hz, 1H), 8.54-8.43 (m, 2H), 8.37 (s, 1H), 8.28 (t, J=8.7 Hz, 1H), 8.15 (s, 1H), 7.88 (d, J=9.1 Hz, 1H), 7.62 (dd, J=8.5, 4.2 Hz, 1H), 7.58-7.50 (m, 2H), 5.56 (s, 1H), 3.92 (s, 3H), 3.86-3.73 (m, 2H), 3.15 (s, 6H), 1.52 (d, J=6.0 Hz, 3H).

Example 130: (R)-6-((5-((1-(dimethylamino)propan-2-yl)oxy)-7-(1-methyl-1H-pyrazol-4-yl)quinazolin-4-yl)amino)-5-fluoroquinolin-2-ol

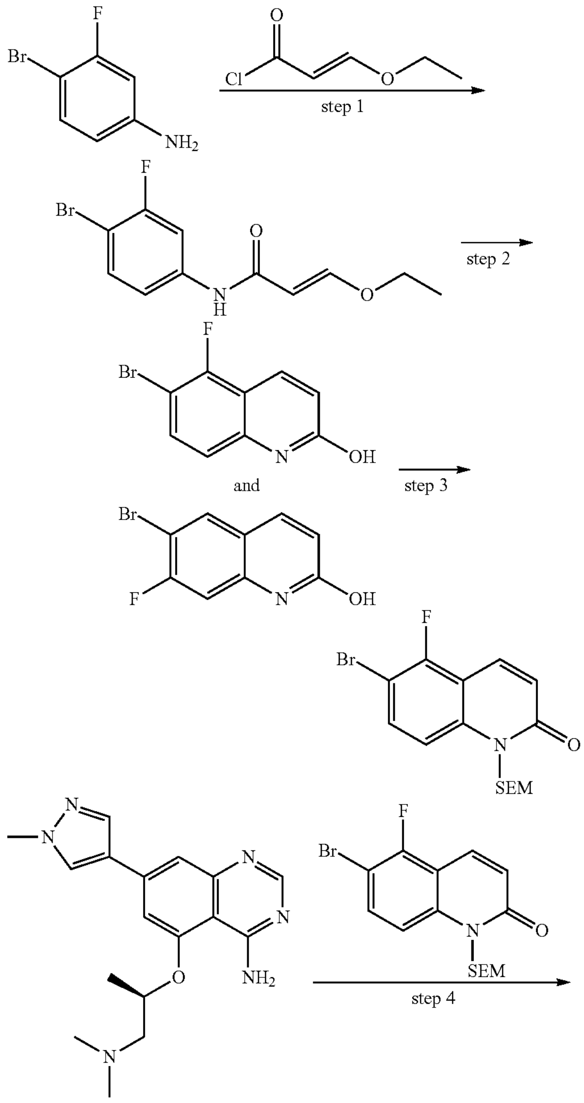

Intermediate 28

-continued

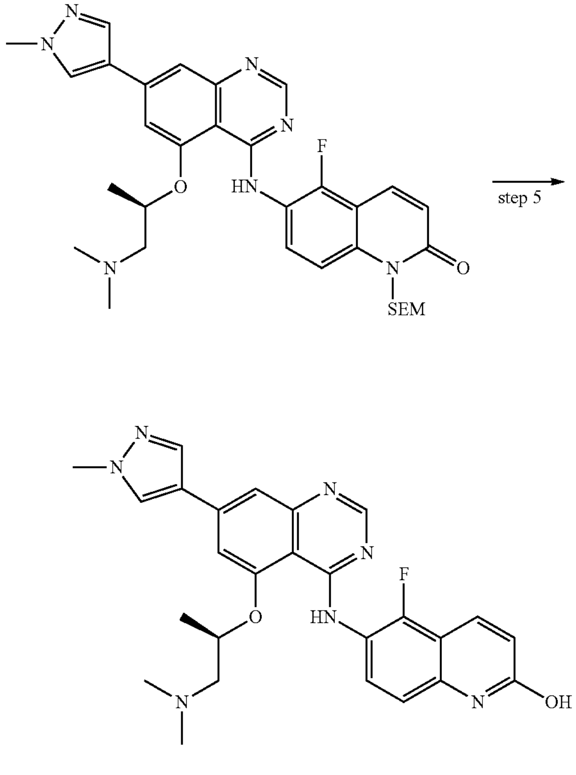

Step 1: (E)-N-(4-bromo-3-fluorophenyl)-3-ethoxy-acrylamide

Pyridine (3.32 g, 42.1 mmol) was added to 4-bromo-3-fluoroaniline (8 g, 42.1 mmol) and (E)-3-ethoxyacryloyl chloride (11.3 g, 84.2 mmol) in DCM at rt. The resulting mixture was stirred at 25° C. for 2 hr. The mixture was diluted with DCM 250 mL and washed with brine 200 mL*3, the organic layer was dried with $Na_2SO_4$ and concentrated under vacuum. The residue was purified by a silica gel column using PE:EA=15:1 to afford the title compound (6 g, yield: 75%) as a light yellow solid. LC-MS: (ES, m/z): RT=1.353 min, LCMS: m/z=288 [M+1].

Step 2: Synthesis of a Mixture of 6-bromo-5-fluoroquinolin-2-ol and 6-bromo-7-fluoroquinolin-2-ol $H_2SO_4$ (30 mL) was added to (E)-N-(4-bromo-3-fluorophenyl)-3-ethoxyacrylamide (6 g, 20.8 mmol) with sealed tube at 0° C. The resulting mixture was stirred at 100° C. for 2 hr. The resulting mixture was poured into ice-water and adjusted to pH=8 with sat NaOH (aq). The mixture was diluted with EA 100 mL and washed with brine 50 mL*2, the organic layer was dried with $Na_2SO_4$ and concentrated under vacuum. The residue was purified by a silica gel column using DCM:MeOH=25:1. This resulted in the title compound (4 g, yield: 66.7%) as a light yellow solid. LC-MS: (ES, m/z): RT=1.080 min, LCMS: m/z=242 [M+1].

Step 3: 6-bromo-5-fluoro-1-((2-(trimethylsilyl)ethoxy)methyl)quinolin-2(1H)-one

LiHMDS (6.07 g, 33.0 mmol) was added to the mixture of 6-bromo-5-fluoroquinolin-2-ol and 6-bromo-7-fluoroquinolin-2-ol (4 g, 16.5 mmol) in THF (50 mL) at −10° C. The resulting mixture was stirred at −10° C. for 0.5 h under $N_2$ then SEMCl (2.57 g, 66.0 mmol) was added to the mixture at −10° C. The resulting solution was stirred at 25° C. for 2 h. The mixture was diluted with DCM 500 mL and washed with brine 250 mL*2, the organic layer was dried with $Na_2SO_4$ and concentrated under vacuum. The residue was purified by a silica gel column using PE:EA=20:1 to afford the title compound (300 mg, yield: 7.5%) as a light yellow solid. LC-MS: (ES, m/z): RT=1.452 min, LCMS: m/z=372 [M+1].

Step 4: (R)-6-((5-((1-(dimethylamino)propan-2-yl)oxy)-7-(1-methyl-1H-pyrazol-4-yl)quinazolin-4-yl)amino)-5-fluoro-1-((2-(trimethylsilyl)ethoxy)methyl)quinolin-2(1H)-one The reaction mixture of $Cs_2CO_3$ (391 mg, 1.20 mmol) and $Pd_2(dba_3)$ (45.7 mg, 80.5 μmol) Xantphos (61.0 mg, 80.5 μmol) and Intermediate 28 (262 mg, 805 μmol) and 6-bromo-5-fluoro-1-((2-(trimethylsilyl)ethoxy)methyl)quinolin-2(1H)-one (300 mg, 805 μmol) in 1,4-dioxane (16 mL) was stirred at 100° C. for 4 h under $N_2$. The mixture was diluted with EA 100 mL and washed with water 50 mL*2, the organic layer was dried with $Na_2SO_4$ and concentrated under vacuum. The residue was purified by a silica gel column using DCM:MeOH=18:1. This resulted in the title compound (200 mg, yield: 66.7%) a white solid. LC-MS: (ES, m/z): RT=1.125 min, LCMS: m/z=618 [M+1].

Step 5: (R)-6-((5-((1-(dimethylamino)propan-2-yl)oxy)-7-(1-methyl-1H-pyrazol-4-yl)quinazolin-4-yl)amino)-5-fluoroquinolin-2-ol TFA (3 mL) was added to (R)-6-((5-((1-(dimethylamino)propan-2-yl)oxy)-7-(1-methyl-1H-pyrazol-4-yl)quinazolin-4-yl)amino)-5-fluoro-1-((2-(trimethylsilyl)ethoxy)methyl)quinolin-2(1H)-one (200 mg, 727.5 μmol) in DCM (10 mL) at rt. The resulting mixture was stirred at rt for 2 hr. The resulting solution was concentrated under vacuum. The crude product was purified by prep-HPLC: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 8% B to 45% B in 10 min, 45% B; Wavelength: 254/220 nm; to afford the title compound (62.8 mg, yield: 31.4%) of as an off-white solid. LC-MS: (ES, m/z): RT=0.652 min, LCMS: m/z=488 [M+1]. $^1H$ NMR (400 MHz, DMSO-$d_6$) δ 11.98 (s, 1H), 10.35 (s, 1H), 8.45 (s, 1H), 8.38 (s, 1H), 8.17-8.08 (m, 2H), 8.04 (d, J=9.8 Hz, 1H), 7.53 (d, J=1.5 Hz, 1H), 7.37 (d, J=1.5 Hz, 1H), 7.19 (d, J=8.8 Hz, 1H), 6.60 (d, J=9.7 Hz, 1H), 5.04 (s, 1H), 3.91 (s, 3H), 2.84 (dd, J=13.0, 8.6 Hz, 1H), 2.49-2.41 (m, 1H), 2.16 (s, 6H), 1.49 (d, J=6.0 Hz, 3H).

Example 131; (2S,3R)-3-((4-((5-fluoroquinolin-6-yl)amino)-7-(1-methyl-1H-pyrazol-4-yl)quinazolin-5-yl)oxy)butan-2-ol or (2R,3S)-3-((4-((5-fluoroquinolin-6-yl)amino)-7-(1-methyl-1H-pyrazol-4-yl)quinazolin-5-yl)oxy)butan-2-ol Example 132: (2R,3S)-3-((4-((5-fluoroquinolin-6-yl)amino)-7-(1-methyl-1H-pyrazol-4-yl)quinazolin-5-yl)oxy)butan-2-ol or (2S,3R)-3-((4-((5-fluoroquinolin-6-yl)amino)-7-(1-methyl-1H-pyrazol-4-yl)quinazolin-5-yl)oxy)butan-2-ol

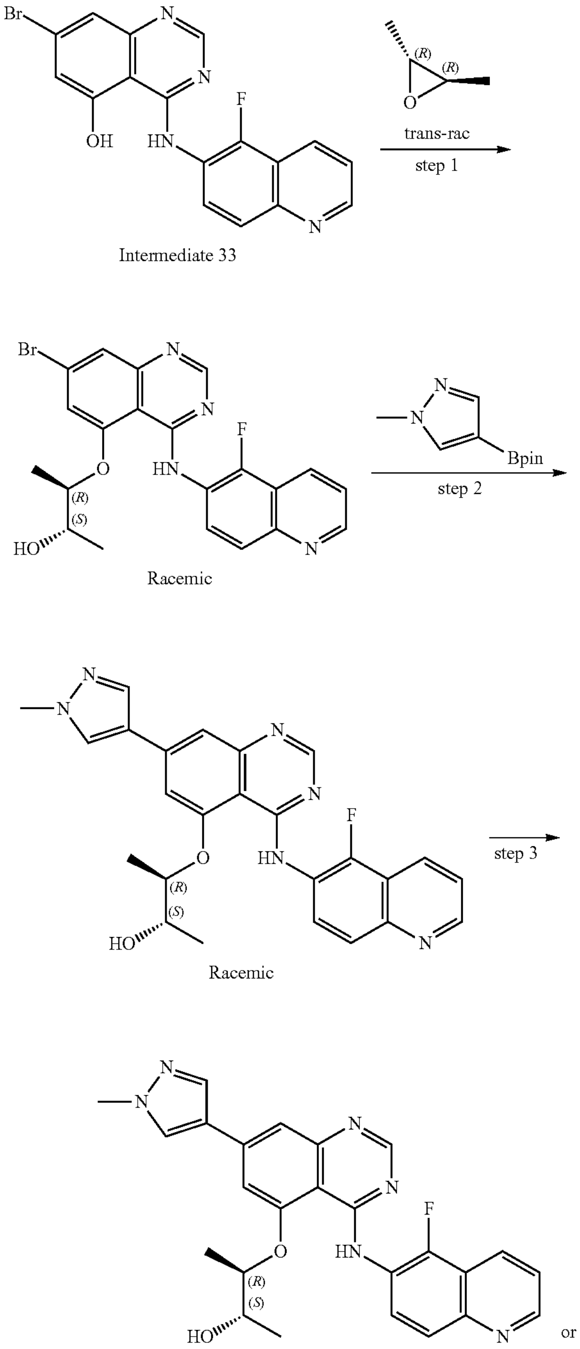

Intermediate 33

Racemic

Racemic or

-continued

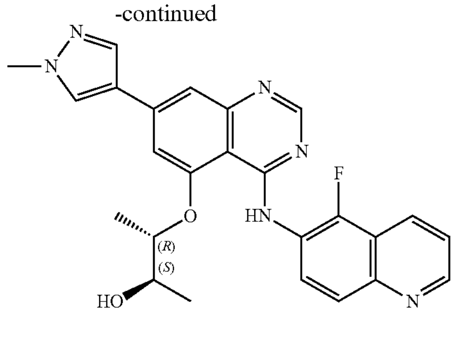

Step 1: (2S,3R)-3-((7-bromo-4-((5-fluoroquinolin-6-yl)amino)quinazolin-5-yl)oxy)butan-2-ol and (2R,3S)-3-((7-bromo-4-((5-fluoroquinolin-6-yl)amino)quinazolin-5-yl)oxy)butan-2-ol NaOH (129 mg, 3.24 mmol) was added to Intermediate 33 (250 mg, 649 μmol) and trans-rac-2,3-dimethyloxirane (233 mg, 3.24 mmol) in dioxane/$H_2O$ (4 mL/1 mL) at rt. The resulting mixture was heated to 100° C. for 3 hr. The reaction mixture was diluted with EtOAc (120 mL) and washed with water (60 mL). The organic layer was dried over $Na_2SO_4$, filtered and evaporated to afford crude product. The mixture was concentrated under vacuum. The crude product was purified by Prep-TLC with DCM:MeOH=10:1 to afford the title compound (100 mg) as a white solid. LC-MS: (ES, m/z): RT=1.108 min, LCMS: m/z=457 [M+1], Step 2: (2S,3R)-3-((4-((5-fluoroquinolin-6-yl)amino)-7-(1-methyl-1H-pyrazol-4-yl)quinazolin-5-yl)oxy)butan-2-ol and (2R,3S)-3-((4-((5-fluoroquinolin-6-yl)amino)-7-(1-methyl-1H-pyrazol-4-yl)quinazolin-5-yl)oxy)butan-2-ol $Pd(dppf)Cl_2$ (17.7 mg, 21.8 μmol) and $K_2CO_3$ (45.1 mg, 327 μmol) were added the product of step 1 (100 mg, 218 μmol) and 1-methyl-4-(4,4,5,5-tetramethyl-1,3,2-dioxaborolan-2-yl)-1H-pyrazole (68.0 mg, 327 μmol) in dioxane/$H_2O$ (4 mL/1 mL) at rt. This resulting mixture was heated at 80° C. for 3 hr. The reaction mixture was diluted with EtOAc (120 mL) and washed with water (60 mL). The organic layer was dried over $Na_2SO_4$, filtered and evaporated to afford crude product. The mixture was concentrated under vacuum. The crude product was purified by Prep-TLC with DCM:MeOH=10:1, to afford 10.3 mg. The residue was purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 29% B to 44% B in 8 min, 44% B; Wavelength: 254; 220 nm to afford the title compound (9.4 mg) as a white solid. LC-MS: (ES, m/z): RT=0.734 min, LCMS: m/z=459 [M+1], Chiral Separation:

The product of step 2 (9.4 mg, 20.5 μmol) in MeOH was Purified by Prep-Chiral-HPLC with following conditions: Column: CHIRALPAK IF, 2*25 cm, 5 μm; Mobile Phase A: Hex (0.5% 2M NH3-MeOH)-HPLC, Mobile Phase B: EtOH-HPLC; Flow rate: 20 mL/min; Gradient: 25% B to 25% B in 40 min; Wavelength: 220/254 nm; RT1(min): 22.856; RT2(min): 31.618; Sample Solvent: EtOH-HPLC; This resulted in:

Example 131: First eluting isomer, (1.2 mg) as a white solid, LC-MS: (ES, m/z): RT=0.897 min, LCMS: m/z=459 [M+1], Chiral-HPLC (ES): RT=3.441 min, 1H NMR (400 MHz, DMSO-d6) δ 10.46 (s, 1H), 8.95 (dd, J=4.2, 1.7 Hz, 1H), 8.60 (t, J=8.8 Hz, 1H), 8.55-8.47 (m, 3H), 8.17 (s, 1H), 7.95 (d, J=9.2 Hz, 1H), 7.65 (dd, J=8.5, 4.2 Hz, 2H), 7.47 (d, J=1.6 Hz, 1H), 5.17 (d, J=4.9 Hz, 1H), 4.99 (dd, J=6.2, 3.9 Hz, 1H), 4.10 (q, J=5.0 Hz, 1H), 3.92 (s, 3H), 1.43 (d, J=6.1 Hz, 3H), 1.33 (s, 1H), 1.26-1.18 (m, 3H).

Example 132: Second eluting isomer, (1.5 mg) as a white solid, LC-MS: (ES, m/z): RT=0.905 min, LCMS: m/z=459 [M+1], Chiral-HPLC (ES): RT=4.928 min, 1H NMR (400 MHz, DMSO-d6) δ 10.46 (s, 1H), 8.95 (dd, J=4.3, 1.7 Hz, 1H), 8.55-8.47 (m, 4H), 8.17 (s, 1H), 7.95 (d, J=9.2 Hz, 1H), 7.65 (dd, J=8.5, 4.3 Hz, 2H), 7.47 (d, J=1.6 Hz, 1H), 5.17 (d, J=4.9 Hz, 1H), 4.99 (dd, J=6.4, 4.0 Hz, 1H), 4.14-4.07 (m, 1H), 3.92 (s, 3H), 1.43 (d, J=6.1 Hz, 3H), 1.33 (s, 1H), 1.26-1.18 (m, 3H).

Example 135: (R)-2-((4-((5-fluoroquinolin-6-yl)amino)-7-(1-methyl-1H-pyrazol-4-yl)quinazolin-5-yl)oxy)propan-1-ol

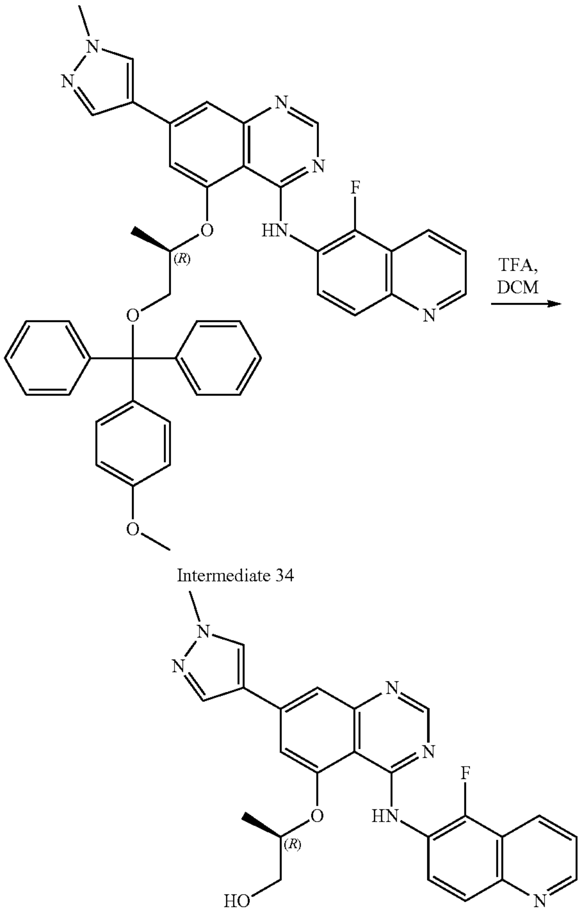

The mixture of Intermediate 34 (150 mg, 0.2092 mmol), TFA (2 mL) and DCM (5 mL) was stirred at 25° C. for 1 hr. The mixture was concentered in vacuum. The residue was purified by prep-HPLC (Column: Xselect CSH F-Phenyl OBD column, 19*250 mm, 5 μm; Mobile Phase A: Water (0.1% FA), Mobile Phase B: ACN; Flow rate: 25 mL/min; Gradient: 25% B to 35% B in 8 min; Wavelength: 254/220 nm) to give the title compound (21.7 mg, yield: 23.3%) as an off-white solid. LC-MS: (ES, m/z): RT=1.202 min, LCMS: m/z=445 [M+1]. $^1$H NMR (300 MHz, DMSO-$d_6$) δ 10.49 (d, J=1.7 Hz, 1H), 8.94 (dd, J=4.2, 1.6 Hz, 1H), 8.84 (t, J=8.9 Hz, 1H), 8.59-8.46 (m, 3H), 8.17 (s, 1H), 7.96 (d, J=9.3 Hz, 1H), 7.66 (d, J=4.2 Hz, 1H), 7.63-7.56 (m, 1H), 7.47 (d, J=1.5 Hz, 1H), 5.40-5.01 (m, 2H), 3.92 (s, 3H), 3.79 (tt, J=11.6, 6.4 Hz, 2H), 1.49 (d, J=6.1 Hz, 3H).

Example 136: (R)-2-((4-((5-fluoroquinolin-6-yl)amino)-7-(1-methyl-1H-pyrazol-4-yl)quinazolin-5-yl)oxy)-N,N-dimethylpropanamide or (S)-2-((4-((5-fluoroquinolin-6-yl)amino)-7-(1-methyl-1H-pyrazol-4-yl)quinazolin-5-yl)oxy)-N,N-dimethylpropanamide Example 137: (S)-2-((4-((5-fluoroquinolin-6-yl)amino)-7-(1-methyl-1H-pyrazol-4-yl)quinazolin-5-yl)oxy)-N,N-dimethylpropanamide or (R)-2-((4-((5-fluoroquinolin-6-yl)amino)-7-(1-methyl-1H-pyrazol-4-yl)quinazolin-5-yl)oxy)-N,N-dimethylpropanamide

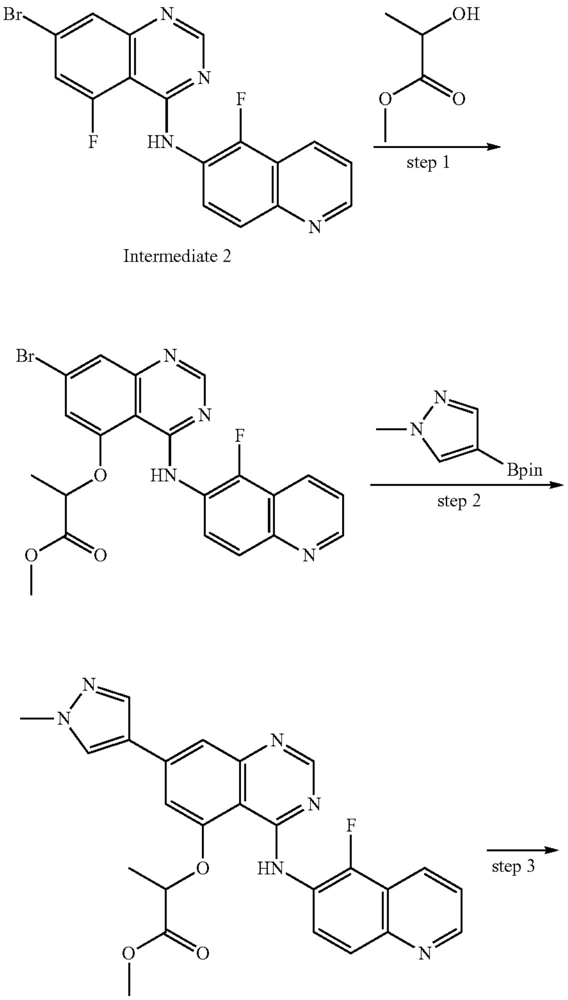

-continued

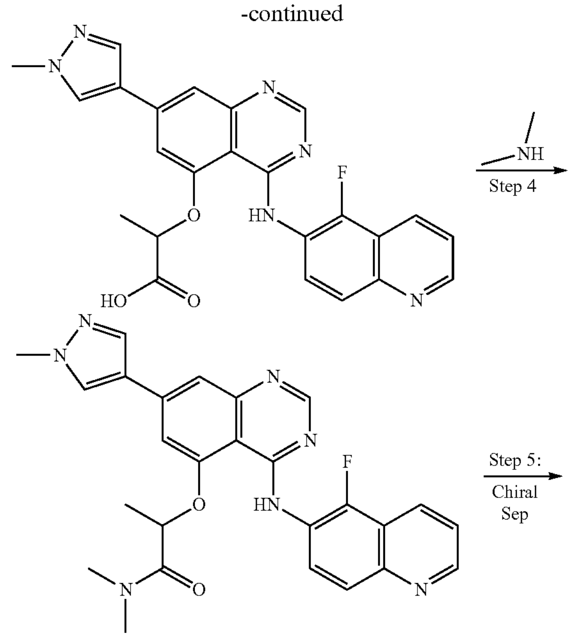

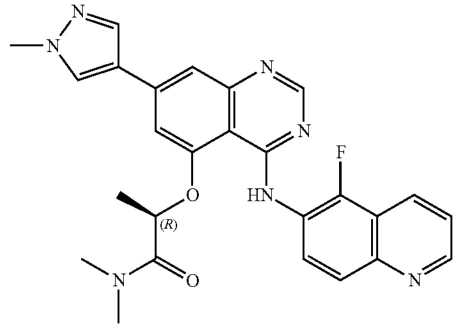

or

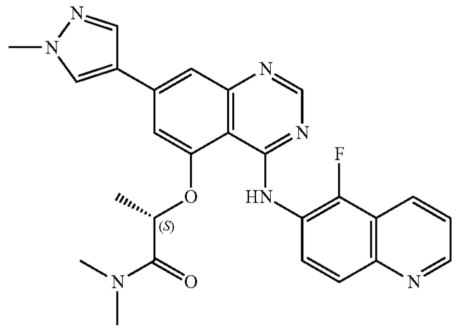

Step 1: Methyl 2-((7-bromo-4-((5-fluoroquinolin-6-yl)amino)quinazolin-5-yl)oxy)propanoate To a mixture of methyl 2-hydroxypropanoate (240 mg, 2.31 mmol) in THF (15 mL) was added NaH (73.9 mg, 3.08 mmol) at 0° C., the reaction mixture was stirred at 0° C. for 15 min, then Intermediate 2 (600 mg, 1.54 mmol) was added to the reaction mixture, and stirred at 80° C. overnight. The reaction mixture was added to ice water and was concentrated under vacuum to afford the title compound (450 mg, yield: 62.0%) as a white solid. LC-MS: (ES, m/z): RT=1.539 min, LCMS: m/z=472 [M+1]

Step 2: Methyl-2-((4-((5-fluoroquinolin-6-yl)amino)-7-(1-methyl-1H-pyrazol-4-yl)quinazolin-5-yl)oxy)propanoate To a mixture of methyl 2-((7-bromo-4-((5-fluoroquinolin-6-yl)amino)quinazolin-5-yl)oxy)propanoate (450 mg, 954 μmol) and 1-methyl-4-(4,4,5,5-tetramethyl-1,3,2-dioxaborolan-2-yl)-1H-pyrazole (297 mg, 1.43 mmol) in 1,4-dioxane (10.00 mL) and $H_2O$ (2.50 mL) was added Pd(dppf)$Cl_2$ (77.8 mg, 95.4 μmol) and $K_2CO_3$ (394 mg, 2.86 mmol) at 25° C., the reaction mixture was stirred at 80° C. for 4 hrs under $N_2$. The reaction was diluted with 20 mL of water. The solution was extracted with 2×20 mL of ethyl acetate and the organic layers combined. The resulting mixture was washed with 20 mL of brine. Dried over anhydrous sodium sulfate and concentrated under vacuum. The product was purified by TLC eluting with DCM:MeOH (10:1) to give the title compound (370 mg, yield: 82.2%) as a yellow solid. LC-MS: (ES, m/z): RT=1.320 min, LCMS: m/z=473 [M+1].

Step 3: 2-((4-((5-fluoroquinolin-6-yl)amino)-7-(1-methyl-1H-pyrazol-4-yl)quinazolin-5-yl)oxy)propanoic acid To a mixture of methyl-2-((4-((5-fluoroquinolin-6-yl)amino)-7-(1-methyl-1H-pyrazol-4-yl)quinazolin-5-yl)oxy)propanoate (370 mg, 783 μmol) in THF (10 mL), $H_2O$ (2.5 mL) and MeOH (2.5 mL) was added LiOH (62.6 mg, 3.13 mmol) at 25° C., the reaction mixture was stirred at 35° C. for 2 hrs. The mixture was concentrated under vacuum to give the title compound (300 mg, yield: 83.7%) as a white solid. LC-MS: (ES, m/z): RT=0.901 min, LCMS: m/z=459 [M+1]

Step 4: 2-((4-((5-fluoroquinolin-6-yl)amino)-7-(1-methyl-1H-pyrazol-4-yl)quinazolin-5-yl)oxy)-N,N-dimethylpropanamide To a solution 2-((4-((5-fluoroquinolin-6-yl)amino)-7-(1-methyl-1H-pyrazol-4-yl)quinazolin-5-yl)oxy)propanoic acid (150 mg, 327 μmol) in DMF (10 mL) was added dimethylamine (44.1 mg, 980 μmol), HATU (248 mg, 654 μmol) and DIEA (253 mg, 1.96 mmol), the reaction mixture was stirred at 60° C. for 3 hrs. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The product was purified by prep-TLC eluting with DCM:MeOH (10:1). The residue was purified by prep-HPLC (Column: XBridge Shield RP18 OBD Column, 30*150 mm, 5 m; Mobile Phase A: Water (10 mmol/L $NH_4HCO_3$+0.1% $NH_3 \cdot H_2O$), Mobile Phase B: ACN; Flow rate: 60 mL/min; Gradient: 17% B to 53% B in 7 min; Wavelength: 254/220 nm) to give the title compound as a yellow solid.

Step 5: Chiral Separation

The product of Step 4 was purified by Prep-Chiral-HPLC with following conditions: Column: CHIRAL ART Amylose-SA, 2*25 cm, 5 μm; Mobile Phase A: MTBE (0.5% 2M $NH_3$-MeOH)-HPLC, Mobile Phase B: MeOH-HPLC; Flow rate: 20 mL/min; Gradient: 10% B to 10% B in 20 min; Wavelength: 220/254 nm to afford:

Example 136: First eluting isomer, (15.5 mg) as a white solid, LC-MS: (ES, m/z): RT=1.152 min, LCMS: m/z=486

[M+1]. Chiral-HPLC R=2.528, $^1$H NMR (300 MHz, DMSO-d6) δ 10.23 (s, 1H), 8.90 (dd, J=4.2, 1.7 Hz, 1H), 8.78 (t, J=8.9 Hz, 1H), 8.55-8.46 (m, 1H), 8.31 (s, 1H), 7.91 (d, J=9.3 Hz, 1H), 7.61 (dd, J=8.5, 4.3 Hz, 1H), 6.52 (d, J=2.1 Hz, 1H), 6.30 (d, J=2.0 Hz, 1H), 5.11 (s, 1H), 4.13 (s, 1H), 3.71-3.37 (m, 5H), 3.05 (s, 1H), 2.33 (s, 6H), 2.09 (d, J=12.7 Hz, 2H), 1.47 (d, J=5.9 Hz, 3H), 1.36 (s, 0H), 1.21 (s, 0H).

Example 137: Second eluting isomer, (16.9 mg) as a white solid, LC-MS: (ES, m/z): RT=1.150 min, LCMS: m/z=486 [M+1]. Chiral-HPLC R=4.169, $^1$H NMR (300 MHz, DMSO-$d_6$) δ 10.98 (s, 1H), 8.93 (dd, J=4.2, 1.7 Hz, 1H), 8.56-8.41 (m, 3H), 8.41-7.88 (m, 3H), 7.63 (dd, J=8.5, 4.2 Hz, 1H), 7.50 (dd, J=43.3, 1.4 Hz, 2H), 5.98 (q, J=6.4 Hz, 1H), 3.91 (s, 3H), 3.16 (s, 3H), 2.85 (s, 3H), 1.65 (d, J=6.4 Hz, 3H).

Example 138: (R)-2-((4-((5-fluoroquinolin-6-yl)amino)-7-(1-methyl-1H-pyrazol-4-yl)quinazolin-5-yl)oxy)-1-morpholinopropan-1-one or (S)-2-((4-((5-fluoroquinolin-6-yl)amino)-7-(1-methyl-1H-pyrazol-4-yl)quinazolin-5-yl)oxy)-1-morpholinopropan-1-one Example 139: (S)-2-((4-((5-fluoroquinolin-6-yl)amino)-7-(1-methyl-1H-pyrazol-4-yl)quinazolin-5-yl)oxy)-1-morpholinopropan-1-one or (R)-2-((4-((5-fluoroquinolin-6-yl)amino)-7-(1-methyl-1H-pyrazol-4-yl)quinazolin-5-yl)oxy)-1-morpholinopropan-1-one

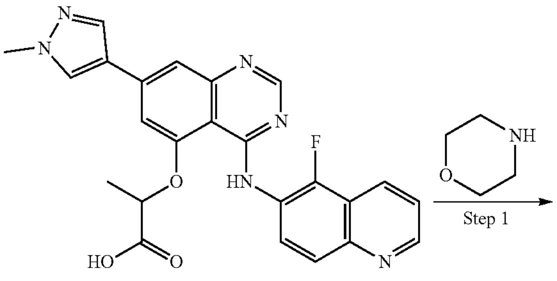

Product of Example 137, Step 3

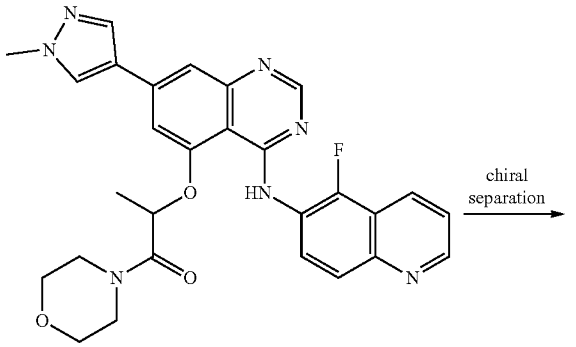

-continued

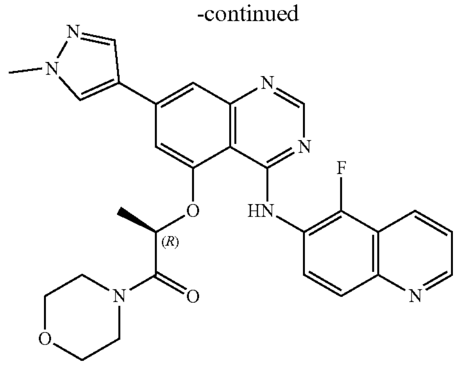

or

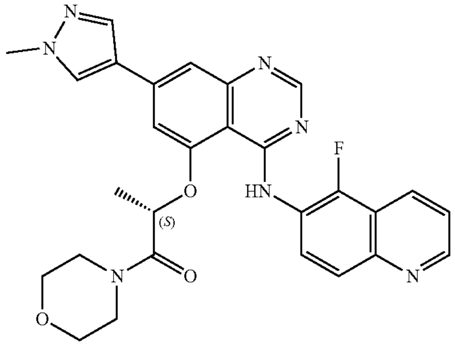

Step 1: 2-((4-((5-fluoroquinolin-6-yl)amino)-7-(1-methyl-1H-pyrazol-4-yl)quinazolin-5-yl)oxy)-1-morpholinopropan-1-one To a solution of 2-((4-((5-fluoroquinolin-6-yl)amino)-7-(1-methyl-1H-pyrazol-4-yl)quinazolin-5-yl)oxy)propanoic acid (Product of Example 137, step 3), 150 mg, 327 μmol) in DMF (10 mL) was added morpholine (85.3 mg, 980 μmol), HATU (248 mg, 654 μmol) and DIEA (168 mg, 1.30 mmol), the reaction mixture was stirred at 60° C. for 3 hrs. The resulting solution was diluted with 20 mL of water. The resulting solution was extracted with 2×20 mL of ethyl acetate and the organic layers combined. The resulting mixture was washed with 20 mL of brine. The mixture was dried over anhydrous sodium sulfate and concentrated under vacuum. The product was purified by prep-TLC eluting with DCM:MeOH (10:1). The residue was purified by prep-HPLC (Column: Xselect CSH F-Phenyl OBD column, 19*250 mm, 5 μm; Mobile Phase A: Water (0.1% FA), Mobile Phase B: ACN; Flow rate: 25 mL/min; Gradient: 25% B to 35% B in 8 min; Wavelength: 254/220 nm) to give the title compound as a yellow solid.

Step 2: Chiral Separation

The product of step 1 was purified by Prep-Chiral-HPLC with following conditions: Column: CHIRALPAK IF, 2*25 cm, 5 μm; Mobile Phase A: Hex: DCM=3:1 (0.5% 2M $NH_3$-MeOH)-HPLC, Mobile Phase B: EtOH-HPLC; Flow rate: 20 mL/min; Gradient: 30% B to 30% B in 17 min; Wavelength: 254/220 nm. To afford:

Example 138: First eluting isomer, (21.4 mg) as a white solid, LC-MS: (ES, m/z): RT=1.137 min, LCMS: m/z=528 [M+1]. Chiral-HPLC R=2.172, 1H NMR (300 MHz, DMSO-d6) δ 10.82 (s, 1H), 8.83 (dd, J=4.2, 1.6 Hz, 1H), 8.47-8.22 (m, 4H), 8.01 (d, J=0.8 Hz, 1H), 7.83 (d, J=9.2 Hz, 1H), 7.61-7.44 (m, 2H), 7.32 (d, J=1.5 Hz, 1H), 5.88 (q, J=6.4 Hz, 1H), 3.81 (s, 3H), 3.69-3.15 (m, 8H), 1.55 (d, J=6.3 Hz, 3H).

Example 139: Second eluting isomer, (18.9 mg) as a white solid, LC-MS: (ES, m/z): RT=1.132 min, LCMS: m/z=528 [M+1]. Chiral-HPLC R=2.726, 1H NMR (300 MHz, DMSO-d6) δ 10.96 (s, 1H), 8.96 (dd, J=4.2, 1.7 Hz, 1H), 8.57-8.37 (m, 4H), 8.14 (s, 1H), 7.96 (d, J=9.2 Hz, 1H), 7.71-7.60 (m, 2H), 7.45 (d, J=1.5 Hz, 1H), 6.01 (d, J=6.5 Hz, 1H), 3.94 (s, 3H), 3.86-3.28 (m, 8H), 1.67 (d, J=6.3 Hz, 3H).

Example 140: 5-((1S,2S)-2-(dimethylamino)cyclobutoxy)-N-(5-fluoroquinolin-6-yl)-7-(1-methyl-1H-pyrazol-4-yl)quinazolin-4-amine or 5-((1R,2R)-2-(dimethylamino)cyclobutoxy)-N-(5-fluoroquinolin-6-yl)-7-(1-methyl-1H-pyrazol-4-yl)quinazolin-4-amine

Example 141: 5-((1R,2R)-2-(dimethylamino)cyclobutoxy)-N-(5-fluoroquinolin-6-yl)-7-(1-methyl-1H-pyrazol-4-yl)quinazolin-4-amine or 5-((1S,2S)-2-(dimethylamino)cyclobutoxy)-N-(5-fluoroquinolin-6-yl)-7-(1-methyl-1H-pyrazol-4-yl)quinazolin-4-amine

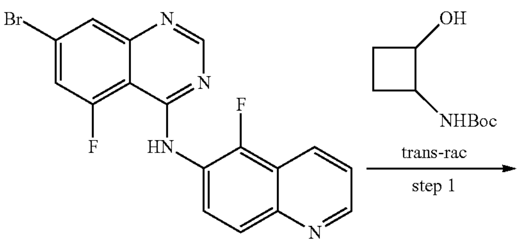

Intermediate 2

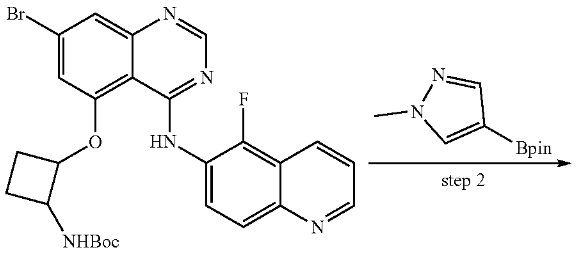

trans-rac

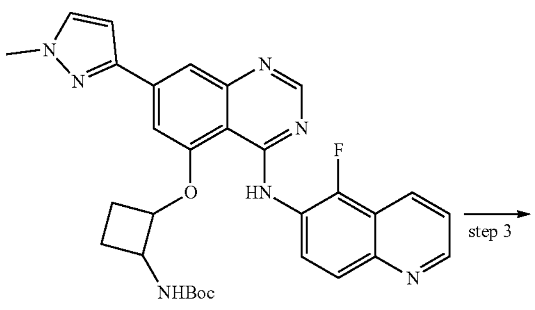

trans-rac

-continued

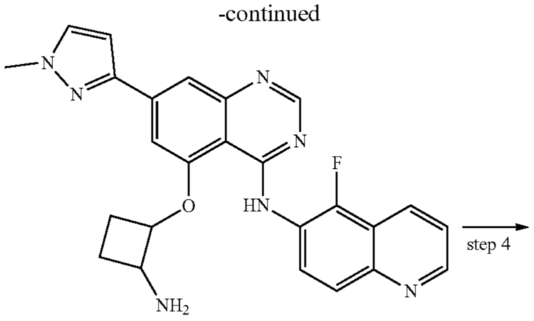

trans-rac

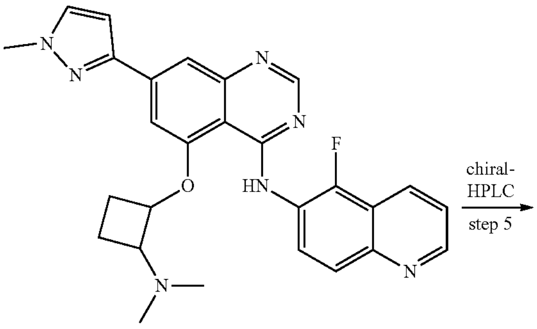

trans-rac

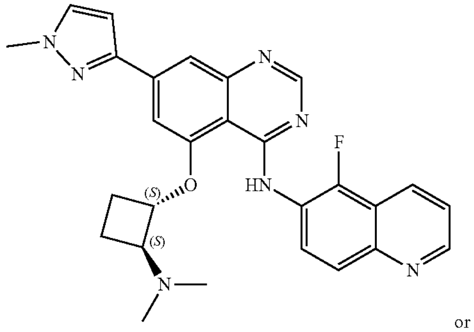

or

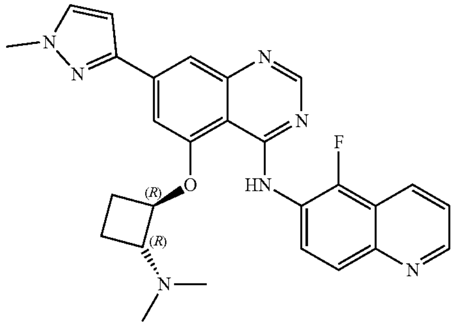

Step 1: trans-rac-tert-butyl (2-((7-bromo-4-((5-fluoroquinolin-6-yl)amino)quinazolin-5-yl)oxy)cyclobutyl)carbamate t-BuOK (143 mg, 1.28 mmol) was added to Intermediate 2 (250 mg, 645 μmol), trans-rac-tert-butyl (2-hydroxycyclobutyl)carbamate (239 mg, 1.28 mmol) in THF (10 mL) at rt. The resulting mixture was stirred at 80° C. for 3 h under $N_2$. The mixture was diluted with EA 100 mL and washed with brine 50 mL*2, the organic layer was dried with $Na_2SO_4$ and concentrated under vacuum. The residue was purified by a silica gel column using DCM: EA=18:1 to afford the title compound (200 mg, yield: 80%) as a light yellow solid. LC-MS: (ES, m/z): RT=1.633 min, LCMS: m/z=554 [M+1].

Step 2: trans-rac-tert-butyl (2-((4-((5-fluoroquinolin-6-yl)amino)-7-(1-methyl-1H-pyrazol-4-yl)quinazolin-5-yl)oxy)cyclobutyl)carbamate Pd(dppf)$Cl_2$ (35.8 mg, 43.9 μmol) and $K_2CO_3$ (90.8 mg, 658 μmol) were added to 1-methyl-4-(4,4,5,5-tetramethyl-1,3,2-dioxaborolan-2-yl)-1H-pyrazole (136 mg, 658 μmol) and trans-rac-tert-butyl (2-((7-bromo-4-((5-fluoroquinolin-6-yl)amino)quinazolin-5-yl)oxy)cyclobutyl)carbamate (200 mg, 439 μmol) in $H_2O$ (4 mL) and dioxane (16 mL) at rt. The resulting mixture was stirred at 80° C. for 2 h under $N_2$. The mixture was diluted with DCM 100 mL and washed with water 50 mL*2, the organic layer was dried with $Na_2SO_4$ and concentrated under vacuum. The residue was purified by a silica gel column using DCM:MeOH=20:1 to afford the title compound (180 mg, yield: 90%) as a yellow oil. LC-MS: (ES, m/z): RT=1.326 min, LCMS: m/z=556 [M+1].

Step 3: trans-rac-5-(2-aminocyclobutoxy)-N-(5-fluoroquinolin-6-yl)-7-(1-methyl-1H-pyrazol-4-yl)quinazolin-4-amine TFA (2 mL) was added to trans-rac-tert-butyl (2-((4-((5-fluoroquinolin-6-yl)amino)-7-(1-methyl-1H-pyrazol-4-yl)quinazolin-5-yl)oxy)cyclobutyl)carbamate (180 mg, 323 μmol) in DCM (6 mL) at rt. The resulting mixture was stirred at rt for 1 hr. The mixture was concentrated under vacuum. This resulted in the title compound (100 mg, yield: 56%) as a white solid. LC-MS: (ES, m/z): RT=1.094 min, LCMS: m/z=456 [M+1].

Step 4: trans-rac-5-(2-(dimethylamino)cyclobutoxy)-N-(5-fluoroquinolin-6-yl)-7-(1-methyl-1H-pyrazol-4-yl)quinazolin-4-amine STAB (18.15 mg, 83.2 μmol) was added to HCHO (0.1 ml) and trans-rac-5-(2-aminocyclobutoxy)-N-(5-fluoroquinolin-6-yl)-7-(1-methyl-1H-pyrazol-4-yl)quinazolin-4-amine (50 mg, 43.2 μmol) in DCM (3 mL) at rt The mixture was stirred at r.t for 2 hr. The mixture was diluted with EA 100 mL and washed with brine 50 mL*2, the organic layer was dried with $Na_2SO_4$ and concentrated under vacuum. The residue was purified by a Prep-TLC with DCM:MeOH=25:1. This resulted in the title compound (35 mg, yield: 70%) as an off-white solid. LC-MS: (ES, m/z): RT=1.245 min, LCMS: m/z=484 [M+1].

Step 5: Chiral Separation trans-rac-5-(2-(dimethylamino)cyclobutoxy)-N-(5-fluoroquinolin-6-yl)-7-(1-methyl-1H-pyrazol-4-yl)quinazolin-4-amine (30 mg, 62.0 μmol) in MeOH was Purified by Prep-Chiral-HPLC with following conditions: Column: CHIRALPAK IE, 2*25 cm, 5 μm; Mobile Phase A: MtBE (0.5% 2M $NH_3$-MeOH)-HPLC, Mobile Phase B: MeOH-HPLC; Flow rate: 20 mL/min; Gradient: 50% B to 50% B in 16 min; Wavelength: 220/254 nm; RT1(min): 8.76; RT2 (min): 12.69; Sample Solvent: EtOH-HPLC; This resulted in Example 140: First eluting isomer, (10.7 mg) as a white solid, LC-MS: (ES, m/z): RT=0.998 min, LCMS: m/z=484 [M+1]. Chiral-HPLC R=1.913, $^1H$ NMR (400 MHz, DMSO-$d_6$) δ 10.24 (d, J=2.1 Hz, 1H), 9.02 (t, J=8.9 Hz, 1H), 8.94 (dd, J=4.2, 1.7 Hz, 1H), 8.58 (s, 1H), 8.56-8.50 (m, 1H), 8.48 (s, 1H), 8.16 (d, J=0.8 Hz, 1H), 7.97 (d, J=9.3 Hz, 1H), 7.66 (dd, J=8.5, 4.2 Hz, 1H), 7.61 (d, J=1.5 Hz, 1H), 7.34 (d, J=1.6 Hz, 1H), 5.02 (q, J=7.2 Hz, 1H), 3.92 (s, 3H), 3.33 (s, 1H), 2.62 (q, J=8.9 Hz, 1H), 2.23 (s, 6H), 2.08 (q, J=9.1 Hz, 1H), 1.77 (p, J=10.1 Hz, 1H), 1.59 (p, J=9.7 Hz, 1H).

Example 141: Second eluting isomer, (12.6 mg) as a white solid, LC-MS: (ES, m/z): RT=0.999 min, LCMS: m/z=484 [M+1]. Chiral-HPLC R=3.119, $^1H$ NMR (400 MHz, DMSO-$d_6$) δ 10.26 (d, J=2.2 Hz, 1H), 9.04 (t, J=8.9 Hz, 1H), 8.94 (dd, J=4.2, 1.7 Hz, 1H), 8.59 (s, 1H), 8.56-8.48 (m, 2H), 8.17 (s, 1H), 7.98 (d, J=9.3 Hz, 1H), 7.70-7.60 (m, 2H), 7.35 (d, J=1.6 Hz, 1H), 5.03 (q, J=7.2 Hz, 1H), 3.93 (s, 3H), 3.33 (s, 1H), 2.62 (q, J=9.0 Hz, 1H), 2.24 (s, 6H), 2.08 (q, J=9.4 Hz, 1H), 1.85-1.71 (m, 1H), 1.59 (p, J=9.6 Hz, 1H).

Example 142: 5-(1-(3-(dimethylamino)oxetan-3-yl)ethoxy)-N-(5-fluoroquinolin-6-yl)-7-(1-methyl-1H-pyrazol-4-yl)quinazolin-4-amine

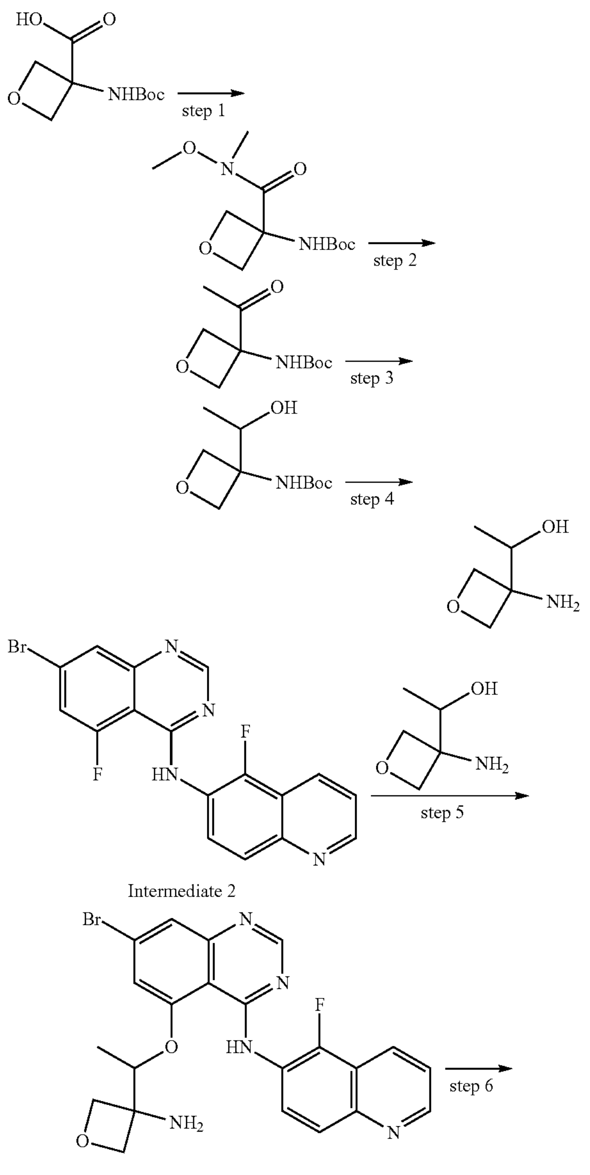

-continued

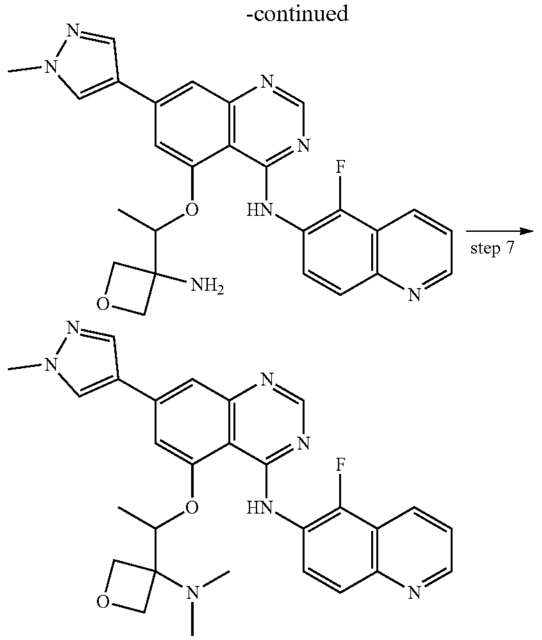

Step 1: tert-butyl (3-(methoxy(methyl)carbamoyl)oxetan-3-yl)carbamate 3-((tert-butoxycarbonyl)amino)oxetane-3-carboxylic acid (500 mg, 2.30 mmol), methoxy(methyl)amine (140 mg, 2.30 mmol), EDCI (883 mg, 4.60 mmol), HOBT (155 mg, 1.15 mmol) and DIEA (630 mg, 4.60 mmol) was added into 15 ml DMF. The mixture was stirred at 25° C. for 16 hours. The reaction was extracted by EA and purified by Prep-TLC (PE:EA=4:1), to afford the title compound (420 mg, 70.2%) as a white solid. LC-MS: (ES, m/z): RT=0.927 min, LCMS: m/z=261 [M+1]

Step 2: tert-butyl (3-acetyloxetan-3-yl)carbamate

MeMgBr (2.41 mL, 2M in THF, 4.83 mmol) was added into tert-butyl (3-(methoxy(methyl)carbamoyl)oxetan-3-yl) carbamate (420 mg, 1.61 mmol) in THF at −10° C. The reaction mixture was stirred at 0° C. for 2 hours. The reaction was quenched by solution of NH4Cl and extracted by EA. The crude compound was purified by Prep-TLC: (PE:EA=2:1). To afford the title compound (300 mg, yield=86.7%) as a white solid. LC-MS: (ES, m/z): RT=0.935 min, LCMS: m/z=216 [M+1]

Step 3: tert-butyl (3-(1-hydroxyethyl)oxetan-3-yl)carbamate

Into a 25 ml vial was added tert-butyl (3-acetyloxetan-3-yl)carbamate (300 mg, 1.39 mmol) in 10 mL MeOH. NaBH4 (158 mg, 4.17 mmol) was added into the solution and stirred at 25° C. for 2 hours. The reaction mixture was quenched by $NH_4Cl$ saturated solution and extracted with EA (50 ml*3). The crude compound was purified by Prep-TLC: (EA:PE=1:1) to afford the title compound (150 mg, yield: 49.8%) as a white solid. LC-MS: (ES, m/z): RT=1.159 min, LCMS: m/z=218 [M+1]

Step 4: 1-(3-amino oxetan-3-yl) ethan-1-ol

TFA (0.5 mL) was added into tert-butyl (3-(1-hydroxyethyl)oxetan-3-yl)carbamate (130 mg, 0.5983 mmol) in DCM. The mixture was stirred at 25° C. for 1 hour. The reaction mixture was evaporated under vacuum and used to next step directly.

Step 5: 5-(1-(3-aminooxetan-3-yl)ethoxy)-7-bromo-N-(5-fluoroquinolin-6-yl)quinazolin-4-amine NaH (6.15 mg, 154 μmol) was added into 1-(3-aminooxetan-3-yl)ethan-1-ol (18.0 mg, 154 μmol) in THF and stirred for 10 min, Intermediate 2 (20 mg, 0.05165 mmol) was added into the reaction mixture and stirred at 80° C. for 3 hours. The reaction was quenched by ice and water and extracted by EA. The crude compound was purified by Prep-TLC: (DCM:MeOH=10:1) to afford the title compound (10 mg, yield: 40.1%) as a light yellow solid. LC-MS: (ES, m/z): RT=1.167 min, LCMS: m/z=484[M+1]

Step 6: 5-(1-(3-aminooxetan-3-yl)ethoxy)-N-(5-fluoroquinolin-6-yl)-7-(1-methyl-1H-pyrazol-4-yl) quinazolin-4-amine Into a 8 ml vial and maintained a $N_2$ atmosphere was added 5-(1-(3-aminooxetan-3-yl)ethoxy)-7-bromo-N-(5-fluoroquinolin-6-yl)quinazolin-4-amine (10 mg, 0.02064 mmol), 1-methyl-4-(4,4,5,5-tetramethyl-1,3,2-dioxaborolan-2-yl)-1H-pyrazole (5.13 mg, 24.7 μmol), Pd(dppf)$Cl_2$ (1.68 mg, 2.06 μmol) and $K_2CO_3$ (5.68 mg, 41.2 μmol) in 1 mL 1,4-dioxane and 0.25 mL $H_2O$. The mixture was stirred at 80° C. for 3 hours. The solution was extracted by EA and purified by Prep-TLC: (DCM: MeOH=10:1) to afford the title compound (7 mg, yield: 70%) as a white solid. LC-MS: (ES, m/z): RT=0.998 min, LCMS: m/z=486 [M+1]

Step 7: (5-(1-(3-(dimethylamino)oxetan-3-yl) ethoxy)-N-(5-fluoroquinolin-6-yl)-7-(1-methyl-1H-pyrazol-4-yl)quinazolin-4-amine Into a 25 ml vial was added 5-(1-(3-aminooxetan-3-yl) ethoxy)-N-(5-fluoroquinolin-6-yl)-7-(1-methyl-1H-pyrazol-4-yl)quinazolin-4-amine (10 mg, 0.02 mmol) and STAB (13.0 mg, 61.7 μmol) in 2 mL DCM and 1 mL MeOH. The mixture was stirred at 25° C. for 10 min. 37% Formaldehyde Solution (0.5 mL) was added into the mixture. The reaction was stirred overnight. The reaction was quenched by $NH_4Cl$ solution and extracted by EA and $H_2O$. The crude compound was purified by HPLC: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 18% B to 54% B in 7 min, 54% B; Wavelength: 254/220 nm; RT1(min): 6.32; to afford the title compound (2.8 mg, 26.6%) as a white solid. LC-MS: (ES, m/z): RT=0.784 min, LCMS: m/z=514[M+1]; 1H NMR (300 MHz, Methanol-d4) δ 8.93 (dd, J=4.3, 1.6 Hz, 1H), 8.65-8.56 (m, 1H), 8.36 (d, J=11.0 Hz, 2H), 8.14 (d, J=0.8 Hz, 1H), 8.09 (dd, J=9.1, 8.0 Hz, 1H), 7.92 (d, J=9.0 Hz, 1H), 7.66 (dd, J=8.6, 4.4 Hz, 1H), 7.58 (d, J=1.4 Hz, 1H), 7.46 (d, J=1.6 Hz, 1H), 5.36 (q, J=6.0 Hz, 1H), 4.93 (d, J=6.9 Hz, 1H), 4.81 (d, J=7.3 Hz, 1H), 4.70 (d, J=6.6 Hz, 1H), 4.02 (s, 3H), 2.45 (s, 6H), 1.64 (d, J=6.0 Hz, 3H).

Example 143: 5-(((3R,4R)-3-fluoro-1-methylpiperidin-4-yl)oxy)-N-(5-fluoroquinolin-6-yl)-7-(1-methyl-1H-pyrazol-4-yl)quinazolin-4-amine or 5-(((3S,4S)-3-fluoro-1-methylpiperidin-4-yl)oxy)-N-(5-fluoroquinolin-6-yl)-7-(1-methyl-1H-pyrazol-4-yl)quinazolin-4-amine Example 144: 5-(((3S,4S)-3-fluoro-1-methylpiperidin-4-yl)oxy)-N-(5-fluoroquinolin-6-yl)-7-(1-methyl-1H-pyrazol-4-yl)quinazolin-4-amine or 5-(((3R,4R)-3-fluoro-1-methylpiperidin-4-yl)oxy)-N-(5-fluoroquinolin-6-yl)-7-(1-methyl-1H-pyrazol-4-yl)quinazolin-4-amine

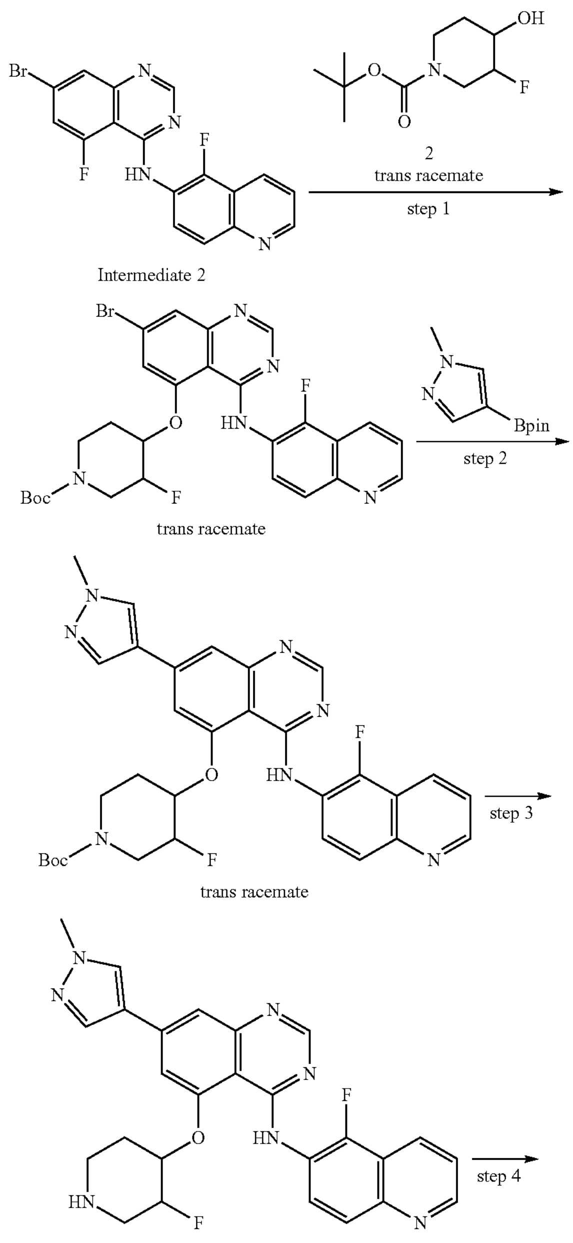

-continued

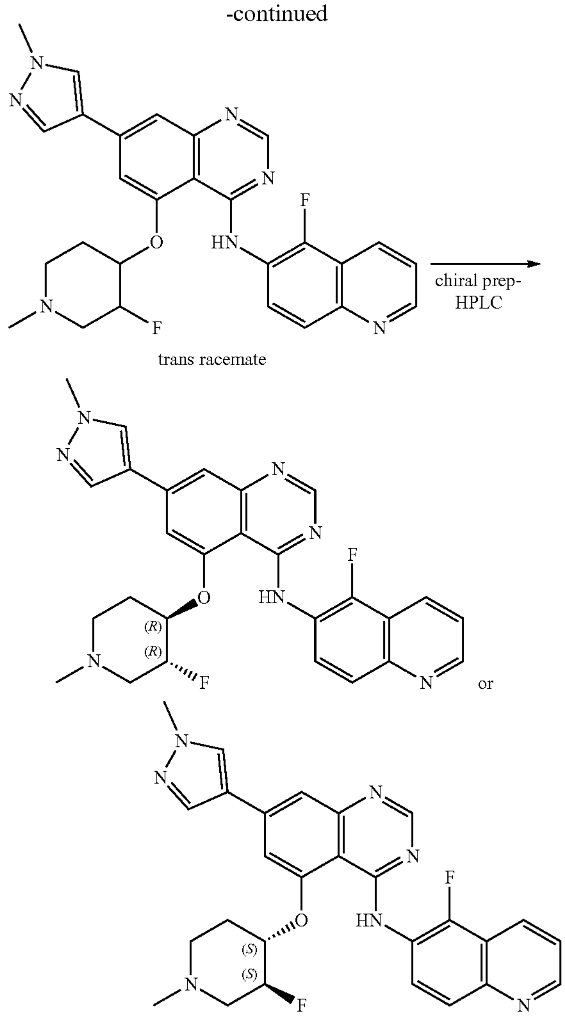

Step 1: trans-rac-tert-butyl 4-((7-bromo-4-((5-fluoroquinolin-6-yl)amino)quinazolin-5-yl)oxy)-3-fluoropiperidine-1l-carboxylate NaH (80 mg, 2 mmol) was added to a mixture of Intermediate 2 (387 mg, 1 mmol) and trans-rac-tert-butyl 3-fluoro-4-hydroxypiperidine-1-carboxylate (436 mg, 2 mmol) in THF (1 mL) and stirred 80° C. for 10 hrs, then the reaction mixture was poured into ice-water, and extracted with EA, washed with water, dried with $Na_2SO_4$, and concentrated to afford the title compound (500 mg, yield: 85%) LC-MS: (ES, m/z): RT=1.267 min, LCMS: m/z=586 588 [M+1].

Step 2: trans-rac-tert-butyl 3-fluoro-4-((4-((5-fluoroquinolin-6-yl)amino)-7-(1-methyl-1H-pyrazol-4-yl)quinazolin-5-yl)oxy)piperidine-1-carboxylate The product of step 1 (500 mg, 0.852 mmol), 1-methyl-4-(4,4,5,5-tetramethyl-1,3,2-dioxaborolan-2-yl)-1H-pyrazole (264 mg, 1.27 mmol), $Pd(dppf)Cl_2$ (66.4 mg, 0.085 mmol) and $K_2CO_3$ (234 mg, 1.70 mmol) in dioxane (4 mL) and water (1 mL), were stirred at 80° C. under $N_2$ for 4 hrs, then poured into water. The title compound was collected by filtration (600 mg, crude). LC-MS: (ES, m/z): RT=1.200 min, LCMS: m/z=588 [M+1].

Step 3: trans-rac-5-((3-fluoropiperidin-4-yl)oxy)-N-(5-fluoroquinolin-6-yl)-7-(1-methyl-1H-pyrazol-4-yl)quinazolin-4-amine HCl in dioxane (5 mL) was added to the product of step 2 (587 mg, 1 mmol) in EA (25 mL) and stirred at rt for 2 hrs. The title compound (320 mg, crude) was collected by filtration. LC-MS: (ES, m/z): RT=1.042 min, LCMS: m/z=488 [M+1].

Step 4: trans-rac-5-((3-fluoro-1-methylpiperidin-4-yl)oxy)-N-(5-fluoroquinolin-6-yl)-7-(1-methyl-1H-pyrazol-4-yl)quinazolin-4-amine $NaBH_3CN$ (103 mg, 1.64 mmol) was added to a mixture of the product of step 3 (200 mg, 0.41 mmol), (CHO)n (36 mg, 0.41 mmol) in $CH_3OH$ (5 mL) and stirred for 10 hrs, then quenched with saturated $NH_4Cl$, and extracted with EA, and concentrated and purified by prep-HPLC to afford the title compound (50 mg, yield: 40%) LC-MS: (ES, m/z): RT=0.792 min, LCMS: m/z=502 [M+1].

Step 5: Chiral Separation

The product of step 4 was separated by chiral prep-HPLC (Column: CHIRALPAK IG-3, 4.6*50 mm, 3.0 um; Mobile Phase A: Hex (0.1% DEA): EtOH=50:50; Flow rate: 1 mL/min; Gradient: 0% B to 0% B; to afford:

Example 143: First eluting isomer (4.4 mg) as a yellow solid. LC-MS: (ES, m/z): RT=0.765 min, LCMS: m/z=502 [M+1], $^1H$ NMR (400 MHz, DMSO-$d_6$) δ 10.24 (d, J=2.1 Hz, 1H), 8.97 (t, J=8.9 Hz, 1H), 8.94 (dd, J=4.2, 1.6 Hz, 1H), 8.59-8.48 (m, 3H), 8.20 (s, 1H), 7.97 (d, J=9.3 Hz, 1H), 7.68-7.61 (m, 2H), 7.55 (d, J=1.5 Hz, 1H), 5.16 (ddd, J=13.7, 9.4, 4.6 Hz, 1H), 5.06-4.95 (m, H), 3.93 (s, 3H), 3.24 (tt, J=6.6, 3.2 Hz, 1H), 2.81 (d, J=11.4 Hz, 1H), 2.31 (s, 3H), 2.35-2.23 (m, 1H), 1.88 (qd, J=11.7, 4.1 Hz, 1H).

Example 144: Second eluting isomer (3.7 mg) as a white solid. LC-MS: (ES, m/z): RT=0.781 min, LCMS: m/z=502 [M+1], $^1H$ NMR (400 MHz, DMSO-$d_6$) δ 10.24 (d, J=2.1 Hz, 1H), 8.97 (t, J=8.9 Hz, 1H), 8.93 (dd, J=4.2, 1.7 Hz, 1H), 8.59-8.48 (m, 3H), 8.20 (d, J=0.7 Hz, 1H), 7.97 (dd, J=9.3, 1.4 Hz, 1H), 7.68-7.60 (m, 2H), 7.55 (d, J=1.6 Hz, 1H), 5.16 (ddd, J=13.6, 9.4, 4.7 Hz, 1H), 5.06-4.95 (m, 1H), 3.93 (s, 3H), 3.24 (tt, J=6.8, 3.9 Hz, 1H), 2.81 (d, J=11.1 Hz, 1H), 2.35 (s, 1H), 2.31 (s, 3H), 2.34-2.23 (m, 2H), 1.89 (qd, J=11.9, 4.1 Hz, 1H).

Intermediate 36 tert-butyl (S)-2-((S)-1-((4-((5-fluoroquinolin-6-yl)amino)-7-(1-methyl-1H-pyrazol-4-yl)quinazolin-5-yl)oxy)ethyl)pyrrolidine-1-carboxylate and tert-butyl (R)-2-((R)-1-((4-((5-fluoroquinolin-6-yl)amino)-7-(1-methyl-1H-pyrazol-4-yl)quinazolin-5-yl)oxy)ethyl)pyrrolidine-1-carboxylate Or tert-butyl (S)-2-((R)-1-((4-((5-fluoroquinolin-6-yl)amino)-7-(1-methyl-1H-pyrazol-4-yl)quinazolin-5-yl)oxy)ethyl)pyrrolidine-1-carboxylate and tert-butyl (R)-2-((S)-1-((4-((5-fluoroquinolin-6-yl)amino)-7-(1-methyl-1H-pyrazol-4-yl)quinazolin-5-yl)oxy)ethyl)pyrrolidine-1-carboxylate Intermediate 37 tert-butyl (S)-2-((R)-1-((4-((5-fluoroquinolin-6-yl)amino)-7-(1-methyl-1H-pyrazol-4-yl)quinazolin-5-yl)oxy)ethyl)pyrrolidine-1-carboxylate and tert-butyl (R)-2-((S)-1-((4-((5-fluoroquinolin-6-yl)amino)-7-(1-methyl-1H-pyrazol-4-yl)quinazolin-5-yl)oxy)ethyl)pyrrolidine-1-carboxylate or tert-butyl (S)-2-((S)-1-((4-((5-fluoroquinolin-6-yl)amino)-7-(1-methyl-1H-pyrazol-4-yl)quinazolin-5-yl)oxy)ethyl)pyrrolidine-1-carboxylate and tert-butyl (R)-2-((R)-1-((4-((5-fluoroquinolin-6-yl)amino)-7-(1-methyl-1H-pyrazol-4-yl)quinazolin-5-yl)oxy)ethyl)pyrrolidine-1-carboxylate

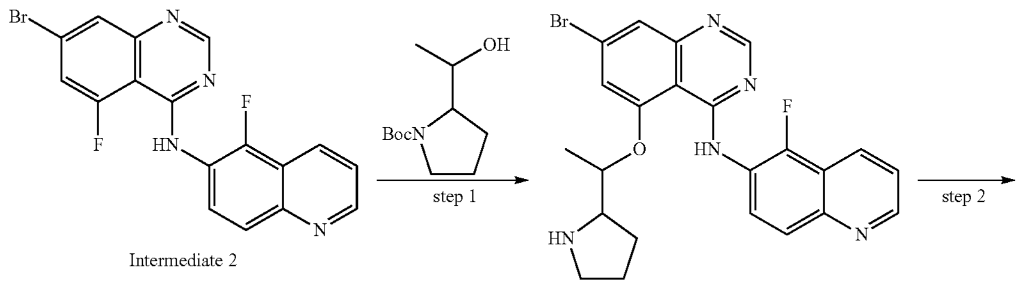

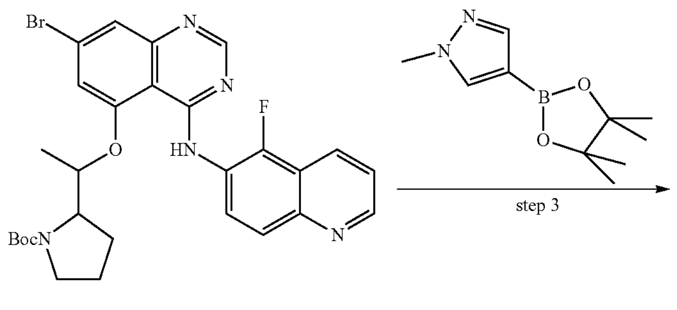

-continued

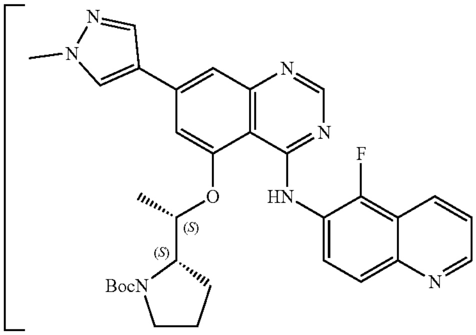

and

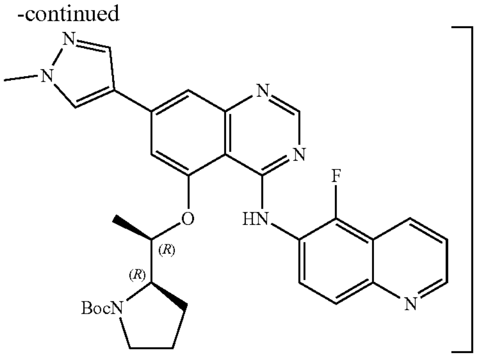

or

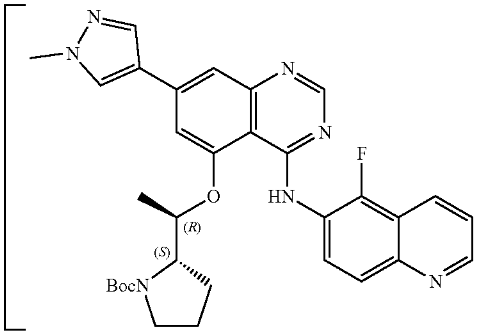

and

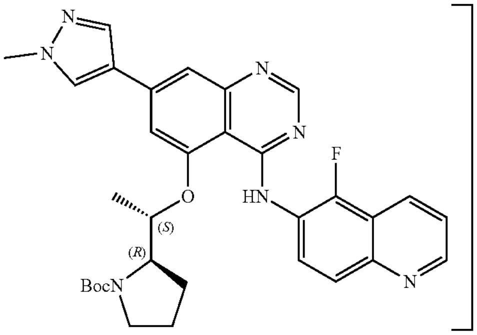

Intermediate 36

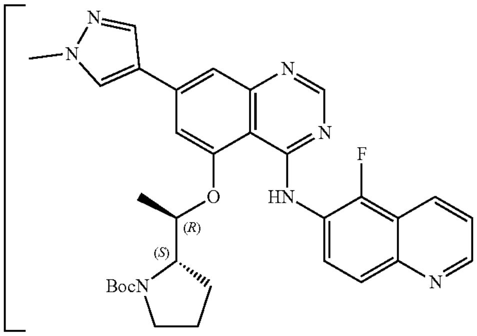

and

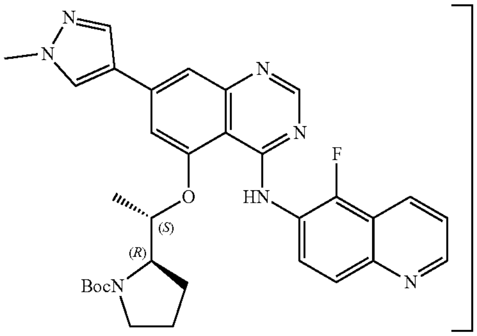

or

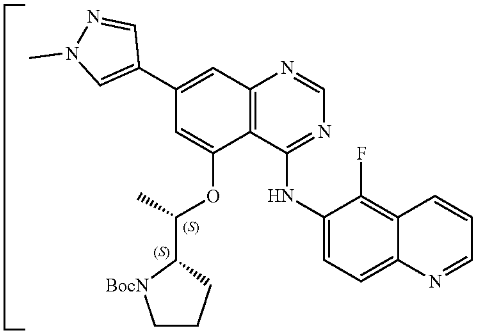

and

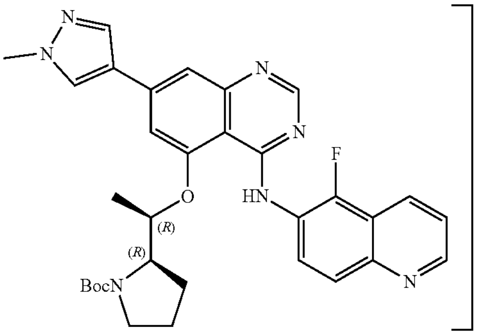

Intermediate 37

Step 1: 7-bromo-N-(5-fluoroquinolin-6-yl)-5-(1-(pyrrolidin-2-yl)ethoxy)quinazolin-4-amine NaH (185 mg, 9.27 mmol) was added batchwise to Intermediate 2 (1.2 g, 3.09 mmol) and tert-butyl 2-(1-hydroxyethyl)pyrrolidine-1-carboxylate (1.99 g, 9.27 mmol) in THF (40 mL) at rt. The resulting mixture was heated to 80° C. for 16 hr. The reaction mixture was diluted with EA (200 mL), washed with water (200 mL*3) and washed with saturated brine (200 mL*1). The organic layer was dried over $Na_2SO_4$, filtered and evaporated under vacuum. The crude product was purified by Prep-TLC with DCM: MeOH=20:1 to afford the title compound (700 mg, yield: 46.9%) as a brown solid. LC-MS: (ES, m/z): RT=1.432 min, LCMS: m/z=482 [M+1], Step 2: tert-butyl 2-(1-((7-bromo-4-((5-fluoroquinolin-6-yl)amino)quinazolin-5-yl)oxy)ethyl)pyrrolidine-1-carboxylate Di-tert-butyl dicarbonate (1.26 g, 5.80 mmol) was added to 7-bromo-N-(5-fluoroquinolin-6-yl)-5-(1-(pyrrolidin-2-yl)

ethoxy)quinazolin-4-amine (700 mg, 1.45 mmol) and $Na_2CO_3$ (461 mg, 4.35 mmol) in THF/$H_2O$ (30 mL/6 mL) at rt. The resulting mixture was stirred at room temperature for 3 hr. The reaction mixture was diluted with EA (100 mL), washed with water (100 mL*3) and saturated brine (100 mL*1). The organic layer was dried over $Na_2SO_4$, filtered and evaporated under vacuum. The crude product was purified by Prep-TLC with DCM:MeOH=20:1 to afford the title compound (480 mg, yield: 56.8%) as a yellow solid. LC-MS: (ES, m/z): RT=1.171 min, LCMS: m/z=582 [M+1], Step 3: Intermediate 36 and Intermediate 37

The reaction mixture of Pd(dppf)$Cl_2$ (57.6 mg, 78.9 μmol) and $K_2CO_3$ (162 mg, 1.18 mmol), tert-butyl 2-(1-((7-bromo-4-((5-fluoroquinolin-6-yl)amino)quinazolin-5-yl)oxy)ethyl) pyrrolidine-1-carboxylate (460 mg, 789 μmol) and 1-methyl-4-(4,4,5,5-tetramethyl-1,3,2-dioxaborolan-2-yl)-1H-pyrazole (196 mg, 946 μmol) in dioxane/$H_2O$ (20 mL/4 mL) was heated to 80° C. for 16 hr. The reaction mixture was diluted with EA (100 mL), and washed with water (100 mL*3) and saturated brine (100 mL*1). The organic layer was dried over $Na_2SO_4$, filtered and evaporated to afford crude product. The crude product was purified by Prep-TLC with DCM:MeOH=20:1. The residue was further purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 45% B to 65% B in 7 min, 65% B to 90% B in 10 min, 90% B; Wavelength: 254; 220 nm. This resulted in:

First Eluting compound, Intermediate 36, (170 mg, 36.9%) as a white solid LC-MS: (ES, m z): RT=1.412 min. LCMS: m/z=584 [M+1] and Second Eluting compound, Intermediate 37, (120 mg, 26%) as a white solid. LC-MS: (ES, m z): RT=1.586 min. LCMS: m/z=584 [M+1].

Examples 145-148

Intermediate 36
or
Intermediate 37

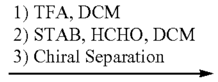

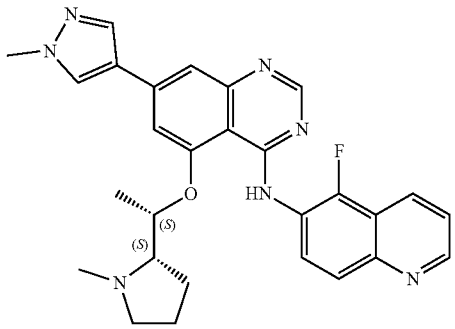

or

-continued

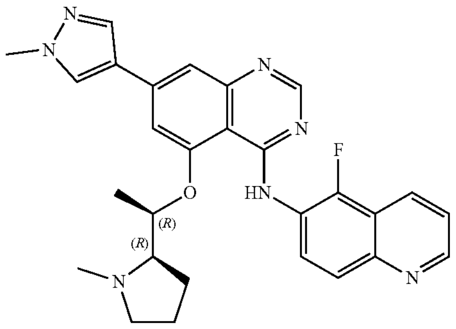

or

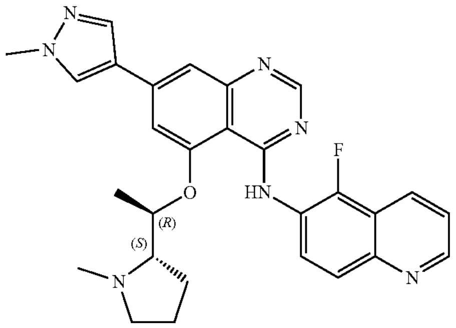

or

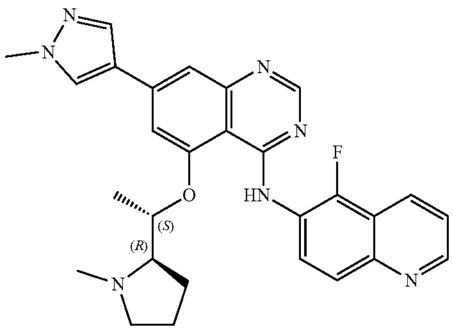

Examples 145, 146, 147, 148 each of which can be represented by any of these 4 structures.

Example 145

N-(5-fluoroquinolin-6-yl)-7-(1-methyl-1H-pyrazol-4-yl)-5-((S)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((R)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((S)-1-((R)-1-methylpyrrolidin-2-yl)ethoxy)quinazolin-4-amine Example 146

N-(5-fluoroquinolin-6-yl)-7-(1-methyl-1H-pyrazol-4-yl)-5-((S)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((R)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((S)-1-((R)-1-methylpyrrolidin-2-yl)ethoxy)quinazolin-4-amine TFA (3 mL) was added to Intermediate 36 (170 mg, 291 μmol) in DCM (9 mL) at rt. The resulting mixture was hold to room temperature for 2 hr. The mixture was concentrated under vacuum. The crude product was purified by Prep-TLC with DCM:MeOH=20:1 to afford a yellow solid (110 mg). LC-MS: (ES, m/z): RT=0.764 min, LCMS: m/z=484 [M+1], STAB (87.3 mg, 412 μmol) was added to the yellow solid (100 mg, 206 μmol) and HCHO (1 mL) in DCM (10 mL) at rt. The resulting mixture was stirred at room temperature for 2 hr. The mixture was concentrated under vacuum. The crude product was purified by Prep-TLC with DCM:MeOH=20:1. The residue was purified by Prep-HPLC using the following conditions: Column: Xselect CSH C18 OBD Column 30*150 mm 5 μm, n; Mobile Phase A: Water (10 mmol/L $NH_4HCO_3$+0.1% $NH_3 \cdot H_2O$), Mobile Phase B: ACN; Flow rate: 60 mL/min; Gradient: 45% B to 65% B in 8 min, 65% B; to afford a white solid (70 mg) which was further separated by dissolving in MeOH and Purified by Prep-Chiral-HPLC with following condition: Column: CHIRALPAK AD-H, 2*25 cm, 5 μm; Mobile Phase A: Hex (0.5% 2M $NH_3$-MeOH)-HPLC, Mobile Phase B: IPA-HPLC; Flow rate: 20 mL/min; Gradient: 30% B to 30% B in 33 min; Wave Length: 220/254 nm. This resulted in Example 145: First Eluting isomer (26.6 mg, 38.2%) as a white solid. LC-MS: (ES, m/z): RT=1.253 min, LCMS: m/z=498 [M+1], HPLC: RT=5.530 min; $^1H$ NMR (400 MHz, DMSO-d6) δ 10.50 (s, 1H), 8.98 (dd, J=4.3, 1.6 Hz, 1H), 8.54-8.49 (m, 2H), 8.42 (s, 1H), 8.32 (t, J=8.7 Hz, 1H), 8.16 (s, 1H), 7.96 (d, J=9.1 Hz, 1H), 7.66 (dd, J=8.6, 4.2 Hz, 1H), 7.57 (d, J=1.3 Hz, 1H), 7.42 (s, 1H), 5.06 (t, J=5.2 Hz, 1H), 3.92 (s, 3H), 2.80 (t, J=8.2 Hz, 1H), 2.53 (s, 1H), 2.30 (s, 3H), 2.15 (q, J=8.8 Hz, 1H), 1.90 (s, 2H), 1.53 (m, 4H), 1.40 (q, J=9.0 Hz, 1H).

Example 146: Second Eluting isomer (31.5 mg, 45.2%) as a white solid. LC-MS: (ES, m/z): RT=1.521 min, LCMS: m/z=498 [M+1], HPLC: RT=8.769 min; $^1H$ NMR (400 MHz, DMSO-d6) δ 10.51 (s, 1H), 8.98 (dd, J=4.3, 1.7 Hz, 1H), 8.54-8.50 (m, 2H), 8.42 (s, 1H), 8.32 (t, J=8.7 Hz, 1H), 8.16 (s, 1H), 7.96 (d, J=9.2 Hz, 1H), 7.67 (dd, J=8.5, 4.2 Hz, 1H), 7.57 (d, J=1.4 Hz, 1H), 7.43 (d, J=1.6 Hz, 1H), 5.06 (dd, J=6.4, 3.7 Hz, 1H), 3.92 (s, 3H), 2.81 (t, J=8.2 Hz, 1H), 2.51 (s, 1H), 2.30 (s, 3H), 2.16 (q, J=9.0 Hz, 1H), 1.91 (s, 2H), 1.54 (m, 4H), 1.46-1.36 (m, 1H).

Example 147

N-(5-fluoroquinolin-6-yl)-7-(1-methyl-1H-pyrazol-4-yl)-5-((S)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((R)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((S)-1-((R)-1-methylpyrrolidin-2-yl)ethoxy)quinazolin-4-amine Example 148

N-(5-fluoroquinolin-6-yl)-7-(1-methyl-1H-pyrazol-4-yl)-5-((S)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((R)-1-methylpyrrolidin-2-yl)ethoxy)quinazolin-4-amine Or N-(5-fluoroquinolin-6-yl)-7-(1-methyl-1H-pyrazol-4-yl)-5-((R)-1-((S)-1-methylpyrrolidin-2-yl)ethoxy)quinazolin-4-amine Or N-(5-fluoroquinolin-6-yl)-7-(1-methyl-1H-pyrazol-4-yl)-5-((S)-1-((R)-1-methylpyrrolidin-2-yl)ethoxy)quinazolin-4-amine TFA (3 mL) was added to Intermediate 37 (120 mg, 205 μmol) in DCM (9 mL) at rt. The resulting mixture was stirred at room temperature for 2 h. The mixture was concentrated under vacuum. The crude product was purified by Pre-TLC with DCM:MeOH=20:1 to afford a yellow solid (80 mg, yield: 80%). LC-MS: (ES, m/z): RT=0.775 min, LCMS: m/z=484 [M+1].

STAB (69.9 mg, 330 μmol) was added to the yellow solid (80 mg, 165 μmol) and HCHO (1 mL) in DCM (10 mL) at rt. The resulting mixture was stirred at room temperature for 2 h. The mixture was concentrated under vacuum. The crude product was purified by prep-TLC using DCM:MeOH=20:1. The residue was further purified by Prep-HPLC using the following conditions: Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 20% B to 66% B in 7 min, 66% B; Wavelength: 254/220 nm. This resulted in a white solid (40 mg) that was dissolved in MeOH and further separated by prep-Chiral-HPLC with following condition: Column: CHIRALPAK IE, 3*25 cm, 5 μm; Mobile Phase A: MtBE (0.5% 2M $NH_3$-MeOH)-HPLC, Mobile Phase B: EtOH-HPLC; Flow rate: 40 mL/min; Gradient: 10% B to 10% B in 33 min; Wavelength: 220/254 nm. This resulted in:

Example 147: First Eluting isomer (16.2 mg, 40.6%) as a white solid. LC-MS: (ES, m/z): RT=1.520 min, LCMS: m/z=498 [M+1], HPLC: RT=4.654 min; $^1$H NMR (400 MHz, DMSO-d6) δ 10.54 (s, 1H), 8.96 (dd, J=4.2, 1.6 Hz, 1H), 8.57-8.44 (m, 4H), 8.17 (s, 1H), 7.96 (d, J=9.2 Hz, 1H), 7.66 (dd, J=8.5, 4.2 Hz, 1H), 7.59 (d, J=1.4 Hz, 1H), 7.49 (d, J=1.6 Hz, 1H), 5.14 (dd, J=6.4, 4.0 Hz, 1H), 3.92 (s, 3H), 2.80-2.71 (m, 2H), 2.40 (s, 3H), 2.18 (td, J=9.4, 6.7 Hz, 1H), 2.01-1.87 (m, 1H), 1.85-1.74 (m, 1H), 1.71-1.57 (m, 2H), 1.47 (d, J=6.2 Hz, 3H).

Example 148: Second Eluting isomer (5.6 mg, 14%) as a white solid. LC-MS: (ES, m/z): RT=1.514 min, LCMS: m/z=498 [M+1], HPLC: RT=6.087 min; $^1$H NMR (400 MHz, DMSO-d6) δ 10.54 (s, 1H), 8.97 (dd, J=4.2, 1.7 Hz, 1H), 8.58-8.44 (m, 4H), 8.17 (s, 1H), 7.97 (d, J=9.2 Hz, 1H), 7.66 (dd, J=8.5, 4.2 Hz, 1H), 7.59 (d, J=1.4 Hz, 1H), 7.49 (d, J=1.6 Hz, 1H), 5.14 (dd, J=6.3, 4.0 Hz, 1H), 3.92 (s, 3H), 2.80-2.72 (m, 2H), 2.41 (s, 3H), 2.26-2.13 (m, 1H), 2.02-1.88 (m, 1H), 1.85-1.74 (m, 1H), 1.71-1.57 (m, 2H), 1.47 (d, J=6.2 Hz, 3H).

Example 149: (R)-7-cyclopropyl-5-((1-(dimethylamino)propan-2-yl)oxy)-N-(5-fluoroquinolin-6-yl)quinazolin-4-amine

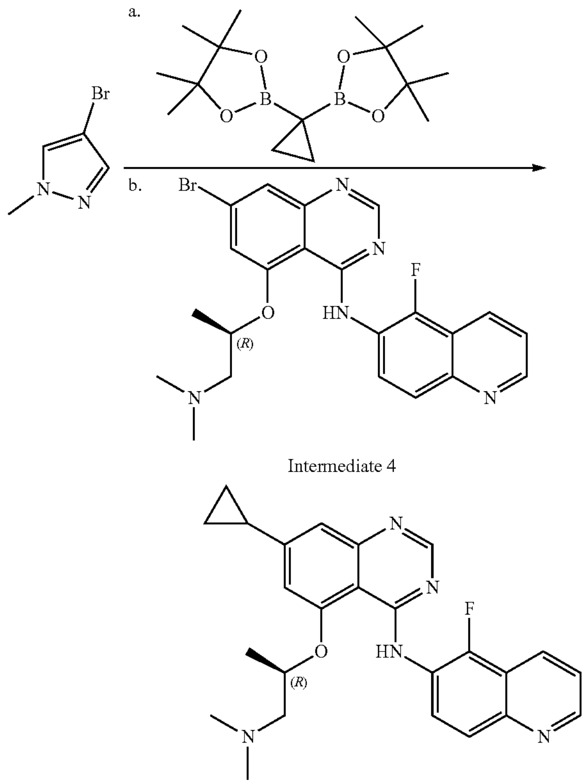

Intermediate 4

[(Di(1-adamantyl)-butylphosphine)-2-(2'-amino-1,1'-biphenyl)]palladium(II) methanesulfonate (12.39 mg, 0.017 mmol), cesium carbonate (332 mg, 1.020 mmol), 2,2'-(cyclopropane-1,1-diyl)bis(4,4,5,5-tetramethyl-1,3,2-dioxaborolane) (100 mg, 0.340 mmol) and 4-bromo-1-methyl-1H-pyrazole (110 mg, 0.680 mmol) with Water (0.2 mL) and 1,4-Dioxane (2 mL) were combined at rt and sparged with nitrogen. The resulting mixture was stirred at 100° C. for 16 hr under $N_2$. Filtered through a pad of celite and concentrated to dryness. To the reaction was added Intermediate 4 (103 mg, 0.220 mmol, 0.65 eq), cesium carbonate (331 mg, 1.016 mmol) and cataCXium® a Pd G3 (12.33 mg, 0.017 mmol) in 1,4-Dioxane (2.000 mL) and Water (0.2 mL) were combined at rt and sparged with nitrogen. The resulting mixture was stirred at 100° C. for 1 h under $N_2$. The reaction mixture was diluted with dichloromethane and water. The mixture was extracted with DCM and the organic layer was concentrated. Purified by prep HPLC using 0-40% (0.10% TFA modified water/Acetonitrile) gradient. Only the title compound (a byproduct) (21.9 mg, 15%) was recovered. LC-MS: (ES, m/z): RT=1.68 min, LC-MS: m/z=432 [M+1]; $^1$H NMR (MeOD) δ: 9.08-9.01 (m, 1H), 8.80 (d, J=7.1 Hz, 2H), 8.70-8.59 (m, 1H), 8.06 (d, J=8.9 Hz, 1H), 7.80 (dd, J=8.6, 4.5 Hz, 1H), 7.42 (d, J=1.5 Hz, 1H), 7.14 (t, J=2.0 Hz, 1H), 5.73-5.64 (m, 1H), 4.87 (s, 1H), 4.06 (ddd, J=12.9, 9.7, 3.0 Hz, 1H), 3.67 (dd, J=14.2, 2.0 Hz, 1H), 3.09 (s, 6H), 2.27 (tt, J=8.5, 4.9 Hz, 1H), 1.62 (d, J=6.2 Hz, 3H), 1.34 (dt, J=8.3, 2.1 Hz, 2H), 1.15-1.02 (m, 2H)

Example 150: 7-(3,6-diazabicyclo[3.1.1]heptan-3-yl)-5-(((R)-1-(dimethylamino)propan-2-yl)oxy)-N-(5-fluoroquinolin-6-yl)quinazolin-4-amine

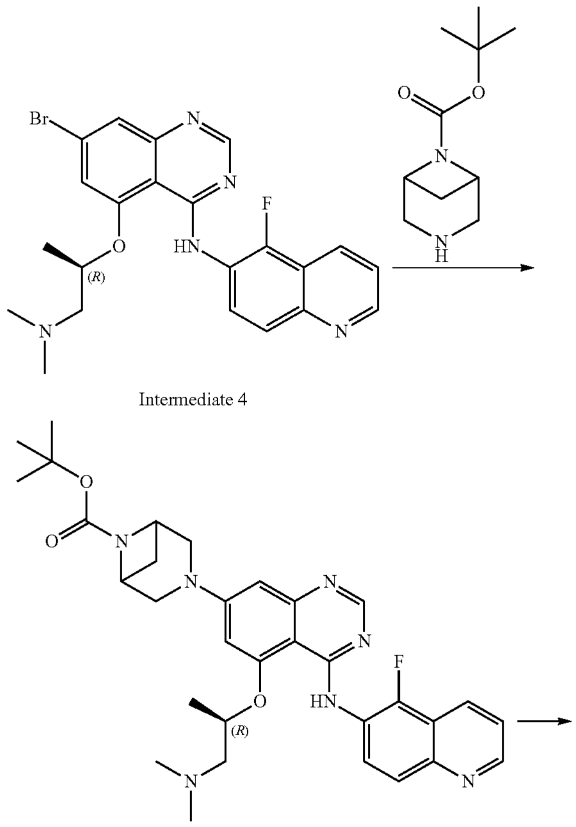

Intermediate 4

-continued

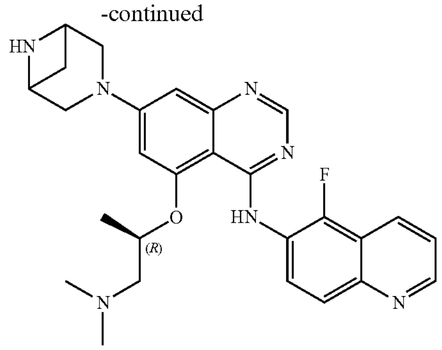

Step 1: tert-butyl 3-(5-(((R)-1-(dimethylamino)propan-2-yl)oxy)-4-((5-fluoroquinolin-6-yl)amino)quinazolin-7-yl)-3,6-diazabicyclo[3.1.1]heptane-6-carboxylate RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (36.8 mg, 0.383 mmol, 3.00 eq), Intermediate 4 (60 mg, 0.128 mmol, 1.00 eq), 3,6-diazabicyclo[3.1.1]heptane-6-carboxylic acid, 1,1-dimethylethyl ester (76.0 mg, 0.383 mmol, 3.0 eq) and dimethylformamide (2.3 mL) were combined at rt and sparged with nitrogen. The resulting mixture was stirred at 95° C. for 1 h under $N_2$. The reaction mixture was concentrated down and purified on a silica gel column using 0-100% (EtOAc/dichloromethane) to afford the title compound (68.0 mg, 91%) as a solid. LC-MS: (ES, m/z): RT=1.832 min, LC-MS: m/z=588 [M+1].

Step 2: 7-(3,6-diazabicyclo[3.1.1]heptan-3-yl)-5-(((R)-1-(dimethylamino)propan-2-yl)oxy)-N-(5-fluoroquinolin-6-yl)quinazolin-4-amine The product of step 1 was treated with 3 mL of trifluoroacetic acid and 3 mL of DCM at RT for 16 hr. Concentrated down and half the batch was taken and purified by prep HPLC using 0-40% (1% TFA modified Water/Acetonitrile) to afford the title compound (30.2 mg, 100%) as a solid. LC-MS: (ES, m/z): RT=1.29 min, LC-MS: m/z=488 [M+1]; $^1$H NMR (MeOD) δ: 9.03 (dd, J=4.5, 1.6 Hz, 1H), 8.75 (d, J=8.5 Hz, 1H), 8.66 (d, J=3.0 Hz, 1H), 8.66-8.56 (m, 2H), 8.03 (d, J=9.3 Hz, 1H), 7.77 (dd, J=8.5, 4.4 Hz, 1H), 7.01 (d, J=2.1 Hz, 1H), 6.72 (d, J=2.0 Hz, 1H), 5.80-5.72 (m, 1H), 4.67 (d, J=6.5 Hz, 2H), 4.22 (d, J=12.5 Hz, 1H), 4.17-4.00 (m, 4H), 3.73-3.64 (m, 1H), 3.19 (dt, J=12.2, 6.7 Hz, 1H), 3.09 (d, J=8.9 Hz, 6H), 2.08 (d, J=10.7 Hz, 1H), 1.63 (dd, J=14.0, 6.1 Hz, 3H)

Example 151: 1-(3-(5-(((R)-1-(dimethylamino)propan-2-yl)oxy)-4-((5-fluoroquinolin-6-yl)amino)quinazolin-7-yl)-3,6-diazabicyclo[3.1.1]heptan-6-yl)ethan-1-one

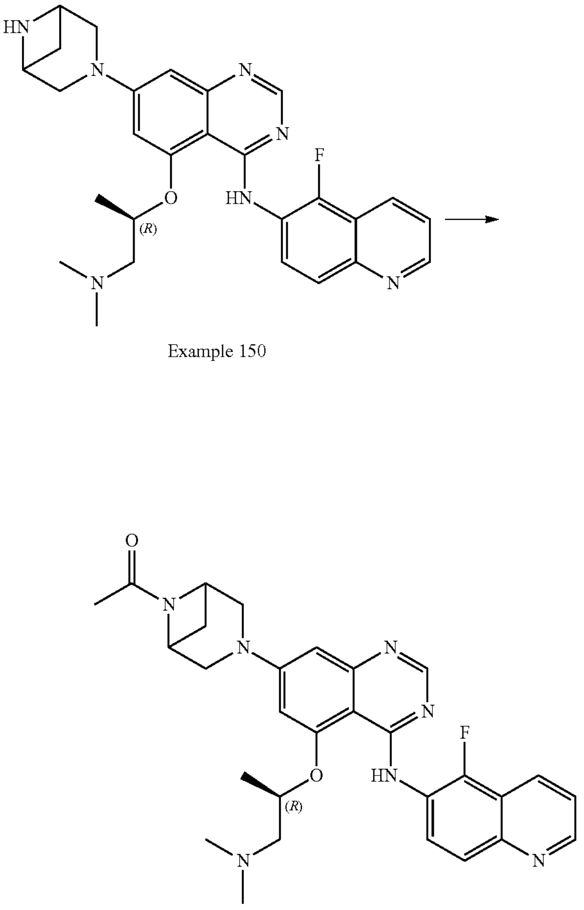

Example 150

To a solution of Example 150 (34 mg, 0.062 mmol, 1.00 eq) in 1 mL of DCM with triethylamine (16.13 μL, 0.116 mmol, 2 eq) followed by acetic anhydride (10.92 μL, 0.116 mmol, 1.5 eq) stirred at RT for 20 min. Concentrated and purified by prep HPLC using 0-40% (1% TFA modified Water/Acetonitrile) to afford the title compound (20.5 mg, 67%) as a solid. LC-MS: (ES, m/z): RT=1.62 min, LC-MS: m/z=530 [M+1]; Rotamers were observed in the NMR. $^1$H NMR (MeOD) δ: 9.01 (dd, J=4.3, 1.7 Hz, 1H), 8.72 (dd, J=8.4, 3.0 Hz, 1H), 8.69-8.58 (m, 2H), 8.02 (dd, J=9.4, 3.9 Hz, 1H), 7.75 (ddd, J=8.6, 4.4, 2.2 Hz, 1H), 6.94 (s, 0.5H), 6.81 (bs, 0.5H), 6.61 (s, 0.5H), 6.45 (s, 0.5H), 5.67 (d, J=20.6 Hz, 1H), 4.81 (s, 1H), 4.67 (d, J=5.5 Hz, 1H), 4.81-4.66 (m, 2H), 4.21-4.16 (m, 1H), 4.08-3.96 (m, 2H), 3.88-3.76 (m, 1H), 3.67 (dd, J=14.0, 5.9 Hz, 2H), 3.12-3.07 (m, 6H), 2.99-2.90 (m, 1H), 2.07-2.00 (m, 3H), 1.84-1.76 (m, 1H), 1.66-1.56 (m, 3H)]]

Example 152: (R)-5-((1-(dimethylamino)propan-2-yl)oxy)-N-(5-fluoroquinolin-6-yl)-7-(2,6-diazaspiro[3.3]heptan-2-yl)quinazolin-4-amine

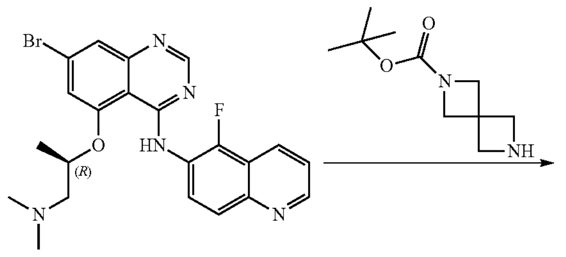

Intermediate 4

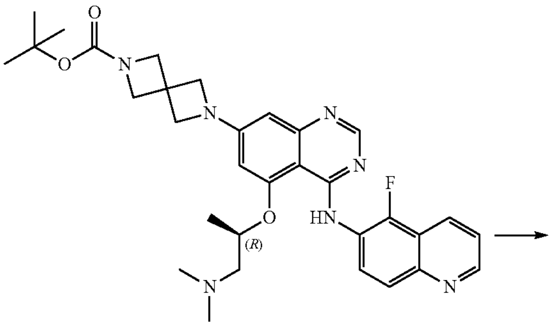

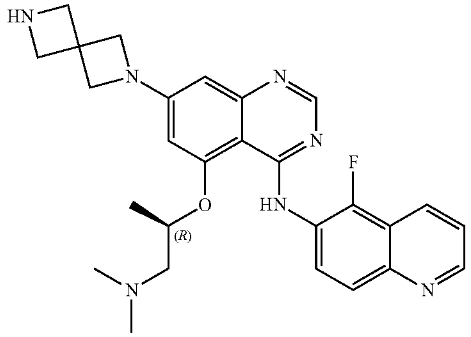

Example 152

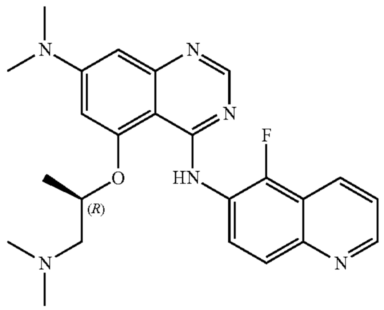

Example 153

Step 1: tert-butyl (R)-6-(5-((1-(dimethylamino)propan-2-yl)oxy)-4-((5-fluoroquinolin-6-yl)amino)quinazolin-7-yl)-2,6-diazaspiro[3.3]heptane-2-carboxylate RuPhos Pd (5.33 mg, 6.38 μmol, 0.05 eq), 2,2'-bis(diphenylphosphaneyl)-1,1'-binaphthalene (3.97 mg, 6.38 μmol), Tris(dibenzylideneacetone)dipalladium(0) (3.50 mg, 3.83 μmol), sodium t-butoxide (61.3 mg, 0.638 mmol, 5.00 eq), Intermediate 4 (60 mg, 0.128 mmol, 1.00 eq), 2-Boc-2,6-diazaspiro[3.3]heptane (76 mg, 0.383 mmol, 3.0 eq) and dimethylformamide (2.3 mL) were combined at rt and sparged with nitrogen. The resulting mixture was stirred at 100° C. for 4 h under $N_2$. The reaction mixture was concentrated down and purified on a silica gel column using 0-100% (EtOAc/dichloromethane) the title compound as a solid. LC-MS: (ES, m/z): RT=2.0 min, LC-MS: m/z=588 [M+1].

Step 2: (R)-5-((1-(dimethylamino)propan-2-yl)oxy)-N-(5-fluoroquinolin-6-yl)-7-(2,6-diazaspiro[3.3]heptan-2-yl)quinazolin-4-amine The product of step 1 was dissolved in 1 mL of DCM and 1 mL of TFA and stirred at RT. The reaction was neutralized with sat $NaHCO_3$ and concentrated Example 153 and the title compound (Example 152) (42.0 mg, 67%) as a solid. LC-MS: (ES, m/z): RT=1.35 min, LC-MS: m/z=488; $^1$H NMR (MeOD) δ: 9.06 (dd, J=4.6, 1.6 Hz, 1H), 8.84 (d, J=8.4 Hz, 1H), 8.70 (t, J=8.7 Hz, 1H), 8.57 (s, 1H), 8.04 (d, J=9.3 Hz, 1H), 7.83 (dd, J=8.5, 4.6 Hz, 1H), 6.58 (d, J=1.9 Hz, 1H), 6.21 (d, J=1.8 Hz, 1H), 5.69-5.59 (m, 1H), 4.49-4.28 (m, 8H), 4.02 (dd, J=14.2, 9.6 Hz, 1H), 3.66 (dd, J=14.2, 1.8 Hz, 1H), 3.08 (s, 6H), 1.67-1.58 (m, 3H).

Example 153: (R)-5-((1-(dimethylamino)propan-2-yl)oxy)-N4-(5-fluoroquinolin-6-yl)-N7,N7-dimethylquinazoline-4,7-diamine

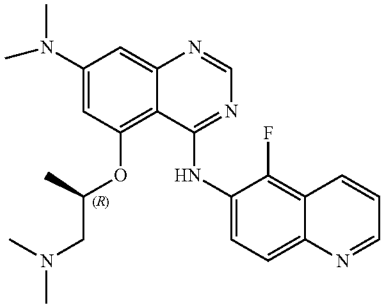

(R)-5-((1-(dimethylamino)propan-2-yl)oxy)-N4-(5-fluoroquinolin-6-yl)-N7,N7-dimethylquinazoline-4,7-diamine, (25.9 mg, 46.7%) as a solid, was isolated during purification of Example 152. LC-MS: (ES, m/z): RT=1.62 min, LC-MS: m/z=435; $^1$H NMR (MeOD) δ: 9.04 (dd, J=4.5, 1.5 Hz, 1H), 8.79 (d, J=8.5 Hz, 1H), 8.70 (t, J=8.8 Hz, 1H), 8.58 (s, 1H), 8.03 (d, J=9.4 Hz, 1H), 7.79 (dd, J=8.6, 4.5 Hz, 1H), 6.88 (d, J=2.2 Hz, 1H), 6.50 (d, J=2.1 Hz, 1H), 5.67 (dd, J=8.9, 5.6 Hz, 1H), 4.02 (dd, J=14.2, 9.6 Hz, 1H), 3.67 (dd, J=14.3, 2.0 Hz, 1H), 3.28 (s, 6H), 3.10 (s, 6H), 1.62 (d, J=6.1 Hz, 3H)

Example 154: (R)-1-(6-(5-((1-(dimethylamino)propan-2-yl)oxy)-4-((5-fluoroquinolin-6-yl)amino)quinazolin-7-yl)-2,6-diazaspiro[3.3]heptan-2-yl)ethan-1-one

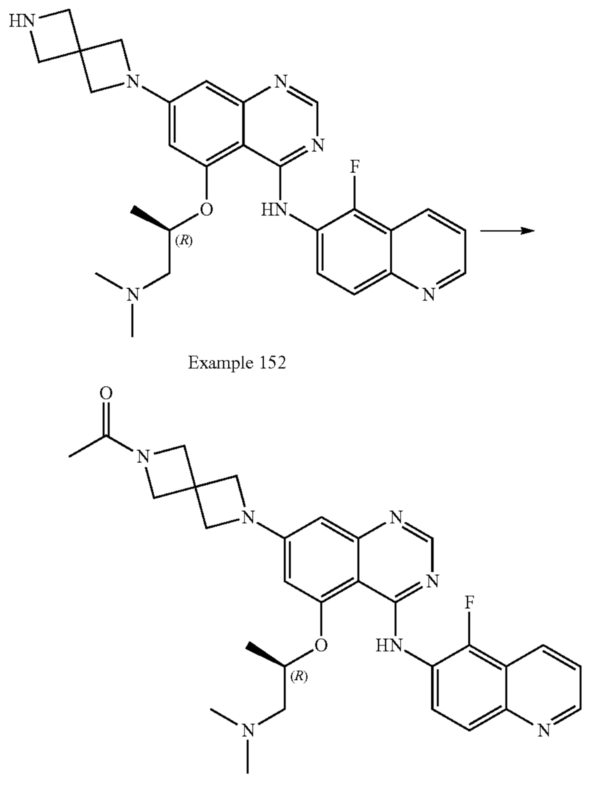

Example 152

To a solution of Example 152 (21.1 mg, 0.043 mmol, 1.00 eq) in 1 ml of DCM with triethylamine (17.08 μl, 0.123 mmol, 2.8 eq) followed by acetic anhydride (8.6 μL, 0.084 mmol, 2.0 eq) stirred at RT for 20 min. Concentrated down and purified by prep HPLC using 0-40% (1% TFA modified Water/Acetonitrile) to afford the title compound (13.8 mg, 60%) as a solid. LC-MS: (ES, m/z): RT=1.54 min, LC-MS: m/z=530 [M+1]; $^1$H NMR (MeOD) δ: 9.00 (dd, J=4.5, 1.8 Hz, 1H), 8.69 (d, J=8.7 Hz, 1H), 8.60 (t, J=8.9 Hz, 1H), 8.57 (s, 1H), 8.01 (d, J=9.3 Hz, 1H), 7.73 (dd, J=8.5, 4.3 Hz, 1H), 6.58 (d, J=1.7 Hz, 1H), 6.17 (d, J=1.8 Hz, 1H), 5.61 (s, 1H), 4.50 (s, 2H), 4.40 (s, 4H), 4.25 (s, 2H), 4.02 (dd, J=14.3, 9.6 Hz, 1H), 3.67 (d, J=14.1 Hz, 1H), 3.10 (s, 6H), 1.92 (s, 3H), 1.61 (d, J=6.1 Hz, 3H)

Example 155: (R)-5-((1-(dimethylamino)propan-2-yl)oxy)-N-(5-fluoroquinolin-6-yl-2-d)-7-(1-methyl-1H-pyrazol-4-yl)quinazolin-4-amine

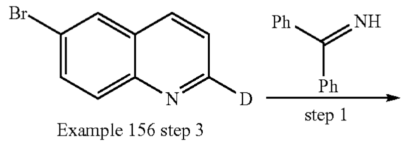

Example 156 step 3

-continued

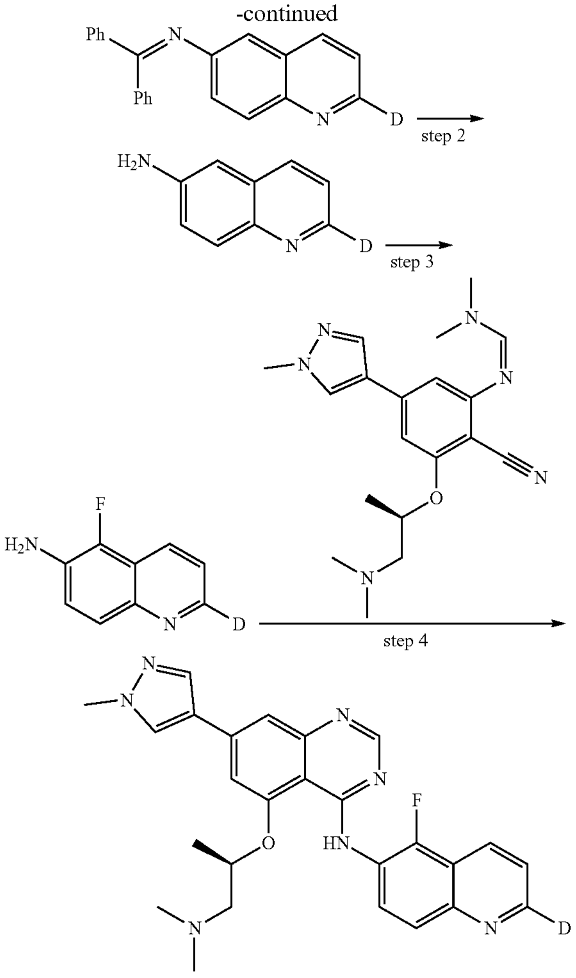

Step 1: 1,1-diphenyl-N-(quinolin-6-yl-2-d)methanimine

A mixture of the product of Example 156 step 3 (1.0 g, 4.78 mmol), diphenylmethanimine (1.73 g, 9.56 mmol), XantPhos Pd (796 mg, 478 μmol) and XantPhos (276 mg, 478 μmol) in dioxane (20 mL) was stirred at 100° C. for 16 hr. The mixture was diluted with EA 100 mL and washed with brine 50 mL*2, the organic layer was dried with $Na_2SO_4$ and concentrated under vacuum. The residue was purified by a silica gel column using PE:EA=5:1. This resulted in 1.2 g 1,1-diphenyl-N-(quinolin-6-yl-2-d)methanimine as a yellow solid. LC-MS: (ES, m/z): RT=0.879 min, LCMS: m/z=310[M+1].

Step 2: Quinolin-2-d-6-amine

HCl (4M, 10 mL) was added to 1,1-diphenyl-N-(quinolin-6-yl-2-d)methanimine (1.2 g, 3.87 mmol) in THF (10 mL) at rt. The resulting mixture was stirred at rt for 2 hr. The mixture was diluted with EA (100 mL) The aqueous layer was adjusted to pH=8 and extracted with EA (100 mL*3), the organic layer was dried with $Na_2SO_4$ and concentrated under vacuum. The residue was purified by a silica gel column using DCM:MeOH=25:1. This resulted in 500 mg of quinolin-2-d-6-amine as a brown solid. LC-MS: (ES, m/z): RT=0.454 min, LCMS: m/z=146 [M+1].

Step 3: 5-fluoroquinolin-2-d-6-amine

Selectfluor (970 mg, 2.74 mmol) was added to quinolin-2-d-6-amine (200 mg, 1.37 mmol) in THF (20 mL) at rt. The resulting mixture was stirred at 60° C. for 2 hr. The mixture was diluted with EA 100 mL and washed with brine 50 mL*2, the organic layer was dried with $Na_2SO_4$ and concentrated under vacuum. The residue was purified by a Prep-TLC with PE:EA=1:2 to afford 100 mg 5-fluoroquinolin-2-d-6-amine as a yellow solid. LC-MS: (ES, m/z): RT=0.551 min, LCMS: m/z=164[M+1].

Step 4: (R)-5-((1-(dimethylamino)propan-2-yl)oxy)-N-(5-fluoroquinolin-6-yl-2-d)-7-(1-methyl-1H-pyrazol-4-yl)quinazolin-4-amine The reaction mixture of 5-fluoroquinolin-2-d-6-amine (100 mg, 612 μmol) and Intermediate 28b (325 mg, 918 μmol) in AcOH (10 mL) was stirred at 100° C. for 16 hr. The resulting mixture was concentrated under vacuum. The mixture was diluted with EA (100 mL) and washed with brine (50 mL*2), the organic layer was dried with $Na_2SO_4$ and concentrated under vacuum. The residue was purified by a Prep-TLC with DCM:MeOH=25:1. The residue was further purified by Prep-HPLC using the following conditions: Column: XBridge Prep OBD C18 Column, 30*150 mm, 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 36% B to 51% B in 8 min, 51% B; Wavelength: 254; 220 nm; This resulted in 10.9 mg of the title compound as white solid. LC-MS: (ES, m/z): RT=1.873 min, LCMS: m/z=473[M+1], $^1$H NMR (400 MHz, DMSO-d6) δ 10.54 (s, 1H), 8.63 (t, J=8.9 Hz, 1H), 8.49-8.39 (m, 3H), 8.09 (d, J=0.8 Hz, 1H), 7.89 (d, J=9.2 Hz, 1H), 7.58 (d, J=8.5 Hz, 1H), 7.51 (d, J=1.4 Hz, 1H), 7.37 (d, J=1.6 Hz, 1H), 5.05 (d, J=11.0 Hz, 1H), 3.85 (s, 3H), 2.83 (dd, J=12.9, 8.3 Hz, 1H), 2.55-2.50 (m, 1H), 2.11 (s, 6H), 1.45 (d, J=6.0 Hz, 3H).

Example 156: (R)-5-((1-(dimethylamino)propan-2-yl)oxy)-7-(1-methyl-1H-pyrazol-4-yl)-N-(quinolin-6-yl-2-d)quinazolin-4-amine

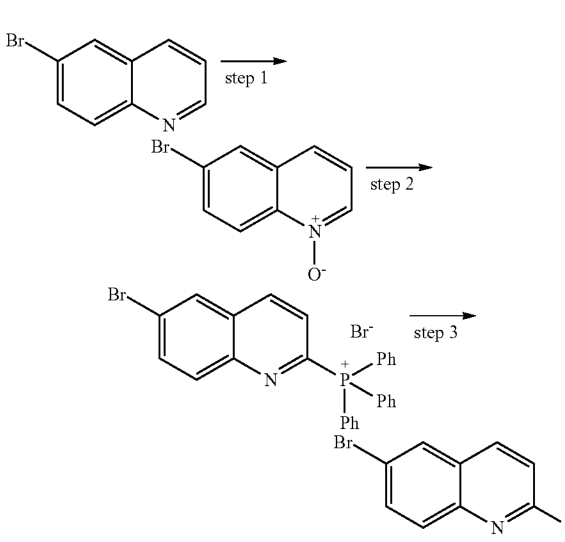

-continued

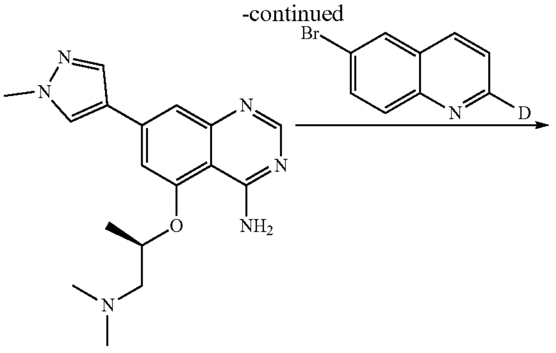

Intermediate 28

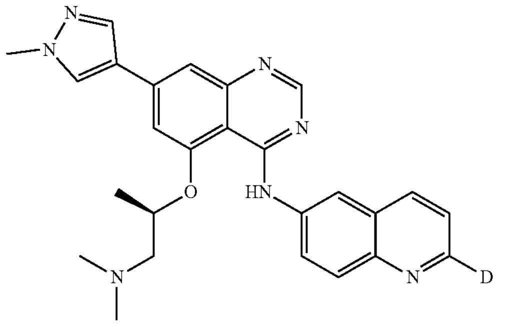

Step 1: 6-bromoquinoline 1-oxide 3-chlorobenzene-1-carboperoxoic acid (16.5 g, 96.0 mmol) was added batchwise to 6-bromoquinoline (10 g, 48.0 mmol) in DCM (150 mL) at rt. The resulting mixture was stirred at rt for 16 hr. The mixture was diluted with DCM 200 mL and washed with KOH (aq, 5M). The organic layer was dried with $Na_2SO_4$ and concentrated under vacuum. The residue was purified by a silica gel column using PE:EA=5:1. This resulted in the title compound (10.0 g) as a brown solid. LC-MS: (ES, m/z): RT=0.835 min, LCMS: m/z=224[M+1].

Step 2: (6-bromoquinolin-2-yl)triphenylphosphoniumbromide 2,2,2-trifluoroacetyl 2,2,2-trifluoroacetate (14.0 g, 66.9 mmol) was added dropwise to 6-bromoquinoline 1-oxide (10.0 g, 44.6 mmol) and triphenylphosphine (17.5 g, 66.9 mmol) in DCM (100 mL) at 0° C. The resulting solution was stirred at rt 7 h. DCM (150 mL) and NaBr (30% w/v) solution (100 mL) were added to the mixture. The mixture was vigorously stirred for 30 min and the organic layer was separated. Aqueous layer was extracted with $CH_2Cl_2$ (1'10 mL). All organic layers were combined, dried with $Na_2SO_4$, and the solvent was removed under reduced pressure. This resulted in the title compound (9.5 g) as a brown oil. LC-MS: (ES, m/z): RT=1.116 min, LCMS: m/z=470 [M-Br].

Step 3: 6-bromoquinoline-2-d 1,4-diazabicyclo[2.2.2]octane (9.47 g, 84.5 mmol) was added batchwise to (6-bromoquinolin-2-yl)triphenylphosphonium (9.5 g, 17.2 mmol) in $D_2O/CD_3OD$ (100 mL/100 mL) at rt. The resulting mixture was stirred at rt for 2d. The mixture was diluted with DCM 200 mL and washed with brine 100 mL*2. The organic layer was dried with $Na_2SO_4$ and concentrated under vacuum. The residue was purified by a Prep-TLC with DCM:MeOH=20:1. The resulted in the title compound (3.0 g) as a yellow solid. LC-MS: (ES, m/z): RT=0.644 min, LCMS: m/z=209[M+1].

Step 4: (R)-5-((1-(dimethylamino)propan-2-yl)oxy)-7-(1-methyl-1H-pyrazol-4-yl)-N-(quinolin-6-yl-2-d)quinazolin-4-amine Intermediate 28 (250 mg, 765 μmol), 6-bromoquinoline-2-d (191 mg, 917 μmol), XantPhos Pd (127 mg, 76.5 μmol), $Cs_2CO_3$ (371 mg, 1.14 mmol) in dioxane (20 mL) was stirred at 100° C. for 16 hr. The mixture was diluted with EA 100 mL and washed with brine 50 mL*2, the organic layer was dried with $Na_2SO_4$ and concentrated under vacuum. The residue was purified by a prep-HPLC using the following conditions: Column: YMC-Actus Triart C18 ExRS, 30*150 mm, 5 μm; Mobile Phase A: Water (10 mmol/L $NH_4HCO_3$+ 0.1% $NH_3 \cdot H_2O$), Mobile Phase B: ACN; Flow rate: 60 mL/min; Gradient: 38% B to 52% B in 8 min, 52% B; Wavelength: 254; 220 nm; This resulted in title compound (129.2 mg) as a white solid. LC-MS: (ES, m/z): RT=0.645 min, LCMS: m/z=455[M+1], $^1$H NMR (400 MHz, DMSO-d6) δ 10.69 (s, 1H), 8.61-8.55 (m, 2H), 8.47 (s, 1H), 8.35 (d, J=8.4 Hz, 1H), 8.15 (d, J=0.8 Hz, 1H), 8.05 (d, J=1.5 Hz, 2H), 7.57 (d, J=1.5 Hz, 1H), 7.52 (d, J=8.3 Hz, 1H), 7.40 (d, J=1.6 Hz, 1H), 5.17-5.08 (m, 1H), 3.92 (s, 3H), 3.04 (dd, J=12.9, 8.9 Hz, 1H), 2.55-2.50 (m, 1H), 2.27 (s, 6H), 1.53 (d, J=5.8 Hz, 3H).

Example 157: N-(5-fluoroquinolin-6-yl)-7-(1-methyl-1H-pyrazol-4-yl)-5-((S)-1-((S)-morpholin-3-yl)ethoxy)quinazolin-4-amine

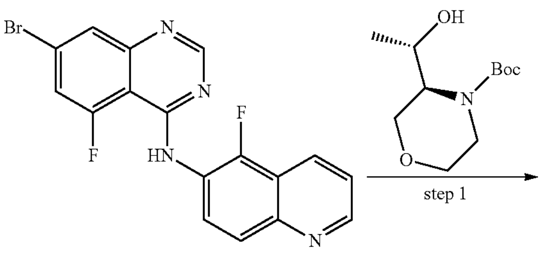

Intermediate 2

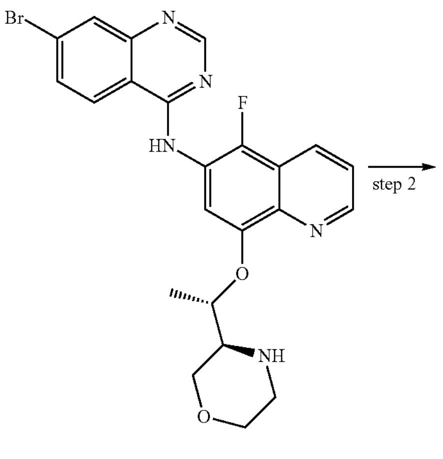

-continued

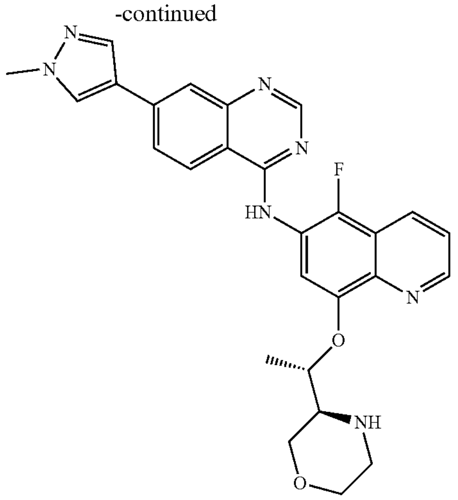

Step 1: 7-bromo-N-(5-fluoroquinolin-6-yl)-5-((S)-1-((S)-morpholin-3-yl)ethoxy)quinazolin-4-amine To a mixture of Intermediate 2 (85 mg, 0.220 mmol) in DMA (1.000 mL) and was added a solution of tert-butyl (S)-3-((S)-1-hydroxyethyl)morpholine-4-carboxylate (53.3 mg, 0.231 mmol), potassium bis(trimethylsilyl)amide in Toluene (878 μL, 0.439 mmol) and heated to 90° C. After 5 hr the reaction was cooled to rt and NaH (1 eq) was added and the reaction was heated at 90° C. After 3 hr the reaction was cooled to room temperature. Added water and extracted with DCM. Concentrated the organic layer and purified by prep HPLC to afford the title compound (5.8 mg, 0.012 mmol, 5.30% yield). LC-MS: (ES, m/z): RT=2.15 min, LC-MS: m/z=499 [M+1]

Step 2: N-(5-fluoroquinolin-6-yl)-7-(1-methyl-1H-pyrazol-4-yl)-5-((S)-1-((S)-morpholin-3-yl)ethoxy)quinazolin-4-amine To a mixture of the product of step 1 (5.8 mg, 0.012 mmol), 1-methyl-4-(4,4,5,5-tetramethyl-1,3,2-dioxaborolan-2-yl)-1H-pyrazole (2.91 mg, 0.014 mmol), Methanesulfonato[9,9-dimethyl-4,5-bis(diphenylphosphino)xanthene][2'-amino-1,1'-biphenyl]palladium(II) dichloromethane adduct (0.552 mg, 0.582 μmol) in DMF (1.0 mL) was added an aqueous solution of potassium phosphate 2M solution (11.64 μL, 0.023 mmol) under inert atmosphere and heated for 16 hr at 110° C. Cooled the reaction and filtered through a pad of celite/silica and rinsed with more DMF. The crude product was purified by prep-HPLC: 0-40% (0.1% TFA modified water/Acetonitrile gradient to afford the title compound (2.2 mg, 4.40 μmol, 37.8% yield) LC-MS: (ES, m/z): RT=1.96 min, LC-MS: m/z=500 [M+1]; $^1$H NMR (DMSO) δ: 13.18 (s, 1H), 9.15-9.08 (m, 1H), 8.92 (s, 1H), 8.62-8.52 (m, 3H), 8.21 (d, J=3.5 Hz, 1H), 8.03 (s, 1H), 8.00-7.95 (m, 1H), 7.89 (d, J=3.5 Hz, 1H), 7.75 (d, J=22.0 Hz, 1H), 7.68-7.52 (m, 2H), 4.89 (s, 1H), 4.21 (d, J=11.4 Hz, 1H), 3.93 (d, J=3.6 Hz, 3H), 3.85-3.75 (m, 4H), 3.20-3.14 (m, 1H), 3.05 (d, J=12.2 Hz, 1H), 0.98 (d, J=5.3 Hz, 3H)

Example 158: (R)-5-((1-(dimethylamino)propan-2-yl)oxy)-N-(5-fluoroquinolin-6-yl)-7-(1-methyl-1H-pyrazol-4-yl)quinazolin-8-d-4-amine

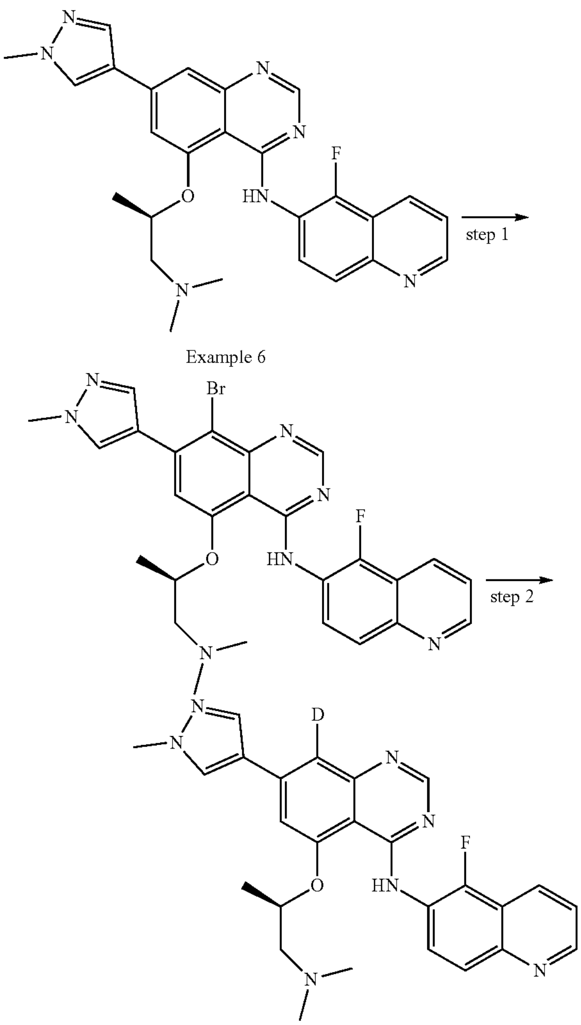

Step 1: (R)-8-bromo-5-((1-(dimethylamino)propan-2-yl)oxy)-N-(5-fluoroquinolin-6-yl)-7-(1-methyl-1H-pyrazol-4-yl)quinazolin-4-amine To a solution of Example 6 (120 mg, 0254 mmol) in 1 mL of chloroform was added a solution of bromine (14.42 μL, 0.280 mmol) in 0.5 mL of Chloroform. Reaction was stirred for 1 hr and quenched with saturated sodium bicarbonate and extracted product with dichloromethane. Organic layer was dried with anhydrous $Na_2SO_4$ and concentrated to give crude solid. Purified by prep-HPLC from 0-40% 0.1 TFA Water/Acetonitrile. Isolated the title compound (63.4 mg, 99% Purity) LC-MS: (ES, m/z): RT=1.99 min, LC-MS: m/z=551-553 [M+1]; $^{1}$H NMR (500 MHz, DMSO) δ 10.77 (s, 1H), 8.96 (dd, J=4.3, 1.6 Hz, 1H), 8.61 (s, 1H), 8.54 (dd, J=9.0, 9.0 Hz, 1H), 8.53 (ddd, J=8.6, 1.1, 1.1 Hz, 1H), 8.44 (s, 1H), 8.09 (s, 1H), 7.96 (d, J=9.1 Hz, 1H), 7.65 (dd, J=8.5, 4.2 Hz, 1H), 7.34 (s, 1H), 5.10 (ddq, J=8.7, 6.0, 4.2 Hz, 1H), 3.95 (s, 3H), 2.89 (dd, J=13.0, 8.6 Hz, 1H), 2.46 (dd, J=13.0, 4.1 Hz, 1H), 2.15 (s, 6H), 1.51 (d, J=5.9 Hz, 3H).

Step 2 (R)-5-((1-(dimethylamino)propan-2-yl)oxy)-N-(5-fluoroquinolin-6-yl)-7-(1-methyl-1H-pyrazol-4-yl)quinazolin-8-d-4-amine To a vial was added (R)-8-bromo-5-((1-(dimethylamino)propan-2-yl)oxy)-N-(5-fluoroquinolin-6-yl)-7-(1-methyl-1H-pyrazol-4-yl)quinazolin-4-amine (15 mg, 0.027 mmol), tri-tert-butylphosphine (0.662 mg, 1.635 μmol), tris(dibenzylideneacetone)dipalladium(0) (0.499 mg, 0.545 μmol) in DMSO and then added sodium borodeuteride (2.281 mg, 0.055 mmol) and heated to 80° C. for 15 min. Cooled to room temperature. Material was passed through a plug of silica and then reverse phase purified by prep-HPLC 0-40% 1% TFA ACN/Water. Isolated product=(R)-5-((1-(dimethylamino)propan-2-yl)oxy)-N-(5-fluoroquinolin-6-yl)-7-(1-methyl-1H-pyrazol-4-yl)quinazolin-8-d-4-amine (10.2 mg, 0.022 mmol, 79% yield) LC-MS: (ES, m/z): RT=1.59 min, LC-MS: m/z=473 [M+1]; 1H NMR (DMSO) δ: 10.60 (s, 1H), 8.95 (d, J=4.1 Hz, 1H), 8.72 (s, 1H), 8.61-8.44 (m, 3H), 8.17 (s, 1H), 7.97 (d, J=9.2 Hz, 1H), 7.66 (dd, J=8.5, 3.8 Hz, 1H), 7.46 (s, 1H), 5.14 (s, 1H), 3.93 (s, 3H), 2.20 (s, 6H), 1.52 (d, J=5.9 Hz, 3H)

Example 159: (R)-5-((1-(dimethylamino)propan-2-yl)oxy)-N-(5-fluoroquinolin-6-yl)-7-(1-methyl-1H-pyrazol-4-yl-5-d)quinazolin-4-amine

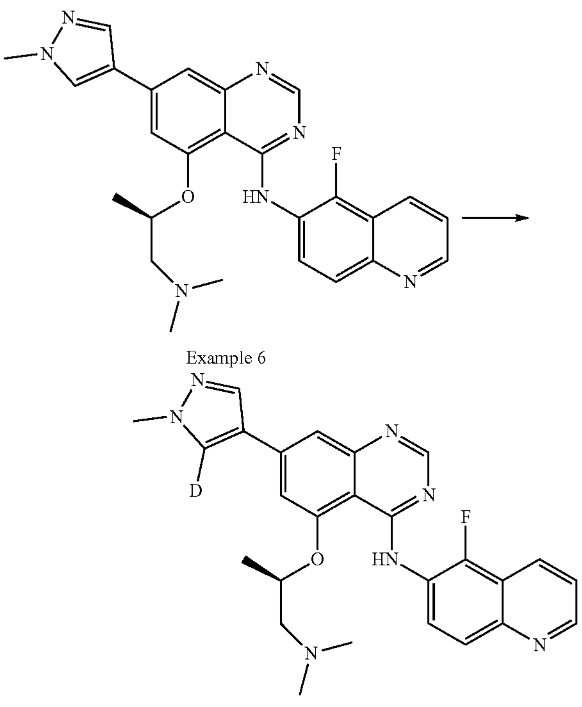

To a solution of ((1-(dimethylamino)propan-2-yl)oxy)-N-(5-fluoroquinolin-6-yl)-7-(1-methyl-1H-pyrazol-4-yl)quinazolin-4-amine (50 mg, 0.106 mmol) in 1 mL of MeOD was added 1 eq of cesium carbonate. Stirred at RT for 16 hr. The reaction was concentrated and purified by prep-HPLC from 0-40% 0.1 TFA Water/Acetonitrile. Isolated the title compound (50 mg, 99% purity). LC-MS: (ES, m/z): RT=1.64 min, LC-MS: m/z=473 [M+1]; 1H NMR (DMSO) δ: 10.48 (s, 1H), 10.30 (s, 1H), 9.05 (s, 1H), 8.80 (s, 1H), 8.63 (s, 0H), 8.35 (s, 0H), 8.03 (s, 1H), 7.77-7.67 (m, 2H), 7.64 (s, 1H), 5.70 (tt, J=7.6, 5.4 Hz, 1H), 4.10 (dd, J=14.0, 9.4 Hz, 1H), 3.62 (d, J=13.9 Hz, 1H), 2.97 (s, 6H), 1.51 (d, J=6.0 Hz, 3H)

Biological Example 1. Biochemical EGFR Inhibition Assays

Inhibitory effects of the compounds of the disclosure were measured in biochemical assays that measure the phosphorylation activity of EGFR enzyme phosphorylates 2.5 micromolar 5-FAM-EEPLYWSFPAKKK-$CONH_2$ peptide substrate (ProfilerPro Kinase Peptide Substrate 22, PerkinElmer, Part #760366) in the presence of adenosine-5'-triphosphate (ATP) and varying concentrations of the test compound in 100 mM 2-[4-(2-hydroxyethyl)piperazin-1-yl] ethanesulfonic acid (HEPES), pH 7.5, 10 mM $MgCl_2$, 0.015% Brij-35, 1 mM dithiothreitol (DTT), 1.0% dimethylsulfoxide (DMSO). Assays were performed at 1.0 mM ATP or at ATP $K_m$ of the EGFR enzymes. Reactions proceeded until between 10% to 20% total peptides were phosphorylated at room temperature (25° C.) and were terminated with 35 mM 2,2',2",2'"-(ethane-1,2-diyldinitrilo) tetraacetic acid (EDTA). Product was detected using the Caliper mobility shift detection method where the phosphorylated peptide (product) and substrate were electrophoretically separated and measured. Percent activity was plotted against log concentration of compound and points to generate an apparent $IC_{50}$. The following enzyme forms of EGFR were examples that were used in these assays:

EGFR WT (SignalChem, E10-112G)
EGFR L858R (SignalChem, E10-122BG)
EGFR (d746-750) (SignalChem, E10-122JG)
EGFR L858R C797S (SignalChem, E10-122ZG)
EGFR (d746-750) C797S (SignalChem, E10-122TG)

Biological Example 2. Cellular EGFR Inhibition Assays

PC-9/A431 pEGFR AlphaLISA Assays

Inhibitory effects of compounds were evaluated in cellular assays that measure level of intracellular phosphorylation of EGFR in PC-9 (ECACC, #90071810, Milipore/Sigma) and A431 cell lines (ATCC, CRL-1555) using AlphaLISA sureFire ultra p-EGFR (Tyr1068) assay kit (PerkinElmer, ALSU-PEGFR-A50K). PC-9 cells were seeded at 3.125×10ˆ5 cells/ml in 40 μL phenol-free DMEM supplemented with 10% FBS per well of a 384 well plate (Corning, 3764), while A431 were seeded at 3.125×10≡cells/ml in 40 μL in phenol-free DMEM with 0.5% FBS. Cells were allowed to adhere overnight at 37° C./5% $CO_2$. On the next day, compounds were transferred at 4-fold, 10-point serial dilution from compound source plate to cell plates using liquid handler Echo550 and were incubated at 37° C./5% $CO_2$ for 4 hours. A431 cells were stimulated prior harvesting for 10 min with EGF at final concentration of 30 ng/ml in the incubator. Medium was removed from the plates and cells were lysed with 10 μL of 1× AlphaLISA lysis buffer (supplemented with 1× protease/phosphatase inhibitor cocktail) followed by shaking at 600 rpm for 30 minutes at room temperature. Lysates were transferred to Optiplate (Apricot designs) and 5 ul of 1× acceptor bead mix (prepared just before use) was added to each well followed by incubation at room temperature for 1.5-2 h in dark. Then 5 μL of freshly-made donor bead mix is added to each well under subdued lighting or green filters, was mixed well on the shaker and the plate was sealed and left for an overnight incubation at room temperature in dark. On the next day, the plate was read the Envision using standard AlphaLisa settings. Percent of pEGFR inhibition was plotted against log concentration of compounds to generate $IC_{50}$ values. Biological assay data of the test compounds are provided in Table 2 below. For inhibitory activity against EGFR L858R C797S and EGFR (d746-750) C797S mutants, and for inhibition of phosphorylation of mutant EGFR in cells the following designations are used: ≤10 nM=A; 10.1-50 nM=B; and >50.1 nm=C.

TABLE 2

| Example # | Enz EGFR_L858R $IC_{50}$ (nM) | Enz EGFR_Exon19-del746-750 $IC_{50}$ (nM) | Ext pEGFR_PC-9 Ex19Del $IC_{50}$ (nM) |
|---|---|---|---|
| 1 | A | A | A |
| 2 | A | A | A |
| 3 | A | A | A |
| 4 | B | B | C |
| 5 | A | A | A |
| 6 | A | A | A |
| 7 | A | A | A |
| 8 | A | A | A |
| 9 | A | A | A |
| 10 | A | A | A |
| 11 | C | B | C |
| 12 | B | A | C |
| 13 | A | A | A |
| 14 | A | A | A |
| 15 | A | A | A |
| 16 | A | A | A |
| 17 | A | A | A |
| 18 | A | A | A |
| 19 | A | A | B |
| 20 | A | A | A |
| 21 | B | A | B |
| 22 | A | A | A |
| 23 | A | A | A |
| 24 | A | A | A |
| 25 | A | A | B |
| 26 | C | C | C |
| 27 | B | A | A |
| 28 | A | A | A |
| 29 | A | A | A |
| 30 | A | A | A |
| 31 | A | A | A |
| 32 | A | A | C |
| 33 | A | A | B |
| 34 | B | A | B |
| 35 | A | A | A |
| 36 | B | A | B |
| 37 | A | A | A |
| 38 | B | A | B |
| 39 | A | A | A |
| 40 | B | A | A |
| 41 | C | B | C |
| 42 | A | A | A |
| 43 | C | B | C |
| 44 | A | A | A |
| 45 | A | A | A |
| 46 | A | A | A |
| 47 | A | A | A |
| 48 | A | A | A |
| 49 | A | A | A |
| 50 | A | A | A |
| 51 | A | A | A |
| 52 | A | A | A |
| 53 | A | A | A |
| 54 | A | A | A |
| 55 | A | A | A |
| 56 | A | A | A |
| 57 | B | A | B |
| 58 | C | B | C |
| 59 | A | A | A |
| 60 | B | A | B |
| 61 | A | A | A |
| 62 | A | A | A |
| 63 | A | A | A |
| 64 | A | A | A |

TABLE 2-continued

| Example # | Enz EGFR_L858R $IC_{50}$ (nM) | Enz EGFR_Exon19-del746-750 $IC_{50}$ (nM) | Ext pEGFR_PC-9 Ex19Del $IC_{50}$ (nM) |
|---|---|---|---|
| 65 | B | A | A |
| 66 | B | A | A |
| 67 | B | B | B |
| 68 | B | A | A |
| 69 | C | B | C |
| 70 | B | A | A |
| 71 | A | A | A |
| 72 | B | A | B |
| 73 | A | A | A |
| 74 | B | A | B |
| 75 | B | A | B |
| 76 | A | A | A |
| 77 | B | A | B |
| 78 | A | A | A |
| 79 | A | A | A |
| 80 | A | A | A |
| 81 | C | C | C |
| 82 | A | A | A |
| 83 | A | A | A |
| 84 | A | A | A |
| 85a | A | A | A |
| 85b | A | A | A |
| 86 | A | A | A |
| 87a | A | A | A |
| 87b | A | A | A |
| 88 | A | A | A |
| 89 | C | C | C |
| 90 | B | A | A |
| 91 | C | B | C |
| 92 | B | A | B |
| 93 | B | A | B |
| 94 | B | A | B |
| 95 | B | A | B |
| 96 | B | A | A |
| 97 | A | A | A |
| 98 | B | A | A |
| 99a | A | A | A |
| 99b | B | A | B |
| 100 | B | B | B |
| 101 | B | A | A |
| 102 | B | B | C |
| 103 | B | A | B |
| 104 | B | A | B |
| 105 | B | A | B |
| 106 | A | A | A |
| 107 | B | A | B |
| 108 | B | A | B |
| 109 | C | B | C |
| 110 | A | A | C |
| 111 | A | A | A |
| 112 | A | A | A |
| 113 | A | A | A |
| 114 | A | A | A |
| 115 | A | A | A |
| 116 | A | A | C |
| 117 | B | A | B |
| 118 | A | A | A |
| 119 | A | A | A |
| 120 | A | A | A |
| 121 | A | A | A |
| 122 | A | A | A |
| 123 | A | A | A |
| 124 | A | A | B |
| 125 | A | A | B |
| 126 | A | A | A |
| 127 | A | A | B |
| 128 | B | B | C |
| 129 | B | A | B |
| 130 | C | B | C |
| 131 | A | A | A |
| 132 | A | A | A |
| 135 | A | A | A |
| 136 | A | A | A |
| 137 | A | A | A |
| 138 | A | A | A |

TABLE 2-continued

| Example # | Enz EGFR_L858R $IC_{50}$ (nM) | Enz EGFR_Exon19-del746-750 $IC_{50}$ (nM) | Ext pEGFR_PC-9 Ex19Del $IC_{50}$ (nM) |
|---|---|---|---|
| 139 | A | A | A |
| 140 | A | A | A |
| 141 | B | B | C |
| 142 | A | A | A |
| 143 | A | A | B |
| 144 | A | A | B |
| 145 | B | B | C |
| 146 | A | A | A |
| 147 | A | A | A |
| 148 | B | B | C |
| 149 | C | B | C |
| 150 | C | C | C |
| 151 | C | B | C |
| 152 | A | A | B |
| 153 | B | A | A |
| 154 | A | A | A |
| 155 | A | A | A |
| 156 | A | A | A |
| 157 | C | C | C |
| 158 | A | A | A |
| 159 | B | A | A |

Additional compounds falling within the scope of formula (I) not disclosed herein were also tested in the assays described in Biological Examples 1 and 2, and all but one had inhibitory activities of less than 10 micromolar in these assays. The following compound had an inhibitory activity greater than 10 micromolar in Biological Assay 1.

TABLE 3

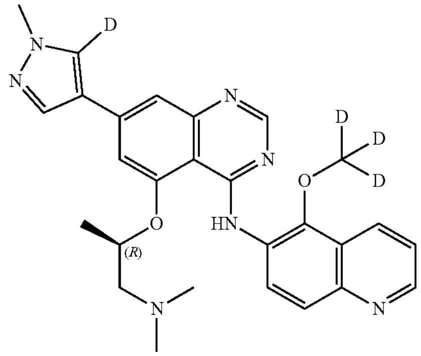

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula (I-0)

(I-0)

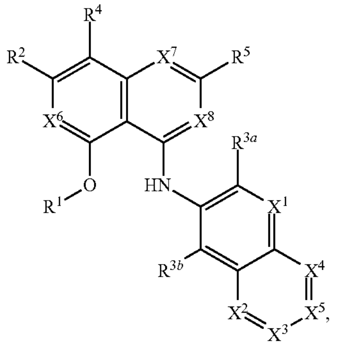

or a pharmaceutically acceptable salt thereof, wherein $X^1$, $X^2$, $X^3$, $X^4$, and $X^5$ is $CR^{3c}$, N, or $N^+$—$O^-$, provided that at least 3 of $X^1$, $X^2$, $X^3$, $X^4$, and $X^5$ is $CR^{3c}$;

$X^6$ is CH;

$X^7$ and $X^8$ is N $R^1$ is $C_1$-$C_6$alkyl, $C_3$-$C_6$cycloalkyl, or 4- to 12-membered heterocyclyl, wherein the alkyl, cycloalkyl, and heterocyclyl represented by $R^1$ is optionally substituted with 1 to 4 groups independently selected from deuterium, halo, $C_1$-$C_4$alkyl, ═O, OH, $C_1$-$C_4$alkoxy, $NR^{1a}R^{1b}$, and 4 to 8 membered heterocyclyl, wherein the heterocyclyl is optionally substituted with methyl, ethyl, or —$(CH_2)_m NR^{1a}R^{1b}$;

$R^2$ is halo, $NR^{1a}R^{1b}$, $C_1$-$C_4$alkyl, $C_1$-$C_4$alkoxy, $C_3$-$C_6$cycloalkyl, 4- to 12-membered heterocyclyl, or 5 or 6 membered heteroaryl, wherein the alkyl, alkoxy, cycloalkyl, heterocycyl, and heteroaryl represented by $R^2$ are each optionally substituted with 1 to 4 groups selected from deuterium, halo, ═O (as valence permits), OH, $NR^{1a}R^{1b}$, $C(O)CH_3$, $C_1$-$C_4$alkyl and $C_1$-$C_4$alkoxy, wherein the $C_1$-$C_4$alkyl and $C_1$-$C_4$alkoxy are each optionally substituted with 1 to 3 groups selected from deuterium, halo, OH, and $OCH_3$;

$R^{3a}$ is H, deuterium, halo, OH, $C_{1-4}$alkyl, or $C_1$-$C_4$alkoxy;

$R^{3b}$ is H, deuterium, halo, OH, $C_{1-4}$alkyl, or $C_1$-$C_4$alkoxy;

Each $R^{3c}$ is independently selected from H, deuterium, halo, OH, $C_{1-4}$alkyl, and $C_1$-$C_4$alkoxy, wherein no more than 3 $R^{3c}$ are halo, OH, $C_{1-4}$alkyl, or $C_1$-$C_4$alkoxy;

$R^{1a}$ is H, deuterium, $C_1$-$C_4$alkyl, or $C_3$-$C_6$cycloalkyl;

$R^{1b}$ is H, deuterium, $C_1$-$C_4$alkyl, or $C_3$-$C_6$cycloalkyl;

$R^4$ is H or deuterium;

$R^5$ is H or deuterium; and m is 0 or 1.

2. The compound of claim 1, or a pharmaceutically acceptable salt thereof, wherein $R^1$ is $C_3$alkyl substituted with $N(CH_3)_2$.

3. A pharmaceutical composition comprising a pharmaceutically acceptable carrier and an effective amount of a compound of any of claim 1, or a pharmaceutically acceptable salt thereof.

4. A method of treating a cancer, comprising administering a subject in need thereof an effective amount of a compound of claim 1, wherein the cancer is non-small cell lung cancer (NSCLC).

5. The method of claim 4, wherein the cancer in the subject in need thereof has metastasized and wherein the cancer is characterized by: (i) epidermal growth factor receptor EGFR L858R mutation or exon 19 deletion; ii) C797S mutation; and (iii) EGFR T790M mutation.

6. The method of claim 4, further comprises administering the subject in need thereof an effective amount of afatinib or osimertinib.

7. A compound of Formula (I)

(I)

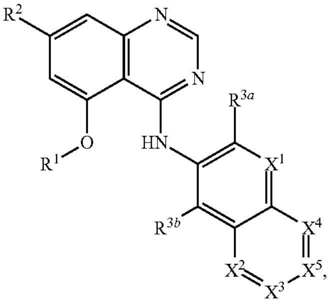

or a pharmaceutically acceptable salt thereof, wherein $X^1$, $X^2$, $X^3$, $X^4$, and $X^5$ is $CR^{3c}$ or N, provided that at least 3 of $X^1$, $X^2$, $X^3$, $X^4$, and $X^5$ is $CR^{3c}$;

$R^1$ is $C_1$-$C_6$ alkyl, $C_3$-$C_6$cycloalkyl, 4 to 12 membered heterocyclyl, wherein the alkyl, cycloalkyl, and heterocyclyl represented by $R^1$ is optionally substituted with 1 to 4 groups independently selected from halo, $C_1$-$C_4$alkyl, ═O, OH, $C_1$-$C_4$alkoxy, $NR^{1a}R^{1b}$, and 4 to 8 membered heterocyclyl, wherein the heterocyclyl is optionally substituted with —$(CH_2)_m NR^{1a}R^{1b}$;

$R^2$ is $C_1$-$C_4$alkoxy, 4 to 12 membered heterocyclyl, 5 or 6 membered heteroaryl, wherein the heterocycyl, and heteroaryl represented by $R^2$ are each optionally substituted with 1 to 4 groups selected from $C_1$-$C_4$alkyl and $C_1$-$C_4$alkoxy, wherein the $C_1$-$C_4$ alkyl and $C_1$-$C_4$alkoxy are each optionally substituted with 1 to 3 groups selected from halo, OH and $OCH_3$;

$R^{3a}$ is H, halo, OH, $C_{1-4}$alkyl, or $C_1$-$C_4$alkoxy;

$R^{3b}$ is H, halo, OH, $C_{1-4}$alkyl, or $C_1$-$C_4$ alkoxy;

Each $R^{3c}$ is independently selected from H, halo, OH, $C_{1-4}$alkyl, and $C_1$-$C_4$ alkoxy, wherein no more than 3 $R^{3c}$ are halo, OH, $C_{1-4}$alkyl, or $C_1$-$C_4$alkoxy;

$R^{1a}$ is H, $C_1$-$C_4$alkyl, or $C_3$-$C_6$cycloalkyl;

$R^{1b}$ is H, $C_1$-$C_4$alkyl, or $C_3$-$C_6$cycloalkyl; and m is 0 or 1.

8. The compound of claim 7, wherein the compound is of Formula (II), (IIA), (IIB), (IIC), (IID), (III), (IIIA), (IIIB), (IIIC), (IIID), or (IIIE), (II)

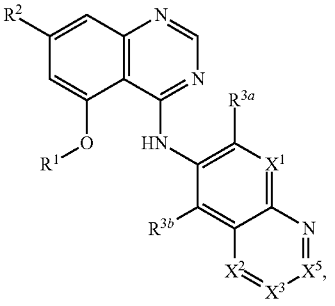

-continued
(IIA)
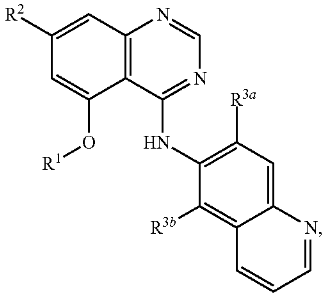
(IIB)
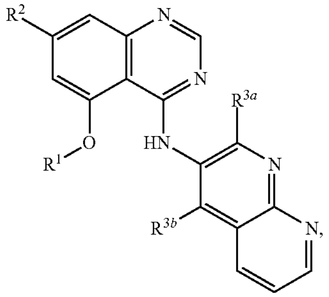
(IIC)
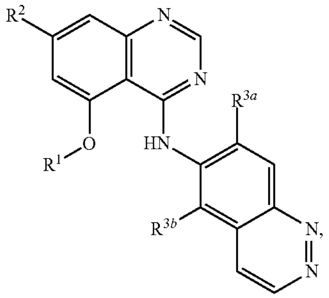
(IID)
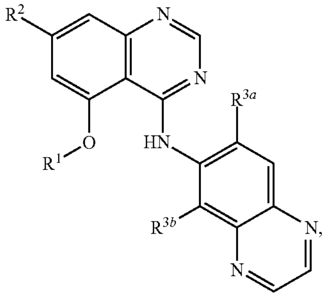
(III)
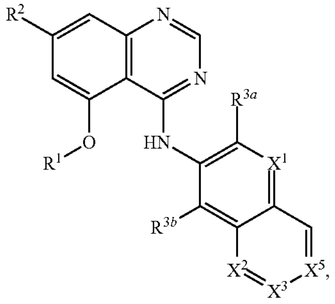
-continued
(IIIA)
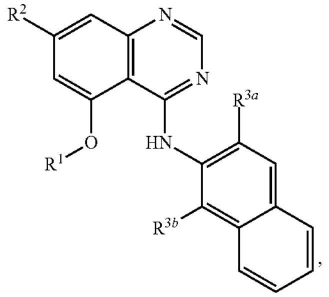
(IIIB)
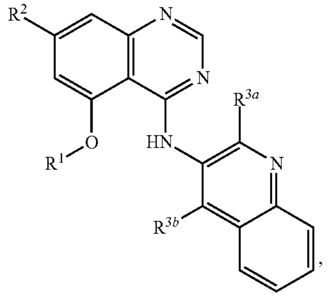
(IIIC)
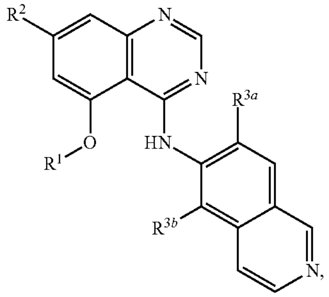
(IIID)
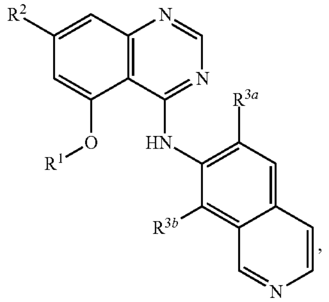
(IIIE)
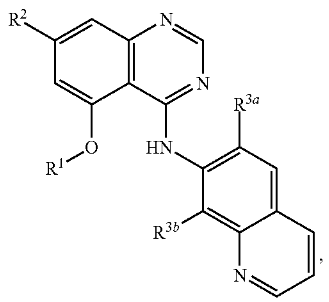
or a pharmaceutically acceptable salt thereof.
9. The compound of claim 8, or a pharmaceutically acceptable salt thereof, wherein $R^1$ is $C_1$-$C_5$ alkyl optionally substituted with 1 to 3 groups independently selected from F, Cl, =O, OH, $OCH_3$, $NR^{1a}R^{1b}$, 3-oxabicyclo[3.1.0]hexanyl, azetidinyl, oxetanyl, tetrahydrofuranyl, and morpholinyl, wherein the oxetanyl is optionally substituted with $N(CH_3)_2$ or $CH_2N(CH_3)_2$;

$R^{1a}$ is H, methyl, cyclopropyl, or cyclobutyl; and $R^{1b}$ is methyl.

10. The compound of claim 9, or a pharmaceutically acceptable salt thereof, wherein $R^1$ is ethyl substituted with oxetanyl.

11. The compound of claim 9, or a pharmaceutically acceptable salt thereof, wherein $R^2$ is pyrazolyl optionally substituted with $C_1$-$C_4$alkyl or $C_1$-$C_4$alkoxy, each of which are optionally substituted with 1 to 3 groups selected from halo and OH.

12. The compound of claim 11, or a pharmaceutically acceptable salt thereof, wherein $R^2$ is pyrazolyl optionally substituted with methyl.

13. The compound of claim 12, or a pharmaceutically acceptable salt thereof, wherein $R^{3a}$ is halo; $R^{3b}$ is halo, and each $R^{3c}$ is H; or $R^{3a}$ is H; $R^{3b}$ is H, and each $R^{3c}$ is H; or $R^{3a}$ is H; $R^{3b}$ is halo, and each $R^{3c}$ is H; or $R^{3a}$ is halo; $R^{3b}$ is H, and each $R^{3c}$ is H.

14. The compound of claim 7, or a pharmaceutically acceptable salt thereof, wherein $R^1$ is $C_1$-$C_6$alkyl optionally substituted with 1 to 4 groups independently selected from halo, =O, OH, $C_1$-$C_4$alkoxy, $NR^{1a}R^{1b}$, and 4 to 8 membered heterocyclyl, wherein the heterocyclyl is optionally substituted with $-(CH_2)_mNR^{1a}R^{1b}$;

$R^{1a}$ is H, $C_{1-4}$alkyl, or $C_3$-$C_6$cycloalkoxy; and $R^{1b}$ is H or $C_{1-4}$alkyl.

15. The compound of claim 14, or a pharmaceutically acceptable salt thereof, wherein $R^2$ is 5 or 6 membered heteroaryl optionally substituted with 1 to 3 groups selected from $C_1$-$C_4$alkyl, and $C_1$-$C_4$alkoxy, wherein the $C_1$-$C_4$alkyl and $C_1$-$C_4$alkoxy represented by $R^2$ are each optionally substituted with 1 to 3 groups selected from halo and OH.

16. The compound of claim 7, or a pharmaceutically acceptable salt thereof, wherein $R^1$ is $C_3$-$C_6$cycloalkyl optionally substituted with 1 to 4 groups independently selected from halo, $C_1$-$C_4$alkyl, =O, OH, $C_1$-$C_4$alkoxy, and $NR^{1a}R^{1b}$;

$R^{1a}$ is H, $C_1$-$C_4$alkyl, or $C_3$-$C_6$cycloalkyl; and $R^{1b}$ is H or $C_1$-$C_4$alkyl.

17. The compound of claim 7, or a pharmaceutically acceptable salt thereof, wherein $R^1$ is 4 to 8 membered monocyclic heterocyclyl optionally substituted with 1 to 2 groups independently selected from halo, $C_1$-$C_4$alkyl, =O, OH, $C_1$-$C_4$alkoxy, and $NR^{1a}R^{1b}$;

$R^{1a}$ is H, $C_1$-$C_4$alkyl, or $C_3$-$C_6$cycloalkyl; and $R^{1b}$ is H or $C_1$-$C_4$alkyl.

18. The compound of claim 7, or a pharmaceutically acceptable salt thereof, wherein $R^2$ is $C_1$-$C_4$alkoxy; or $R^2$ is 4 to 12 membered heterocyclyl optionally substituted with 1 to 3 groups selected from $C_1$-$C_4$alkyl or $C_1$-$C_4$ alkoxy, wherein the alkyl represented by $R^2$ is optionally substituted with OH.

* * * * *